US012419960B2

(12) United States Patent
Snyder

(10) Patent No.: US 12,419,960 B2
(45) Date of Patent: Sep. 23, 2025

(54) COMPOUNDS AND METHODS FOR THE TARGETED DEGRADATION OF ANDROGEN RECEPTOR AND ASSOCIATED METHODS OF USE

(71) Applicant: Arvinas Operations, Inc., New Haven, CT (US)

(72) Inventor: Lawrence B. Snyder, Killingworth, CT (US)

(73) Assignee: Arvinas Operations, Inc., New Haven, CT (US)

( * ) Notice: Subject to any disclaimer, the term of this patent is extended or adjusted under 35 U.S.C. 154(b) by 122 days.

(21) Appl. No.: 17/506,324

(22) Filed: Oct. 20, 2021

(65) Prior Publication Data

US 2023/0084249 A1 Mar. 16, 2023

Related U.S. Application Data

(60) Provisional application No. 63/094,554, filed on Oct. 21, 2020.

(51) Int. Cl.
*A61K 45/06* (2006.01)
*A61K 47/54* (2017.01)
*A61K 47/55* (2017.01)
*A61P 35/00* (2006.01)
*C07D 401/14* (2006.01)
*C07D 405/14* (2006.01)
*C07D 413/14* (2006.01)
*C07D 487/04* (2006.01)
*C07D 498/08* (2006.01)
*C07D 498/10* (2006.01)

(52) U.S. Cl.
CPC ............ *A61K 47/545* (2017.08); *A61K 45/06* (2013.01); *A61K 47/55* (2017.08); *A61P 35/00* (2018.01); *C07D 401/14* (2013.01); *C07D 405/14* (2013.01); *C07D 413/14* (2013.01); *C07D 487/04* (2013.01); *C07D 498/08* (2013.01); *C07D 498/10* (2013.01)

(58) Field of Classification Search
CPC ...... A61K 47/545; A61K 45/06; A61K 47/55; A61P 35/00; C07D 401/14; C07D 405/14; C07D 413/14; C07D 487/04; C07D 498/08; C07D 498/10
See application file for complete search history.

(56) References Cited

U.S. PATENT DOCUMENTS

| 4,522,811 | A | 6/1985 | Eppstein et al. |
| 10,584,101 | B2 | 3/2020 | Crew et al. |
| 2014/0356322 | A1 | 12/2014 | Crews et al. |
| 2015/0291562 | A1 | 10/2015 | Crew et al. |
| 2016/0058872 | A1 | 3/2016 | Crew et al. |
| 2018/0099940 | A1 | 4/2018 | Crew et al. |
| 2018/0228907 | A1 | 8/2018 | Crew et al. |
| 2022/0144809 | A1 | 5/2022 | Dong et al. |
| 2023/0091225 | A1 | 3/2023 | Du et al. |
| 2023/0183209 | A1 | 6/2023 | Crew et al. |

FOREIGN PATENT DOCUMENTS

| CN | 110317192 A | 10/2019 |
| CN | 110746400 A | 2/2020 |
| CN | 110790750 A | 2/2020 |
| CN | 118085015 A | 5/2024 |
| EP | 1466902 A1 | 10/2004 |
| WO | 2018071606 A1 | 4/2018 |
| WO | 2021081108 A1 | 4/2021 |
| WO | WO-2022098544 A1 | 5/2022 |

OTHER PUBLICATIONS

Elancheran, R., et al., "Design and Development of Oxobenzimidazoles as Novel Androgen Receptor Antagonists", Medicinal Chemistry Research (Jan. 21, 2016); 25(4): 539-552.
Guo, C., et al., "Design of oxobenzimidazoles and oxindoles as novel androgen receptor antagonists", Bioorganic & Medicinal Chemistry Letters (2012); 22: 2572-2578.
Heinlein, C. A., et al., "Androgen receptor in prostate cancer", Endocrine Reviews (2004); 25(2): 276-308.
Heinlein, C. A., et al., "The roles of androgen receptors and androgen-binding proteins in nongenomic androgen actions", Molecular Endocrinology (2002); 16(10): 2181-2187.
Lu, N. Z., et al., "International Union of Pharmacology. LXV. The pharmacology and classification of the nuclear receptor superfamily: glucocorticoid, mineralocorticoid, progesterone, and androgen receptors", Pharmacological Reviews (2006); 58(4): 782-797.
Mooradian, A. D., et al., "Biological actions of androgens", Endocrine Reviews (1987); 8(1): 1-28.
Roy, A. K., et al., "Regulation of androgen action", Vitamins & Hormones (1998); 55: 309-352.
Trewartha, D., et al., "Advances in prostate cancer treatment", Nature Reviews, Drug Discovery (2013); 12(11): 823-824.
Scott, DE., et al., Systematic Investigation of the Permeability of Androgen Receptor PROTACs, ACS Med. Chem. Lett. Jun. 8, 2020, 11, 1539-1547.

(Continued)

*Primary Examiner* — Sun Jae Yoo
(74) *Attorney, Agent, or Firm* — Sheppard Mullin Richter & Hampton LLP

(57) ABSTRACT

Bifunctional compounds, which find utility as modulators of androgen receptor (AR), are described herein. In particular, the bifunctional compounds of the present disclosure contain on one end a moiety that binds to the cereblon E3 ubiquitin ligase and on the other end a moiety which binds AR, such that the target protein is placed in proximity to the ubiquitin ligase to effect degradation (and inhibition) of target protein. The bifunctional compounds of the present disclosure exhibit a broad range of pharmacological activities associated with degradation/inhibition of target protein. Diseases or disorders that result from aberrant regulation of the target protein are treated or prevented with compounds and compositions of the present disclosure.

20 Claims, 1 Drawing Sheet

(56) References Cited

OTHER PUBLICATIONS

Shibata, N., et al., Development of Protein Degradation Inducers of Androgen Receptor by Conjugation of Androgen Receptor Ligands and Inhibitor of Apoptosis Protein Ligands, Jun. 8, 2017, J. Med Chem. 2018, 61, 543-575.
International Search Report and Written Opinion for PCT/US2021/1055836 issued Feb. 7, 2022.
Yamamoto, S., et al., "Design, synthesis, and biological evaluation of 4-phenylpyrrole derivatives as novel androgen receptor antagonists", Bioorganic & Medicinal Chemistry (Oct. 28, 2011); 20: 422-434.

COMPOUNDS AND METHODS FOR THE TARGETED DEGRADATION OF ANDROGEN RECEPTOR AND ASSOCIATED METHODS OF USE

CROSS-REFERENCE TO RELATED APPLICATIONS

The present application claims priority to and the benefit of U.S. Provisional Application No. 63/094,554, filed 21 Oct. 2020, titled COMPOUNDS AND METHODS FOR THE TARGETED DEGRADATION OF ANDROGEN RECEPTOR AND ASSOCIATED METHODS OF USE, which is incorporated by reference herein in its entirety for all purposes

INCORPORATION BY REFERENCE

All cited references are hereby incorporated herein by reference in their entirety, including U.S. patent application Ser. No. 14/686,640, filed on 14 Apr. 2015, published as U.S. Patent Application Publication No. 2015/0291562; and U.S. patent application Ser. No. 14/792,414, filed on 6 Jul. 2015, published as U.S. Patent Application Publication No. 2016/0058872; and U.S. patent application Ser. No. 15/953,108, filed on 13 Apr. 2018, published as U.S. Patent Application Publication No. 2018/0228907; and U.S. patent application Ser. No. 15/730,728, filed 11 Oct. 2017, issued as U.S. Pat. No. 10,584,101 on 10 Mar. 2020.

FIELD OF THE INVENTION

The description provides hetero-bifunctional compounds comprising a target protein binding moiety and a E3 ubiquitin ligase binding moiety, and associated methods of use. The bifunctional compounds are useful as modulators of targeted ubiquitination of androgen receptor (AR), which is then degraded and/or inhibited.

BACKGROUND

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and therefore, are more attractive therapeutic targets than general proteasome inhibitors due to their specificity for certain protein substrates. The development of ligands of E3 ligases has proven challenging, in part because they must disrupt protein-protein interactions. However, recent developments have provided specific ligands which bind to these ligases. For example, since the discovery of nutlins, the first small molecule E3 ligase inhibitors, additional compounds have been reported that target E3 ligases.

Cereblon is a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism which has not been completely elucidated, cereblon ubiquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this ubiquitin ligase complex is important for limb outgrowth in embryos. In the absence of cereblon, DDB1 forms a complex with DDB2 that functions as a DNA damage-binding protein.

Bifunctional compounds such as those described in U.S. Patent Application Publications 2015/0291562 and 2014/0356322 (incorporated herein by reference), function to recruit endogenous proteins to an E3 ubiquitin ligase for ubiquitination and subsequent degradation in the proteasome degradation pathway. In particular, the publications cited above describe bifunctional or proteolysis-targeting chimeric (PROTAC®) protein degrader compounds, which find utility as modulators of targeted ubiquitination of a variety of polypeptides and other proteins, which are then degraded and/or inhibited by the bifunctional compounds.

Androgen Receptor (AR) belongs to a nuclear hormone receptor family that is activated by androgens, such as testosterone and dihydrotestosterone (Pharmacol. Rev. 2006, 58(4), 782-97; Vitam. Horm. 1999, 55:309-52.). In the absence of androgens, AR is bound by Heat Shock Protein 90 (Hsp90) in the cytosol. When an androgen binds AR, its conformation changes to release AR from Hsp90 and to expose the Nuclear Localization Signal (NLS). The latter enables AR to translocate into the nucleus where AR acts as a transcription factor to promote gene expression responsible for male sexual characteristics (Endocr. Rev. 1987, 8(1):1-28; Mol. Endocrinol. 2002, 16(10), 2181-7). AR deficiency leads to Androgen Insensitivity Syndrome, formerly termed testicular feminization.

While AR is responsible for development of male sexual characteristics, it is also a well-documented oncogene in certain forms of cancers, including prostate cancers (Endocr. Rev. 2004, 25(2), 276-308). A commonly measured target gene of AR activity is the secreted Prostate Specific Antigen (PSA) protein. The current treatment regimen for prostate cancer involves inhibiting the androgen-AR axis by two methods. The first approach relies on reduction of androgens, while the second strategy aims to inhibit AR function (Nat. Rev. Drug Discovery, 2013, 12,823-824). Despite the development of effective targeted therapies, most patients develop resistance and the disease progresses. An alternative approach for the treatment of prostate cancer involves eliminating the AR protein. Because AR is a critical driver of tumorigenesis in many forms of prostate cancers, its elimination should lead to therapeutically beneficial response.

There exists an ongoing need in the art for effective treatments for diseases, especially cancer, prostate cancer, and Kennedy's Disease. However, non-specific effects, and the inability to target and modulate certain classes of proteins altogether, such as transcription factors, remain as obstacles to the development of effective anti-cancer agents. As such, an ongoing need exists in the art for effective treatments for AR related disease and discorders, e.g., cancer, prostate cancer, and Kennedy's Disease.

SUMMARY

The present disclosure describes hetero-bifunctional compounds that function to recruit androgen receptor (AR) to an E3 ubiquitin ligase for targeted ubiquitination and subsequent proteasomal degradation, and methods of making and using the same. In particular, compounds as described herein preferentially bind to AR proteins. In addition, the description provides methods of using an effective amount of a compound of the invention, as described herein, for the treatment or amelioration of a disease condition or one or more symptoms thereof, such as Kennedy's Disease or cancer, e.g. prostate cancer.

As such, in one aspect the disclosure provides hetero-bifunctional compounds that comprise an E3 ubiquitin ligase binding moiety (i.e., a ligand for an E3 ubiquitin ligase (a "ULM" group)), and a protein targeting moiety that preferentially binds to AR, such that the AR protein is thereby preferentially placed in proximity to the ubiquitin ligase to effect ubiquitination and subsequent preferential degradation (and/or inhibition) of the AR protein. In a preferred embodiment, the ULM (ubiquitin ligase binding moiety) is a cereblon E3 ubiquitin ligase binding moiety (CLM). For example, the structure of the bifunctional compound can be depicted as:

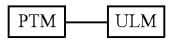

The respective positions of the PTM and ULM moieties (e.g., CLM), as well as their number as illustrated herein, is provided by way of example only and is not intended to limit the compounds in any way. As would be understood by the skilled artisan, the bifunctional compounds as described herein can be synthesized such that the number and position of the respective functional moieties can be varied as desired.

In certain embodiments, the bifunctional compound further comprises a chemical linker ("L"). In this example, the structure of the bifunctional compound can be depicted as:

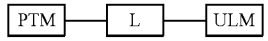

where PTM is a moiety that selectively or preferentially binds to an AR protein, L is a linker, e.g., a bond or a chemical linking group coupling PTM to ULM, and ULM is a cereblon E3 ubiquitin ligase binding moiety (CLM).

For example, the structure of the bifunctional compound can be depicted as:

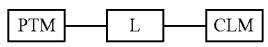

wherein: PTM is a moiety that selectively or preferentially binds to an AR protein; "L" is a linker (e.g. a bond or a chemical linking group) coupling the PTM and CLM; and CLM is cereblon E3 ubiquitin ligase binding moiety that binds to cereblon.

In certain embodiments, the compounds as described herein comprise multiple independently selected ULMs, multiple PTMs, multiple chemical linkers or a combination thereof.

In an embodiment, the CLM comprises a chemical group derived from an imide, a thioimide, an amide, or a thioamide. In a particular embodiment, the chemical group is a phthalimido group, or an analog or derivative thereof. In a certain embodiment, the CLM is selected from thalidomide, lenalidomide, pomalidomide, analogs thereof, isosteres thereof, and derivatives thereof. Other contemplated CLMs are described in U.S. Patent Application Publication No. 2015/0291562, which is incorporated herein by reference in its entirety.

In certain embodiments, "L" is a bond. In additional embodiments, the linker "L" is a connector with a linear non-hydrogen atom number in the range of 1 to 20. The connector "L" can contain, but is not limited to one or more functional groups such as ether, amide, alkane, alkene, alkyne, ketone, hydroxyl, carboxylic acid, thioether, sulfoxide, and sulfone. The linker can contain aromatic, heteroaromatic, cyclic, bicyclic or tricyclic moieties. Substitution with halogen, such as Cl, F, Br and I can be included in the linker. In the case of fluorine substitution, single or multiple fluorines can be included.

In certain embodiments, CLM is a derivative of piperidine-2,6-dione, where piperidine-2,6-dione can be substituted at the 3-position, and the 3-substitution can be bicyclic hetero-aromatics with the linkage as C—N bond or C—C bond. Examples of CLM can be, but are not limited to, pomalidomide, lenalidomide and thalidomide and their analogs.

In an additional aspect, the description provides therapeutic compositions comprising an effective amount of a compound as described herein, or a salt form thereof, and a pharmaceutically acceptable carrier. The therapeutic compositions can be used to trigger targeted degradation and/or inhibition of an AR protein in a patient or subject in need thereof, for example, an animal such as a human, and can be used for treating or ameliorating one or more disease states, conditions, or symptoms causally related to the AR protein, which treatment is accomplished through the degradation of the AR protein to control, stabilize or lower levels of protein of the AR protein in a patient or subject. In certain embodiments, the therapeutic compositions as described herein may be used to effectuate the degradation of AR for the treatment or amelioration of a disease, disorder or symptom, such as, e.g., an infection, an inflammatory or immunological disorder, or cancer.

In yet another aspect, the present disclosure provides a method of ubiquitinating an AR in a cell. In certain embodiments, the method comprises administering a hetero-bifunctional compound as described herein comprising a PTM that binds to an AR, and a CLM, preferably linked together through a chemical linker moiety, as described herein, to effectuate degradation of the AR protein. Though not wanting to be limited by theory, the inventors believe that, pursuant to the invention, poly-ubiquitination of the AR protein will occur when it is placed in proximity to the E3 ubiquitin ligase via use of the hetero-bifunctional compound, thereby triggering subsequent degradation of the ar protein via the proteasomal pathway, thereby controlling or reducing ar protein levels in cells of the subject. The control or reduction in AR protein levels afforded by the present disclosure provides treatment of a disease state, condition or at least one causally related symptom, as modulated through a lowering or stabilization of the amount of AR protein in cells of the subject.

In still another aspect, the description provides methods for treating or ameliorating a disease, condition, or symptom thereof in a subject or a patient, e.g., an animal such as a human, comprising administering to a subject in need thereof a composition comprising an effective amount, e.g., a therapeutically effective amount, of a hetero-bifunctional compound as described herein or salt form thereof, and a pharmaceutically acceptable carrier, wherein the composition is effective for treating or ameliorating the disease or disorder or symptom thereof in the subject.

In another aspect, the description provides methods for identifying the effects of the degradation of an AR protein according to the disclosure in a biological system using compounds according to the present disclosure.

In another aspect, the description provides processes and intermediates for making a hetero-bifunctional compound of the invention capable of targeted ubiquitination and degradation of an AR protein according to the disclosure in a cell.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the disclosure may be utilized in numerous combinations, all of which are expressly contemplated by the present description. These additional aspects and embodiments are expressly included within the scope of the present disclosure. The publications and other materials used herein to illuminate the background of the disclosure, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating embodiments of the disclosure and are not to be construed as limiting the disclosure. Further objects, features and advantages of the disclosure will become apparent from the following detailed description taken in conjunction with the accompanying figures showing illustrative embodiments of the disclosure.

FIG. 1A. Exemplary hetero-bifunctional protein degrading compounds comprise a protein targeting moiety (PTM; darkly shaded rectangle), a ubiquitin ligase binding moiety (ULM; lightly shaded triangle), and optionally a linker moiety (L; black line) coupling or tethering the PTM to the ULM. FIG. 1B Illustrates the functional use of the hetero-bifunctional protein degrading compounds (commercially known as PROTAC® brand compounds) as described herein. Briefly, the ULM (triangle) recognizes and binds to a specific E3 ubiquitin ligase, and the PTM (large rectangle) binds and recruits a target protein bringing it into close proximity to the E3 ubiquitin ligase. Typically, the E3 ubiquitin ligase is complexed with an E2 ubiquitin-conjugating protein (E2), and either alone or via the E2 protein catalyzes attachment of multiple ubiquitin molecules (black circles) to a lysine on the target protein via an isopeptide bond. The poly-ubiquitinated protein (far right) has thereby been targeted for degradation by the proteosomal machinery of the cell.

DETAILED DESCRIPTION

The following is a detailed description provided to aid those skilled in the art in practicing the present invention. Those of ordinary skill in the art may make modifications and variations in the embodiments described herein without departing from the spirit or scope of the present disclosure.

All publications, patent applications, patents, and other references mentioned herein are expressly incorporated by reference in their entirety.

Figure 1A:
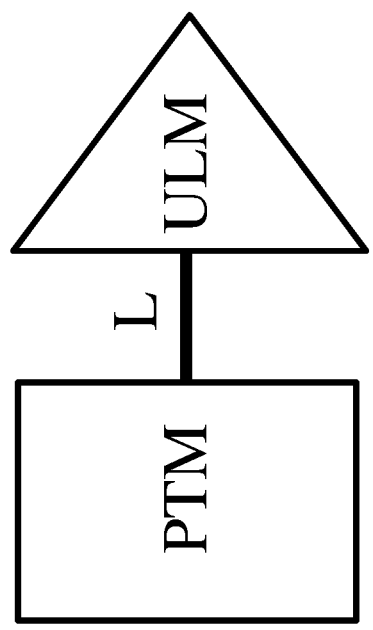
FIGS. 1A and 1B. Illustration of general principle for the functioning of hetero-bifunctional protein degrading compounds as described herein.
Figure 1B:
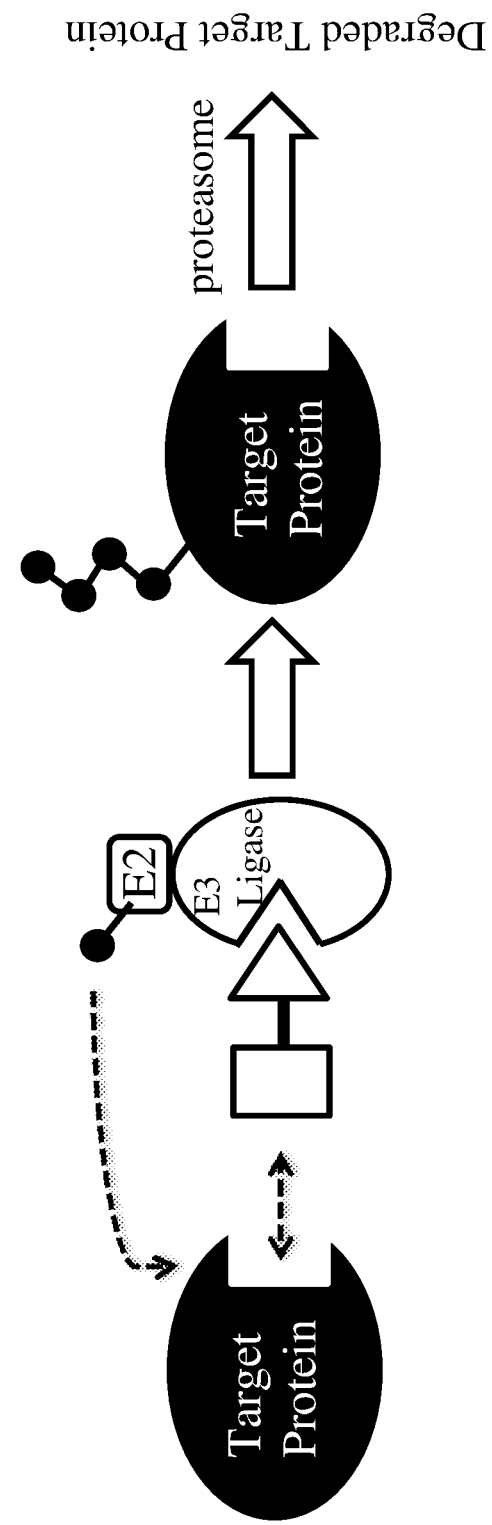

Presently described are compounds, compositions and methods that relate to the surprising and unexpected discovery that an E3 ubiquitin ligase (e.g., a cereblon E3 ubiquitin ligase) ubiquitinates the androgen receptor (AR) protein once the E3 ubiquitin ligase and the AR protein are placed in proximity via a bifunctional compound that binds both the E3 ubiquitin ligase and the AR protein. Accordingly the present disclosure provides compounds and compositions comprising an E3 ubiquitin ligase binding moiety ("ULM") coupled by a bond or chemical linking group (L) to a protein targeting moiety ("PTM") that targets the AR protein, which results in the ubiquitination of the AR protein, and which leads to degradation of the AR protein by the proteasome (see FIG. 1).

In one aspect, the description provides compounds in which the PTM preferably binds the AR protein. The present disclosure also provides a library of compositions and the use thereof to produce targeted degradation of the AR protein in a cell.

In certain aspects, the present disclosure provides hetero-bifunctional compounds which comprise a ligand, e.g., a small molecule ligand (i.e., having a molecular weight of below 2,000, 1,000, 500, or 200 Daltons), which is capable of binding to an E3 ubiquitin ligase, such as cereblon. The compounds also comprise a small molecule moiety that is capable of binding to AR in such a way that the AR protein is placed in proximity to the ubiquitin ligase to effect ubiquitination and degradation (and/or inhibition) of the AR protein. "Small molecule" means, in addition to the above, that the molecule is non-peptidyl, that is, it is not considered a peptide, e.g., comprises fewer than 4, 3, or 2 amino acids. In accordance with the present description, each of the PTM, ULM and hetero-bifunctional molecule is a small molecule.

Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

Where a range of values is provided, it is understood that each intervening value in the range, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either/or both of those included limits are also included in the disclosure.

The following terms are used to describe the present disclosure. In instances where a term is not specifically defined herein, that term is given an art-recognized meaning by those of ordinary skill applying that term in context to its use in describing the present disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element, unless otherwise indicated.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

It should also be understood that, in certain methods or processes described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time-varied administration (administration of one or more therapeutic agents at a time different from that of the administration of an additional therapeutic agent or agents), as long as the two or more therapeutic agents are present in the patient to some extent, preferably at effective amounts, at the same time. In certain preferred aspects, one or more of the hetero-bifunctional compounds described herein are coadministered with at least one additional bioactive agent, e.g., an anticancer agent. In particularly preferred aspects, the co-administration of such compounds results in synergistic activity and/or therapy such as, e.g., anticancer activity.

The term "compound", as used herein, unless otherwise indicated, refers to any specific hetero-bifunctional compound disclosed herein, pharmaceutically acceptable salts and solvates thereof, and deuterated forms of any of the aforementioned molecules, where applicable. Deuterated compounds contemplated are those in which one or more of the hydrogen atoms contained in the drug molecule have been replaced by deuterium. Such deuterated compounds preferably have one or more improved pharmacokinetic or pharmacodynamic properties (e.g., longer half-life) compared to the equivalent "undeuterated" compound.

The term "ubiquitin ligase" refers to a family of proteins that facilitate the transfer of one or more ubiquitins to a specific substrate protein. Addition of a chain of several ubiquitins (poly-ubiquitination) targets the substrate protein for degradation. For example, cereblon is an E3 ubiquitin ligase that alone, or in combination with an E2 ubiquitin-conjugating enzyme, can ultimately cause the attachment of a chain of four ubiquitins to a lysine residue on the target protein, thereby targeting the protein for degradation by the proteasome. The ubiquitin ligase is involved in poly-ubiquitination such that a first ubiquitin is attached to a lysine on the target protein; a second ubiquitin is attached to the first; a third is attached to the second, and a fourth is attached to the third. Such poly-ubiquitination marks proteins for degradation by the proteasome.

The term "patient" or "subject" is used throughout the specification to describe an animal, preferably a human or a domesticated animal, to whom treatment, including prophylactic treatment, with the compositions according to the present disclosure is provided. For treatment of those diseases, conditions or symptoms that are specific for a specific animal, such as a human patient, the term "patient" refers to that specific animal, including a domesticated animal such as a dog or cat, or a farm animal such as a horse, cow, sheep, etc. In general, in the present disclosure, the terms "patient" and "subject" refer to a human patient unless otherwise stated or implied from the context of the use of the term.

The terms "effective" and "therapeutically effective" are used to describe an amount of a compound or composition which, when used within the context of its intended use, and either in a single dose or, more preferably after multiple doses within the context of a treatment regimen, effects an intended result such as an improvement in a disease or condition, or amelioration or reduction in one or more symptoms associated with a disease or condition. The terms "effective" and "therapeutically effective" subsume all other "effective amount" or "effective concentration" terms, which are otherwise described or used in the present application.

Compounds and Compositions

In one aspect, the description provides hetero-bifunctional compounds comprising an E3 ubiquitin ligase binding moiety ("ULM") that is a cereblon E3 ubiquitin ligase binding moiety (a "CLM"), The CLM is covalently coupled to a protein targeting moiety (PTM) that binds to the protein, which coupling is either directly by a bond or via a chemical linking group (L) according to the structure:

PTM-L-CLM (A)

wherein L is the bond or chemical linking group, and PTM is a protein targeting moiety that binds to the protein AR, where the PTM is a small molecule AR targeting moiety. The term CLM is inclusive of all cereblon binding moieties.

In any of the aspects or embodiments, the CLM demonstrates a half maximal inhibitory concentration ($IC_{50}$) for the E3 ubiquitin ligase (e.g., cereblon E3 ubiquitin ligase) of less than about 200 µM. The $IC_{50}$ can be determined according to any suitable method known in the art, e.g., a fluorescent polarization assay.

In certain embodiments, the hetero-bifunctional compounds described herein demonstrate an $IC_{50}$ or a half maximal degradation concentration ($DC_{50}$) of less than about 100, 50, 10, 1, 0.5, 0.1, 0.05, 0.01, 0.005, 0.001 mM, or less than about 100, 50, 10, 1, 0.5, 0.1, 0.05, 0.01, 0.005, 0.001 µM, or less than about 100, 50, 10, 1, 0.5, 0.1, 0.05, 0.01, 0.005, 0.001 nM, or less than about 100, 50, 10, 1, 0.5, 0.1, 0.05, 0.01, 0.005, 0.001 µM.

The term "alkyl" shall mean within its context a linear, branch-chained or cyclic fully saturated hydrocarbon radical, preferably a $C_1$-$C_{10}$, preferably a $C_1$-$C_6$, or more preferably a $C_1$-$C_3$ alkyl group, which may be optionally substituted with any suitable functional group or groups. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others. In certain embodiments, the alkyl group is end-capped with a halogen group (At, Br, Cl, F, or I).

The term "Alkenyl" refers to linear, branch-chained or cyclic $C_2$-$C_{10}$ (preferably $C_2$-$C_6$) hydrocarbon radicals containing at least one C=C bond.

The term "Alkynyl" refers to linear, branch-chained or cyclic $C_2$-$C_{10}$ (preferably $C_2$-$C_6$) hydrocarbon radicals containing at least one C≡C bond.

The term "alkylene" when used, refers to a —$(CH_2)_n$— group (n is an integer generally from 0-6), which may be optionally substituted. When substituted, the alkylene group preferably is substituted on one or more of the methylene groups with a $C_1$-$C_6$ alkyl group (including a cyclopropyl group or a t-butyl group), but may also be substituted with one or more halo groups, preferably from 1 to 3 halo groups or one or two hydroxyl groups, O—($C_1$-$C_6$ alkyl) groups or amino acid sidechains as otherwise disclosed herein. In certain embodiments, an alkylene group may be substituted with a urethane or alkoxy group (or other suitable functional group) which may be further substituted with a polyethylene glycol chain (of from 1 to 10, preferably 1 to 6, or more preferably 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (e.g., methylene) group, may be substituted with an amino acid sidechain group such as a sidechain group of a natural or unnatural amino acid, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon.

The term "substituted" or "optionally substituted" shall mean independently (i.e., where more than one substituent occurs, each substituent is selected independent of another substituent) one or more substituents (independently up to five substituents, preferably up to three substituents, more preferably 1 or 2 substituents on a moiety in a compound according to the present disclosure and may include substituents which themselves may be further substituted) at a carbon (or nitrogen) position anywhere on a molecule within context, and includes as possible substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl, for example benzyl or benzoyl), alkoxy group (preferably, $C_1$-$C_6$ alkyl or aryl, including phenyl and substituted phenyl), thioether (preferably, $C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), halogen (preferably, F or Cl), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which are preferably independently substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present disclosure may include, for example —$SiR_1R_2R_3$ groups where each of $R_1$ and $R_2$ is as otherwise described herein and $R_3$ is H or a $C_1$-$C_6$ alkyl group, preferably $R_1$, $R_2$, $R_3$ together is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heteroaryl moiety) through an optionally substituted —$(CH_2)_m$— or alternatively an optionally substituted —$(OCH_2)_m$—, —$(OCH_2CH_2)_m$— or —$(CH_2CH_2O)_m$— group, which may be substituted with any one or more of the above-described substituents. Alkylene groups —$(CH_2)_m$— or —$(CH_2)_n$— groups or other chains such as ethylene glycol chains, as identified above, may be substituted anywhere on the chain. Preferred substituents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halo groups (preferably F), or a side chain of an amino acid as otherwise described herein and optionally substituted amide (preferably carboxamide substituted as described above) or urethane groups (often with one or two $C_0$-$C_6$ alkyl substituents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present disclosure, a moiety in a molecule may be optionally substituted with up to five substituents, preferably up to three substituents. Most often, in the present disclosure moieties which are substituted are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane —O—C(O)—$NR_1R_2$ or —N($R_1$)—C(O)—O—$R_1$, nitro, cyano and amine (especially including a $C_1$-$C_6$ alkylene-$NR_1R_2$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, =O, —$(CH_2)_m$— (here, m and n are in context, 1, 2, 3, 4, 5 or 6), —S—, —S(O)—, $SO_2$— or —NH—C(O)—NH—, —$(CH_2)_n$OH, —$(CH_2)_n$SH, —$(CH_2)_n$COOH, $C_1$-$C_6$ alkyl, —$(CH_2)_n$O—($C_1$-$C_6$ alkyl), —$(CH_2)_n$C(O)—($C_1$-$C_6$ alkyl), —$(CH_2)_n$OC(O)—($C_1$-$C_6$ alkyl), —$(CH_2)_n$C(O)O—($C_1$-$C_6$ alkyl), —$(CH_2)_n$NHC(O)—$R_1$, —$(CH_2)_n$C(O)—$NR_1R_2$, —$(OCH_2)_n$OH, —$(CH_2O)_n$COOH, $C_1$-$C_6$ alkyl, —$(OCH_2)_n$O—($C_1$-$C_6$ alkyl), —$(CH_2O)_n$C(O)—($C_1$-$C_6$ alkyl), —$(OCH_2)_n$NHC(O)—$R_1$, —$(CH_2O)_n$C(O)—$NR_1R_2$, —$S(O)_2$—$R_S$, —S(O)—$R_S$ ($R_S$ is $C_1$-$C_6$ alkyl or a —$(CH_2)_m$—$NR_1R_2$ group), $NO_2$, CN or halogen (F, Cl, Br, I, preferably F or Cl), depending on the context of the use of the substituent. $R_1$ and $R_2$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group O—C(O)—$NR_1R_2$ group where $R_1$ and $R_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical (e.g., a 5-16 membered ring) having a single ring (e.g., benzene, phenyl, benzyl, or 5, 6, 7 or 8 membered ring) or condensed rings (e.g., naphthyl, anthracenyl, phenanthrenyl, 10-16 membered ring, etc.) and can be bound to the compound according to the present disclosure at any available stable position on the ring(s) or as otherwise indicated in the chemical structure presented. Other examples of aryl groups, in context, may include heterocyclic aromatic ring systems, "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, pyrimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: —$(CH_2)_n$OH, —$(CH_2)_n$—O—$(C_1$-$C_6)$alkyl, —$(CH_2)_n$—O—$(CH_2)$, —$(C_1$-$C_6)$alkyl, —$(CH_2)_n$—C(O)($C_0$-$C_6$) alkyl, —$(CH_2)_n$—C(O)O($C_0$-$C_6$) alkyl, —$(CH_2)_n$—OC(O)($C_0$-$C_6$)alkyl, amine, mono- or di- ($C_1$-$C_6$ alkyl) amine wherein the alkyl group on the amine is optionally substituted with 1 or 2 hydroxyl groups or up to three halo (preferably F, Cl) groups, OH, COOH, $C_1$-$C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is preferably connected to a PTM group, including a ULM group, via a linker group), and/or at least one of F, Cl, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methyl substituted isoxazole, an optionally substituted oxazole including a methyl substituted oxazole, an optionally substituted thiazole including a methyl substituted thiazole, an optionally substituted isothiazole including a methyl substituted isothiazole, an optionally substituted pyrrole including a methyl substituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methyl substituted triazole group, an optionally substituted pyridine group, including a halo-(preferably, F) or methyl substituted pyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

"Carboxyl" denotes the group —C(O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

The term "heteroaryl" or "hetaryl" can mean but is in no way limited to a 5-16 membered heteroaryl (e.g., 5, 6, 7 or 8 membered monocylic ring or a 10-16 membered heteroaryl having multiple condensed rings), an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —$(CH_2)_m$—O—$C_1$-$C_6$ alkyl group or an optionally substituted —$(CH_2)_m$—C(O)—O—$C_1$-$C_6$ alkyl group), an optionally substituted pyridine (2-, 3, or 4-pyridine) or a group according to the chemical structure:

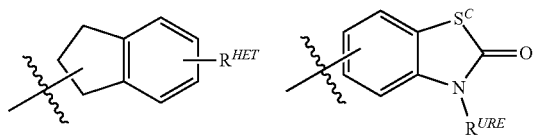

-continued

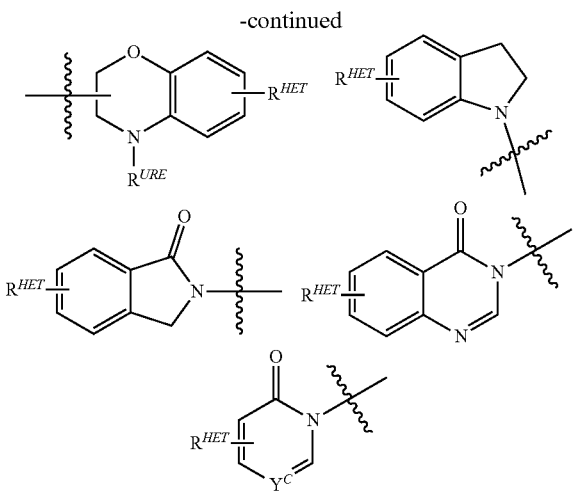

wherein:
$S^c$ is $CHR^{SS}$, $NR^{URE}$, or O;
$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);
$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O) ($C_1$-$C_6$ alkyl) (preferably substituted with one or two hydroxyl groups or up to three halo groups);
$R^{URE}$ is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and
$Y^C$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C— $R_a$ where $R_a$ is H or a $C_1$-$C_6$ alkyl group (preferably $C_1$-$C_3$ alkyl).

The terms "aralkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

The term "arylalkyl" as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above.

The term "Heterocycle" refers to a cyclic group which contains at least one heteroatom, e.g., N, O or S, and may be aromatic (heteroaryl) or non-aromatic. Thus, the heteroaryl moieties are subsumed under the definition of heterocycle, depending on the context of its use. Exemplary heteroaryl groups are described hereinabove.

Exemplary heterocyclics include: azetidinyl, benzimidazolyl, 1,4-benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, ethyleneurea, 1,3-dioxolane, 1,3-dioxane, 1,4-dioxane, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocylooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SOaryl, —SO-heteroaryl, —SO2-alkyl, —SO2-substituted alkyl, —SO2-aryl, oxo (=O), and —SO2-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles. The term "heterocyclic" also includes bicyclic groups in which any of the heterocyclic rings is fused to a benzene ring or a cyclohexane ring or another heterocyclic ring (for example, indolyl, quinolyl, isoquinolyl, tetrahydroquinolyl, and the like).

The term "cycloalkyl" can mean but is in no way limited to univalent groups derived from monocyclic or polycyclic alkyl groups or cycloalkanes, as defined herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like. The term "substituted cycloalkyl" can mean but is in no way limited to a monocyclic or polycyclic alkyl group and being substituted by one or more substituents, for example, amino, halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group in which at least one ring carbon atom of its cyclic structure being replaced with a heteroatom selected from the group consisting of N, O, S or P. "Substituted heterocycloalkyl" refers to a monocyclic or polycyclic alkyl group in which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "independently" is used herein to indicate that the variable, which is independently applied, varies independently from application to application.

The term "lower alkyl" refers to methyl, ethyl or propyl

The term "lower alkoxy" refers to methoxy, ethoxy or propoxy.

Exemplary CLMs

Neo-Imide Compounds

In any aspect or embodiment described herein, the description provides CLMs useful for binding and recruiting cereblon. In certain embodiments, the CLM is selected from the group consisting of chemical structures:

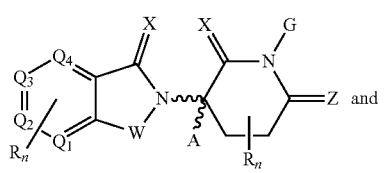

(a1)

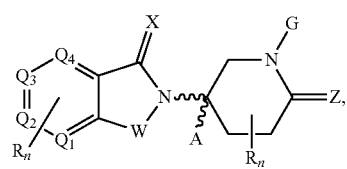

(a3)

wherein:
- W of Formulas (a1) and (a3) is independently selected from the group $CH_2$, O, CHR, C=O, $SO_2$, NH, N, optionally substituted cyclopropyl group, optionally substituted cyclobutyl group, and N-alkyl;
- X of Formulas (a1) and (a3) is independently selected from the group absent, O, S and $CH_2$;
- Z of Formulas (a1) and (a3) is independently selected from the group absent, O, and S or $CH_2$ except that both X and Z cannot be $CH_2$ or absent;
- G of Formulas (a1) and (a3) is selected from the group H, optionally substituted linear or branched alkyl, OH, R'OCOOR, R'OCONRR", $CH_2$-heterocyclyl optionally substituted with R', and benzyl optionally substituted with R';
- $Q_1$-$Q_4$ of Formulas (a1) and (a3) represent a carbon C or N substituted with a group independently selected from H, R, N or N-oxide;
- A of Formulas (a1) and (a3) is independently selected from the group H, optionally substituted linear or branched alkyl, cycloalkyl, —CN, Cl and F;
- n of Formulas (a1) and (a3) represent an integer from 1 to 10 (e.g., 1-4, 1, 2, 3, 4, 5, 6, 7, 8, 9, or 10);

R of Formulas (a1) and (a3) comprises, but is not limited to: H, —C(=O)R' (e.g., a carboxy group), —CONR'R" (e.g., an amide group), —$OR_2$, —OR' (e.g., OH), —NR'R" (e.g., an amine group), —SR', —$SO_2$R', —$SO_2$NR'R", —CR'R"—, —CR'NR'R"—, (—CR'O)$_{n'}$, R", optionally substituted heterocyclyl, optionally substituted aryl, (e.g., an optionally substituted $C_5$-$C_7$ aryl), optionally substituted alkyl-aryl (e.g., an alkyl-aryl comprising at least one of an optionally substituted $C_1$-$C_6$ alkyl, an optionally substituted $C_5$-$C_7$ aryl, or combinations thereof), optionally substituted heteroaryl, optionally substituted alkyl (e.g., a $C_1$-$C_6$ linear or branched alkyl optionally substituted with one or more halogen, deuterium, cycloalkyl (e.g., a $C_3$-$C_6$ cycloalkyl), or aryl (e.g., $C_5$-$C_7$ aryl)), optionally substituted alkoxyl group (e.g., a methoxy, ethoxy, butoxy, propoxy, pentoxy, or hexoxy; wherein the alkoxyl may be substituted with one or more halogen, deuterium, alkyl, haloalky, fluoroalkyl, cycloalkyl (e.g., a $C_3$-$C_6$ cycloalkyl), or aryl (e.g., $C_5$-$C_7$ aryl)), optionally substituted cycloalkyl, optionally substituted heterocyclyl, —P(O)(OR')R", —P(O)R'R", —OP(O)(OR')R", —OP(O)R'R", —Cl, —F, —Br, —I, —$CF_3$, —CN, —$NR'SO_2NR'R"$, —NR'CONR'R", —CONR'COR", —NR'C(=N—CN)NR'R", —C(=N—CN)NR'R", —NR'C(=N—CN)R", —NR'C(=C—$NO_2$)NR'R", —$SO_2$NR'COR", —$NO_2$, —$CO_2$R', —C(C=N—OR')R", —CR'=CR'R", —CCR', —S(C=O)(C=N—R')R", —$SF_5$ and —$OCF_3$, each optionally substituted with deuterium, wherein at least one W, X, Z, G, R, $R^2$, R', R", $Q_1$-$Q_4$, or A is the point of attachment or is modified to be covalently joined to a PTM, a chemical linking group (L), a ULM, CLM, or combination thereof;

R' and R" of Formulas (a1) and (a3) are independently selected from H, optionally substituted linear or branched alkyl (e.g., optionally substituted linear or branched C1-6 alkyl), optionally substituted cycloalkyl (e.g., optionally substituted 3-7 membered cycloalkyl), optionally substituted aryl (e.g., optionally substituted 5-7 membered aryl), optionally substituted heteroaryl (e.g., optionally substituted 5-7 membered hetaryl), optionally substituted heterocyclic (e.g., optionally substituted 3-7 membered heterocyclic), —C(=O)R, optionally substituted heterocyclyl (e.g., optionally substituted 3-7 membered heterocyclyl);

$R^2$ is independently selected from the group consisting of H and an unsubstituted or substituted $C_{1-3}$ alkyl (e.g., methyl, ethyl, or isopropyl group, each optionally deuterated);

n' of Formulas (a1) and (a3) is an integer from 1-10 (e.g. 1-4, 1, 2, 3, 4, 5, 6, 7, 8, 9, or 10); and ∿∿ of Formulas (a1) and (a3) represents a bond that may be stereospecific ((R) or (S)) or non-stereospecific.

In any aspect or embodiment described herein, the CLM comprises a chemical structure selected from the group consisting of:

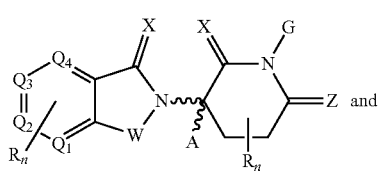

(a1)

-continued

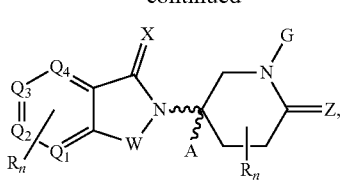
(a3)

wherein:
W of Formulas (a1) and (a3) is independently selected from the group $CH_2$, O, CHR, C=O, $SO_2$, NH, N, optionally substituted cyclopropyl group, optionally substituted cyclobutyl group, and N-alkyl;

X of Formulas (a1) and (a3) is independently selected from the group O, S and $CH_2$;

Z of Formulas (a1) and (a3) is independently selected from the group O, and S or CH2 except that both X and Z cannot be $CH_2$ or absent;

G of Formulas (a1) and (a3) is independently selected from the group H, optionally substituted linear or branched alkyl, OH, R'OCOOR, R'OCONRR", $CH_2$-heterocyclyl optionally substituted with R', and benzyl optionally substituted with R';

$Q_1$-$Q_4$ of Formulas (a1) and (a3) represent a carbon C or N substituted with a group independently selected from H, R, N or N-oxide;

A of Formulas (a1) and (a3) is independently selected from the group H, optionally substituted linear or branched alkyl, cycloalkyl, —CN, Cl and F;

n of Formulas (a1) and (a3) represent an integer from 1 to 10 (e.g., 1-4, 1, 2, 3, 4, 5, 6, 7, 8, 9, or 10);

R of Formulas (a1) and (a3) comprises, but is not limited to: H, —$OR_2$ (e.g., methoxy or ethoxy), —C(=O)R' (e.g., a carboxy group), —CONR'R" (e.g., an amide group), —OR' (e.g., OH), —NR'R" (e.g., an amine group), —SR', —$SO_2$R', —$SO_2$NR'R", —CR'R"—, —CR'NR'R"—, (—CR'O)$_n$R", optionally substituted aryl (e.g., an optionally substituted $C_5$-$C_7$ aryl), optionally substituted alkyl-aryl (e.g., an alkyl-aryl comprising at least one of an optionally substituted $C_1$-$C_6$ alkyl, an optionally substituted $C_5$-$C_7$ aryl, or combinations thereof), optionally substituted hetaryl, -optionally substituted linear or branched alkyl (e.g., a $C_1$-$C_6$ linear or branched alkyl optionally substituted with one or more halogen, deuterium, cycloalkyl (e.g., a $C_3$-$C_6$ cycloalkyl), or aryl (e.g., $C_5$-$C_7$ aryl)), optionally substituted alkoxyl group (e.g., a methoxy, ethoxy, butoxy, propoxy, pentoxy, or hexoxy; wherein the alkoxyl may be substituted with one or more halogen, deuterium, alkyl, haloalky, fluoroalkyl, cycloalkyl (e.g., a $C_3$-$C_6$ cycloalkyl), or aryl (e.g., $C_5$-$C_7$ aryl)), optionally substituted cycloalkyl, optionally substituted heterocyclyl, —P(O)(OR')R", —P(O)R'R", —OP(O)(OR')R", —OP(O)R'R", —Cl, —F, —Br, —I, —$CF_3$, —CN, —NR'SO2NR'R", —NR'CONR'R", —CONR'COR", —NR'C(=N—CN)NR'R", —C(=N—CN)NR'R", —NR'C(=N—CN)R", —NR'C(=C—NO2)NR'R", —SO2NR'COR", —NO2, —$CO_2$R', —C(C=N—OR')R", —CR'=CR'R", —CCR', —S(C=O)(C=N—R')R", —SF5 and —$OCF_3$, each optionally substituted with deuterium, wherein at least one of W, X, Z, G, R, $R^2$, R', R", Q1-Q4, or A is the point of attachment or is covalently joined (directly or indirectly, e.g., via a functional group or an atom, such as O, S, N) to a PTM, a chemical linking group (L), a ULM, CLM, or combination thereof;

R' and R" of Formulas (a1) through (e) are independently selected from a bond, H, optionally substituted linear or branched alkyl, optionally substituted cycloalkyl, optionally substituted aryl, optionally substituted heteroaryl, optionally substituted heterocyclic, —C(=O)R, optionally substituted heterocyclyl;

$R_2$ is independently selected from the group consisting of H and an unsubstituted or substituted $C_{1-3}$ alkyl (e.g., methyl, ethyl, or isopropyl group, each optionally deuterated);

n' of Formulas (a1) through (e) is an integer from 1-10 (e.g., 1-4, 1, 2, 3, 4, 5, 6, 7, 8, 9, or 10); and ∿∿ of Formulas (a1) through (e) represents a bond that may be stereospecific ((R) or (S)) or non-stereospecific.

In any aspect or embodiment described herein, the clm or ulm has a chemical structure represented by:

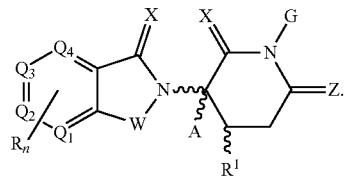

wherein:
W is selected from the group consisting of $CH_2$, O, C=O, NH, and N-alkyl;

each X is O or S;

Z is O or S;

G is H, OH, or an unsubstituted linear or branched $C_{1-3}$ alkyl;

$Q_1$, $Q_2$, $Q_3$, and $Q_4$ represent a N or a C substituted with a group selected from H and R;

A is independently selected from the group H, unsubstituted linear or branched $C_{1-3}$ alkyl, cycloalkyl, —CN, Cl and F;

n is an integer from 1 to 4 (e.g., 1, 2, 3, or 4);

each R is selected from the group consisting of H, an unsubstituted or substituted linear or branched $C_{1-4}$ alkyl, —OR', $OR_2$ (e.g., methoxy or ethoxy), —Cl, —F, —Br, —I, —$CF_3$, —CN, and —$NO_2$, wherein one or two R groups are the point of attachment or are modified to be covalently joined to the chemical linking group (L);

R' is independently selected from the group consisting of H and an unsubstituted or substituted $C_{1-3}$ alkyl e.g., methyl, ethyl, or isopropyl group, each optionally deuterated), each optionally substituted with deuterium;

$R^2$ is independently selected from the group consisting of H and an unsubstituted or substituted $C_{1-3}$ alkyl (e.g., methyl, ethyl, or isopropyl group, each optionally deuterated), each optionally substituted with deuterium; and ∿∿ represents a bond that may be stereospecific ((R) or (S)) or non-stereospecific.

In any aspect or embodiment described herein, the CLM or ULM is selected from the structure of Formula (g):

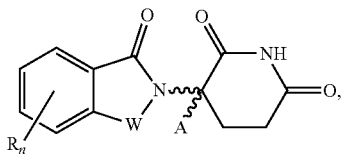

Formula (g)

wherein:
W of Formula (g) is independently selected from the group CH$_2$, O, C=O, NH, and N-alkyl;
A of Formula (g) is selected from a H, methyl, CN, or optionally substituted linear or branched alkyl;
n is an integer from 1 to 4;
R of Formula (g) is independently selected from a H, O, OH, N, NH, NH$_2$, Cl, —F, —Br, —I, methyl, optionally substituted linear or branched alkyl (e.g., optionally substituted linear or branched C$_1$-C$_6$ alkyl), optionally substituted linear or branched alkoxy (e.g., optionally substituted linear or branched C$_1$-C$_6$ alkoxy), -alkyl-aryl (e.g., an -alkyl-aryl comprising at least one of C$_1$-C$_6$ alkyl, C$_4$-C$_7$ aryl, or a combination thereof), aryl (e.g., C$_5$-C$_7$ aryl), amine, amide, or carboxy), wherein at least one R or W is the point of attachment or is modified to be covalently joined to a PTM, a chemical linking group (L), a ULM, CLM, or combination thereof; and
∼∼∼ of Formula (g) represents a bond that may be stereospecific ((R) or (S)) or non-stereospecific.

In any aspect or embodiment described herein, the CLM or ULM is selected from the group consisting of:

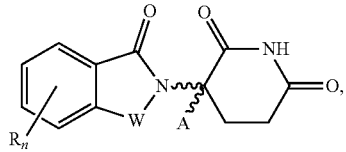

wherein:
W is independently selected from the group CH$_2$ and C=O;
A is selected from a H, —CN, or methyl, preferably H;
n is 1 or 2;
each R is independently selected from a H, O, OH, N, NH, NH$_2$, Cl, —F, —Br, —I, methyl, optionally substituted linear or branched C$_{1-3}$ alkyl, optionally substituted linear or branched C$_{1-3}$ alkoxy, wherein an R is the point of attachment or is modified to be covalently joined to the chemical linking group (L); and
∼∼∼ represents a bond that may be stereospecific ((R) or (S)) or non-stereospecific.

In any aspect or embodiment described herein, the CLM or ULM is selected from the group consisting of:

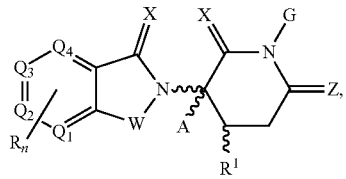

wherein:
W is selected from the group consisting of CH$_2$, O, C=O, cyclopropane, NH, and N-alkyl;
each X is O or S;
Z is O or S;
G is H, OH, or an unsubstituted linear or branched C$_{1-3}$ alkyl; each of Q$_1$, Q$_2$, Q$_3$, and Q$_4$ represent a N or a C substituted with a group selected from H and R;
A is independently selected from the group H, unsubstituted linear or branched C$_{1-3}$ alkyl (e.g. methyl), —CN, Cl and F;
n is an integer from 1 to 4 (e.g., 1, 2, 3, or 4);
each R is selected from the group consisting of H, OH, NH$_2$, an unsubstituted or substituted linear or branched C$_{1-4}$ alkyl (e.g., methyl or ethyl), —OR$_2$ (e.g., methoxy or ethoxy), —Cl, —F, —Br, —CF$_3$, —CN, and —NO$_2$, each optionally substituted with deuterium;
R$^1$ is H or an unsubstituted or substituted C$_{1-3}$ alkyl (e.g., methyl);
R$^2$ is independently selected from the group consisting of H and an unsubstituted or substituted C$_{1-3}$ alkyl (e.g., methyl, ethyl, or isopropyl group, each optionally deuterated); and
∼∼∼ represents a bond that may be stereospecific ((R) or (S)) or non-stereospecific,
wherein one or two R groups are the point of attachment or are modified to be covalently joined to the chemical linking group (L).

In any aspect or embodiment described herein, the CLM or ULM is selected from the group consisting of:

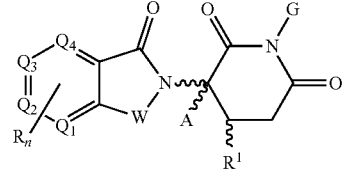

wherein:
W is selected from the group consisting of CH$_2$, O, C=O, cyclopropane, NH, and N-alkyl;
G is H, OH, or an unsubstituted linear or branched C$_{1-3}$ alkyl; each of Q$_1$, Q$_2$, Q$_3$, and Q$_4$ represent a N or a C substituted with a group selected from H and R;
A is independently selected from the group H, unsubstituted linear or branched C$_{1-3}$ alkyl (e.g. methyl), —CN, Cl and F;
n is an integer from 1 to 4 (e.g., 1, 2, 3, or 4);
each R is selected from the group consisting of H, OH, NH$_2$, an unsubstituted or substituted linear or branched C$_{1-4}$ alkyl (e.g., methyl or ethyl), —OR$_2$ (e.g., methoxy or ethoxy), —Cl, —F, —Br, —CF$_3$, and, —CN, each optionally substituted with deuterium;
R$^1$ is H or an unsubstituted or substituted C$_{1-3}$ alkyl (e.g., methyl);
R$^2$ is independently selected from the group consisting of H and an unsubstituted or substituted C$_{1-3}$ alkyl (e.g., methyl, ethyl, or isopropyl group, each optionally deuterated); and
∼∼∼ represents a bond that may be stereospecific ((R) or (S)) or non-stereospecific, wherein one or two R groups are the point of attachment or are modified to be covalently joined to the chemical linking group (L).

In any aspect or embodiment described herein, the CLM or ULM is:

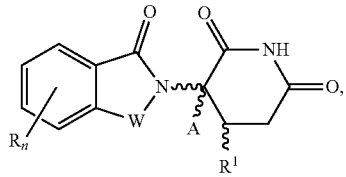

wherein:
W is independently selected from the group CH$_2$, C=O, and cyclopropane;
A is selected from a H, F, —CN, or methyl;
n is 1 or 2;
each R is independently selected from a H, OH, NH$_2$, —Cl, —F, —Br, methyl, optionally substituted linear or branched C$_{1-3}$ alkyl (e.g., methyl or ethyl), optionally substituted linear or branched C$_{1-3}$ alkoxy (e.g., methoxy, ethoxy, or —OCH(CH$_3$)$_2$);
wherein one or two R groups are the point of attachment or are modified to be covalently joined to the chemical linking group (L); and
∿∿ represents a bond that may be stereospecific ((R) or (S)) or non-stereospecific In any aspect or embodiment described herein, the CLM or ULM is:

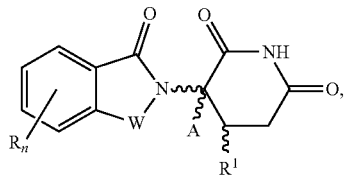

wherein:
W is independently selected from the group CH$_2$, C=O, and cyclopropane;
A is selected from a H, F, —CN, or methyl;
R$^1$ is H or methyl;
n is 1 or 2;
each R is independently selected from a H, —Cl, —F, —Br, optionally substituted linear or branched C$_{1-3}$ alkyl (e.g., methyl or ethyl), optionally substituted linear or branched C$_{1-3}$ alkoxy (e.g., methoxy, ethoxy, or —OCH(CH$_3$)$_2$;
wherein one or two R groups are the point of attachment or are modified to be covalently joined to the chemical linking group (L); and
∿∿ represents a bond that may be stereospecific ((R) or (S)) or non-stereospecific.

In any aspect or embodiment described herein, the CLM or ULM is selected from the group consisting of:

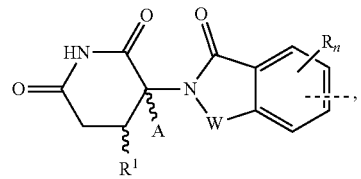

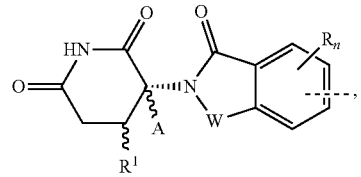

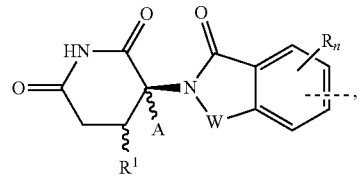

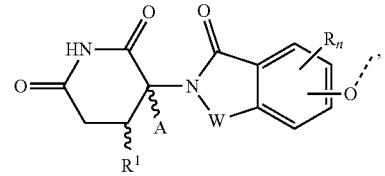

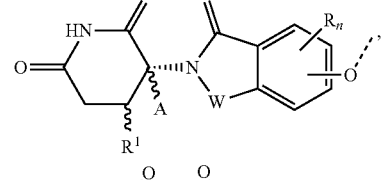

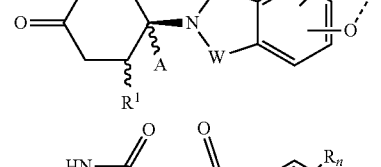

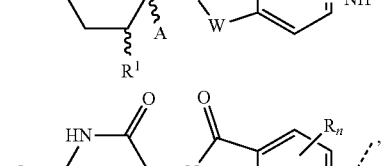

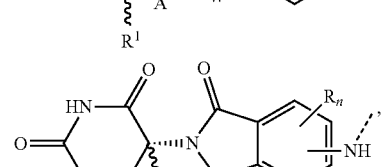

23

-continued

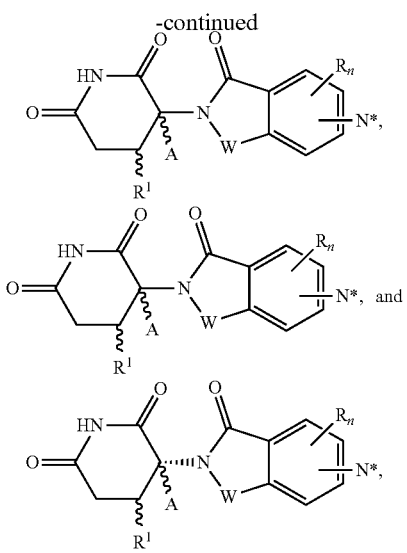

wherein:
- ``´´`` of the CLM indicates the point of attachment with the chemical linking group;
- N* is a nitrogen atom that is shared with the chemical linking group;
- n is 1 or 2; and
- the other variables are as defined in any aspect or embodiment described herein,
- wherein an R can be the point of attachment or can be modified to be covalently joined to the chemical linking group (L).

In any aspect or embodiment described herein, the CLM or ULM is selected from the group consisting of:

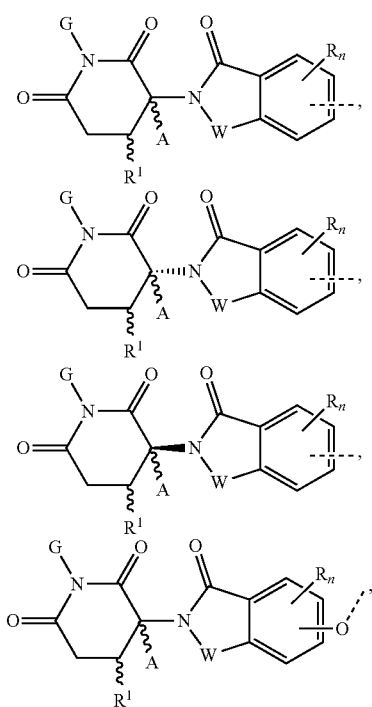

24

-continued

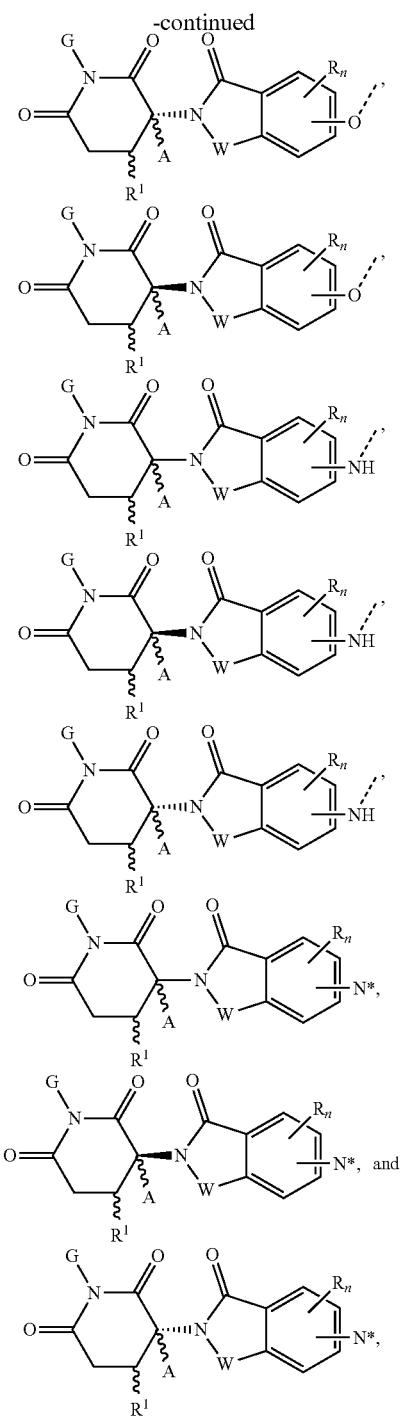

wherein:
- W is selected from the group consisting of $CH_2$, O, C=O, cyclopropane, NH, and N-alkyl;
- G is H, OH, or methyl; each of $Q_1$, $Q_2$, $Q_3$, and $Q_4$ represent a N or a C substituted with a group selected from H and R;
- A is independently selected from the group H, unsubstituted linear or branched $C_{1-3}$ alkyl (e.g. methyl), —CN, Cl and F;
- n is 1 or 2;
- each R is selected from the group consisting of H, OH, $NH_2$, an unsubstituted or substituted linear or branched $C_{1-4}$ alkyl (e.g., methyl or ethyl), —$OR_2$ (e.g., methoxy or ethoxy), —Cl, —F, —Br, —$CF_3$, —CN, and —$NO_2$, each optionally substituted with deuterium;

$R^1$ is H or an unsubstituted or substituted $C_{1-3}$ alkyl (e.g., methyl);

$R^2$ is independently selected from the group consisting of H and an unsubstituted or substituted $C_{1-3}$ alkyl (e.g., methyl, ethyl, or isopropyl group, each optionally deuterated); and ∼∼ represents a bond that may be stereospecific ((R) or (S)) or non-stereospecific, ⸝⸝ of the CLM indicates the point of attachment with the chemical linking group; and N* is a nitrogen atom that is shared with the chemical linking group, wherein an R can be the point of attachment or can be modified to be covalently joined to the chemical linking group (L).

In any aspect or embodiment described herein, the CLM or ULM is selected from the group consisting of:

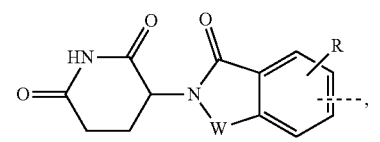

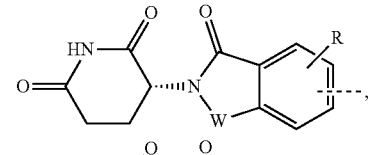

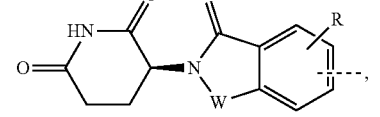

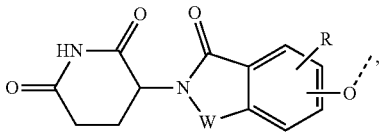

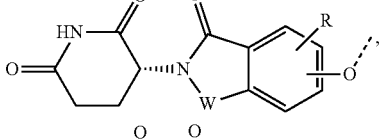

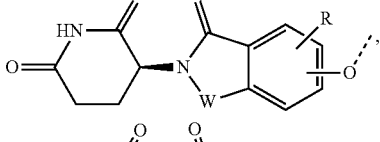

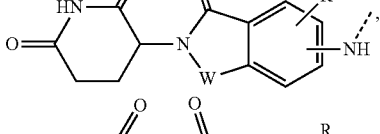

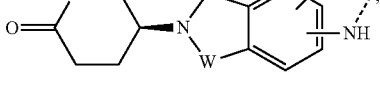

-continued

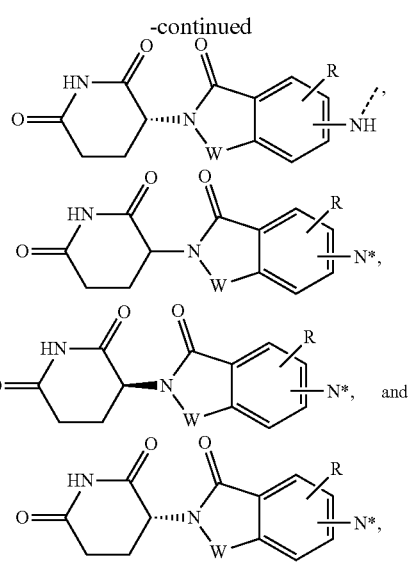

wherein:
- ⸝⸝ of the CLM indicates the point of attachment with the chemical linking group;
- N* is a nitrogen atom that is shared with the chemical linking group; and
- the other variable are as defined in any aspect or embodiment described herein,
- wherein an R can be the point of attachment or can be modified to be covalently joined to the chemical linking group (L).

In any aspect or embodiment described herein, at least one of:

W is C=O, $CH_2$, or

A is H, halogen (e.g., F), methyl, or —CN;

R is an H, $C_1$-$C_3$ alkyl (e.g., methyl or ethyl) optionally substituted with deuterium, $C_1$-$C_3$ alkoxy (e.g. methox, ethoxy, or

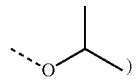

optionally substituted with deuterium (e.g., —$CD_3$), or halogen (e.g., F); and $R^1$ is H.

In any aspect or embodiment described herein, wherein at least one of:

W is C=O, $CH_2$, or

A is H, F, methyl, or —CN;

R is an H, methyl, ethyl, methoxy, ethoxy, or —OCH$(CH_3)_2$, each optionally substituted with deuterium (e.g., —$CD_3$) or F; and $R^1$ is H.

In any aspect or embodiment described herein, the CLM or ULM is selected from the group consisting of:

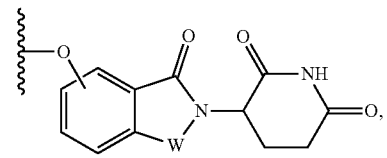

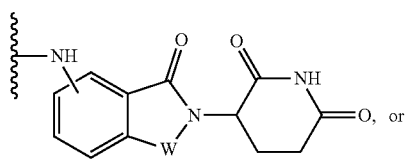

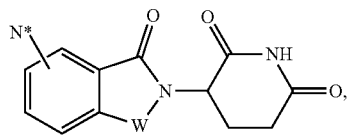

wherein:

W is C=O or CH$_2$;

N* is a nitrogen atom that is shared with the chemical linking group; and

⸹— indicates the point of attachment of the CLM or ULM to the linker (L) or PTM.

In any aspect or embodiment described herein, R is selected from: H, O, OH, N, NH, NH$_2$, C$_1$-C$_6$ alkyl, C$_1$-C$_6$ alkoxy, -alkyl-aryl (e.g., an -alkyl-aryl comprising at least one of C$_1$-C$_6$ alkyl, C$_4$-C$_7$ aryl, or a combination thereof), aryl (e.g., C$_5$-C$_7$ aryl), amine, amide, or carboxy), each optionally substituted with deuterium.

In any aspect or embodiment described herein, at least one R (e.g. an R group selected from the following H, O, OH, N, NH, NH$_2$, C$_1$-C$_6$ alkyl, C$_1$-C$_6$ alkoxy, -alkyl-aryl (e.g., an -alkyl-aryl comprising at least one of C$_1$-C$_6$ alkyl, C$_4$-C$_7$ aryl, or a combination thereof), aryl (e.g., C$_5$-C$_7$ aryl), amine, amide, or carboxy, each optionally substituted with deuterium) or W is the point of attachment or is modified to be covalently joined to a PTM, a chemical linker group (L), a ULM, a CLM, or a combination thereof In any aspect or embodiment described herein, the W, X, Z, G, R, R$^2$, R', R", Q$_1$-Q$_4$, and A of Formulas (a) through (g) can independently be covalently coupled to a linker and/or a linker to which is attached one or more PTM, ULM, or CLM groups.

In any of the aspects or embodiments described herein, n is an integer from 1 to 4, and each R is independently selected functional groups or atoms, for example, O, OH, N, —Cl, —F, C$_1$-C$_6$ alkyl, C$_1$-C$_6$ alkoxy, -alkyl-aryl (e.g., an -alkyl-aryl comprising at least one of C$_1$-C$_6$ alkyl, C$_4$-C$_7$ aryl, or a combination thereof), aryl (e.g., C$_5$-C$_7$ aryl), amine, amide, or carboxy, on the aryl or heteroaryl of the CLM, each optionally substituted with deuterium, and optionally, one of which is the point of attachment or is modified to be covalently joined to a PTM, a chemical linker group (L), a ULM, CLM or combination thereof.

In any aspect or embodiment descried herein, W of the CLM or ULM is

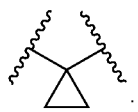 [SMILES: *C1(*)CC1]

More specifically, non-limiting examples of CLMs include those shown below as well as those "hybrid" molecules that arise from the combination of one or more of the different features shown in the molecules below wherein at least one R is the point of attachment or is modified to be covalently joined to a PTM, a chemical linking group (L), a ULM, CLM, or combination thereof.

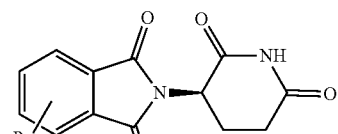

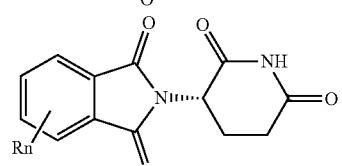

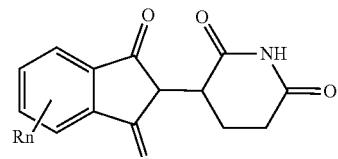

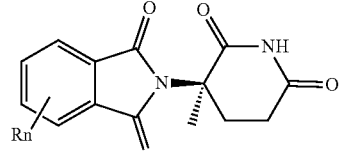

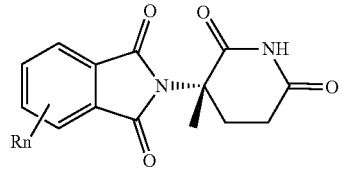

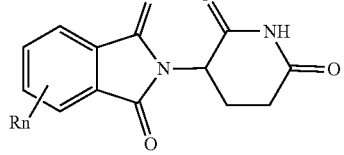

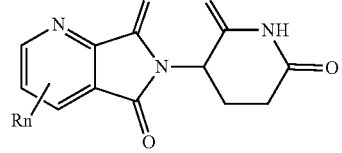

-continued
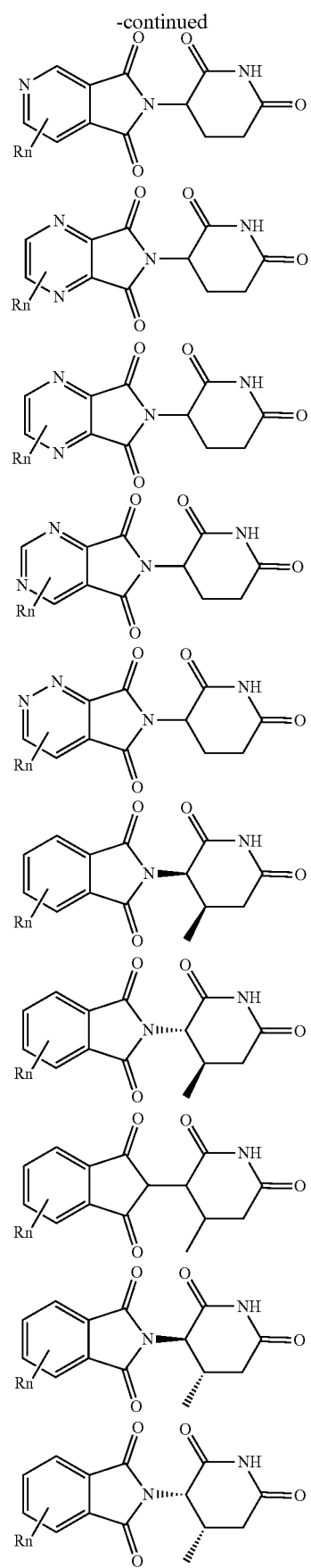
-continued
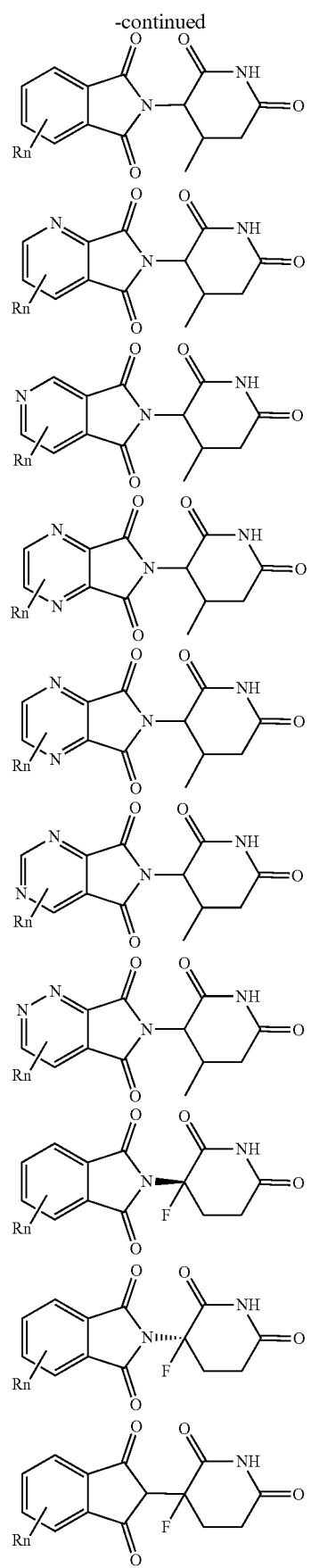

-continued
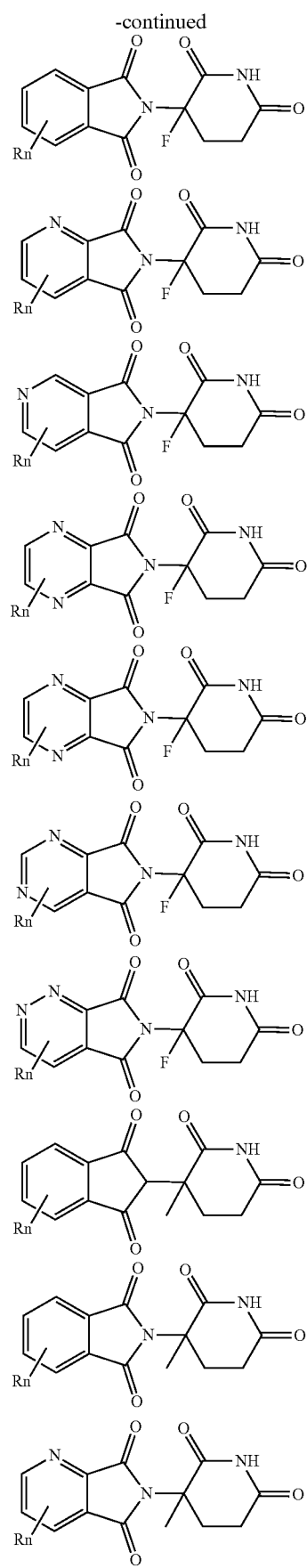
-continued
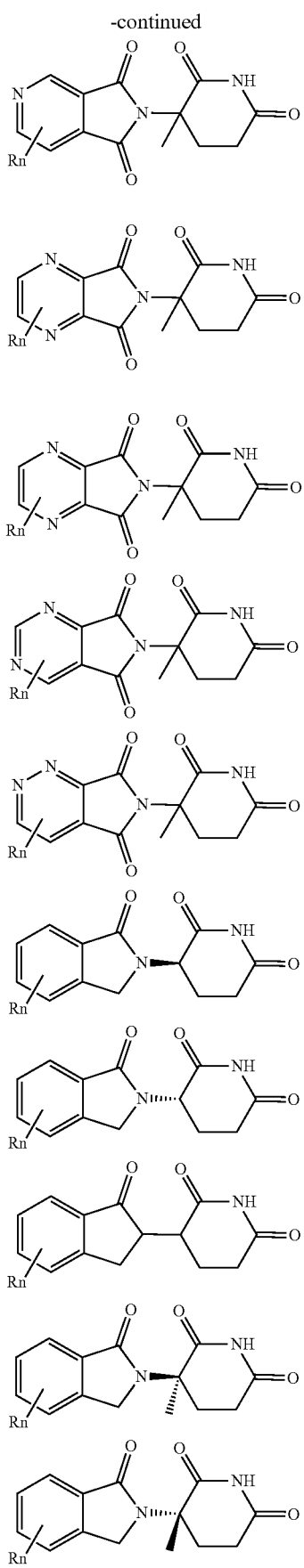

-continued
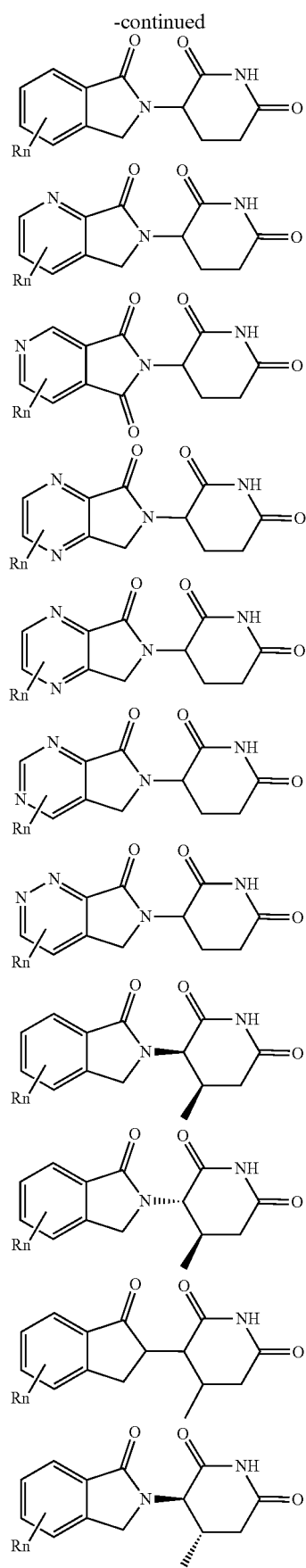
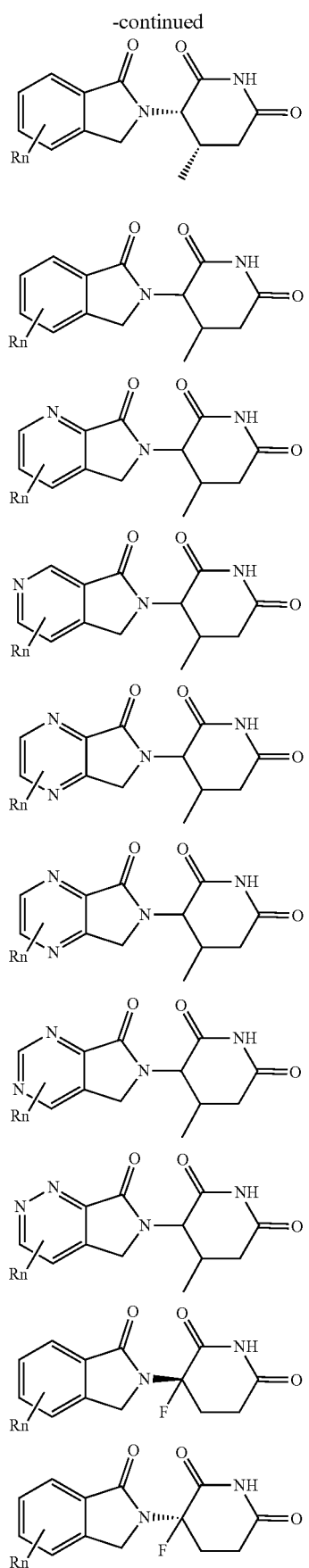

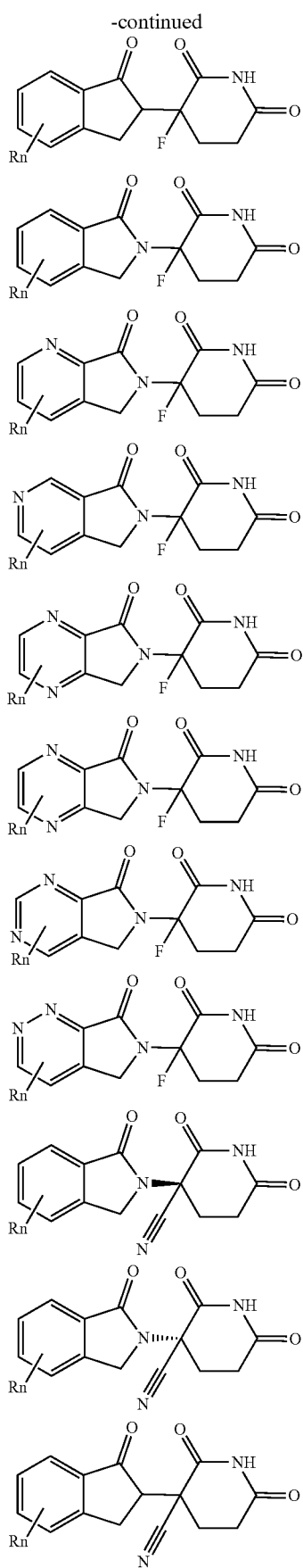
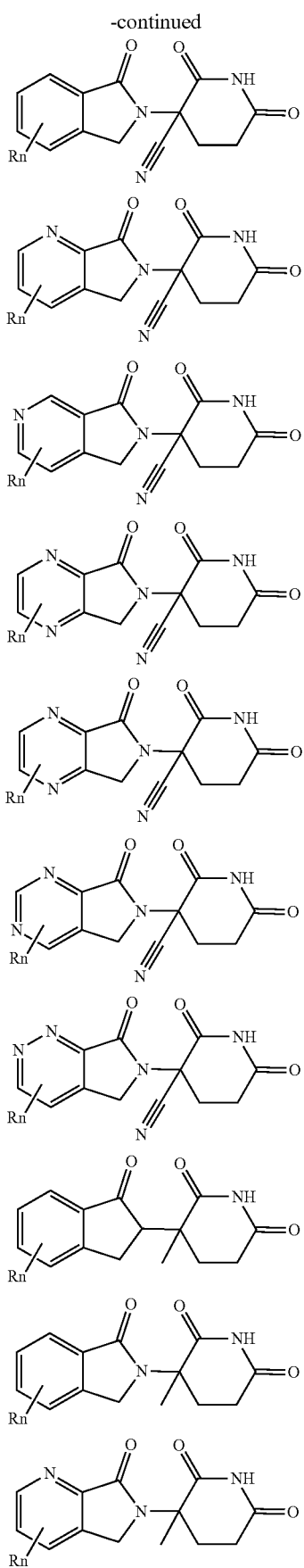

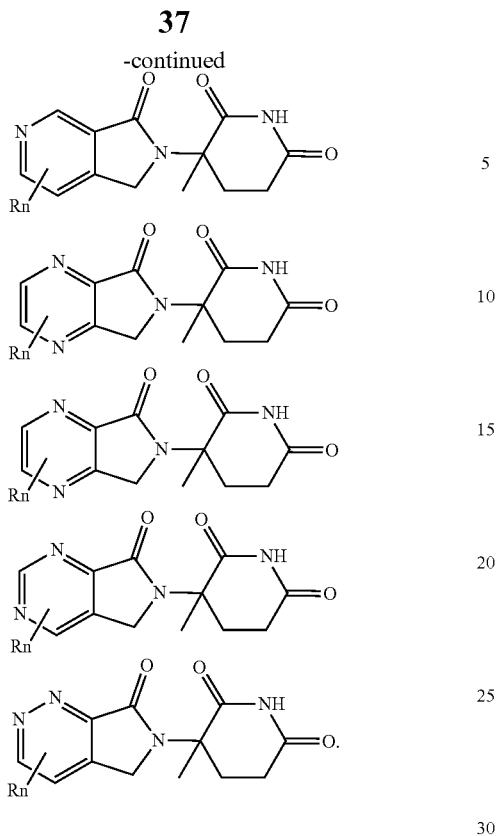

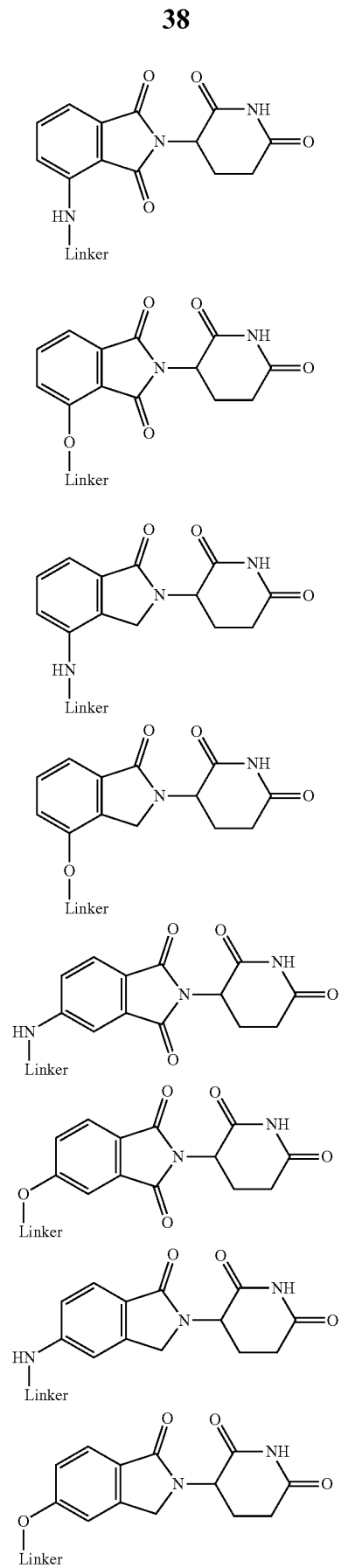

In any aspect or embodiment described herein, the CLM is covalently joined to a PTM or a chemical linker group (L) via an R group (such as, R, $R^1$, $R^2$, R', or R"), W, X, or a Q group (such as, $Q_1$, $Q_2$, $Q_3$, $Q_4$).

In any aspect or embodiment described herein, the CLM is covalently joined to a PTM or a chemical linker group (L) via W, X, R, $R^1$, $R^2$, R', R", $Q_1$, $Q_2$, $Q_3$, and $Q_4$.

In any aspect or embodiment described herein, the W, X, $R^1$, $R^2$, R', R", $Q_1$, $Q_2$, $Q_3$, and $Q_4$ can independently be covalently coupled to a linker and/or a linker to which is attached to one or more PTM, ULM, CLM groups.

In any aspect or embodiment described herein, the W, $R^1$, $R^2$, $Q_1$, $Q_2$, $Q_3$, $Q_4$, R, R', and R" can independently be covalently coupled to a linker and/or a linker to which is attached one or more PTM groups.

In any aspect or embodiment described herein, the $R^1$, $R^2$, $Q_1$, $Q_2$, $Q_3$, $Q_4$, R, R', and R" can independently be covalently coupled to a linker and/or a linker to which is attached one or more PTM groups.

In any aspect or embodiment described herein, the $Q_1$, $Q_2$, $Q_3$, $Q_4$, R, R', and R" can independently be covalently coupled to a linker and/or a linker to which is attached one or more PTM groups.

In any aspect or embodiment described herein, R is modified to be covalently joined to the linker group (L), or a PTM, or combination thereof.

In any aspect or embodiment described herein, "CLM" can be an imide that binds to cereblon E3 ligase. In any aspect or embodiment described herein, the imides and linker attachment point can be, but not be limited to, one of the following structures (e.g., any of the following attachment points can be utilized for any CLM chemical structure described herein):

-continued
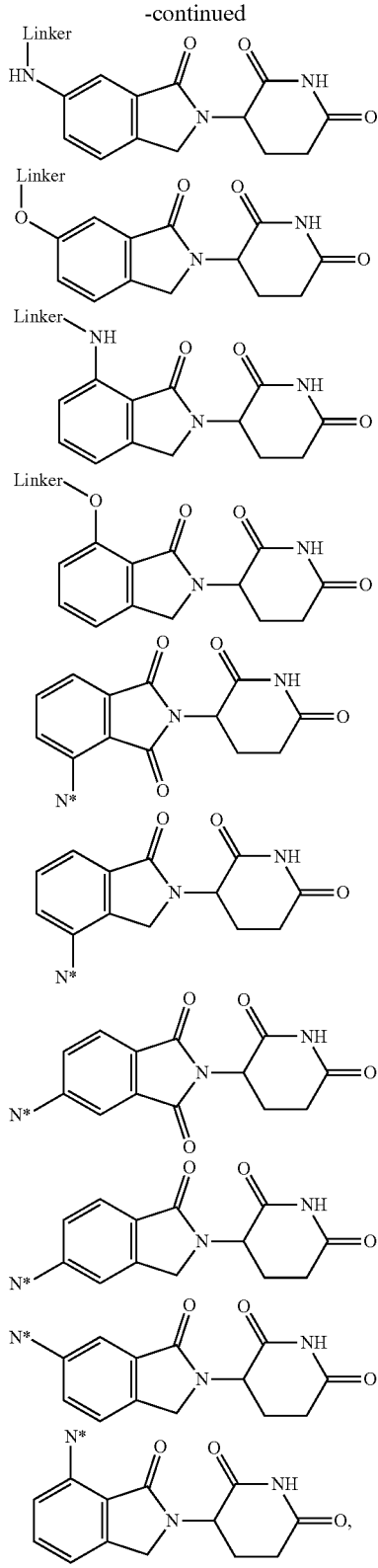
wherein:
- of the ULM indicates the point of attachment with a linker group or a PTM; and
N* is a nitrogen atom that is shared with the chemical linker group or PTM.
In any aspect or embodiment described herein, the ULM is selected from the group consisting of:
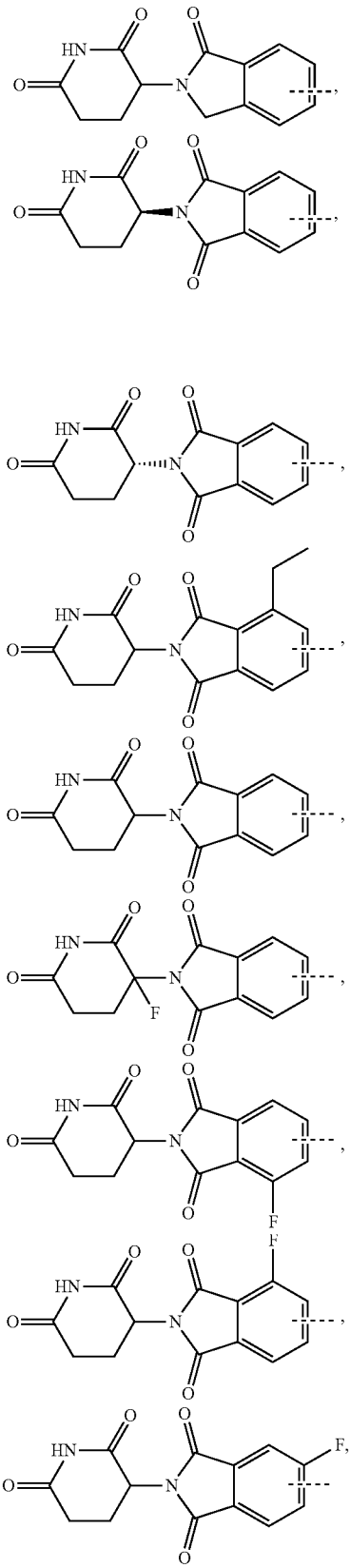

-continued
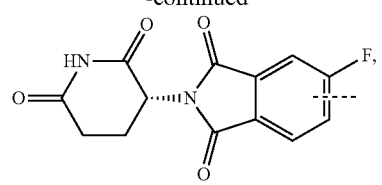
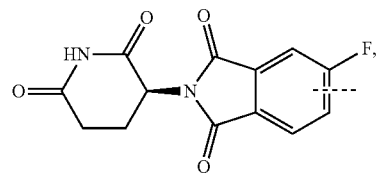
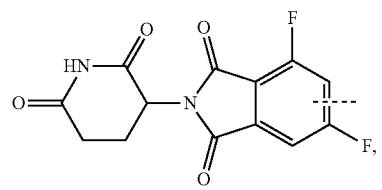
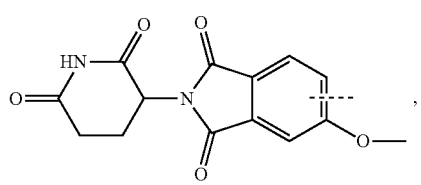
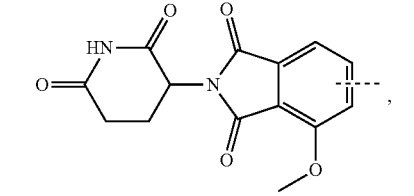
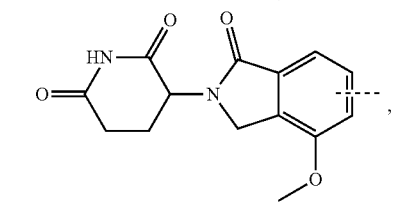
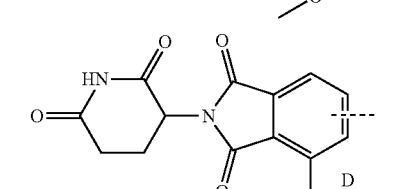
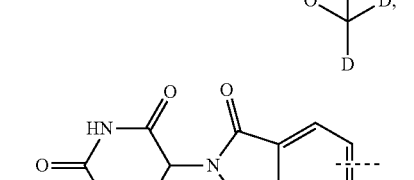
-continued
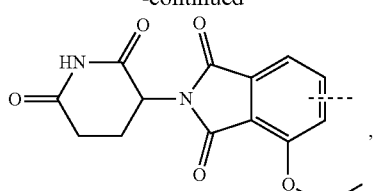
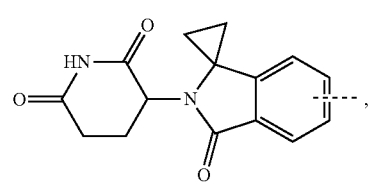
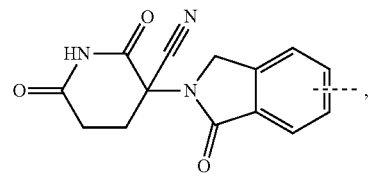
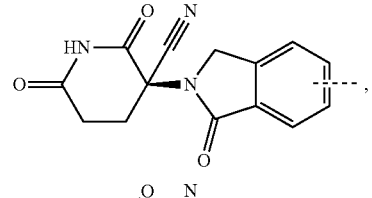
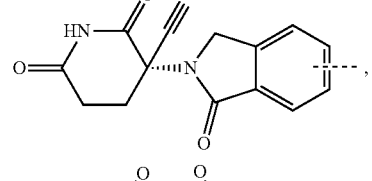
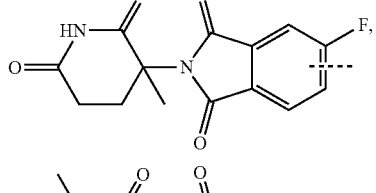
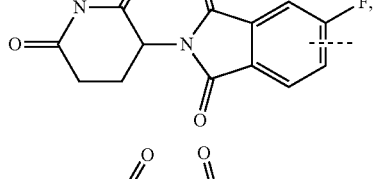
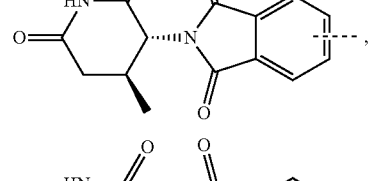

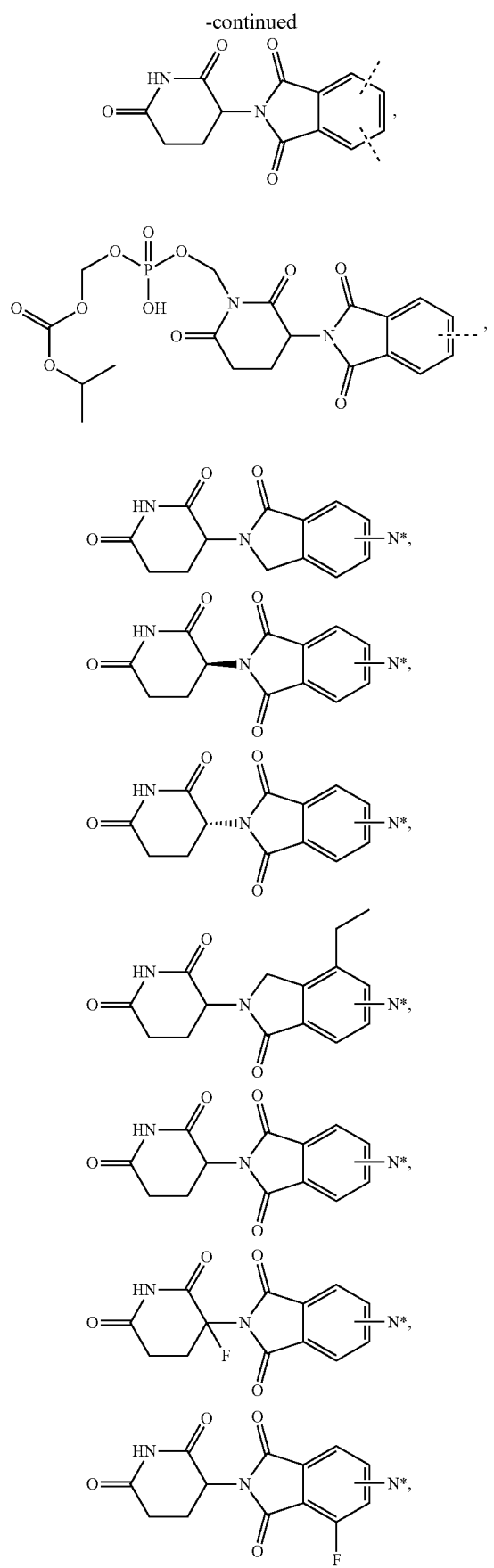
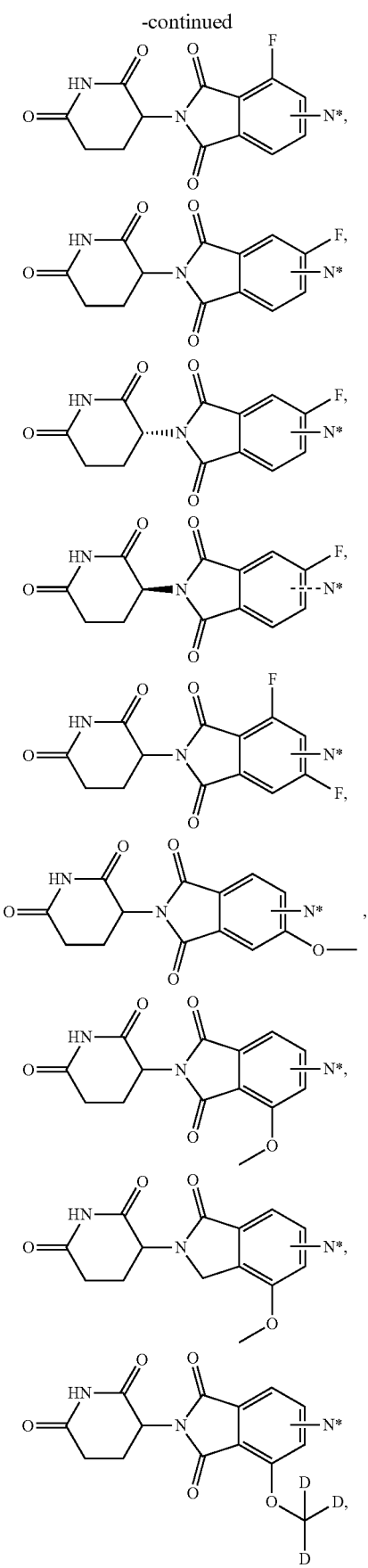

-continued
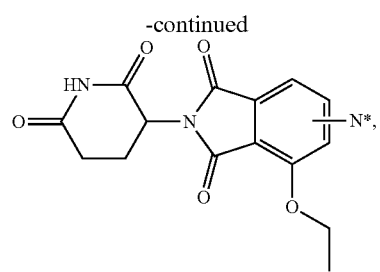
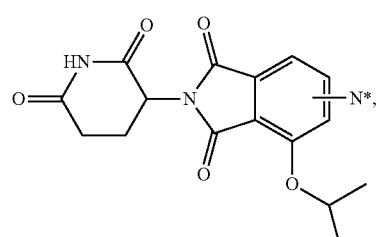
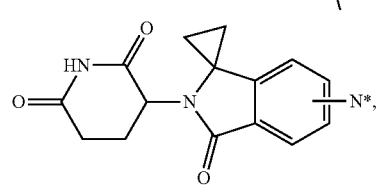
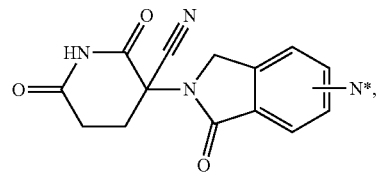
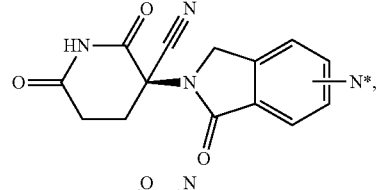
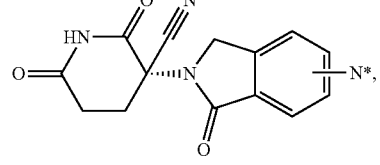
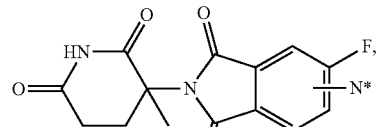
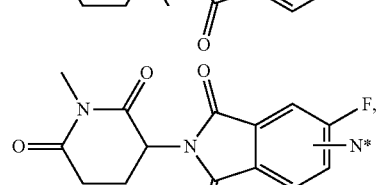
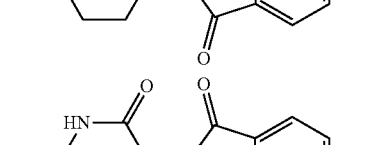
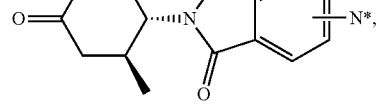
-continued
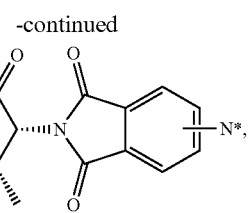
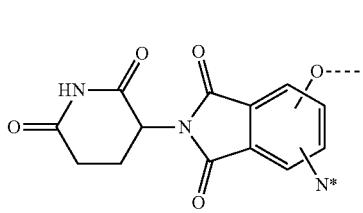
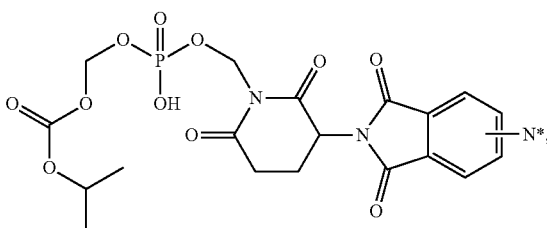
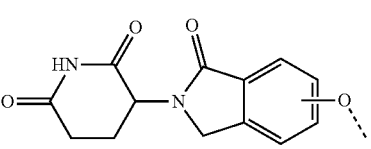
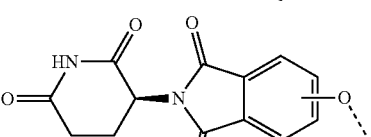
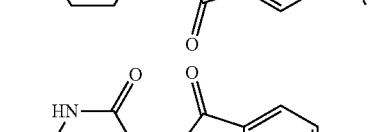
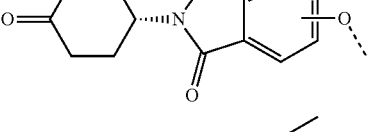
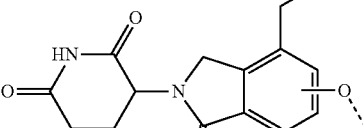
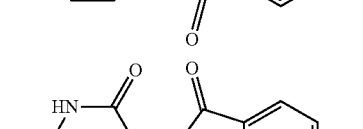
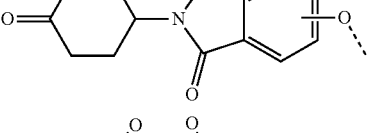
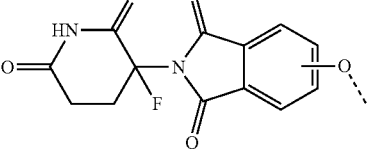

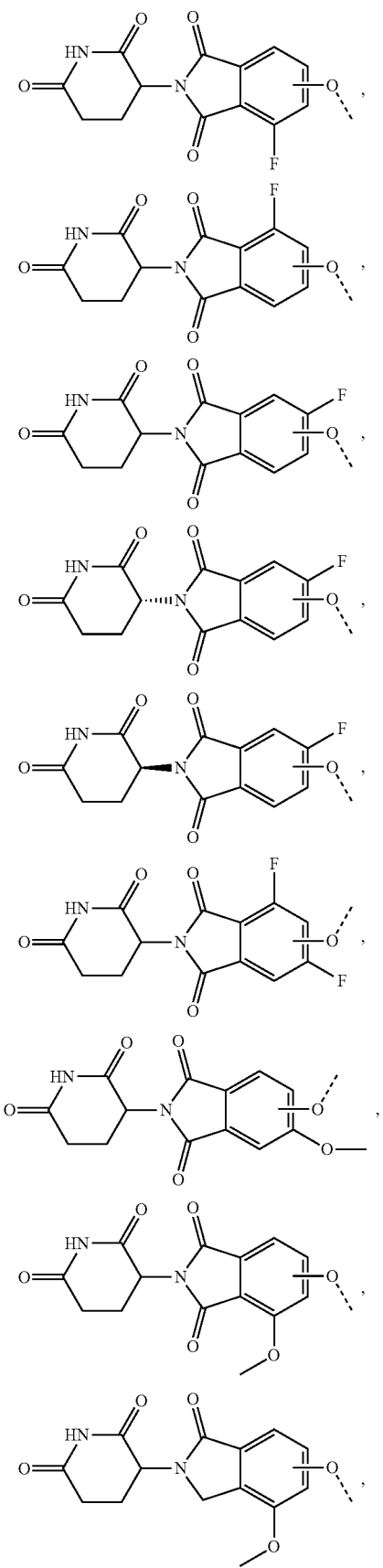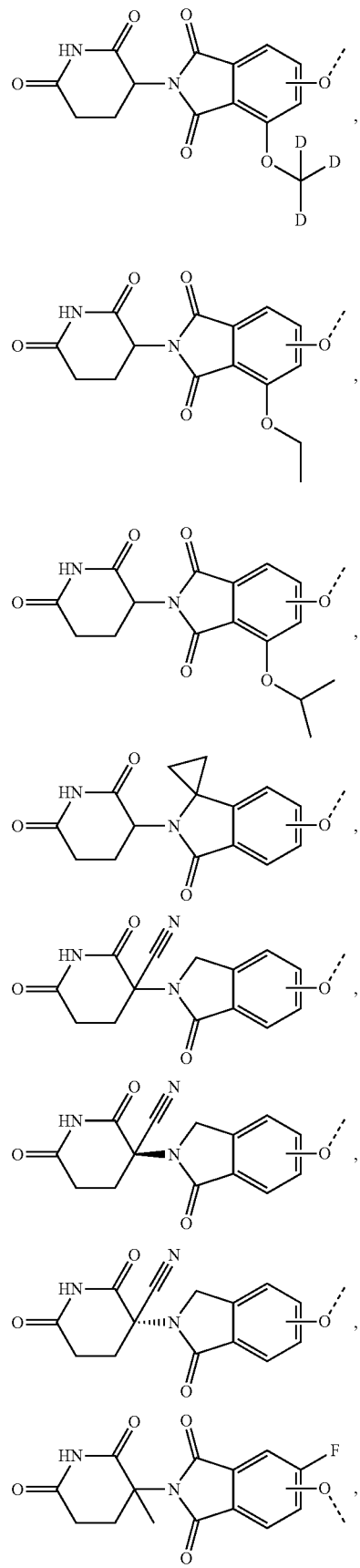

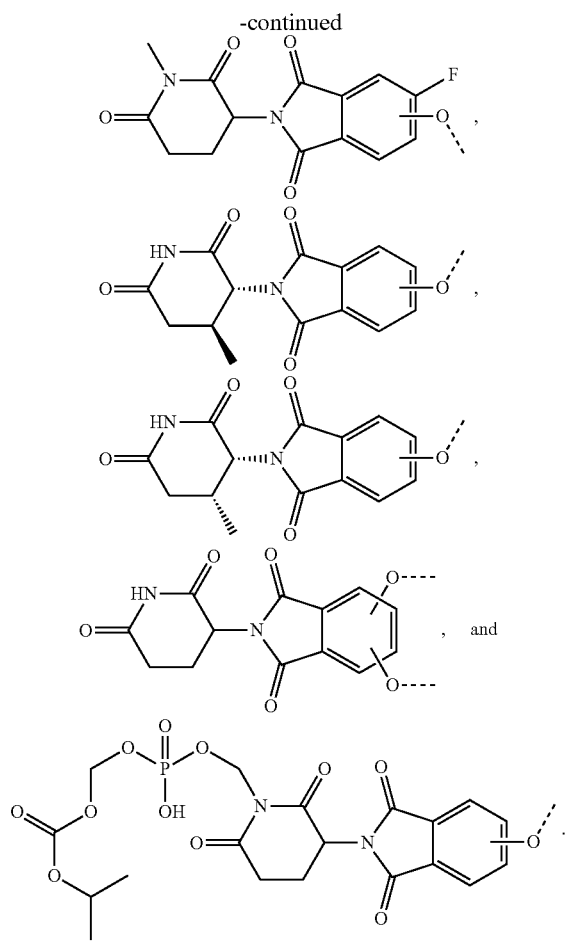

wherein:
- ⌇ of the ULM indicates the point of attachment with a linker group or a PTM; and
- N* is a nitrogen atom that is shared with the chemical linker group or PTM.

Exemplary Linkers

In any aspect or embodiment described herein, the compounds as described herein include a PTM chemically linked to a ULM (e.g., CLM) via a chemical linker (L). In certain embodiments, the linker group L comprises one or more covalently connected structural units (e.g., -$A^L_1$ ... ($A^L$)$_q$- or -($A^L$)$_q$-), wherein $A^L_1$ is a group coupled to PTM, and ($A^L$)$_q$ is a group coupled to ULM.

In any aspect or embodiment described herein, the linker (L) to a ULM (e.g., CLM) connection is a stable L-ULM connection. For example, in certain embodiments, when a linker (L) and a ULM are connected via a heteroatom (e.g., N, O, S), any additional heteroatom, if present, is separated by at least a carbon atom (e.g., —CH$_2$—), such as with an acetal or aminal group. By way of further example, in certain embodiments described herein, when a linker (L) and a ULM are connected via a heteroatom, the heteroatom is not part of an ester.

In any aspect or embodiment described herein, the linker group L is a bond or a chemical linker group represented by the formula -($A^L$)$_q$-, wherein A is a chemical moiety and q is an integer from 1-100 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80), and wherein L is covalently bound to both the PTM and the ULM, and provides for binding of the PTM to the protein target and the ULM to an E3 ubiquitin ligase to effectuate target protein ubiquitination.

In any aspect or embodiment described herein, the linker group L is a bond or a chemical linker group represented by the formula -($A^L$)$_q$-, wherein A is a chemical moiety and q is an integer from 6-30 (e.g., 1, 2, 3, 4, 5, 6, 7, 8, 9, 10, 11, 12, 13, 14, 15, 16, 17, 18, 19, 20, 21, 22, 23, 24, or 25), and wherein L is covalently bound to both the PTM and the ULM, and provides for binding of the PTM to the protein target and the ULM to an E3 ubiquitin ligase in sufficient proximity to result in target protein ubiquitination.

In any aspect or embodiment described herein, the linker group L is -($A^L$)$_q$-, wherein:
- ($A^L$)$_q$ is a group which connects a ULM (e.g., CLM), to PTM;
- q of the linker is an integer greater than or equal to 1;
- each $A^L$ is independently selected from the group consisting of, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}$=$CR^{L2}$, C≡C, $SiR^{L1}R^{L2}$, $P(O)R^{L1}$, $P(O)OR^{L1}$, $NR^{L3}C$(=NCN)$NR^{L4}$, $NR^{L3}C$(=NCN), $NR^{L3}C$(=CNO$_2$)$NR^{L4}$, $C_{3-11}$cycloalkyl optionally substituted with 1-6 $R^{L1}$ and/or $R^{L2}$ groups, $C_{5-3}$ spirocycloalkyl optionally substituted with 1-9 $R^{L1}$ and/or $R^{L2}$ groups, $C_{3-11}$ heterocyclyl optionally substituted with 1-6 $R^{L1}$ and/or $R^{L2}$ groups, $C_{5-13}$ spiroheterocyclyl optionally substituted with 1-8 $R^{L1}$ and/or $R^{L2}$ groups, aryl optionally substituted with 1-6 $R^{L1}$ and/or $R^{L2}$ groups, heteroaryl optionally substituted with 1-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 1-4 $R^{L5}$ groups; and
- $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}$alkyl)$_2$, $C_{3-11}$cycloalkyl, aryl, heteroaryl, $C_{3-11}$heterocyclyl, $OC_{3-8}$cycloalkyl, $SC_{3-8}$cycloalkyl, $NHC_{3-8}$cycloalkyl, $N(C_{3-8}$cycloalkyl)$_2$, $N(C_{3-8}$cycloalkyl)($C_{1-8}$alkyl), OH, $NH_2$, SH, $SO_2C_{1-8}$alkyl, $P(O)(OC_{1-8}$alkyl)($C_{1-8}$alkyl), $P(O)(OC_{1-8}$alkyl)$_2$, CC—$C_{1-8}$ alkyl, CCH, CH=CH($C_{1-8}$alkyl), C($C_{1-8}$alkyl)=CH ($C_{1-8}$alkyl), C($C_{1-8}$alkyl)=C($C_{1-8}$alkyl)$_2$, Si(OH)$_3$, Si($C_{1-8}$alkyl)$_3$, Si(OH)($C_{1-8}$alkyl)$_2$, COC$_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}$alkyl)$_2$, $SONHC_{1-8}$alkyl, $SON(C_{1-8}$alkyl)$_2$, $CONHC_{1-8}$alkyl, $CON(C_{1-8}$alkyl)$_2$, $N(C_{1-8}$alkyl)$CONH(C_{1-8}$alkyl), $N(C_{1-8}$alkyl)$CON(C_{1-8}$alkyl)$_2$, $NHCONH(C_{1-8}$alkyl), $NHCON(C_{1-8}$alkyl)$_2$, $NHCONH_2$, N(C-alkyl)$SO_2NH(C_{1-8}$alkyl), $N(C_{1-8}$alkyl) $SO_2N(C_{1-8}$alkyl)$_2$, NH $SO_2NH(C_{1-8}$alkyl), NH $SO_2N(C_{1-8}$alkyl)$_2$, NH $SO_2NH_2$.

In certain embodiments, q is an integer greater than or equal to 1.

In certain embodiments, e.g., where q of the linker is greater than 2, ($A^L$)$_q$ is a group which is $A^{L1}$ and ($A^L$)$_q$ wherein the linker couples a PTM to a ULM.

In certain embodiments, e.g., where q of the linker is 2, $A^{L2}$ is a group which is connected to $A^{L1}$ and to a ULM.

In certain embodiments, e.g., where q of the linker is 1, the structure of the linker group L is -$A^{L1}$-, and $A^{L1}$ is a group which connects a ULM moiety to a PTM moiety.

In any aspect or embodiment described herein, the unit $A^L$ of linker (L) comprises a group represented by a general structure selected from the group consisting of:

—NR(CH$_2$)$_n$-(lower alkyl)-, —NR(CH$_2$)$_n$-(lower alkoxyl)-, —NR(CH$_2$)$_n$-(lower alkoxyl)-OCH$_2$—, —NR(CH$_2$)$_n$-(lower alkoxyl)-(lower alkyl)-OCH$_2$—, —NR(CH$_2$)$_n$-(cycloalkyl)-(lower alkyl)-OCH$_2$—, —NR(CH$_2$)$_n$-(heterocycloalkyl)-, —NR(CH$_2$CH$_2$O)$_n$-(lower alkyl)-O—CH$_2$—, —NR(CH$_2$CH$_2$O)$_n$-(heterocycloalkyl)-O—CH$_2$—, —NR(CH$_2$CH$_2$O)$_n$-Aryl-O—CH$_2$—, —NR(CH$_2$CH$_2$O)$_n$-(heteroaryl)-O—CH$_2$—, —NR(CH$_2$CH$_2$O)$_n$-(cyclo alkyl)-O-(heteroaryl)-O—CH$_2$—, —NR(CH$_2$CH$_2$O)$_n$-(cyclo alkyl)-O-Aryl-O—CH$_2$—, —NR(CH$_2$CH$_2$O)$_n$-(lower alkyl)-NH-Aryl-O—CH$_2$—, —NR(CH$_2$CH$_2$O)$_n$-(lower alkyl)-O-Aryl-CH$_2$, —NR(CH$_2$CH$_2$O)$_n$-cycloalkyl-O-Aryl-, —NR(CH$_2$CH$_2$O)$_n$-cycloalkyl-O-(heteroaryl)l-, —NR(CH$_2$CH$_2$)$_n$-(cycloalkyl)-O-(heterocyclyl)-CH$_2$, —NR(CH$_2$CH$_2$)$_n$-(heterocyclyl)-(heterocyclyl)-CH$_2$, and —N(R1R2)-(heterocyclyl)-CH$_2$; where n of the linker can be 0 to 10;

R of the linker can be H, or lower alkyl; and

R1 and R2 of the linker can form a ring with the connecting N.

In any aspect or embodiment described herein, the linker (L) includes an optionally substituted C$_1$-C$_{50}$alkyl (e.g., C$_1$, C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, C$_{20}$, C$_{21}$, C$_{22}$, C$_{23}$, C$_{24}$, C$_{25}$, C$_{26}$, C$_{27}$, C$_{28}$, C$_{29}$, C$_{30}$, C$_{31}$, C$_{32}$, C$_{33}$, C$_{34}$, C$_{35}$, C$_{36}$, C$_{37}$, C$_{38}$, C$_{39}$, C$_{40}$, C$_{41}$, C$_{42}$, C$_{43}$, C$_{44}$, C$_{45}$, C$_{46}$, C$_{47}$, C$_{48}$, C$_{49}$, or C$_{50}$ alkyl, and including all implied subranges, e.g., C1-C10, C1-C20; C2-C10, C2-20; C10-C20, C10-C50 etc.), wherein each carbon is optionally independently substituted or replaced with (1) a heteroatom selected from N or O atoms that has an appropriate number of hydrogens, substitutions, or both to complete valency, (2) an optionally substituted cycloalkyl or bicyclic cycloalkly, (3) an optionally substituted heterocyloalkyl or bicyclic heterocyloalkyl, (4) an optionally substituted aryl or bicyclic aryl, or (5) optionally substituted heteroaryl or bicyclic heteroaryl. In any aspect or embodiment described herein, the linker (L) does not have heteroatom-heteroatom bonding (e.g., no heteroatoms are covalently linked or adjacently located).

In any aspect or embodiment described herein, the linker (L) includes an optionally substituted C$_1$-C$_{50}$ alkyl (e.g., C$_1$, C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, C$_{20}$, C$_{21}$, C$_{22}$, C$_{23}$, C$_{24}$, C$_{25}$, C$_{26}$, C$_{27}$, C$_{28}$, C$_{29}$, C$_{30}$, C$_{31}$, C$_{32}$, C$_{33}$, C$_{34}$, C$_{35}$, C$_{36}$, C$_{37}$, C$_{38}$, C$_{39}$, C$_{40}$, C$_{41}$, C$_{42}$, C$_{43}$, C$_{44}$, C$_{45}$, C$_{46}$, C$_{47}$, C$_{48}$, C$_{49}$, or C$_{50}$alkyl), wherein:

each carbon is optionally independently substituted or replaced with CR$^{L1}$R$^{L2}$, O, NR$^{L3}$, CONR$^{L3}$, CO, CR$^{L1}$=CR$^{L2}$, C≡C, C$_{3-11}$cycloalkyl optionally substituted with 1-6 R$^{L1}$ and/or R$^{L2}$ groups, C$_{5-13}$ spirocycloalkyl optionally substituted with 1-9 R$^{L1}$ and/or R$^L$ groups, C$_{3-11}$ heterocyclyl optionally substituted with 1-6 R$^{L1}$ and/or R$^{L2}$ groups, C$_{5-13}$ spiroheterocyclyl optionally substituted with 1-8 R$^{L1}$ and/or R$^{L2}$ groups, aryl optionally substituted with 1-6 R$^{L1}$ and/or R$^{L2}$ groups, and heteroaryl optionally substituted with 1-6 R$^{L1}$ and/or R$^{L2}$ groups, where R$^{L1}$ or R$^{L2}$, each independently are optionally linked to other groups to form a cycloalkyl and/or a heterocyclyl moiety, optionally substituted with 1-4 R$^{L5}$ groups; and R$^{L1}$, R$^{L2}$, R$^{L3}$, R$^{L4}$ and R$^{L5}$ are, each independently, H, halo, C$_{1-8}$alkyl, OC$_{1-8}$alkyl, NHC$_{1-8}$alkyl, N(C$_{1-8}$alkyl)$_2$, C$_{3-11}$cycloalkyl, aryl, heteroaryl, C$_{3-11}$ heterocyclyl, OC$_{3-8}$cycloalkyl, NHC$_{3-8}$cycloalkyl, NN(C$_{3-8}$cycloalkyl)(C$_{1-8}$alkyl), OH, NH$_2$, CC—C$_{1-8}$alkyl, CCH, CH=CH(C$_{1-8}$alkyl), C(C$_{1-8}$alkyl)=CH(C$_{1-8}$alkyl), C(C$_{1-8}$alkyl)=C(C$_{1-8}$alkyl)$_2$, COC$_{1-8}$alkyl, CO$_2$H, halogen, CN, CF$_3$, CHF$_2$, CH$_2$F, or NO$_2$.

In any aspect or embodiment described herein, the linker group is optionally substituted an optionally substituted C$_1$-C$_{50}$alkyl (e.g., C$_1$, C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, C$_{20}$, C$_{21}$, C$_{22}$, C$_{23}$, C$_{24}$, C$_{25}$, C$_{26}$, C$_{27}$, C$_{28}$, C$_{29}$, C$_{30}$, C$_{31}$, C$_{32}$, C$_{33}$, C$_{34}$, C$_{35}$, C$_{36}$, C$_{37}$, C$_{38}$, C$_{39}$, C$_{40}$, C$_{41}$, C$_{42}$, C$_{43}$, C$_{44}$, C$_{45}$, C$_{46}$, C$_{47}$, C$_{48}$, C$_{49}$, or C$_{50}$alkyl, and including all implied subranges, e.g., C1-C10, C1-C20; C2-C10, C2-20; C10-C20, C10-C50 etc.), wherein each carbon atom optionally substituted or replaced with: a O or N atom that has an appropriate number of hydrogens, substitutions (e.g., OH, halo, alkyl, methyl, ethyl, haloalkyl, hydroxyalkyl, alkoxy, methoxy, etc.), or both to complete valency; an optionally substituted C5 or C6 aryl aryl or C5-C20 bicyclic aryl; an optionally substituted 5-6 membered heteroaryl or 5-20 membered bicyclic heteroaryl (e.g., an optionally substituted heteroaryl or bicyclic heteroaryl having one or more heteroatoms selected from N and O that has an appropriate number of hydrogens, substitutions (e.g., OH, halo, alkyl, methyl, ethyl, haloalkyl, hydroxyalkyl, alkoxy, methoxy, etc.), or both to complete valency); an optionally substituted C1-C6 alkyl; an optionally substituted C1-C6 alkenyl; an optionally substituted C1-C6 alkynyl; an optionally substituted C3-C7 cycloalkyl or C5-C20 bicyclic cycloalkyl; or an optionally substituted 3-7 membered heterocycloalkyl or 5-20 membere bicyclicheteroalkyl (e.g., an optionally substituted heterocycloalkyl bicyclicheteroalkyl having one or more heteroatoms selected from N and O atoms that has an appropriate number of hydrogens, substitutions (e.g., OH, halo, alkyl, methyl, ethyl, haloalkyl, hydroxyalkyl, alkoxy, methoxy, etc.), or both to complete valency). In any aspect or embodiment described herein, the optionally substituted alkyl linker is optionally substituted with one or more OH, halo, linear or branched C1-C6 alkyl (such as methyl or ethyl), linear or branched C1-C6 haloalkyl, linear or branched C1-C6 hydroxyalkyl, or linear or branched C1-C6 alkoxy (e.g., methoxy).

In any aspect or embodiment described herein, the linker (L) does not have heteroatom-heteroatom bonding (e.g., no heteroatoms are covalently linked or adjacently located).

In any aspect or embodiment described herein, the linker (L) includes about 1 to about 50 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) alkylene glycol units that are optionally substituted, wherein carbon or oxygen may be substituted with a heteroatom selected from N, S, P, or Si atoms with an appropriate number of hydrogens to complete valency.

In any aspect or embodiment described herein, the linker (L) comprises or is the chemical structure:

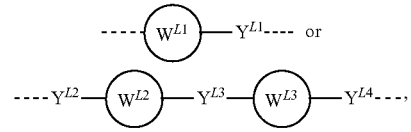

wherein:

W$^{L1}$ is a 5- or 6-membered ring (e.g., 5- or 6-membered cycloalkyl or 5- or 6-membered cycloalkyl heterocycloalkyl) with 0-3 heteroatoms (e.g., 1, 2, or 3 heteroatoms selected from O and N) or a C$_{8-11}$ spiroheterocycloalkyl with 0-3 heteroatoms (e.g., 0, 1, 2, or 3 heteroatoms selected from O and N), each optionally substituted with a halogen (e.g., F, Cl, Br) or methyl;

$Y^{L1}$ is a bond, a unsubstituted or substituted linear or branched $C_{1-8}$ alkyl ($C_1$, $C_2$, $C_3$, $C_4$, or $C_5$ alkyl), wherein one or more C atoms are optionally replace with O (e.g., a unsubstituted or substituted linear or branched $C_{1-5}$ alkyl-O ($C_1$, $C_2$, $C_3$, $C_4$, or $C_5$ alkyl)) and each carbon is optionally substituted with a halogen (e.g., F, Cl, Br), methyl, or ethyl);

$Y^{L2}$ is a bond, O, or an unsubstituted or substituted linear or branched $C_{1-3}$ alkyl ($C_1$, $C_2$, or $C_3$ alkyl), wherein each carbon is optionally substituted with a halogen (e.g., F, Cl, Br), methyl, or ethyl);

$W^{L2}$ is a 3-7 membered ring (e.g., 4-6 membered cycloalkyl or 4-6 membered heterocycloalkyl) with 0-3 heteroatoms (e.g., 1, 2, or 3 heteroatoms selected from O and N), a $C_{5-11}$ spiroheterocycloalkyl (e.g., $C_{5-8}$ or a $C_{6-7}$ spiroheterocycloalkyl), 6-10 membered fused bicyclic cycloalkyl, or 6-10 membered fused bicyclic heteocycloalkyl, each optionally substituted with a halogen (e.g., F, Cl, Br), deuterium, or methyl;

$Y^{L3}$ is a bond or a $C_1$-$C_4$ alkyl ($C_1$, $C_2$, $C_3$, or $C_4$ alkyl), wherein one or more C atoms (e.g., one carbon atom) are optionally replaced with O or $NR^L$, and wherein: each carbon is optionally substituted with a halogen (e.g., F, Cl, Br) or a linear or branched C1-C4 alkyl;

$R^L$ is: H; linear or branched C1-4 alkyl that is optionally substituted with one or more halogen (e.g., F), deuterium, or C=O (e.g., methyl, ethyl, isopropyl group, —CH$_2$—CF$_3$, —CH$_2$—CHF$_2$, or —(C=O)CH$_3$); linear or branched CL-3 hydroxyalkyl (e.g., a C2 hydroxyalkyl); (CH$_2$)$_n$-4 to 6 membered heerocycloalkyl having 1-3 heteroatoms (e.g., 1 or 2 heteroatoms selected from O and N), such as

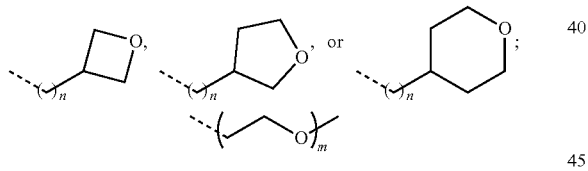

that is optionally substituted with a halogen (e.g., F, Cl, or Br), methyl, or deuterium;

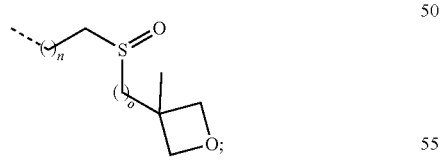

m is an integer from 1 to 6 (e.g., 1, 2, 3, 4, 5, or 6);
n is an integer from 0 to 3 (e.g., 0, 1, 2, or 3);
is an integer from 1 to 3 (e.g., 1, 2, or 3);
$W^{L3}$ is a 3-7 membered ring (e.g., 4-6 membered cycloalkyl or 4-6 membered heterocycloalkyl), each with 0-3 heteroatoms (e.g., 1, 2, or 3 heteroatoms selected from O and N) and optionally substituted with halo (e.g., F, Cl, Br), or methyl; and
$Y^{L4}$ is bond, O, or (CH$_2$)$_o$—O, optionally substituted with a halogen (e.g., F, Cl, Br) or methyl.

In any aspect or embodiment described herein, the linker (L) comprises a structure selected from the group consisting of:

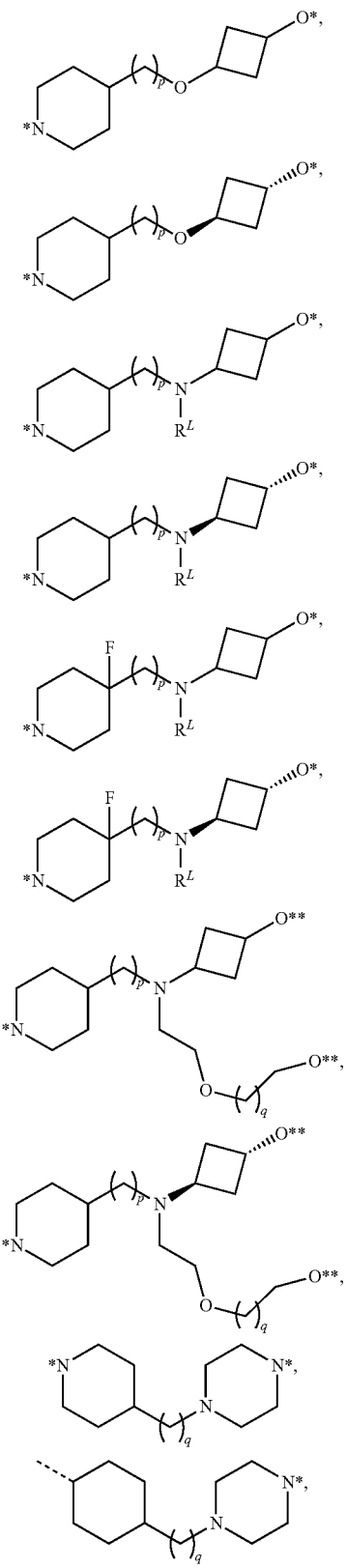

-continued
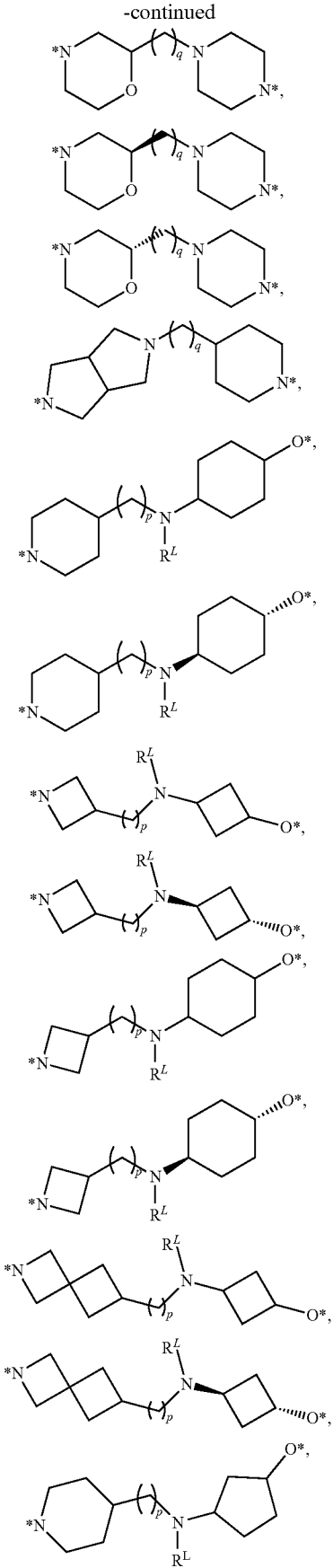
-continued
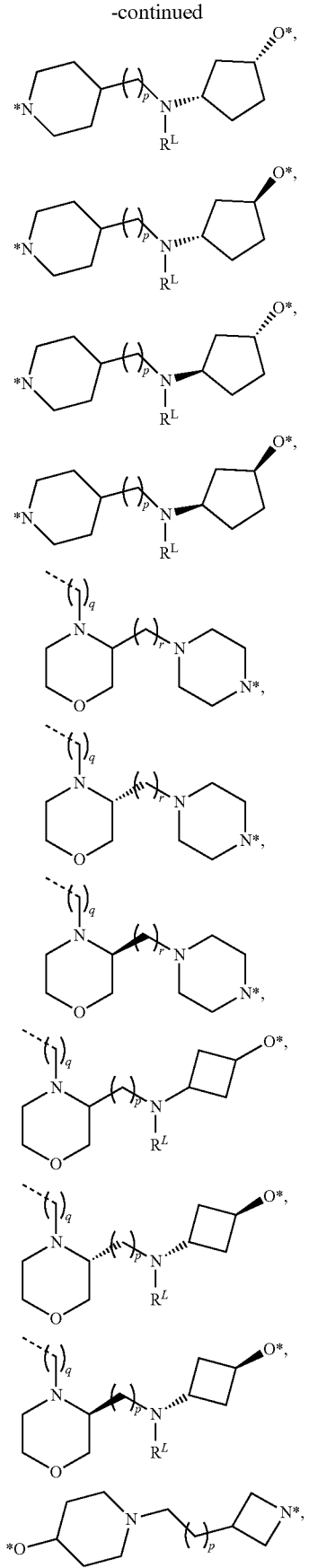

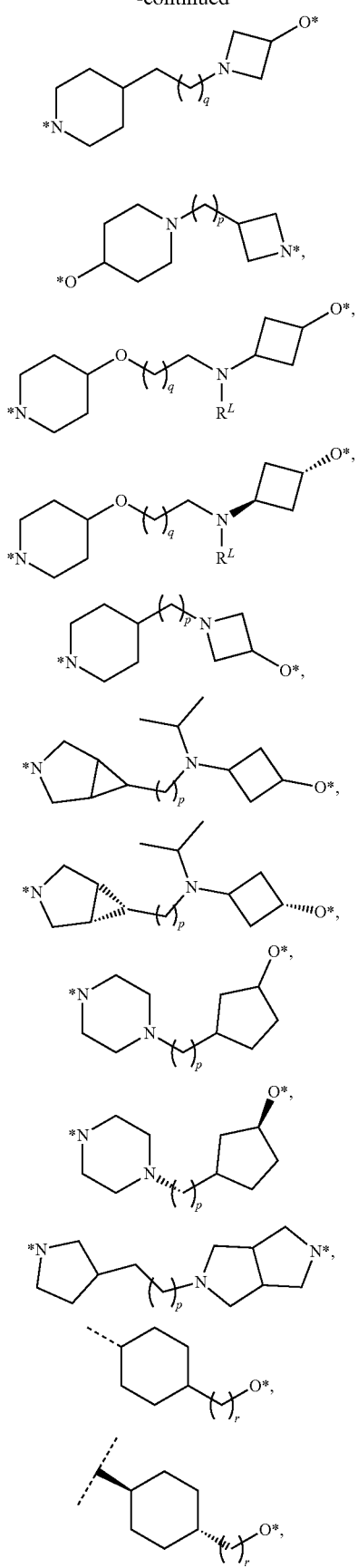
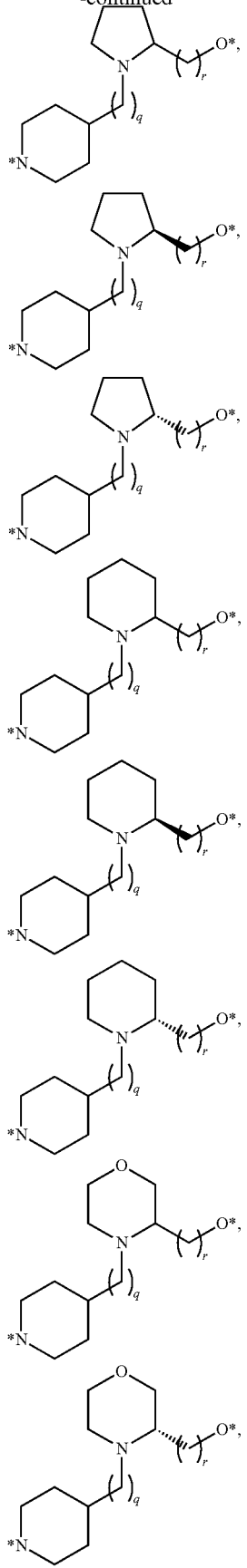

-continued

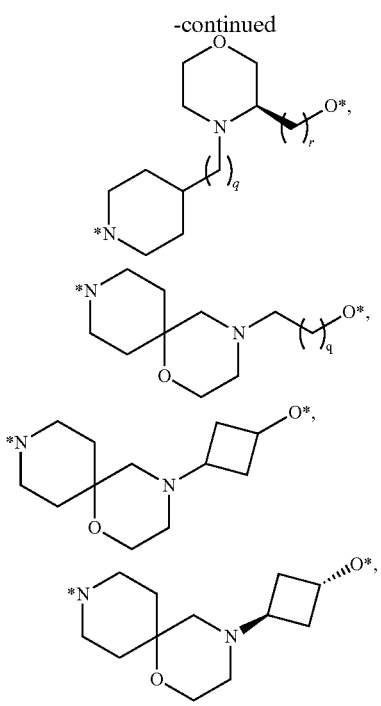

wherein:
R$^L$ is: H; linear or branched C$_{1-4}$ alkyl that is optionally substituted with one or more halogen (e.g., F), deuterium, or C=O (e.g., methyl, ethyl, isopropyl group, —CH$_2$—CF$_3$, —CH$_2$—CHF$_2$, or —(C=O)CH$_3$); linear or branched C$_{1-3}$ hydroxyalkyl (e.g., a C$_2$ hydroxyalkyl); (CH$_2$)$_n$-4 to 6 membered heerocycloalkyl having 1-3 heteroatoms (e.g., 1 or 2 heteroatoms selected from O and N), such as

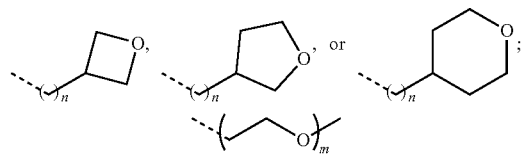

that is optionally substituted with a halogen (e.g., F, Cl, or Br), methyl, or deuterium;

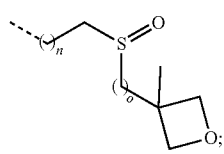

p is an integer from 0 to 3 (e.g., 0, 1, 2, or 3);
q is an integer from 1 to 3 (e.g., 1, 2, or 3);
r is an integer from 1 to 3 (e.g., 1, 2, or 3);
s is an integer from 0 to 4 (e.g., 0, 1, 2, 3, or 4);

╲╲╲ indicates the site that is covalently linked to the CLM or PTM; and
* indicates the site that is covalently linked to the CLM or PTM, or is an atom that is shared with the CLM or PTM.

In any aspect or embodiment described herein, the linker (L) comprises a structure selected from the group consisting of:

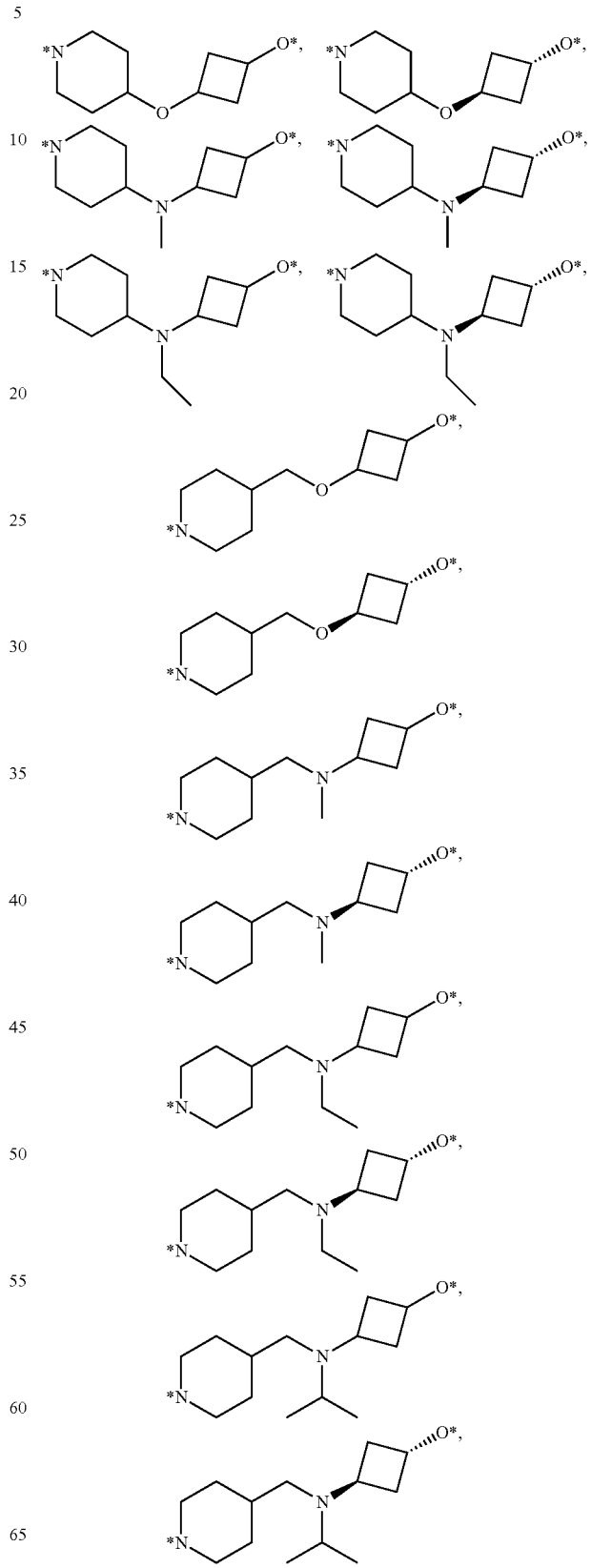

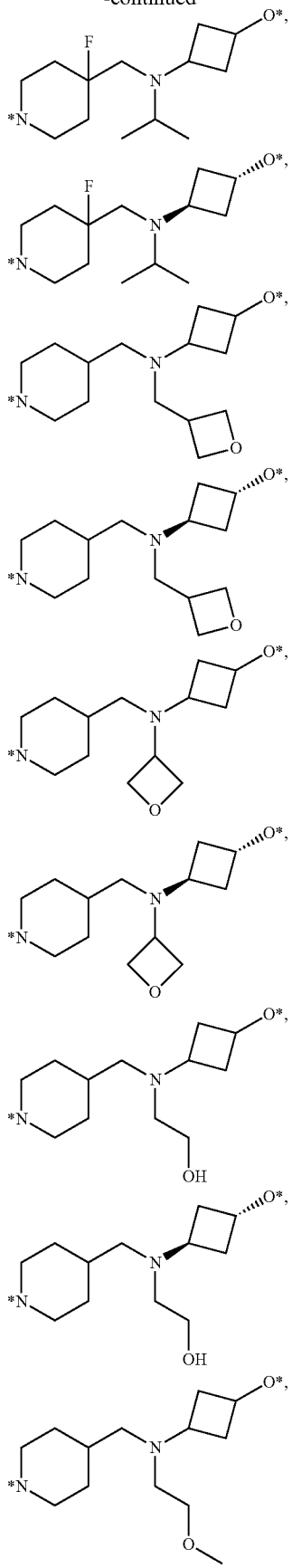
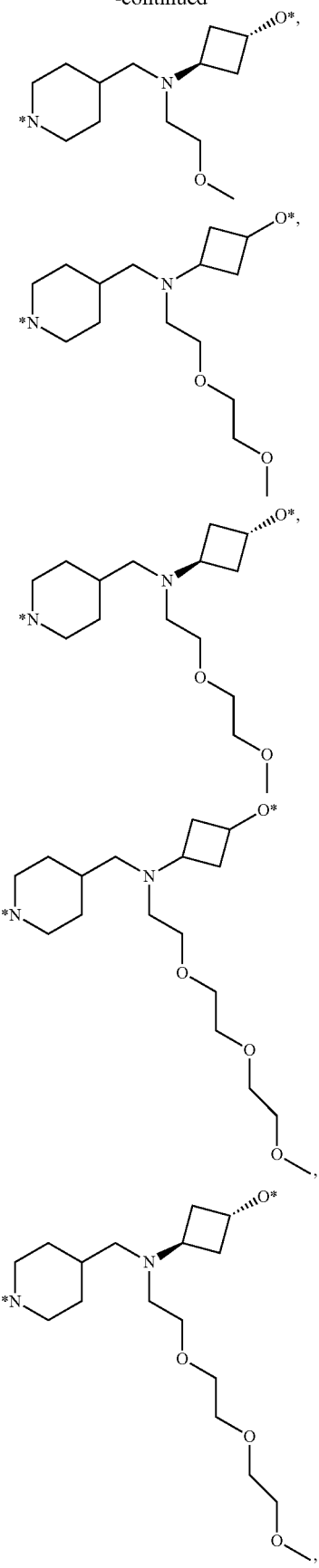

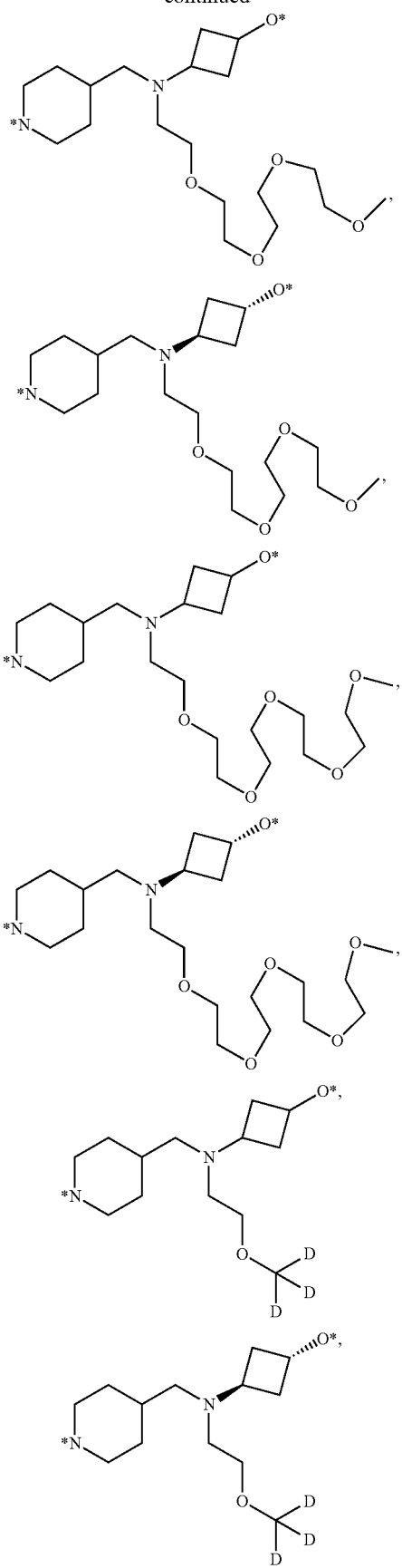
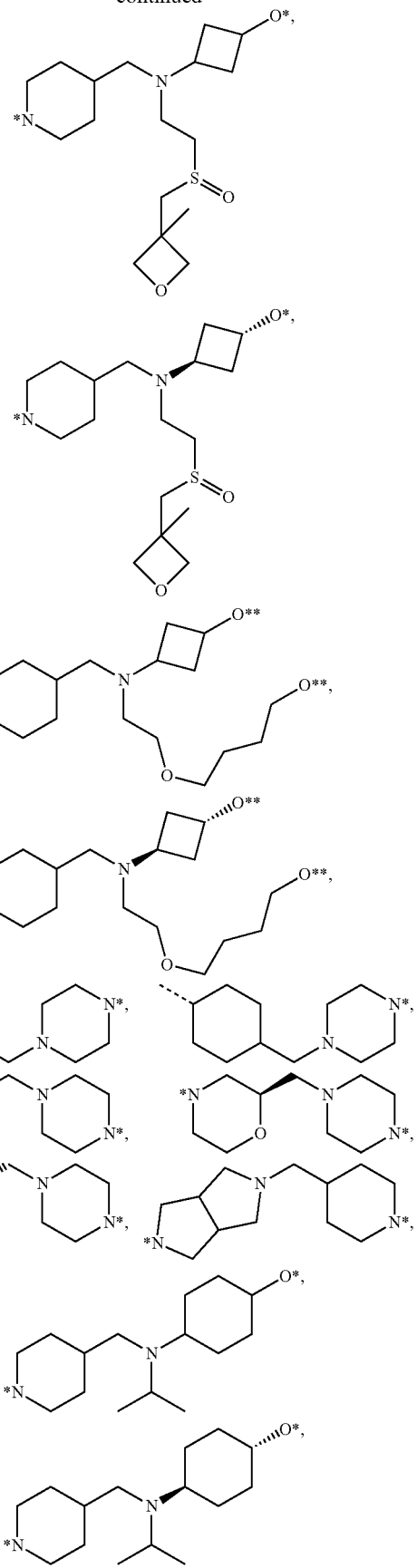

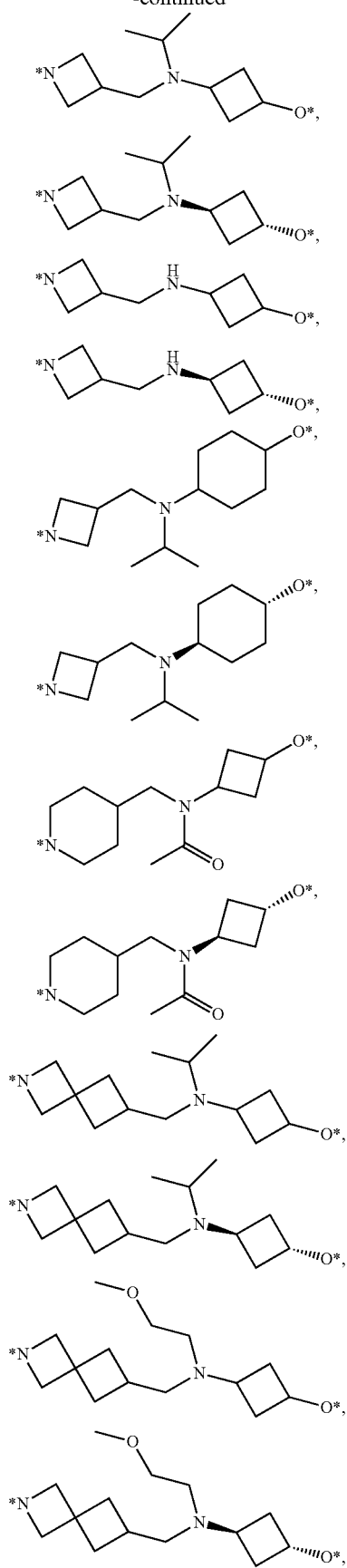
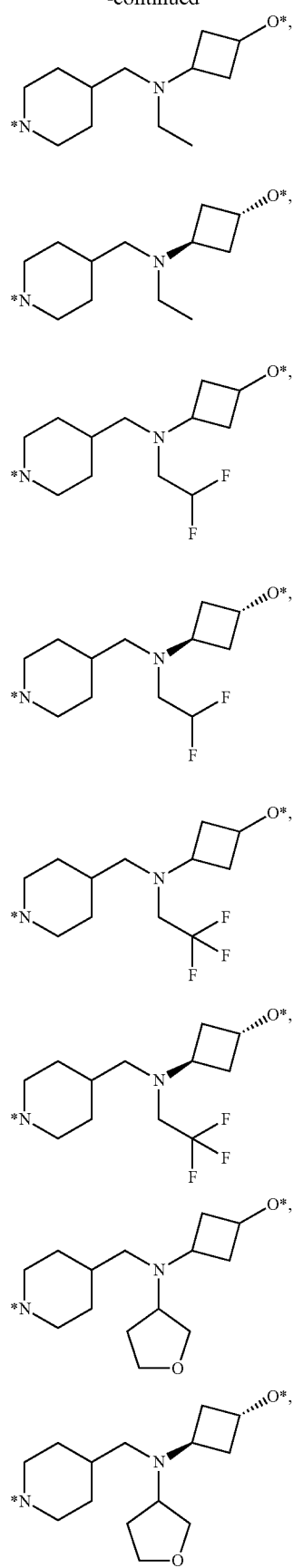

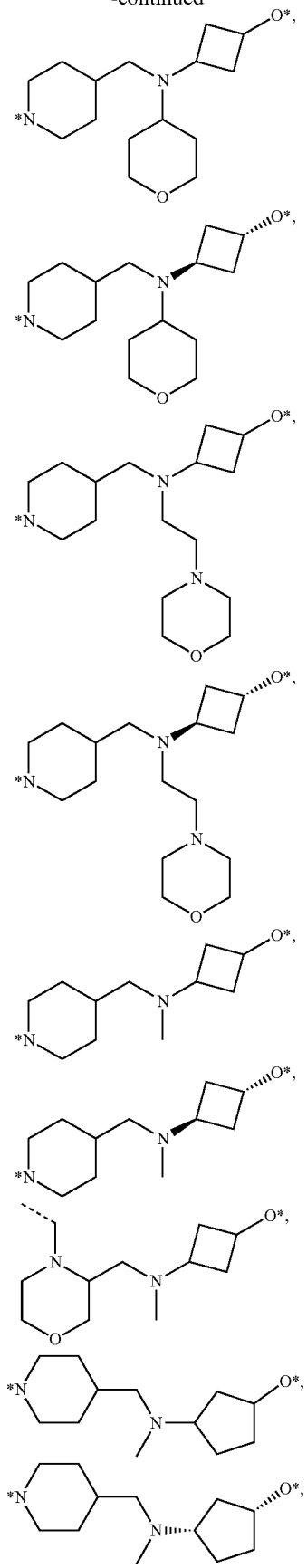
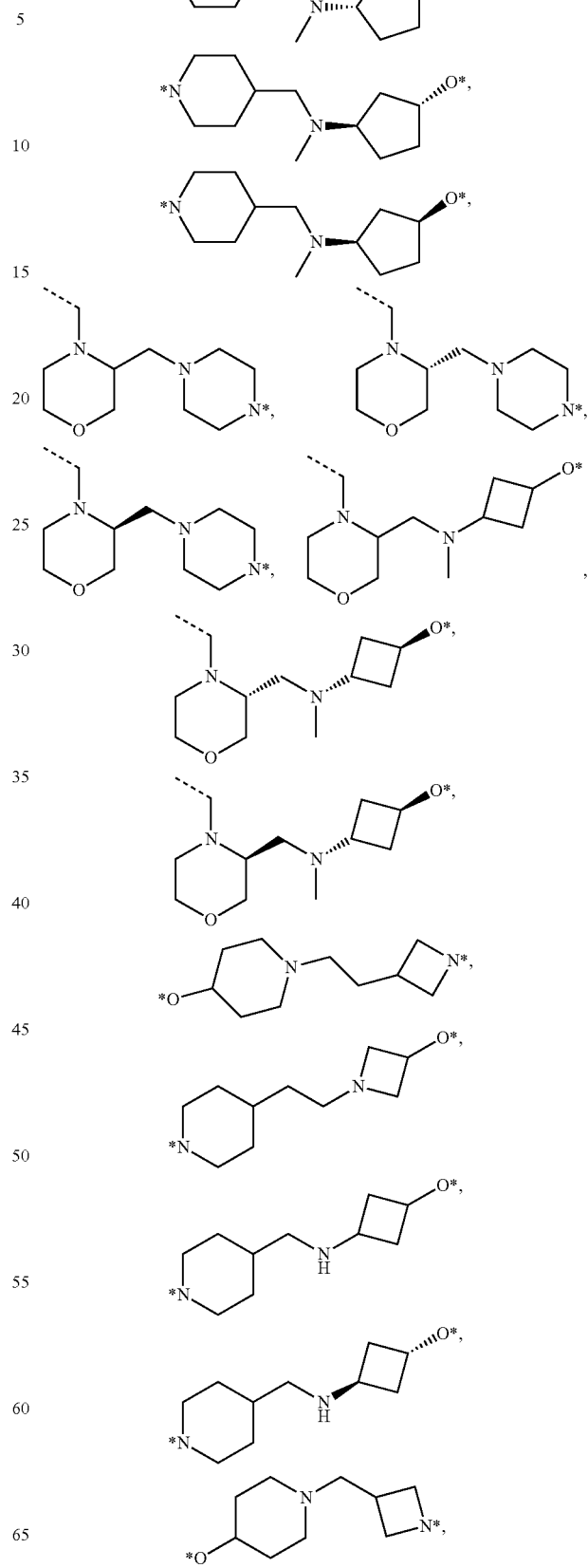

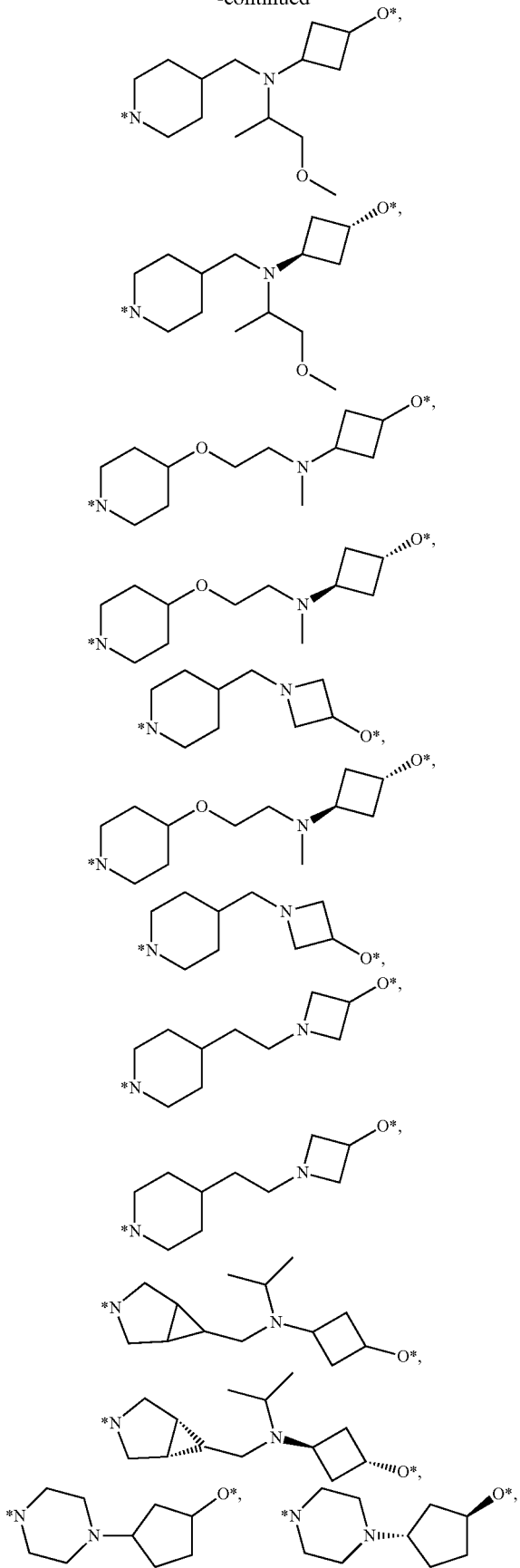
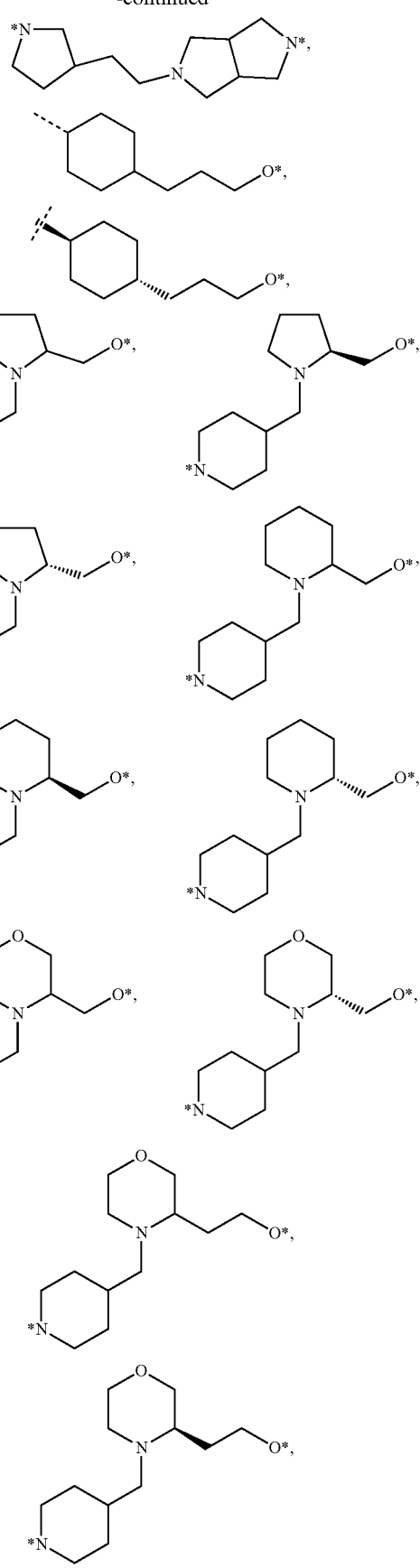

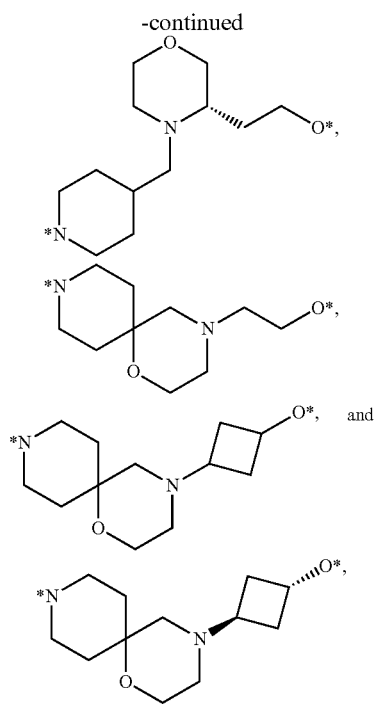

wherein:

- ⸺ indicates the site that is covalently linked to the ULM or PTM;
- indicates the site that is covalently linked to the ULM or PTM or is an atom that is shared with the ULM or PTM; and
- ** indicates the site that is covalently linked to the ULM or is an atom that is shared with the ULM.

In any aspect or embodiment described herein, the linker (L) comprises a structure selected from the group consisting of:

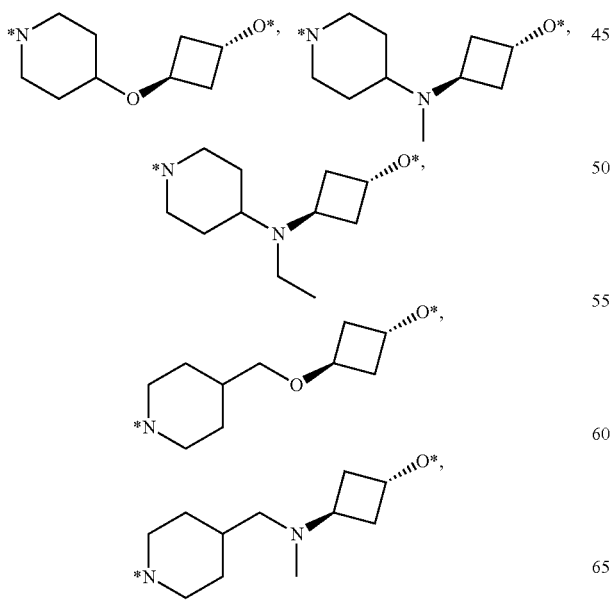

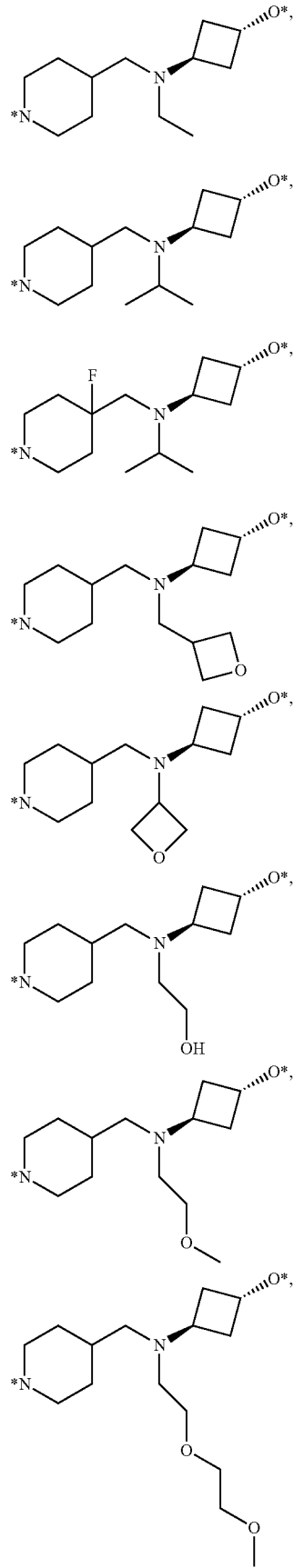

73
-continued
74
-continued
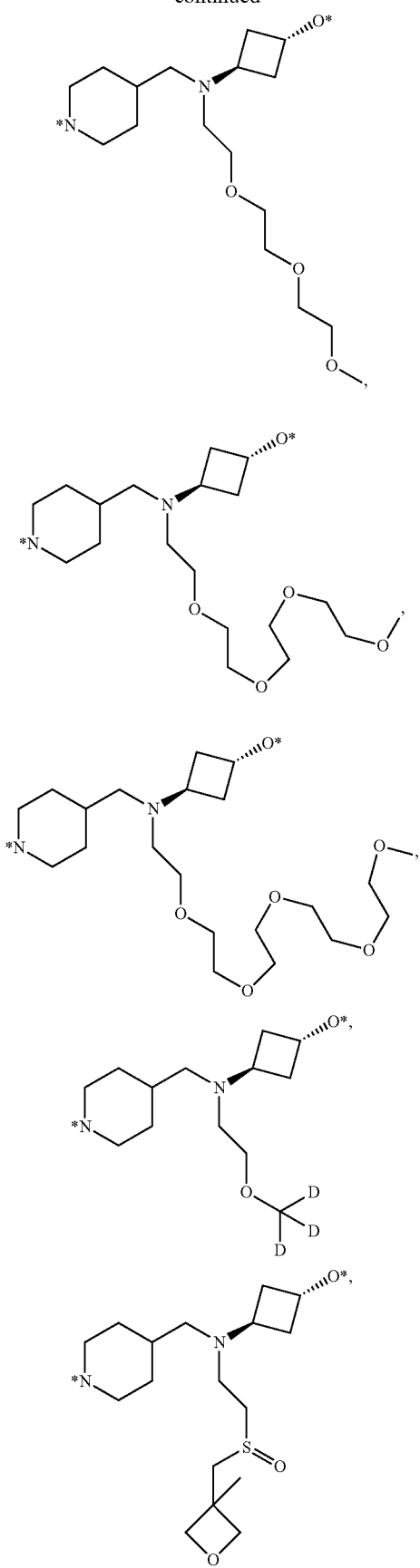
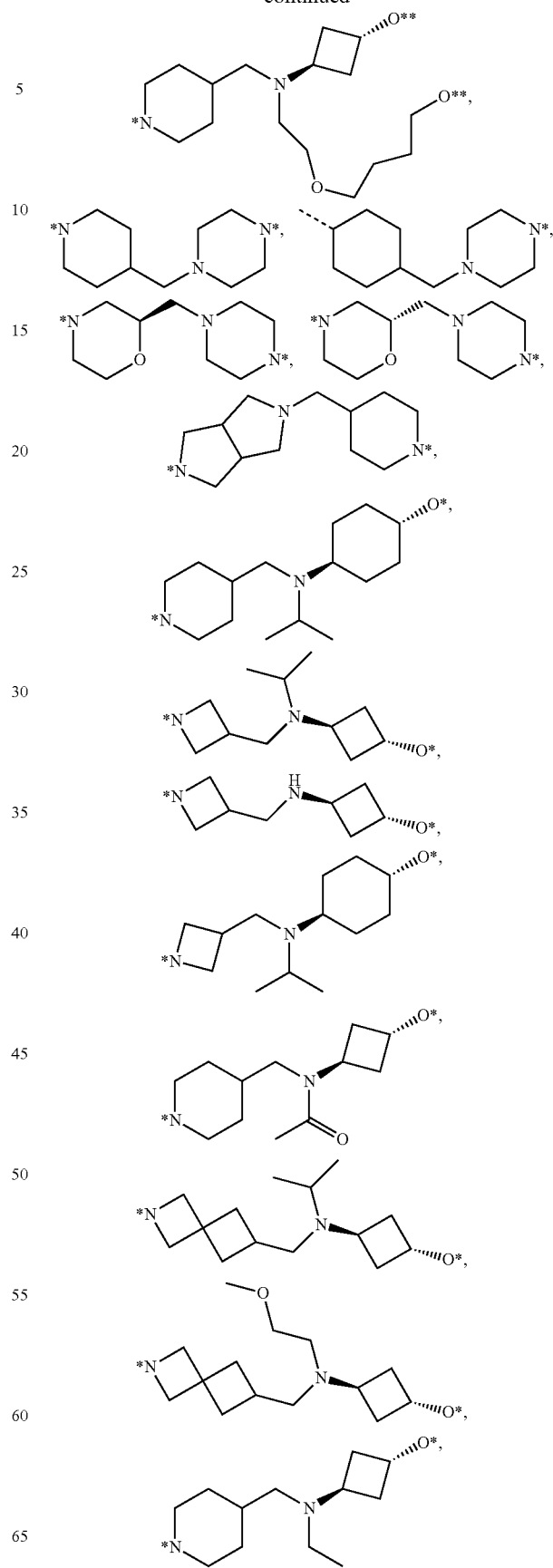

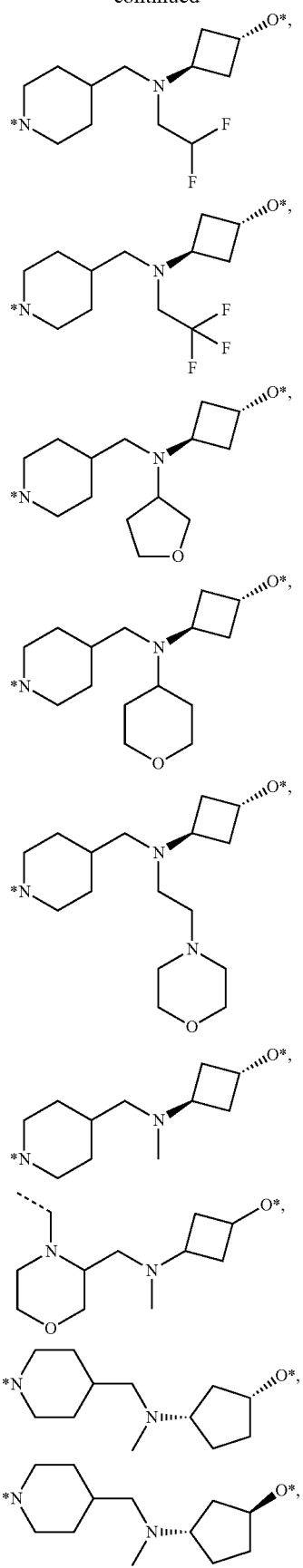
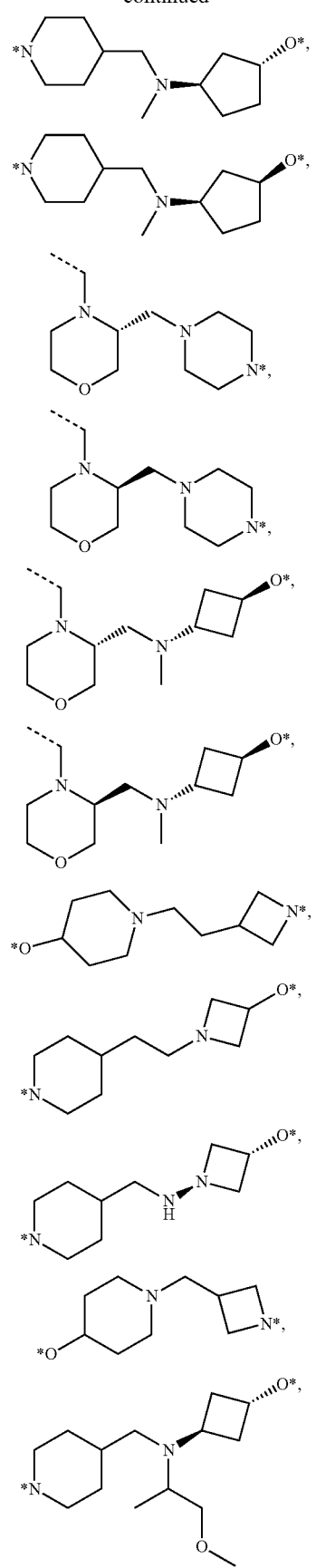

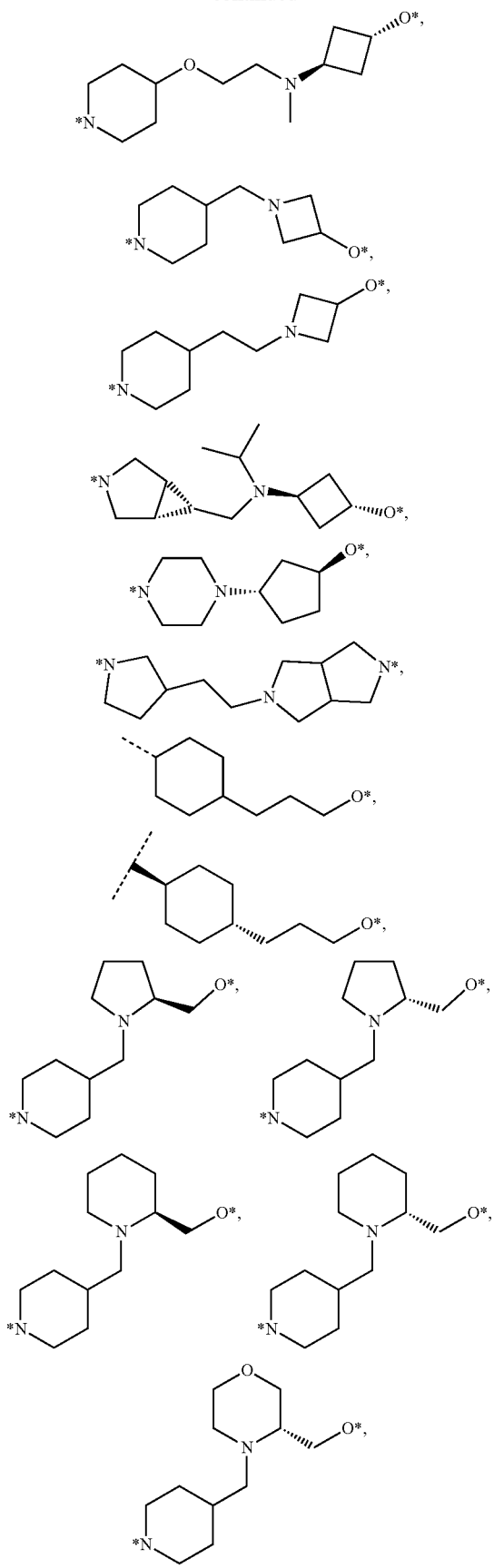

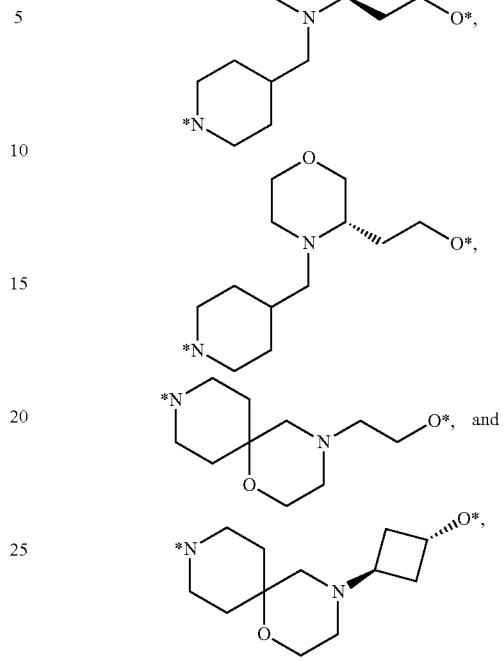

wherein:

indicates the site that is covalently linked to the ULM or PTM;

* indicates the site that is covalently linked to the ULM or PTM or is an atom that is shared with the ULM or PTM; and

** indicates the site that is covalently linked to the ULM or is an atom that is shared with the ULM.

In any aspect or embodiment described herein, the linker (L) comprises a structure selected from the structure shown below:

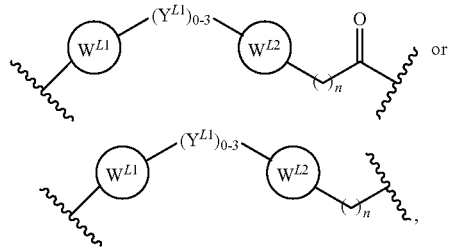

wherein:

$W^{L1}$ and $W^{L2}$ are each independently absent, a 4-8 membered ring with 0-4 heteroatoms, optionally substituted with $R^Q$, each $R^Q$ is independently a H, halo, OH, CN, $CF_3$, optionally substituted linear or branched $C_1$-$C_6$ alkyl, optionally substituted linear or branched $C_1$-$C_6$ alkoxy, or 2 $R^Q$ groups taken together with the atom they are attached to, form a 4-8 membered ring system containing 0-4 heteroatoms;

$Y^{L1}$ is each independently a bond, optionally substituted linear or branched $C_1$-$C_6$ alkyl and optionally one or more C atoms are replaced with O or $NR^{YL1}$, optionally substituted $C_1$-$C_6$ alkene and optionally one or more C atoms are replaced with O, optionally substituted $C_1$-$C_6$ alkyne, and optionally one or more C atoms are replaced with O, or optionally substituted linear or branched $C_1$-$C_6$ alkoxy;

$R^{YL1}$ is H, or optionally substituted linear or branched $C_{1-6}$ alkyl;

n is 0-10; and

✓ and ⌇ indicates the attachment point to the PTM or ULM moieties.

In any aspect or embodiment described herein, the linker (L) comprises a structure selected from the structure shown below:

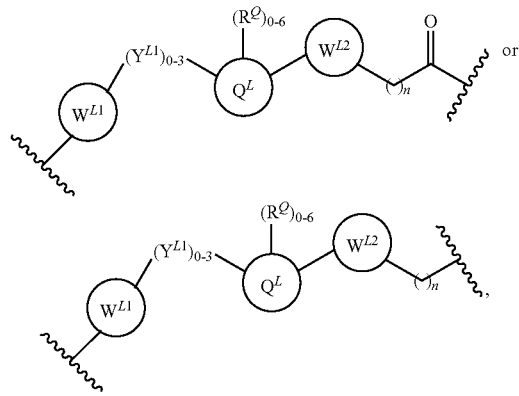

wherein:
- $W^{L1}$ and $W^{L2}$ are each independently absent, aryl, heteroaryl, cyclic, heterocyclic, $C_{1-6}$ alkyl and optionally one or more C atoms are replaced with O or $NR^{YL1}$, $C_{1-6}$ alkene and optionally one or more C atoms are replaced with O, $C_{1-6}$ alkyne and optionally one or more C atoms are replaced with O, bicyclic, biaryl, biheteroaryl, or biheterocyclic, each optionally substituted with $R^Q$, each $R^Q$ is independently a H, halogen, OH, CN, $CF_3$, hydroxyl, nitro, C≡CH, $C_{2-6}$ alkenyl, $C_{2-6}$ alkynyl, optionally substituted linear or branched $C_1$-$C_6$ alkyl, optionally substituted linear or branched $C_1$-$C_6$ alkoxy, optionally substituted $OC_{1-3}$alkyl (e.g., optionally substituted by 1 or more —F), OH, $NH_2$, $NR^{Y1}R^{Y2}$, CN, or 2 $R^Q$ groups taken together with the atom they are attached to, form a 4-8 membered ring system containing 0-4 heteroatoms;
- $Y^{L1}$ is each independently a bond, $NR^{YL1}$, O, S, $NR^{YL2}$, $CR^{YL1}R^{YL2}$, C=O, C=S, SO, $SO_2$, optionally substituted linear or branched $C_1$-$C_6$ alkyl and optionally one or more C atoms are replaced with O; optionally substituted linear or branched $C_1$-$C_6$ alkoxy;
- $Q^L$ is absent, a 3-6 membered alicyclic, bicyclic, or aromatic ring with 0-4 heteroatoms, optionally bridged, optionally substituted with 0-6 $R^Q$, each $R^Q$ is independently H, optionally substitute linear or branched $C_{1-6}$ alkyl (e.g., optionally substituted by 1 or more halo, $C_{1-6}$ alkoxyl), or 2 $R^Q$ groups taken together with the atom they are attached to, form a 3-8 membered ring system containing 0-2 heteroatoms;
- $R^{YL1}$, $R^{YL2}$ are each independently H, OH, optionally substituted linear or branched $C_{1-6}$ alkyl (e.g., optionally substituted by 1 or more halo, $C_{1-6}$ alkoxyl), or $R^1$, $R^2$ together with the atom they are attached to, form a 3-8 membered ring system containing 0-2 heteroatoms;

n is 0-10; and

✓ and ⌇ indicates the attachment point to the PTM or ULM moieties.

In any aspect or embodiment described herein, the linker (L) comprises a structure selected from the structure shown below:

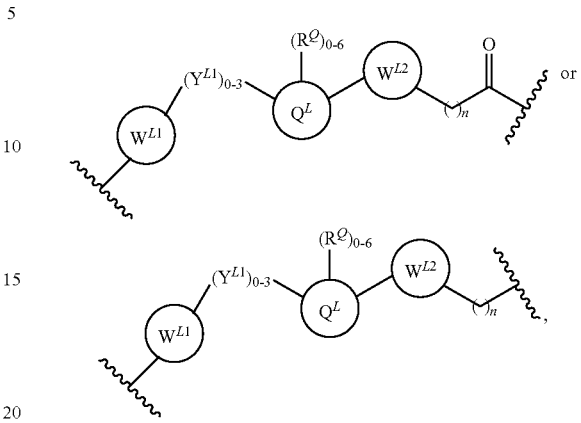

wherein:
- $W^{L1}$ and $W^{L2}$ are each independently absent, cyclohexane, cyclopentane, piperazine, piperidine, morpholine, $C_{1-6}$ alkyl and optionally one or more C atoms are replaced with O or $NR^{YL1}$, $C_{1-6}$ alkene and optionally one or more C atoms are replaced with O, or $C_{1-6}$ alkyne and optionally one or more C atoms are replaced with O, each optionally substituted with $R^Q$, each $R^Q$ is independently a H, Cl—, —F—, OH, CN, $CF_3$, hydroxyl, optionally substituted linear or branched $C_1$-$C_6$ alkyl (e.g. methyl, ethyl), optionally substituted linear or branched $C_1$-$C_6$ alkoxy;
- $Y^{L1}$ is each independently a bond, $NR^{YL1}$, O, $CR^{YL1}R^{YL2}$, C=O, optionally substituted linear or branched $C_1$-$C_6$ alkyl and optionally one or more C atoms are replaced with O or $NR^{YL1}$, $C_{1-6}$ alkene and optionally one or more C atoms are replaced with O, $C_{1-6}$ alkyne and optionally one or more C atoms are replaced with O, or optionally substituted linear or branched $C_1$-$C_6$ alkoxy;
- $Q^L$ is a 3-6 membered heterocyclic, heterobicyclic, or heteroaryl ring, optionally substituted with 0-6 $R^Q$, each $R^Q$ is independently H, or optionally substituted linear or branched $C_{1-6}$ alkyl (e.g., methyl or ethyl, optionally substituted by 1 or more halo, $C_{1-6}$ alkoxyl);
- $R^{YL1}$, $R^{YL2}$ are each independently H, optionally substituted linear or branched $C_{1-6}$ alkyl (e.g., optionally substituted by 1 or more halo, $C_{1-6}$ alkoxyl);

n is 0-10; and

✓ and ⌇ indicates the attachment point to the PTM or ULM moieties.

Exemplary PTMs

The term "protein target moiety" or PTM is used to describe a small molecule which binds to AR, and can be used to target the PTM for ubiquitination and degradation. The compositions described below exemplify members of AR binding moieties that can be used according to the present disclosure. These binding moieties are linked to the ubiquitin ligase binding moiety preferably through a chemical linking group in order to present the AR protein in proximity to the ubiquitin ligase for ubiquitination and subsequent degradation.

In certain contexts, the term "target protein" is used to refer to the AR protein, which is a target protein to be ubiquitinated and degraded.

The compositions described herein exemplify the use of some of the members of these types of small molecule target protein binding moieties.

In any aspect or embodiment described herein, the PTM is a small molecule that binds AR. For example, in any aspect or embodiment described herein, the PTM is represented by the chemical structure:

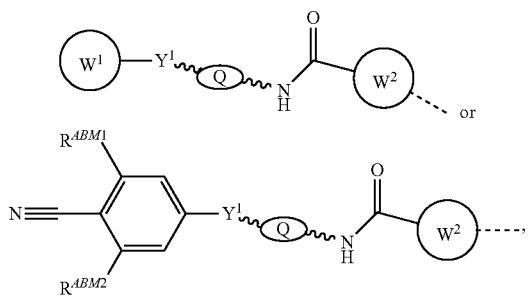

or wherein:
W¹ is

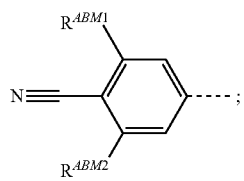

$R^{ABM1}$ and $R^{ABM2}$ are each independently a H, —CN (e.g., $R^{ABM1}$ is H and $R^{ABM2}$ is CN, or $R^{ABM1}$ is CN and $R^{ABM2}$ is H), an unsubstituted or substituted C1-C3 alkyl (e.g., an unsubstituted or substituted C1-C2 alkyl or a methyl), halogen (e.g. Cl, Br, or F), an unsubstituted or substituted C1-C3 alkoxyl (e.g., a deuterated C1-C3 alkoxyl, a methoxy, ethoxy, or deuterated methoxy);

Y¹ is a CH₂ or O;

Q is a 4-6 membered cycloalkyl, a 8-10 membered fused bicyclic cycloalkyl, a 8-10 membered fused bicyclic heterocycloalkyl with 1 or 2 hetereoatoms (e.g., 1 or 2 nitrogen atoms), a 7-9 membered spirocycloalkyl, or a 7-9 membered spiroheterocycloalkyl with 1 or 2 hetereoatoms (e.g., 1 or 2 nitrogen atoms), wherein each is optionally substituted with 1, 2, 3, or 4 substitutions selected from the group consisting of: H, OH, and $C_1$-$C_2$ alkyl (e.g., the 4-6 membered cycloalkyl is optionally substituted with up to four $C_1$-$C_2$ alkyls, such as four $C_1$-$C_2$ alkyls or four methyl groups);

W² is a 5- or 6-membered aromatic group with 0 to 2 heteroatoms (e.g., 0, 1, or 2 nitrogen atoms), optionally substituted by 1 or 2 $R^{W2}$;

each $R^{W2}$ is independently: H; OH; halogen; linear or branched $C_{1-3}$ alkyl (e.g., methyl);

~~~ represents a bond that may be stereospecific ((R) or (S)) or non-stereospecific; and ˙˙˙ is the linker attachment point.

In any of the aspects or embodiments described herein, W¹ is selected from:

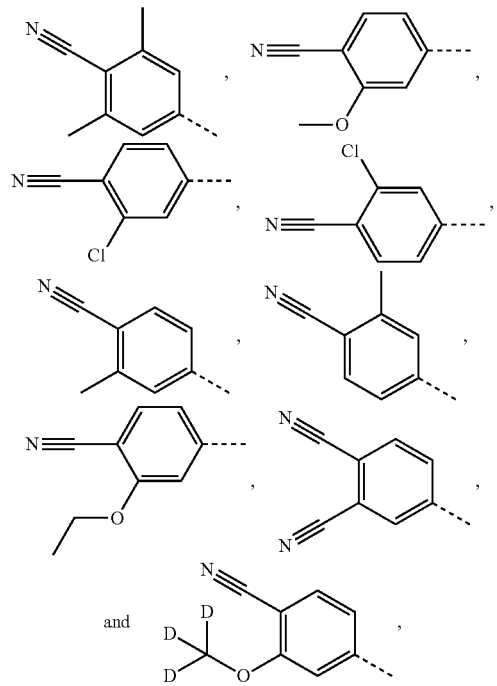

wherein the dashed lines indicate points of attachment.

In any aspect or embodiment described herein, Q is selected from:

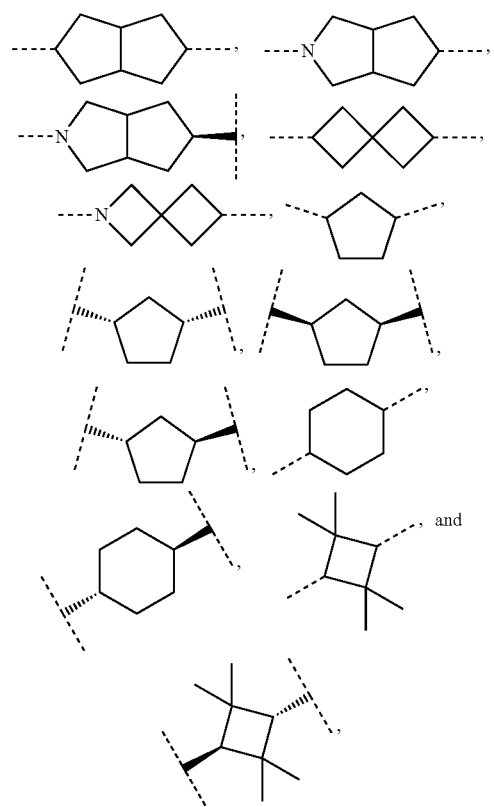

wherein the dashed lines indicate points of attachment.

In any aspect or embodiment described herein, $W^2$ is a bond or selected from:

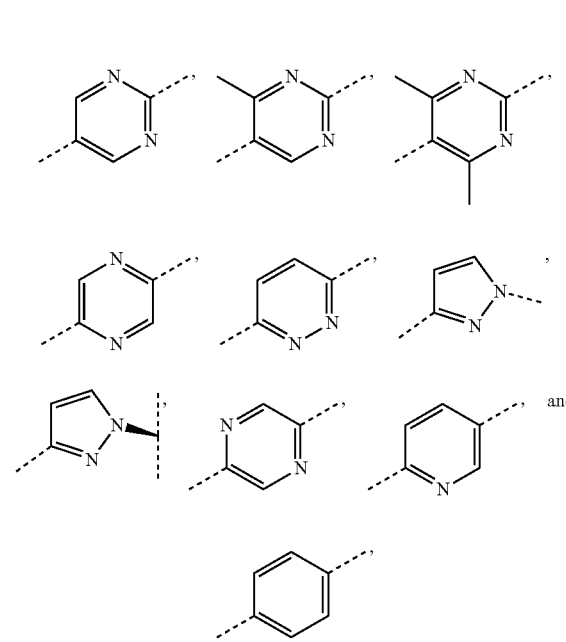

wherein the dashed lines indicate points of attachment.

In any aspect or embodiment described herein, $R^{ABM1}$ and $R^{ABM2}$ are each a methyl.

In any aspect or embodiment described herein, the PTM is represented by the chemical structure:

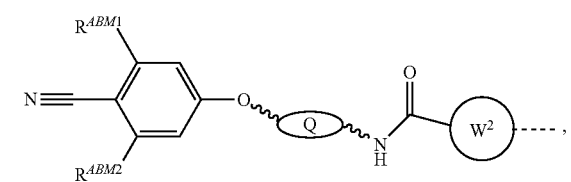

wherein:
- $R^{ABM1}$ and $R^{ABM2}$ are each independently a H, —CN, a methyl, halogen, a methoxy, ethoxy, or deuterated methoxy;
- Q is a 4-6 membered cycloalkyl, a 8-10 membered fused bicyclic cycloalkyl, a 8-10 membered fused bicyclic heterocycloalkyl with 1 or 2 hetereoatoms, a 7-9 membered spirocycloalkyl, or a 7-9 membered spiroheterocycloalkyl with 1 or 2 hetereoatoms, wherein each is optionally substituted with 1, 2, 3, or 4 substitutions selected from the group consisting of: H, OH, and methyl;
- $W^2$ is a 5- or 6-membered aromatic group with 0 to 2 heteroatoms, optionally substituted by 1 or 2 $R^{W2}$;
- each $R^{W2}$ is independently: H; OH; halogen; or methyl;
- 〜〜〜 represents a bond that may be stereospecific ((R) or (S)) or non-stereospecific; and
- ╌╌╌ is the linker attachment point.

In any aspect or embodiment described herein, the PTM is represented by a chemical structure selected from:

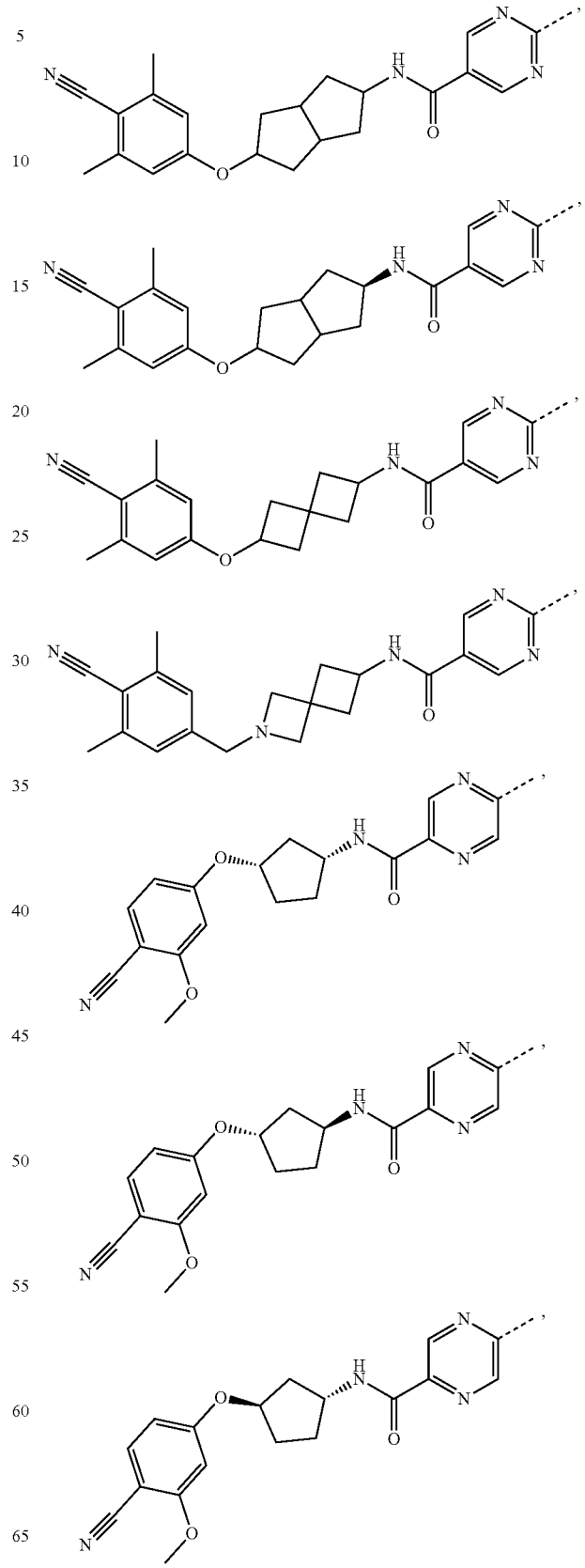

85
-continued
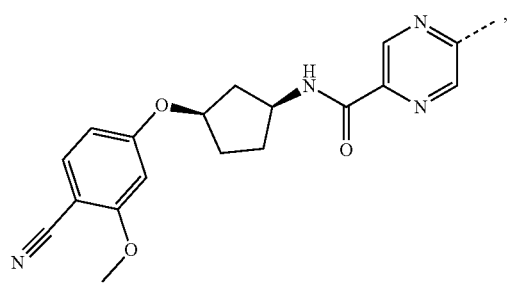
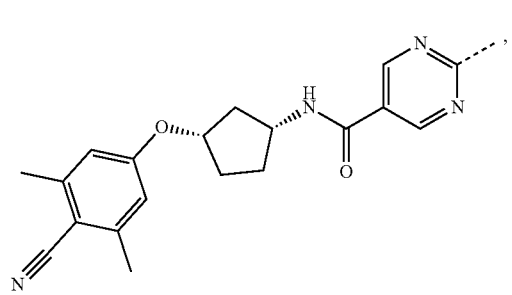
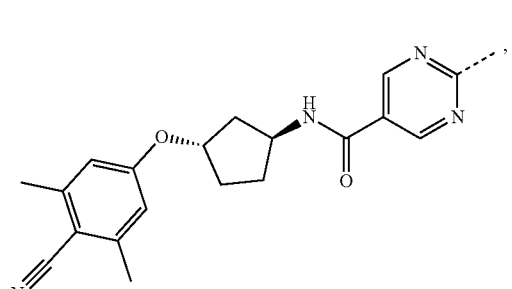
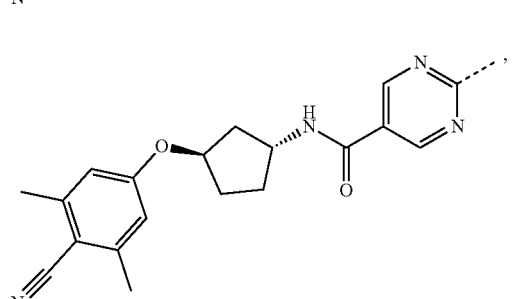
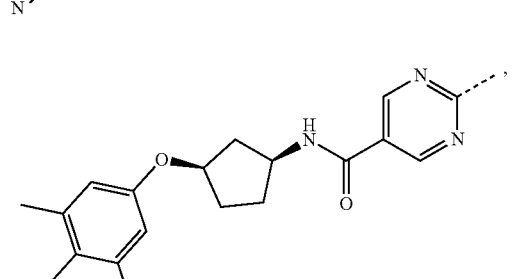
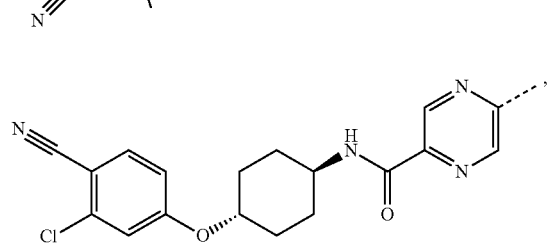
86
-continued
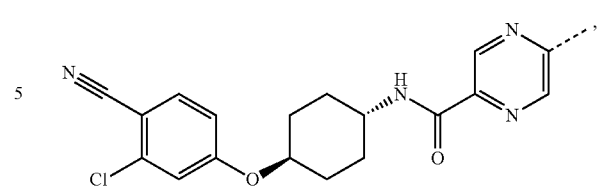
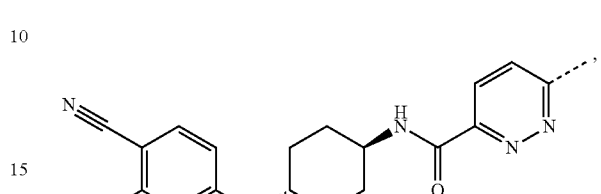
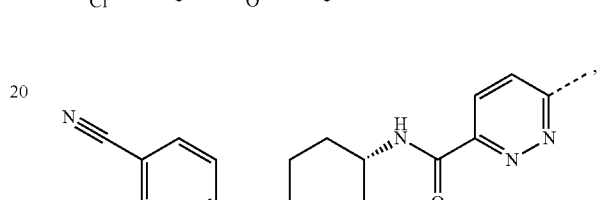
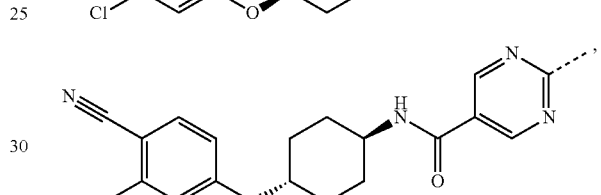
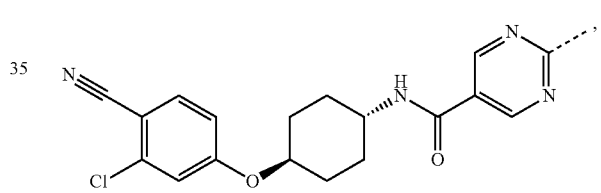
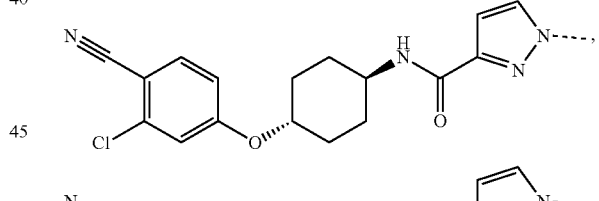
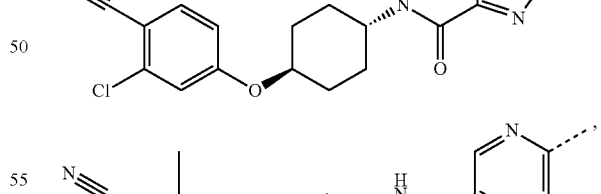
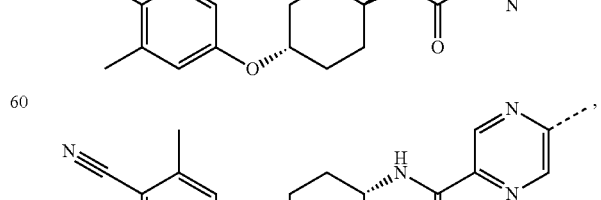

87
-continued
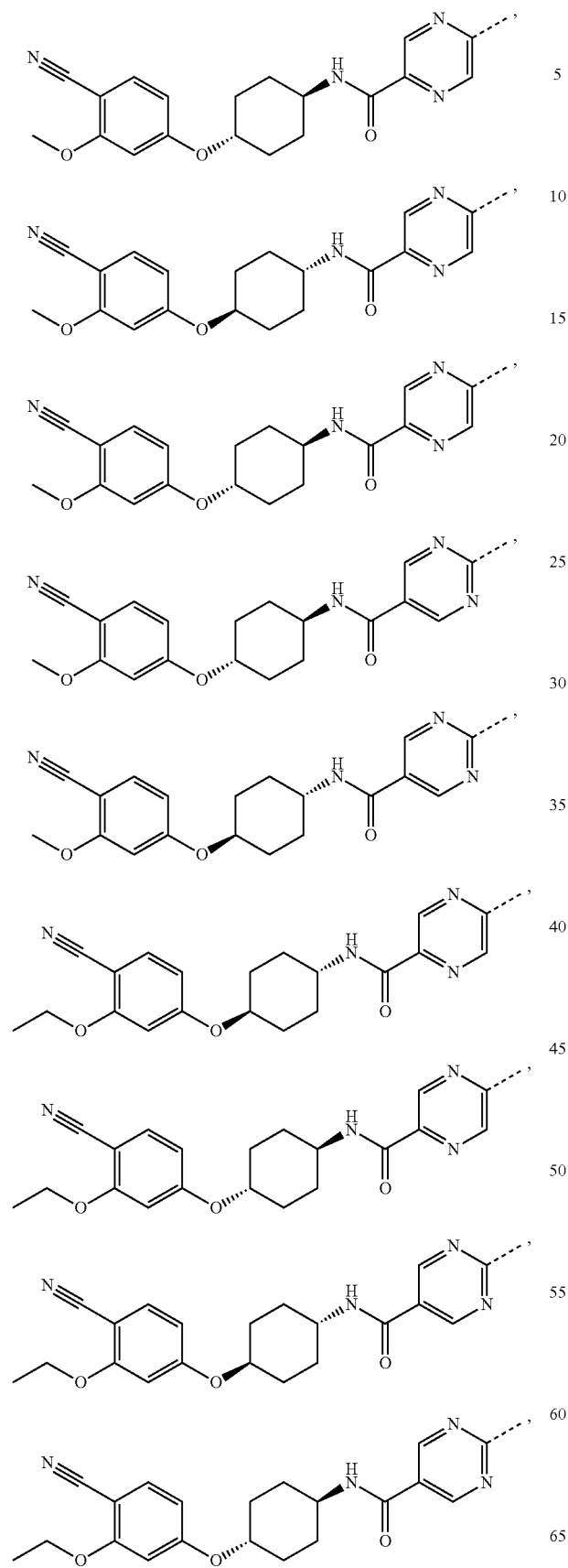
88
-continued
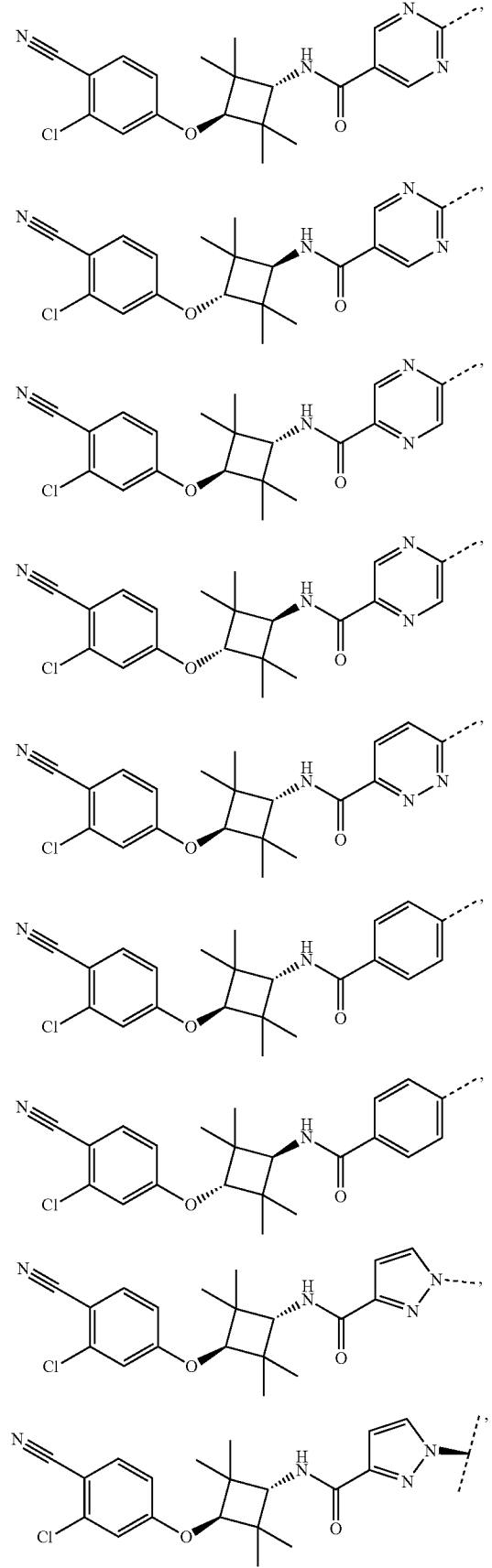

89
-continued
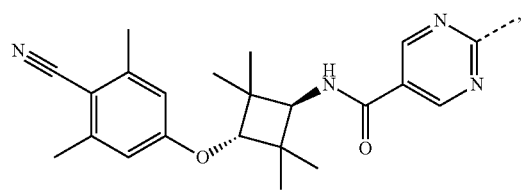
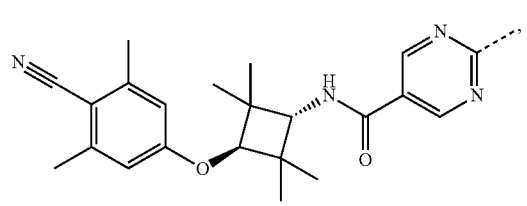
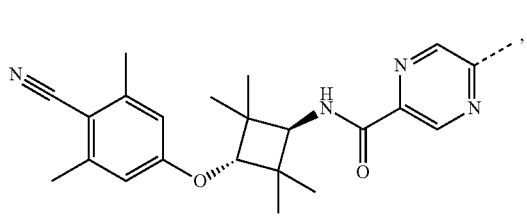
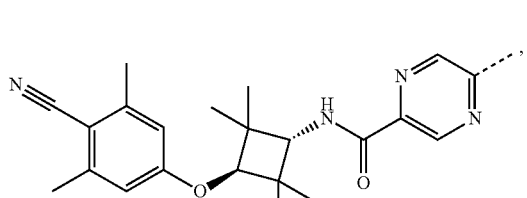
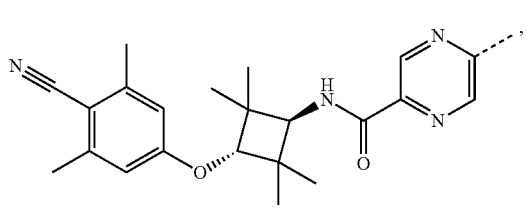
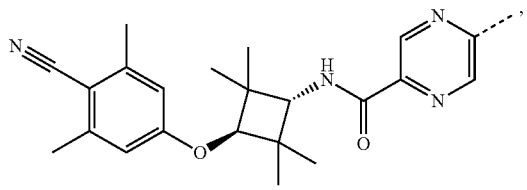
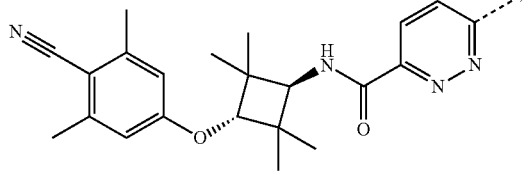
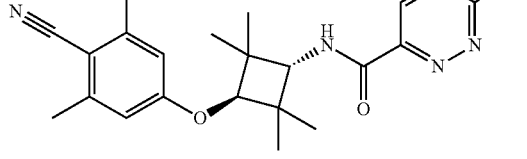
90
-continued
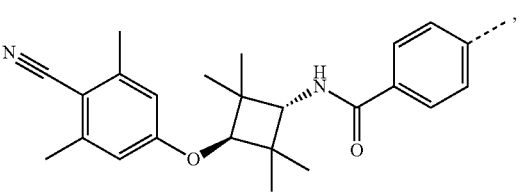
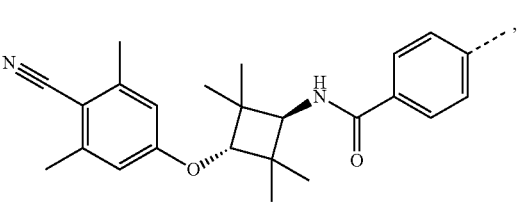
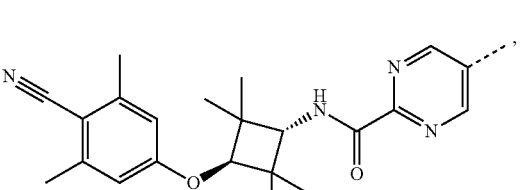
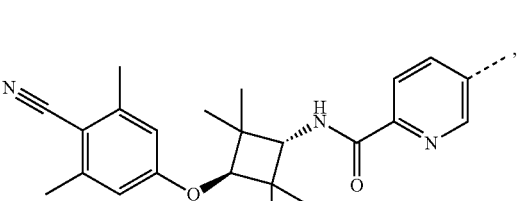
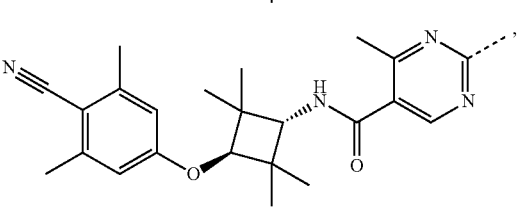
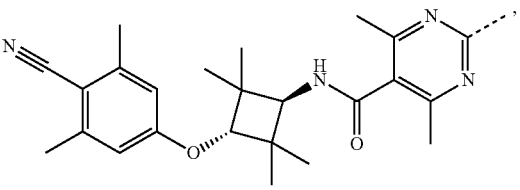
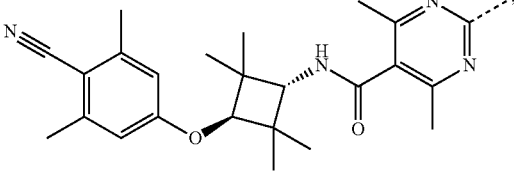
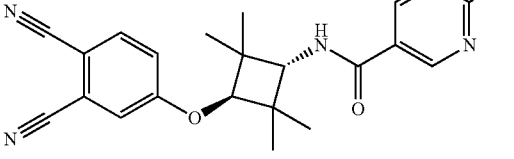

-continued
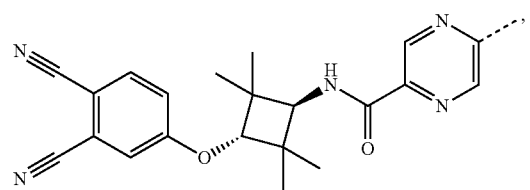
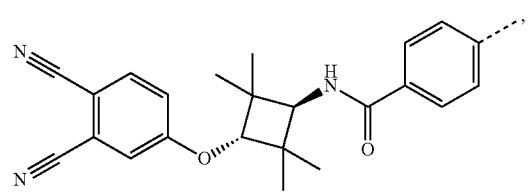
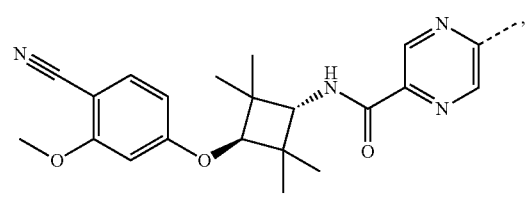
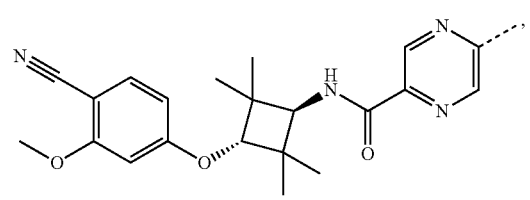
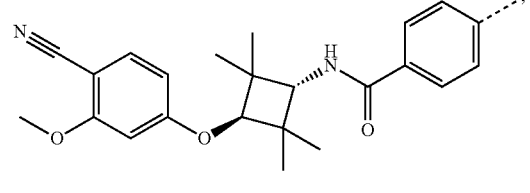
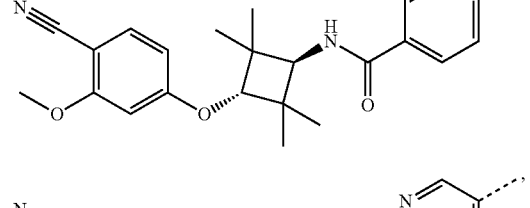
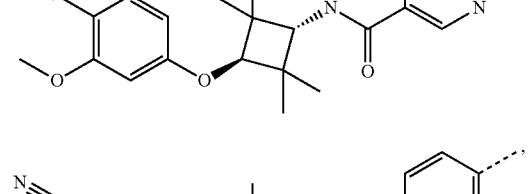
-continued
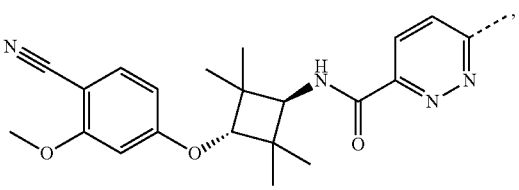
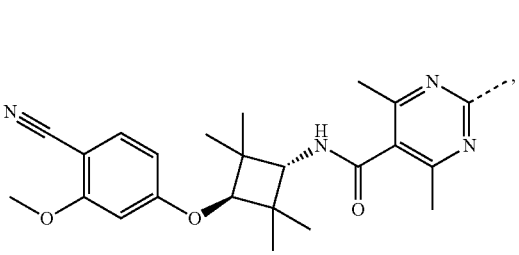
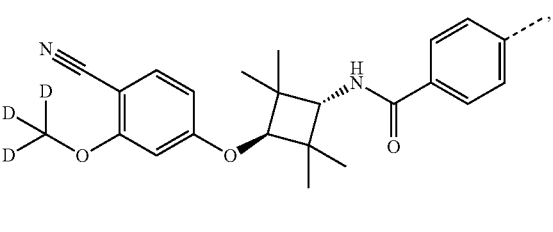
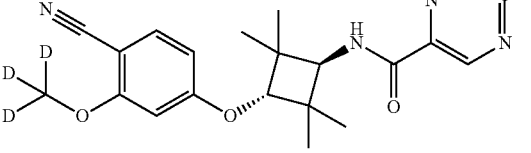
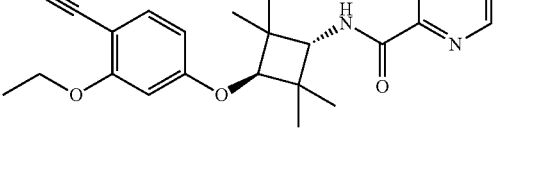
wherein ⌇ of the PTM indicates the point of attachment with the chemical linking group (L) or the ULM or CLM.

In any aspect or embodiment described herein, the heterobifunctional compound is represented by a chemical structure selected from:

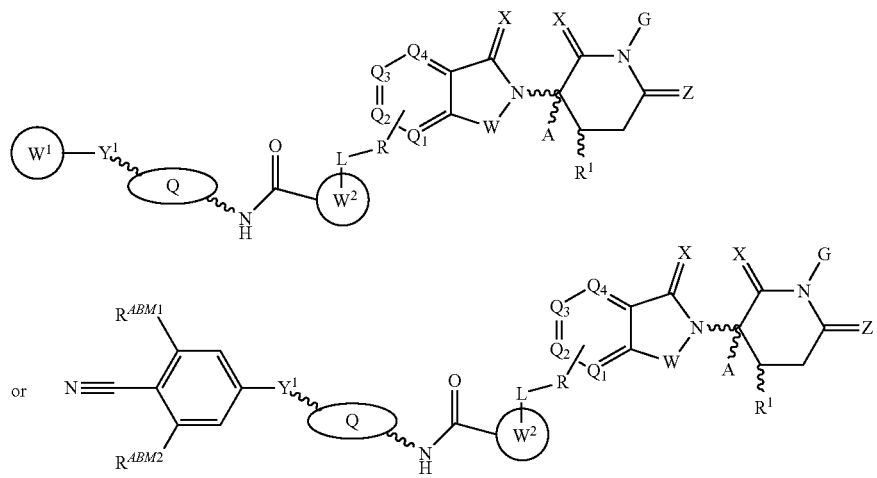

wherein:
the R that is covalently linked to L is O, N*, or NH;
N* is a nitrogen atom that is shared with the chemical linking group; and
the other variables (e.g., $R^{ABM1}$, $R^{ABM2}$, $Y^1$, Q, $W^2$, L, R, $Q_1$, $Q_2$, $Q_3$, $Q_4$, W, X, A, R', G, Z, n) are as defined in any aspect or embodiment described herein.

In any aspect or embodiment described herein, the heterobifunctional compound is represented by a chemical structure selected from:

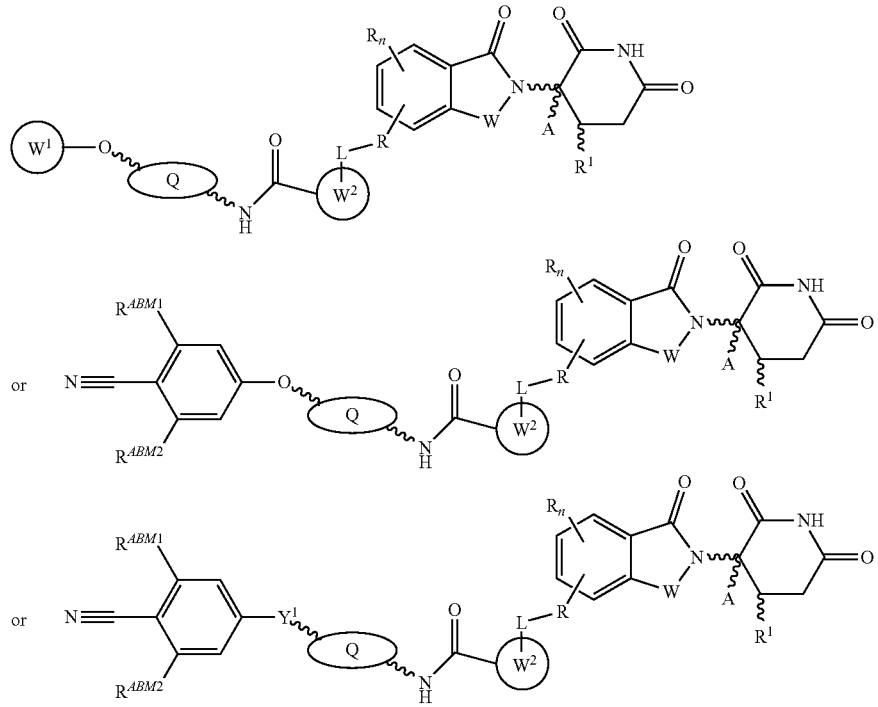

wherein:
the R that is covalently linked to L is O, N*, or NH;
N* is a nitrogen atom that is shared with the chemical linking group; and
the other variables (e.g., $R^{ABM1}$, $R^{ABM2}$, $Y^1$, Q, $W^2$, L, R, n, W, A, $R^1$) are as defined in any aspect or embodiment described herein.

Therapeutic Compositions

The present invention further provides pharmaceutical compositions comprising therapeutically effective amounts of at least one bifunctional compound as described herein, in combination with a pharmaceutically acceptable carrier, additive or excipient.

In an additional aspect, the description provides therapeutic compositions comprising an effective amount of a compound as described herein or salt form thereof, and a pharmaceutically acceptable carrier, additive or excipient, and optionally an additional bioactive agent. The therapeutic compositions effect targeted protein degradation in a patient or subject, for example, an animal such as a human, and can be used for treating or ameliorating disease states or conditions which are modulated by degrading the target protein. In certain embodiments, the therapeutic compositions as described herein may be used to effectuate the degradation of protein for the treatment or amelioration of AR-mediated cancer, such as prostate cancer, Kennedy's disease, or both.

In alternative aspects, the present disclosure relates to a method for treating a disease state or ameliorating one or more symptoms of a disease or condition in a subject in need thereof by degrading the AR protein comprising administering to said patient or subject an effective amount, e.g., a therapeutically effective amount, of at least one compound as described herein, optionally in combination with a pharmaceutically acceptable carrier, additive or excipient, and optionally coadministered with an additional bioactive agent, wherein the composition is effective for treating or ameliorating the disease or disorder or one or more symptoms thereof in the subject. The method according to the present disclosure may be used to treat certain disease states or conditions including cancer and Kennedy's Disease, by virtue of the administration of effective amounts of at least one compound described herein.

The present disclosure further includes pharmaceutical compositions comprising a pharmaceutically acceptable salt, in particular, acid or base addition salts of compounds as described herein. The acids which are used to prepare the pharmaceutically acceptable acid addition salts of the aforementioned compounds useful according to this aspect are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds according to the present disclosure. The chemical bases that may be used as reagents to prepare pharmaceutically acceptable base salts of the present compounds are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium, zinc and magnesium), ammonium or water-soluble amine addition salts such as N-methylglucamine-(meglumine), and the lower alkanolammonium and other base salts of pharmaceutically acceptable organic amines, among others.

The compounds as described herein may, in accordance with the disclosure, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual, intra nasal, intra ocular, intrathecal, and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound as described herein, optionally in combination with a pharmaceutically acceptable carrier, additive or excipient. Compounds according to the present disclosure may be administered in immediate release, intermediate release or sustained or controlled release forms. Sustained or controlled release forms are preferably administered orally, but also in suppository and transdermal or other topical forms. Intramuscular injections in liposomal form or in depot formulation may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions as described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient may be combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. In certain preferred aspects of the disclosure, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of active pharmaceutical ingredient in a pharmaceutical composition as described herein that may be combined with the carrier materials to produce a single dosage form will vary depending upon the condition of the subject and disease treated, as well as the particular mode of administration. Preferably, the compositions should be formulated to contain between about 0.05 milligram and about 750 milligrams or more, more preferably about 1 milligram to about 600 milligrams, and even more preferably about 10 milligrams to about 500 milligrams of active ingredient, alone or in combination with another compound according to the present disclosure.

It should also be understood that a specific dosage and treatment regimen for any particular patient will depend upon a variety of factors, including the activity and bioavailability of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the methods described herein can be treated by administering to the patient (subject) an effective amount of the compound according to the present disclosure depending upon the pharmaceutically acceptable salt, solvate or polymorph, thereof optionally in a pharmaceutically acceptable carrier or diluent, either alone, or in combination with another known therapeutic agent.

The active compound is combined with the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 nanograms per kilograms (ng/kg) to 300 milligrams per kilograms (mg/kg), preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to a dosage form containing less than 1 milligrams (mg), 1 mg to 3000 mg, or 5 mg to 500 mg of active ingredient per unit dosage form. An oral dosage of about 25 mg-250 mg is often convenient.

The active ingredient is preferably administered to achieve peak plasma concentrations of the active compound of about 0.00001-30 millimole (mM), preferably about 0.1-30 micromole (μM). This may be achieved, for example, by the intravenous injection of a solution or formulation of the active ingredient, optionally in saline, or an aqueous medium or administered as a bolus of the active ingredient. Oral administration may also be appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as anti-cancer agents, as described herein among others. In certain preferred aspects of the disclosure, one or more compounds according to the present disclosure are coadministered with another bioactive agent, such as an anti-cancer agent or a wound healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In any aspect or embodiment described herein, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Therapeutic Methods

In an additional aspect, the description provides therapeutic methods comprising administration of an effective amount of a compound as described herein or salt form thereof, and a pharmaceutically acceptable carrier. The therapeutic methods are useful to effect protein degradation in a patient or subject in need thereof, for example, an animal such as a human, for treating or ameliorating a disease state, condition or related symptom that me be treated through targeted protein degradation.

The terms "treat", "treating", and "treatment", etc., as used herein, refer to any action providing a benefit to a patient for which the present compounds may be administered, including the treatment of any disease state, condition, or symptom which is related to the protein to which the present compounds bind. Disease states or conditions, including cancer, which may be treated using compounds according to the present disclosure are set forth hereinabove.

The description provides therapeutic methods for effectuating the degradation of proteins of interest for the treatment or amelioration of a disease, e.g., cancer. In any aspect or embodiment described herein, the disease is prostate cancer or Kenney's Disease or both. As such, in another aspect, the description provides a method of ubiquitinating/degrading a target protein in a cell. In certain embodiments, the method comprises administering a bifunctional compound of the present disclosure. The control or reduction of specific protein levels in cells of a subject as afforded by the present disclosure provides treatment of a disease state, condition, or symptom. In any aspect or embodiment described herein, the method comprises administering an effective amount of a compound as described herein, optionally including a pharmaceutically acceptable excipient, carrier, adjuvant, another bioactive agent or combination thereof.

In additional embodiments, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable excipient, carrier, adjuvant, another bioactive agent or combination thereof, wherein the composition is effective for treating or ameliorating the disease or disorder or symptom thereof in the subject.

In another aspect, the description provides methods for identifying the effects of the degradation of proteins of interest in a biological system using compounds according to the present disclosure.

In another aspect, the description provides a process for making a molecule that can cause degradation of AR in a cell, comprising the steps of: i. providing a small molecule that binds AR; ii. providing and E3 ubiquitin ligase binding moiety (ULM), preferably a CLM such as thalidomide, pomalidomide, lenalidomide or an analog thereof; and iii. covalently coupling the small molecule of step (i) to the ULM of step (ii) via a chemical linking group (L) to form a compound which binds to both a cereblon E3 ubiquitin ligase and AR protein in the cell, such that the cereblon E3 ubiquitin ligase is in proximity to, and ubiquitinates AR protein bound thereto, such that the ubiquitinated AR is then degraded.

In another aspect, the description provides a method for detecting whether a molecule can trigger degradation of an AR protein in a cell, the method comprising the steps of: (i) providing a molecule for which the ability to trigger degradation of AR protein in a cell is to be detected, said molecule comprising the structure: CLM-L-PTM, wherein CLM is a cereblon E3 ubiquitin ligase binding moiety capable of binding a cereblon E3 ubiquitin ligase in a cell, which CLM is thalidomide, pomalidomide, lenalidomide, or an analog thereof; PTM is a protein targeting moiety, which is a small molecule that binds to AR, said AR having at least one lysine residue available to be ubiquitinated by a cereblon E3 ubiquitin ligase bound to the CLM of the molecule; and L is a chemical linking group that covalently links the CLM to the PTM to form the molecule; (ii) incubating an AR protein-expressing cell in the presence of the molecule of step (i); and (iii) detecting whether the AR protein in the cell has been degraded.

In any of the aspects or embodiments described herein, the small molecule capable of binding AR, is a small molecule as described herein.

In another aspect of said treatment, the present disclosure provides a method of treating a human patient in need of said treatment of a disease state, condition, or symptom causally related to AR expression, over-expression, mutation, misfolding or dysregulation where the degradation of the AR protein will produce a therapeutic effect in the patient, the method comprising administering to the patient an effective amount of a compound according to the present disclosure, optionally in combination with another bioactive agent. The disease state, condition, or symptom may be caused by a microbial agent or other exogenous agent such as a virus, bacteria, fungus, protozoa or other microbe, or may be a disease state, which is caused by expression, overexpression, mutation, misfolding, or dysregulation of the protein, which leads to a disease state, condition, or symptom.

In another aspect, the present disclosure provides a method of treating or ameliorating at least one symptom of a disease or condition in a subject, comprising the steps of: providing a subject identified as having a symptom of a disease or condition causally related to expression, overexpression, mutation, misfolding, or dysregulation of AR protein in the subject, and the symptom of the disease or condition is treated or ameliorated by degrading AR protein in cells of the subject; and administering to the subject therapeutically effective amount of a compound comprising a small molecule of the present disclosure such that the AR protein is degraded, thereby treating or ameliorating at least one symptom of a disease or condition in the subject.

The term "disease state or condition" is used to describe any disease state or condition wherein protein expression overexpression, mutation, misfolding, or dysregulation (e.g., the amount of protein expressed in a patient is elevated) occurs and where degradation of the AR protein to reduce or stabilize the level of AR protein (whether mutated or not) in a patient provides beneficial therapy or relief of symptoms to a patient in need thereof. In certain instances, the disease state, condition, or symptom may be cured.

Disease state, condition, or symptom which may be treated using compounds according to the present disclosure include, for example, cancer, prostate cancer, Kenney's disease. In any aspect or embodiment described herein, the cancer is selected from: squamous-cell carcinoma, basal cell carcinoma, adenocarcinoma, hepatocellular carcinomas, and renal cell carcinomas, bladder cancer, head and neck cancer, kidney cancer, ovary, leukemias, benign and malignant lymphomas, Burkitt's lymphoma, Non-Hodgkin's lymphoma, benign and malignant melanomas, myeloproliferative diseases, sarcoma, Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, glioblastomas, neuroblastomas, ganglioneuromas, gangliogliomas, medulloblastomas, pineal cell tumors, meningiomas, meningeal sarcomas, neurofibromas, Schwannomas, bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor or teratocarcinomas. In any aspect or embodiment described herein, the disease to be treated is cancer, e.g., prostate cancer or Kennedy's Disease. In a preferred aspect, the subject is a human.

The term "bioactive agent" is used to describe an agent, other than a compound according to the present disclosure, which is used in combination with a present compound as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

The term "additional anti-cancer agent" is used to describe an anti-cancer therapeutic agent, which may be combined with a compound according to the present disclosure to cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, an androgen receptor inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(Bu t) 6,Azgly 10](pyro-Glu-His-Trp-Ser-Tyr-D-Ser(Bu t)-Leu-Arg-Pro-Azgly-NH$_2$ acetate [C$_{59}$H$_{84}$Ni$_8$Oi$_4$-(C$_2$H$_4$O$_2$)$_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

EXAMPLES

Abbreviations

ACN Acetonitrile
AcOH Acetic acid
DCM Dichloromethane
DMF Dimethylformamide
DMSO Dimethyl Sulfoxide
DIPEA N, N-Diisopropylethylamine
EtOAc/EA Ethyl Acetate
EtOH Ethanol
HATU Hexafluorophosphate Azabenzotriazole Tetramethyl Uronium
HPLC High pressure liquid chromatography
Hz Hertz
KOAc Potassium acetate
LCMS Liquid Chromatography/Mass Spectrometry
MHz Megahertz
NMR Nuclear Magnetic Resonance
MeOH Methanol
MS Mass Spectrometry
PE Petroleum ether
Psi Pound-force per square inch
RT or r.t. Room temperature
TEA Triethylamine
THF Tetrahydrofuran
TFA Trifluoracetic acid
TLC Thin layer chromatography
TMS Trimethylsilyl General Synthetic Approach The synthetic realization and optimization of the heterobifunctional molecules as described herein may be approached in a stepwise or modular fashion. For example, identification of compounds that bind to the target protein, i.e., AR can involve high or medium throughput screening campaigns if no suitable ligands are immediately available. It is not unusual for initial ligands to require iterative design and optimization cycles to improve suboptimal aspects as identified by data from suitable in vitro and pharmacological and/or ADMET assays. Part of the optimization/SAR campaign would be to probe positions of the ligand that are tolerant of substitution and that might be suitable places on which to attach the chemical linking group previously referred to herein. Where crystallographic or NMR structural data are available, these can be used to focus such a synthetic effort.

In a very analogous way one can identify and optimize ligands for an E3 Ligase.

With PTMs and ULMs (e.g. CLMs) in hand, one skilled in the art can use known synthetic methods for their combination with or without a chemical linking group(s). Chemical linking group(s) can be synthesized with a range of compositions, lengths and flexibility and functionalized such that the PTM and ULM groups can be attached sequentially to distal ends of the linker. Thus, a library of bifunctional molecules can be realized and profiled in in vitro and in vivo pharmacological and ADMET/PK studies. As with the PTM and ULM groups, the final bifunctional molecules can be subject to iterative design and optimization cycles in order to identify molecules with desirable properties.

In some instances, protecting group strategies and/or functional group interconversions (FGIs) may be required to facilitate the preparation of the desired materials. Such chemical processes are well known to the synthetic organic chemist and many of these may be found in texts such as "Greene's Protective Groups in Organic Synthesis" Peter G. M. Wuts and Theodora W. Greene (Wiley), and "Organic Synthesis: The Disconnection Approach" Stuart Warren and Paul Wyatt (Wiley).

Synthetic Procedures

Scheme 1

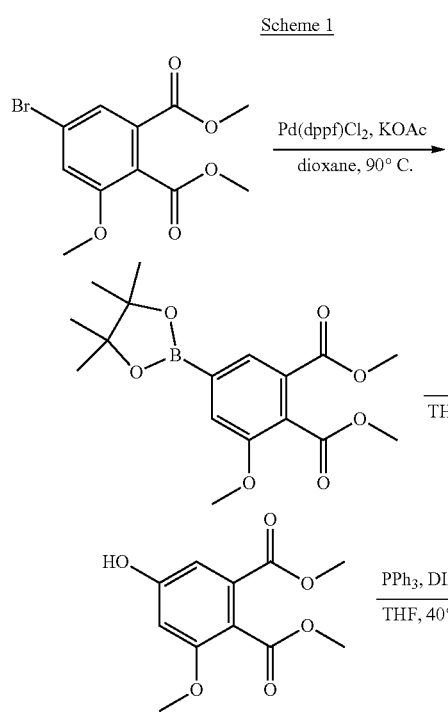

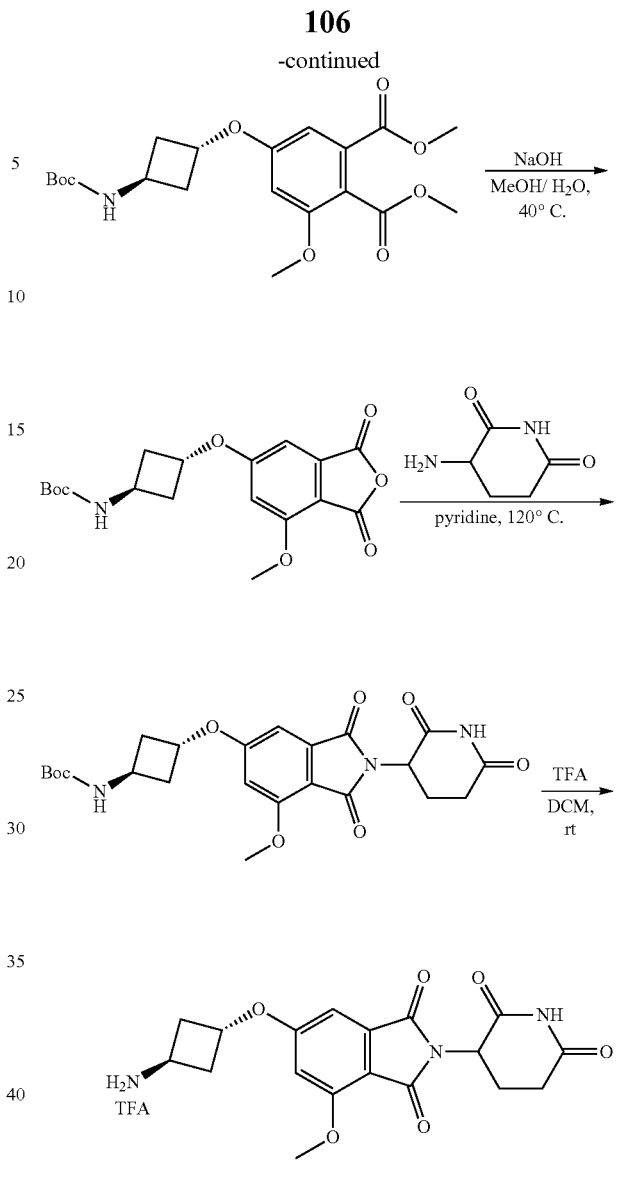

Scheme 2

-continued
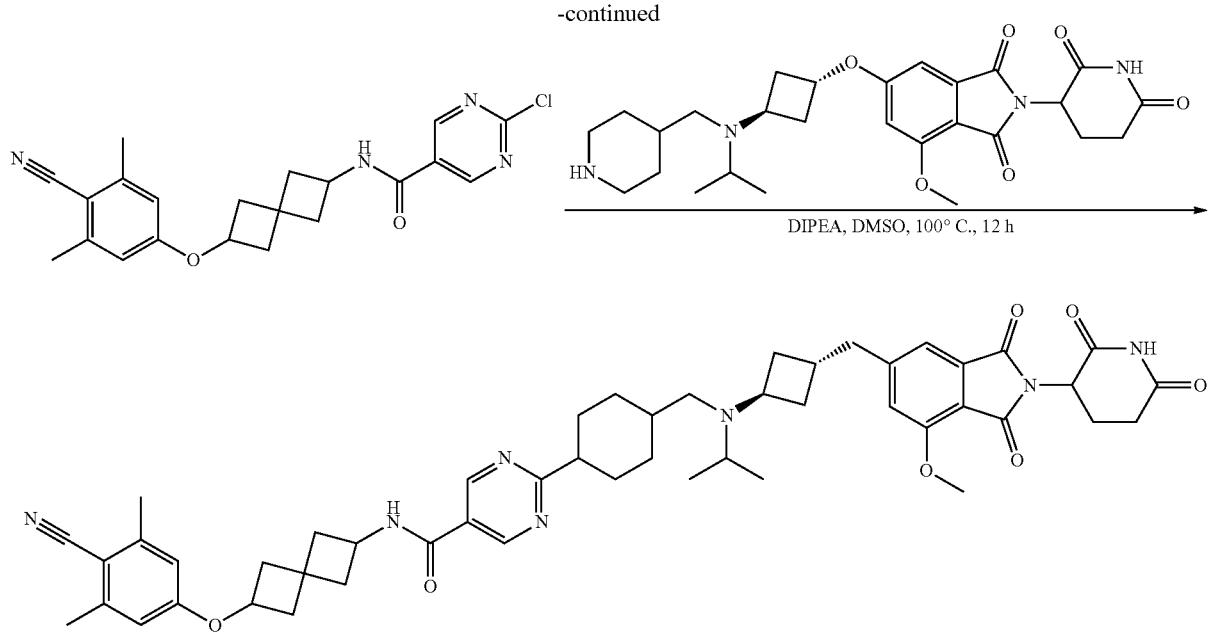
Scheme 3
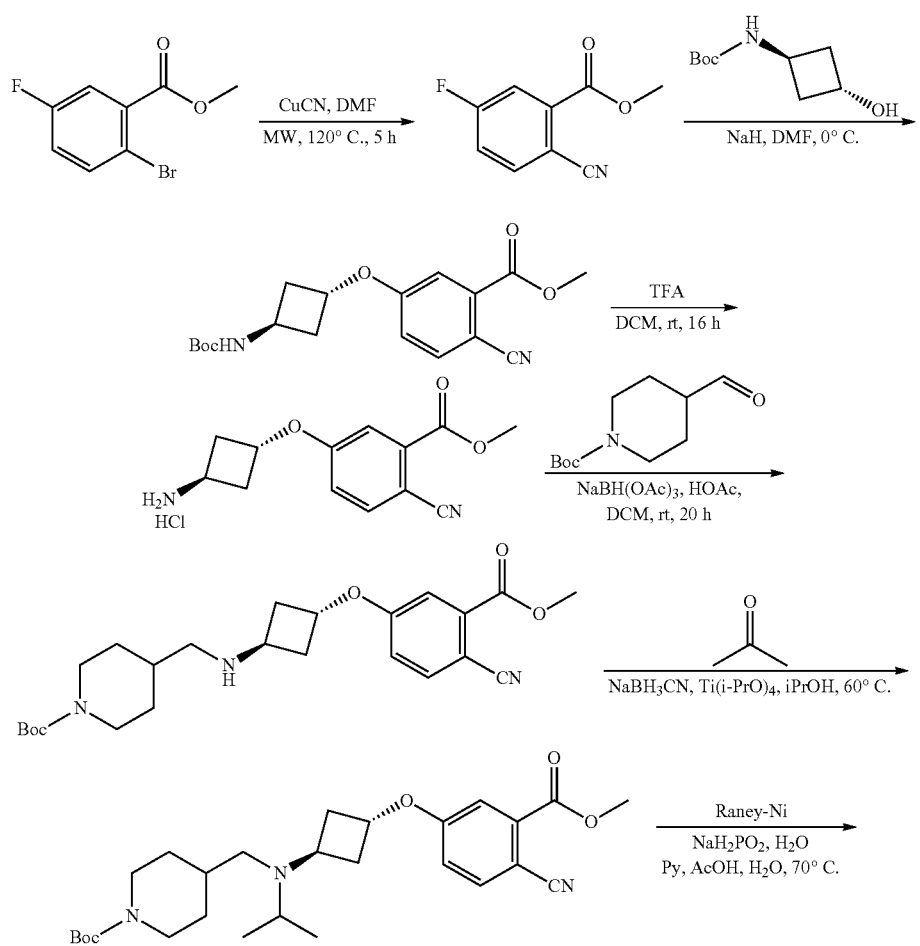

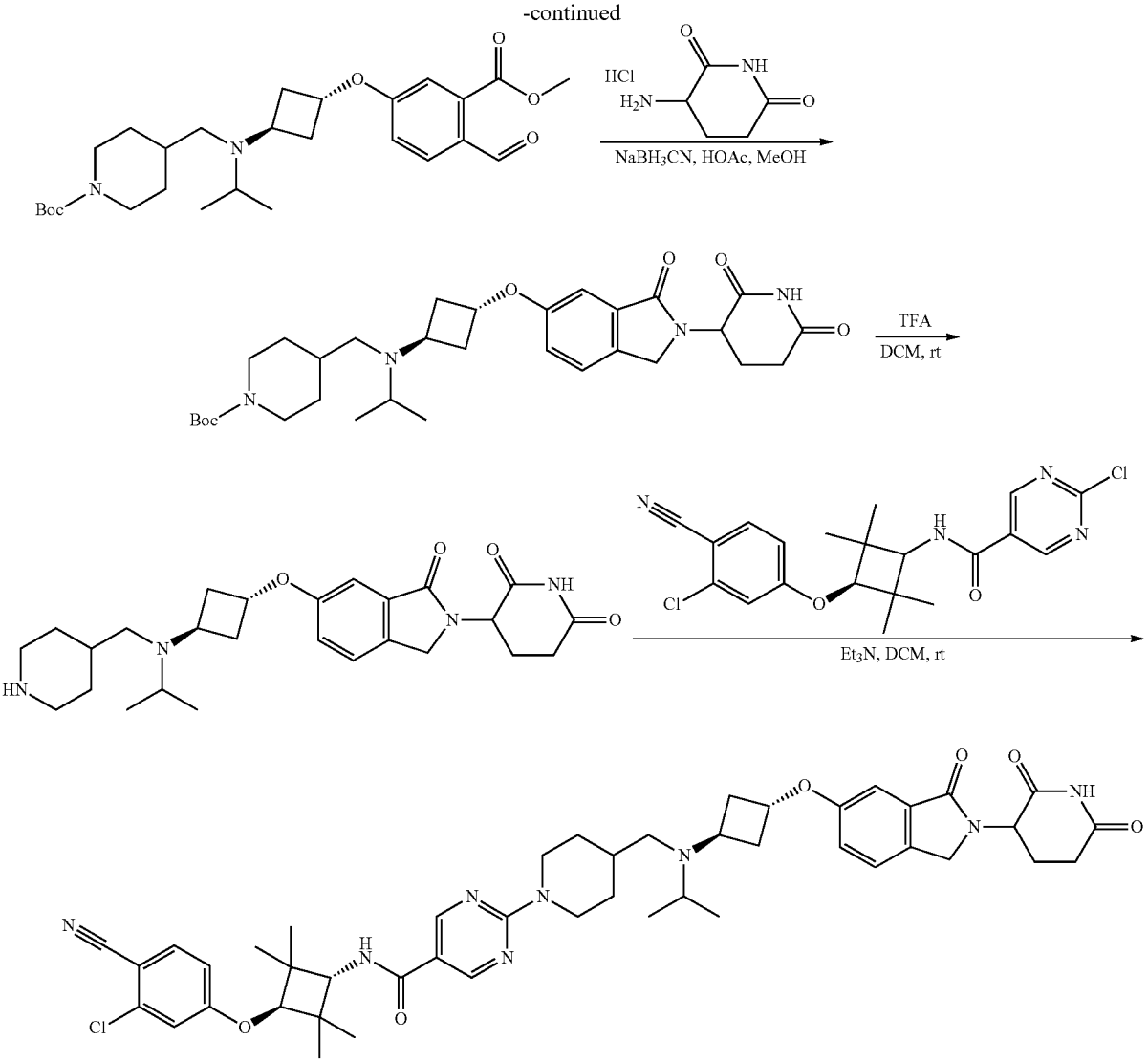
Scheme 4
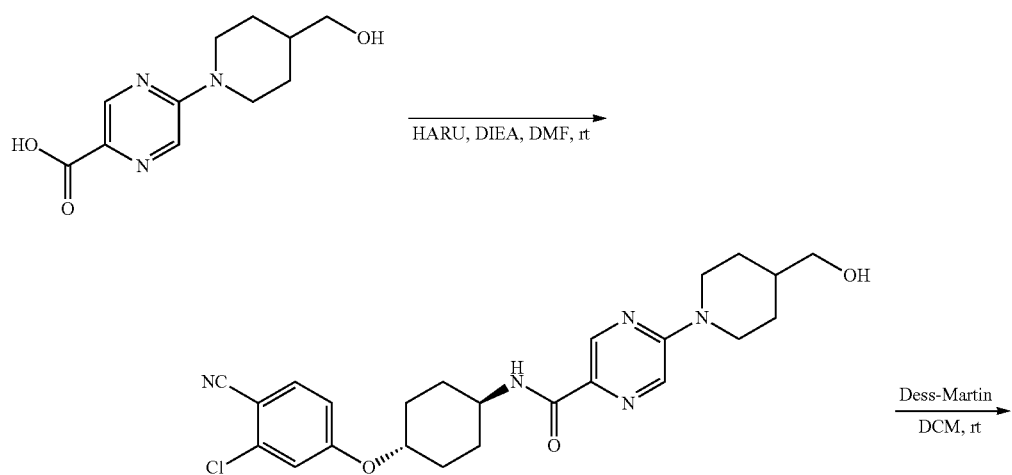

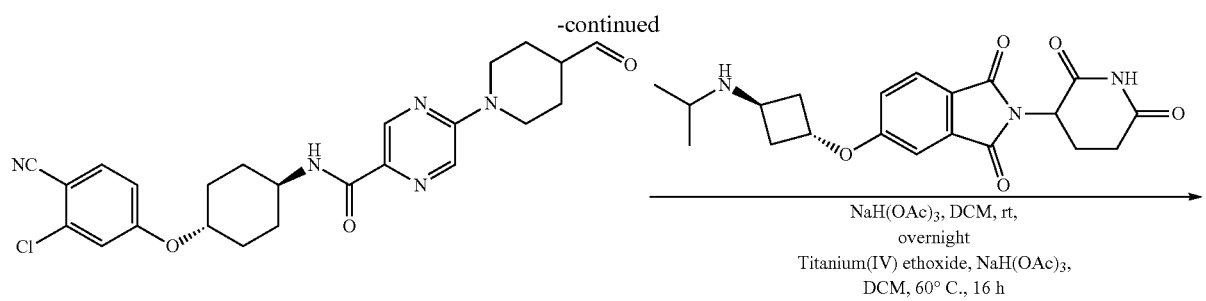
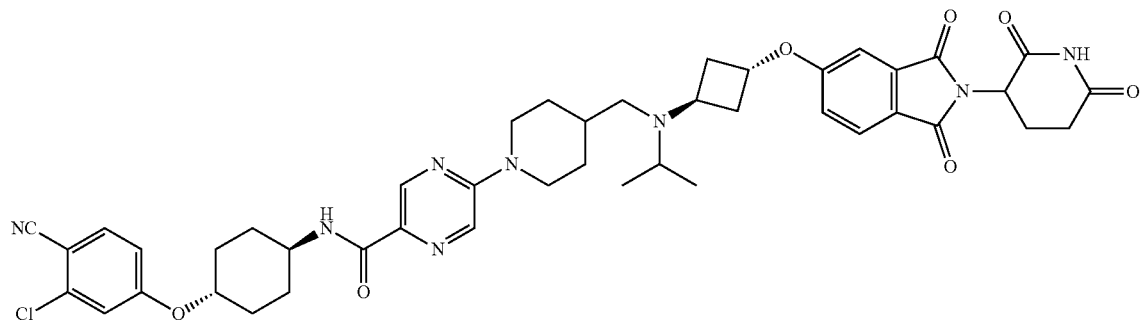
Scheme 5
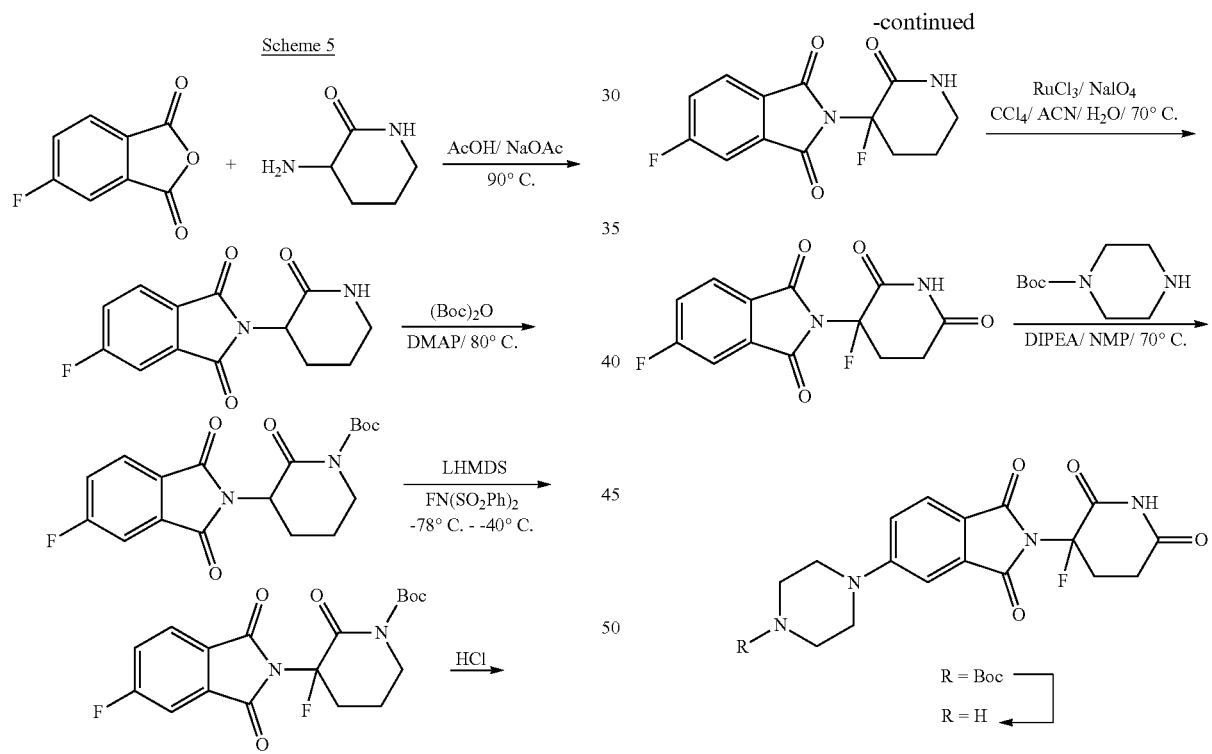
Scheme 6
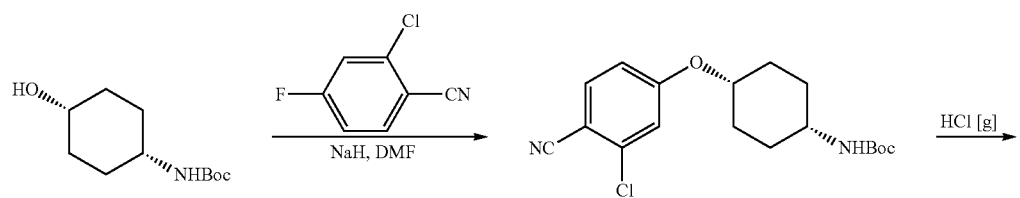

113
114
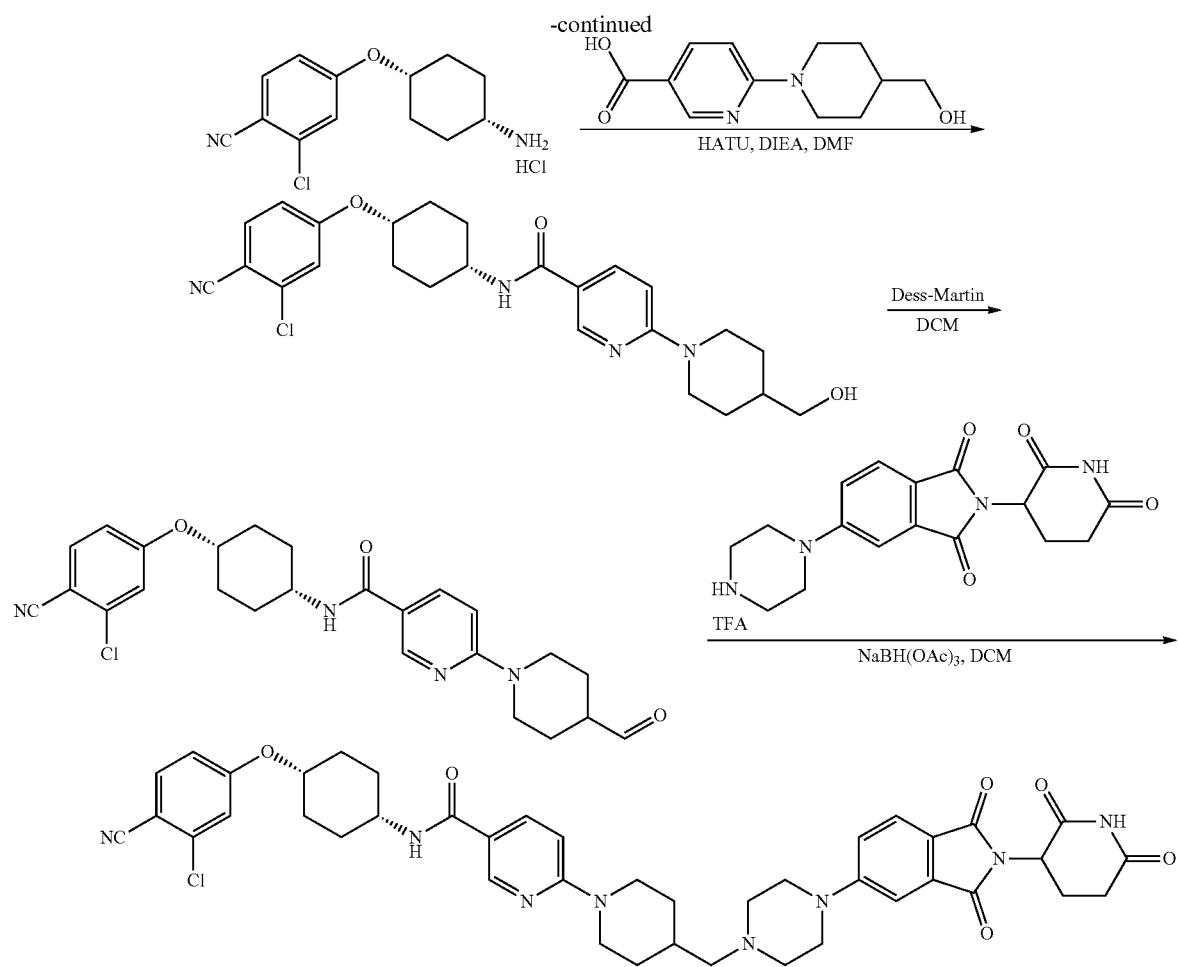

Scheme 7
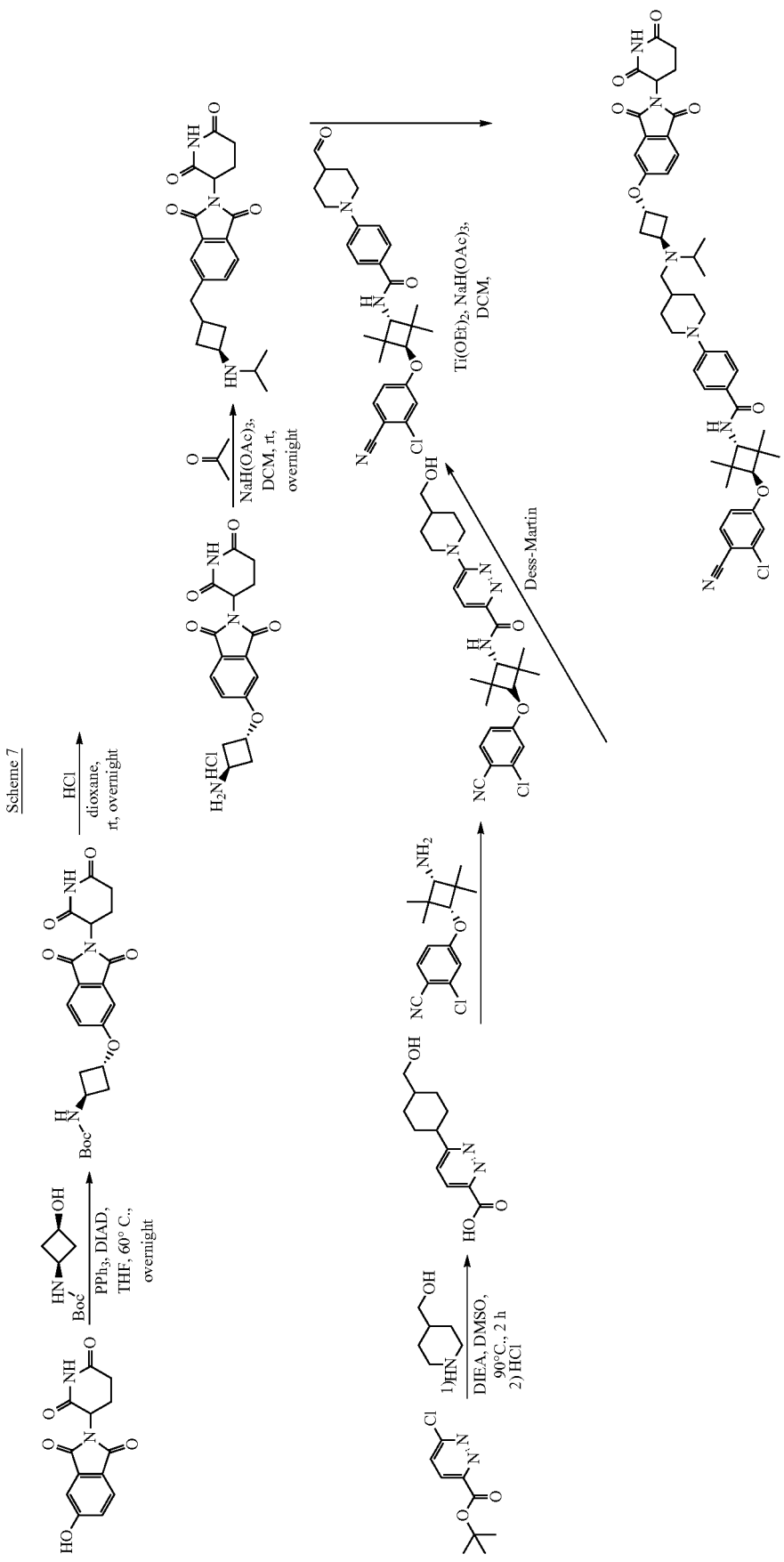

Scheme 8
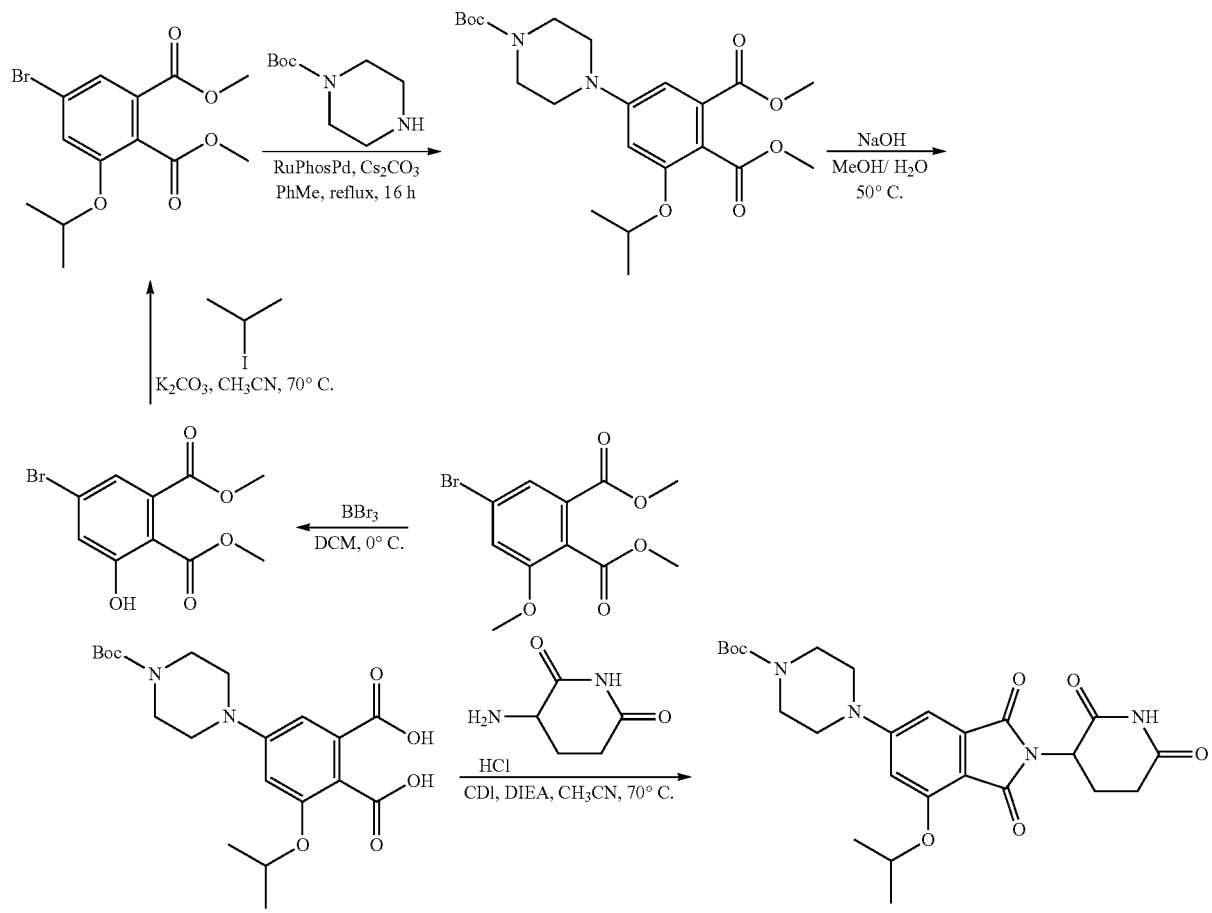
Scheme 9
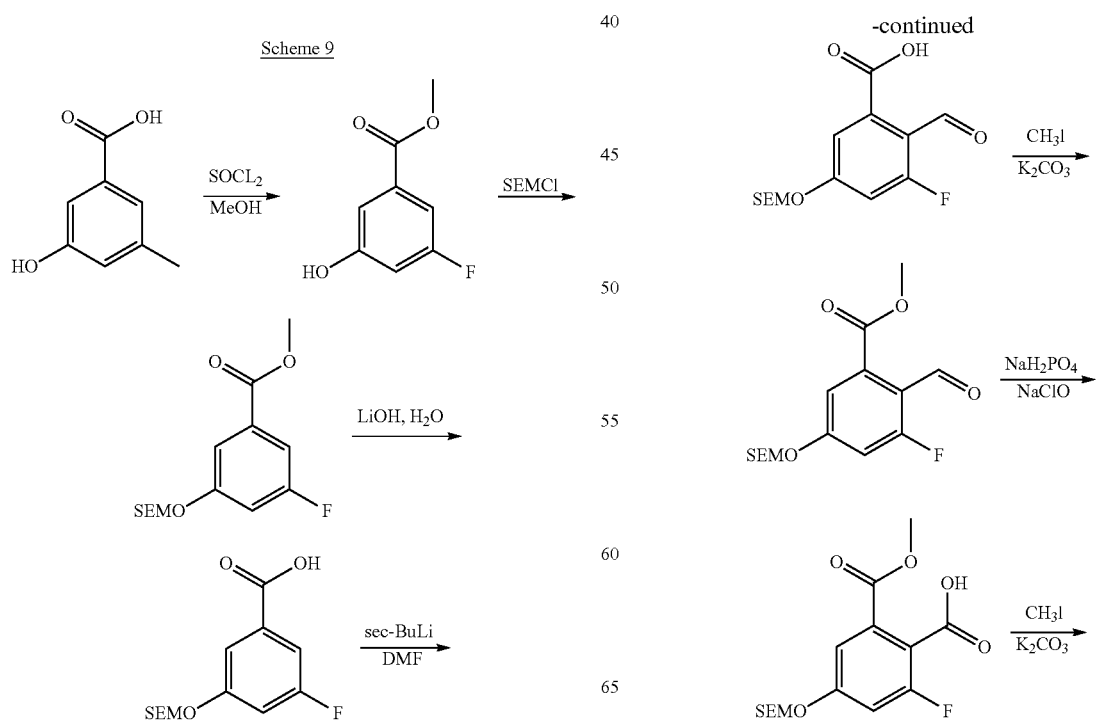

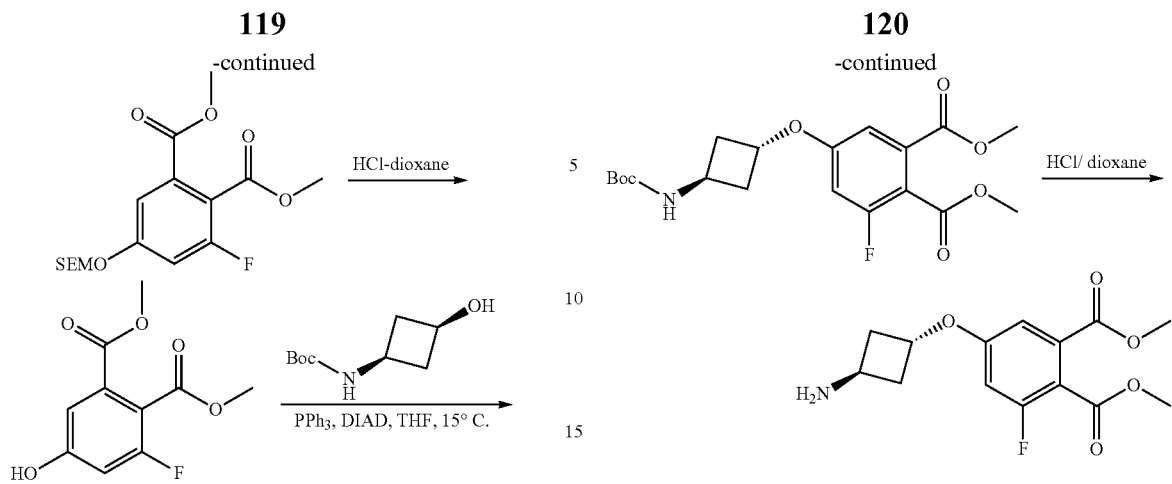
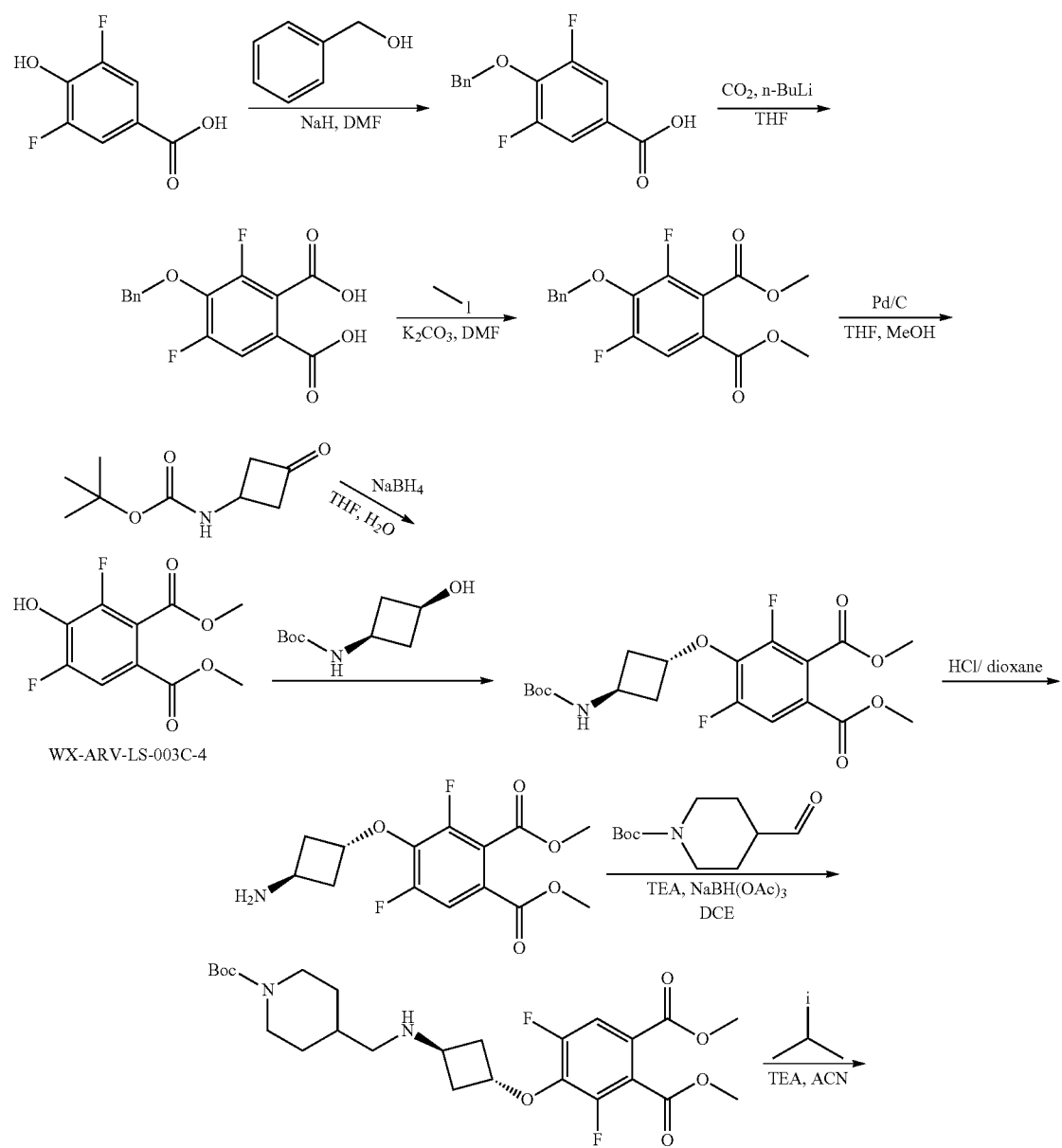

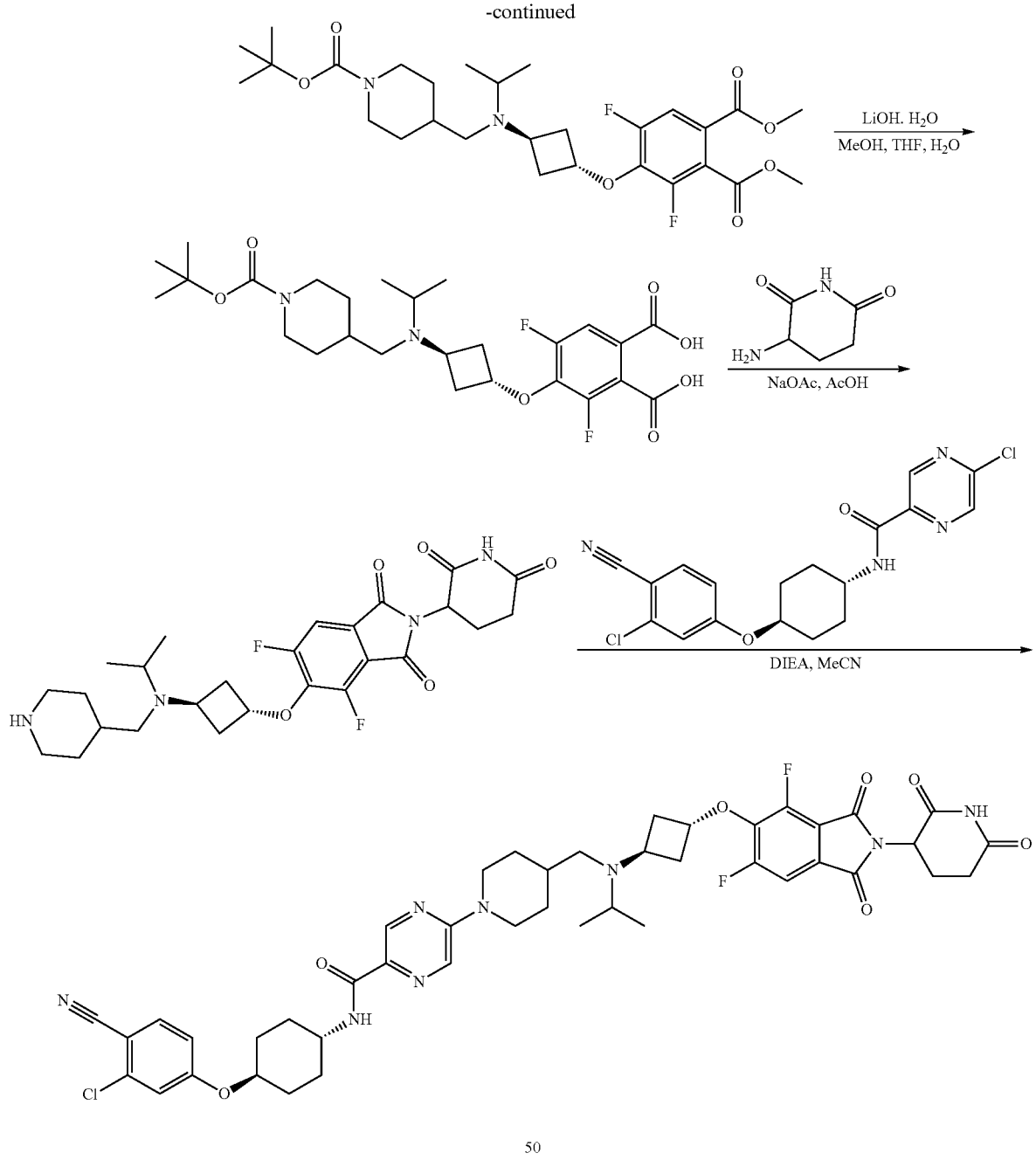
Scheme 11
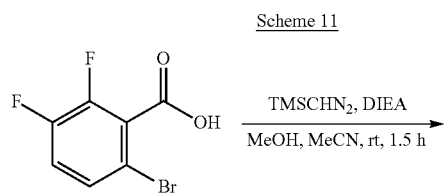
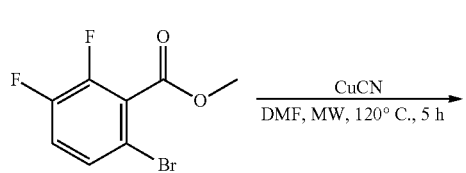
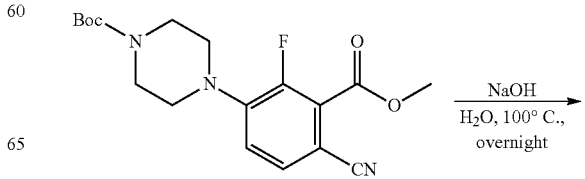

123
-continued
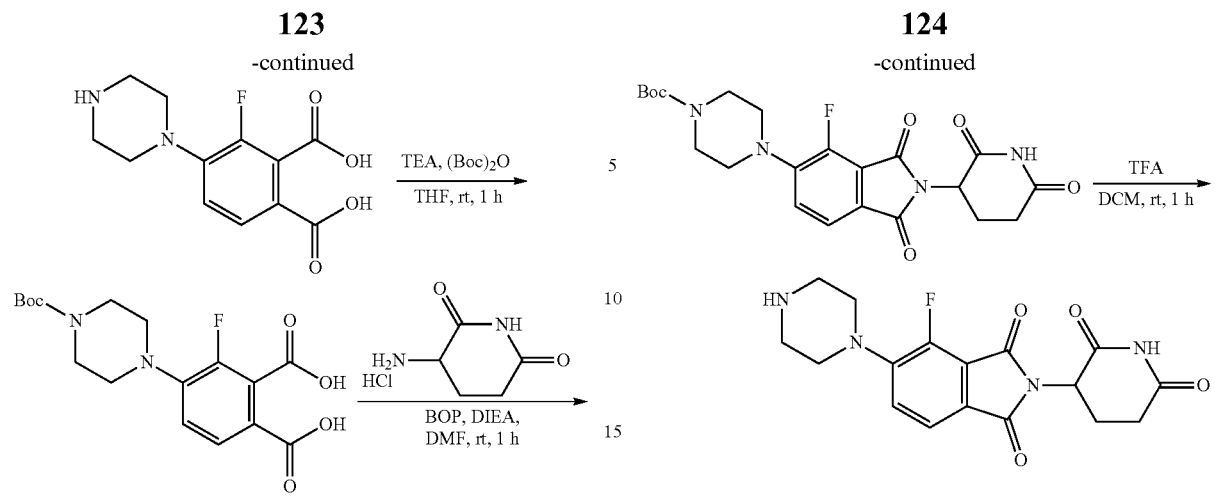
124
-continued
Scheme 12
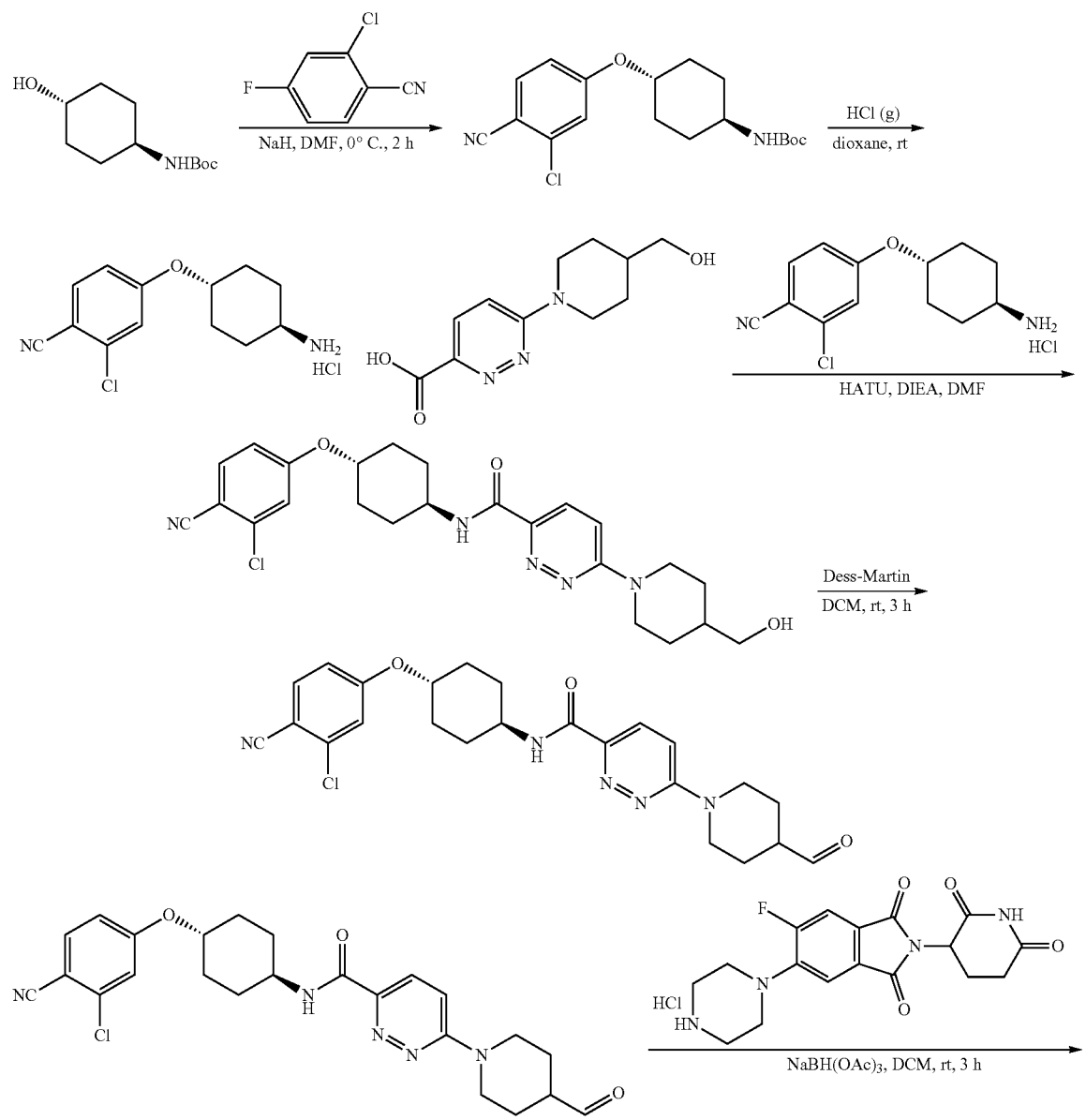

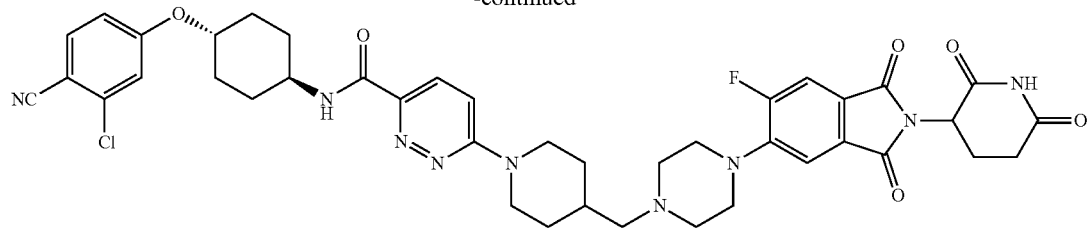
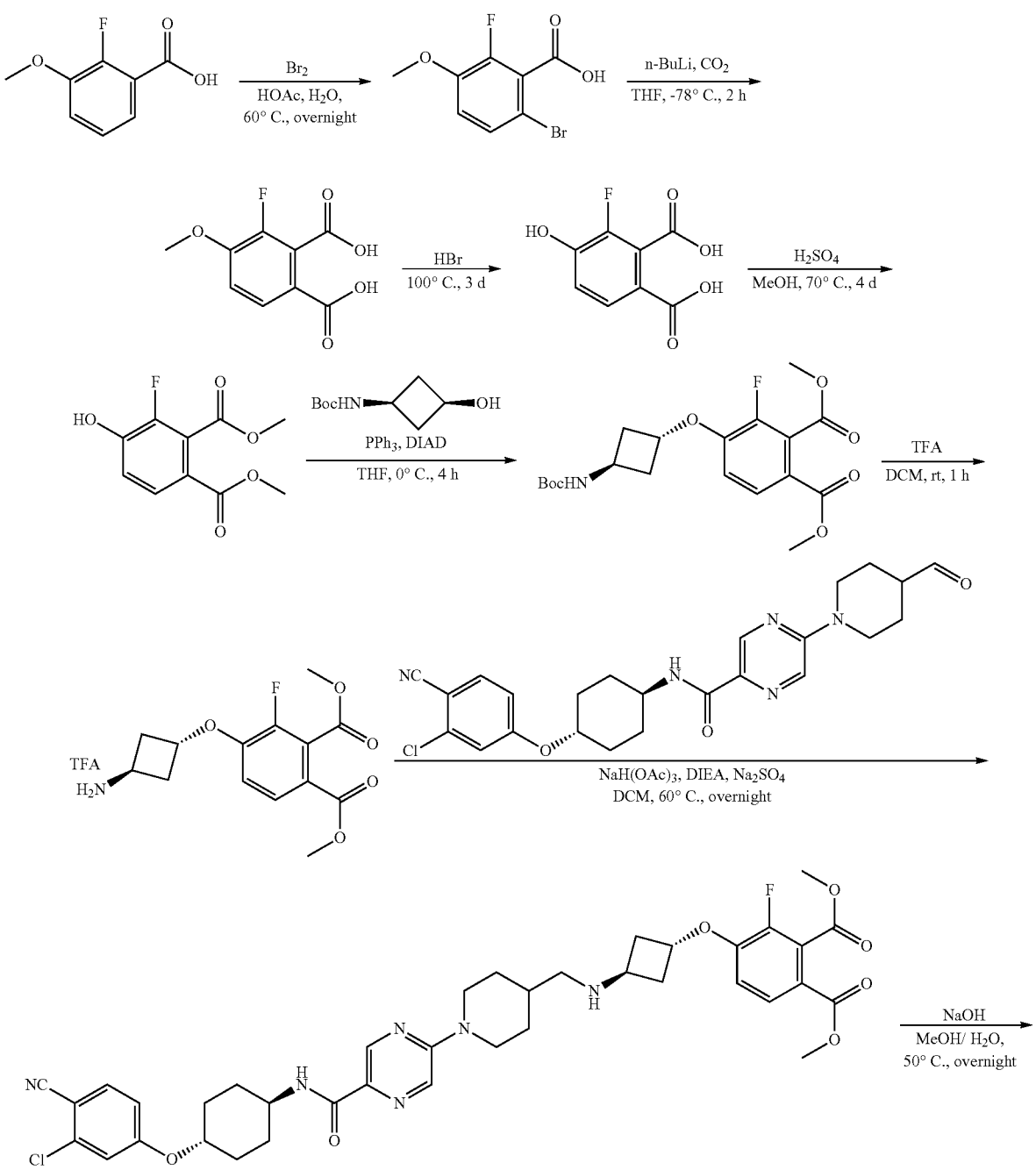
Scheme 13

127 128
-continued
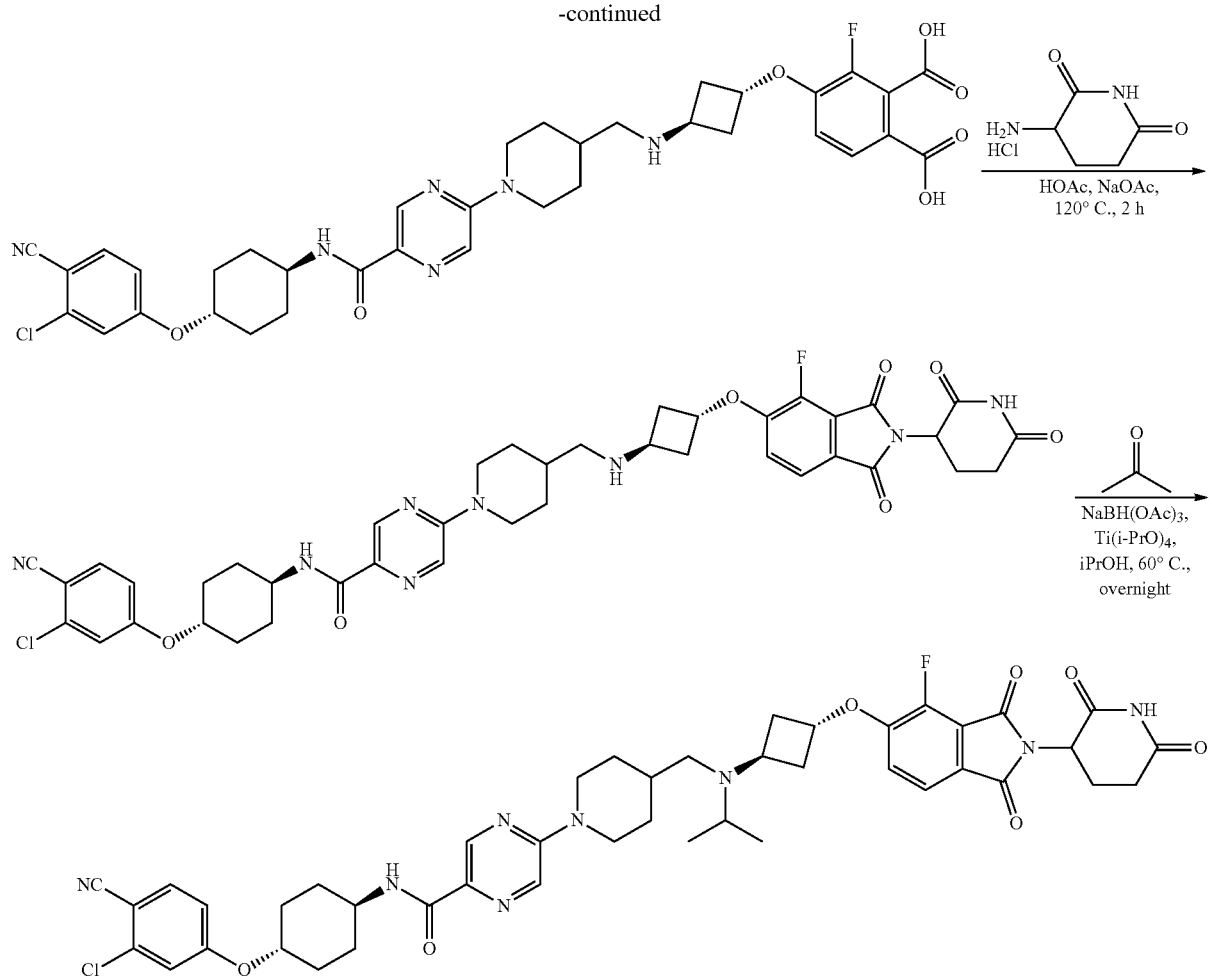
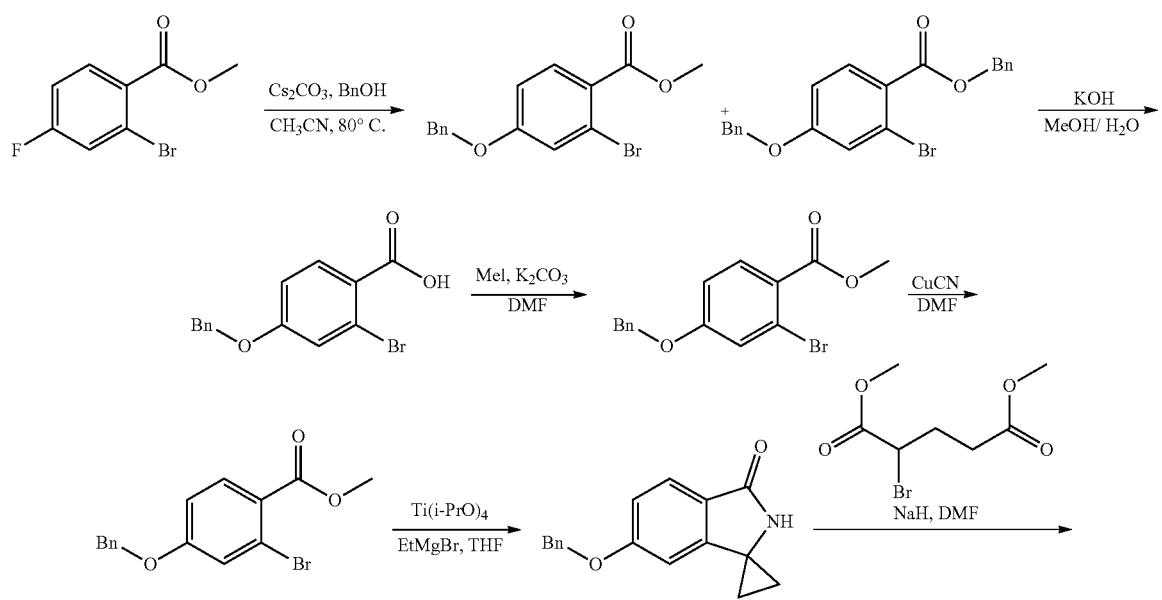
Scheme 14

-continued
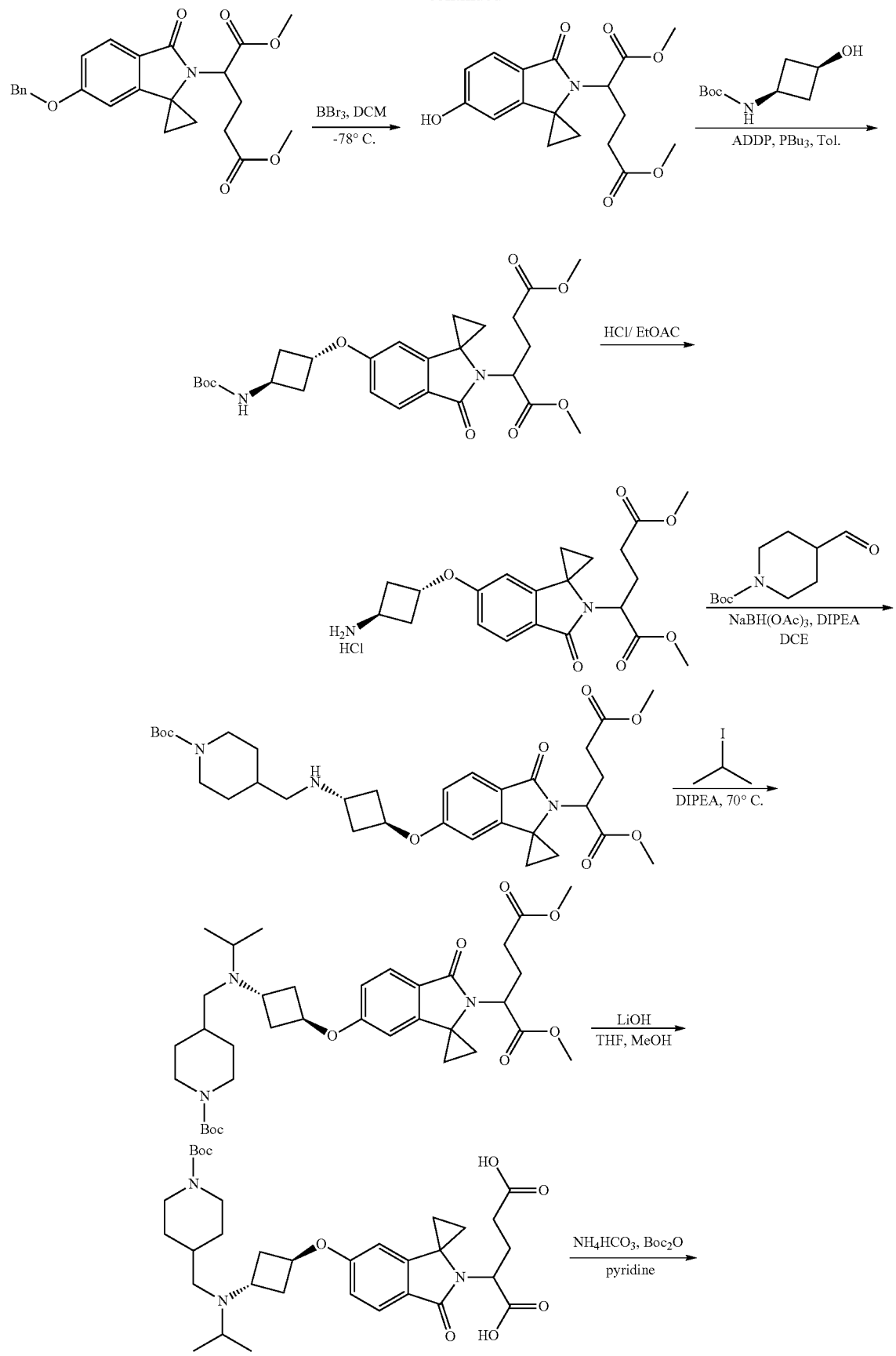

131 132
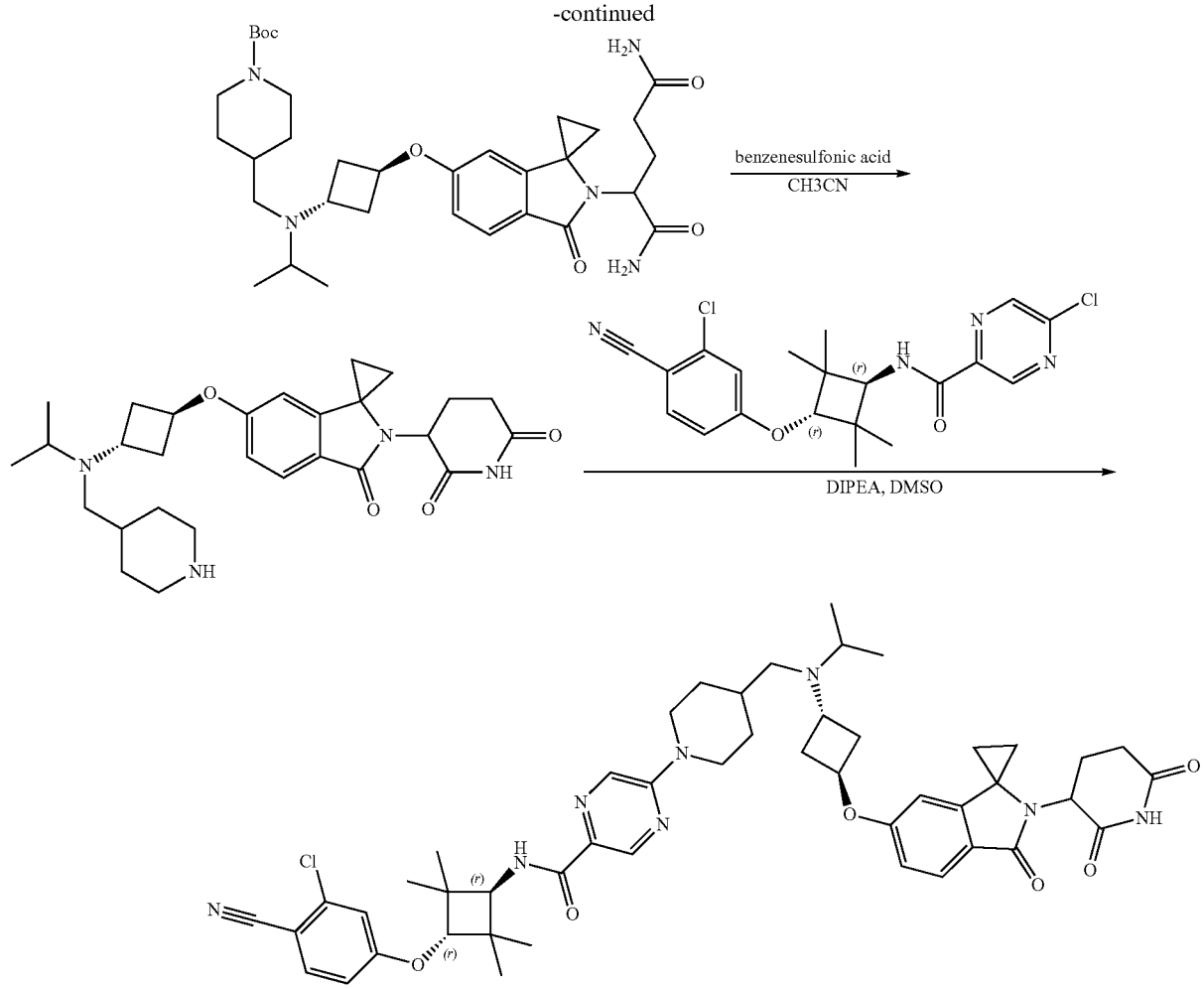
Scheme 15
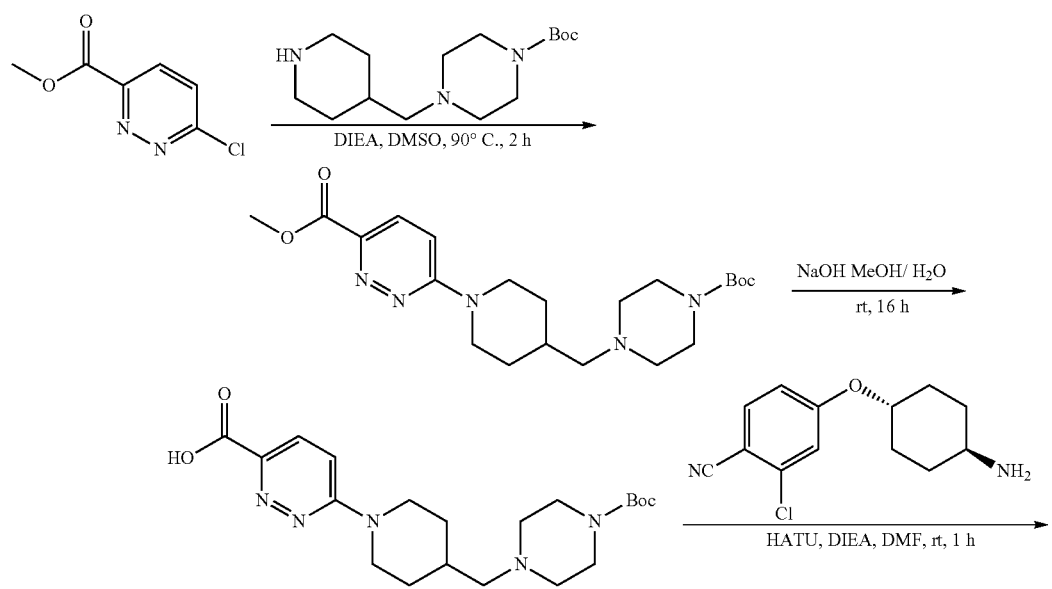

133
-continued
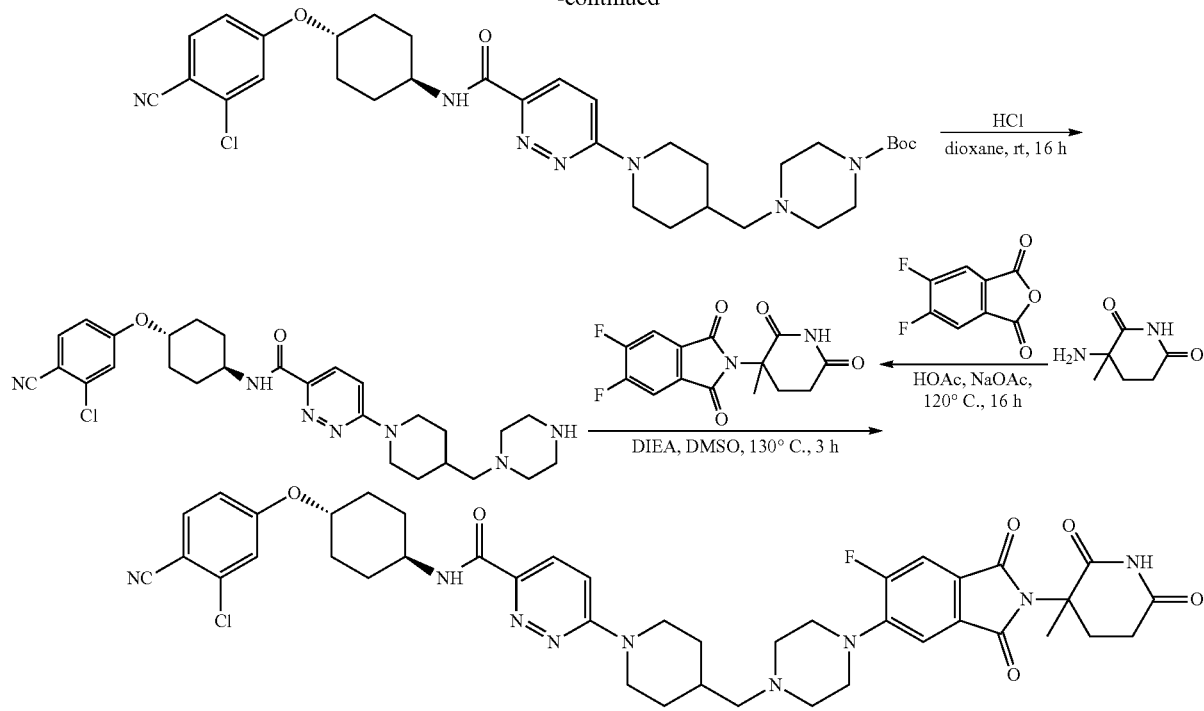
134
-continued
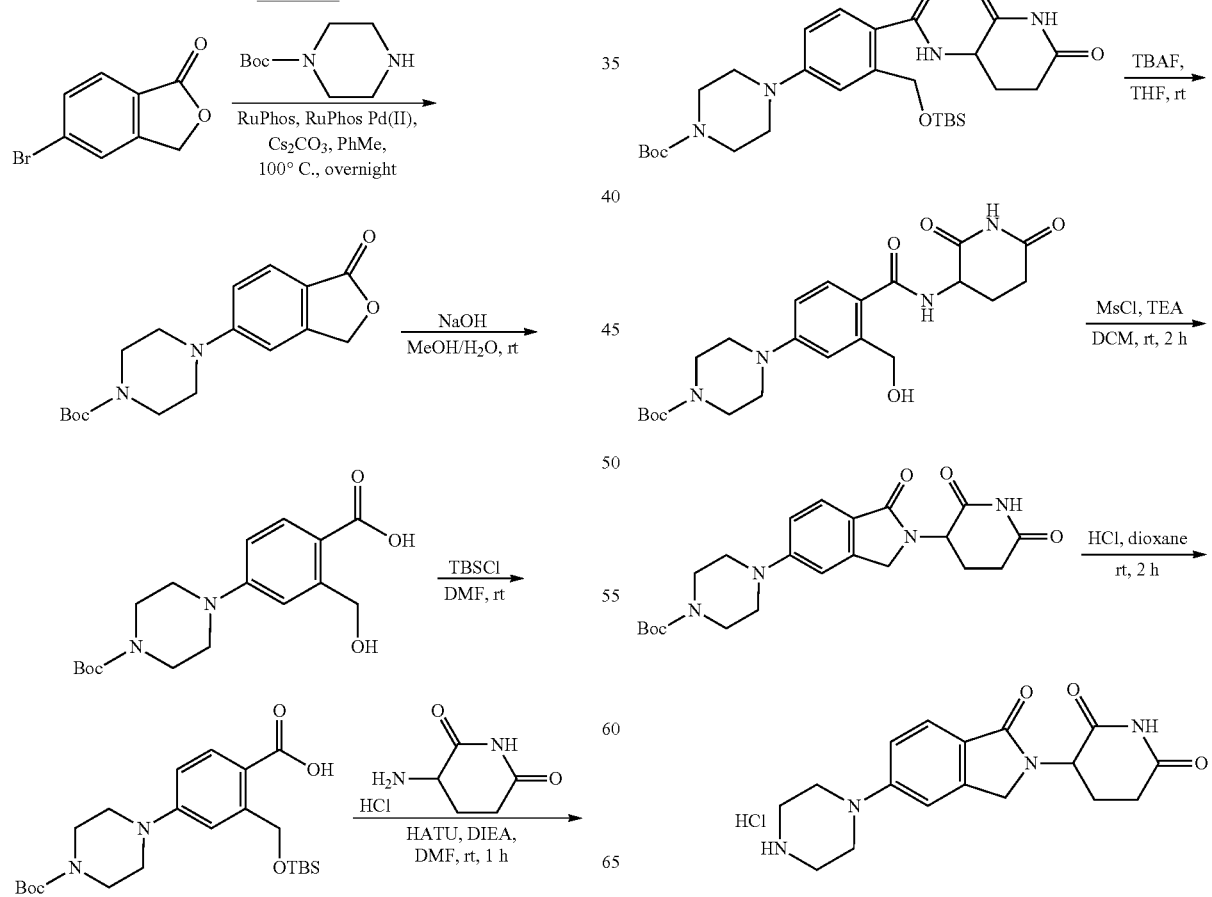
Scheme 16

Scheme 17
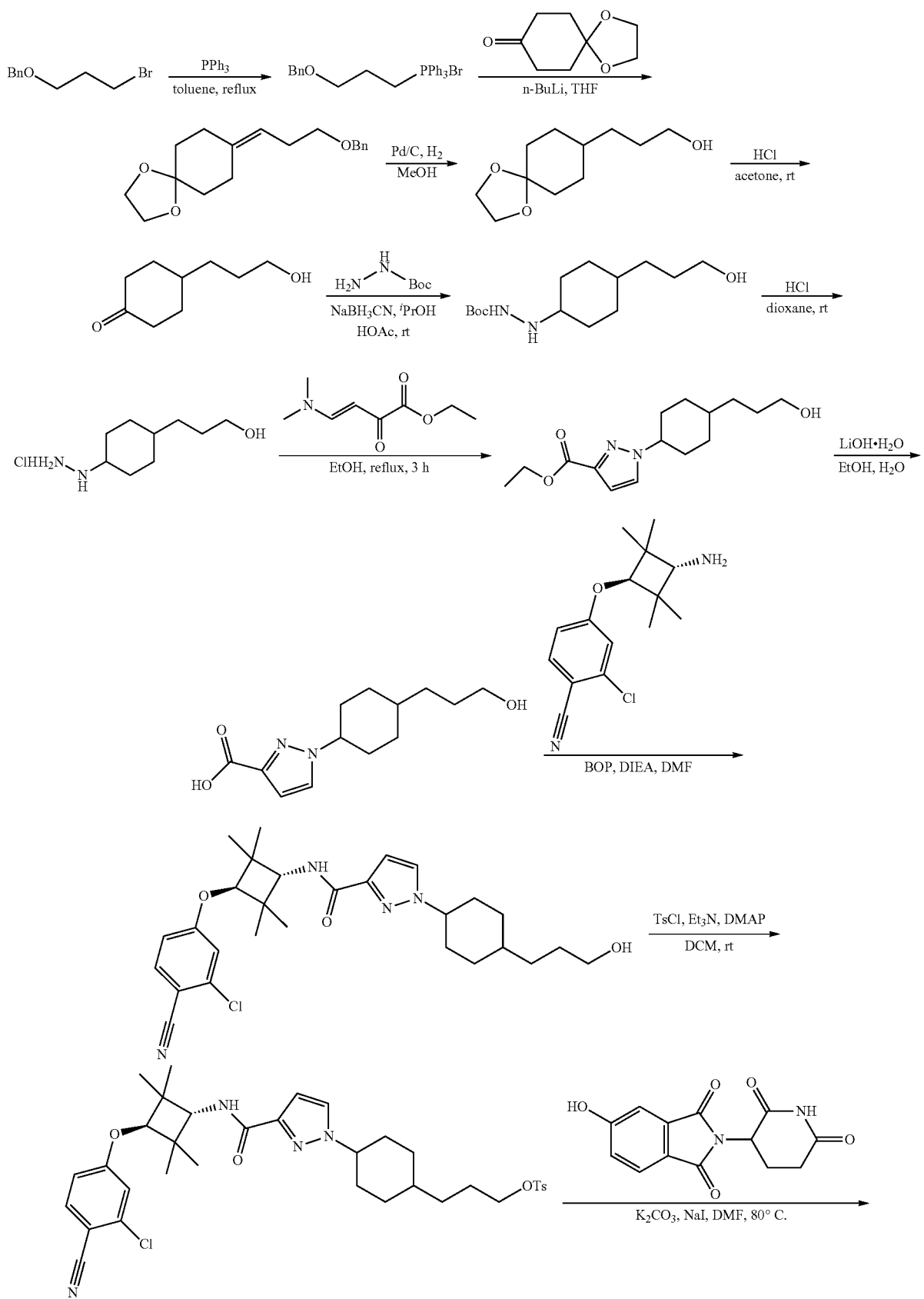

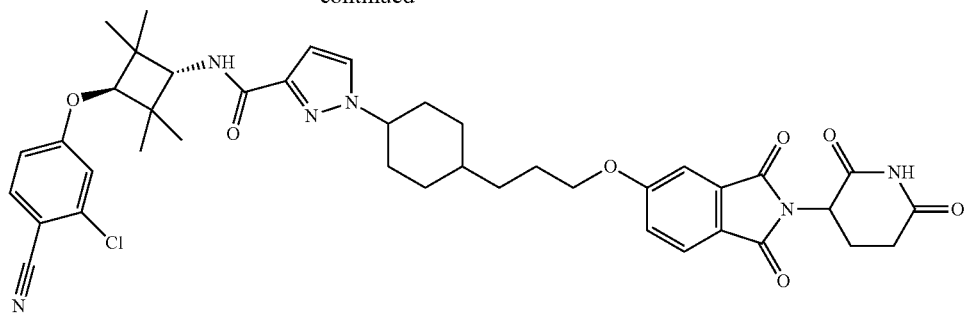
15
Scheme 18
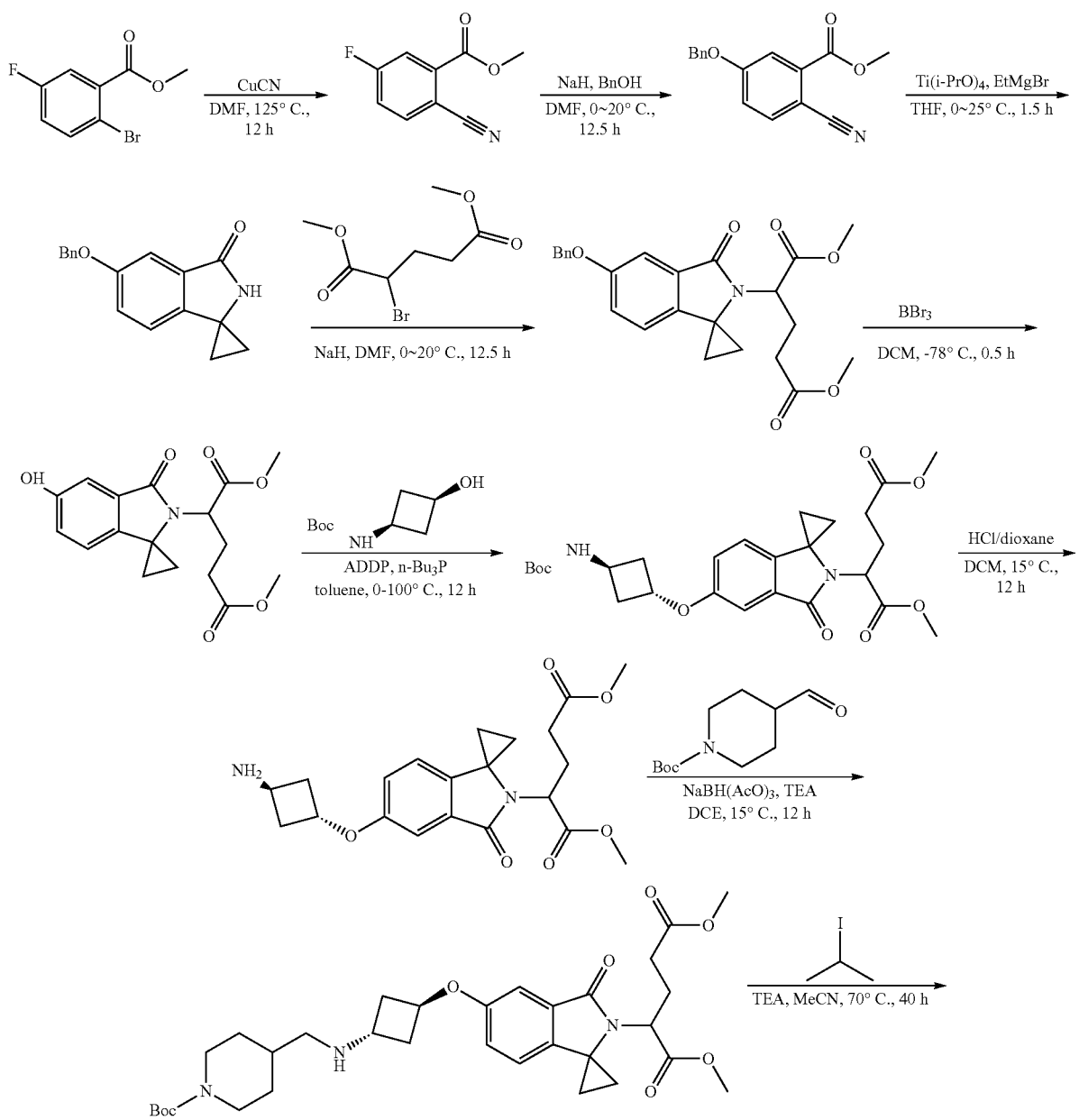

-continued
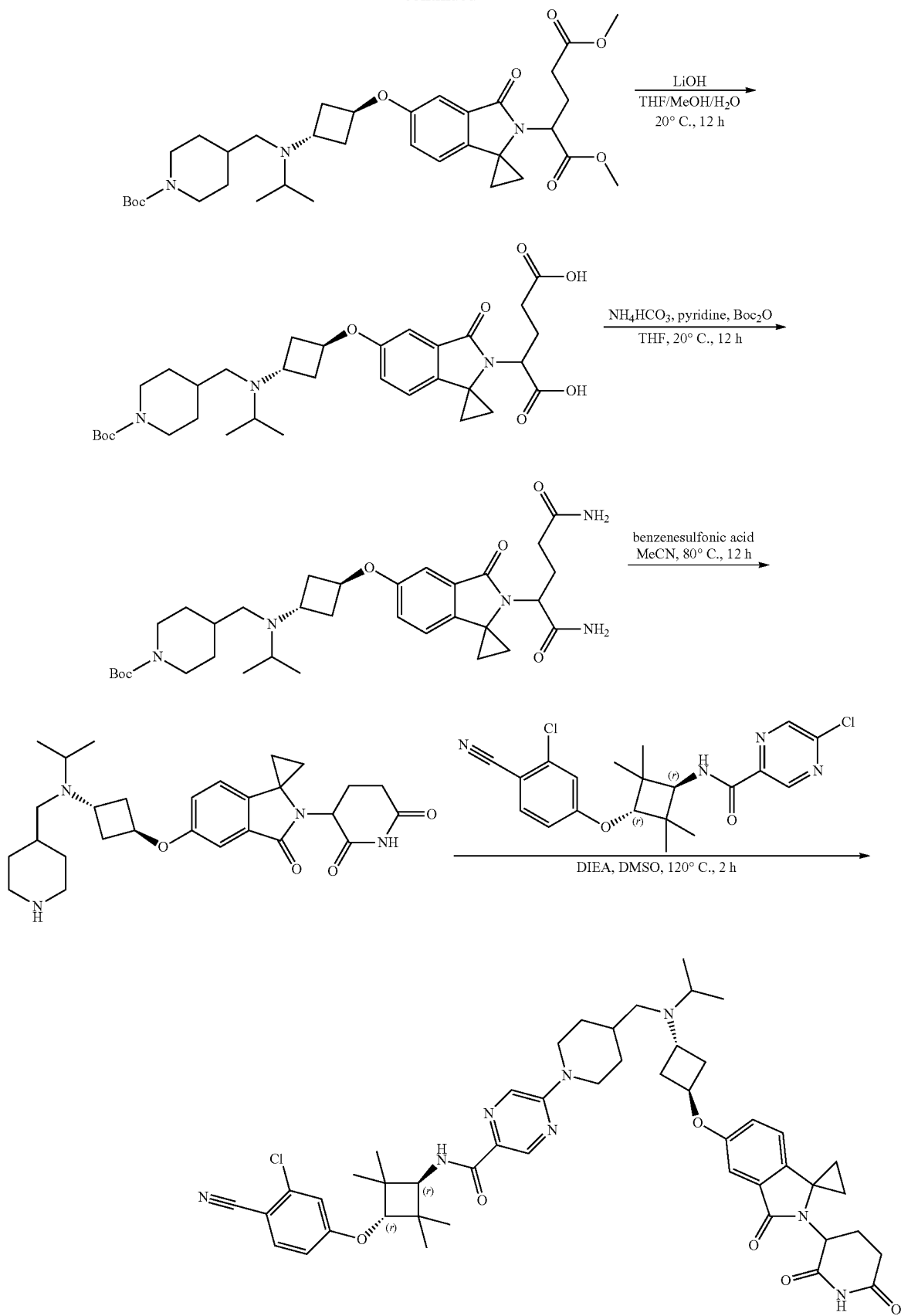

Scheme 19
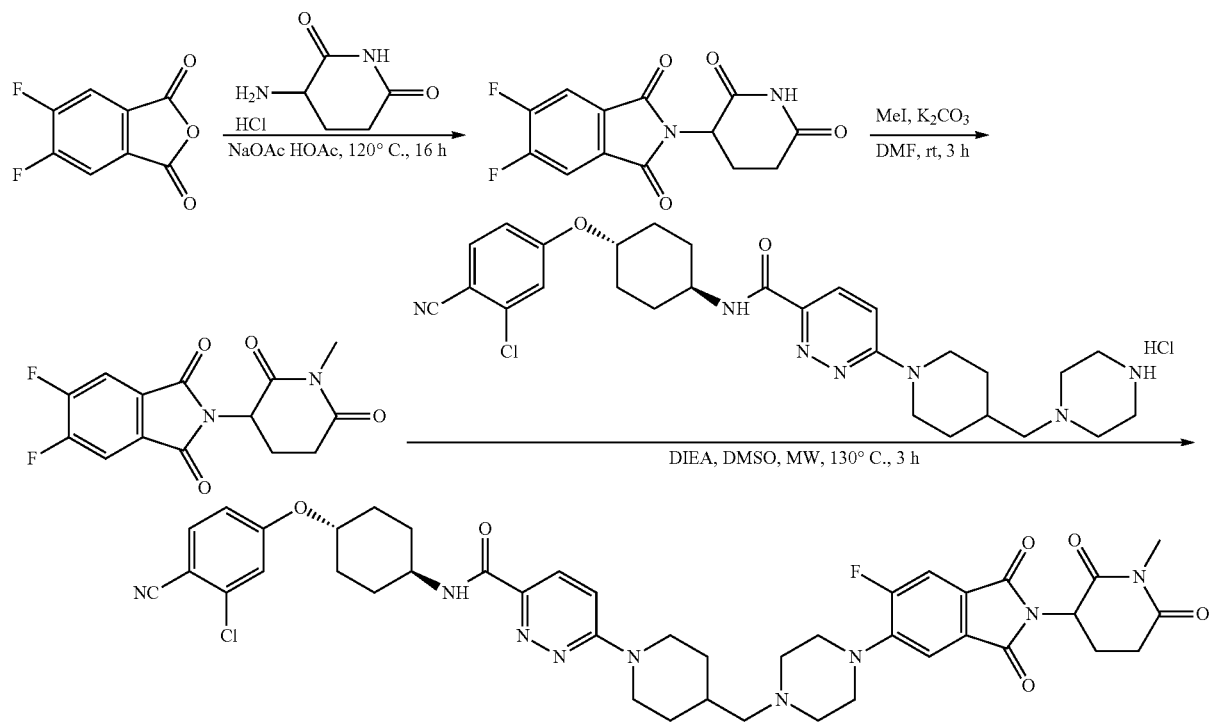
Scheme 20
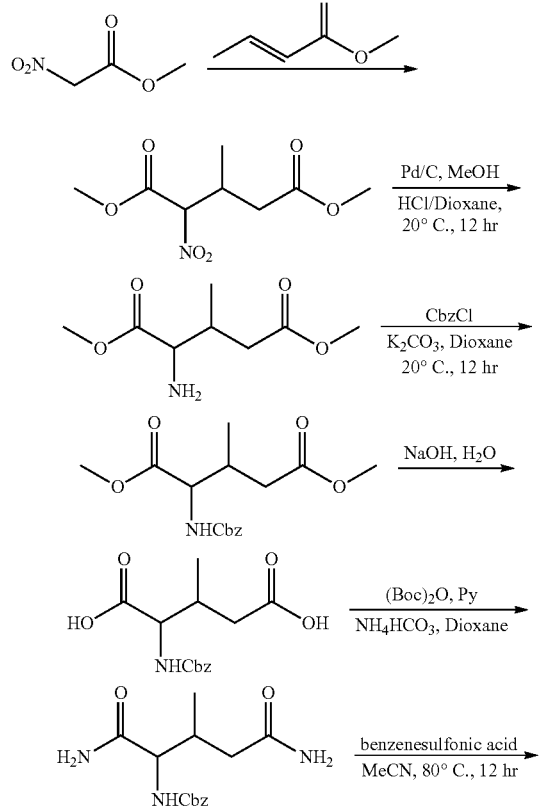
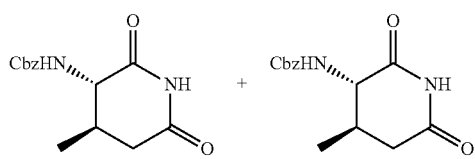
Scheme 21
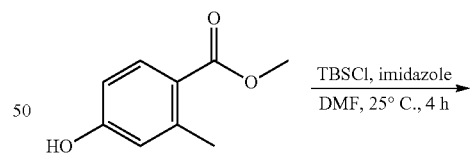
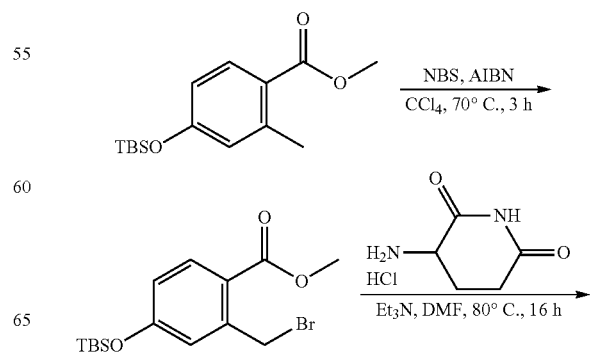

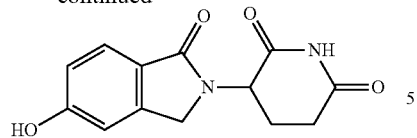
Scheme 22
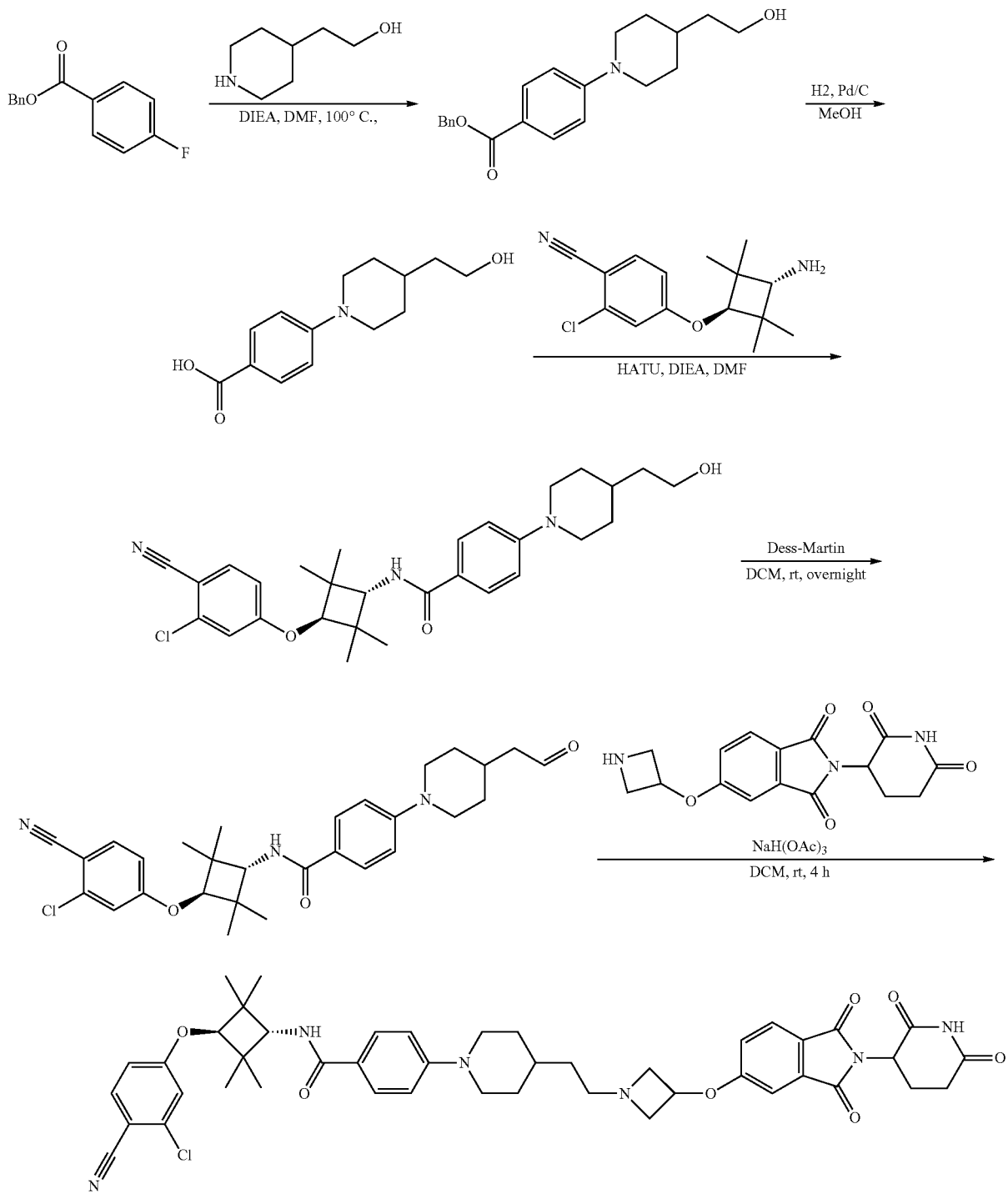

Scheme 23
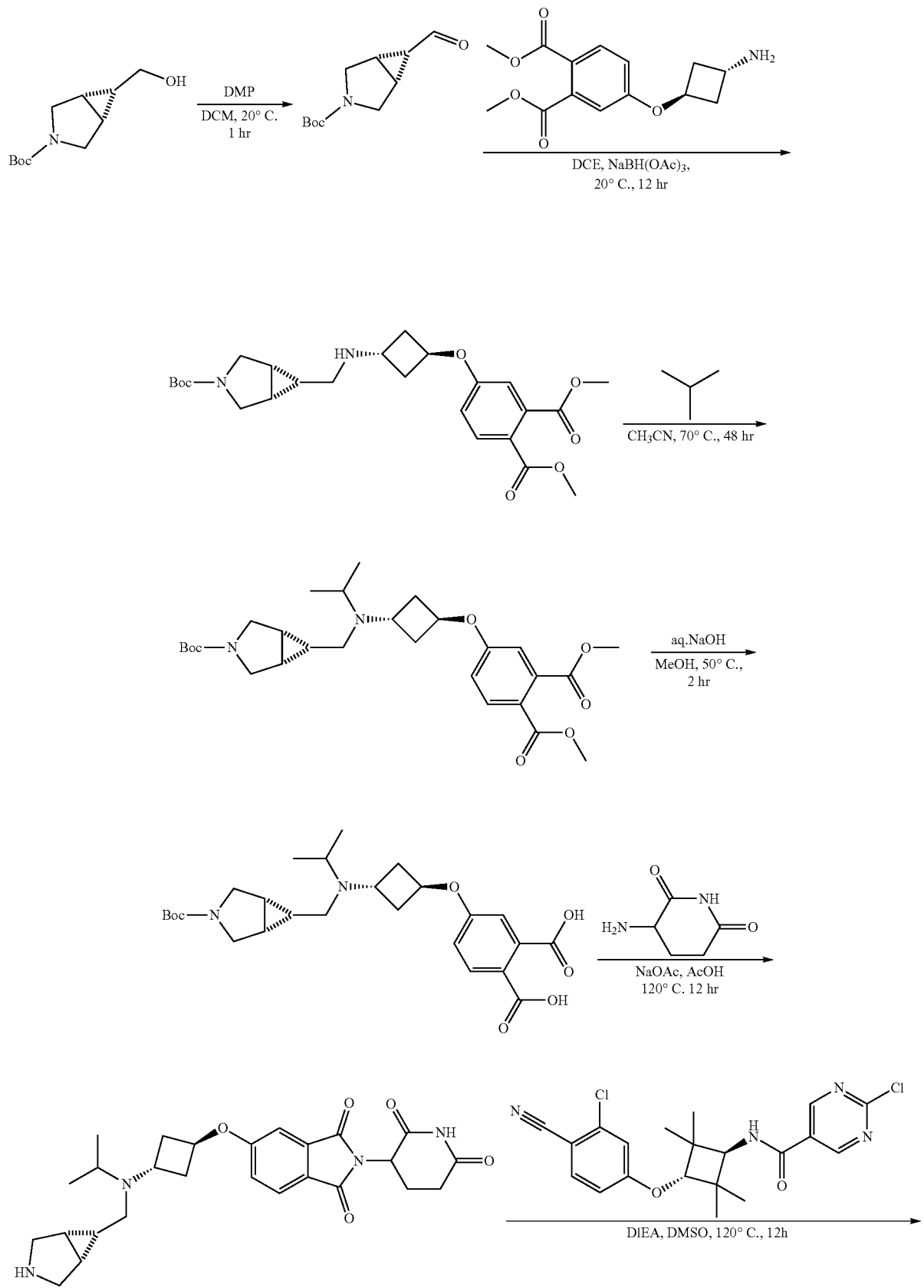

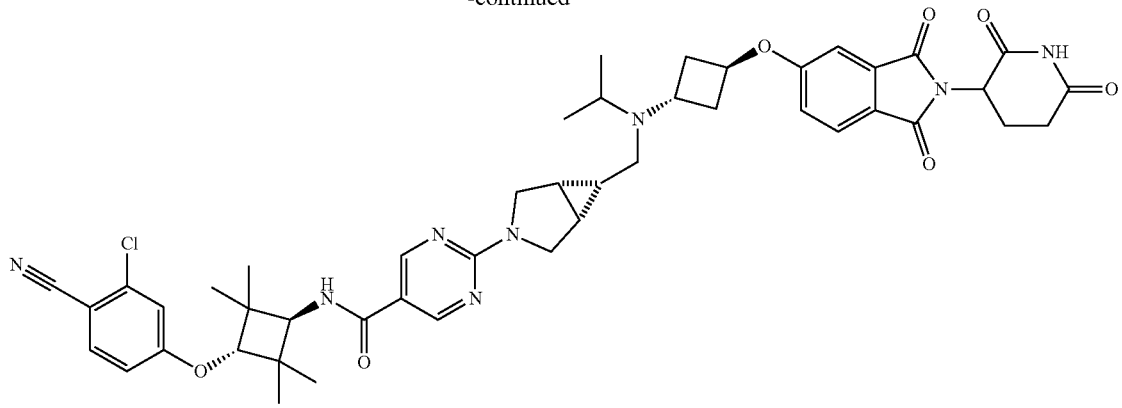
Scheme 24
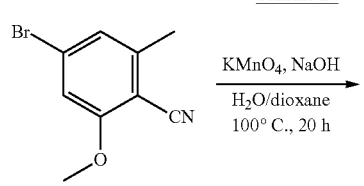
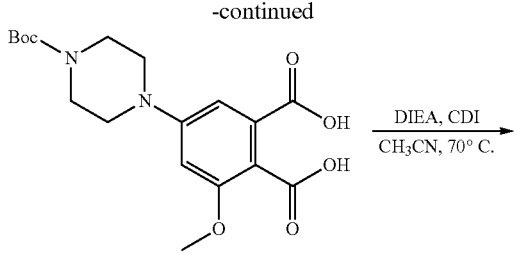
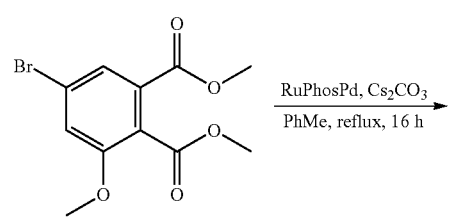
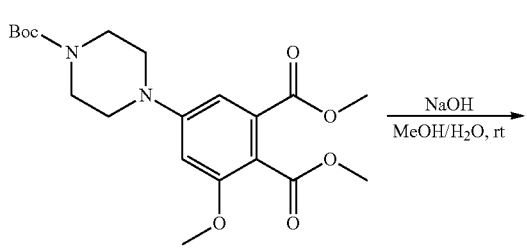
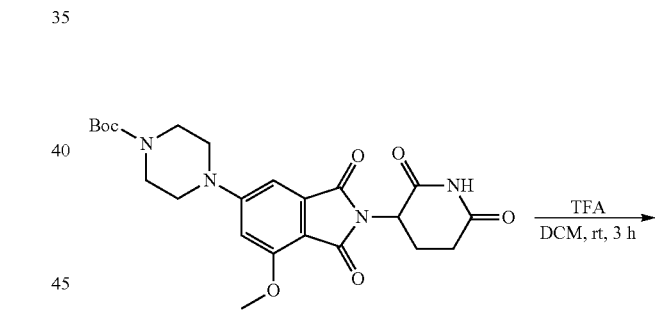
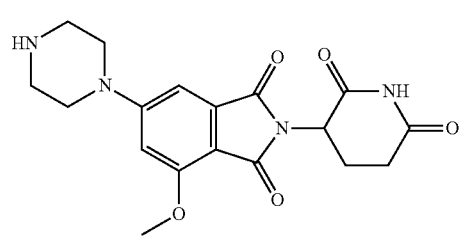

Scheme 25
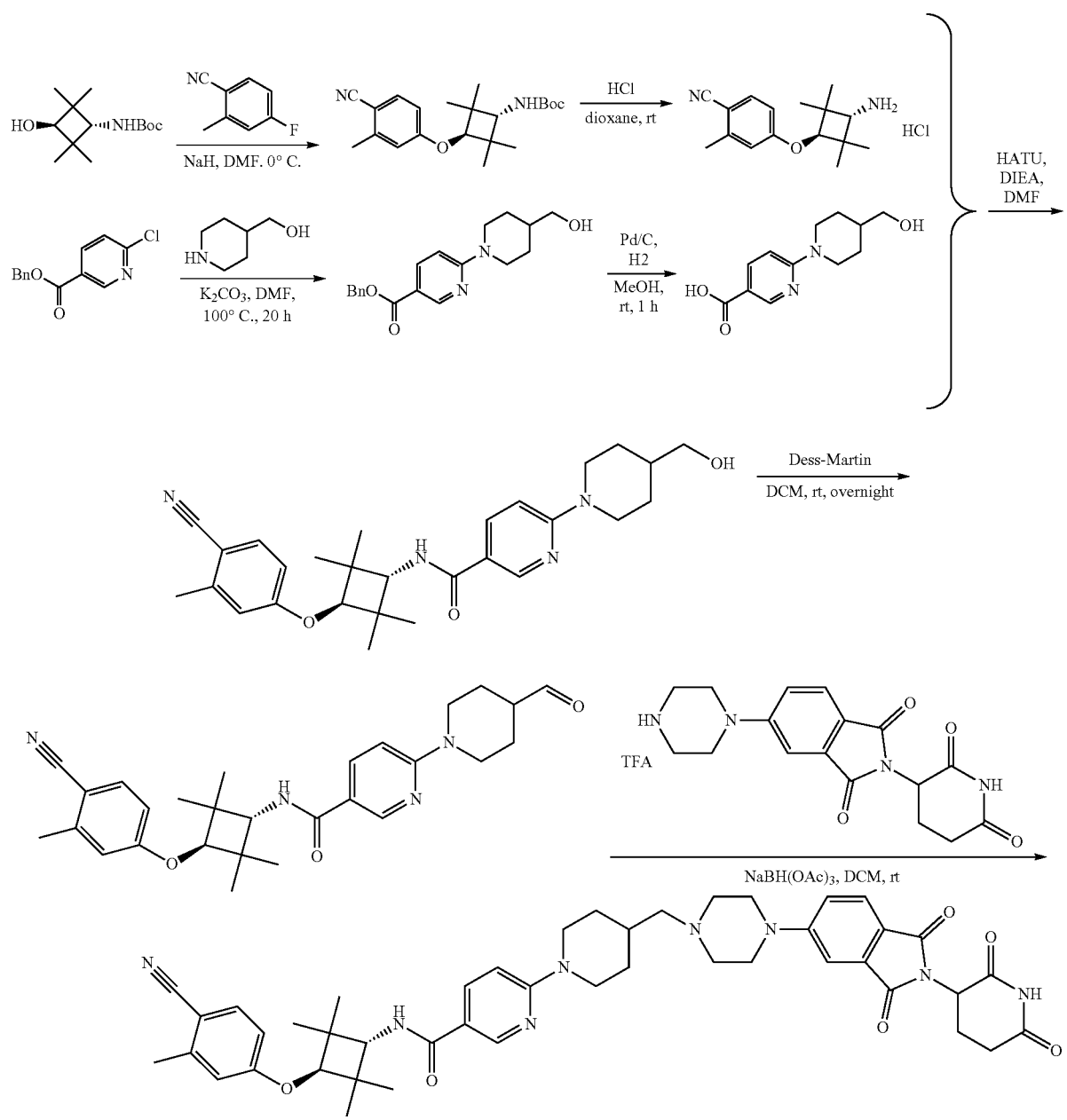
Scheme 26
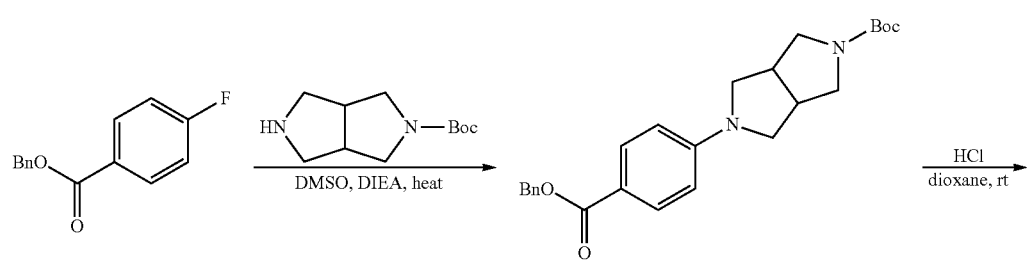

151 152
-continued
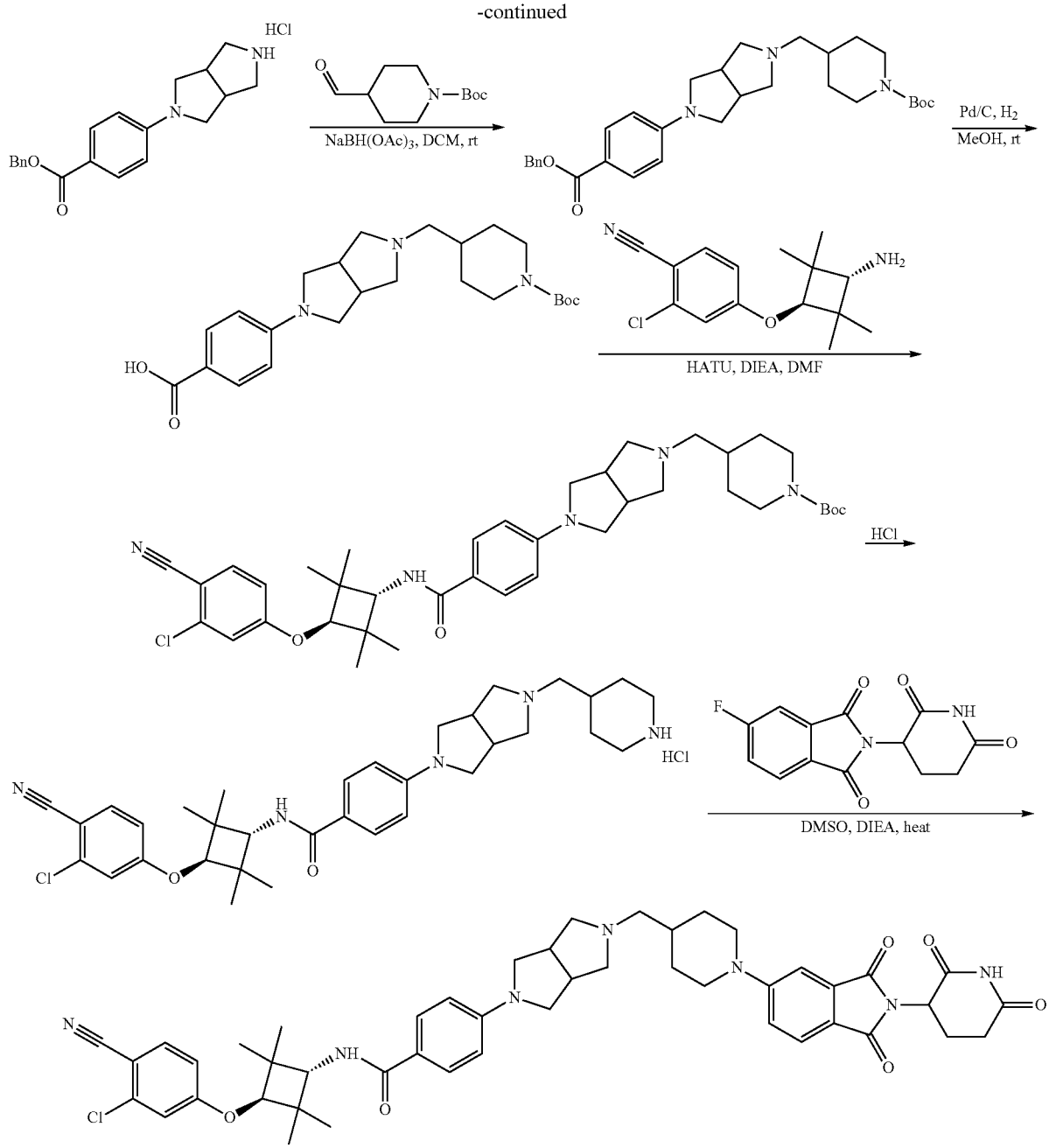

Scheme 27
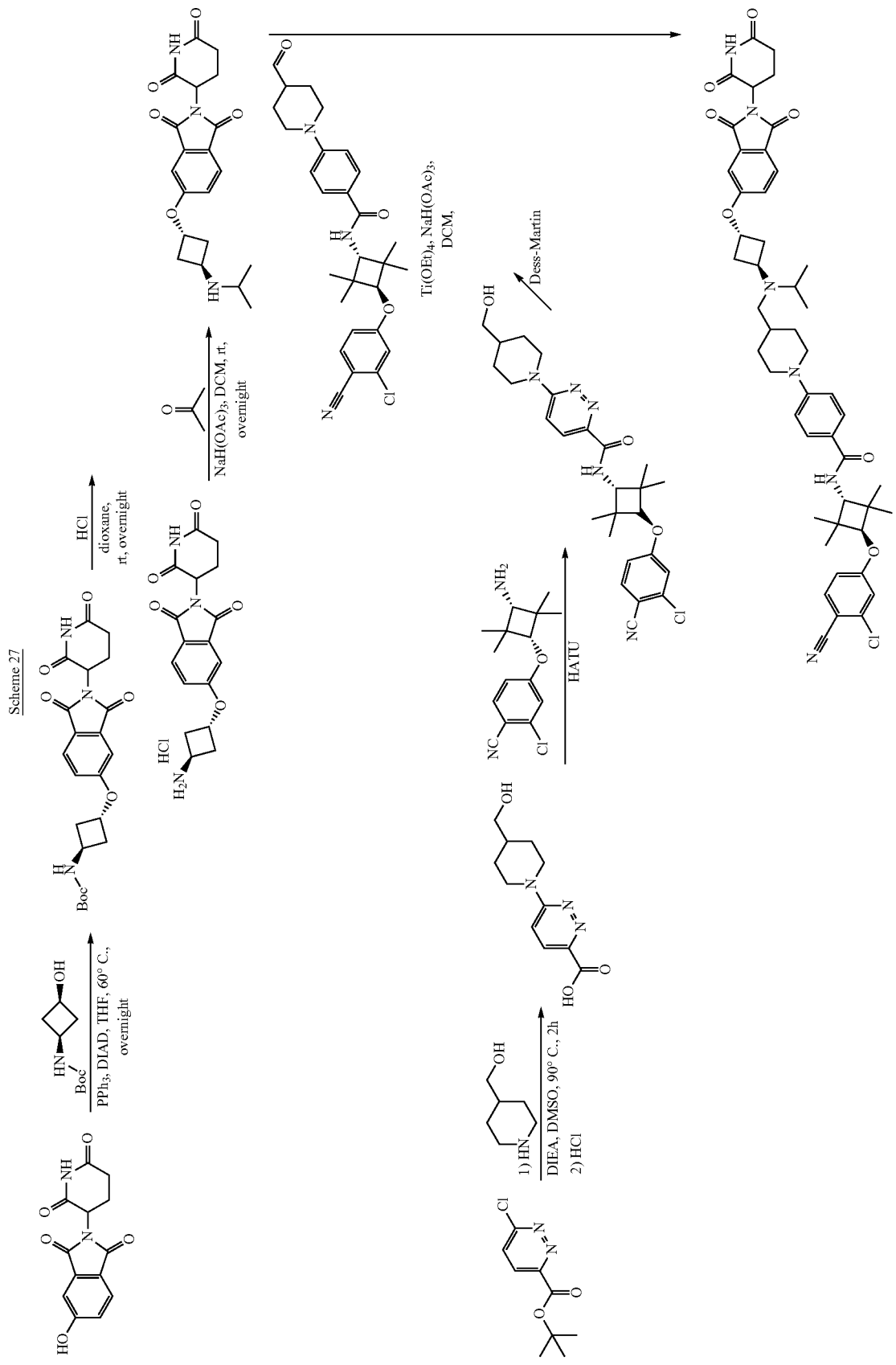

Scheme 28
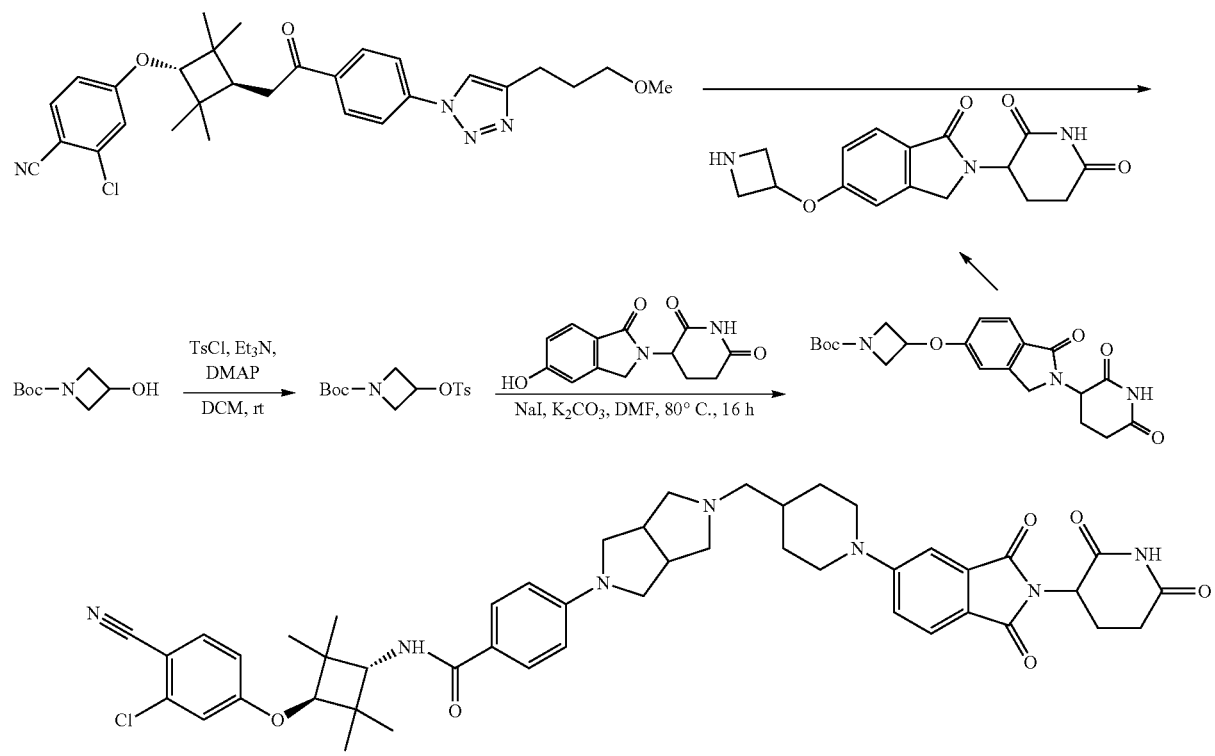
Scheme 29
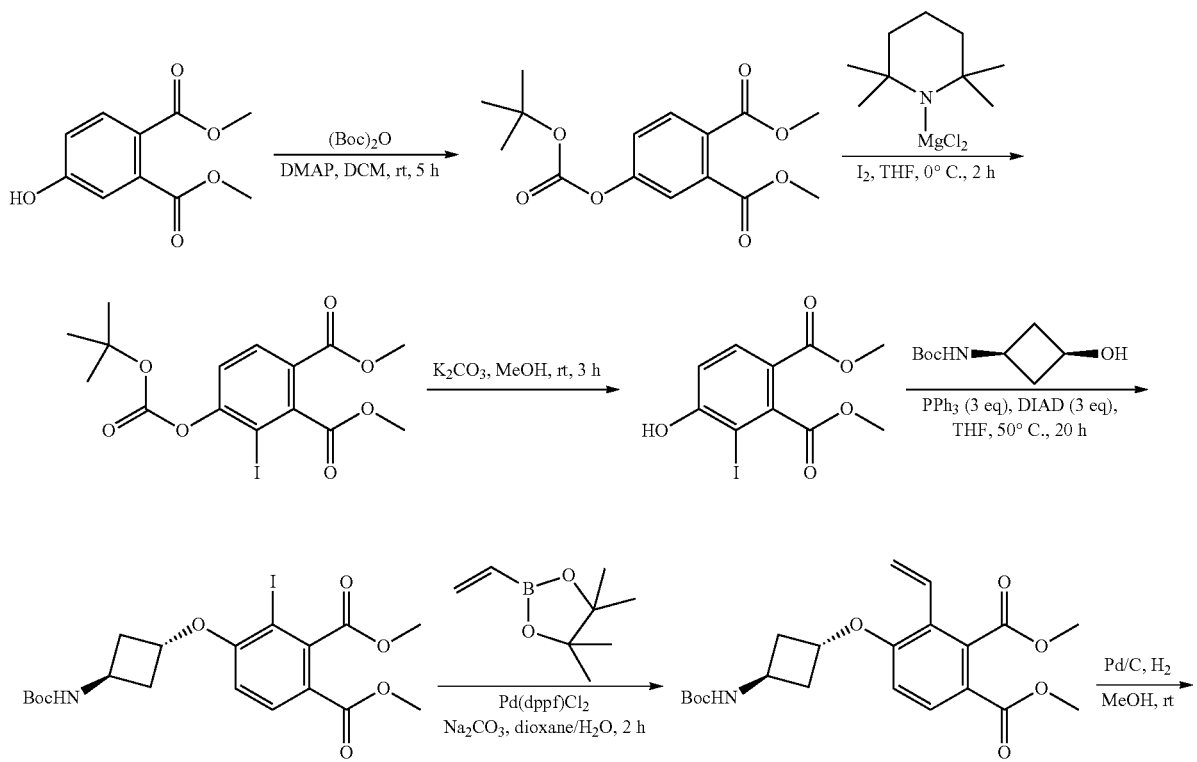

159
160
-continued
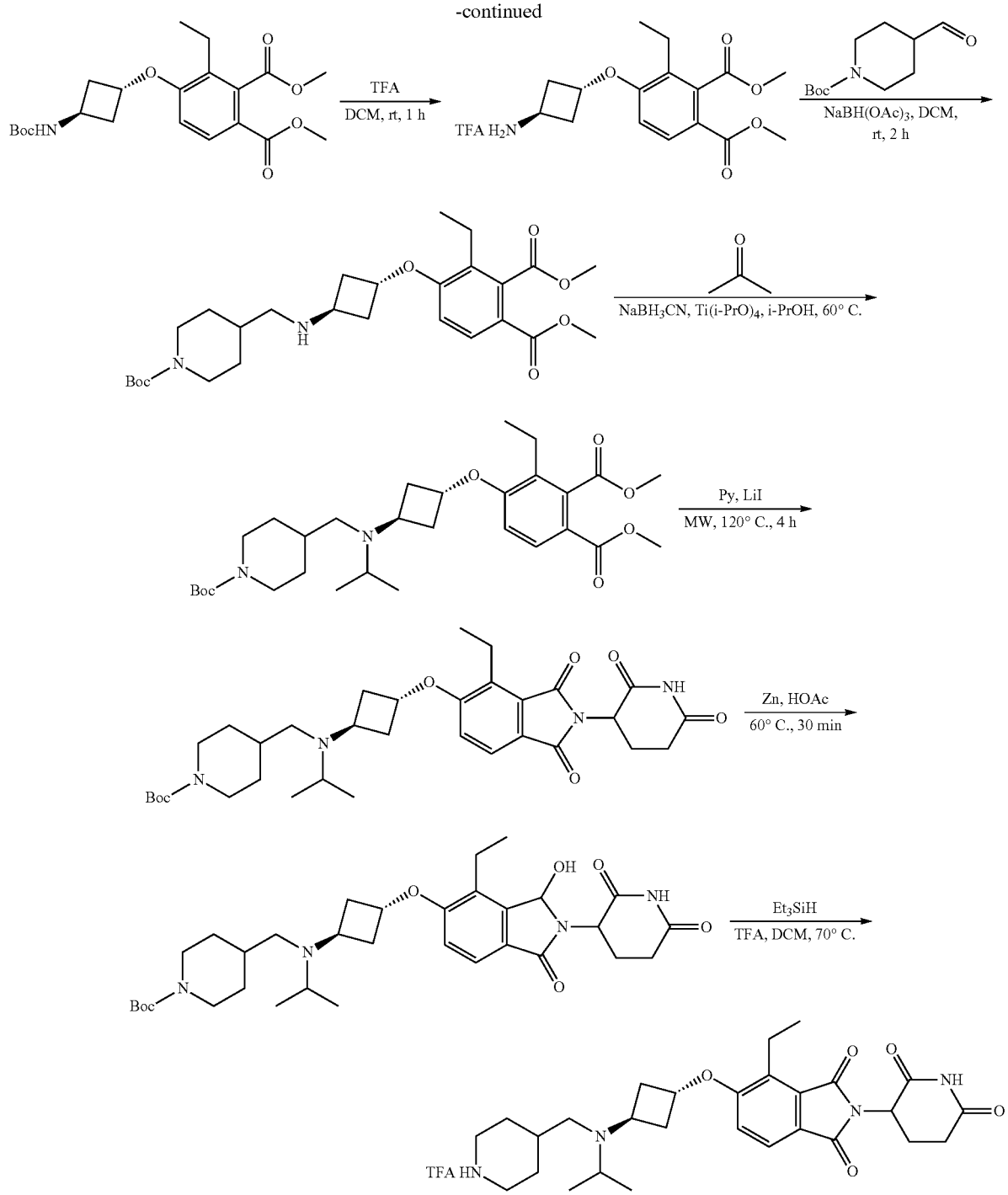
Scheme 30
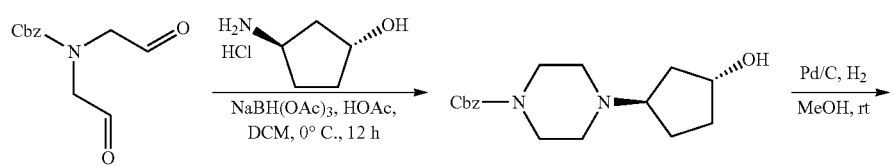

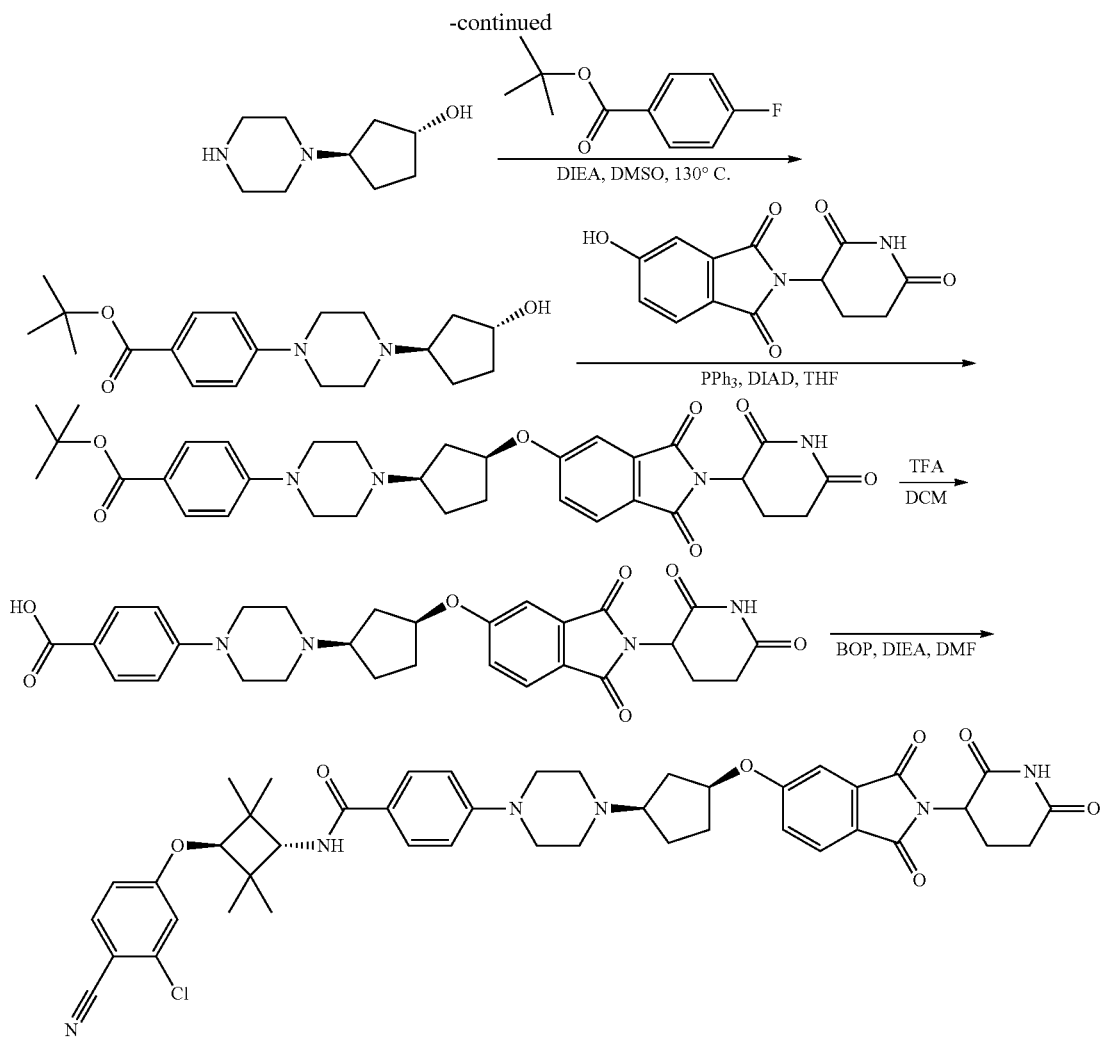

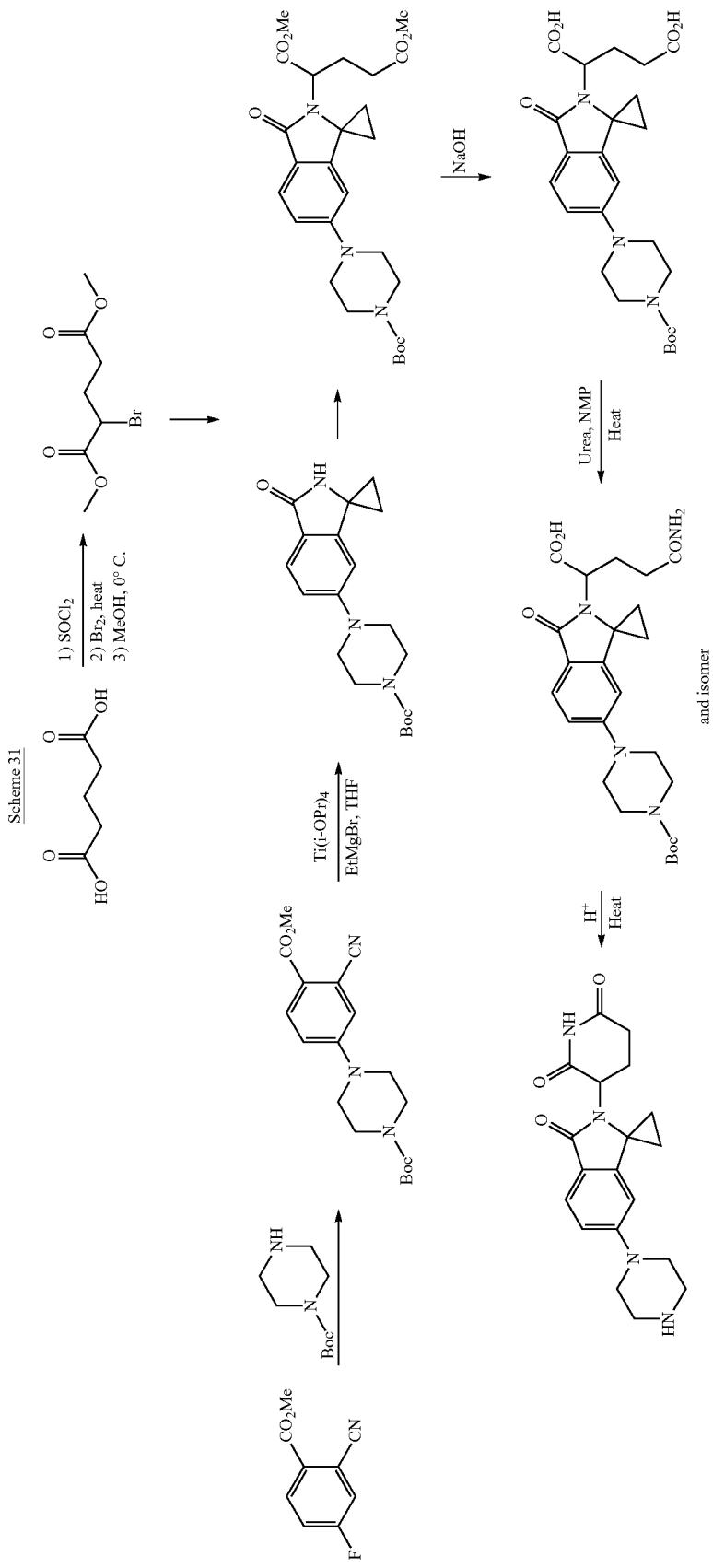
Scheme 31

Scheme 32
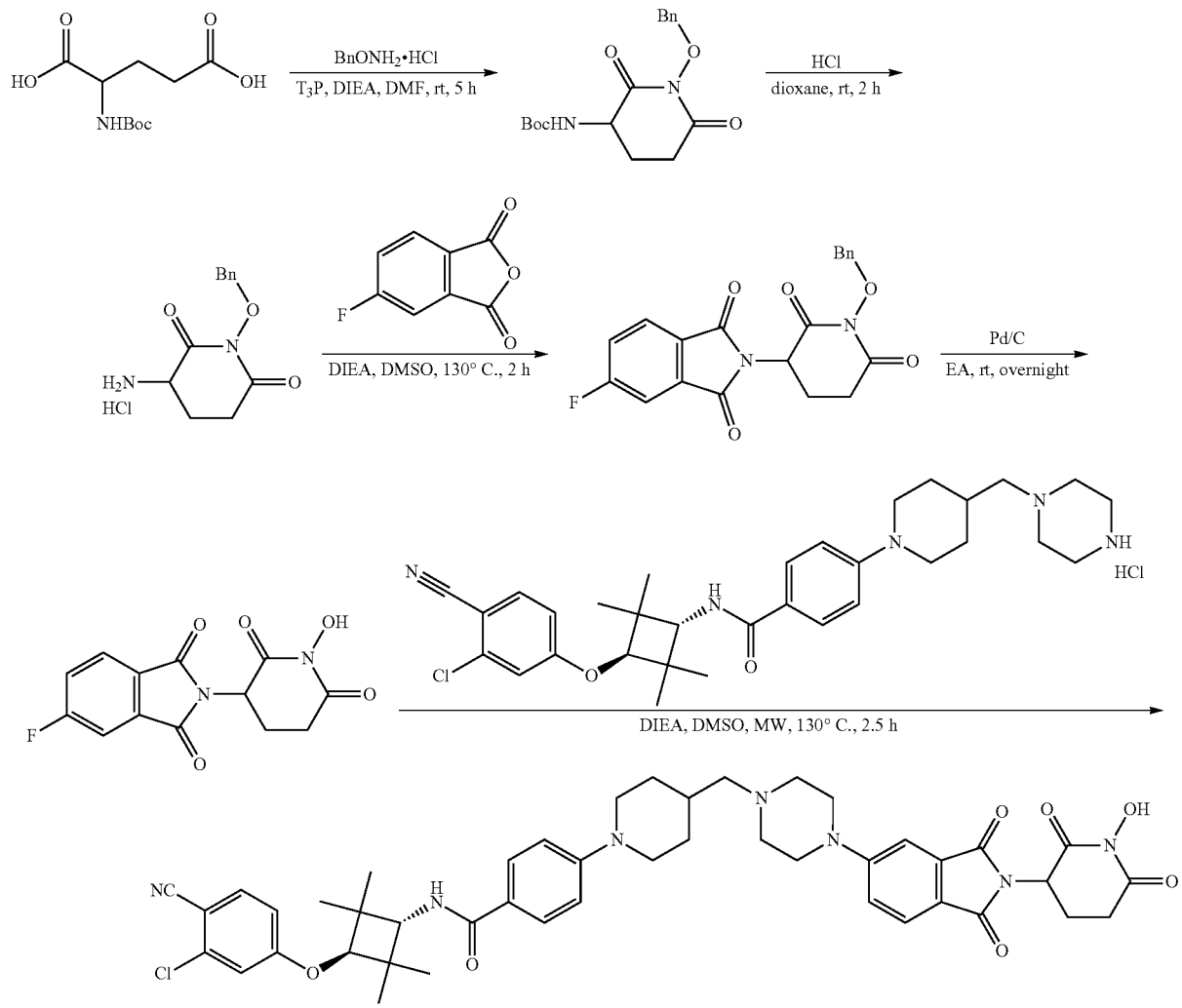
Scheme 33:
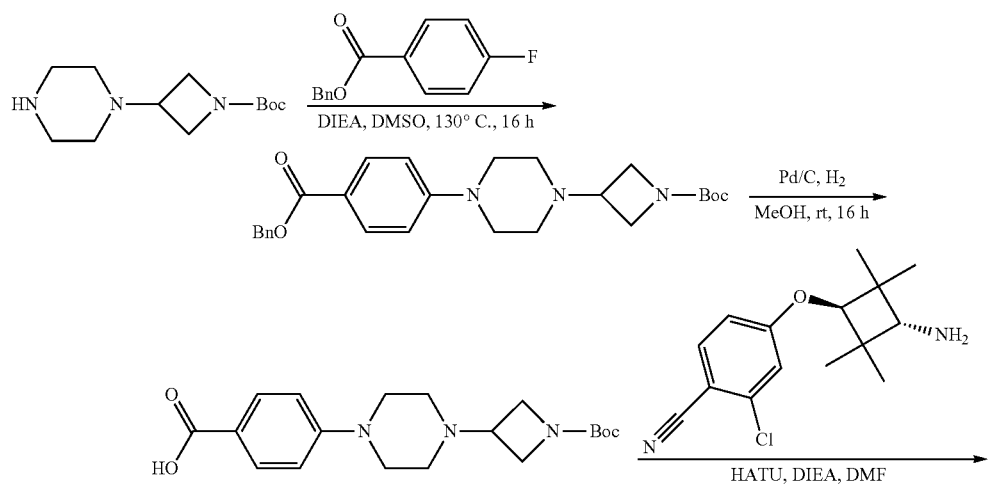

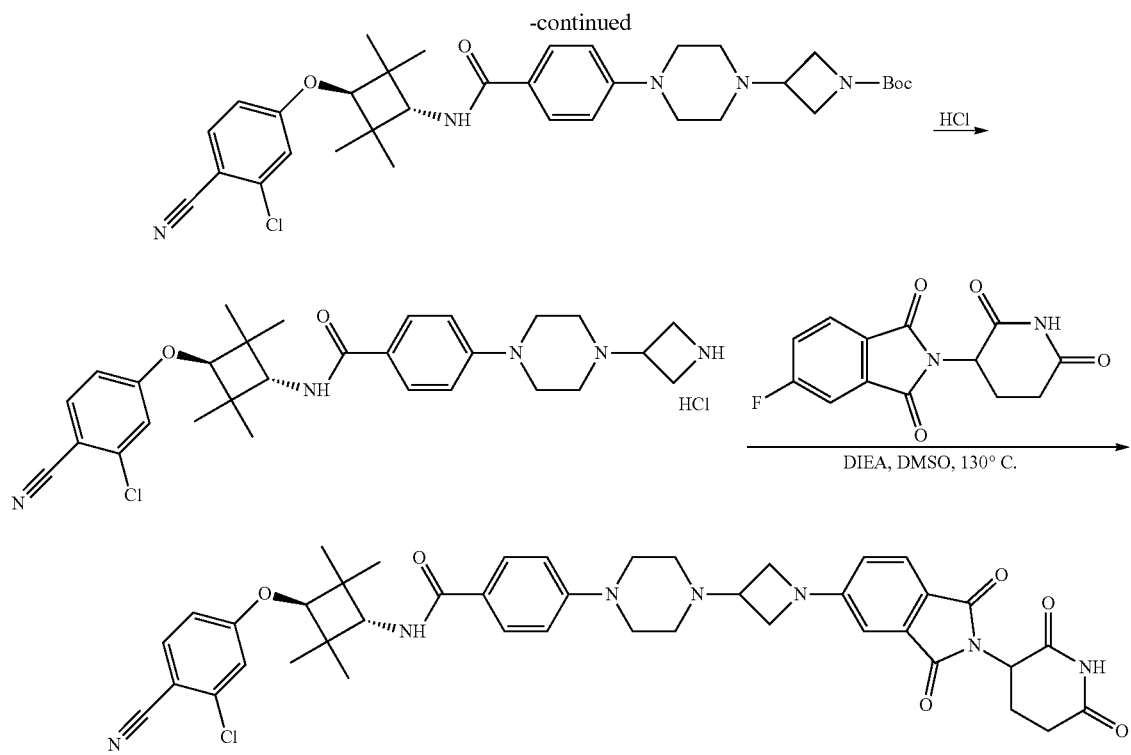
Scheme 34:
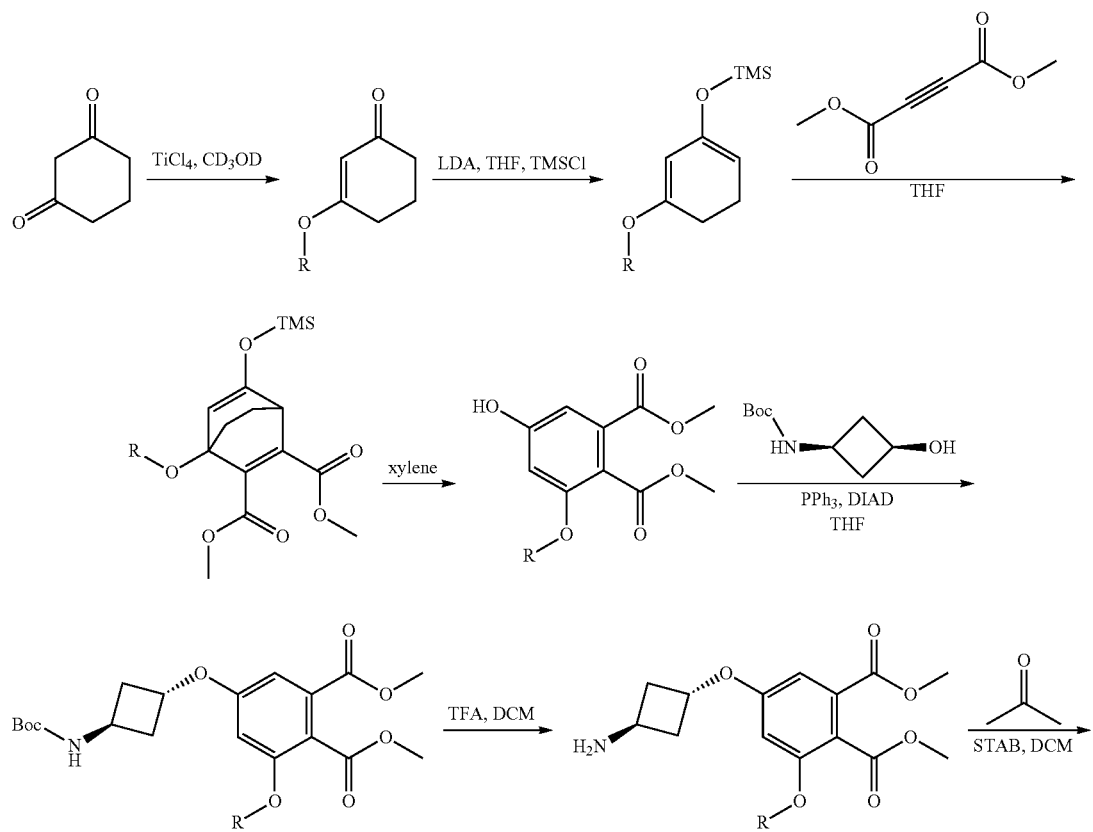

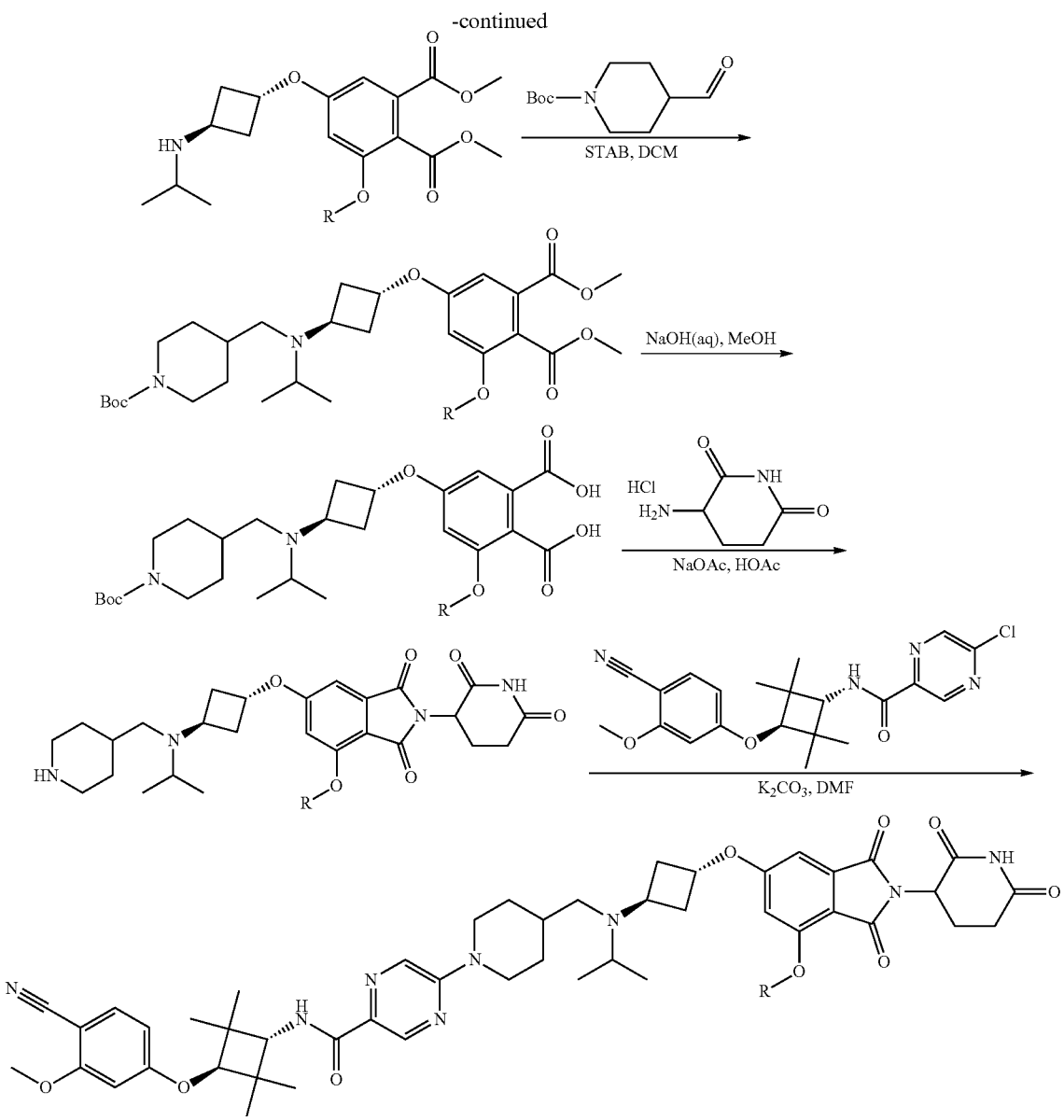
Scheme 36:
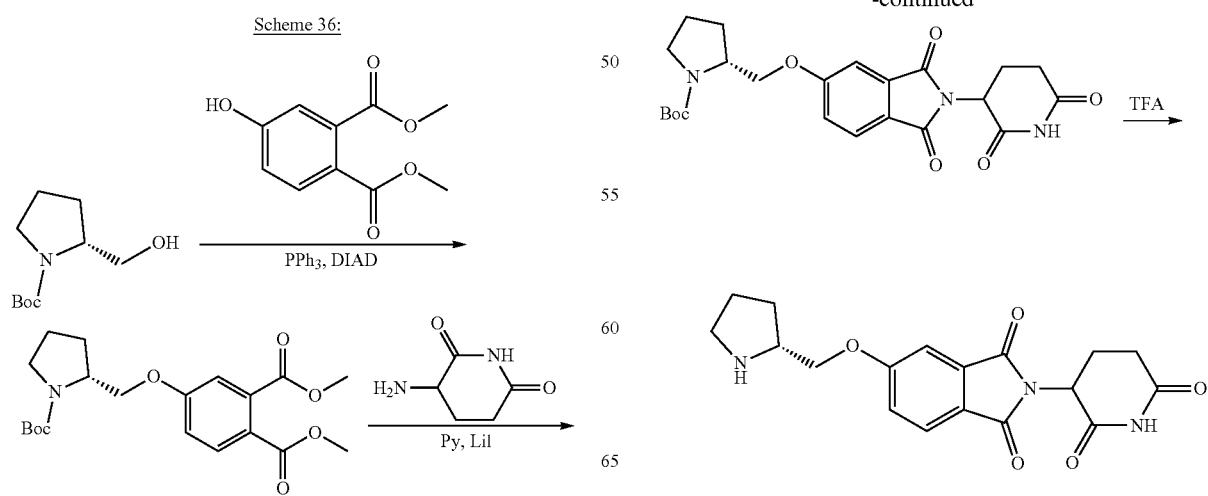

Scheme 38:
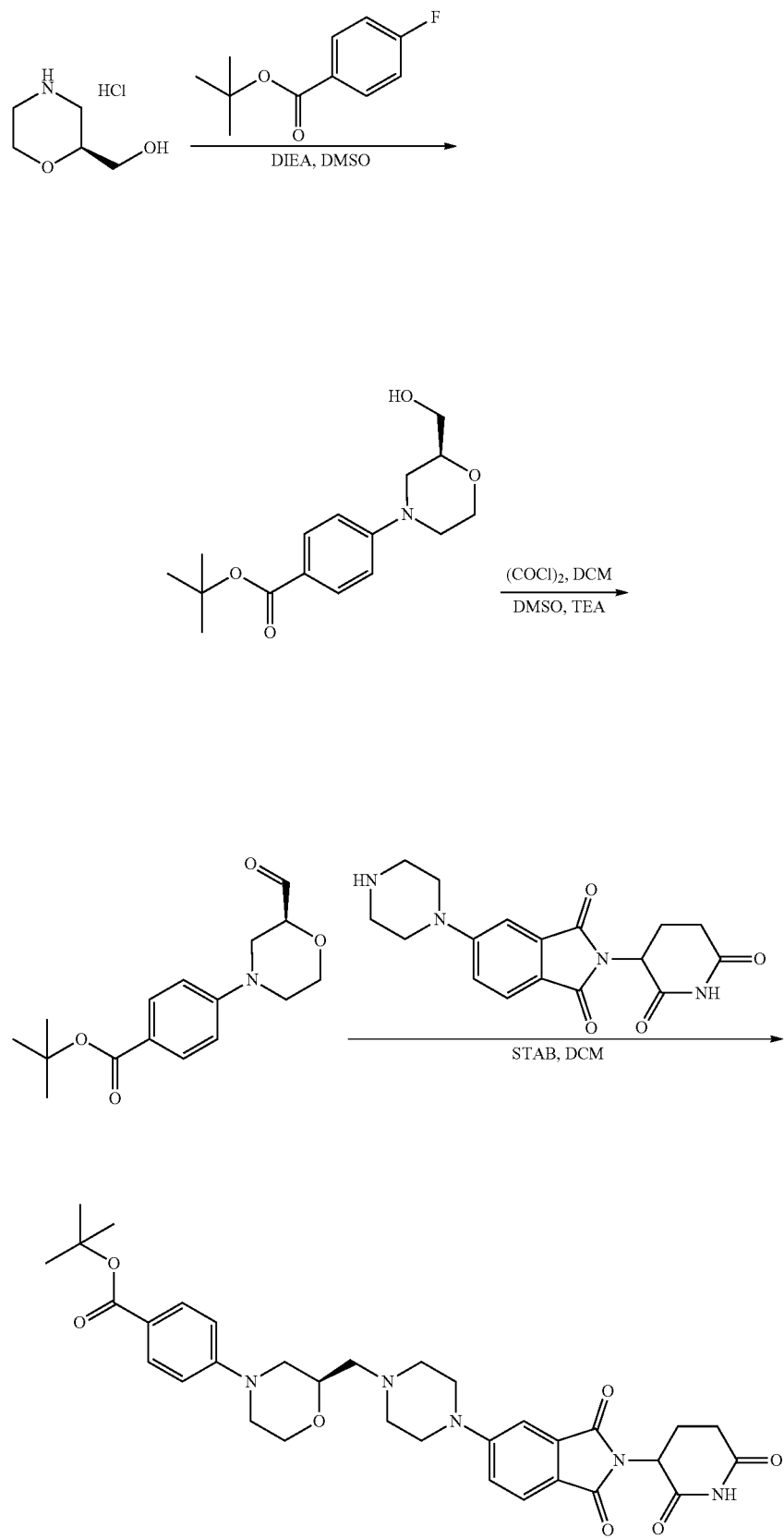

Scheme 39:
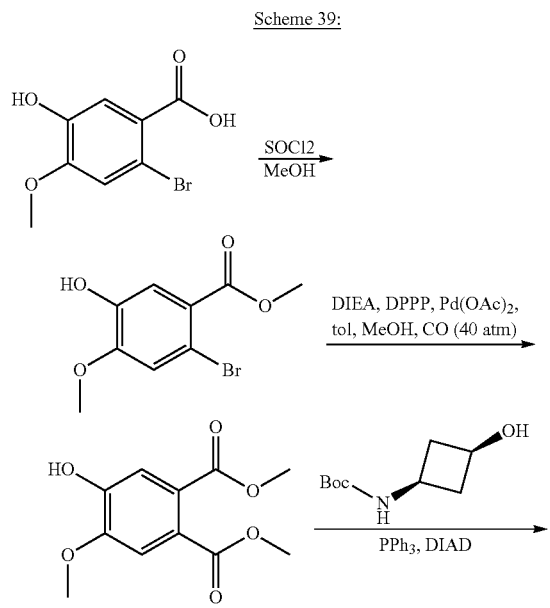
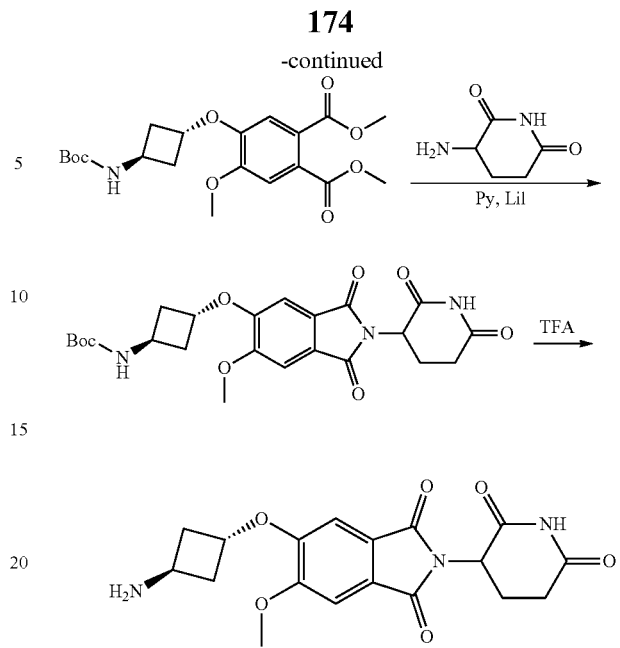
Scheme 40
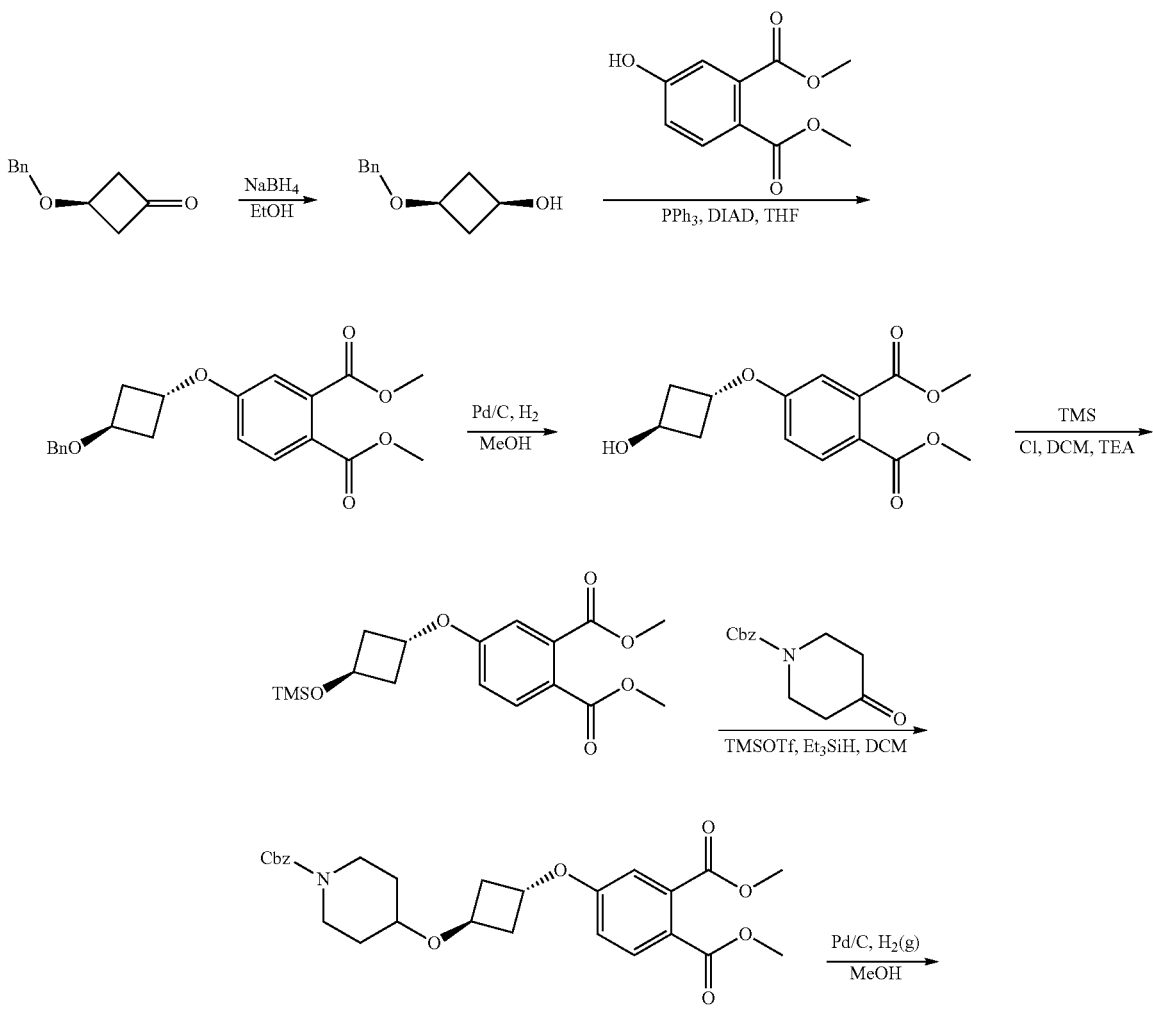

-continued
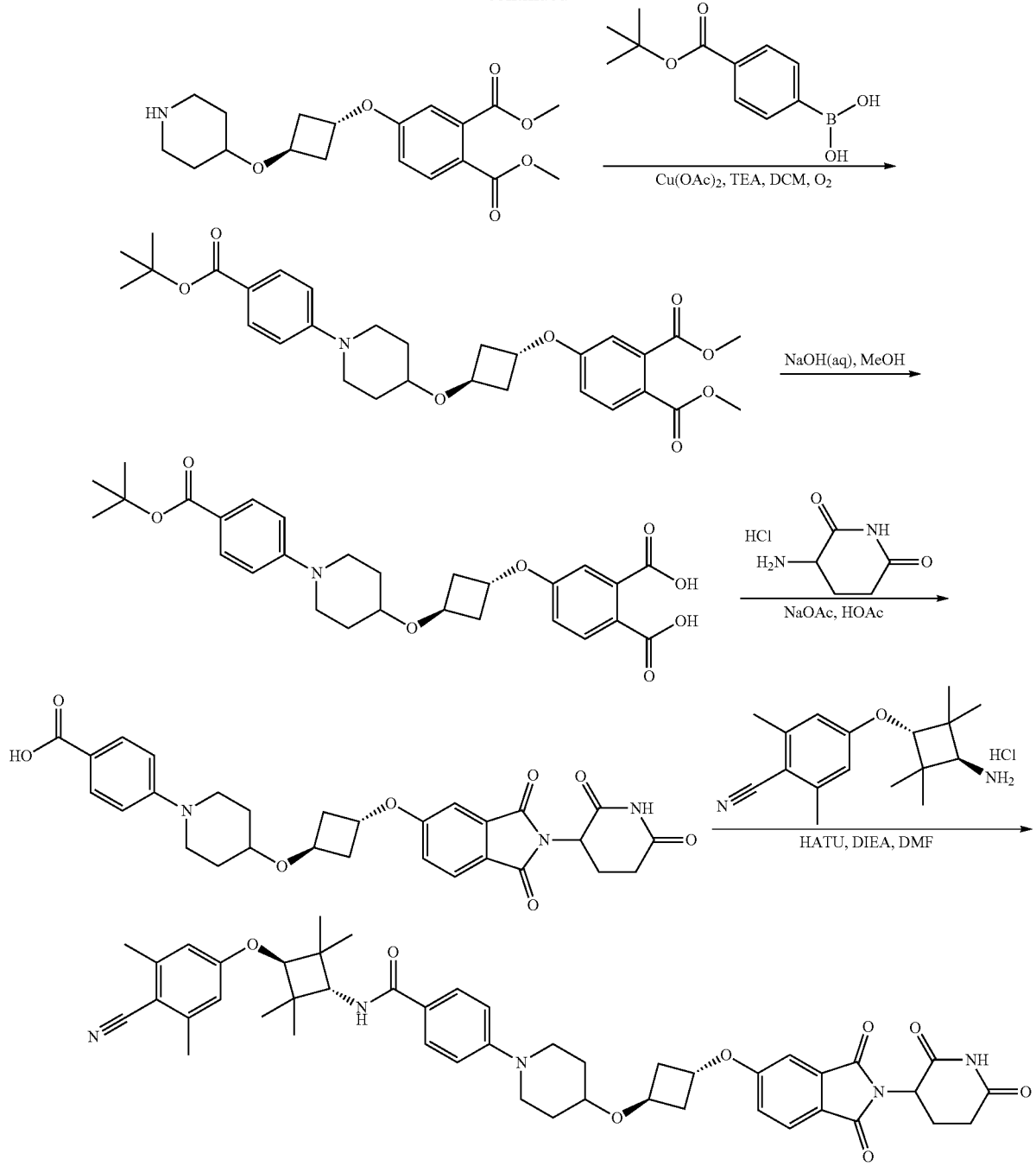
Scheme 41:
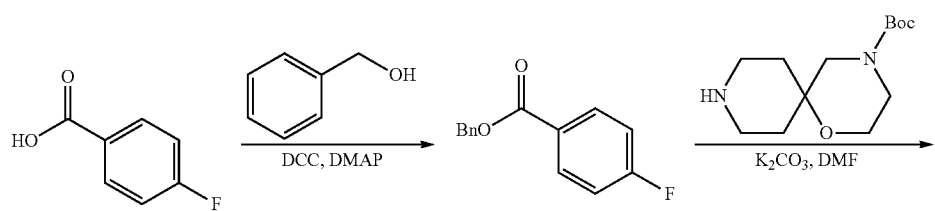

177 178
-continued
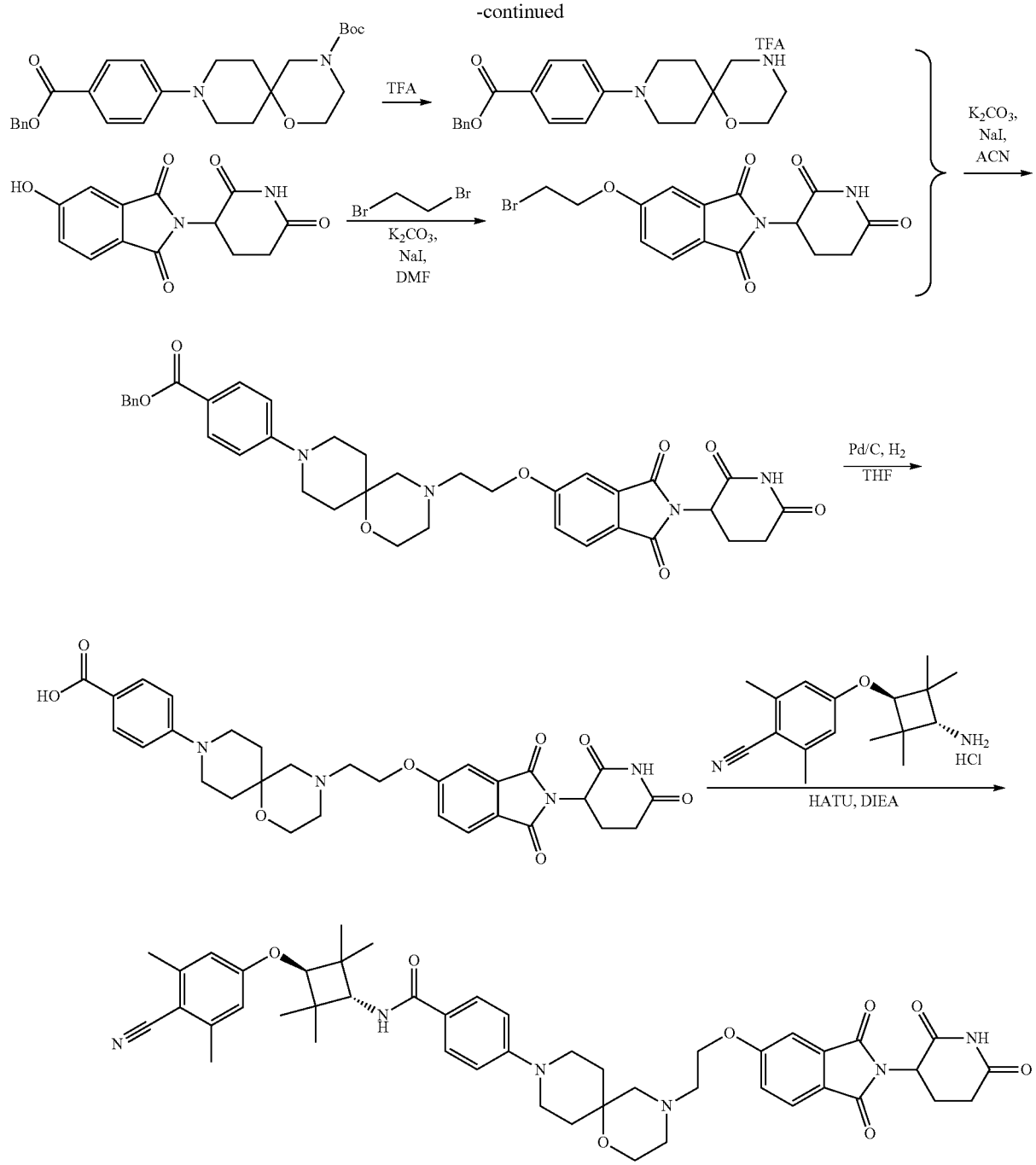
Scheme 42
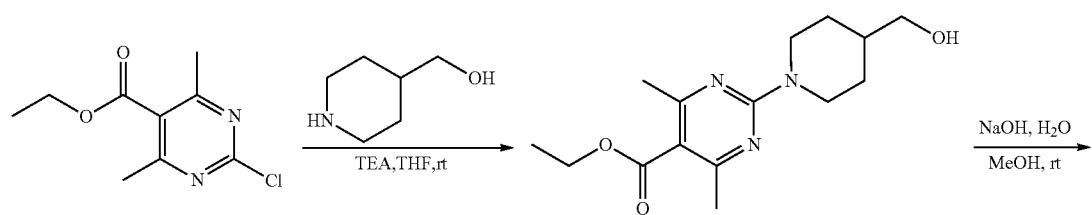

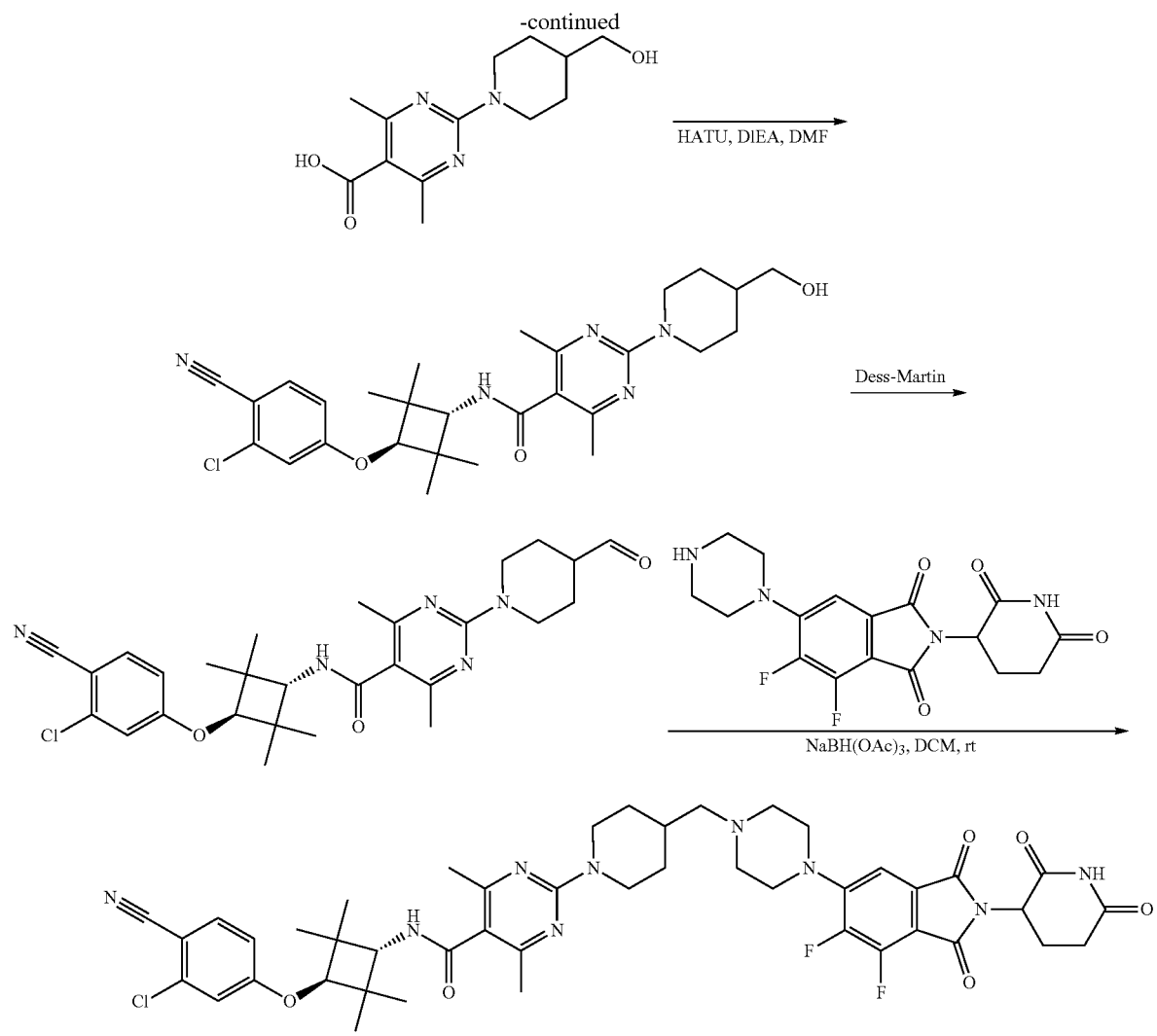
Scheme 43:
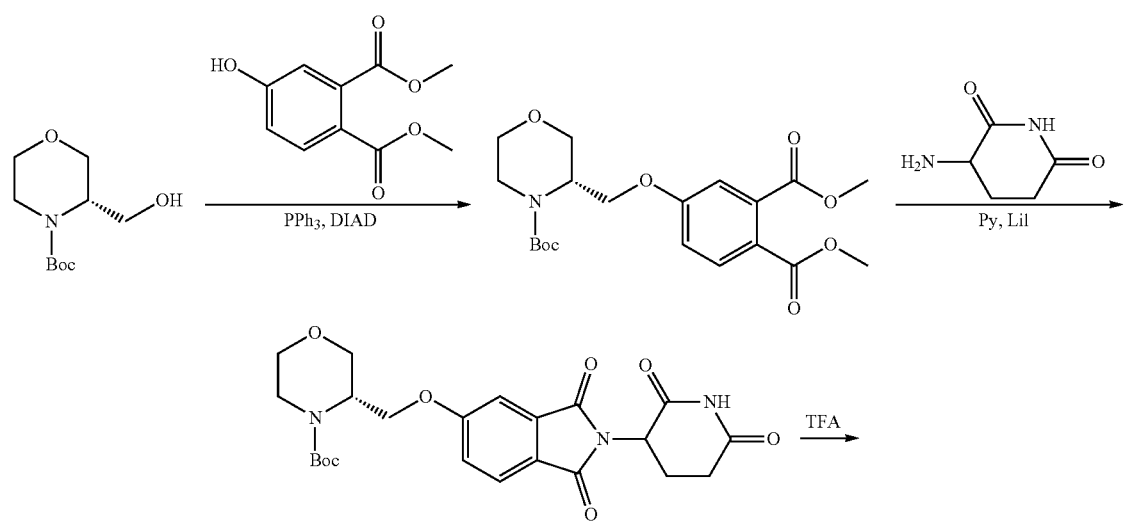

181 182
-continued
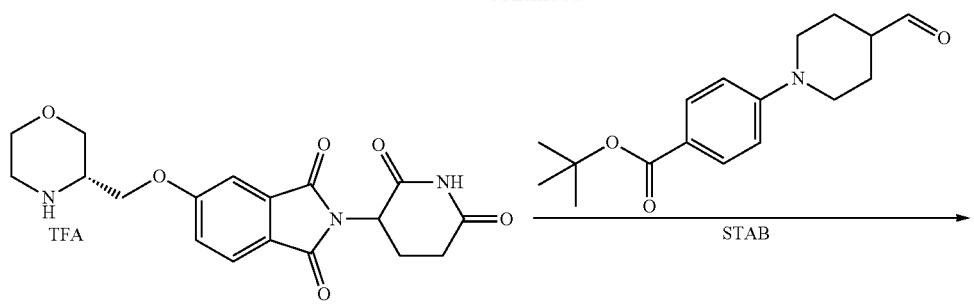
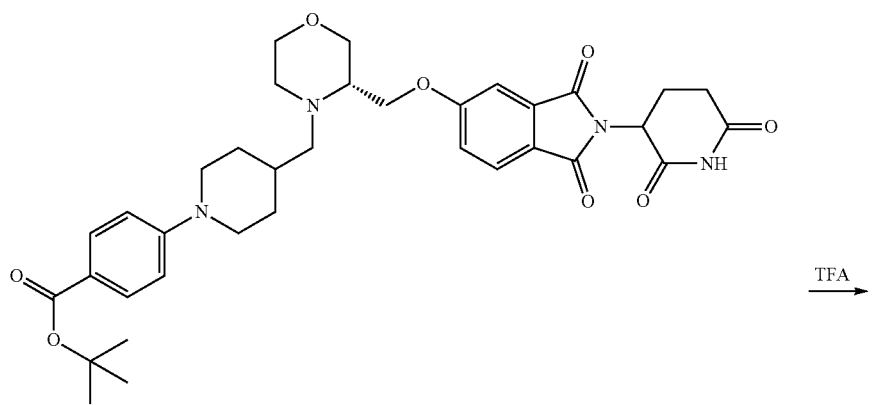
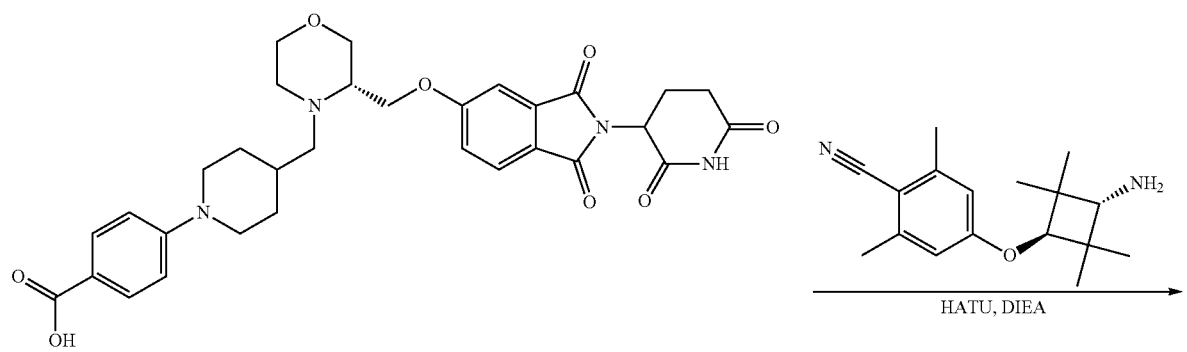
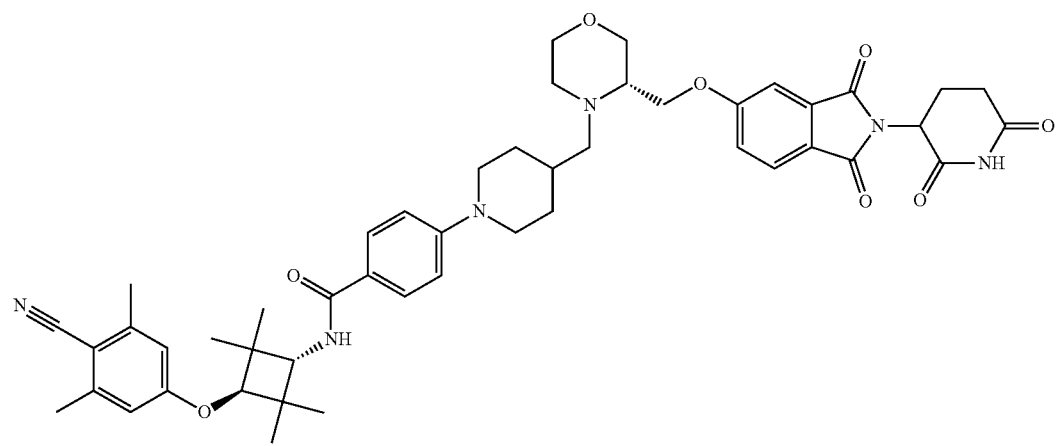

Scheme 44:
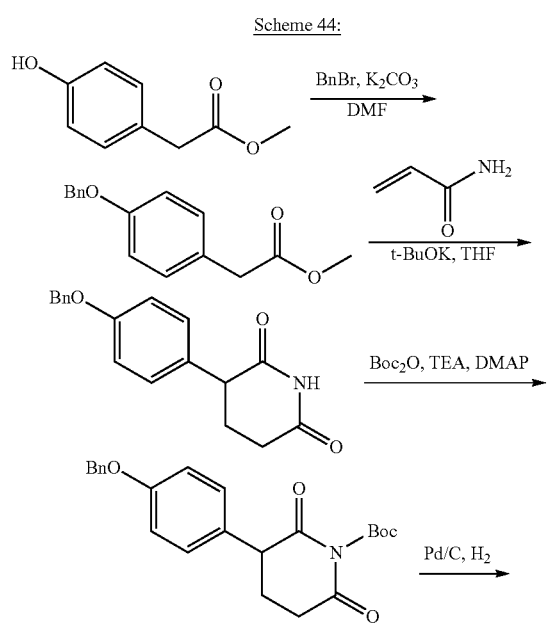
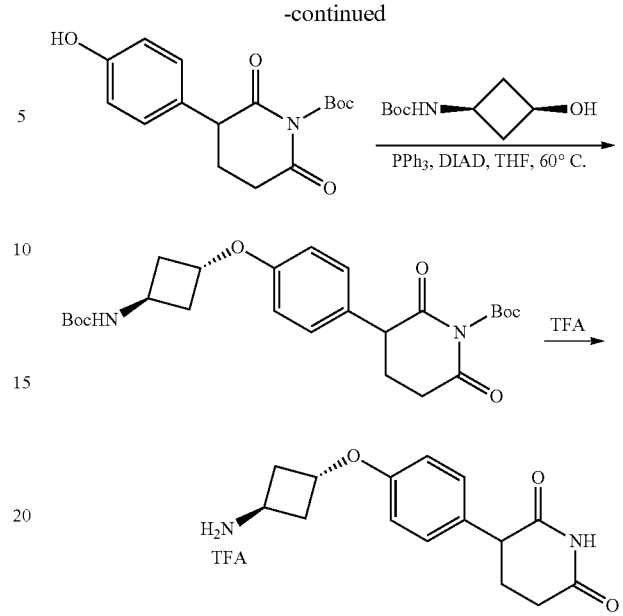
Scheme 45
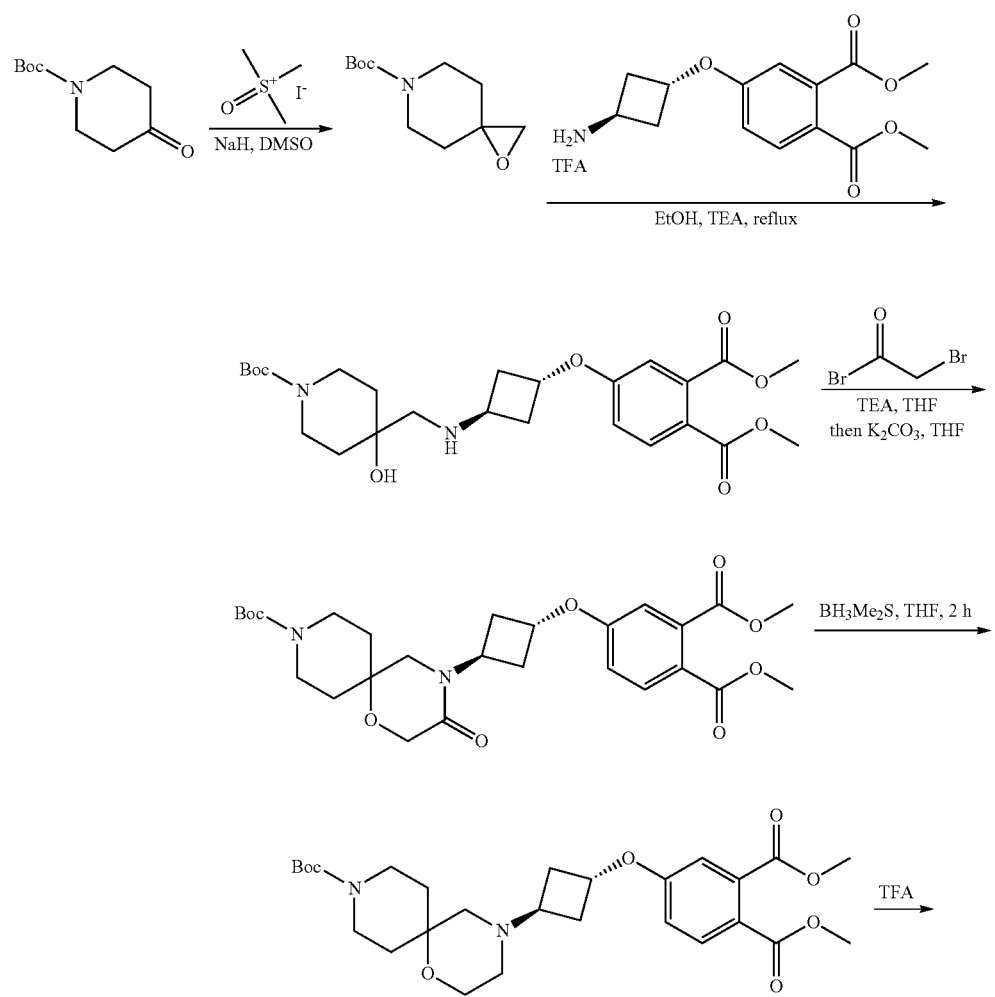

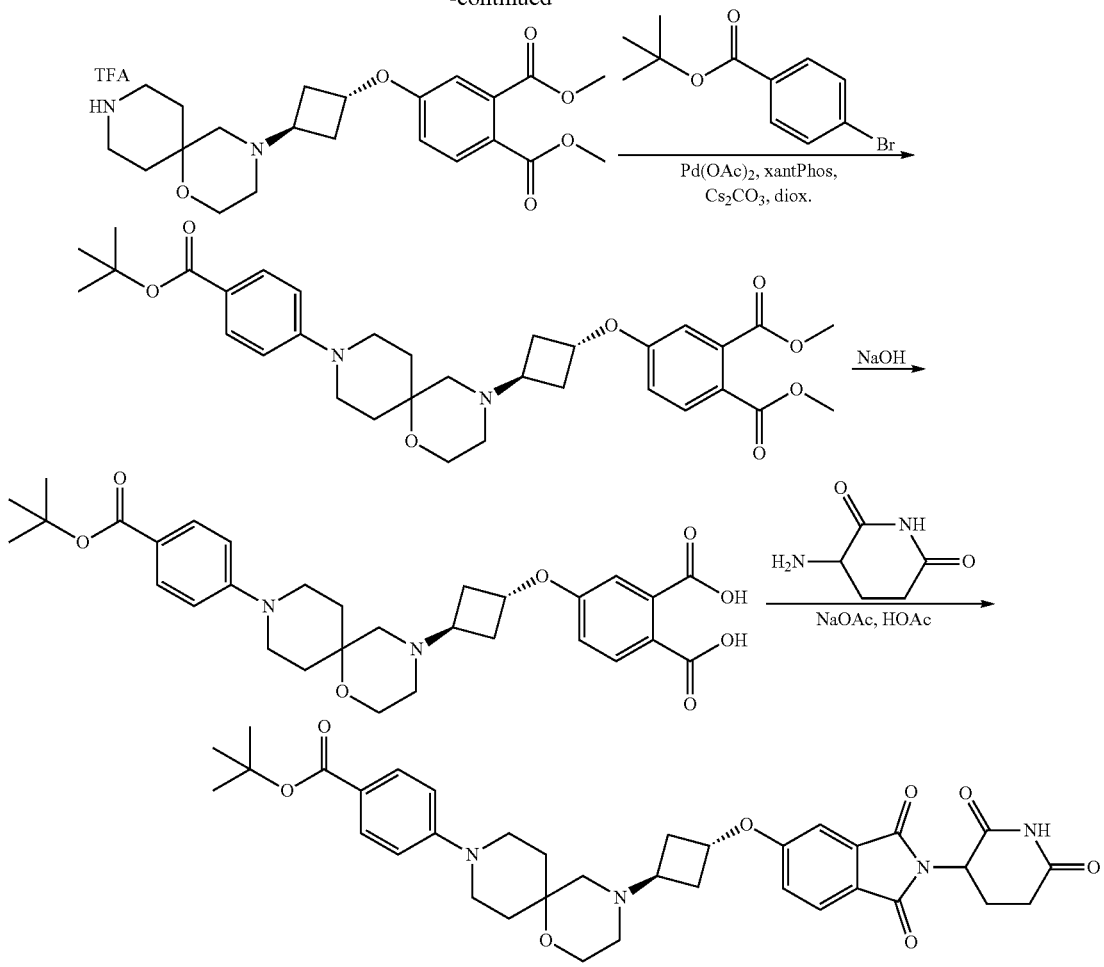
Scheme 46:
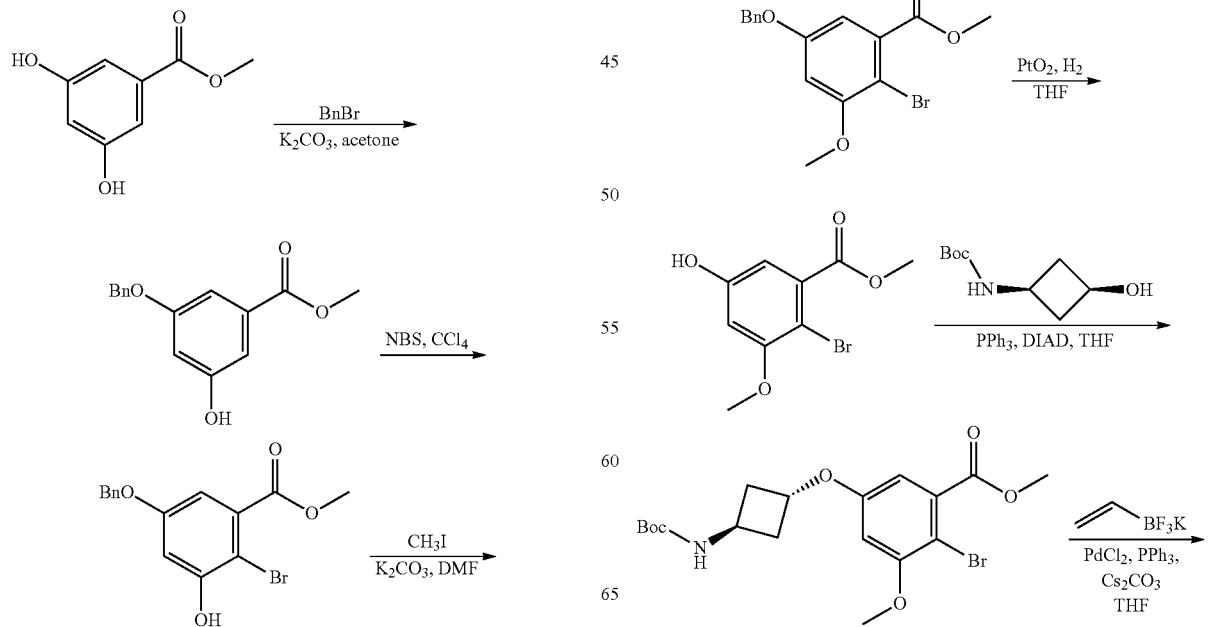

187
-continued
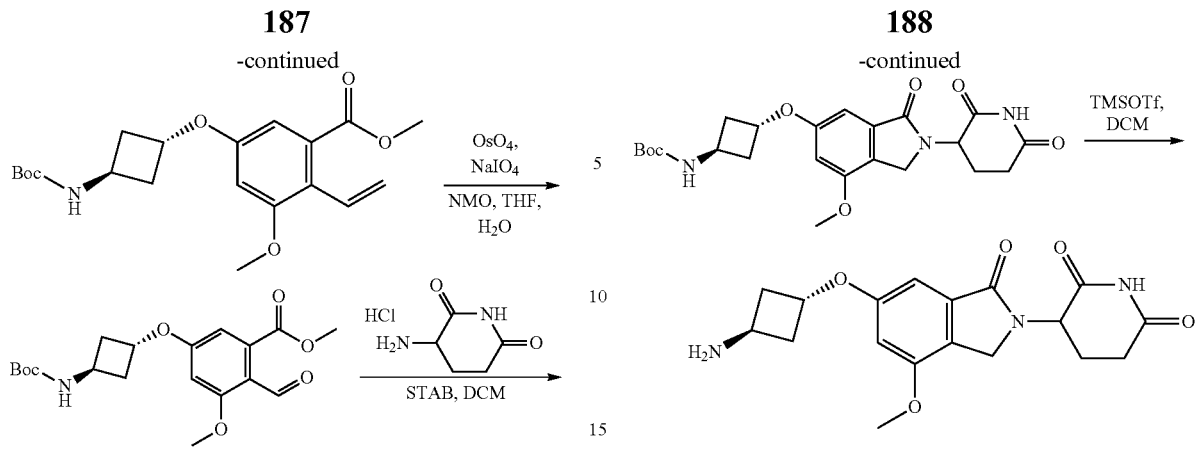
188
-continued
Scheme 47
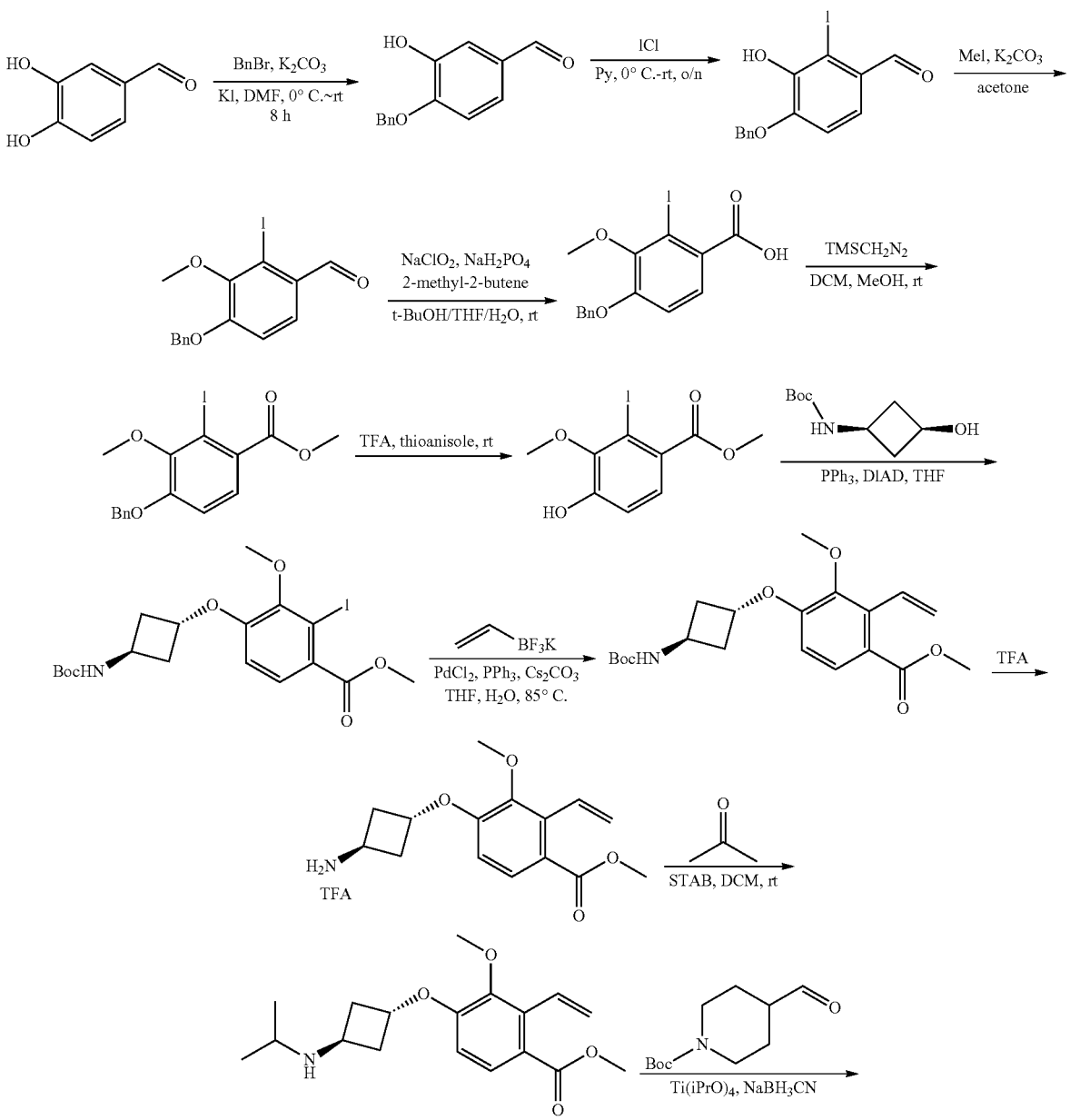

-continued
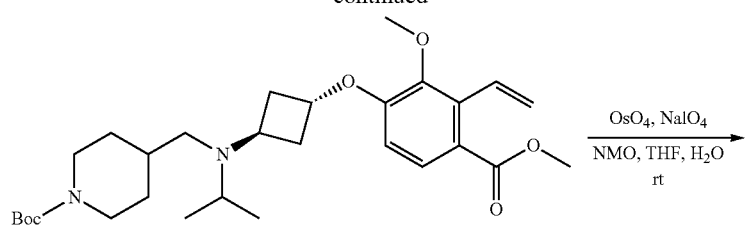
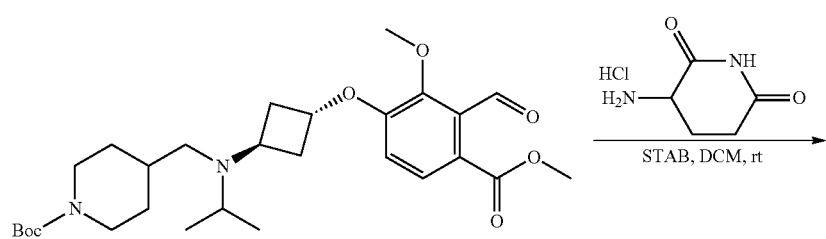
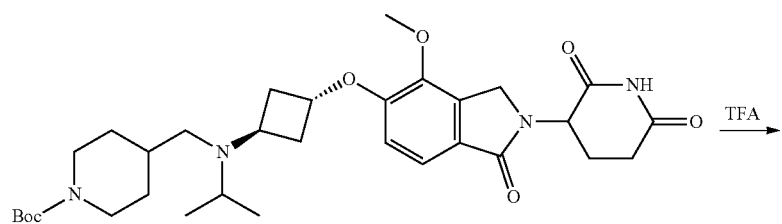
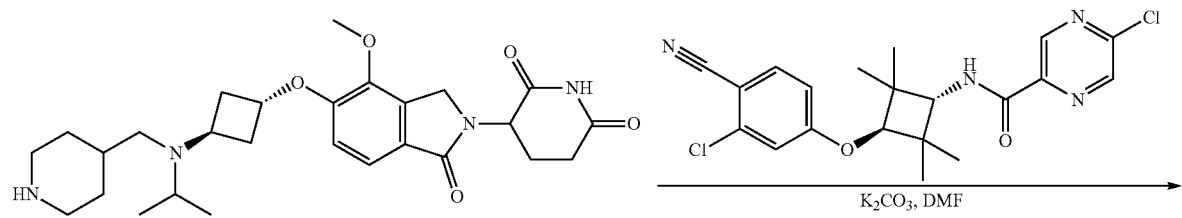
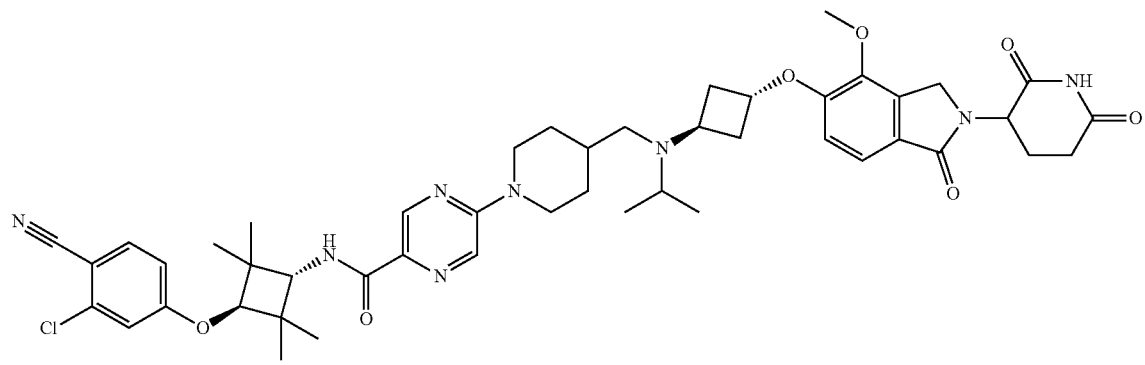

Scheme 48:
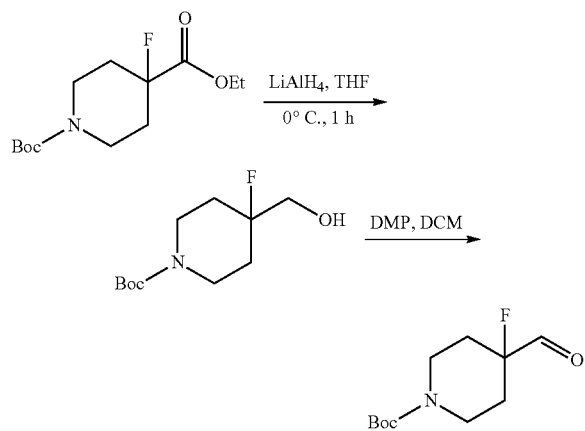
Scheme 49
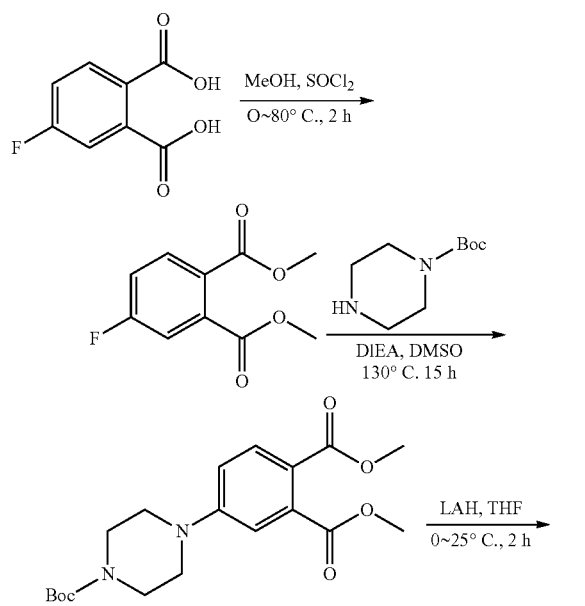
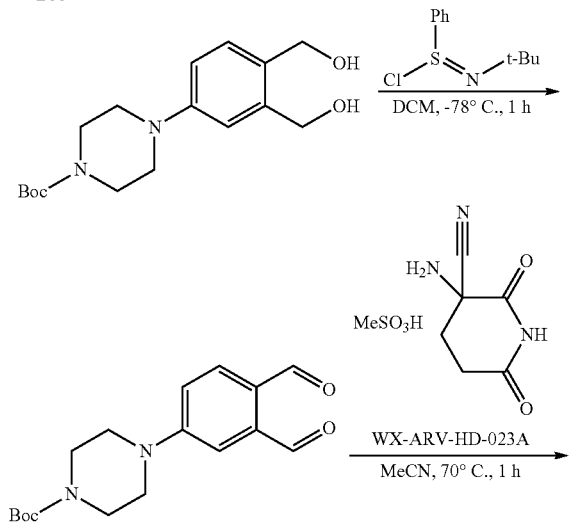
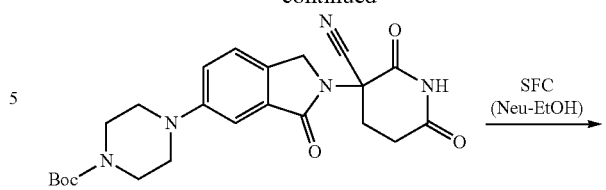
-continued
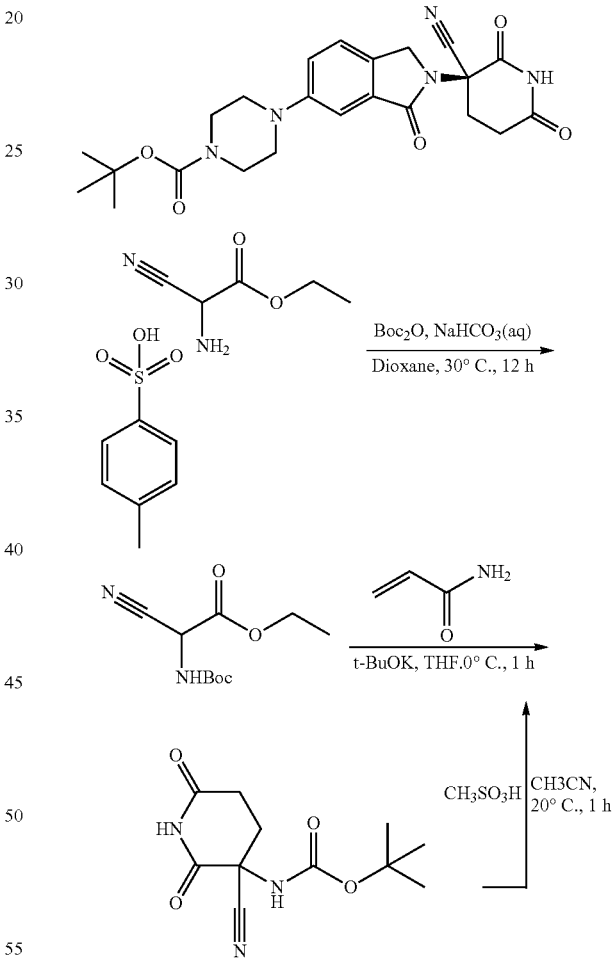
Scheme 50:

193
-continued
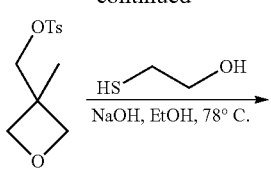
194
-continued
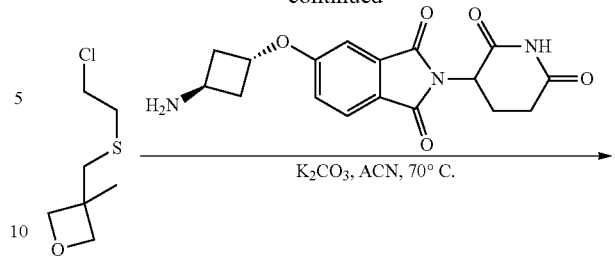
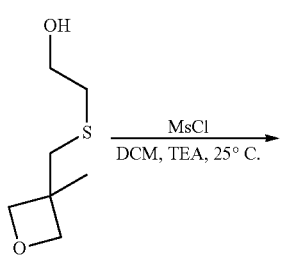
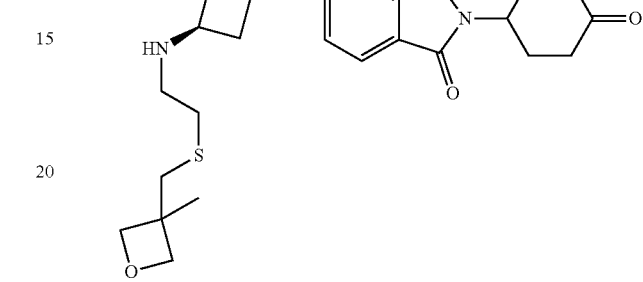
Scheme 51
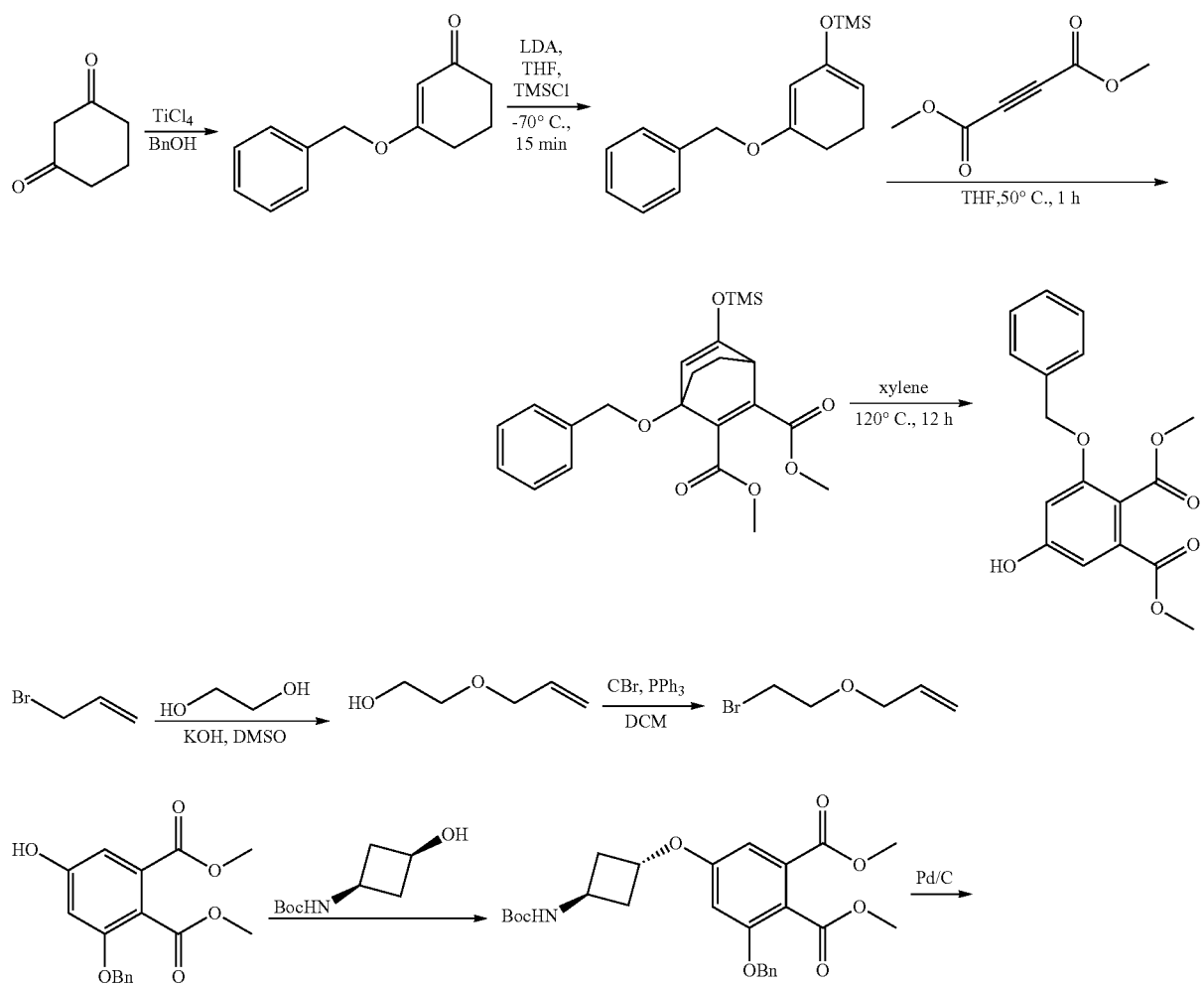

195
196
-continued
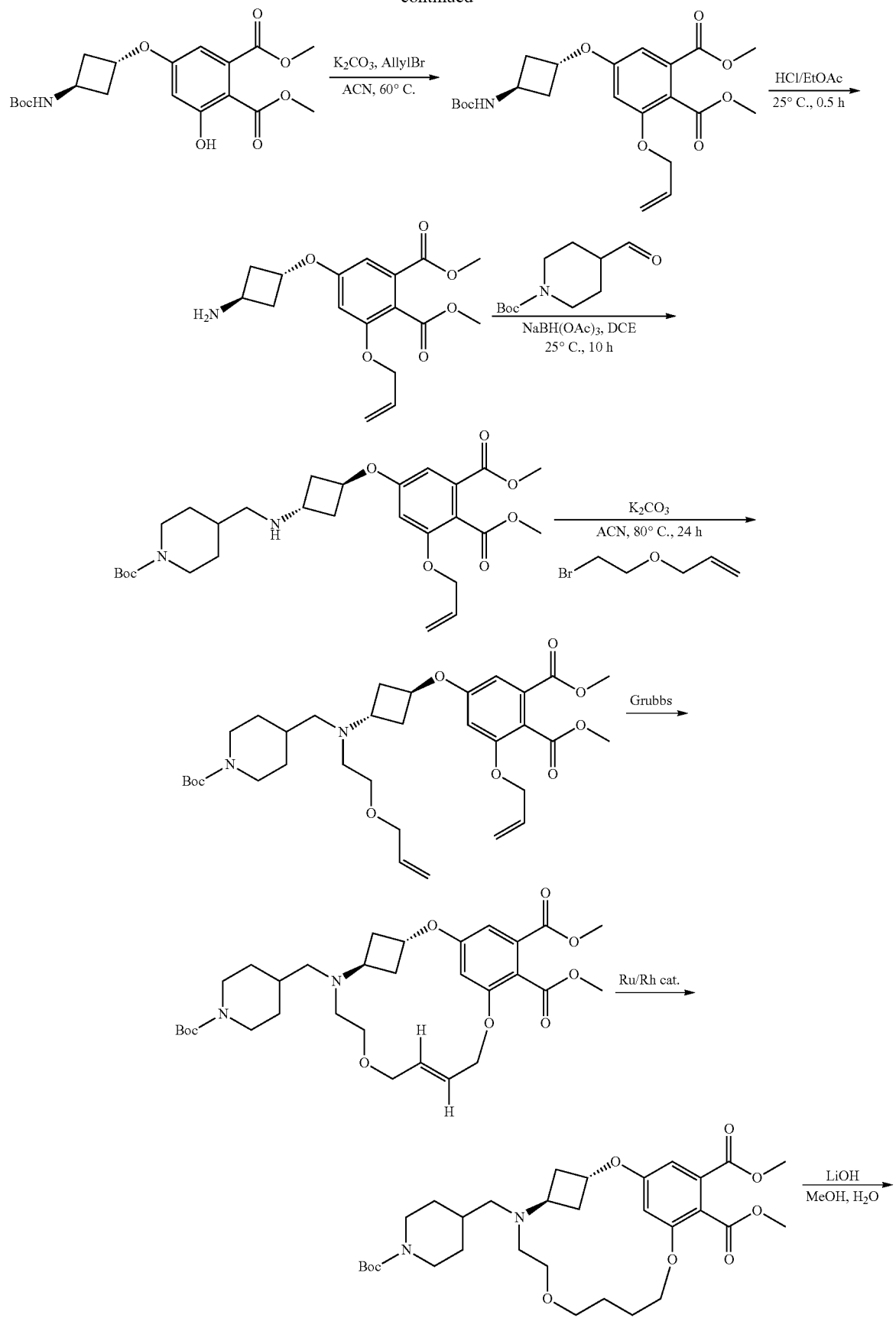

197 198
-continued
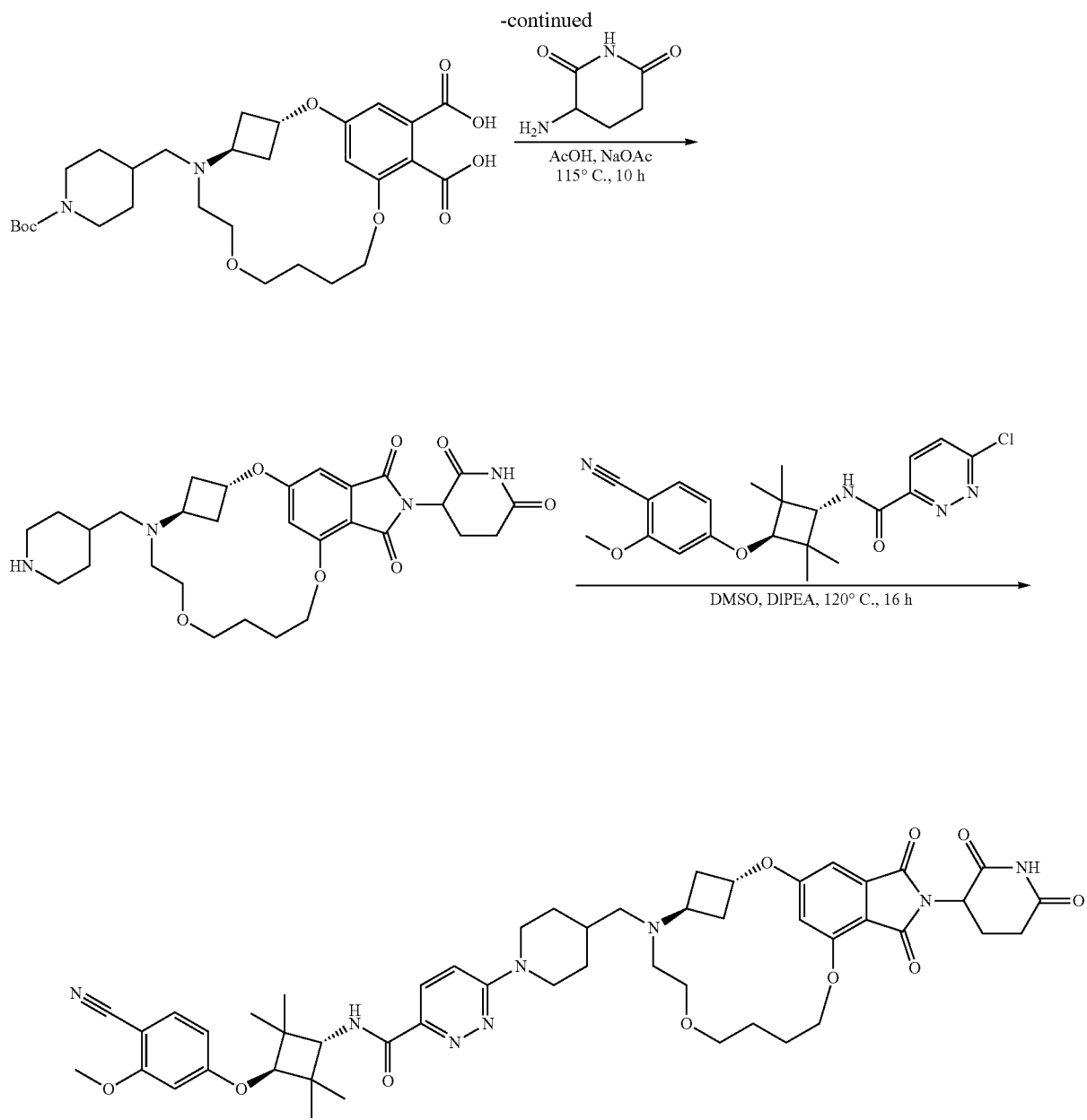
Scheme 52
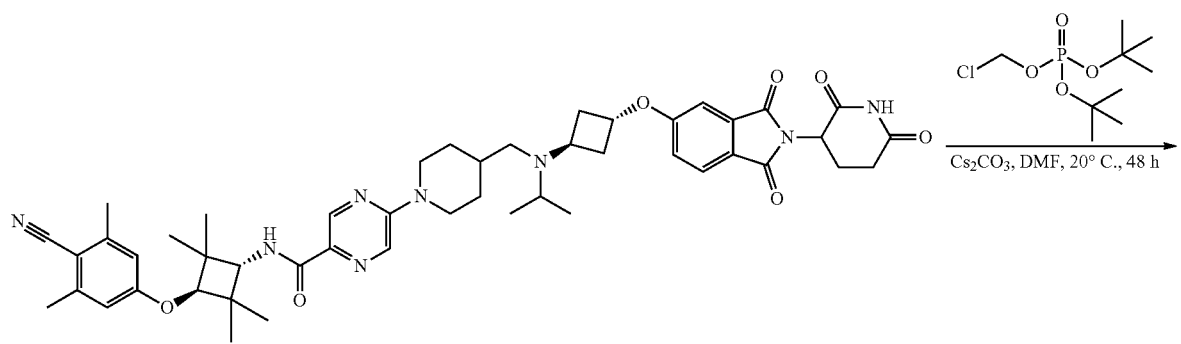

-continued
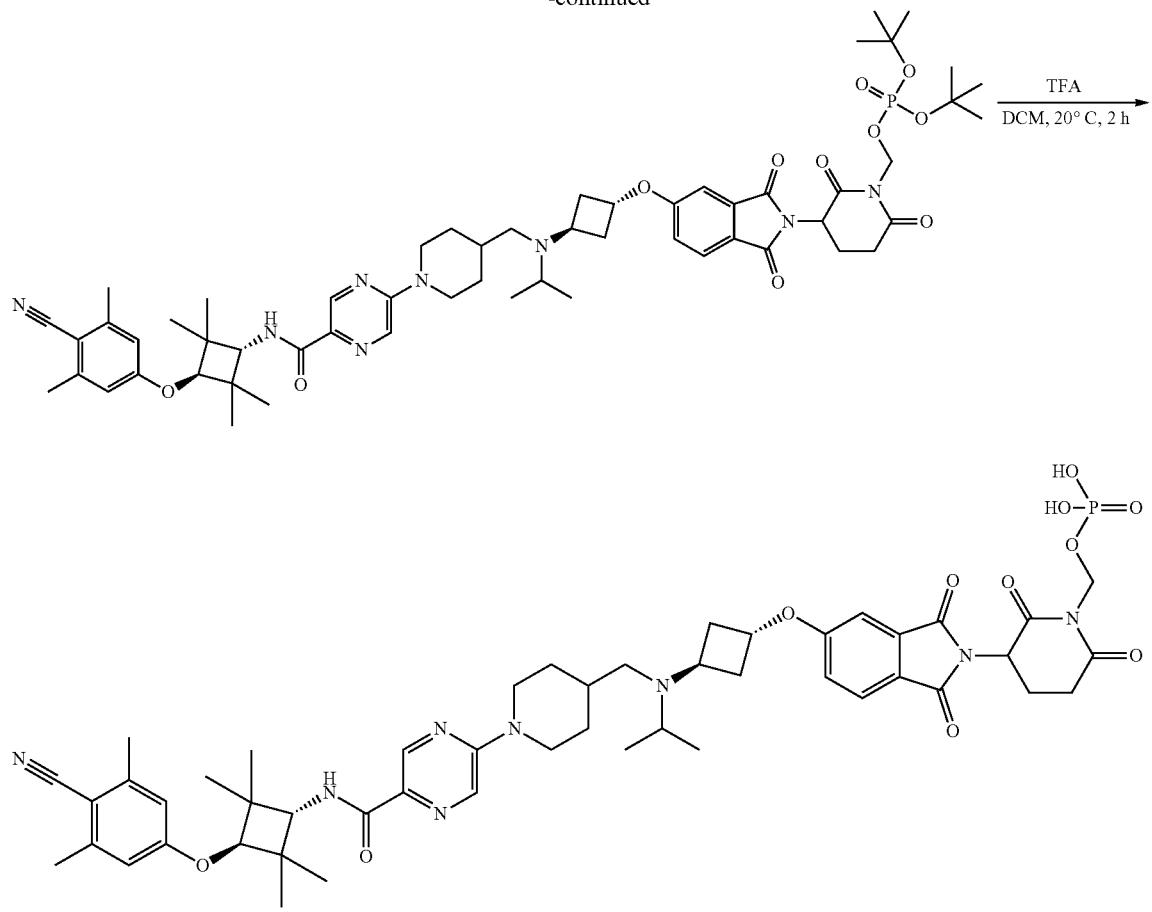
Scheme 53:
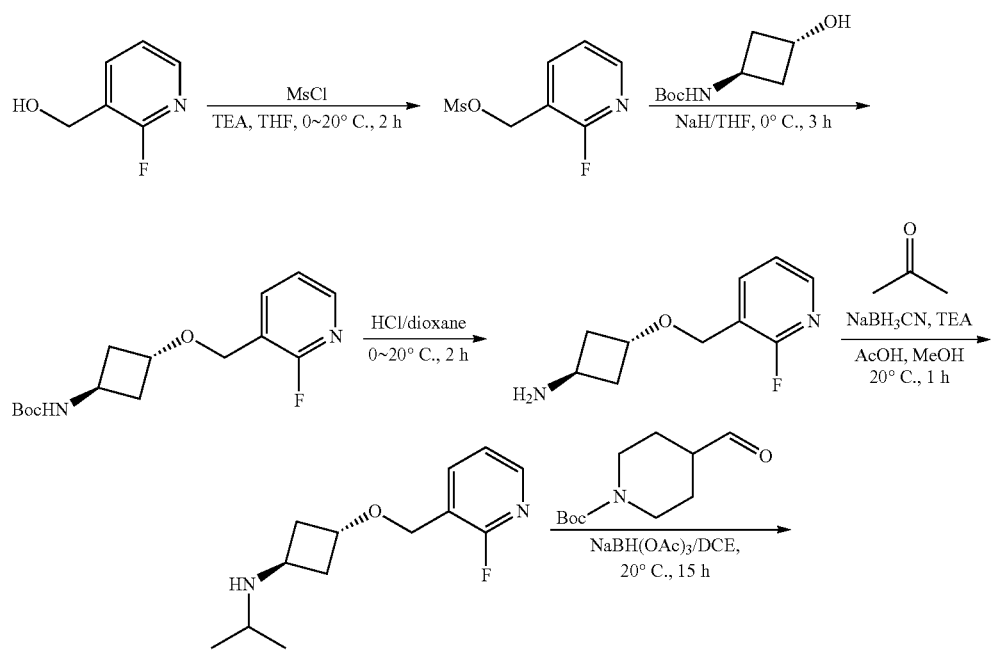

201
202
-continued
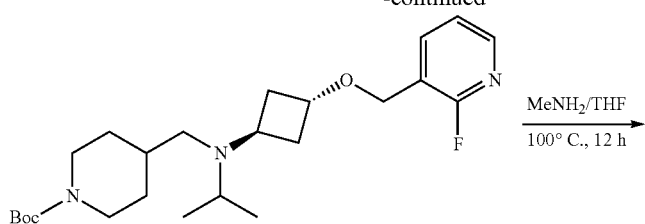
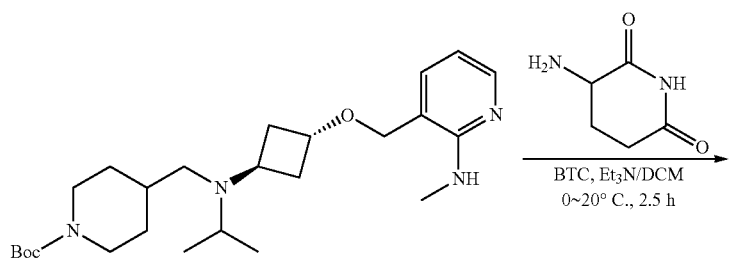
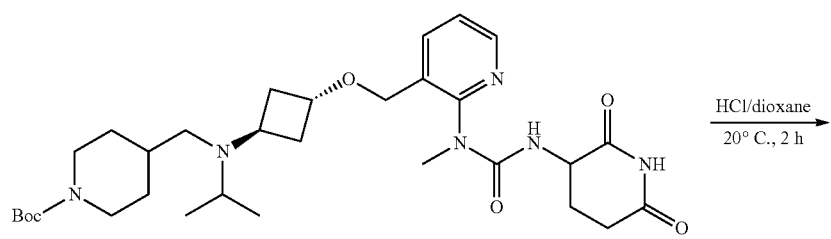
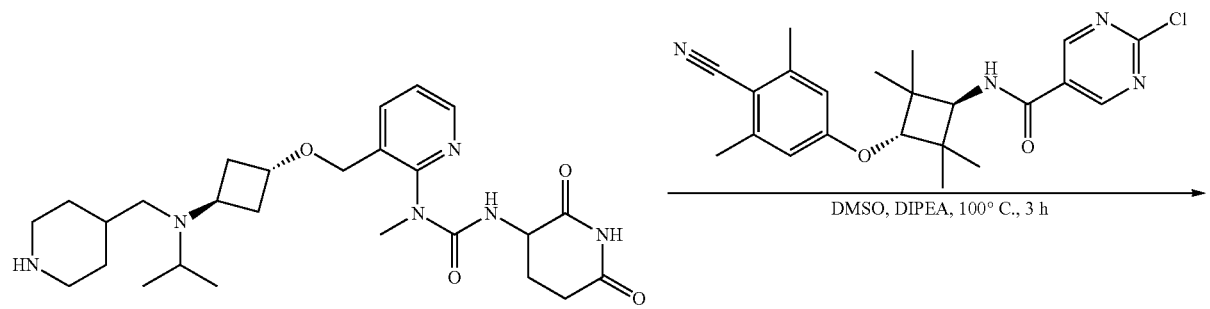
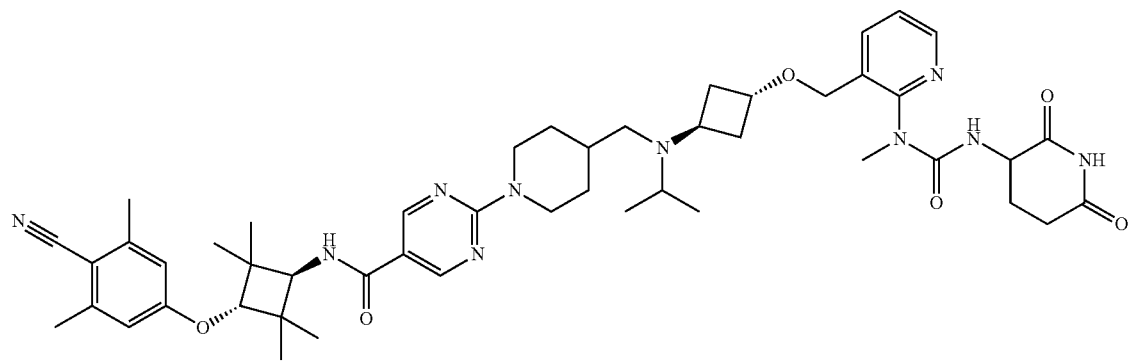

Scheme 54:
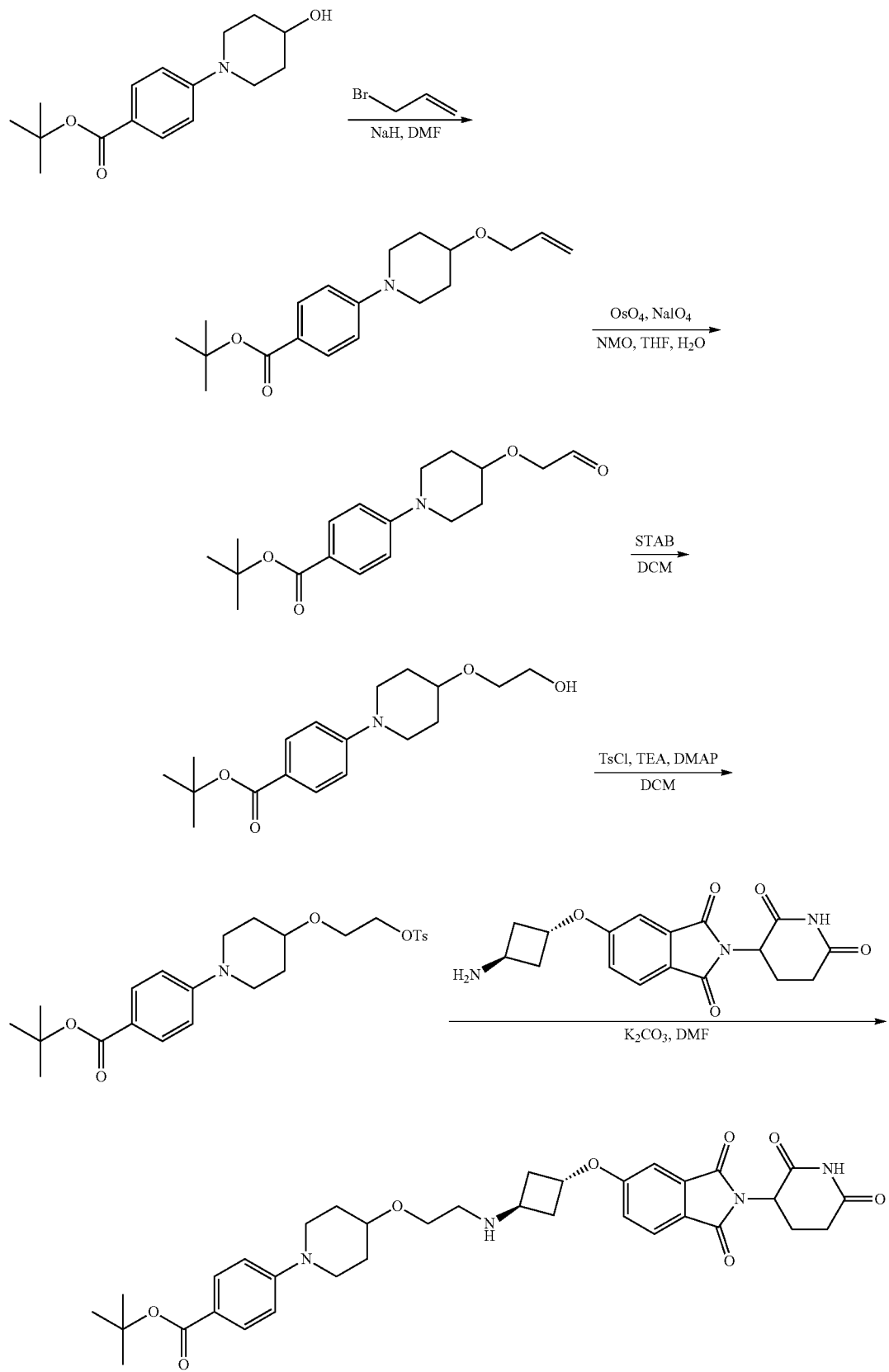

Exemplary Synthesis of Exemplary Compound 147: N-((1r,3r)-3-(4-cyano-3-methoxyphenoxy)-2,2,4,4-tetramethylcyclobutyl)-4-(4-((((1r,3r)-3-((2-(2,6-dioxopiperidin-3-yl)-1,3-dioxoisoindolin-5-yl)oxy)cyclobutyl)(ethyl)amino)methyl)piperidin-1-yl)benzamide Step 1: Preparation of dimethyl 4-((1r,3r)-3-(((1-(tert-butoxycarbonyl)piperidin-4-yl)methyl)amino)cyclobutoxy)phthalate

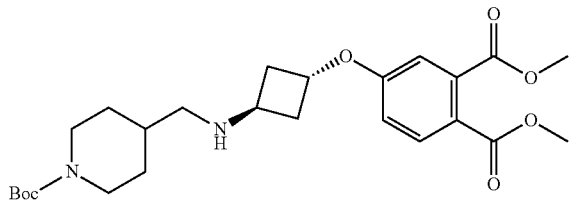 [SMILES: COC(=O)c1ccc(O[C@H]2C[C@H](NCC3CCN(C(=O)OC(C)(C)C)CC3)C2)cc1C(=O)OC]

To a solution of dimethyl 4-(3-aminocyclobutoxy)benzene-1,2-dicarboxylate (6.00 g, 21.48 mmol, 1.00 eq) and tert-butyl 4-formylpiperidine-1-carboxylate (5.04 g, 23.63 mmol, 1.10 eq) in dichloroethane (50 mL) was stirred at 20° C. for 10 h. Then the mixture was added sodium triacetoxyborohydride (13.66 g, 64.45 mmol, 3.00 eq) and stirred at 20° C. for 8 h. The reaction mixture was diluted with methanol (60 mL) and concentrated under reduced pressure to give a residue. The residue was purified by column chromatography on silica gel (petroleum ether: ethyl acetate=1:1 to 0:1) to give dimethyl 4-[3-[(1-tert-butoxycarbonyl-4-piperidyl)methylamino]cyclobutoxy]benzene-1,2-dicarboxylate (9.00 g, 18.89 mmol, 88% yield) as a light yellow oil. LC/MS (ESI) m/z: 499.1 [M+23]+.

Step 2: Preparation of dimethyl 4-((1r,3r)-3-(((1-(tert-butoxycarbonyl)piperidin-4-yl)methyl)(ethyl)amino)cyclobutoxy)phthalate

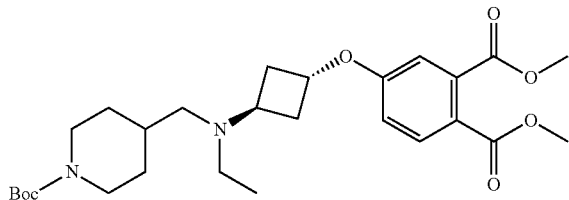 [SMILES: CCN(CC1CCN(C(=O)OC(C)(C)C)CC1)[C@H]1C[C@H](Oc2ccc(C(=O)OC)c(C(=O)OC)c2)C1]

To a solution of dimethyl 4-[3-[(1-tert-butoxycarbonyl-4-piperidyl)methylamino]cyclobutoxy]benzene-1,2-dicarboxylate (2.80 g, 5.88 mmol, 1.00 eq) and iodoethane (3.67 g, 23.50 mmol, 1.88 mL, 4.00 eq) in acetonitrile (30 mL) was added potassium carbonate (2.84 g, 20.56 mmol, 219.30 uL, 3.50 eq). The mixture was stirred at 70° C. for 5 h. The reaction mixture was filtered and concentrated under reduced pressure to give dimethyl 4-[3-[(1-tert-butoxycarbonyl-4-piperidyl)methyl-ethyl-amino]cyclobutoxy]benzene-1,2-dicarboxylate (2.30 g, 4.56 mmol, 78% yield) as a yellow oil. LC/MS (ESI) m/z: 505.4 [M+1]+; 1H-NMR (400 MHz, CDCl3) δ 7.80 (d, J=8.6 Hz, 1H), 6.93 (d, J=2.4 Hz, 1H), 6.87 (dd, J=8.6, 2.4 Hz, 1H), 3.90 (d, J=18.4 Hz, 6H), 3.49-3.41 (m, 1H), 2.69 (br s, 2H), 2.56 (q, J=6.8 Hz, 2H), 2.37-2.23 (m, 4H), 2.17 (br d, J=6.4 Hz, 2H), 1.76 (br d, J=12.4 Hz, 2H), 1.61 (br s, 4H), 1.46 (s, 9H), 1.02 (br d, J=11.2 Hz, 2H), 0.95 (br t, J=7.2 Hz, 3H).

Step 3: Preparation of dimethyl 4-((1r,3r)-3-(ethyl(piperidin-4-ylmethyl)amino)cyclobutoxy)phthalate

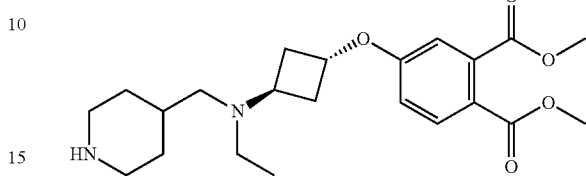

To a solution of dimethyl 4-[3-[(1-tert-butoxycarbonyl-4-piperidyl)methyl-ethyl-amino]cyclobutoxy]benzene-1,2-dicarboxylate (1.30 g, 2.58 mmol, 1.00 eq) in ethyl acetate (13 mL) was added hydrochloride/ethyl acetate (4 M, 5 mL, 7.76 eq). The mixture was stirred at 25° C. for 3 h. The reaction mixture was filtered and concentrated under reduced pressure to give dimethyl 4-[3-[ethyl(4-piperidylmethyl)amino]cyclobutoxy]benzene-1,2-dicarboxylate (1.30 g, hydrochloride salt) as a yellow solid. LC/MS (ESI) m/z: 405.3 [M+1]+.

Step 4: Preparation of dimethyl 4-((1r,3r)-3-(((1-(4-(tert-butoxycarbonyl)phenyl)piperidin-4-yl)methyl)(ethyl)amino)cyclobutoxy)phthalate

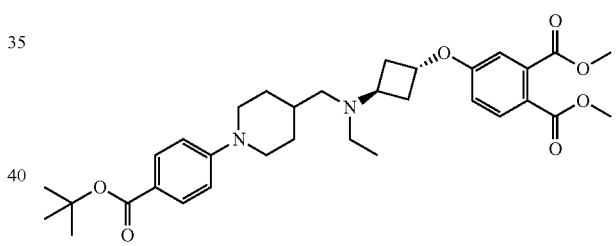

To a solution of dimethyl 4-[3-[ethyl(4-piperidylmethyl)amino]cyclobutoxy]benzene-1,2-dicarboxylate (1.30 g, 3.21 mmol, 1.00 eq, hydrochloride salt) in dioxane (15 mL) was added tert-butyl 4-bromobenzoate (991.63 mg, 3.86 mmol, 1.20 eq), palladium(II) acetate (36.08 mg, 160.69 umol, 0.05 eq), (±)-2,2'-bis(diphenylphosphino)-1,1'-binaphthalene (200.12 mg, 321.39 umol, 0.10 eq) and cesium carbonate (3.66 g, 11.25 mmol, 3.50 eq). The mixture was stirred at 110° C. for 10 h under nitrogen atmosphere. The reaction mixture was diluted with dichloromethane (20 mL) and filtered. The filtrate was concentrated under reduced pressure to give the residue. The residue was purified by column chromatography on silica gel (petroleum ether:ethyl acetate=10:1 to 1:1) to give dimethyl 4-[3-[[1-(4-tert-butoxycarbonylphenyl)-4-piperidyl]methyl-ethyl-amino]cyclobutoxy]benzene-1,2-dicarboxylate (1.10 g, 1.89 mmol, 59% yield) as a light yellow oil. LC/MS (ESI) m/z: 581.4 [M+1]+; 1H-NMR (400 MHz, DMSO-d6) δ 7.77 (d, J=8.8 Hz, 1H), 7.69 (br d, J=8.8 Hz, 2H), 7.06-7.01 (m, 1H), 6.99 (d, J=2.0 Hz, 1H), 6.92 (br d, J=8.8 Hz, 2H), 4.81 (br s, 1H), 3.88 (br d, J=12.8 Hz, 2H), 3.78 (d, J=7.2 Hz, 6H), 3.42-3.36 (m, 1H), 2.80 (br t, J=11.6 Hz, 2H), 2.30 (br d, J=6.4 Hz, 2H), 2.16 (br d, J=6.4 Hz, 4H), 1.99 (s, 2H), 1.79 (br d, J=11.6 Hz, 2H), 1.50 (s, 9H), 1.23 (br s, 1H), 1.14-1.05 (m, 2H), 0.90 (br t, J=6.8 Hz, 3H).

Step 5: Preparation of 4-((1r,3r)-3-(((1-(4-(tert-butoxycarbonyl)phenyl)piperidin-4-yl)methyl)(ethyl)amino)cyclobutoxy)phthalic acid

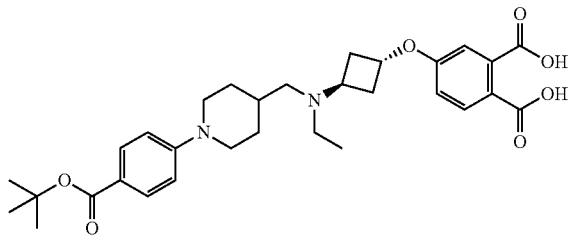 [SMILES: CCN(CC1CCN(c2ccc(C(=O)OC(C)(C)C)cc2)CC1)[C@H]1C[C@H](Oc2ccc(C(=O)O)c(C(=O)O)c2)C1]

To a solution of dimethyl 4-[3-[[1-(4-tert-butoxycarbonylphenyl)-4-piperidyl]methyl-ethyl-amino]cyclobutoxy]benzene-1,2-dicarboxylate (1.10 g, 1.89 mmol, 1.00 eq) in methanol (12 mL) and water (3 mL) was added lithium hydroxide (357.67 mg, 8.52 mmol, 4.50 eq). The mixture was stirred at 40° C. for 2.5 h. The reaction mixture was concentrated under reduced pressure. The residue was diluted with water (20 mL) and neutralized with hydrochloric acid (1 M) to pH=3-4. Then the mixture was extracted with ethyl acetate (80 mL). The organic layer was dried over anhydrous sodium sulfate, filtered and concentrated under reduced pressure to give 4-[3-[[1-(4-tert-butoxycarbonylphenyl)-4-piperidyl]methyl-ethyl-amino]cyclobutoxy]phthalic acid (1.00 g, 1.81 mmol, 95% yield) as a light yellow solid. LC/MS (ESI) m/z: 553.2 [M+1]$^+$.

Step 6: Preparation of 4-(4-((((1r,3r)-3-((2-(2,6-dioxopiperidin-3-yl)-1,3-dioxoisoindolin-5-yl)oxy)cyclobutyl)(ethyl)amino)methyl)piperidin-1-yl)benzoic acid

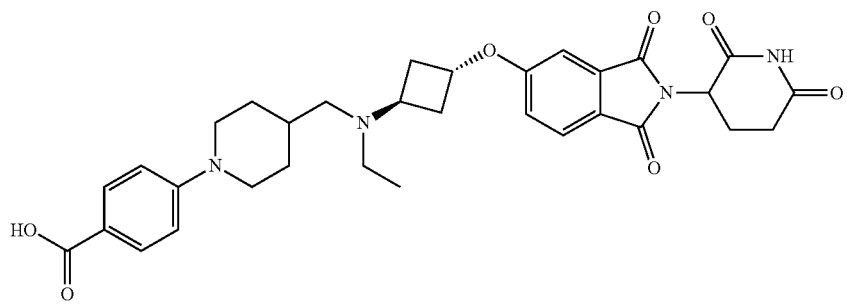 [SMILES: CCN(CC1CCN(c2ccc(C(=O)O)cc2)CC1)[C@H]1C[C@H](Oc2ccc3c(c2)C(=O)N(C2CCC(=O)NC2=O)C3=O)C1]

To a solution of 4-[3-[[1-(4-tert-butoxycarbonylphenyl)-4-piperidyl]methyl-ethyl-amino]cyclobutoxy]phthalic acid (1.00 g, 1.81 mmol, 1.00 eq) and 3-aminopiperidine-2,6-dione (327.60 mg, 1.99 mmol, 1.10 eq, hydrochloride salt) in acetic acid (10 mL) were added sodium acetate (445.29 mg, 5.43 mmol, 3.00 eq). The mixture was stirred at 110° C. for 8 h. The reaction mixture was concentrated under reduced pressure to give the residue. The residue was purified by medium pressure liquid chromatography (formate condition) to give 4-[4-[[[3-[2-(2,6-dioxo-3-piperidyl)-1,3-dioxo-isoindolin-5-yl]oxycyclobutyl]-ethyl-amino]methyl]-1-piperidyl]benzoic acid (640.00 mg, 1.09 mmol, 60% yield) as a black brown solid. LC/MS (ESI) m/z: 589.1 [M+1]$^+$; $^1$H-NMR (400 MHz, DMSO-d$_6$) δ 11.10 (s, 1H), 8.14 (s, 1H), 7.83 (d, J=8.8 Hz, 1H), 7.74 (d, J=9.2 Hz, 2H), 7.29-7.23 (m, 2H), 6.93 (d, J=9.2 Hz, 2H), 5.11 (dd, J=12.8, 5.2 Hz, 1H), 4.98-4.89 (m, 1H), 3.90 (br d, J=12.8 Hz, 2H), 3.45 (td, J=14.8, 7.6 Hz, 2H), 2.94-2.86 (m, 1H), 2.86-2.78 (m, 2H), 2.61-2.52 (m, 3H), 2.38 (td, J=13.6, 6.8 Hz, 2H), 2.27-2.15 (m, 4H), 2.09-2.00 (m, 1H), 1.81 (br d, J=11.2 Hz, 2H), 1.66 (br s, 1H), 1.19-1.07 (m, 2H), 0.92 (t, J=7.2 Hz, 3H).

Step 7: Preparation of N-((1r,3r)-3-(4-cyano-3-methoxyphenoxy)-2,2,4,4-tetramethylcyclobutyl)-4-(4-((((1r,3r)-3-((2-(2,6-dioxopiperidin-3-yl)-1,3-dioxoisoindolin-5-yl)oxy)cyclobutyl)(ethyl)amino)methyl)piperidin-1-yl)benzamide

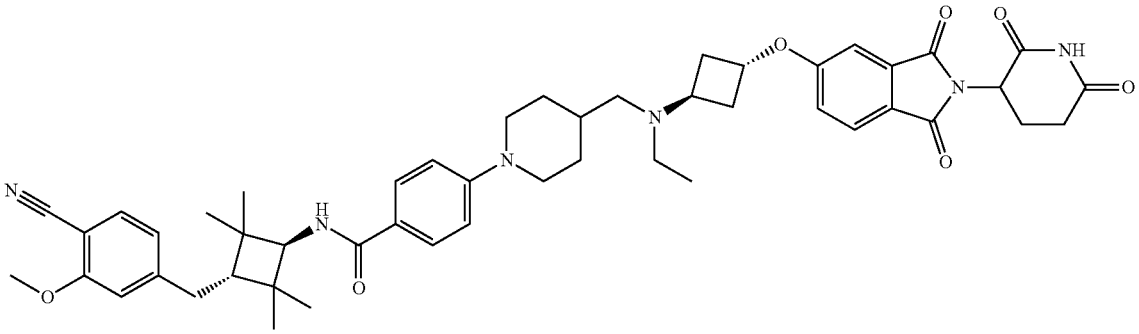 [SMILES: CCN(CC1CCN(c2ccc(C(=O)N[C@H]3C(C)(C)[C@H](Cc4ccc(C#N)c(OC)c4)C3(C)C)cc2)CC1)[C@H]1C[C@H](Oc2ccc3c(c2)C(=O)N(C2CCC(=O)NC2=O)C3=O)C1]

To a solution of 4-[4-[[[3-[2-(2,6-dioxo-3-piperidyl)-1,3-dioxo-isoindolin-5-yl]oxycyclobutyl]-ethyl-amino]methyl]-1-piperidyl]benzoic acid (0.20 g, 339.76 umol, 1.00 eq) in N,N-dimethylformamide (2 mL) was added hydroxybenzotriazole (59.68 mg, 441.69 umol, 1.30 eq), diisopropylethylamine (219.55 mg, 1.70 mmol, 295.89 uL, 5.00 eq), 1-(3-dimethylaminopropyl)-3-ethylcarbodiimide hydrochloride (84.67 mg, 441.69 umol, 1.30 eq) and 4-(3-amino-2,2,4,4-tetramethyl-cyclobutoxy)-2-methoxy-benzonitrile (105.60 mg, 339.76 umol, 1.00 eq, hydrochloride salt). The mixture was stirred at 20° C. for 10 h. The reaction mixture was filtered to give a residue. The residue was purified by prep-HPLC to give N-[3-(4-cyano-3-methoxy-phenoxy)-2,2,4,4-tetramethyl-cyclobutyl]-4-[4-[[[3-[2-(2,6-dioxo-3-piperidyl)-1,3-dioxo-isoindolin-5-yl]oxycyclobutyl]-ethyl-amino]methyl]-1-piperidyl]benzamide (159.40 mg, 174.14 umol, 51% yield, 97% purity, formate) as a light yellow solid. LC/MS (ESI) rm/z: 845.4 [M+1]$^+$; $^1$H-NMR (400 MHz, DMSO-d$_6$) δ 11.10 (s, 1H), 8.15 (s, 1H), 7.83 (d, J=8.4 Hz, 1H), 7.73 (d, J=8.8 Hz, 2H), 7.64 (d, J=8.8 Hz, 1H), 7.47 (d, J=9.2 Hz, 1H), 7.29-7.23 (m, 2H), 6.95 (d, J=9.2 Hz, 2H), 6.64 (d, J=2.0 Hz, 1H), 6.54 (dd, J=8.8, 2.0 Hz, 1H), 5.11 (dd, J=12.8, 5.4 Hz, 1H), 4.94 (br s, 1H), 4.27 (s, 1H), 4.05 (d, J=9.2 Hz, 1H), 3.91 (s, 3H), 3.86 (br d, J=12.8 Hz, 2H), 3.42 (br s, 2H), 2.91-2.85 (m, 1H), 2.78 (br t, J=11.6 Hz, 2H), 2.61 (br s, 1H), 2.57 (br s, 1H), 2.55 (br d, J=7.2 Hz, 2H), 2.41-2.33 (m, 2H), 2.24-2.17 (m, 4H), 2.09-2.00 (m, 1H), 1.81 (br d, J=11.6 Hz, 2H), 1.64 (br s, 1H), 1.22 (s, 6H), 1.16 (br s, 1H), 1.14 (s, 6H), 0.92 (t, J=7.2 Hz, 3H).

Exemplary Synthesis of Exemplary Compound 104: N-((1r,3r)-3-(4-cyano-3,5-dimethylphenoxy)-2,2,4,4-tetramethylcyclobutyl)-4-(4-((((1r,3r)-3-((2-(2,6-dioxopiperidin-3-yl)-1,3-dioxoisoindolin-5-yl)oxy)cyclobutyl)(isopropyl)amino)methyl)piperidin-1-yl)benzamide Step 1: Preparation of dimethyl 4-((1r,3r)-3-(isopropylamino)cyclobutoxy)phthalate

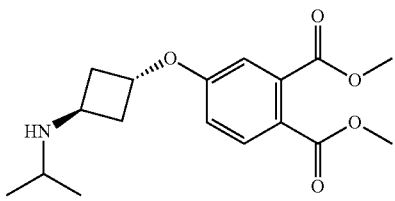 [SMILES: COC(=O)c1ccc(O[C@H]2C[C@H](NC(C)C)C2)cc1C(=O)OC]

To a solution of dimethyl 4-(3-aminocyclobutoxy)benzene-1,2-dicarboxylate (13.00 g, 46.55 mmol, 1.00 eq) in dichloroethane (130 mL) was added acetone (7.90 g, 136.02 mmol, 2.92 eq) at 20° C. The mixture was stirred at 20° C. for 15 h. The mixture was added sodium borohydride acetate (29.60 g, 139.64 mmol, 3.00 eq) at 20° C. Then the mixture was stirred at 20° C. for 16 h. The mixture was quenched with methanol (100 mL) and stirred for 2 h. Then the mixture was filtered and the filtrate was concentrated under reduced pressure to give a residue. The residue was dissolved with dichloromethane (100 mL) and a white solid was separated out. Then the suspension solution was filtered to give dimethyl 4-[3-(isopropylamino)cyclobutoxy]benzene-1,2-dicarboxylate (15.00 g) as a light red oil. LC/MS (ESI) m/z: 322.2 [M+1]$^+$.

Step 2: Preparation of dimethyl 4-((1r,3r)-3-(((1-(tert-butoxycarbonyl)piperidin-4-yl)methyl)(isopropyl)amino)cyclobutoxy)phthalate

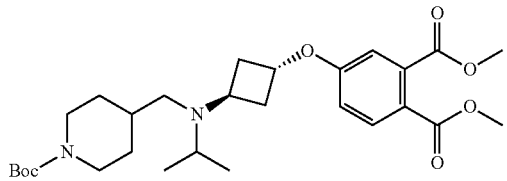 [SMILES: COC(=O)c1ccc(O[C@H]2C[C@H](N(CC3CCN(C(=O)OC(C)(C)C)CC3)C(C)C)C2)cc1C(=O)OC]

To a solution of dimethyl 4-[3-(isopropylamino)cyclobutoxy]benzene-1,2-dicarboxylate (15.00 g, 46.68 mmol, 1.00 eq) in dichloroethane (150 mL) was added tert-butyl 4-formylpiperidine-1-carboxylate (11.95 g, 56.01 mmol, 1.20 eq) at 20° C. for 20 h. The mixture was added sodium borohydride acetate (34.62 g, 163.36 mmol, 3.50 eq). Then the mixture was stirred at 20° C. for 15 h. The mixture was quenched with methanol (150 mL) and the suspension solution was filtered. Then the filtrate was concentrated to give a residue. The residue was purified by column chromatography (petroleum ether:ethyl acetate=3:1 to 0:1) to give dimethyl 4-[3-

[(1-tert-butoxycarbonyl-4-piperidyl)methyl-isopropyl-amino]cyclobutoxy]benzene-1,2-dicarboxylate (16.40 g, 31.62 mmol, 68% yield) as a light yellow oil. LC/MS (ESI) m/z: 519.2 [M+1]$^+$; H-NMR (400 MHz, DMSO-d$_6$) δ 7.73-7.79 (m, 1H), 7.00-7.05 (m, 1H), 6.97-6.99 (m, 1H), 4.77 (t, J=6.0 Hz, 1H), 3.79 (s, 3H), 3.77 (s, 3H), 3.54-3.68 (m, 1H), 3.33 (s, 2H), 2.80-2.93 (m, 1H), 2.57-2.74 (m, 2H), 2.28-2.40 (m, 2H), 2.19 (d, J=6.8 Hz, 2H), 2.08-2.17 (m, 2H), 1.69 (d, J=11.2 Hz, 2H), 1.60 (d, J=12.4 Hz, 1H), 1.42-1.52 (m, 1H), 1.38 (s, 9H), 0.92-1.00 (m, 1H), 0.90 (s, 3H), 0.88 (s, 3H).

Step 3: Preparation of dimethyl 4-((1r,3r)-3-(isopropyl(piperidin-4-ylmethyl)amino)cyclobutoxy)phthalate

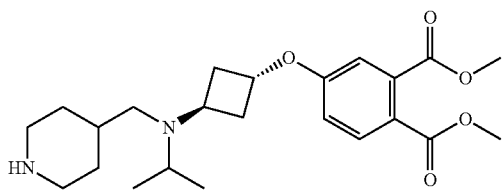 [SMILES: COC(=O)c1ccc(O[C@H]2C[C@H](N(CC3CCNCC3)C(C)C)C2)cc1C(=O)OC]

To a solution of dimethyl 4-[3-[(1-tert-butoxycarbonyl-4-piperidyl)methyl-isopropyl-amino]cyclobutoxy]benzene-1,2-dicarboxylate (850.00 mg, 1.64 mmol, 1.00 eq) in dichloromethane (8 mL) was added hydrochloride/ethyl acetate (4 M, 4.25 mL, 10.37 eq). The mixture was stirred at 20° C. for 2 h. The reaction mixture was concentrated under reduced pressure to give dimethyl 4-[3-[isopropyl(4-piperidylmethyl)amino]cyclobutoxy]benzene-1,2-dicarboxylate (830.00 mg, hydrochloride salt) as a light yellow oil. LC/MS (ESI) m/z: 419.3 [M+1]$^+$.

Step 4: Preparation of dimethyl 4-((1r,3r)-3-(((1-(4-(tert-butoxycarbonyl)phenyl)piperidin-4-yl)methyl)(isopropyl)amino)cyclobutoxy)phthalate To a solution of dimethyl 4-[3-[isopropyl(4-piperidylmethyl)amino]cyclobutoxy]benzene-1,2-dicarboxylate (350.00 mg, 0.77 mmol, 1.00 eq, hydrochloride salt) in dioxane (7 mL) was added tert-butyl 4-bromobenzoate (237.35 mg, 0.92 mmol, 1.20 eq), palladium(II) acetate (8.64 mg, 0.04 umol, 0.05 eq), bis(diphenylosphino)-1,1'-binaphthalene (47.90 mg, 0.08 umol, 0.10 eq) and cesium carbonate (877.23 mg, 2.69 mmol, 3.50 eq). The mixture was purged and degassed with nitrogen for three times. Then the mixture was stirred at 110° C. for 10 h. The reaction mixture was diluted with dichloromethane (10 mL) and filtered. The filtrate was dried over anhydrous sodium sulfate, filtered and concentrated under reduced pressure to give a residue. The residue was purified by prep-thin layer chromatography (silica gel, petroleum ether:ethyl acetate=1:1) to give dimethyl 4-[3-[[1-(4-tert-butoxycarbonylphenyl)-4-piperidyl]methyl-isopropyl-amino]cyclobutoxy]benzene-1,2-dicarboxylate (190.00 mg, 0.32 mmol, 42% yield) as a light yellow solid. LC/MS (ESI) m/z: 595.2 [M+1]$^+$.

Step 5: Preparation of 4-((1r,3r)-3-(((1-(4-(tert-butoxycarbonyl)phenyl)piperidin-4-yl)methyl)(isopropyl)amino)cyclobutoxy)phthalic acid

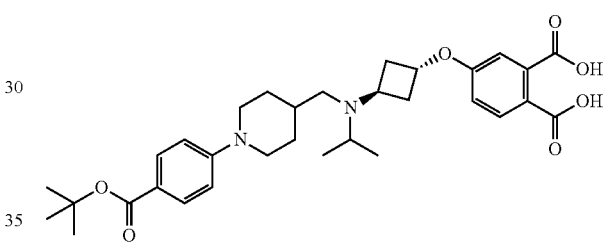

To a solution of dimethyl 4-[3-[[1-(4-tert-butoxycarbonylphenyl)-4-piperidyl]methyl-isopropyl-amino]cyclobutoxy]benzene-1,2-dicarboxylate (300.00 mg, 0.50 mmol, 1.00 eq) in methanol (3 mL) and water (1 mL) was added lithium hydroxide (95.25 mg, 2.27 mmol, 4.50 eq). The mixture was stirred at 50° C. for 4 h. The reaction mixture was concentrated under reduced pressure to give a residue. The residue was diluted with water (15 mL) and neutralized with hydrochloric acid (1 M) to pH=3-4. The mixture was extracted with ethyl acetate (25 mL). The organic layer was dried over anhydrous sodium sulfate, filtered and concentrated under reduced pressure to give 4-[3-[[1-(4-tert-butoxycarbonylphenyl)-4-piperidyl]methyl-isopropyl-amino]cyclobutoxy]phthalic acid (300.00 mg) as a light yellow oil. LC/MS (ESI) m/z: 567.3 [M+1]$^+$.

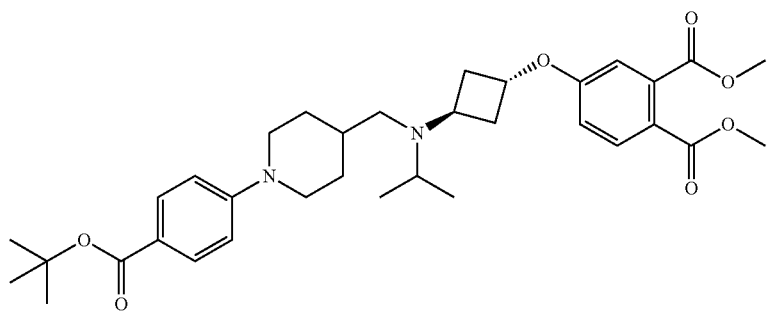 [SMILES: COC(=O)c1ccc(O[C@H]2C[C@H](N(CC3CCN(c4ccc(C(=O)OC(C)(C)C)cc4)CC3)C(C)C)C2)cc1C(=O)OC]

Step 6: Preparation of 4-(4-(((((1r,3r)-3-((2-(2,6-dioxopiperidin-3-yl)-1,3-dioxoisoindolin-5-yl)oxy)cyclobutyl)(isopropyl)amino)methyl)piperidin-1-yl)benzoic acid

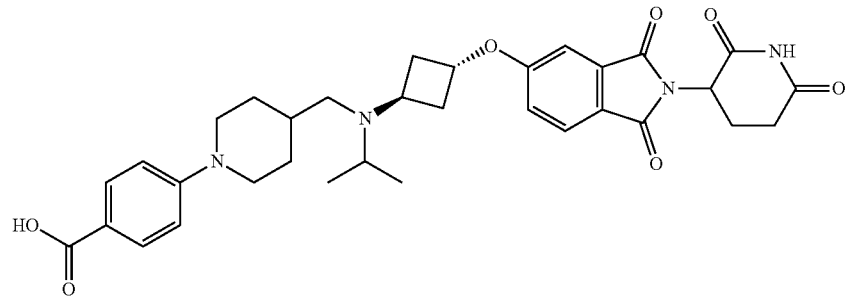 [SMILES: CC(C)N(CC1CCN(c2ccc(C(=O)O)cc2)CC1)[C@H]1C[C@H](Oc2ccc3c(c2)C(=O)N(C2CCC(=O)NC2=O)C3=O)C1]

To a solution of 4-[3-[[1-(4-tert-butoxycarbonylphenyl)-4-piperidyl]methyl-isopropyl-amino]cyclobutoxy]phthalic acid (270.00 mg, 0.48 mmol, 1.00 eq) and 3-aminopiperidine-2,6-dione (94.10 mg, 0.57 mmol, 1.20 eq, hydrochloride salt) in acetic acid (2 mL) were added sodium acetate (117.26 mg, 1.43 mmol, 3.00 eq). The mixture was stirred at 115° C. for 8 h. The reaction mixture was concentrated under reduced pressure to give a residue. The residue was purified by prep-HPLC to give 4-[4-[[[3-[2-(2,6-dioxo-3-piperidyl)-1,3-dioxo-isoindolin-5-yl]oxycyclobutyl]-isopropyl-amino]methyl]-1-piperidyl]benzoic acid (80.00 mg, 0.13 mmol, 28% yield) as a black brown solid. LC/MS (ESI) m/z: 603.2 [M+1]$^+$.

Step 7: Preparation of N-((1r,3r)-3-(4-cyano-3,5-dimethylphenoxy)-2,2,4,4-tetramethylcyclobutyl)-4-(4-(((((1r,3r)-3-((2-(2,6-dioxopiperidin-3-yl)-1,3-dioxoisoindolin-5-yl)oxy)cyclobutyl)(isopropyl)amino)methyl)piperidin-1-yl)benzamide To a solution of 4-[4-[[[3-[2-(2,6-dioxo-3-piperidyl)-1,3-dioxo-isoindolin-5-yl]oxycyclobutyl]-isopropyl-amino]methyl]-1-piperidyl]benzoic acid (80.00 mg, 0.13 mmol, 1.00 eq) in N,N-dimethylformamide (1 mL) was added hydroxybenzotriazole (23.32 mg, 0.17 mmol, 1.30 eq), diisopropylethylamine (85.78 mg, 0.66 mmol, 0.12 mL, 5.00 eq), 1-(3-dimethylaminopropyl)-3-ethylcarbodiimide hydrochloride (33.08 mg, 0.17 mmol, 1.30 eq) and 4-(3-amino-2,2,4,4-tetramethyl-cyclobutoxy)-2,6-dimethyl-benzonitrile (49.20 mg, 0.16 mmol, 1.2 eq, hydrochloride salt). The mixture was stirred at 20° C. for 10 h. The reaction mixture was filtered to give a residue. The residue was purified by prep-HPLC to give N-[3-(4-cyano-3,5-dimethylphenoxy)-2,2,4,4-tetramethyl-cyclobutyl]-4-[4-[[[3-[2-(2,6-dioxo-3-piperidyl)-1,3-dioxo-isoindolin-5-yl]oxycyclobutyl]-isopropyl-amino]methyl]-1-piperidyl]benzamide (45.00 mg, 52.51 umol, 39.56% yield) as a white solid. LC/MS (ESI) m/z: 857.5 [M+1]$^+$; $^1$H-NMR (400 MHz, DMSO-d$_6$) δ 11.12 (brs, 1H), 8.26 (s, 1H), 7.84 (d, J=8.0 Hz, 1H), 7.74 (d, J=8.8 Hz, 2H), 7.48 (d, 1=9.6 Hz, 1H), 7.30-7.24 (m, 2H), 6.96 (d, J=8.8 Hz, 2H), 6.74 (s, 2H), 5.12 (dd, J=12.8, 5.6 Hz, 1H), 4.91 (br s, 1H), 4.23 (s, 1H), 4.04 (d, J=9.2 Hz, 1H), 3.89 (br d, J=12.0 Hz, 2H), 3.72-3.62 (m, 1H), 2.95-2.83 (m, 3H), 2.76 (br t, J=12.0 Hz, 2H), 2.68 (br s, 1H), 2.61 (br s, 1H), 2.44 (s, 7H), 2.26 (br d, J=6.8 Hz, 2H), 2.21 (br d, J=8.0 Hz, 2H), 2.10-1.99 (m, 1H), 1.83 (br d, J=12.4 Hz, 2H), 1.57 (br s, 1H), 1.22 (s, 6H), 1.18 (hr s, 2H), 1.12 (s, 6H), 0.93 (d, J=6.4 Hz, 6H).

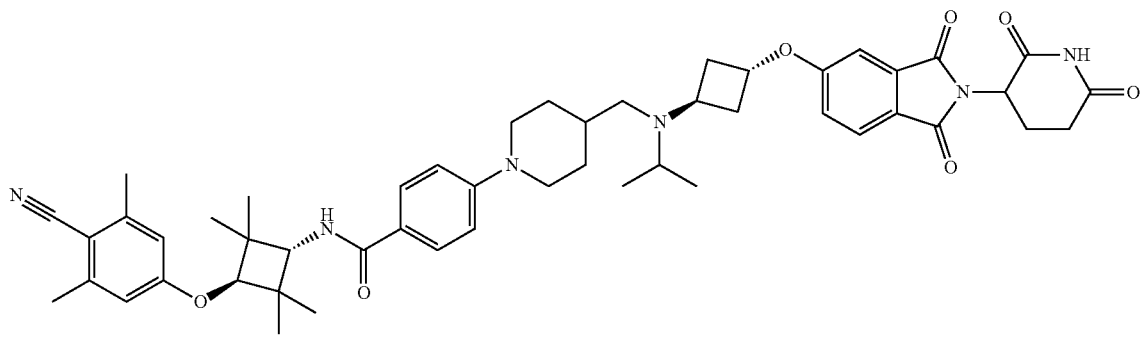 [SMILES: Cc1cc(O[C@H]2C(C)(C)[C@H](NC(=O)c3ccc(N4CCC(CN(C(C)C)[C@H]5C[C@H](Oc6ccc7c(c6)C(=O)N(C6CCC(=O)NC6=O)C7=O)C5)CC4)cc3)C2(C)C)cc(C)c1C#N]

Exemplary Synthesis of Exemplary Compound 72: N-((1r,3r)-3-(3-chloro-4-cyanophenoxy)-2,2,4,4-tetramethylcyclobutyl)-1-(4-(3-((2-(2,6-dioxopiperidin-3-yl)-1,3-dioxoisoindolin-5-yl)oxy)propyl)cyclohexyl)-1H-pyrazole-3-carboxamide Step 1: Preparation of (3-(benzyloxy)propyl)bromotriphenyl-15-phosphane

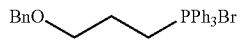

A mixture of [(3-bromopropoxy)methyl]benzene (20 g, 87.3 mmol, 1.0 equiv) and triphenylphosphane (22.9 g, 87.3 mmol, 1.0 equiv) in toluene (100 mL) was stirred for 22 hr under reflux condition in an oil bath. Toluene was removed under vacuum. The crude product was re-crystallized from acetonitrile/petroleum ether in the ratio of 4:1. This resulted in 18.4 g (42.9%) of (3-(benzyloxy)propyl)bromotriphenyl-15-phosphane as a white solid. LC/MS (ESI) m/z: 411.2 [M-79]$^+$.

Step 2: Preparation of 8-(3-(benzyloxy)propylidene)-1,4-dioxaspiro[4.5]decane

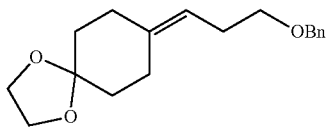 [SMILES: C(CCOCc1ccccc1)=C1CCC2(CC1)OCCO2]

To a mixture of [3-(benzyloxy)propyl](bromo)triphenyl-$\$1^{[5]}$-phosphane (1.5759 g, 3.21 mmol, 1.001 equiv) in oxolane (8 mL) was added dropwise over 30 min (s) butyllithium (1.28 mL, 3.20 mmol, 0.999 equiv) in hexane at 0° C. The mixture was stirred at 0° C. for 30 min (s), followed by dropwise addition of a solution of 1,4-dioxaspiro[4.5]decan-8-one (500.3 mg, 3.20 mmol, 1 equiv) in THF (2 mL). The reaction mixture was warmed to room temperature and stirred for 15 hr. The reaction was then quenched by the addition of water (30 mL×3). The resulting solution was extracted with ethoxyethane (40 mL×3) and the organic layers combined. The resulting mixture was washed with brine (20 mL×1). The mixture was dried over anhydrous sodium sulfate. The residue was applied onto a silica gel column with ethyl acetate/petroleum ether (1:20 to 1:10). This resulted in 531.2 mg (57.5%) of 8-[3-(benzyloxy)propylidene]-1,4-dioxaspiro[4.5]decane as a colorless liquid. LC/MS (ESI) m/z: 289.35 [M+1]$^+$.

Step 3: Preparation of 3-(1,4-dioxaspiro[4.5]decan-8-yl)propan-1-ol

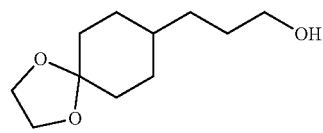 [SMILES: OCCCC1CCC2(CC1)OCCO2]

To a solution of 8-[3-(benzyloxy)propylidene]-1,4-dioxaspiro[4.5]decane (999.7 mg, 3.47 mmol, 1 equiv) in methanol (50 mL) was added Pd/C (424.8 mg, 10%) under N$_2$. The reaction mixture was vacuumed and flushed with H$_2$ (5 times). The resulting mixture was hydrogenated for 8 hr at room temperature. The mixture was filtered and the filtrate was concentrated and dried under vacuum. This resulted in 678.3 mg (97.7%) of 3-[1,4-dioxaspiro[4.5]decan-8-yl]propan-1-ol as a colorless oil. LC/MS (ESI) m/z: 201.15 [M+1]$^+$.

Step 4: Preparation of 4-(3-hydroxypropyl)cyclohexan-1-one

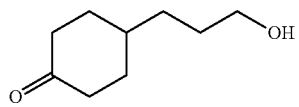

To a solution of 3-[1,4-dioxaspiro[4.5]decan-8-yl]propan-1-ol (676.2 mg, 3.38 mmol, 1.0 equiv) in acetone (6.0 mL) was added H$_2$O (4.2 mL) and hydrogen chloride (2.5 mL, 30.0 mmol, 8.9 equiv). The resulting solution was stirred for 24 hr at room temperature. Acetone was removed under vacuum and then diluted with water (10 mL). The resulting solution was extracted with ethyl acetate (20 mL×3) and the combined organic layers were washed with brine (10 mL×1). The mixture was dried over anhydrous sodium sulfate. This resulted in 532.5 mg (100%) of 4-(3-hydroxypropyl)cyclohexan-1-one as brown oil.

Step 5: Preparation of tert-butyl 2-(4-(3-hydroxypropyl)cyclohexyl)hydrazine-1-carboxylate

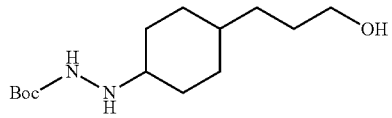 [SMILES: CC(C)(C)OC(=O)NNC1CCC(CCCO)CC1]

A mixture of 4-(3-hydroxypropyl)cyclohexan-1-one (477.8 mg, 3.06 mmol, 1.0 equiv) and (tert-butoxy)carbohydrazide (461.9 mg, 3.49 mmol, 1.14 equiv) in i-PrOH (8 mL) was stirred for 19 hr at room temperature. Then to this was added NaBH$_3$CN (590.5 mg, 9.40 mmol, 3.07 equiv) and HOAc (0.2 mL, 3.49 mmol, 1.14 equiv). The reaction mixture was stirred for additional 28 hr at room temperature. The reaction was then quenched by the addition of water (15 mL×3). i-PrOH was removed under vacuum. The residue was extracted with ethyl acetate (20 mL×3) and the organic layers combined. The organic layer was washed with water (20 mL×3) and dried over anhydrous sodium sulfate. The crude was subjected to a silica gel column with ethyl acetate/petroleum ether (2:3). This resulted in 606.3 mg (72.8%) of N-[4-(3-hydroxypropyl)cyclohexyl](tert-butoxy)carbohydrazide as a white solid. LC/MS (ESI) n/z: 217.10 [M-55]$^+$.

Step 6: Preparation of 3-(4-hydrazineylcyclohexyl)propan-1-ol hydrochloride

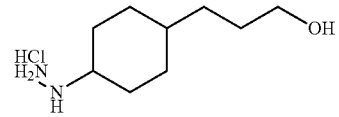

To a solution of N-[4-(3-hydroxypropyl)cyclohexyl](tert-butoxy)carbohydrazide (478.9 mg, 1.76 mmol, 1 equiv) in 7 mL dioxane was added hydrogen chloride in dioxane (5 mL, 20.00 mmol, 11.38 equiv). The resulting solution was stirred for 15 hr at room temperature. The resulting mixture was evaporated to dryness and dried under vacuum. This resulted in 367 mg (100%) of 3-(4-hydrazinylcyclohexyl)propan-1-ol hydrochloride as light yellow oil. LC/MS (ESI) m/z: 173.20 [M-35]$^+$.

Step 7: Preparation of ethyl 1-(4-(3-hydroxypropyl) cyclohexyl)-1H-pyrazole-3-carboxylate

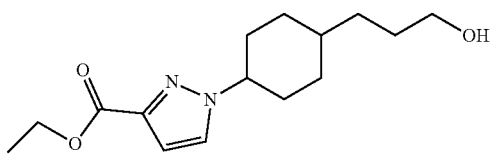 [SMILES: CCOC(=O)c1ccn(C2CCC(CCCO)CC2)n1]

Into a 25-mL round-bottom flask, was placed ethyl (3E)-4-(dimethylamino)-2-oxobut-3-enoate (307.7 mg, 1.80 mmol, 1 equiv), 3-(4-hydrazinylcyclohexyl)propan-1-ol hydrochloride (367 mg, 1.76 mmol, 0.98 equiv), ethanol (9 mL). The resulting solution was heated to reflux for 5 hr. The resulting solution was concentrated under vacuum. The resulting solution was extracted with ethyl acetate (20 mL×3) and the organic layers combined. The organic layer was washed with brine (20 mL×1). The mixture was dried over anhydrous sodium sulfate. The residue was applied onto a silica gel column with ethyl acetate/hexane (1:1). This resulted in 197.9 mg (39.3%) of ethyl 1-[4-(3-hydroxypropyl)cyclohexyl]-1H-pyrazole-3-carboxylate as colorless oil. LC/MS (ESI) m/z: 281.20 [M+1]$^+$; $^1$H-NMR (300 MHz, CDCl$_3$) δ 1.14-1.48 (m, 9H), 1.57-1.67 (m, 3H), 1.73-1.85 (m, 2H), 1.87-2.03 (m, 2H), 2.04-2.18 (m, 1H), 2.19-2.30 (m, 1H), 3.64-3.69 (m, 2H), 4.12-4.37 (m, 1H), 4.40-4.45 (m, 2H), 6.80-6.81 (m, 1H), 7.44-7.49 (m, 1H).

Step 8: Preparation of 1-(4-(3-hydroxypropyl)cyclohexyl)-1H-pyrazole-3-carboxylic acid

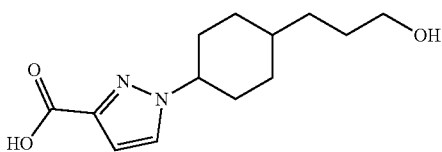 [SMILES: O=C(O)c1ccn(C2CCC(CCCO)CC2)n1]

To a solution of ethyl 1-[4-(3-hydroxypropyl)cyclohexyl]-1H-pyrazole-3-carboxylate (136.8 mg, 0.49 mmol, 1 equiv) in ethanol (2.4 mL) was added lithium hydroxide monohydrate (89.2 mg, 2.13 mmol, 4.36 equiv) and water (0.6 mL). The reaction solution was stirred for 17 hr at room temperature. The solution was then concentrated and diluted with water (10 mL). To this was added 1 M HCl to adjust pH=4. The resulting solution was extracted with ethyl acetate (20 mL×3). The organic layer was dried over anhydrous sodium sulfate and evaporated to dryness. This resulted in 123.2 mg (100%) of 1-[4-(3-hydroxypropyl) cyclohexyl]-1H-pyrazole-3-carboxylic acid as colorless oil. LC/MS (ESI) m/z: 253.00 [M+1]$^+$.

Step 9: Preparation of N-((1r,3r)-3-(3-chloro-4-cyanophenoxy)-2,2,4,4-tetramethylcyclobutyl)-1-(4-(3-hydroxypropyl)cyclohexyl)-1H-pyrazole-3-carboxamide

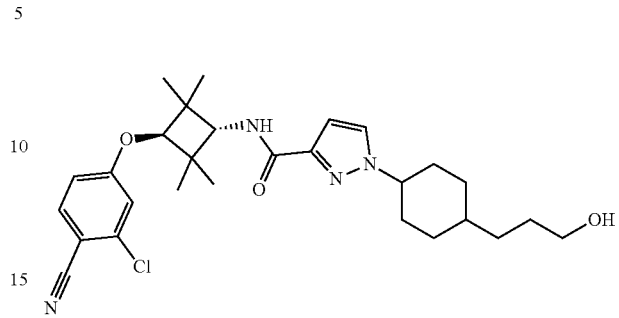

To a solution of 1-[4-(3-hydroxypropyl)cyclohexyl]-1H-pyrazole-3-carboxylic acid (119.8 mg, 0.47 mmol, 1 equiv) and 2-chloro-4-[(1r,3r)-3-amino-2,2,4,4-tetramethylcyclobutoxy]benzonitrile (164.9 mg, 0.52 mmol, 1.10 equiv) in DMF (5.0 mL) was added DIEA (0.4 mL, 2.42 mmol, 5.10 equiv) and BOP (231.2 mg, 0.52 mmol, 1.10 equiv). The reaction solution was stirred for 2 hr at room temperature. To this was added water (20 mL). The mixture was extracted with ethyl acetate (20 mL×4) and the organic layers combined. The organic layer was washed with brine (20 mL×1). The mixture was dried over anhydrous sodium sulfate. The residue was purified by preparative TLC with ethyl acetate/petroleum ether (2:1). This resulted in 246 mg (100%) of 1-[4-(3-hydroxypropyl)cyclohexyl]-N-[(1r,3r)-3-(3-chloro-4-cyanophenoxy)-2,2,4,4-tetramethylcyclobutyl]-1H-pyrazole-3-carboxamide as a white solid. LC/MS (ESI) m/z: 513.25 [M+1]$^+$.

Step 10: Preparation of 3-(4-(3-(((1r,3r)-3-(3-chloro-4-cyanophenoxy)-2,2,4,4-tetramethylcyclobutyl)carbamoyl)-1H-pyrazol-1-yl)cyclohexyl) propyl 4-methylbenzenesulfonate

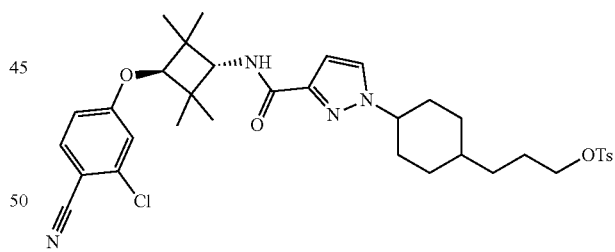

A solution of 1-[4-(3-hydroxypropyl)cyclohexyl]-N-[(1r,3r)-3-(3-chloro-4-cyanophenoxy)-2,2,4,4-tetramethylcyclobutyl]-1H-pyrazole-3-carboxamide (100.1 mg, 0.20 mmol, 1 equiv), TsCl (57.4 mg, 0.30 mmol, 1.54 equiv), Et$_3$N (0.1 mL, 0.72 mmol, 3.69 equiv) and DMAP (2.8 mg, 0.02 mmol, 0.12 equiv) in dichloromethane (2 mL) was stirred for 14 hr at room temperature. The reaction solution was evaporated to dryness. The residue was purified by preparative TLC with ethyl acetate/petroleum ether (2:3). This resulted in 109.7 mg (84.3%) of 3-[4-(3-[[(1r,3r)-3-(3-chloro-4-cyanophenoxy)-2,2,4,4-tetramethylcyclobutyl]carbamoyl]-1H-pyrazol-1-yl)cyclohexyl]propyl 4-methylbenzene-1-sulfonate as a colorless semi-solid. LC/MS (ESI) m/z: 667.30 [M+1]$^+$.

Step 11: Preparation of N-((1r,3r)-3-(3-chloro-4-cyanophenoxy)-2,2,4,4-tetramethylcyclobutyl)-1-(4-(3-((2-(2,6-dioxopiperidin-3-yl)-1,3-dioxoisoindolin-5-yl)oxy)propyl)cyclohexyl)-1H-pyrazole-3-carboxamide

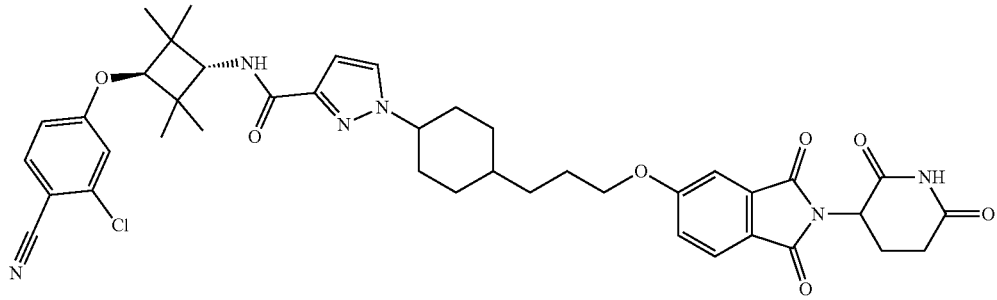 [SMILES: CC1(C)[C@H](NC(=O)c2ccn(C3CCC(CCCOc4ccc5c(c4)C(=O)N(C4CCC(=O)NC4=O)C5=O)CC3)n2)C(C)(C)[C@H]1Oc1ccc(C#N)c(Cl)c1]

To a solution of 3-[4-(3-[[(1r,3r)-3-(3-chloro-4-cyanophenoxy)-2,2,4,4-tetramethylcyclobutyl]carbamoyl]-1H-pyrazol-1-yl)cyclohexyl]propyl 4-methylbenzene-1-sulfonate (106.7 mg, 0.16 mmol, 1 equiv) and 2-(2,6-dioxopiperidin-3-yl)-5-hydroxy-2,3-dihydro-1H-isoindole-1,3-dione (87.9 mg, 0.32 mmol, 2.00 equiv) in DMF (3 mL) was added K$_2$CO$_3$ (68.2 mg, 0.49 mmol, 3.09 equiv) and NaI (4.9 mg, 0.03 mmol, 0.20 equiv). The resulting mixture was stirred for 4 hr at 80° C. To this was added water (10 mL). The mixture was extracted with dichloromethane (20 mL×3). The combined organic layer was washed with brine (20 mL×1) and dried over anhydrous sodium sulfate. The crude product was purified by Prep-HPLC. This resulted in 44.9 mg (36.5%) of 1-[4-(3-[[2-(2,6-dioxopiperidin-3-yl)-1,3-dioxo-2,3-dihydro-1H-isoindol-5-yl]oxy]propyl)cyclohexyl]-N-[(1r,3r)-3-(3-chloro-4-cyanophenoxy)-2,2,4,4-tetramethylcyclobutyl]-1H-pyrazole-3-carboxamide as a white solid. LC/MS (ESI) m/z: 769.35/771.35 [M+1]$^+$; $^1$H-NMR (300 MHz, DMSO-d$_6$) δ 1.05-1.08 (m, 7H), 1.13 (s, 6H), 1.25-1.90 (m, 10H), 1.92-2.18 (m, 3H), 2.46-2.65 (m, 2H), 2.75-2.96 (m, 1H), 3.80-3.96 (m, 1H), 4.02-4.34 (m, 3H), 4.36-4.48 (m, 1H), 4.95-5.18 (m, 1H), 6.59-6.61 (m, 1H), 6.94-6.97 (m, 1H), 7.15-7.21 (m, 1H), 7.24-7.28 (m, 1H), 7.30-7.34 (m, 1H), 7.35-7.37 (m, 1H), 7.75-7.88 (m, 3H), 11.05 (s, 1H).

Exemplary Synthesis of Exemplary Compound 129: N-((1r,3r)-3-(3-chloro-4-cyanophenoxy)-2,2,4,4-tetramethylcyclobutyl)-4-(4-((4-(2-(2-fluoro-2,6-dioxopiperidin-3-yl)-1,3-dioxoisoindolin-5-yl)piperazin-1-yl)methyl)piperidin-1-yl)benzamide Step 1: Preparation of 5-fluoro-2-(2-oxopiperidin-3-yl)isoindoline-1,3-dione

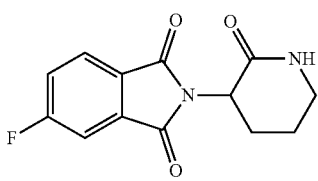 [SMILES: O=C1NCCCC1N1C(=O)c2ccc(F)cc2C1=O]

To a solution of 5-fluoro-1,3-dihydro-2-benzofuran-1,3-dione (1.32 g, 7.99 mmol) and 3-aminopiperidin-2-one (830 mg, 7.27 mmol) in acetic acid (20 mL) was added sodium acetate (1.18 g, 14.5 mmol), the reaction mixture was heated to 90° C. for 4 hrs. Dichloromethane (50 mL) and water (50 mL) were added and the organic layer was washed by sat. NaHCO$_3$, water, dried with Na$_2$SO$_4$, the solvent was evaporated to give 5-fluoro-2-(2-oxopiperidin-3-yl)-2,3-dihydro-1H-isoindole-1,3-dione as brown solid (1.61 g, yield 84.2%). LC/MS (ESI) m/z: 285.21 [M+23]$^+$; $^1$H-NMR (400 MHz, CDCl$_3$) δ 7.84 (m, 1H), 7.50 (m, 1H), 7.36 (m, 1H), 5.84 (br. S, 1H), 4.74 (m, 1H), 3.53 (m, 1H), 3.40 (m, 11H), 2.44-2.35 (m, 11H), 2.12-1.95 (m, 3H).

Step 2: Preparation of tert-butyl 3-(5-fluoro-1,3-dioxoisoindolin-2-yl)-2-oxopiperidine-1-carboxylate

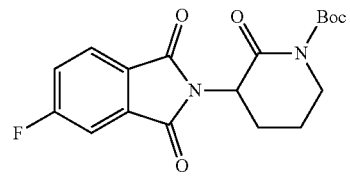 [SMILES: CC(C)(C)OC(=O)N1CCCC(N2C(=O)c3ccc(F)cc3C2=O)C1=O]

To a solution of 5-fluoro-2-(2-oxopiperidin-3-yl)-2,3-dihydro-1H-isoindole-1,3-dione (1.86 g, 7.09 mmol) in acetonitrile (50 mL) was added ditertbutyl dicarbonate (1.54 g, 7.09 mmol), N,N-dimethylpyridin-4-amine (1.29 g, 10.6 mmol) was added and it was heated to 80° C. for 1.5 hrs. ditertbutyl dicarbonate (1.54 g, 7.09 mmol) was added and it was stirred at 80° C. for 1.5 hrs. Citric acid solution (3%, 10 mL) was added and most of solvent was evaporated, ethyl acetate (30 mL) was added and the organic layer was separated and dried with Na$_2$SO$_4$, the solvent was evaporated to give the crude product. The mixture was purified by silica gel chromatography (0-80% EtOAc/Hexane). The product tert-butyl 3-(5-fluoro-1,3-dioxo-2,3-dihydro-1H-isoindol-2-yl)-2-oxopiperidine-1-carboxylate was obtained as light brown solid (2.1 g, yield 82%). LC/MS (ESI) m/z: 747.55 [2M+23]$^+$; $^1$H-NMR (400 MHz, CDCl$_3$) δ 7.84 (m, 1H), 7.50 (m, 1H), 7.37 (m, 1H), 4.85 (m, 1H), 3.86 (m, 1H), 3.73 (m, 1H), 2.48 (m, 1H), 2.10 (m, 2H), 1.98 (m, 1H), 1.49 (s, 9H).

Step 3: Preparation of tert-butyl 3-fluoro-3-(5-fluoro-1,3-dioxoisoindolin-2-yl)-2-oxopiperidine-1-carboxylate

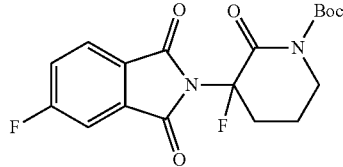 [SMILES: CC(C)(C)OC(=O)N1CCCC(F)(N2C(=O)c3ccc(F)cc3C2=O)C1=O]

To the solution of tert-butyl 3-(5-fluoro-1,3-dioxo-2,3-dihydro-1H-isoindol-2-yl)-2-oxopiperidine-1-carboxylate (2.1 g, 5.79 mmol) in THF (50 mL) was added lithium bis(trimethylsilyl)azanide (6.94 mL, 6.94 mmol) in dryice-acetone bath at −78° C. The bath was warmed to −40° C. slowly and N-(benzenesulfonyl)-N-fluorobenzenesulfonamide (3.27 g, 10.4 mmol) was added and then the reaction mixture was warmed up naturally. One hour later the bath was removed, and it was stirred at room temperature for 3 hrs. Aqueous NH$_4$Cl (15 mL) was added and it was extracted with ethyl acetate (40 mL×2), dried with Na$_2$SO$_4$, the solvent was evaporated to give crude product. The mixture was purified by silica gel chromatography (0-80% EtOAc/Hexane). The product tert-butyl 3-fluoro-3-(5-fluoro-1,3-dioxo-2,3-dihydro-1H-isoindol-2-yl)-2-oxopiperidine-1-carboxylate was obtained as white solid (1.83 g, yield 83%). LC/MS (ESI) m/z: 403.30 [M+23]$^+$; $^1$H-NMR (400 MHz, CDCl$_3$) δ 7.88 (m, 1H), 7.54 (m, 1H), 7.43 (m, 1H), 3.95 (m, 1H), 3.59 (m, 1H), 3.18 (m, 1H), 2.39 (m, 1H), 2.07 (m, 1H), 1.87 (m, 1H), 1.55 (s, 9H).

Step 4: Preparation of 5-fluoro-2-(3-fluoro-2-oxopiperidin-3-yl)isoindoline-1,3-dione

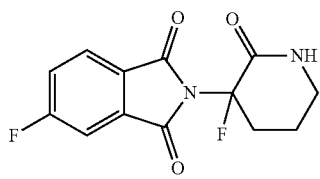 [SMILES: O=C1c2ccc(F)cc2C(=O)N1C1(F)CCCNC1=O]

To the solution of tert-butyl 3-fluoro-3-(5-fluoro-1,3-dioxo-2,3-dihydro-1H-isoindol-2-yl)-2-oxopiperidine-1-carboxylate (1.83 g, 4.81 mmol) in dichloromethane (10 mL) was added 4N HCl in dioxane (5 mL, 24.0 mmol), it was stirred at room temperature for 2 hrs. The solvent was evaporated and it was exchanged with dichloromethane (20 mL×2), dried under high vacuum over the night to give the product 5-fluoro-2-(3-fluoro-2-oxopiperidin-3-yl)-2,3-dihydro-1H-isoindole-1,3-dione as light brown solid (1.3 g, yield 98%). LC/MS (ESI) m/z: 303.21 [M+23]$^+$; $^1$H-NMR (400 MHz, CDCl$_3$) δ 7.85 (m, 1H), 7.52 (m, 11H), 7.41 (m, 1H), 6.16 (br. S, 1H), 3.46 (m, 2H), 2.80 (m, 1H), 2.51 (m, 1H), 2.09 (m, 1H), 1.88 (m, 1H).

Step 5: Preparation of 5-fluoro-2-(3-fluoro-2,6-dioxopiperidin-3-yl)isoindoline-1,3-dione

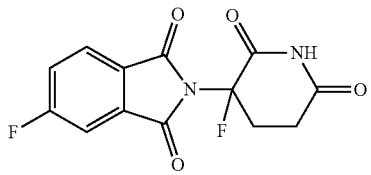 [SMILES: O=C1CCC(F)(N2C(=O)c3ccc(F)cc3C2=O)C(=O)N1]

A solution of sodium periodate (1.91 g, 8.97 mmol) in water (18 mL) was added to a solution of 5-fluoro-2-(3-fluoro-2-oxopiperidin-3-yl)-2,3-dihydro-1H-isoindole-1,3-dione (840 mg, 2.99 mmol) in acetonitrile (12 mL) and CCl$_4$ (12 mL), ruthenium (III) chloride (62 mg, 0.30 mmol) was added and it was heated to 75° C. for 4.5 hrs. The reaction mixture was cooled to room temperature and water (30 mL) and ethyl acetate (50 mL) were added, dried with Na$_2$SO$_4$, the solvent was evaporated to give the crude product. It was loaded with dichloromethane and purified by silica gel chromatography (20-100% EtOAc/Hexane). The product 5-fluoro-2-(3-fluoro-2,6-dioxopiperidin-3-yl)-2,3-dihydro-1H-isoindole-1,3-dione was obtained as white solid (0.37 g, 42% yield). LC/MS (ESI) m/z: 317.20 [M+23]$^+$; $^1$H-NMR (400 MHz, DMSO-d$_6$) δ 11.45 (s, 1H), 7.98 (m, 1H), 7.82 (m, 1H), 7.71 (m, 1H), 3.21 (m, 11H), 2.92-2.83 (m, 1H), 2.56-2.44 (m, 2H).

Step 6: Preparation of tert-butyl 4-(2-(3-fluoro-2,6-dioxopiperidin-3-yl)-1,3-dioxoisoindolin-5-yl)piperazine-1-carboxylate

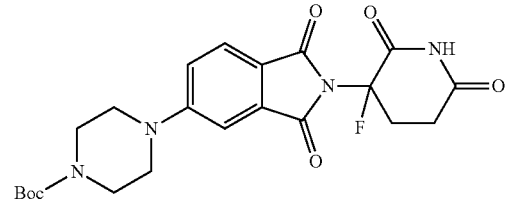 [SMILES: CC(C)(C)OC(=O)N1CCN(c2ccc3c(c2)C(=O)N(C2(F)CCC(=O)NC2=O)C3=O)CC1]

To a solution of 5-fluoro-2-(3-fluoro-2,6-dioxopiperidin-3-yl)-2,3-dihydro-1H-isoindole-1,3-dione (220 mg, 0.7477 mmol) in NMP (6 mL) was added N,N-diisopropylethylamine (258 μL, 1.49 mmol) and tert-butyl piperazine-1-carboxylate (221 mg, 1.19 mmol), it was heated to 75° C. for 2.5 hrs. The reaction mixture was cooled and diluted with water (60 mL), it was extracted with ethyl acetate (30 mL) and 10% MeOH/DCM (30 mL). The combined organic layer was dried with Na$_2$SO$_4$, the solvent was evaporated to give the crude product. The mixture was purified by silica gel chromatography (20-100% EtOAc/Hexane). The product tert-butyl 4-[2-(3-fluoro-2,6-dioxopiperidin-3-yl)-1,3-dioxo-2,3-dihydro-1H-isoindol-5-yl]piperazine-1-carboxylate was obtained as yellow solid (128 mg, yield 38%). LC/MS (ESI) m/z: 483.38 [M+23]$^+$; $^1$H-NMR (400 MHz, CDCl$_3$) δ 8.05 (m, 1H), 7.71 (d, J=12 Hz, 1H), 7.22 (s, 1H), 7.08 (d, J=12 Hz, 1H), 3.60 (m, 5H), 3.43 (m, 4H), 2.86-2.81 (m, 1H), 2.57-2.51 (m, 1H), 2.44-2.37 (m, 1H), 1.47 (s, 9H).

Step 7: Preparation of 2-(3-fluoro-2,6-dioxopiperidin-3-yl)-5-(piperazin-1-yl)isoindoline-1,3-dione hydrochloride

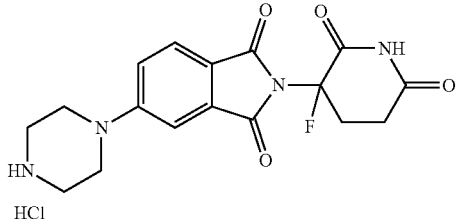 [SMILES: O=C1CCC(F)(N2C(=O)c3ccc(N4CCNCC4)cc3C2=O)C(=O)N1 ; Cl]

To a solution of tert-butyl 4-[2-(3-fluoro-2,6-dioxopiperidin-3-yl)-1,3-dioxo-2,3-dihydro-1H-isoindol-5-yl]piperazine-1-carboxylate (128 mg, 0.2779 mmol) in dichloromethane (2 mL) was added 4N HCl in dioxane (1 mL, 20.3 mmol). The reaction mixture was stirred at room temperature for 19 hrs. The solvent was evaporated and the product 2-(3-fluoro-2,6-dioxopiperidin-3-yl)-5-(piperazin-1-yl)isoindoline-1,3-dione hydrochloride was obtained as yellow solid (110 mg, yield 98%). LC/MS (ESI) m/z: 361.31 [M+H]$^+$.

Step 8: Preparation of N-((1r,3r)-3-(3-chloro-4-cyanophenoxy)-2,2,4,4-tetramethylcyclobutyl)-4-(4-((4-(2-(3-fluoro-2,6-dioxopiperidin-3-yl)-1,3-dioxoisoindolin-5-yl)piperazin-1-yl)methyl)piperidin-1-yl)benzamide

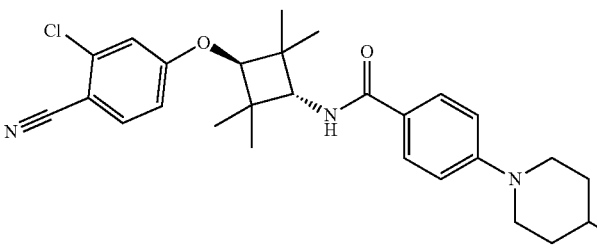

To a solution of 4-(4-formylpiperidin-1-yl)-N-[(1r,3r)-3-(3-chloro-4-cyanophenoxy)-2,2,4,4-tetramethylcyclobutyl]benzamide (49.7 mg, 0.1008 mmol) in dichloroethane (2 mL) was added 2-(3-fluoro-2,6-dioxopiperidin-3-yl)-5-(piperazin-1-yl)-2,3-dihydro-1H-isoindole-1,3-dione hydrochloride (40 mg, 0.1008 mmol), triethylamine (42.0 μL, 0.3023 mmol) was added and it was stirred for 5 mins, sodium bis(acetyloxy)boranuidyl acetate (21.3 mg, 0.1008 mmol) was added slowly and the white suspension was stirred at room temperature for 16 hrs. Water (5 mL) was added and it was extracted by dichloromethane (10 mL×2), dried with Na$_2$SO$_4$, the solvent was evaporated to give the crude product. It was purified by silica gel chromatography (0-20% MeOH/DCM). The product 4-[4-({4-[2-(3-fluoro-2,6-dioxopiperidin-3-yl)-1,3-dioxo-2,3-dihydro-1H-isoindol-5-yl]piperazin-1-yl}methyl)piperidin-1-yl]-N-[(1r,3r)-3-(3-chloro-4-cyanophenoxy)-2,2,4,4-tetramethylcyclobutyl]benzamide was obtained as yellow solid (60 mg, yield 71%). LC/MS (ESI) m/z: 838.67 [M+1]$^+$; $^1$H NMR (400 Hz, DMSO-d$_6$) δ 11.39 (s, 1H), 7.87 (d, J=8 Hz, 1H), 7.71-7.64 (m, 3H), 7.46 (d, J=8 Hz, 1H), 7.29 (m, 2H), 7.18 (s, 1H), 6.98-6.91 (m, 3H), 4.29 (s, 1H), 4.02 (d, J=8 Hz, 1H), 3.83 (d, J=12 Hz, 2H), 3.41 (m, 3H), 3.25 (m, 3H), 2.73 (m, 3H), 2.68-2.63 (m, 2H), 2.38 (m, 1H), 2.18-2.12 (m, 4H), 1.90-1.76 (m, 5H), 1.18 (s, 7H), 1.09 (s, 5H).

Exemplary Synthesis of Exemplary Compound 178: N-((1r,3r)-3-(4-cyano-3,5-dimethylphenoxy)-2,2,4,4-tetramethylcyclobutyl)-4-(4-((1r,3r)-3-((2-(2,6-dioxopiperidin-3-yl)-1,3-dioxoisoindolin-5-yl)oxy)cyclobutoxy)piperidin-1-yl)benzamide Step 1: Preparation of dimethyl 4-((1r,3r)-3-(benzyloxy)cyclobutoxy)phthalate

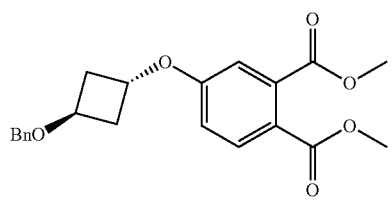 [SMILES: COC(=O)c1ccc(O[C@H]2C[C@H](OCc3ccccc3)C2)cc1C(=O)OC]

Into a 100-mL round-bottom flask, was placed 1,2-dimethyl 4-hydroxybenzene-1,2-dicarboxylate (2.50 g, 11.89 mmol, 1.00 equiv) in THF (30.00 mL), to which was added (1s,3s)-3-(benzyloxy)cyclobutan-1-ol (2.12 g, 11.89 mmol, 1.00 equiv), PPh$_3$ (6.24 g, 23.79 mmol, 2.00 equiv), this was followed by the addition of a solution of DIAD (4.81 g, 23.79 mmol, 2.00 equiv) in THF (15 mL) dropwise with stirring at 0° C. in 5 min. The resulting solution was stirred for 15 min at 0° C. The resulting solution was allowed to react, with stirring, for an additional 15 hr at 60° C. The reaction mixture was cooled to room temperature. The resulting mixture was concentrated under vacuum. The crude product was purified by Flash-Prep-HPLC. This resulted in 4.00 g (65%) of 1,2-dimethyl 4-[(1r,3r)-3-(benzyloxy)cyclobutoxy]benzene-1,2-dicarboxylate as a light yellow solid. LC/MS (ESI) m/z: 371.05 [M+1]$^+$.

Step 2: Preparation of dimethyl 4-((1r,3r)-3-hydroxycyclobutoxy)phthalate

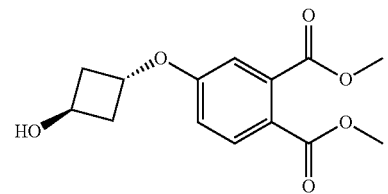 [SMILES: COC(=O)c1ccc(O[C@H]2C[C@H](O)C2)cc1C(=O)OC]

Into a 100-mL round-bottom flask, was placed 1,2-dimethyl 4-[(1r,3r)-3-(benzyloxy)cyclobutoxy]benzene-1,2-dicarboxylate (1.99 g, 5.37 mmol, 1.00 equiv) and Pd/C (10%, 1.15 g, 10.74 mmol, 2.00 equiv) in MeOH (20.00 mL) and AcOH (1.50 mL) under nitrogen atmosphere. The flask was then vacuumed and flushed with hydrogen. The reaction mixture was hydrogenated at room temperature for 3 hours under hydrogen atmosphere using a hydrogen balloon. Then the reaction mixture was filtered through a celite pad and the filtrate was concentrated under reduced pressure. The crude product was purified by Flash-Prep-HPLC. This resulted in 1.35 g (90%) of 1,2-dimethyl 4-[(1r,3r)-3-hydroxycyclobutoxy]benzene-1,2-dicarboxylate as colorless oil. LC/MS (ESI) m/z: 280.95 [M+1]+.

Step 3: Preparation of dimethyl 4-((1r,3r)-3-((trimethylsilyl)oxy)cyclobutoxy)phthalate

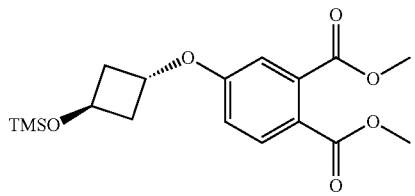

Into a 50-mL round-bottom flask, was placed 1,2-dimethyl 4-[(1r,3r)-3-hydroxycyclobutoxy]benzene-1,2-dicarboxylate (1.35 g, 4.82 mmol, 1.00 equiv) in DCM (15.00 mL), to which was added TEA (975.00 mg, 9.64 mmol, 2.00 equiv), TMSCl (681.00 mg, 6.27 mmol, 1.30 equiv). The resulting solution was stirred for 30 min at 0° C. in a water/ice bath. The resulting solution was allowed to react, with stirring, for an additional 2 hr at room temperature. The resulting mixture was concentrated under vacuum. The residue was dissolved in 30.00 mL of EA. The solids were filtered out. This filtrate was concentrated under vacuum, this resulted in 1.60 g of 1,2-dimethyl 4-[(1r,3r)-3-[(trimethylsilyl)oxy]cyclobutoxy]benzene-1,2-dicarboxylate as brown oil.

Step 4: Preparation of dimethyl 4-((1r,3r)-3-((1-((benzyloxy)carbonyl)piperidin-4-yl)oxy)cyclobutoxy)phthalate

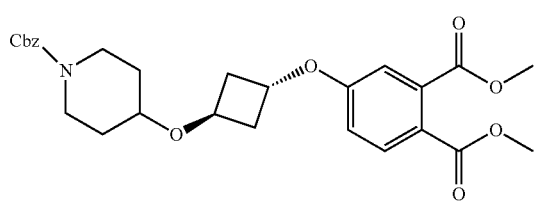 [SMILES: COC(=O)c1ccc(O[C@H]2C[C@H](OC3CCN(C(=O)OCc4ccccc4)CC3)C2)cc1C(=O)OC]

Into a 250-mL 3-necked round-bottom flask purged and maintained with an inert atmosphere of nitrogen, was placed 1,2-dimethyl 4-[(1r,3r)-3-[(trimethylsilyl)oxy]cyclobutoxy]benzene-1,2-dicarboxylate (1.80 g, 5.11 mmol, 1.00 equiv) in DCM (50.00 mL), to which was added benzyl 4-oxopiperidine-1-carboxylate (1.90 g, 8.15 mmol, 1.59 equiv), Et$_3$SiH (2.40 g, 20.64 mmol, 4.04 equiv), TMSOTf (2.27 g, 10.21 mmol, 2.00 equiv). The resulting solution was stirred for 5 hr at −78° C. in a liquid nitrogen bath. The resulting solution was allowed to react, with stirring, for an additional 30 min at 0° C. The resulting solution was allowed to react, with stirring, for an additional 2 hr at room temperature. The reaction was then quenched by the addition of 20 mL of water. The pH value of the solution was adjusted to 4-5 with H$_3$PO$_4$ (1 mol/L). The resulting solution was extracted with (2×20 mL) of dichloromethane dried over anhydrous sodium sulfate and concentrated under vacuum. The crude product was purified by Flash-Prep-HPLC. This resulted in 1.26 g (50%) of 1,2-dimethyl 4-[(1r,3r)-3-([1-[(benzyloxy)carbonyl]piperidin-4-yl]oxy) cyclobutoxy]phthalate as colorless oil. LC/MS (ESI) m/z: 498.05 [M+1]+.

Step 5: Preparation of dimethyl 4-((1r,3r)-3-(piperidin-4-yloxy)cyclobutoxy)phthalate

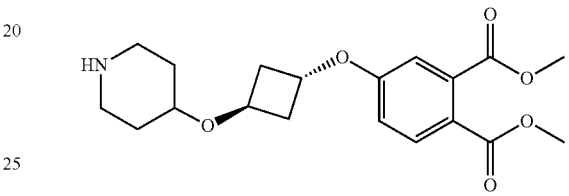

Into a 50-mL round-bottom flask, was placed 1,2-dimethyl 4-[(1r,3r)-3-([1-[(benzyloxy)carbonyl]piperidin-4-yl]oxy)cyclobutoxy]benzene-1,2-dicarboxylate (1.26 g, 2.53 mmol, 1.00 equiv) and Pd/C (10%, 541 mg, 5.06 mmol, 2.00 equiv) in MeOH (15.00 mL) under nitrogen atmosphere. The flask was then vacuumed and flushed with hydrogen. The reaction mixture was hydrogenated at room temperature for 1 hour under hydrogen atmosphere using a hydrogen balloon. Then the reaction mixture was filtered through a celite pad and the filtrate was concentrated under reduced pressure. This resulted in 778.00 mg of 1,2-dimethyl 4-[(1r,3r)-3-(piperidin-4-yloxy)cyclobutoxy]benzene-1,2-dicarboxylate as light yellow oil. LC/MS (ESI) m/z: 364.00 [M+1]+.

Step 6: Preparation of dimethyl 4-((1r,3r)-3-((1-(4-(tert-butoxycarbonyl)phenyl)piperidin-4-yl)oxy)cyclobutoxy)phthalate

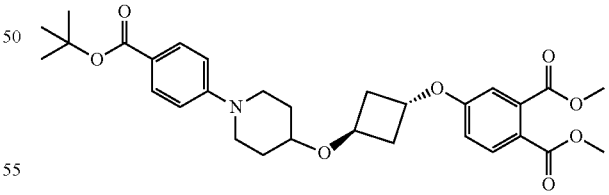

Into a 50-ml round-bottom flask, was placed 1,2-dimethyl 4-[(1r,3r)-3-(piperidin-4-yloxy)cyclobutoxy]benzene-1,2-dicarboxylate (778.00 mg, 2.14 mmol, 1.00 equiv) in DCM (30.00 mL), to which was added TEA (1.10 g, 10.87 mmol, 5.08 equiv), Cu(OAc)$_2$ (1.20 g, 6.61 mmol, 3.09 equiv), [4-[(tert-butoxy)carbonyl]phenyl]boronic acid (1.43 g, 6.42 mmol, 3.00 equiv) under nitrogen atmosphere. The flask was then vacuumed and flushed with oxygen. The resulting solution was stirred for 48 hr at room temperature under oxygen atmosphere using an oxygen balloon. The solids were filtered out. The resulting mixture was concentrated under vacuum. The crude product was purified by Flash-Prep-HPLC. This resulted in 330.00 mg (29%) of 1,2-dimethyl 4-[(1r,3r)-3-[(1-[4-[(tert-butoxy)carbonyl]phenyl]piperidin-4-yl)oxy]cyclobutoxy]benzene-1,2-dicarboxylate as light yellow oil. LC/MS (ESI) m/z: 540.10 [M+1]⁺.

Step 7: Preparation of 4-((1r,3r)-3-((1-(4-(tert-butoxycarbonyl)phenyl)piperidin-4-yl)oxy)cyclobutoxy)phthalic acid

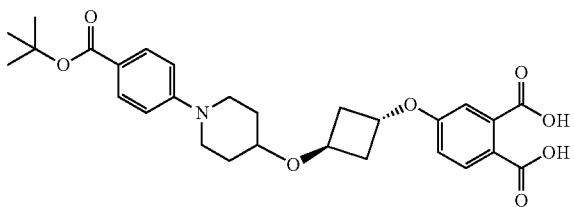 [SMILES: CC(C)(C)OC(=O)c1ccc(N2CCC(O[C@H]3C[C@H](Oc4ccc(C(=O)O)c(C(=O)O)c4)C3)CC2)cc1]

Into a 50-mL round-bottom flask, was placed 1,2-dimethyl 4-[(1r,3r)-3-[(1-[4-[(tert-butoxy) carbonyl]phenyl]piperidin-4-yl)oxy]cyclobutoxy]benzene-1,2-dicarboxylate (185.00 mg, 0.34 mmol, 1.00 equiv) in MeOH (16.00 mL) and THF (2.00 mL), to which was added NaOH(aq) (1 mol/L, 4.00 mL, 11.76 equiv). The resulting solution was stirred for 12 hr at 40° C. The reaction mixture was cooled to 0° C. with a water/ice bath. The pH value of the solution was adjusted to 2-3 with HCl (aq) (4 mol/L). The resulting mixture was concentrated under vacuum. The residue was dissolved in HOAC:DCM (5 mL:15 mL). The solids were filtered out. This resulting mixture was concentrated under vacuum, This resulted in 150.00 mg of 4-[(1r,3r)-3-[(1-[4-[(tert-butoxy) carbonyl]phenyl]piperidin-4-yl)oxy]cyclobutoxy]benzene-1,2-dicarboxylic acid as brown oil. LC/MS (ESI) m/z: 512.25 [M+1]⁺.

Step 8: Preparation of 4-(4-((1r,3r)-3-((2-(2,6-dioxopiperidin-3-yl)-1,3-dioxoisoindolin-5-yl)oxy)cyclobutoxy)piperidin-1-yl)benzoic acid

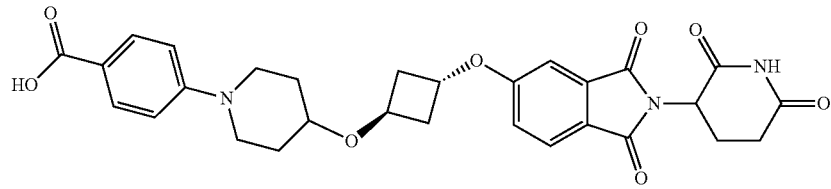 [SMILES: O=C1CCC(N2C(=O)c3ccc(O[C@H]4C[C@H](OC5CCN(c6ccc(C(=O)O)cc6)CC5)C4)cc3C2=O)C(=O)N1]

Into a 50-mL round-bottom flask, was placed 4-[(1r,3r)-3-[(1-[4-[(tert-butoxy)carbonyl]phenyl]piperidin-4-yl)oxy]cyclobutoxy]benzene-1,2-dicarboxylic acid (150.00 mg, 0.29 mmol, 1.00 equiv) in HOAc (5.00 mL), to which was added NaOAc (73.00 mg, 0.89 mmol, 3.03 equiv), 3-aminopiperidine-2,6-dione hydrochloride (95.12 mg, 0.58 mmol, 2 equiv). The resulting solution was stirred for 2 hr at 120° C. The reaction mixture was cooled to room temperature. The resulting mixture was concentrated under vacuum. The residue was applied onto a silica gel column with dichloromethane/methanol (8:1). This resulted in 87.00 mg (54%) of 4-[4-[(1r,3r)-3-[[2-(2,6-dioxopiperidin-3-yl)-1,3-dioxo-2,3-dihydro-1H-isoindol-5-yl]oxy]cyclobutoxy]piperidin-1-yl]benzoic acid as a light yellow solid. LC/MS (ESI) m/z: 548.15 [M+1]⁺.

Step 9: Preparation of N-((1r,3r)-3-(4-cyano-3,5-dimethylphenoxy)-2,2,4,4-tetramethylcyclobutyl)-4-(4-((1r,3r)-3-((2-(2,6-dioxopiperidin-3-yl)-1,3-dioxoisoindolin-5-yl)oxy)cyclobutoxy)piperidin-1-yl)benzamide

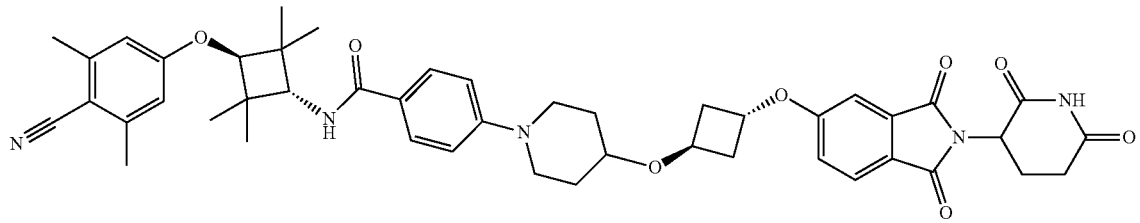 [SMILES: Cc1cc(O[C@H]2C(C)(C)[C@H](NC(=O)c3ccc(N4CCC(O[C@H]5C[C@H](Oc6ccc7c(c6)C(=O)N(C6CCC(=O)NC6=O)C7=O)C5)CC4)cc3)C2(C)C)cc(C)c1C#N]

Into a 25-mL round-bottom flask purged and maintained with an inert atmosphere of argon, was placed 4-[4-[(1r,3r)-3-[[2-(2,6-dioxopiperidin-3-yl)-1,3-dioxo-2,3-dihydro-1H-isoindol-5-yl]oxy]cyclobutoxy]piperidin-1-yl]benzoic acid (87.00 mg, 0.16 mmol, 1.00 equiv) in DMF (3.00 mL), to which was added DIEA (103.00 mg, 0.80 mmol, 5.02 equiv), HATU (96.00 mg, 0.25 mmol, 1.59 equiv), 2,6-dimethyl-4-[(1r,3r)-3-amino-2,2,4,4-tetramethylcyclobutoxy]benzonitrile hydrochloride (70.84 mg, 0.23 mmol, 1.44 equiv), The resulting solution was stirred for 4 hr at room temperature. The reaction was then quenched by the addition of 20 mL of water. The resulting solution was extracted with (5×30 mL) of ethyl acetate. The resulting mixture was washed with (3×30 mL) of brine. The mixture was dried over anhydrous sodium sulfate and concentrated under vacuum. The crude product was purified by Prep-HPLC. This resulted in 73.60 mg (58%) of N-[(1r,3r)-3-(4-cyano-3,5-dimethylphenoxy)-2,2,4,4-tetramethylcyclobutyl]-4-[4-[(1r,3r)-3-[[2-(2,6-dioxopiperidin-3-yl)-1,3-dioxo-2,3-dihydro-1H-isoindol-5-yl]oxy]cyclobutoxy]piperidin-1-yl]

benzamide as a white solid. LC/MS (ESI) m/z: 802.25 [M+1]+; 1H NMR (400 Hz, DMSO-d6) δ 11.12 (s, 1H), 7.85-7.83 (m, 1H), 7.75-7.73 (m, 2H), 7.51-7.49 (m, 1H), 7.28-7.21 (m, 2H), 6.98-6.96 (m, 2H), 6.55 (s, 2H), 5.14-5.05 (m, 2H), 4.42-4.39 (m, 1H), 4.22 (s, 1H), 4.04-4.02 (m, 1H), 3.69-3.66 (m, 2H), 3.07-2.94 (m, 2H), 2.93-2.81 (m, 1H), 2.64-2.53 (m, 1H), 2.46-2.37 (m, 9H), 2.07-1.83 (m, 4H), 1.45 (m, 2H), 1.21 (m, 7H), 1.13 (m, 7H).

Exemplary Synthesis of Exemplary Compound 24: N-((1r,4r)-4-(3-chloro-4-cyanophenoxy)cyclohexyl)-5-(4-((((1r,3r)-3-((2-(2,6-dioxopiperidin-3-yl)-3-oxoisoindolin-5-yl)oxy)cyclobutyl)(2-methoxyethyl)amino)methyl)piperidin-1-yl)pyrazine-2-carboxamide Step 1: Preparation of tert-butyl ((1r,4r)-4-(3-chloro-4-cyanophenoxy)cyclohexyl)carbamate

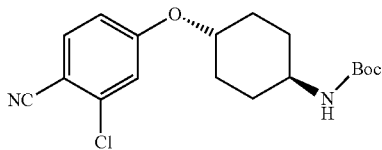

Into a 50.0-mL round-bottom flask, was placed tert-butyl N-[(1r,4r)-4-hydroxycyclohexyl]carbamate (500.0 mg, 2.32 mmol, 1.00 equiv), N,N-dimethylformamide (10.0 mL), sodium hydride (82.8 mg, 3.45 mmol, 1.50 equiv), 2-chloro-4-fluorobenzonitrile (432.6 mg, 2.78 mmol, 1.20 equiv). The resulting solution was stirred for 2 h at 0° C. in a water/ice bath. The reaction was then quenched by the addition of 20.0 mL of water. The resulting solution was extracted with ethyl acetate (40.0 mL) and the organic layers combined. The resulting mixture was washed with sodium chloride (40.0 mL). The mixture was dried over anhydrous sodium sulfate. The residue was applied onto a silica gel column with ethyl acetate/petroleum ether (1/2). The collected fractions were combined and concentrated under vacuum. This resulted in 470.0 mg (58%) of tert-butyl N-[(1r,4r)-4-(3-chloro-4-cyanophenoxy)cyclohexyl]carbamate as yellow oil. LC/MS (ESI) m/z: 295.0 [M+1]+.

Step 2: Preparation of 4-(((1r,4r)-4-aminocyclohexyl)oxy)-2-chlorobenzonitrile

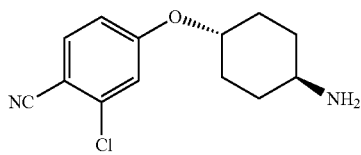 [SMILES: N#Cc1ccc(O[C@H]2CC[C@H](N)CC2)cc1Cl]

Into a 50.0-mL round-bottom flask, was placed tert-butyl N-[(1r,4r)-4-(3-chloro-4-cyanophenoxy)cyclohexyl]carbamate (470.0 mg, 1.34 mmol, 1.00 equiv), methanol (5.0 mL), hydrogen chloride. The resulting solution was stirred for 2 h at room temperature. The resulting mixture was concentrated under vacuum. This resulted in 340.0 mg (88%) of 2-chloro-4-[[(1r,4r)-4-aminocyclohexyl]oxy]benzonitrile hydrochloride as a yellow solid. LC/MS (ESI) m/z: 250.90 [M+1]+.

Step 3: Preparation of methyl 5-(4-(hydroxymethyl)piperidin-1-yl)pyrazine-2-carboxylate

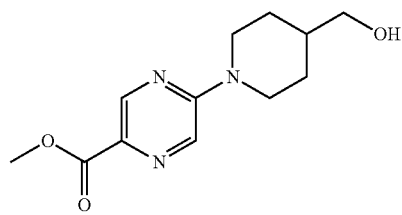 [SMILES: COC(=O)c1cnc(N2CCC(CO)CC2)cn1]

Into a 50-mL round-bottom flask, was placed methyl 5-chloropyrazine-2-carboxylate (2 g, 11.59 mmol, 1 equiv), DMSO (15 mL, 0.19 mmol, 0.017 equiv), DIEA (0.2 mL, 0.000 equiv), piperidin-4-ylmethanol (1.3 mg, 0.01 mmol, 1 equiv). The resulting solution was stirred for 16 h at 120° C. in an oil bath. The resulting solution was extracted ethyl acetate (30 mL×3) and the organic layers combined. The resulting mixture was washed with brine (10 mL×1). The resulting mixture was concentrated under vacuum. The residue was applied onto a silica gel column with dichloromethane/methanol (1:1). This resulted in 2.21 g (65%) of methyl 5-[4-(hydroxymethyl)piperidin-1-yl]pyrazine-2-carboxylate as a white solid. LC/MS (ESI) m/z: 251.13 [M+1]+.

Step 4: Preparation of 5-(4-(hydroxymethyl)piperidin-1-yl)pyrazine-2-carboxylic acid

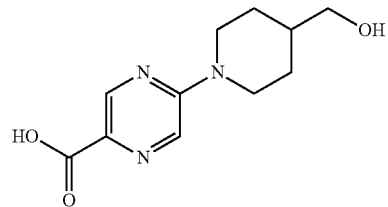 [SMILES: O=C(O)c1cnc(N2CCC(CO)CC2)cn1]

Into a 100-mL round-bottom flask, was placed methyl 5-[4-(hydroxymethyl)piperidin-1-yl]pyrazine-2-carboxylate (2.21 g, 8.79 mmol, 1 equiv), methanol (40 mL), lithiumol (0.633 mg, 0.03 mmol, 0.003 equiv), water (10 mL). The resulting solution was stirred for 16 h at room temperature. The resulting mixture was concentrated. The PH was adjusted to 4 with 1M HCl. The resulting solution was extracted dichloromethane (30 mL×3) and the organic layers combined. The resulting mixture was washed with brine (10 mL×1). The resulting mixture was concentrated under vacuum. This resulted in 1.7042 g (81.67%) of 5-[4-(hydroxymethyl)piperidin-1-yl]pyrazine-2-carboxylic acid as a white solid. LC/MS (ESI) m/z: 237.11 [M+1]+.

Step 5: Preparation of N-((1r,4r)-4-(3-chloro-4-cyanophenoxy)cyclohexyl)-5-(4-(hydroxymethyl)piperidin-1-yl)pyrazine-2-carboxamide

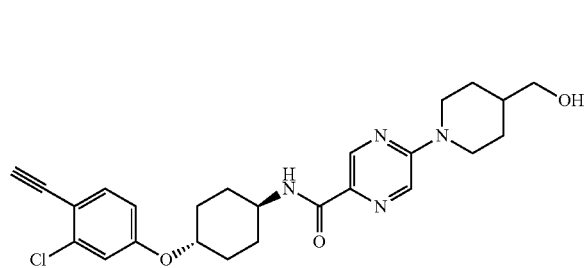 [SMILES: C#Cc1ccc(O[C@H]2CC[C@H](NC(=O)c3cnc(N4CCC(CO)CC4)cn3)CC2)cc1Cl]

Into a 100-mL round-bottom flask, was placed 5-[4-(hydroxymethyl)piperidin-1-yl]pyrazine-2-carboxylic acid (310 mg), DMF (15 mL), DIEA (563.69 mg), 2-chloro-4-[[(1s,4s)-4-aminocyclohexyl]oxy]benzonitrile (250 mg), BOP (386.28 mg). The resulting solution was stirred for 2 hr at room temperature. The resulting mixture was extracted with ethyl acetate (50 mL×3) and the organic layer was washed with brine (30 mL×1). The organic was dried over anhydrous sodium sulfate and concentrated under vacuum. The residue was applied onto a silica gel column with dichloromethane/methanol (10:1). The collected fractions were combined and concentrated under vacuum. This resulted in 243.5 mg of 5-[4-(hydroxymethyl)piperidin-1-yl]-N-[(1s,4s)-4-(3-chloro-4-cyanophenoxy)cyclohexyl]pyrazine-2-carboxamide as a white solid. LC/MS (ESI) m/z: 469.19 [M+1]$^+$.

Step 6: Preparation of N-((1r,4r)-4-(3-chloro-4-cyanophenoxy)cyclohexyl)-5-(4-formylpiperidin-1-yl)pyrazine-2-carboxamide

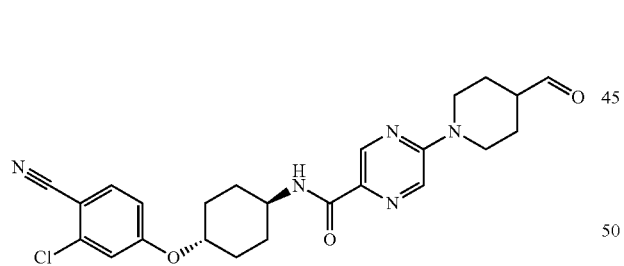

Into a 100-mL round-bottom flask, was placed 5-[4-(hydroxymethyl)piperidin-1-yl]-N-[(1r,4r)-4-(3-chloro-4-cyanophenoxy)cyclohexyl]pyrazine-2-carboxamide (150.1 mg, 0.32 mmol, 1 equiv), dichloromethane (15 mL, 0.18 mmol, 0.553 equiv), Dess-martin (271.37 mg). The resulting mixture was extracted with dichloromethane (50 mL×3) and the organic layer was washed with brine (30 mL×1). The organic was dried over anhydrous sodium sulfate and concentrated under vacuum. This resulted in 200 mg of 5-(4-formylpiperidin-1-yl)-N-[(1r,4r)-4-(3-chloro-4-cyanophenoxy)cyclohexyl]pyrazine-2-carboxamide as a white solid. LC/MS (ESI) m/z: 467.17 [M+1]$^+$.

Step 7: Preparation of methyl 2-cyano-5-fluorobenzoate

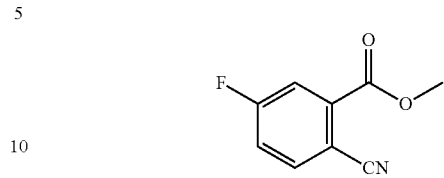

Into a 100-mL round-bottom flask purged and maintained with an inert atmosphere of nitrogen, was placed methyl 2-bromo-5-fluorobenzoate (5 g, 21.46 mmol, 1 equiv) in DMF (30 mL), to which was added Pd$_2$(dba)$_3$ (1.95 g, 2.13 mmol, 0.10 equiv), Zn(CN)$_2$ (5 g, 42.57 mmol, 1.98 equiv) at room temperature under nitrogen atmosphere. The resulting mixture was stirred for 4 hr at 120° C. under nitrogen atmosphere. The reaction was then quenched by the addition of 150 mL water. The resulting mixture was extracted with ethyl acetate (3×150 mL) and the organic layers were combined, washed with brine (3×100 mL), dried over anhydrous sodium sulfate and concentrated under vacuum. The residue was applied onto a silica gel column eluting with ethyl acetate/petroleum ether (0:100 to 1:4). This resulted in 1.5 g (39.02%) of methyl 2-cyano-5-fluorobenzoate as a yellow solid. LC/MS (ESI) m/z: 179.95 [M+1]$^+$.

Step 8: Preparation of methyl 5-((1r,3r)-3-((tert-butoxycarbonyl)amino)cyclobutoxy)-2-cyanobenzoate

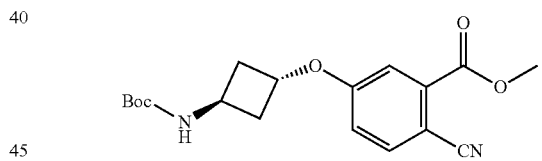

Into a 100-mL round-bottom flask, was placed tert-butyl N-[(1r,3r)-3-hydroxycyclobutyl]carbamate (3 g, 16.02 mmol, 1 equiv) in DMF (20 mL), to which was added NaH (1 g, 25 mmol, 1.56 equiv, 60%) at 0° C. The resulting mixture was stirred for 30 min and then was added by methyl 2-cyano-5-fluorobenzoate (3.2 g, 17.86 mmol, 1.11 equiv) at 0° C. The reaction mixture was stirred for 1.5 hr at room temperature. The reaction was then quenched by the addition of 100 mL water. The resulting mixture was extracted with ethyl acetate (3×150 mL) and the organic layers were combined, washed with brine (3×100 mL), dried over anhydrous sodium sulfate and concentrated under vacuum. The residue was applied onto a silica gel column eluting with ethyl acetate/petroleum ether (0:100 to 1:4). This resulted in 2.9 g (52.16%) of methyl 2-cyano-5-[(1r,3r)-3-[[(tert-butoxy)carbonyl]amino]cyclobutoxy]benzoate as yellow oil.

Step 9: Preparation of methyl 5-((1r,3r)-3-((tert-butoxycarbonyl)amino)cyclobutoxy)-2-formylbenzoate

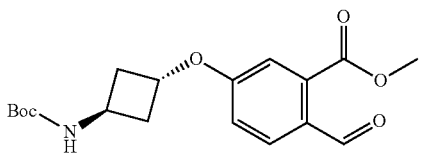 [SMILES: COC(=O)c1cc(O[C@H]2C[C@H](NC(=O)OC(C)(C)C)C2)ccc1C=O]

Into a 250-mL round-bottom flask purged and maintained with an inert atmosphere of nitrogen, was placed methyl 2-cyano-5-[(1r,3r)-3-[[(tert-butoxy)carbonyl]amino]cyclobutoxy]benzoate (2.9 g, 8.37 mmol, 1 equiv) in pyridine (20 mL), to which was added AcOH (10 mL), $H_2O$ (10 mL), Raney Ni (3.6 g, 42.02 mmol, 5.02 equiv), $NaH_2PO_2$ (4.5 g, 42.45 mmol, 5.07 equiv) in sequence at room temperature under nitrogen atmosphere. The reaction mixture was stirred for 12 hr at 70° C. and then was quenched by the addition of 50 mL HCl aqueous solution (1 M). The resulting mixture was extracted with ethyl acetate (3×50 mL) and the organic layers were combined, washed with brine, dried over anhydrous sodium sulfate and concentrated under vacuum. The residue was applied onto a silica gel column eluting with ethyl acetate/petroleum ether (0:100 to 1:4). This resulted in 1.2 g (41.02%) of methyl 2-formyl-5-[(1r,3r)-3-[[(tert-butoxy)carbonyl]amino]cyclobutoxy]benzoate as light yellow oil.

Step 10: Preparation of tert-butyl ((1r,3r)-3-((2-(2,6-dioxopiperidin-3-yl)-3-oxoisoindolin-5-yl)oxy)cyclobutyl)carbamate

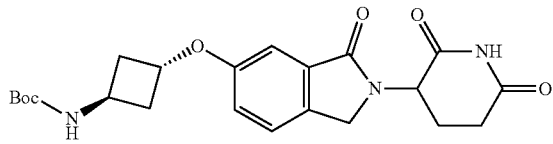 [SMILES: CC(C)(C)OC(=O)N[C@H]1C[C@H](Oc2ccc3c(c2)C(=O)N(C2CCC(=O)NC2=O)C3)C1]

Into a 50-mL round-bottom flask, was placed methyl 2-formyl-5-[(1r,3r)-3-[[(tert-butoxy)carbonyl]amino]cyclobutoxy]benzoate (380 mg, 1.09 mmol, 1 equiv) in DCM (5 mL), to which was added 3-aminopiperidine-2,6-dione hydrochloride (360 mg, 2.19 mmol, 2.01 equiv), $NaBH(OAc)_3$ (350 mg, 1.65 mmol, 1.52 equiv) at room temperature. The resulting solution was stirred for 24 hr at room temperature, and then was quenched by the addition of 50 mL water. The resulting mixture was extracted with ethyl acetate (3×30 mL) and the organic layers were combined, washed with brine, dried over anhydrous sodium sulfate and concentrated under vacuum. The residue was applied onto a silica gel column eluting with ethyl acetate/petroleum ether (0:100 to 3:1). This resulted in 346 mg (74.07%) of tert-butyl N-[(1r,3r)-3-[[2-(2,6-dioxopiperidin-3-yl)-3-oxo-2,3-dihydro-1H-isoindol-5-yl]oxy]cyclobutyl]carbamate as light yellow oil. LC/MS (ESI) m/z: 452.10 $[M+23]^+$.

Step 11: Preparation of 3-(6-((1r,3r)-3-aminocyclobutoxy)-1-oxoisoindolin-2-yl)piperidine-2,6-dione

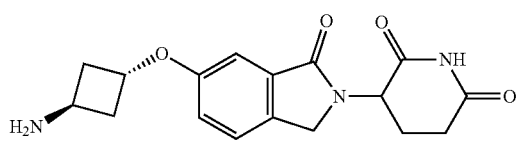 [SMILES: N[C@H]1C[C@H](Oc2ccc3c(c2)C(=O)N(C2CCC(=O)NC2=O)C3)C1]

Into a 50-mL round-bottom flask, was placed tert-butyl N-[(1r,3r)-3-[[2-(2,6-dioxopiperidin-3-yl)-3-oxo-2,3-dihydro-1H-isoindol-5-yl]oxy]cyclobutyl]carbamate (620 mg, 1.44 mmol, 1 equiv) in DCM (2 mL), to which was added TFA (2 mL). The resulting solution was stirred for 1.5 hr at room temperature. The mixture was concentrated under vacuum. This resulted in 450 mg of 3-[1-oxo-6-[(1r,3r)-3-aminocyclobutoxy]-2,3-dihydro-1H-isoindol-2-yl]piperidine-2,6-dione as brown oil. LC/MS (ESI) m/z: 330.10 $[M+23]^+$.

Step 12: Preparation of N-((1r,4r)-4-(3-chloro-4-cyanophenoxy)cyclohexyl)-5-(4-((((1r,3r)-3-((2-(2,6-dioxopiperidin-3-yl)-3-oxoisoindolin-5-yl)oxy)cyclobutyl)amino)methyl)piperidin-1-yl)pyrazine-2-carboxamide

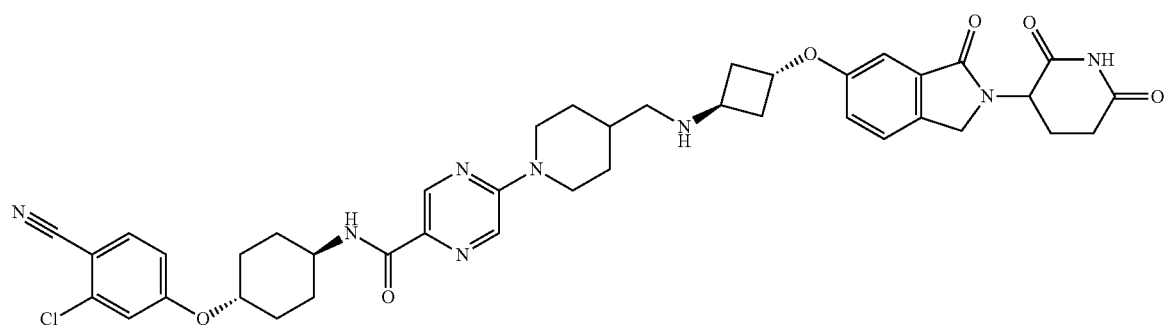 [SMILES: N#Cc1ccc(O[C@H]2CC[C@H](NC(=O)c3cnc(N4CCC(CN[C@H]5C[C@H](Oc6ccc7c(c6)C(=O)N(C6CCC(=O)NC6=O)C7)C5)CC4)cn3)CC2)cc1Cl]

Into a 50-mL round-bottom flask, was placed 3-[1-oxo-6-[(1r,3r)-3-aminocyclobutoxy]-2,3-dihydro-1H-isoindol-2-yl]piperidine-2,6-dione (340 mg, 1.03 mmol, 1 equiv) in DCM (10 mL), to which was added 5-(4-formylpiperidin-1-yl)-N-[(1r,4r)-4-(4-cyano-3-methylphenoxy)cyclohexyl]pyrazine-2-carboxamide (480 mg, 1.03 mmol, 1 equiv), NaBH(OAc)₃ (330 mg, 1.56 mmol, 1.51 equiv) at room temperature. The resulting solution was stirred for 3 hr at room temperature and then was quenched by the addition of 50 mL water. The resulting mixture was extracted with ethyl acetate (3×30 mL) and the organic layers were combined, washed with brine, dried over anhydrous sodium sulfate and concentrated under vacuum. The residue was applied onto a silica gel column eluting with dichloromethane/methanol (10:1). This resulted in 320 mg (39.68%) of 5-[4-([[(1r,3r)-3-[[2-(2,6-dioxopiperidin-3-yl)-3-oxo-2,3-dihydro-1H-isoindol-5-yl]oxy]cyclobutyl]amino]methyl)piperidin-1-yl]-N-[(1r,4r)-4-(4-cyano-3-methylphenoxy)cyclohexyl]pyrazine-2-carboxamide as a yellow solid. LC/MS (ESI) m/z: 781.25 [M+23]⁺.

Step 13: Preparation of N-((1r,4r)-4-(3-chloro-4-cyanophenoxy)cyclohexyl)-5-(4-((((1r,3r)-3-((2-(2,6-dioxopiperidin-3-yl)-3-oxoisoindolin-5-yl)oxy)cyclobutyl)(2-methoxyethyl)amino)methyl)piperidin-1-yl)pyrazine-2-carboxamide

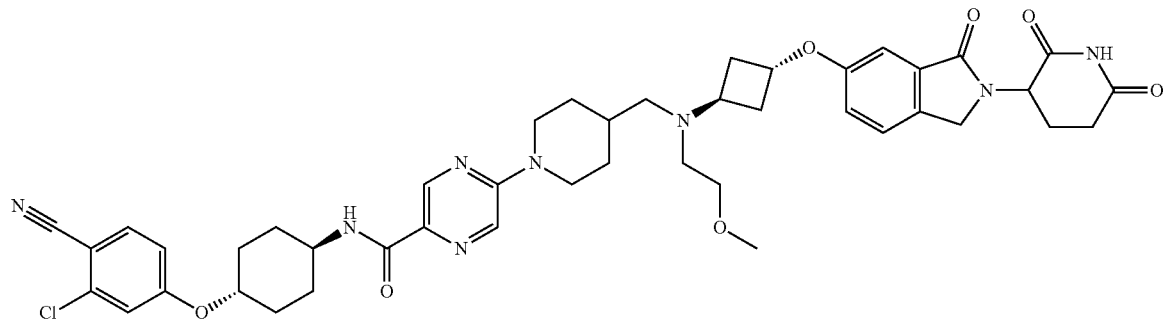 [SMILES: COCCN(CC1CCN(c2cnc(C(=O)N[C@H]3CC[C@H](Oc4ccc(C#N)c(Cl)c4)CC3)cn2)CC1)[C@H]1C[C@H](Oc2ccc3c(c2)C(=O)N(C2CCC(=O)NC2=O)C3)C1]

Into a 50-mL round-bottom flask, was placed 5-[4-([[(1r,3r)-3-[[2-(2,6-dioxopiperidin-3-yl)-3-oxo-2,3-dihydro-1H-isoindol-5-yl]oxy]cyclobutyl]amino]methyl)piperidin-1-yl]-N-[(1r,4r)-4-(3-chloro-4-cyanophenoxy)cyclohexyl]pyrazine-2-carboxamide (120 mg, 0.15 mmol, 1 equiv) in DMSO (5 mL), to which was added 1-bromo-2-methoxyethane (33 mg, 0.24 mmol, 1.55 equiv), DIEA (40 mg, 0.31 mmol, 2.02 equiv) at room temperature. The resulting solution was stirred for 36 hr at room temperature. The mixture was then concentrated and the crude product was purified by Prep-HPLC. This resulted in 12.4 mg (9.64%) of 5-(4-[[[(oxetan-3-yl)[(1r,3r)-3-[[2-(2,6-dioxopiperidin-3-yl)-3-oxo-2,3-dihydro-1H-isoindol-5-yl]oxy]cyclobutyl]amino]methyl]piperidin-1-yl)-N-[(1r,4r)-4-(3-chloro-4-cyanophenoxy)cyclohexyl]pyrazine-2-carboxamide as an off-white solid. LC/MS (ESI) m/z: 839.30 [M+1]⁺; ¹H-NMR (400 MHz, DMSO-d₆) δ 10.97 (s, 1H), 8.59 (s, 1H), 8.25 (s, 1H), 8.08-8.06 (d, 1H), 7.87-7.84 (d, 1H), 7.52-7.49 (d, 1H), 7.38-7.37 (m, 1H), 7.14-7.11 (m, 2H), 7.01-7.00 (m, 1H), 5.09 (m, 1H), 4.80 (m, 1H), 4.49-4.40 (m, 3H), 4.34-4.26 (m, 2H), 3.87-3.75 (m, 1H), 3.48-3.38 (m, 3H), 3.24 (s, 3H), 3.02-2.91 (m, 3H), 2.62-2.51 (m, 2H), 2.40-2.00 (m, 10H), 1.86-1.82 (m, 5H), 1.63-1.48 (m, 4H), 1.24 (m, 1H), 1.10-1.06 (m, 2H).

Synthesis of 5-chloro-N-((1r,3r)-3-(4-cyano-3,5-dimethylphenoxy)-2,2,4,4-tetramethylcyclobutyl)pyrazine-2-carboxamide Step 1: Preparation of 5-chloro-N-((1r,3r)-3-(4-cyano-3,5-dimethylphenoxy)-2,2,4,4-tetramethylcyclobutyl)pyrazine-2-carboxamide

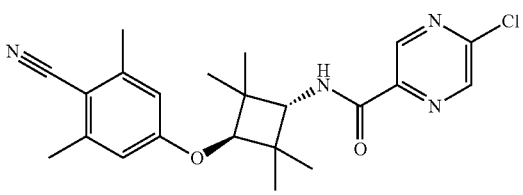 [SMILES: Cc1cc(O[C@H]2C(C)(C)[C@H](NC(=O)c3cnc(Cl)cn3)C2(C)C)cc(C)c1C#N]

To a solution of 5-chloropyrazine-2-carboxylic acid (2.00 g, 12.63 mmol, 1.30 eq) in dichloromethane (35 mL) was added 2,4,6-tripropyl-1,3,5,2,4,6-trioxatriphosphinane 2,4,6-trioxide (12.36 g, 19.43 mmol, 11.55 mL, 50% purity, 2.00 eq), triethylamine (3.93 g, 38.85 mmol, 5.41 mL, 4.00 eq) and 4-(3-amino-2,2,4,4-tetramethyl-cyclobutoxy)-2,6-dimethyl-benzonitrile (3.00 g, 9.71 mmol, 1.00 eq, hydrochloride salt) at 20° C. The mixture was stirred at 20° C. for 15 h. The mixture was diluted with water (40 mL). The organic layer was washed with brine (2×30 mL), dried over anhydrous sodium sulfate and concentrated under reduced pressure to give a residue. The residue was purified by column chromatography (petroleum ether:ethyl acetate=8:1 to 1:1) to give 5-chloro-N-[3-(4-cyano-3,5-dimethyl-phenoxy)-2,2,4,4-tetramethyl-cyclobutyl]pyrazine-2-carboxamide (3.60 g, 8.72 mmol, 90% yield) as a light yellow solid. LC/MS (ESI) m/z: 413.1 [M+1]⁺; ¹H-NMR (400 MHz, DMSO-d₆) δ 9.02 (d, J=1.2 Hz, 1H), 8.91 (d, J=1.2 Hz, 1H), 8.18 (d, J=9.2 Hz, 1H), 6.74 (s, 2H), 4.32 (s, 1H), 4.00 (d, J=9.2 Hz, 1H), 2.42 (s, 6H), 1.22 (s, 6H), 1.14 (s, 6H).

Exemplary Synthesis of Exemplary Compound 207: N-((1r,3r)-3-(4-cyano-3,5-dimethylphenoxy)-2,2,4,4-tetramethylcyclobutyl)-5-(4-((((1r,3r)-3-((2-(2,6-dioxopiperidin-3-yl)-7-methoxy-1,3-dioxoisoindolin-5-yl)oxy)cyclobutyl)(ethyl)amino)methyl)piperidin-1-yl)pyrazine-2-carboxamide Step 1: Preparation of 3-methoxycyclohex-2-en-1-one

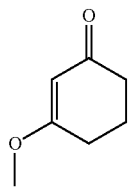

To a solution of cyclohexane-1,3-dione (15 g, 133.78 mmol, 1 eq) in MeOH (260 mL) was added titanium tetrachloride (1 M, 4 mL, 0.03 eq) in dichloromethan (4 mL), at 15° C., the mixture was stirred at 15° C. for 0.5 h. The mixture was poured into water (200 mL) and the aqueous phase was extracted with ether (50 mL×5). The combined organic phase was washed with brine (50 mL×2), dried with anhydrous sodium sulfate, filtered and concentrated in vacuum. The residue was purified by Prep-HPLC to obtain 3-methoxycyclohex-2-en-1-one as a yellow oil. LC/MS (ESI) m/z: 127.2 [M+1]⁺.

Step 2: Preparation of ((5-methoxycyclohexa-1,5-dien-1-yl)oxy)trimethylsilane

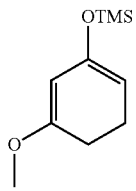

To a solution of 3-methoxycyclohex-2-en-1-one (8.65 g, 68 mmol, 1 eq) in tetrahydrofuran (80 mL) was added lithium diisopropylamide, Lithium (2 M, 41 mL, 1.2 eq) under nitrogen. The mixture was stirred at −70° C. for 10 min, then trimethylchlorosilane (7.45 g, 68 mmol, 8.70 mL, 1 eq) was added into the mixture. The mixture was stirred at −70° C. for 1 h. The mixture was poured into ammonium chloride (sat, 20 mL) and the aqueous phase was extracted with ethyl acetate (50 mL×3). The combined organic phase was washed with brine (50 mL×2), dried with anhydrous sodium sulfate, filtered and concentrated in vacuum. (5-methoxycyclohexa-1,5-dien-1-yl)oxy-trimethyl-silane (13.5 g) was obtained as a yellow oil.

Step 3: Preparation of dimethyl 1-methoxy-5-((trimethylsilyl)oxy)bicyclo[2.2.2]octa-2,5-diene-2,3-dicarboxylate

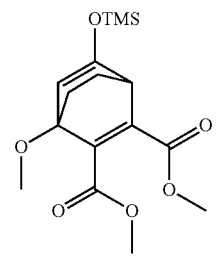

To a solution of (5-methoxycyclohexa-1,5-dien-1-yl)oxy-trimethyl-silane (13.5 g, 68 mmol, 1 eq) in tetrahydrofuran (100 mL) was added dimethyl but-2-ynedioate (9.77 g, 68 mmol, 1.01 eq) dropwise at −70° C. The reaction temperature was then raised to 50° C. over a period of 1 h. The mixture was stirred at 50° C. for 1 h. The mixture was concentrated in vacuum to obtain dimethyl 1-methoxy-5-((trimethylsilyl)oxy)bicyclo[2.2.2]octa-2,5-diene-2,3-dicarboxylate (20 g) as a yellow oil.

Step 4: Preparation of dimethyl 5-hydroxy-3-methoxyphthalate

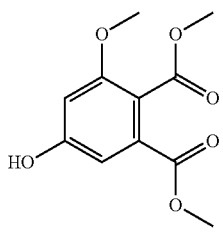 [SMILES: COC(=O)c1cc(O)cc(OC)c1C(=O)OC]

A solution of dimethyl 1-methoxy-5-((trimethylsilyl)oxy)bicyclo[2.2.2]octa-2,5-diene-2,3-dicarboxylate (20 g, 58.75 mmol, 1 eq) in xylene (5 mL) was stirred at 120° C. for 12 h. The mixture was concentrated in vacuum. The residue was purified by Prep-HPLC. Dimethyl 5-hydroxy-3-methoxyphthalate (11 g, 45.79 mmol, 77% yield) was obtained as a white solid. LC/MS (ESI) m/z: 503.1 [2M+23]⁺.

Step 5: Preparation of dimethyl 5-((1r,3r)-3-((tert-butoxycarbonyl)amino)cyclobutoxy)-3-methoxyphthalate

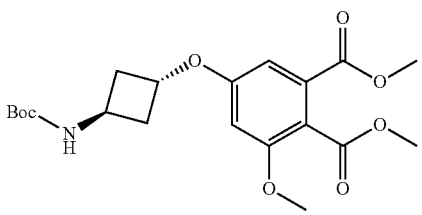 [SMILES: COC(=O)c1cc(O[C@H]2C[C@H](NC(=O)OC(C)(C)C)C2)cc(OC)c1C(=O)OC]

To a solution of dimethyl 5-hydroxy-3-methoxy-benzene-1,2-dicarboxylate (2 g, 8.33 mmol, 1 eq) in tetrahydrofuran (40 mL) was added tert-butyl N-(3-hydroxycyclobutyl)carbamate (1.71 g, 9 mmol, 1.1 eq), triphenylphosphine (2.62 g, 9.99 mmol, 1.2 eq) at 0° C. Then Diisopropyl azodicarboxylate (2.02 g, 9.99 mmol, 1.9 mL, 1.2 eq) in tetrahydrofuran (10 mL) was added into the mixture. The mixture was stirred at 15° C. for 12 h. The mixture was poured into water (20 mL) and the aqueous phase was extracted with ethyl acetate (20 mL×3). The combined organic phase was washed with brine (20 mL×2), dried with anhydrous sodium sulfate, filtered and concentrated in vacuum. The residue was purified by silica gel chromatography (Petroleum ether/Ethyl acetate=20/1-5/1). Dimethyl 5-((1r,3r)-3-((tert-butoxycarbonyl)amino)cyclobutoxy)-3-methoxyphthalate (2.7 g, 6.59 mmol, 79% yield) was obtained as a white solid. LC/MS (ESI) m/z: 432.2 [M+23]$^+$.

Step 6: Preparation of dimethyl 5-((1r,3r)-3-aminocyclobutoxy)-3-methoxyphthalate

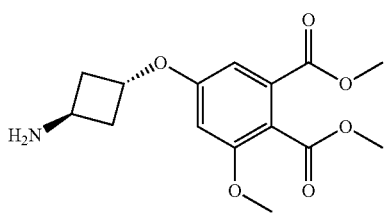 [SMILES: COC(=O)c1cc(O[C@H]2C[C@H](N)C2)cc(OC)c1C(=O)OC]

To a solution of dimethyl 5-[3-(tert-butoxycarbonylamino)cyclobutoxy]-3-methoxy-benzene-1,2-dicarboxylate (3 g, 7.33 mmol, 1 eq) in dichloromethane (5 mL) was added hydrochloric acid/dioxane (4 M, 20 mL, 10 eq). The mixture was stirred at 15° C. for 0.5 h. The reaction mixture was concentrated under reduced pressure to give a residue. The product (2.5 g, hydrochloric acid) was obtained as a yellow solid. LC/MS (ESI) m/z: 310.1 [M+1]$^+$.

Step 7: Preparation of dimethyl 5-((1r,3r)-3-(((1-(tert-butoxycarbonyl)piperidin-4-yl)methyl)amino)cyclobutoxy)-3-methoxyphthalate

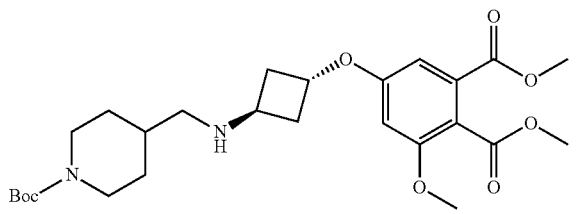 [SMILES: COC(=O)c1cc(O[C@H]2C[C@H](NCC3CCN(C(=O)OC(C)(C)C)CC3)C2)cc(OC)c1C(=O)OC]

To a solution of dimethyl 5-(3-aminocyclobutoxy)-3-methoxy-benzene-1,2-dicarboxylate (2.4 g, 6.94 mmol, 1 eq, hydrochloric acid) in dichloroethane (30 mL) was added dropwise triethylamine (3.51 g, 34 mmol, 4.8 mL, 5 eq) at 15° C. After addition, the mixture was stirred at this temperature for 10 min, and then tert-butyl 4-formylpiperidine-1-carboxylate (1.11 g, 5.21 mmol, 0.75 eq) was added dropwise at 15° C. The resulting mixture was stirred at 15° C. for 20 min. then Sodium borohydride acetate (4.41 g, 20 mmol, 3 eq) was added at 15° C., the mixture was stirred at 15° C. for 0.5 h. The mixture was extracted with dichloromethane (40 mL×5). The combined organic layers were dried over anhydrous sodium sulfate, filtered and concentrated in vacuum. The residue was further purified by silica gel chromatography (Petroleum ether/Ethyl acetate=20/1, 7/1). The product (1.9 g, 3.75 mmol, 54% yield) was obtained as a white solid. LC/MS (ESI) m/z: 407.3 [M-99]$^+$.

Step 8: Preparation of dimethyl 5-((1r,3r)-3-(((1-(tert-butoxycarbonyl)piperidin-4-yl)methyl)(ethyl)amino)cyclobutoxy)-3-methoxyphthalate

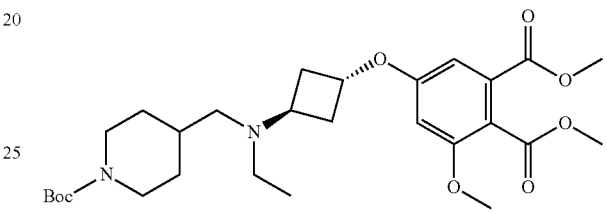

To a solution of iodoethane (753.68 mg, 4.83 mmol, 386.50 uL, 4.00 eq) and dimethyl 5-[3-[(1-tert-butoxycarbonyl-4-piperidyl)methylamino]cyclobutoxy]-3-methoxy-benzene-1,2-dicarboxylate (612.00 mg, 1.21 mmol, 1.00 eq) in acetonitrile (5 mL) was added potassium carbonate (584.38 mg, 4.23 mmol, 3.50 eq). The mixture was stirred at 70° C. for 3 h. The reaction mixture was concentrated under reduced pressure to give the residue. The residue was diluted with water (15 mL) and extracted with ethyl acetate (30 mL×3). The combined organic layers were washed with brine (30 mL×3), dried over anhydrous sodium sulfate, filtered and concentrated under reduced pressure to give a residue. The residue was purified by silica gel chromatography (ethyl acetate/methanol=10/1) to give the product (405.00 mg, 0.76 mmol, 62% yield) as a yellow oil. LC/MS (ESI) m/z: 535.2 [M+1]$^+$; $^1$H-NMR (400 MHz, CDCl$_3$) δ 6.88 (d, J=2.0 Hz, 1H), 6.60 (d, J=2.0 Hz, 1H), 4.76 (s, 1H), 4.14 (s, 1H), 3.89 (d, J=13.6 Hz, 9H), 3.47 (s, 1H), 2.70 (s, 4H), 2.56 (d, J=6.0 Hz, 2H), 2.24-2.44 (m, 4H), 2.19 (d, J=6.8 Hz, 2H), 1.77 (s, 2H), 1.46 (s, 9H), 1.26 (s, 2H), 0.96 (t, J=7.2 Hz, 3H).

Step 9: Preparation of 5-((1r,3r)-3-(((1-(tert-butoxycarbonyl)piperidin-4-yl)methyl)(ethyl)amino)cyclobutoxy)-3-methoxyphthalic acid

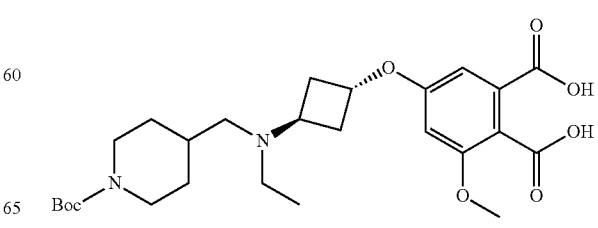

To a solution of dimethyl 5-[3-[(1-tert-butoxycarbonyl-4-piperidyl)methyl-ethyl-amino]cyclobutoxy]-3-methoxy-benzene-1,2-dicarboxylate (405.00 mg, 0.76 mmol, 1.00 eq) in methanol (10 mL) was added lithium hydroxide monohydrate (127.15 mg, 3.03 mmol, 4.00 eq) in water (2 mL). The mixture was stirred at 40° C. for 2 h. The reaction mixture was concentrated under reduced pressure. The residue was diluted with water (20 mL) and adjusted pH to 5-6 with hydrochloric acid (1M). Then the mixture was extracted with ethyl acetate (30 mL×3). The combined organic layers were washed with brine (30 mL×3), dried over anhydrous sodium sulfate, filtered and concentrated under reduced pressure to give the product (200 mg, 0.39 mmol, 52% yield) as a yellow oil. LC/MS (ESI) m/z: 507.2 [M+1]$^+$.

Step 10: Preparation of 2-(2,6-dioxopiperidin-3-yl)-6-((1r,3r)-3-(ethyl(piperidin-4-ylmethyl)amino)cyclobutoxy)-4-methoxyisoindoline-1,3-dione

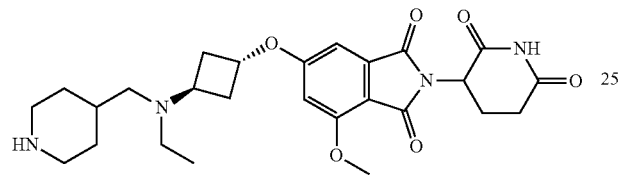

To a solution of 5-[3-[(1-tert-butoxycarbonyl-4-piperidyl)methyl-ethyl-amino]cyclobutoxy]-3-methoxy-phthalic acid (200.00 mg, 0.40 mmol, 1.00 eq) in acetic acid (10 mL) was added sodium acetate (97.16 mg, 1.18 mmol, 3.00 eq) and 3-aminopiperidine-2,6-dione (77.98 mg, 0.47 mmol, 1.20 eq, hydrochloride salt). The mixture was stirred at 110° C. for 1 h. The reaction mixture was concentrated under reduced pressure to give a residue. The residue was purified by prep-HPLC to give the product (138.00 mg, 0.25 mmol, 64% yield, formate) as a black brown oil. LC/MS (ESI) m/z: 499.2 [M+1]$^+$.

Step 11: Preparation of N-((1r,3r)-3-(4-cyano-3,5-dimethylphenoxy)-2,2,4,4-tetramethylcyclobutyl)-5-(4-((((1r,3r)-3-((2-(2,6-dioxopiperidin-3-yl)-7-methoxy-1,3-dioxoisoindolin-5-yl)oxy)cyclobutyl)(ethyl)amino)methyl)piperidin-1-yl)pyrazine-2-carboxamide

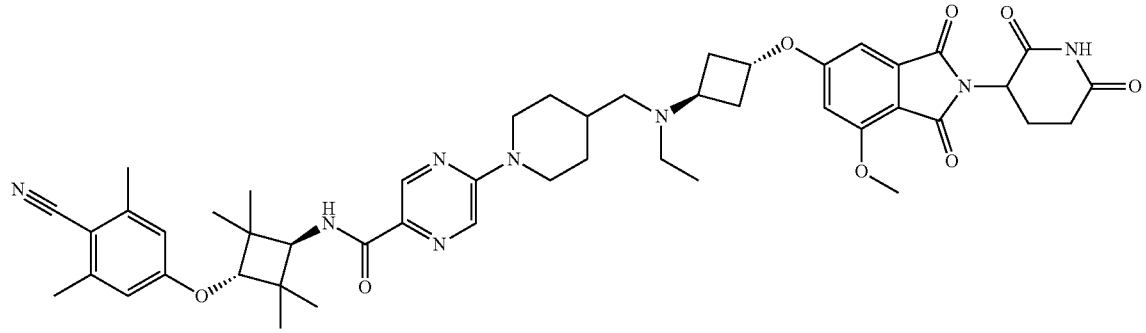 [SMILES: CCN(CC1CCN(c2cnc(C(=O)N[C@H]3C(C)(C)[C@H](Oc4cc(C)c(C#N)c(C)c4)C3(C)C)cn2)CC1)[C@H]1C[C@H](Oc2cc(OC)c3c(c2)C(=O)N(C2CCC(=O)NC2=O)C3=O)C1]

To a solution of 2-(2,6-dioxo-3-piperidyl)-6-[3-[ethyl(4-piperidylmethyl)amino]cyclobutoxy]-4-methoxy-isoindoline-1,3-dione (128.00 mg, 0.24 mmol, 1.00 eq, formate) and 5-chloro-N-[3-(4-cyano-3,5-dimethyl-phenoxy)-2,2,4,4-tetramethyl-cyclobutyl]pyrazine-2-carboxamide (97.05 mg, 0.24 mmol, 1.00 eq) in dimethylsulfoxide (2 mL) was added diisopropylethyllamine (60.75 mg, 0.47 mmol, 81.88 uL, 2.00 eq). The mixture was stirred at 120° C. for 2 h. The reaction mixture was filtered to give a residue. The residue was purified by prep-HPLC to give the product (78.30 mg, 0.078 mmol, 33% yield, 98% purity, trifluoroacetic salt) as an off-white solid. %). LC/MS (ESI) m/z: 875.5 [M+1]$^+$; $^1$H NMR (400 Hz, DMSO-d$_6$) S 11.09 (s, 1H), 9.24-9.42 (m, 1H), 8.62 (s, 1H), 8.38 (s, 1H), 7.81 (d, J=8.8 Hz, 1H), 6.83-6.94 (m, 2H), 6.76 (s, 2H), 4.99-5.12 (m, 2H), 4.52 (d, J=11.2 Hz, 2H), 4.30 (s, 1H), 4.15 (d, J=7.2 Hz, 1H), 3.88-3.99 (m, 5H), 3.46-3.57 (m, 4H), 2.74-3.31 (m, 6H), 2.53-2.71 (m, 3H), 2.43 (s, 6H), 1.76-2.23 (m, 4H), 1.19 (s, 10H), 1.12 (s, 6H).

Exemplary Synthesis of Exemplary Compound 199: N-((1r,3r)-3-(4-cyano-3,5-dimethylphenoxy)-2,2,4,4-tetramethylcyclobutyl)-5-(4-((((1r,3r)-3-((2-(2,6-dioxopiperidin-3-yl)-6-methoxy-1,3-dioxoisoindolin-5-yl)oxy)cyclobutyl)(isopropyl)amino)methyl)piperidin-1-yl)pyrazine-2-carboxamide Step 1: Preparation of methyl 2-bromo-5-hydroxy-4-methoxybenzoate

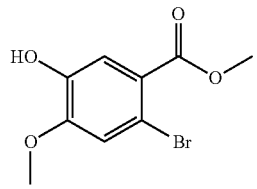

To a stirred solution of 2-bromo-5-hydroxy-4-methoxybenzoic acid (1.00 g, 4.048 mmol, 1.00 equiv) in MeOH was added sulfurooyl dichloride (1.44 g, 12.144 mmol, 3.00 equiv) dropwise portions at 0° C. The resulting mixture was stirred for 2 h at 50° C. The resulting mixture was diluted with ethyl acetate (40 mL). The reaction was quenched with Water/Ice at 0° C. The resulting mixture was washed with 3×30 mL of water. The resulting mixture was concentrated under reduced pressure. This resulted in methyl 2-bromo-5-hydroxy-4-methoxybenzoate (900 mg, 85.16%) as a white solid. LC/MS (ESI) m/z: 261.00 [M+1]$^+$.

Step 2: Preparation of dimethyl 4-hydroxy-5-methoxyphthalate

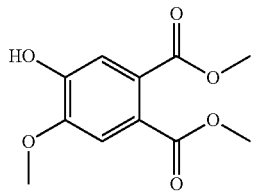 [SMILES: COC(=O)c1cc(O)c(OC)cc1C(=O)OC]

To a solution of methyl 2-bromo-5-hydroxy-4-methoxybenzoate (900.00 mg, 3.447 mmol, 1.00 equiv), DPPP (497.64 mg, 1.207 mmol, 0.35 equiv), DIEA (2004.95 mg, 15.513 mmol, 4.5 equiv) and Pd(OAc)$_2$ (232.19 mg, 1.034 mmol, 0.3 equiv) in 10 mL MeOH was added toluene in a pressure tank. The mixture was purged with nitrogen for 5 min and then was pressurized to 40 atm with carbon monoxide at 100° C. overnight. The reaction mixture was cooled to room temperature and filtered to remove insoluble solids. The aqueous layer was extracted with CH$_2$Cl$_2$ (3×40 mL). The resulting mixture was concentrated under reduced pressure. The residue was purified by Prep-TLC (PE/EtOAc 1:1) to afford the product (760 mg, 91.78%) as a yellow oil. LC/MS (ESI) m/z: 241.06 [M+1]$^+$.

Step 3: Preparation of dimethyl 4-((1r,3r)-3-((tert-butoxycarbonyl)amino)cyclobutoxy)-5-methoxyphthalate

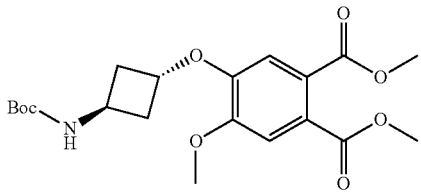 [SMILES: COC(=O)c1cc(OC)c(O[C@H]2C[C@H](NC(=O)OC(C)(C)C)C2)cc1C(=O)OC]

To a stirred solution of 1,2-dimethyl 4-hydroxy-5-methoxybenzene-1,2-dicarboxylate (1.50 g, 6.245 mmol, 1.00 equiv) and tert-butyl N-[(1s,3s)-3-hydroxycyclobutyl]carbamate (1.17 g, 6.245 mmol, 1.00 equiv) in THF were added PPh$_3$ (3.28 g, 12.489 mmol, 2 equiv) and DIAD (2.53 g, 12.489 mmol, 2 equiv) in portions at 0° C. under nitrogen atmosphere. The resulting mixture was stirred for 2 h at 50° C. under nitrogen atmosphere. The resulting mixture was diluted with ethyl acetate (50 mL). The resulting mixture was washed with 3×30 mL of water. The resulting mixture was concentrated under reduced pressure. The residue was purified by reverse flash chromatography. This resulted in 1,2-dimethyl 4-methoxy-5-[(1r,3r)-3-[[(tert-butoxy)carbonyl]amino]cyclobutoxy]benzene-1,2-dicarboxylate (2.5 g, 97.78%) as a yellow oil. LC/MS (ESI) m/z: 410.17 [M+1]$^+$.

Step 4: Preparation of tert-butyl ((1r,3r)-3-((2-(2,6-dioxopiperidin-3-yl)-6-methoxy-1,3-dioxoisoindolin-5-yl)oxy)cyclobutyl)carbamate

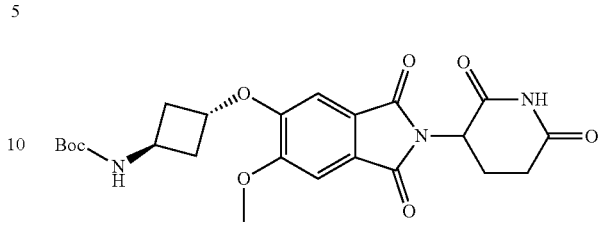

To a stirred solution of 1,2-dimethyl 4-methoxy-5-[(1r,3r)-3-[[(tert-butoxy)carbonyl]amino]cyclobutoxy]benzene-1,2-dicarboxylate (2.56 g, 6.253 mmol, 1.00 equiv) and 3-aminopiperidine-2,6-dione (2.40 g, 18.758 mmol, 3 equiv) in pyridine was added LiI (2.51 g, 18.758 mmol, 3 equiv) in portions at room temperature under nitrogen atmosphere. The final reaction mixture was irradiated with microwave radiation for 3 h at 120° C. The resulting mixture was diluted with ethyl acetate (50 mL). The resulting mixture was washed with 3×30 mL of water. The residue was purified by silica gel column chromatography, eluted with PE/EtOAc (1:1) to afford the product (1.2 g, 40.53%) as a grey solid. LC/MS (ESI) m/z: 418.00 [M+1]$^+$.

Step 5: Preparation of 5-((1r,3r)-3-aminocyclobutoxy)-2-(2,6-dioxopiperidin-3-yl)-6-methoxyisoindoline-1,3-dione

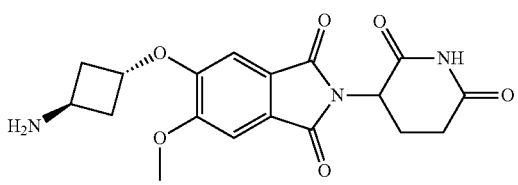 [SMILES: COc1cc2c(cc1O[C@H]1C[C@H](N)C1)C(=O)N(C1CCC(=O)NC1=O)C2=O]

To a stirred solution of tert-butyl N-[(1r,3r)-3-[[2-(2,6-dioxopiperidin-3-yl)-6-methoxy-1,3-dioxo-2,3-dihydro-1H-isoindol-5-yl]oxy]cyclobutyl]carbamate (1.20 g, 2.534 mmol, 1.00 equiv) in DCM was added 2,2,2-trifluoroacetaldehyde (5 mL) dropwise portions at 0° C. under nitrogen atmosphere. The resulting mixture was stirred for 1 h at room temperature under nitrogen atmosphere. The resulting mixture was concentrated under reduced pressure to give the product. LC/MS (ESI) m/z: 374.13 [M+1]$^+$.

Step 6: Preparation of 2-(2,6-dioxopiperidin-3-yl)-5-((1r,3r)-3-(isopropylamino)cyclobutoxy)-6-methoxyisoindoline-1,3-dione

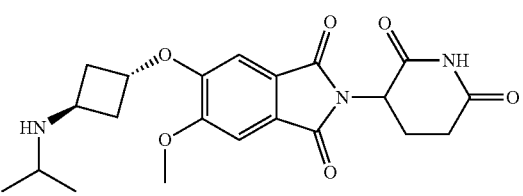 [SMILES: COc1cc2c(cc1O[C@H]1C[C@H](NC(C)C)C1)C(=O)N(C1CCC(=O)NC1=O)C2=O]

To a stirred solution of 2-(2,6-dioxopiperidin-3-yl)-5-methoxy-6-[(1r,3r)-3-aminocyclobutoxy]-2,3-dihydro-1H-isoindole-1,3-dione (1.10 g, 2.946 mmol, 1.00 equiv) and propan-2-one (1.71 g, 29.462 mmol, 10.00 equiv) in DCM and MeOH was added STAB (5.00 g, 23.569 mmol, 8.00 equiv) in portions at room temperature under nitrogen atmosphere. The resulting mixture was stirred for 2 h at room temperature under nitrogen atmosphere. The residue was purified by silica gel column chromatography, eluted with CH$_2$Cl$_2$/MeOH (10:1) to afford the product (1.2 g, 98.04%) as a white solid. LC/MS (ESI) m/z: 416.17 [M+1]$^+$.

Step 7: Preparation of tert-butyl 4-(((((1r,3r)-3-((2-(2,6-dioxopiperidin-3-yl)-6-methoxy-1,3-dioxoisoindolin-5-yl)oxy)cyclobutyl)(isopropyl)amino)methyl)piperidine-1-carboxylate

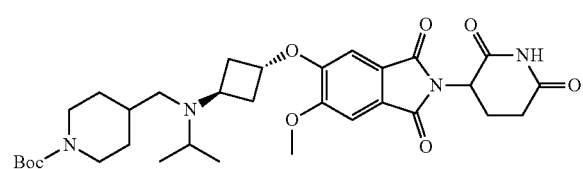 [SMILES: COc1cc2c(cc1O[C@H]1C[C@H](N(CC3CCN(C(=O)OC(C)(C)C)CC3)C(C)C)C1)C(=O)N(C1CCC(=O)NC1=O)C2=O]

To a stirred solution of 2-(2,6-dioxopiperidin-3-yl)-5-methoxy-6-[(1r,3r)-3-[(propan-2-yl)amino]cyclobutoxy]-2,3-dihydro-1H-isoindole-1,3-dione (1.20 g, 2.888 mmol, 1.00 equiv) and tert-butyl 4-formylpiperidine-1-carboxylate (1.85 g, 8.665 mmol, 3.00 equiv) in i-PrOH (30.00 mL) were added Ti(Oi-Pr)$_4$ (2.46 g, 8.665 mmol, 3.00 equiv) and NaBH$_3$CN (1.09 g, 17.331 mmol, 6.00 equiv) in portions at 0° C. under nitrogen atmosphere. The resulting mixture was stirred for 2 h at room temperature under nitrogen atmosphere. The resulting mixture was diluted with ethyl acetate (50 mL). The resulting mixture was washed with 3×20 mL of water. The residue was purified by reverse flash chromatography. This resulted in the product (550 mg, 31.08%) as a light yellow solid. LC/MS (ESI) m/z: 613.32 [M+1]$^+$.

Step 8: Preparation of 2-(2,6-dioxopiperidin-3-yl)-5-((1r,3r)-3-(isopropyl(piperidin-4-ylmethyl)amino)cyclobutoxy)-6-methoxyisoindoline-1,3-dione

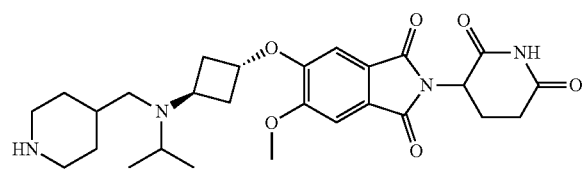 [SMILES: COc1cc2c(cc1O[C@H]1C[C@H](N(CC3CCNCC3)C(C)C)C1)C(=O)N(C1CCC(=O)NC1=O)C2=O]

To a stirred solution of tert-butyl 4-[[(propan-2-yl)[(1r,3r)-3-[[2-(2,6-dioxopiperidin-3-yl)-6-methoxy-1,3-dioxo-2,3-dihydro-1H-isoindol-5-yl]oxy]cyclobutyl]amino]methyl]piperidine-1-carboxylate (550.00 mg, 1 equiv) in DCM was added 2,2,2-trifluoroacetaldehyde (2.00 mL) dropwise portions at 0° C. under nitrogen atmosphere. The resulting mixture was stirred for 1 h at room temperature under nitrogen atmosphere. The resulting mixture was concentrated under reduced pressure to give the product. LC/MS (ESI) m/z: 513.26 [M+1]$^+$.

Step 9: Preparation of N-((1r,3r)-3-(4-cyano-3,5-dimethylphenoxy)-2,2,4,4-tetramethylcyclobutyl)-5-(4-(((((1r,3r)-3-((2-(2,6-dioxopiperidin-3-yl)-6-methoxy-1,3-dioxoisoindolin-5-yl)oxy)cyclobutyl)(isopropyl)amino)methyl)piperidin-1-yl)pyrazine-2-carboxamide

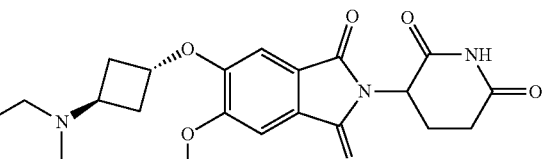

To a stirred solution of 2-(2,6-dioxopiperidin-3-yl)-5-methoxy-6-[(1r,3r)-3-[isopropyl(piperidin-4-ylmethyl)amino]cyclobutoxy]isoindole-1,3-dione (550.00 mg, 1.073 mmol, 1.00 equiv) and 5-chloro-N-[(1r,3r)-3-(4-cyano-3,5-dimethylphenoxy)-2,2,4,4-tetramethylcyclobutyl]pyrazine-2-carboxamide (487.35 mg, 1.180 mmol, 1.1 equiv) in DMF was added K$_2$CO$_3$ (444.86 mg, 3.219 mmol, 3 equiv) in portions at room temperature. The resulting mixture was stirred overnight at 60° C. The resulting mixture was diluted with ethyl acetate (40 mL). The aqueous layer was extracted with EtOAc (3×30 mL). The resulting mixture was washed with 3×20 mL of water. The residue was purified by reverse flash chromatography. This resulted in 5-[4-([isopropyl[(1r,3r)-3-[[2-(2,6-dioxopiperidin-3-yl)-6-methoxy-1,3-dioxoisoindol-5-yl]oxy]cyclobutyl]amino]methyl)piperidin-1-yl]-N-[(1r,3r)-3-(4-cyano-3,5-dimethylphenoxy)-2,2,4,4-tetramethylcyclobutyl]pyrazine-2-carboxamide (363.0 mg, 38.05%) as a white solid. LC/MS (ESI) m/z: 889.30 [M+1]$^+$; $^1$H NMR (400 Hz, DMSO-d$_6$) δ 11.09 (s, 1H), 8.61 (d, J=1.3 Hz, 1H), 8.34 (d, J=1.4 Hz, 1H), 7.80 (d, J=9.0 Hz, 1H), 7.46 (s, 1H), 7.11 (s, 1H), 6.77 (s, 2H), 5.09 (dd, J=13.0, 5.4 Hz, 1H), 4.88 (s, 1H), 4.51 (d, J=12.8 Hz, 2H), 4.30 (s, 1H), 3.99-3.91 (m, 4H), 3.66 (q, J=8.2 Hz, 1H), 3.04-2.82 (m, 4H), 2.64-2.52 (m, 1H), 2.43 (s, 6H), 2.27 (s, 1H), 2.22 (dd, J=19.4, 10.0 Hz, 3H), 2.03 (d, J=13.1 Hz, 1H), 1.86 (d, J=12.8 Hz, 2H), 1.70 (s, 1H), 1.20 (s, 6H), 1.12 (s, 8H), 0.93 (d, J=6.6 Hz, 6H).

Exemplary Synthesis of Exemplary Compound 227: N-((1r,3r)-3-(3-chloro-4-cyanophenoxy)-2,2,4,4-tetramethylcyclobutyl)-5-(4-((((1r,3r)-3-((2-(2,6-dioxopiperidin-3-yl)-4-methoxy-1-oxoisoindolin-5-yl)oxy)cyclobutyl)(isopropyl)amino)methyl)piperidin-1-yl)pyrazine-2-carboxamide Step 1: Preparation of 4-(benzyloxy)-3-hydroxybenzaldehyde

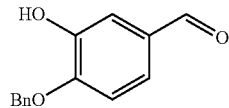

Into a 500-mL round-bottom flask, was placed 3,4-dihydroxybenzaldehyde (50.00 g, 361.999 mmol, 1.00 equiv), DMF (150.00 mL), KI (3.00 g, 18.100 mmol, 0.05 equiv), K₂CO₃ (55.03 g, 398.199 mmol, 1.10 equiv). This was followed by the addition of BnBr (66.87 g, 390.959 mmol, 1.08 equiv) dropwise with stirring at 0° C. The resulting solution was stirred for 5 hr at 0° C. in a water/ice bath. The resulting solution was diluted with 500 mL of EA. The resulting mixture was washed with 2×500 mL of brine. The mixture was dried over anhydrous sodium sulfate and concentrated. The residue was applied onto a silica gel column with ethyl acetate/petroleum ether (0%-50%). This resulted in 13.3 g (16.10%) of 4-(benzyloxy)-3-hydroxybenzaldehyde as a yellow solid. LC/MS (ESI) m/z: 228.90 [M+1]⁺.

Step 2: Preparation of 4-(benzyloxy)-3-hydroxy-2-iodobenzaldehyde

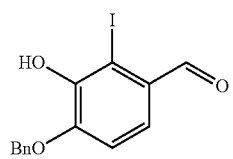

Into a 1000 mL round-bottom flask were added 4-(benzyloxy)-3-hydroxybenzaldehyde (10.00 g, 43.812 mmol, 1.00 equiv) and Pyridine (100.00 mL, 1242.353 mmol, 28.36 equiv) at 0° C. To the above mixture was added iodine monochloride (8.54 g, 52.575 mmol, 1.20 equiv) at 0° C. The resulting mixture was stirred for additional 3 days at 0° C. The resulting mixture was extracted with EtOEt (300×3 mL). The combined organic layers were washed with water (500×5 mL), dried over anhydrous Na₂SO₄. After filtration, the filtrate was concentrated under reduced pressure. The residue was purified by silica gel column chromatography, eluted with PE/EtOAc (1:1) to afford 4-(benzyloxy)-3-hydroxy-2-iodobenzaldehyde (3.5 g, 22.56%) as a light yellow solid. LC/MS (ESI) m/z: 354.98 [M+1]⁺.

Step 3: Preparation of 4-(benzyloxy)-2-iodo-3-methoxybenzaldehyde

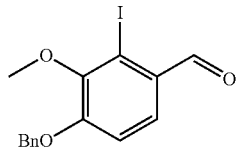 [SMILES: COc1c(OCc2ccccc2)ccc(C=O)c1I]

To a stirred solution/mixture of 4-(benzyloxy)-3-hydroxy-2-iodobenzaldehyde (2.75 g, 0.008 mmol, 1.00 equiv) and MeI (3.31 g, 0.023 mmol, 3 equiv) were added acetone (50.00 mL, 680.107 mmol, 87583.68 equiv) in portions at room temperature under air atmosphere. To the above mixture was added K₂CO₃ (3.22 g, 0.023 mmol, 3 equiv) dropwise portions over 2 min at room temperature. The resulting mixture was stirred for additional 3 h at 50° C. The mixture was allowed to cool down to room temperature. The resulting mixture was extracted with EtOAc (3×100 mL). The combined organic layers were washed with water (5×100 mL), dried over anhydrous Na₂SO₄. After filtration, the filtrate was concentrated under reduced pressure. The residue was purified by silica gel column chromatography, eluted with CH₂Cl₂/MeOH (10:1) to afford 4-(benzyloxy)-2-iodo-3-methoxybenzaldehyde (3 g, 104.93%) as a light yellow solid. LC/MS (ESI) m/z: 368.99 [M+1]⁺.

Step 4: Preparation of 4-(benzyloxy)-2-iodo-3-methoxybenzoic acid

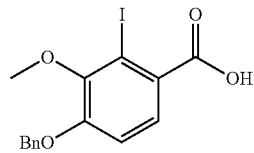 [SMILES: COc1c(OCc2ccccc2)ccc(C(=O)O)c1I]

To a stirred solution/mixture of 4-(benzyloxy)-2-iodo-3-methoxybenzaldehyde (3.00 g, 8.148 mmol, 1.00 equiv) and 2-methyl-2-butene (21.15 g, 301.491 mmol, 37.00 equiv) were added t-BuOH (84.00 mL, 883.953 mmol, 108.48 equiv) and THF (77.00 mL, 950.410 mmol, 116.64 equiv) at room temperature under air atmosphere. To the above mixture was added NaClO₂ (6.63 g, 73.336 mmol, 9.00 equiv) and NaH₂PO₄ (6.84 g, 57.039 mmol, 7.00 equiv) and H₂O (6.50 mL, 360.804 mmol, 44.28 equiv) dropwise portions at room temperature. The resulting mixture was stirred for additional 5 h at room temperature. The residue was purified by silica gel column chromatography, eluted with CH₂Cl₂/MeOH (15:1) to afford 4-(benzyloxy)-2-iodo-3-methoxybenzoic acid (3.5 g, 111.81%) as a light yellow solid.

Step 5: Preparation of methyl 4-(benzyloxy)-2-iodo-3-methoxybenzoate

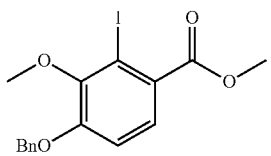

To a stirred mixture of 4-(benzyloxy)-2-iodo-3-methoxybenzoic acid (3.50 g, 9.111 mmol, 1.00 equiv) and TMSCHN₂ (3.12 g, 27.315 mmol, 3.00 equiv) were added MeOH (35.15 mL, 1096.976 mmol, 95.29 equiv) and DCM (35.15 mL, 413.863 mmol, 60.69 equiv) at room temperature under air atmosphere. The resulting mixture was stirred overnight at room temperature. The resulting mixture was concentrated under vacuum. The residue was purified by silica gel column chromatography, eluted with CH₂Cl₂/MeOH (20:1) to afford methyl 4-(benzyloxy)-2-iodo-3-methoxybenzoate (3.23 g, 44.71%) as a light yellow solid. LC/MS (ESI) m/z: 399.05 [M+1]⁺.

Step 6: Preparation of methyl 4-hydroxy-2-iodo-3-methoxybenzoate

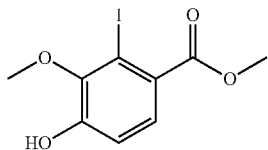

To a stirred solution of methyl 4-(benzyloxy)-2-iodo-3-methoxybenzoate (2.00 g) and dimethyl sulfide (30.00 mL) were added TFA (90.00 mL) in portions at 0° C. under air atmosphere. The resulting mixture was stirred overnight at room temperature. The resulting mixture was concentrated under reduced pressure. The residue was purified by silica gel column chromatography, eluted with PE/EtOAc (1:1) to afford methyl 4-hydroxy-2-iodo-3-methoxybenzoate (1.3 g) as a light yellow solid. LC/MS (ESI) m/z: 309.07 [M+1]⁺.

Step 7: Preparation of methyl 4-((1r,3r)-3-((tert-butoxycarbonyl)amino)cyclobutoxy)-2-iodo-3-methoxybenzoate

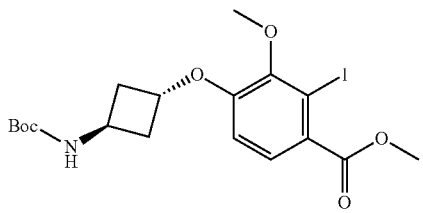

To a stirred mixture of methyl 4-hydroxy-2-iodo-3-methoxybenzoate (1.30 g, 4.220 mmol, 1.00 equiv) and tert-butyl N-[(1s,3s)-3-hydroxycyclobutyl]carbamate (0.79 g, 4.220 mmol, 1.00 equiv) were added THF (20.00 mL, 246.860 mmol, 58.50 equiv) and PPh₃ (2.21 g, 8.440 mmol, 2.00 equiv) at room temperature under air atmosphere. To the above mixture was added DIAD (1.71 g, 8.440 mmol, 2.00 equiv) at 0° C. The resulting mixture was stirred for additional overnight at 50° C. The resulting mixture was extracted with EtOAc (100×3 mL). The combined organic layers were washed with water (100×5 mL), dried over anhydrous Na₂SO₄. After filtration, the filtrate was concentrated under reduced pressure. The residue was purified by silica gel column chromatography, eluted with PE/EtOAc (1:1) to afford methyl 2-iodo-3-methoxy-4-[(1r,3r)-3-[(tert-butoxycarbonyl)amino]cyclobutoxy]benzoate (1.6 g, 79.44%) as a light yellow solid. LC/MS (ESI) m/z: 500.07 [M+23]⁺.

Step 8: Preparation of methyl 4-((1r,3r)-3-((tert-butoxycarbonyl)amino)cyclobutoxy)-3-methoxy-2-vinylbenzoate

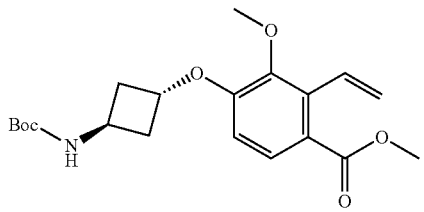 [SMILES: C=Cc1c(C(=O)OC)ccc(O[C@H]2C[C@H](NC(=O)OC(C)(C)C)C2)c1OC]

Into a 100-mL round-bottom flask purged and maintained with an inert atmosphere of nitrogen, was placed methyl 2-iodo-3-methoxy-4-[(1r,3r)-3-[(tert-butoxycarbonyl)amino]cyclobutoxy]benzoate (1.70 g, 3.562 mmol, 1.00 equiv), ethenyltrifluoro-lambda4-borane potassium (2385.47 mg, 17.809 mmol, 5.00 equiv), PPh₃ (186.84 mg, 0.712 mmol, 0.20 equiv), PdCl₂ (63.16 mg, 0.356 mmol, 0.10 equiv), Cs₂CO₃ (4641.94 mg, 14.247 mmol, 4.00 equiv), THF (16.00 mL, 0.222 mmol, 0.06 equiv), H₂O (10.00 mL, 0.555 mmol, 0.16 equiv). The resulting solution was stirred for 6 hr at 85° C. in an oil bath. The resulting mixture was concentrated. The residue was applied onto a silica gel column with ethyl acetate/petroleum ether (0%-100%). This resulted in 530 mg (39%) of the product as a solid. LC/MS (ESI) n/z: 321.95 [M-55]⁺.

Step 9: Preparation of methyl 4-((1r,3r)-3-aminocyclobutoxy)-3-methoxy-2-vinylbenzoate

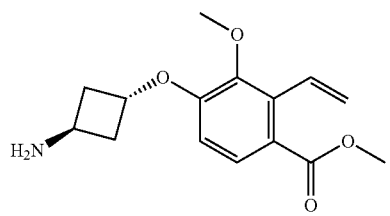 [SMILES: C=Cc1c(C(=O)OC)ccc(O[C@H]2C[C@H](N)C2)c1OC]

Into a 100-mL round-bottom flask, was placed methyl-2-ethenyl-3-methoxy-4-[(1r,3r)-3-[(tert-butoxycarbonyl)amino]cyclobutoxy]benzoate (530.00 mg, 1.404 mmol, 1.00 equiv), DCM (5.00 mL, 0.059 mmol, 0.04 equiv), trifluoroacetaldehyde (3.00 mL, 0.031 mmol, 0.02 equiv). The resulting solution was stirred for 2 hr at room temperature. The resulting mixture was concentrated. This resulted in 500 mg (128.40%) of methyl 2-ethenyl-3-methoxy-4-[(1r,3r)-3-aminocyclobutoxy]benzoate as yellow oil.

Step 10: Preparation of methyl 4-((1r,3r)-3-(isopropylamino)cyclobutoxy)-3-methoxy-2-vinylbenzoate

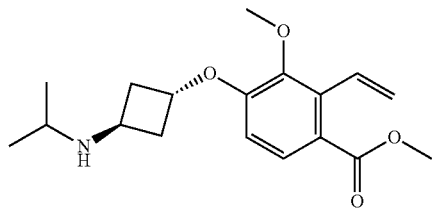 [SMILES: C=Cc1c(C(=O)OC)ccc(O[C@H]2C[C@H](NC(C)C)C2)c1OC]

Into a 50-mL round-bottom flask, was placed methyl 2-ethenyl-3-methoxy-4-[(1r,3r)-3-aminocyclobutoxy]benzoate (500.00 mg, 1.803 mmol, 1.00 equiv), acetone (523.58 mg, 9.015 mmol, 5.00 equiv), DCM (5.00 mL). This was followed by the addition of STAB (1146.37 mg, 5.409 mmol, 3.00 equiv) in several batches at 0° C. The resulting solution was stirred for 2 hr at room temperature. The residue was applied onto a silica gel column with dichloromethane/methanol (10:1). This resulted in 610 mg of the product as yellow oil. LC/MS (ESI) m/z: 320.15 [M+1]$^+$.

Step 11: Preparation of tert-butyl 4-((isopropyl((1r,3r)-3-(2-methoxy-4-(methoxycarbonyl)-3-vinylphenoxy)cyclobutyl)amino)methyl)piperidine-1-carboxylate

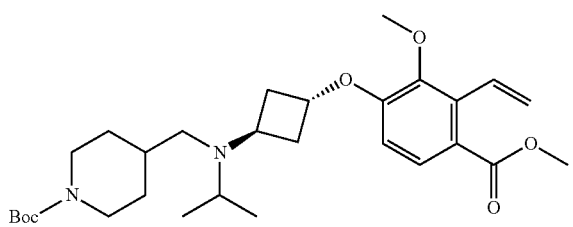 [SMILES: C=Cc1c(C(=O)OC)ccc(O[C@H]2C[C@H](N(CC3CCN(C(=O)OC(C)(C)C)CC3)C(C)C)C2)c1OC]

Into a 50-mL round-bottom flask, was placed methyl-2-ethenyl-3-methoxy-4-[(1r,3r)-3-(isopropylamino)cyclobutoxy]benzoate (610.00 mg, 1.910 mmol, 1.00 equiv), tert-butyl 4-formylpiperidine-1-carboxylate (1221.97 mg, 5.729 mmol, 3.00 equiv), DCM (10.00 mL). This was followed by the addition of STAB (2023.85 mg, 9.549 mmol, 5.00 equiv) in several batches at 0° C. The resulting solution was stirred overnight at room temperature. The solids were filtered out. The resulting mixture was concentrated. The residue was applied onto a silica gel column with H$_2$O:ACN (100%-0%). This resulted in 400 mg (40.54%) of the product as yellow oil. LC/MS (ESI) m/z: 517.40 [M+1]$^+$.

Step 12: Preparation of tert-butyl 4-((((1r,3r)-3-(3-formyl-2-methoxy-4-(methoxycarbonyl)phenoxy)cyclobutyl)(isopropyl)amino)methyl)piperidine-1-carboxylate

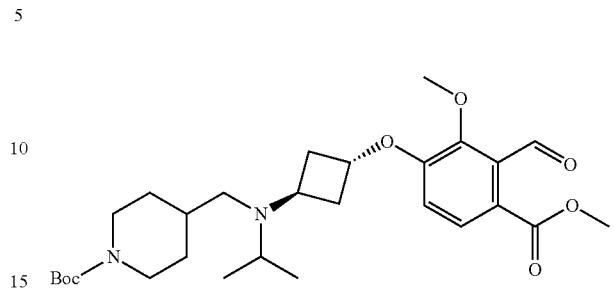

Into a 100-mL round-bottom flask, was placed tert-butyl 4-([isopropyl[(1r,3r)-3-[3-ethenyl-2-methoxy-4-(methoxycarbonyl)phenoxy]cyclobutyl]amino]methyl)piperidine-1-carboxylate (200.00 mg, 0.387 mmol, 1.00 equiv), THF (25.00 mL), NaIO$_4$ (248.38 mg, 1.161 mmol, 3.00 equiv), NMO (136.04 mg, 1.161 mmol, 3.00 equiv), OsO$_4$ (19.68 mg, 0.077 mmol, 0.20 equiv), H$_2$O (5.00 mL). The resulting solution was stirred for 10 min at room temperature. The resulting mixture was concentrated. The residue was applied onto a silica gel column with ethyl acetate/petroleum ether (1:2). This resulted in 61 mg (30.38%) of the product as a light yellow oil. LC/MS (ESI) m/z: 519.25 [M+1]$^+$.

Step 13: Preparation of tert-butyl 4-((((1r,3r)-3-((2-(2,6-dioxopiperidin-3-yl)-4-methoxy-1-oxoisoindolin-5-yl)oxy)cyclobutyl)(isopropyl)amino)methyl)piperidine-1-carboxylate

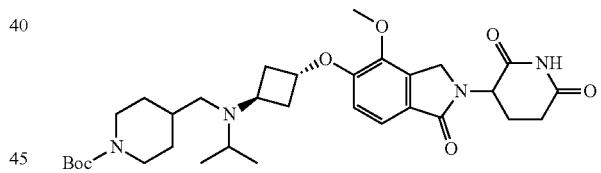

Into a 50-mL round-bottom flask, was placed tert-butyl 4-([isopropyl[(1r,3r)-3-[3-formyl-2-methoxy-4-(methoxycarbonyl)phenoxy]cyclobutyl]amino]methyl)piperidine-1-carboxylate (61.00 mg, 0.118 mmol, 1.00 equiv), 3-aminopiperidine-2,6-dione (15.07 mg, 0.118 mmol, 1.00 equiv), DCM (5.00 mL, 0.059 mmol, 0.50 equiv), AcOH (0.50 mL, 0.008 mmol, 0.07 equiv). This was followed by the addition of STAB (124.63 mg, 0.588 mmol, 5.00 equiv) in several batches at 0° C. The resulting solution was stirred overnight at room temperature. The resulting solution was diluted with 50 mL of DCM. The resulting mixture was washed with 1×50 mL of brine. The solid was dried in an oven under reduced pressure. The residue was applied onto a silica gel column with ethyl acetate/petroleum ether (1:1). This resulted in 50 mg (71.00%) of the product as a yellow solid. LC/MS (ESI) m/z: 599.20 [M+1]$^+$.

Step 14: Preparation of 3-(5-(((1r,3r)-3-(isopropyl (piperidin-4-ylmethyl)amino)cyclobutoxy)-4-methoxy-1-oxoisoindolin-2-yl)piperidine-2,6-dione

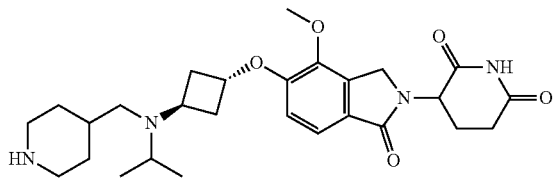 [SMILES: COc1c(O[C@H]2C[C@H](N(CC3CCNCC3)C(C)C)C2)ccc2c1CN(C1CCC(=O)NC1=O)C2=O]

Into a 25-mL round-bottom flask, was placed tert-butyl 4-([isopropyl[(1r,3r)-3-[[2-(2,6-dioxopiperidin-3-yl)-4-methoxy-1-oxo-3H-isoindol-5-yl]oxy]cyclobutyl]amino]methyl)piperidine-1-carboxylate (50.00 mg, 0.084 mmol, 1.00 equiv), DCM (2.00 mL), trifluoroacetaldehyde (1.00 mL, 0.010 mmol, 0.12 equiv). The resulting solution was stirred for 1 hr at room temperature. The resulting mixture was concentrated. This resulted in 45 mg of the product as a yellow solid.

Step 15: Preparation of N-((1r,3r)-3-(3-chloro-4-cyanophenoxy)-2,2,4,4-tetramethylcyclobutyl)-5-(4-((((1r,3r)-3-((2-(2,6-dioxopiperidin-3-yl)-4-methoxy-1-oxoisoindolin-5-yl)oxy)cyclobutyl)(isopropyl) amino)methyl)piperidin-1-yl)pyrazine-2-carboxamide

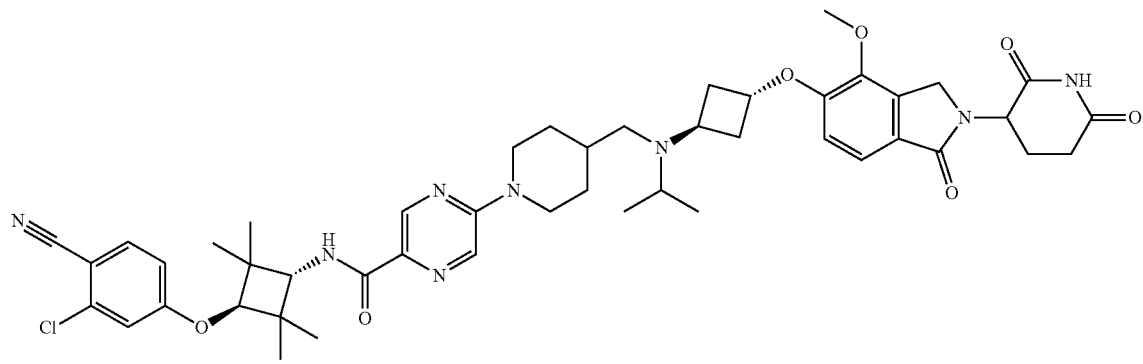 [SMILES: COc1c(O[C@H]2C[C@H](N(CC3CCN(c4cnc(C(=O)N[C@H]5C(C)(C)[C@H](Oc6ccc(C#N)c(Cl)c6)C5(C)C)cn4)CC3)C(C)C)C2)ccc2c1CN(C1CCC(=O)NC1=O)C2=O]

Into a 25-mL round-bottom flask, was placed 3-[4-methoxy-1-oxo-5-[(1r,3r)-3-[isopropyl(piperidin-4-ylmethyl)amino]cyclobutoxy]-3H-isoindol-2-yl]piperidine-2,6-dione (45.00 mg, 0.090 mmol, 1.00 equiv), DMF (1.00 mL), 5-chloro-N-((1r,3r)-3-(3-chloro-4-cyanophenoxy)-2,2,4,4-tetramethylcyclobutyl)pyrazine-2-carboxamide (38.00 mg, 0.090 mmol, 1.00 equiv). $K_2CO_3$ (25.00 mg, 0.180 mmol, 2.00 equiv). The resulting mixture was stirred for 16 hr at 100° C. in an oil bath. The resulting mixture was purified by prep-HPLC. This resulted in 8.2 mg of the product as an off-white solid. LC/MS (ESI) m/z: 881.50 [M+1]$^+$; $^1$H-NMR (400 MHz, CDCl$_3$) δ 8.84 (d, J=1.3 Hz, 1H), 8.02 (d, J=1.5 Hz, 1H), 7.98 (s, 1H), 7.78 (d, J=8.9 Hz, 1H), 7.58 (dd, J=8.8, 4.2 Hz, 2H), 6.99 (d, J=2.4 Hz, 1H), 6.87-6.78 (m, 2H), 5.36 (s, 1H), 5.32 (s, 3H), 5.21 (dd, J=13.3, 5.2 Hz, 1H), 4.78 (s, 1H), 4.57-4.44 (m, 3H), 4.35 (d, J=16.1 Hz, 1H), 4.15 (d, J=8.8 Hz, 1H), 4.09 (s, 11H), 3.98 (s, 3H), 3.77 (s, 2H), 2.98 (s, 3H), 2.95-2.78 (m, 1H), 2.42-2.31 (m, 1H), 2.31-2.19 (m, 1H), 2.02 (d, J=7.0 Hz, 2H), 1.33 (s, 5H), 1.26 (d, J=22.0 Hz, 16H), 1.00 (s, 3H), 0.90 (t, J=6.4 Hz, 1H).

Protein Level Control

This description also provides methods for the control of protein levels within a cell. The method is based on the use of compounds as described herein such that degradation of the target protein AR in vivo will result in the reducing the amount of the target protein in a biological system, preferably to provide a particular therapeutic benefit.

The following examples are used to assist in describing the present disclosure, but should not be seen as limiting the present disclosure in any way.

In certain embodiments, the description provides the following exemplary AR-degrading bifunctional molecules (compounds of Table 1A-1C, or Compounds 1-247), including salts, polymorphs, analogs, derivatives, and deuterated forms thereof.

In any aspect or embodiment described herein, the compound is a compound selected from exemplary compounds 1-247 or from Tables 1A, 1B, and 1C.

Assay for Testing AR Degradation Driven by Compounds of the Present Disclosure.

Androgen Receptor ELISA Assay. Compounds were evaluated in the following assay in LNCaP and/or VCaP cells utilizing similar protocols. The protocols used with VCaP cells are described below. The androgen receptor ELISA assay was performed using PathScan AR Sandwich ELISA (Cell Signaling Catalog #12850) according to the following assay steps.

VCaP cells were seeded at 40,000 cells/well at a volume of 100 μL/well in VCaP assay medium [Phenol red free RPMI (Gibco Cat #11835-030); 5% Charcoal Stripped (Dextran treated) FBS (Omega Scientific, Cat #FB-04); 1% penstrep (Life Technologies, Gibco Cat #: 10378-016)] in Corning 3904 plates. The cells were grown for a minimum of 3 days.

First, cells were dosed with compounds diluted in 0.01% DMSO—in a polypropylene plate avoiding the use of outer columns according to the following protocol: (1)(i) 1000× stock plate in DMSO was made; (ii) 20 mM stock diluted 1/6.7 with DMSO (5 μL+28.3 μL DMSO)=3 mM into row H; (iii) serial dilutions in ½ log doses (10 μL of bifunctional compound+20 μL DMSO) was performed from row H towards row B with row A being reserved for DMSO; (iv) 7 doses total (final concentration in this 1000× plate will be 3 mM, 1 mM, 333 μM, 111 μM, etc). (2)(i) A 10× stock plate in media was made; (ii) 2.5 μL of the 1000× stock was transferred to a new 10× stock plate (use 12 channel pipet, start at A (DMSO control) work thru H. When 247.5 μL of media was added to this plate, it served as a 10× stock; (iii) made media+1 nM R1881 for making 10× stock plate; (iv) added 247.5 µL of media with 1 nM R1881 to each well of the 10× stock plate, mix.

Then 22 µL of 10× stock was added to cells and incubated for 5 hours. 1× Cell Signaling Cell lysis buffer was made (Catalogue #9803; comes with the kit) to have 50 µL/well, and was kept on ice. Media was aspirated, and 100 µL 1× cell lysis buffer/well was added. The cells were placed on a shaker located in a cold room for 10 minutes and shaken at speed 7. The lysate mixture was mix and 20 µL transferred to 100 µl of Diluent in ELISA plate (0.15 µg/ml-0.075 µg/ml). The lysate-diluent mixture was store at 4° C. overnight on a shaker located in a cold room at speed 5 (gentle swirl).

The lysate-diluent mixture was shaken for 30 minutes at 37° C. The mouse AR antibody, anti-mouse antibody, TMB, and STOP solution were allowed to come to room temperature. The 1× ELISA buffer included in kit was made and loaded in reservoir. Media from the plate was discarded, the ELISA plate was tapped hard on paper towel, and washed 4×200 µl ELISA wash buffer using a plate washer for the first three washes and an eight channel aspirator for the fourth wash to more thoroughly aspirate the solution.

Next, 100 µL/well of mouse AR detection Ab was added; the plate was covered and shaken at 37° C. for 1 hour; media was discarded from the plates, the plates tapped on a paper towel and washed four times with 200 µL ELISA wash buffer with a plate washer for the first three washes and an eight channel aspirator for the fourth wash; 100 µL/well of anti-mouse—HRP conjugated Ab (comes with the kit) was added; the plates was cover and shaken at 37° C. for 30 minutes; the TMB reagent was allowed to come to room temperature; the media from the plate was discarded, the plates tapped on paper towel, and washed four times with 200 µL ELISA wash buffer with a plate washer for the first three washes and an eight channel aspirator for the fourth wash; plates were tapped on paper towl; 100 µL TMB was added to each well and the plate shaken for 2 minutes—while watching color. STOP solution (100 µL) was added when light blue color developed. The plates were shake and read at 450 nM.

Progression of prostate cancer in patients treated with anti-androgen therapy usually involves one of several mechanisms of enhanced Androgen Receptor (AR) signaling, including increased intratumoral androgen synthesis, increased AR expression and AR mutations. Bi-functional molecules described herein simultaneously bind a target of choice and an E3 ligase, cause ubiquitination via induced proximity and degradation of the targeted, pathological protein. As opposed to traditional target inhibition, which is a competitive process, degradation is a progressive process. As such, it is less susceptible to increases in endogenous ligand, target expression, or mutations in the target. Thus this technology seems ideal for addressing the mechanisms of AR resistance in patients with prostate cancer.

Data was analyzed and plotted using GraphPad Prism software. Exemplary compounds of Tables 1A, 1B, and 1C were assayed and the data shown below in Tables 2A, 2B, and 2C. DC50 (nM) categories (degradation of AR ELISA in LNCaP and/or VCaP cells) of Tables 2A, 2B, and 2C are as follows: A<1 nM; 1≤B<10 nM; 10≤C<100 nM; D≥100 nM. Dmax (%) categories (degradation of AR ELISA in LNCaP and/or VCaP cells) of Table 2 are as follows: A≥70; 50≤B<70; C<50

TABLE 1A

Exemplary heterobifunctional compounds of the present disclosure.

| Comp No. | Structure | Name | Scheme |
|---|---|---|---|
| 1 | 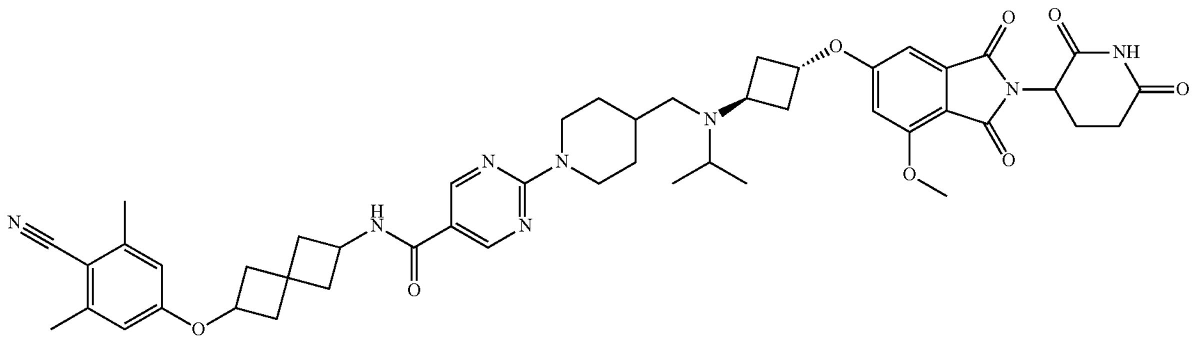 [SMILES: COc1cc(O[C@H]2C[C@H](N(CC3CCN(c4ncc(C(=O)NC5CC6(C5)CC(Oc5cc(C)c(C#N)c(C)c5)C6)cn4)CC3)C(C)C)C2)cc2c1C(=O)N(C1CCC(=O)NC1=O)C2=O] | N-(6-(4-cyano-3,5-dimethylphenoxy)spiro[3.3]heptan-2-yl)-2-(4-((((1r,3r)-3-((2-(2,6-dioxopiperidin-3-yl)-7-methoxy-1,3-dioxoisoindolin-5-yl)oxy)cyclobutyl)(isopropyl)amino)methyl)piperidin-1-yl)pyrimidine-5-carboxamide | 1 and 2 |
| 2 | 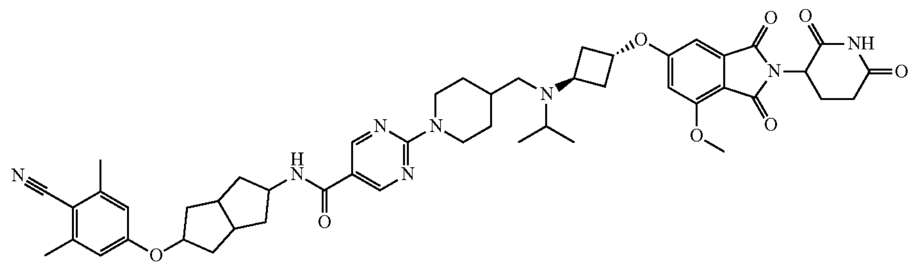 [SMILES: COc1cc(O[C@H]2C[C@H](N(CC3CCN(c4ncc(C(=O)NC5CC6CC(Oc7cc(C)c(C#N)c(C)c7)CC6C5)cn4)CC3)C(C)C)C2)cc2c1C(=O)N(C1CCC(=O)NC1=O)C2=O] | N-(5-(4-cyano-3,5-dimethylphenoxy)octahydropentalen-2-yl)-2-(4-((((1r,3r)-3-((2-(2,6-dioxopiperidin-3-yl)-7-methoxy-1,3-dioxoisoindolin-5-yl)oxy)cyclobutyl)(isopropyl)amino)methyl)piperidin-1-yl)pyrimidine-5-carboxamide | 1 and 2 |
| 3 | 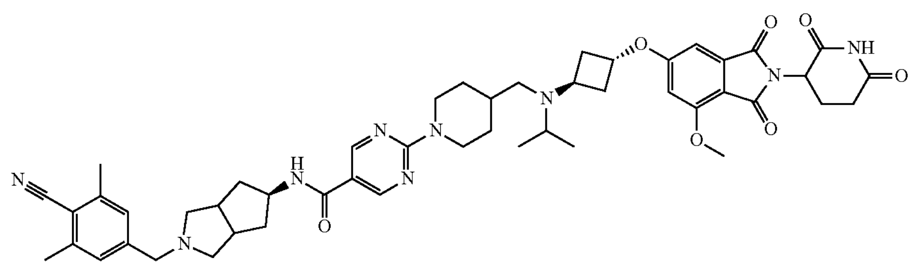 | N-(2-(4-cyano-3,5-dimethylbenzyl)octahydrocyclopenta[c]pyrrol-5-yl)-2-(4-((((1r,3r)-3-((2-(2,6-dioxopiperidin-3-yl)-7-methoxy-1,3-dioxoisoindolin-5-yl)oxy)cyclobutyl)(isopropyl)amino)methyl)piperidin-1-yl)pyrimidine-5-carboxamide | 1 and 2 |

TABLE 1A-continued

Exemplary heterobifunctional compounds of the present disclosure.

| Comp No. | Structure | Name | Scheme |
|---|---|---|---|
| 4 | 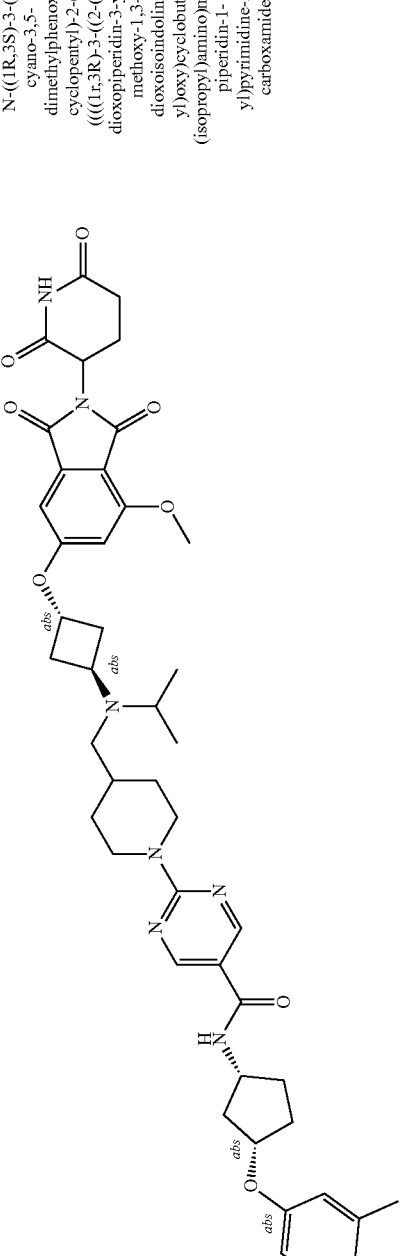 | N-((1R,3S)-3-(4-cyano-3,5-dimethylphenoxy)cyclopentyl)-2-(4-((((1r,3R)-3-((2-(2,6-dioxopiperidin-3-yl)-7-methoxy-1,3-dioxoisoindolin-5-yl)oxy)cyclobutyl)(isopropyl)amino)methyl)piperidin-1-yl)pyrimidine-5-carboxamide | 1 and 2 |
| 5 | 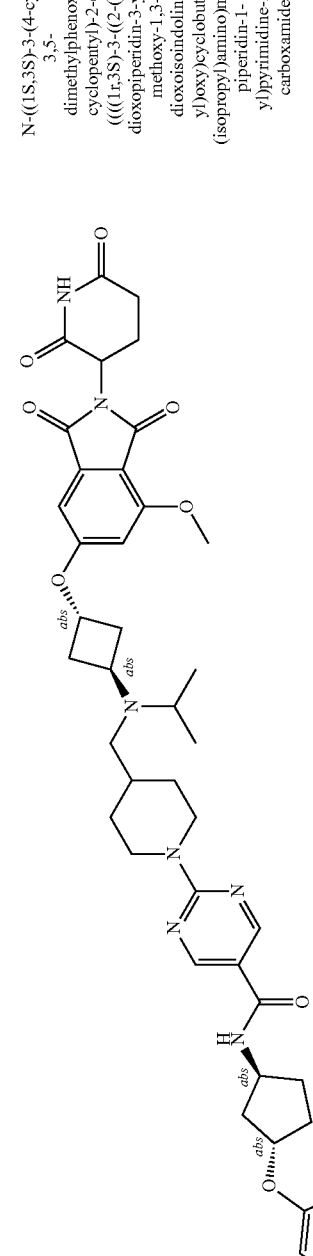 | N-((1S,3S)-3-(4-cyano-3,5-dimethylphenoxy)cyclopentyl)-2-(4-((((1r,3S)-3-((2-(2,6-dioxopiperidin-3-yl)-7-methoxy-1,3-dioxoisoindolin-5-yl)oxy)cyclobutyl)(isopropyl)amino)methyl)piperidin-1-yl)pyrimidine-5-carboxamide | 1 and 2 |

TABLE 1A-continued

Exemplary heterobifunctional compounds of the present disclosure.

| Comp No. | Structure | Name | Scheme |
|---|---|---|---|
| 6 | 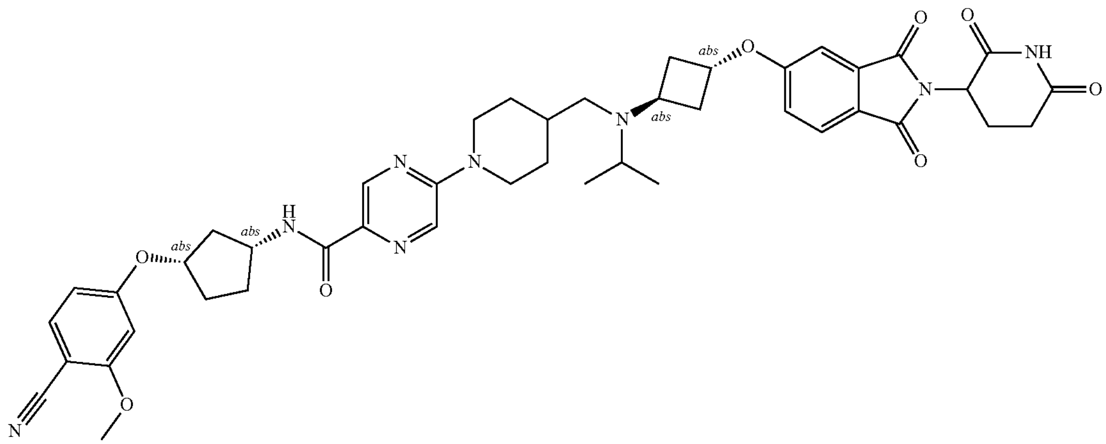 [SMILES: COc1cc(O[C@H]2CC[C@@H](NC(=O)c3cnc(N4CCC(CN(C(C)C)[C@H]5C[C@H](Oc6ccc7c(c6)C(=O)N(C6CCC(=O)NC6=O)C7=O)C5)CC4)cn3)C2)ccc1C#N] | N-((1R,3S)-3-(4-cyano-3-methoxyphenoxy)cyclopentyl)-5-(4-((((1r,3R)-3-(2-(2,6-dioxopiperidin-3-yl)-1,3-dioxoisoindolin-5-yl)oxy)cyclobutyl)(isopropyl)amino)methyl)piperidin-1-yl)pyrazine-2-carboxamide | 1 and 2 |
| 7 | 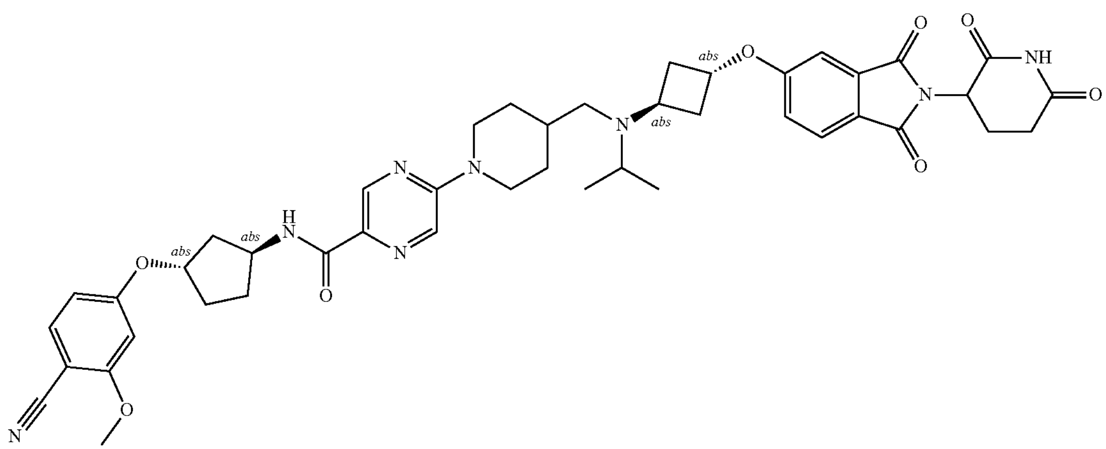 [SMILES: COc1cc(O[C@H]2CC[C@H](NC(=O)c3cnc(N4CCC(CN(C(C)C)[C@H]5C[C@H](Oc6ccc7c(c6)C(=O)N(C6CCC(=O)NC6=O)C7=O)C5)CC4)cn3)C2)ccc1C#N] | N-((1S,3S)-3-(4-cyano-3-methoxyphenoxy)cyclopentyl)-5-(4-((((1r,3S)-3-(2-(2,6-dioxopiperidin-3-yl)-1,3-dioxoisoindolin-5-yl)oxy)cyclobutyl)(isopropyl)amino)methyl)piperidin-1-yl)pyrazine-2-carboxamide | 1 and 2 |

TABLE 1A-continued

Exemplary heterobifunctional compounds of the present disclosure.

| Comp No. | Structure | Name | Scheme |
|---|---|---|---|
| 8 | 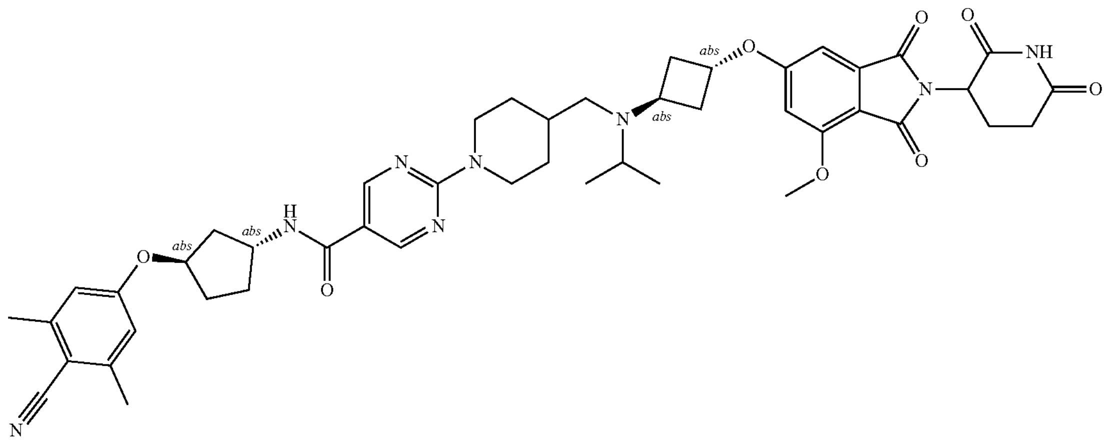 [SMILES: COc1cc(O[C@H]2C[C@H](N(CC3CCN(c4ncc(C(=O)N[C@@H]5CC[C@@H](Oc6cc(C)c(C#N)c(C)c6)C5)cn4)CC3)C(C)C)C2)cc2c1C(=O)N(C1CCC(=O)NC1=O)C2=O] | N-((1R,3R)-3-(4-cyano-3,5-dimethylphenoxy)cyclopentyl)-2-(4-(((1r,3R)-3-((2-(2,6-dioxopiperidin-3-yl)-7-methoxy-1,3-dioxoisoindolin-5-yl)oxy)cyclobutyl)(isopropyl)amino)methyl)piperidin-1-yl)pyrimidine-5-carboxamide | 1 and 2 |
| 9 | 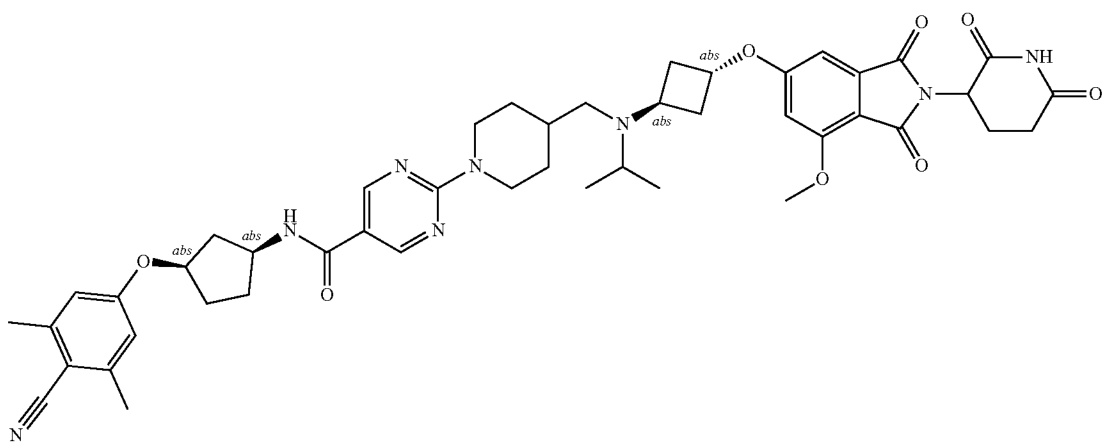 [SMILES: COc1cc(O[C@H]2C[C@H](N(CC3CCN(c4ncc(C(=O)N[C@H]5CC[C@@H](Oc6cc(C)c(C#N)c(C)c6)C5)cn4)CC3)C(C)C)C2)cc2c1C(=O)N(C1CCC(=O)NC1=O)C2=O] | N-((1S,3S)-3-(4-cyano-3,5-dimethylphenoxy)cyclopentyl)-2-(4-(((1r,3R)-3-((2-(2,6-dioxopiperidin-3-yl)-7-methoxy-1,3-dioxoisoindolin-5-yl)oxy)cyclobutyl)(isopropyl)amino)methyl)piperidin-1-yl)pyrimidine-5-carboxamide | 1 and 2 |

TABLE 1A-continued

Exemplary heterobifunctional compounds of the present disclosure.

| Comp No. | Structure | Name | Scheme |
|---|---|---|---|
| 10 | 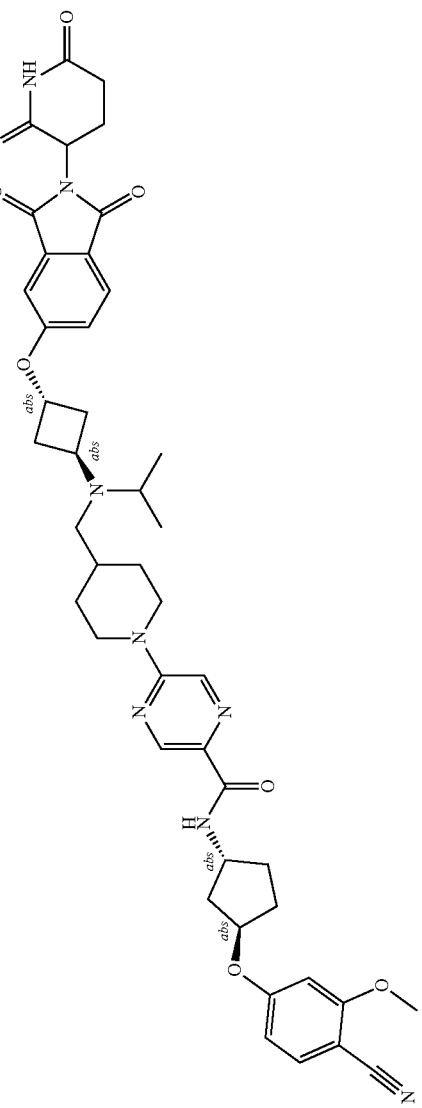 | N-((1R,3R)-3-(4-cyano-3-methoxyphenoxy)cyclopentyl)-5-(4-((((1r,3R)-3-((2-(2,6-dioxopiperidin-3-yl)-1,3-dioxoisoindolin-5-yl)oxy)cyclobutyl)(isopropyl)amino)methyl)piperidin-1-yl)pyrazine-2-carboxamide | 1 and 2 |
| 11 | 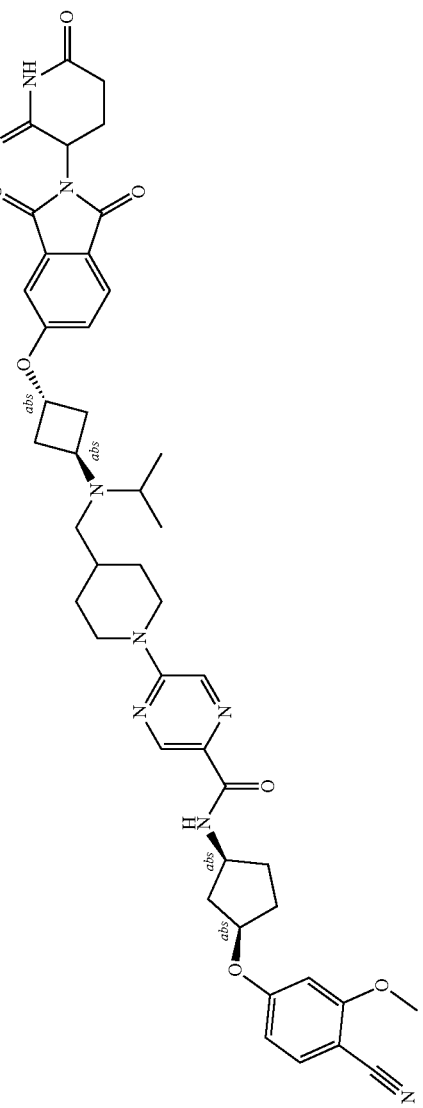 | N-((1S,3R)-3-(4-cyano-3-methoxyphenoxy)cyclopentyl)-5-(4-((((1r,3S)-3-((2-(2,6-dioxopiperidin-3-yl)-1,3-dioxoisoindolin-5-yl)oxy)cyclobutyl)(isopropyl)amino)methyl)piperidin-1-yl)pyrazine-2-carboxamide | 1 and 2 |

TABLE 1A-continued

Exemplary heterobifunctional compounds of the present disclosure.

| Comp. No. | Structure | Name | Scheme |
|---|---|---|---|
| 12 | 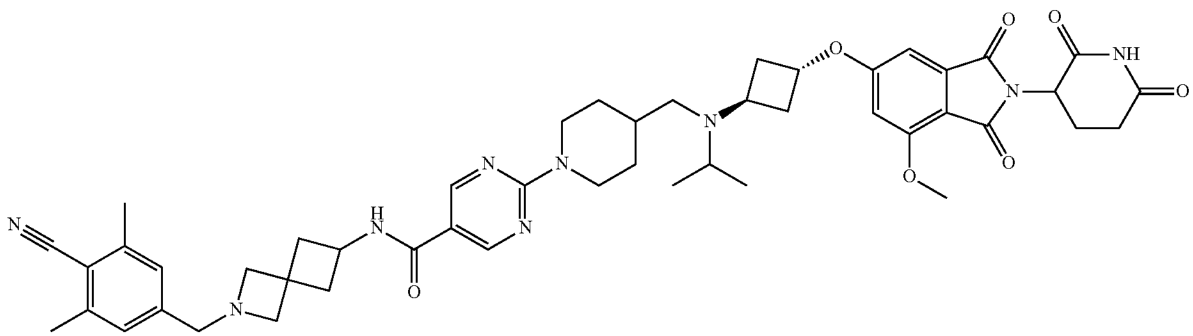 [SMILES: COc1cc(O[C@H]2C[C@H](N(CC3CCN(c4ncc(C(=O)NC5CC6(C5)CN(Cc5cc(C)c(C#N)c(C)c5)C6)cn4)CC3)C(C)C)C2)cc2c1C(=O)N(C1CCC(=O)NC1=O)C2=O] | rac-N-(2-(4-cyano-3,5-dimethylbenzyl)-2-azaspiro[3.3]heptan-6-yl)-2-(4-(((1r,3r)-3-((2-(2,6-dioxopiperidin-3-yl)-7-methoxy-1,3-dioxoisoindolin-5-yl)oxy)cyclobutyl)(isopropyl)amino)methyl)piperidin-1-yl)pyrimidine-5-carboxamide | 1 and 2 |

TABLE 1B

Exemplary heterobifunctional compounds of the present disclosure.

| Comp No. | Structure | Name | Scheme |
|---|---|---|---|
| 13 | 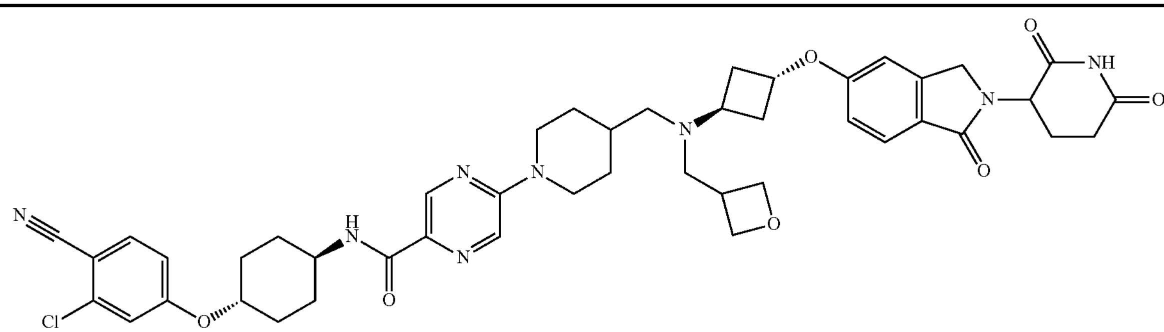 | N-((1r,4r)-4-(3-chloro-4-cyanophenoxy)cyclohexyl)-5-(4-((((1r,3r)-3-((2-(2,6-dioxopiperidin-3-yl)-1-oxoisoindolin-5-yl)oxy)cyclobutyl)(oxetan-3-ylmethyl)amino)methyl)piperidin-1-yl)pyrazine-2-carboxamide | 3 and 4 |
| 14 | 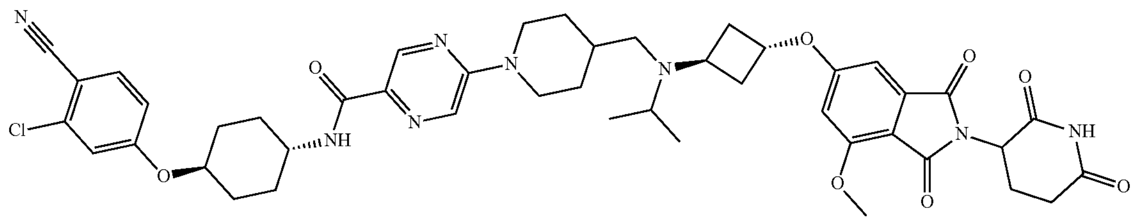 [SMILES: COc1cc(O[C@H]2C[C@H](N(CC3CCN(c4cnc(C(=O)N[C@H]5CC[C@H](Oc6ccc(C#N)c(Cl)c6)CC5)cn4)CC3)C(C)C)C2)cc2c1C(=O)N(C1CCC(=O)NC1=O)C2=O] | N-((1r,4r)-4-(3-chloro-4-cyanophenoxy)cyclohexyl)-5-(4-((((1r,3r)-3-((2-(2,6-dioxopiperidin-3-yl)-7-methoxy-1,3-dioxoisoindolin-5-yl)oxy)cyclobutyl)(isopropyl)amino)methyl)piperidin-1-yl)pyrazine-2-carboxamide | 1 and 4 |
| 15 | 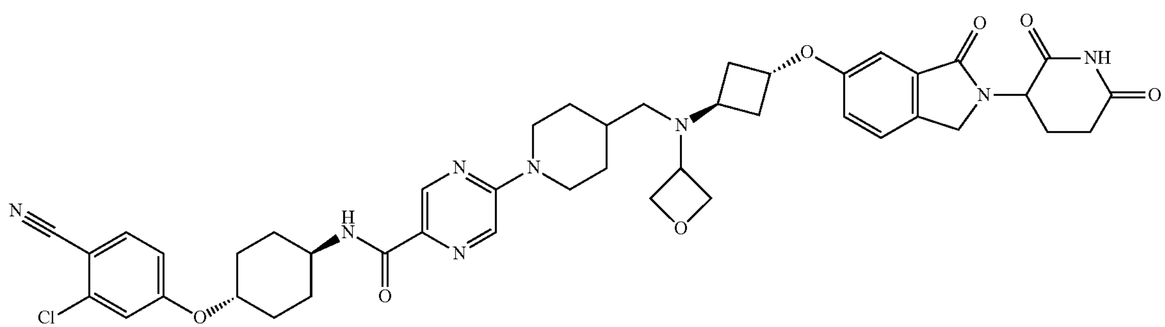 [SMILES: N#Cc1ccc(O[C@H]2CC[C@H](NC(=O)c3cnc(N4CCC(CN(C5COC5)[C@H]5C[C@H](Oc6ccc7c(c6)C(=O)N(C6CCC(=O)NC6=O)C7)C5)CC4)cn3)CC2)cc1Cl] | N-((1r,4r)-4-(3-chloro-4-cyanophenoxy)cyclohexyl)-5-(4-((((1r,3r)-3-((2-(2,6-dioxopiperidin-3-yl)-3-oxoisoindolin-5-yl)oxy)cyclobutyl)(oxetan-3-yl)amino)methyl)piperidin-1-yl)pyrazine-2-carboxamide | 3 and 4 |

TABLE 1B-continued

Exemplary heterobifunctional compounds of the present disclosure.

| Comp No. | Structure | Name | Scheme |
|---|---|---|---|
| 16 | 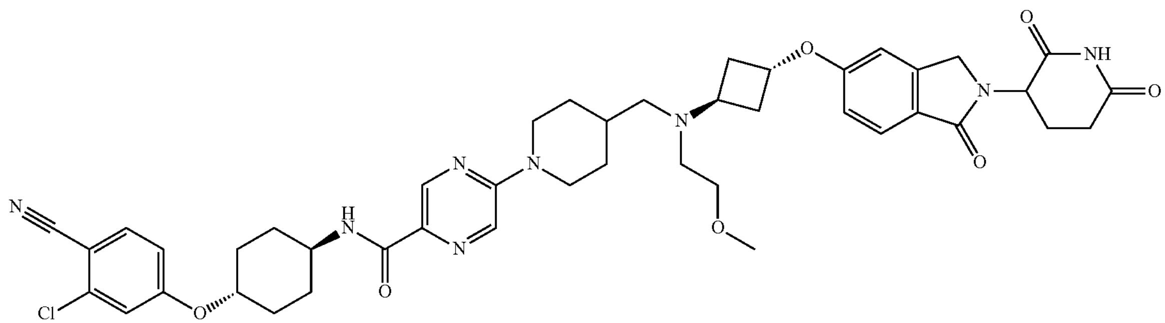 [SMILES: COCCN(CC1CCN(c2cnc(C(=O)N[C@H]3CC[C@H](Oc4ccc(C#N)c(Cl)c4)CC3)cn2)CC1)[C@H]1C[C@H](Oc2ccc3c(c2)CN(C2CCC(=O)NC2=O)C3=O)C1] | N-((1r,4r)-4-(3-chloro-4-cyanophenoxy)cyclohexyl)-5-(4-((((1r,3r)-3-((2-(2,6-dioxopiperidin-3-yl)-1-oxoisoindolin-5-yl)oxy)cyclobutyl)(2-methoxyethyl)amino)methyl)piperidin-1-yl)pyrazine-2-carboxamide | 3 and 4 |
| 17 | 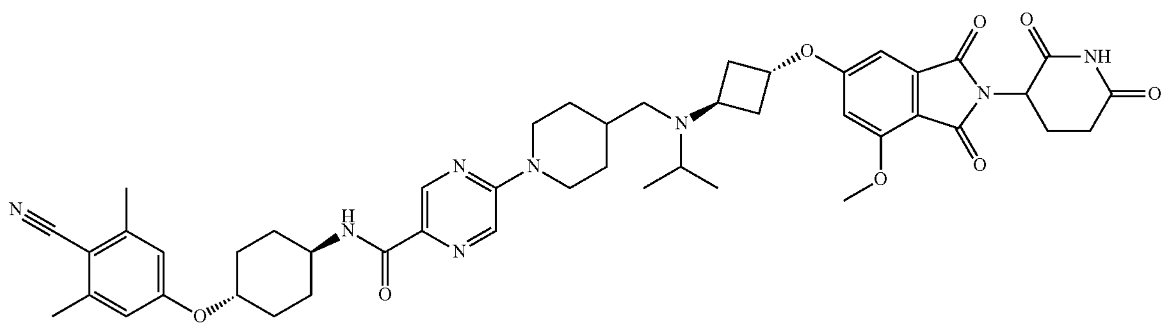 [SMILES: COc1cc(O[C@H]2C[C@H](N(CC3CCN(c4cnc(C(=O)N[C@H]5CC[C@H](Oc6cc(C)c(C#N)c(C)c6)CC5)cn4)CC3)C(C)C)C2)cc2c1C(=O)N(C1CCC(=O)NC1=O)C2=O] | N-((1r,4r)-4-(4-cyano-3,5-dimethylphenoxy)cyclohexyl)-5-(4-((((1r,3r)-3-((2-(2,6-dioxopiperidin-3-yl)-7-methoxy-1,3-dioxoisoindolin-5-yl)oxy)cyclobutyl)(isopropyl)amino)methyl)piperidin-1-yl)pyrazine-2-carboxamide | 1 and 4 |
| 18 | 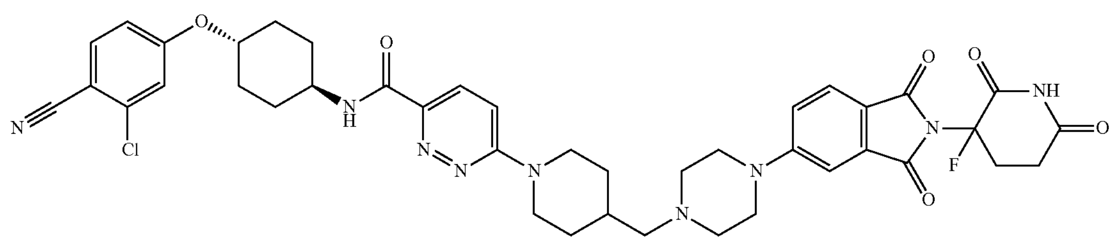 [SMILES: N#Cc1ccc(O[C@H]2CC[C@H](NC(=O)c3ccc(N4CCC(CN5CCN(c6ccc7c(c6)C(=O)N(C6(F)CCC(=O)NC6=O)C7=O)CC5)CC4)nn3)CC2)cc1Cl] | rac-N-((1r,4r)-4-(3-chloro-4-cyanophenoxy)cyclohexyl)-6-(4-((4-(2-(3-fluoro-2,6-dioxopiperidin-3-yl)-1,3-dioxoisoindolin-5-yl)piperazin-1-yl)methyl)piperidin-1-yl)pyridazine-3-carboxamide | 5 and 6 |

TABLE 1B-continued

Exemplary heterobifunctional compounds of the present disclosure.

| Comp No. | Structure | Name | Scheme |
|---|---|---|---|
| 19 | 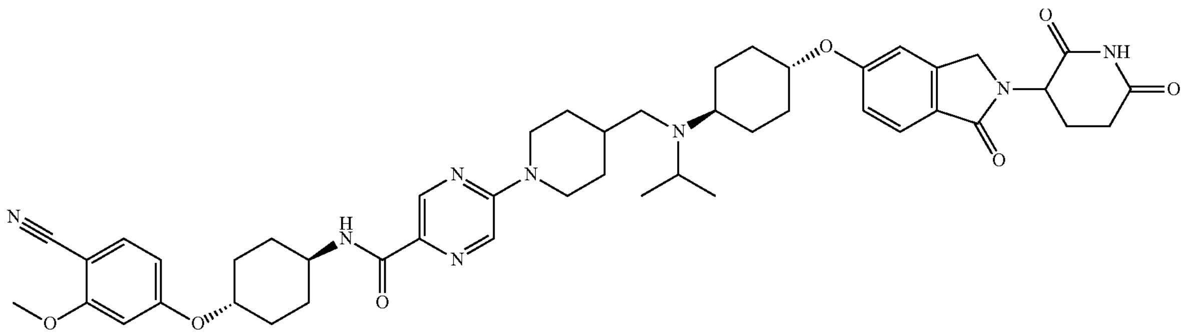 [SMILES: COc1cc(O[C@H]2CC[C@H](NC(=O)c3cnc(N4CCC(CN(C(C)C)[C@H]5CC[C@H](Oc6ccc7c(c6)CN(C6CCC(=O)NC6=O)C7=O)CC5)CC4)cn3)CC2)ccc1C#N] | N-((1r,4r)-4-(4-cyano-3-methoxyphenoxy)cyclohexyl)-5-(4-((((1r,4r)-4-((2-(2,6-dioxopiperidin-3-yl)-1-oxoisoindolin-5-yl)oxy)cyclohexyl)(isopropyl)amino)methyl)piperidin-1-yl)pyrazine-2-carboxamide | 3 and 4 |
| 20 | 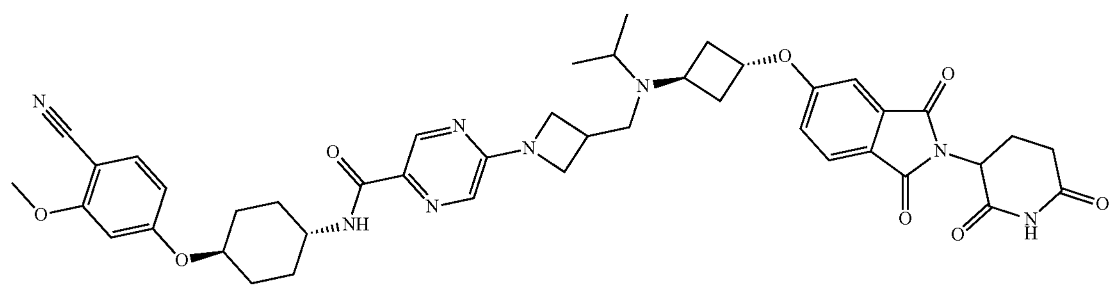 [SMILES: COc1cc(O[C@H]2CC[C@H](NC(=O)c3cnc(N4CC(CN(C(C)C)[C@H]5C[C@H](Oc6ccc7c(c6)C(=O)N(C6CCC(=O)NC6=O)C7=O)C5)C4)cn3)CC2)ccc1C#N] | N-((1r,4r)-4-(4-cyano-3-methoxyphenoxy)cyclohexyl)-5-(3-((((1r,3r)-3-((2-(2,6-dioxopiperidin-3-yl)-1,3-dioxoisoindolin-5-yl)oxy)cyclobutyl)(isopropyl)amino)methyl)azetidin-1-yl)pyrazine-2-carboxamide | 7 and 4 |
| 21 | 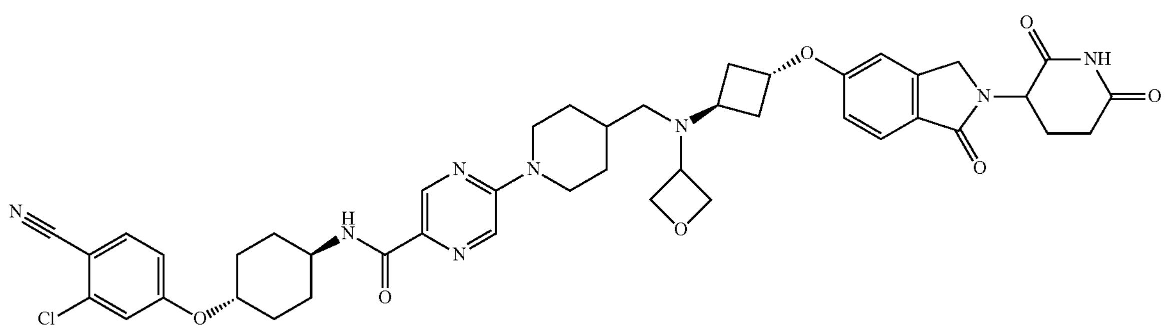 [SMILES: N#Cc1ccc(O[C@H]2CC[C@H](NC(=O)c3cnc(N4CCC(CN(C5COC5)[C@H]5C[C@H](Oc6ccc7c(c6)CN(C6CCC(=O)NC6=O)C7=O)C5)CC4)cn3)CC2)cc1Cl] | N-((1r,4r)-4-(3-chloro-4-cyanophenoxy)cyclohexyl)-5-(4-((((1r,3r)-3-((2-(2,6-dioxopiperidin-3-yl)-1-oxoisoindolin-5-yl)oxy)cyclobutyl)(oxetan-3-yl)amino)methyl)piperidin-1-yl)pyrazine-2-carboxamide | 3 and 4 |

TABLE 1B-continued

Exemplary heterobifunctional compounds of the present disclosure.

| Comp. No. | Structure | Name | Scheme |
|---|---|---|---|
| 22 | 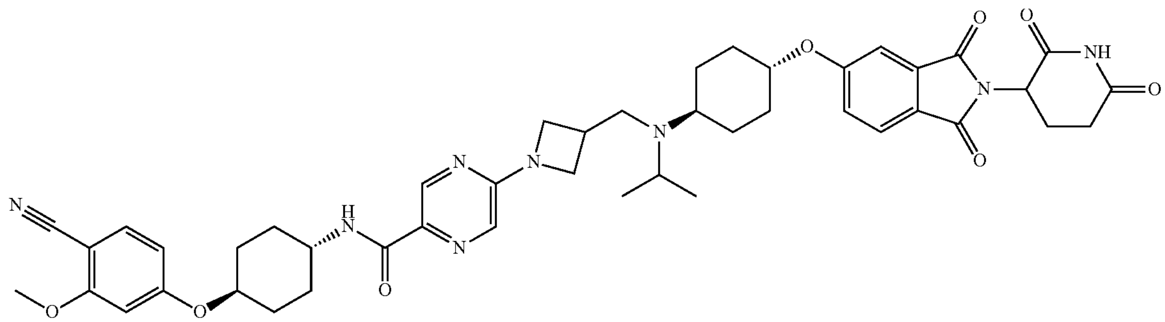 [SMILES: COc1cc(O[C@H]2CC[C@H](NC(=O)c3cnc(N4CC(CN(C(C)C)[C@H]5CC[C@H](Oc6ccc7c(c6)C(=O)N(C6CCC(=O)NC6=O)C7=O)CC5)C4)cn3)CC2)ccc1C#N] | N-((1r,4r)-4-(4-cyano-3-methoxyphenoxy)cyclohexyl)-5-(3-(((1r,4r)-4-((2-(2,6-dioxopiperidin-3-yl)-1,3-dioxoisoindolin-5-yl)oxy)cyclohexyl)(isopropyl)amino)methyl)azetidin-1-yl)pyrazine-2-carboxamide | 7 and 4 |
| 23 | 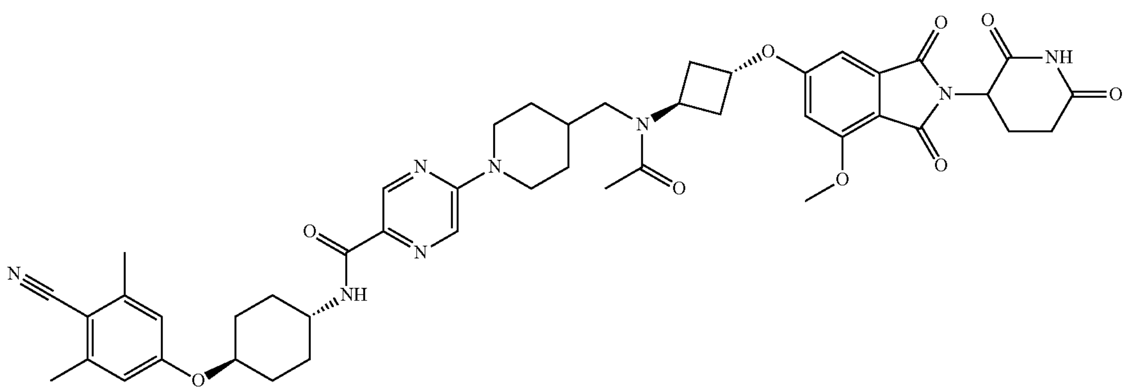 [SMILES: COc1cc(O[C@H]2C[C@H](N(CC3CCN(c4cnc(C(=O)N[C@H]5CC[C@H](Oc6cc(C)c(C#N)c(C)c6)CC5)cn4)CC3)C(C)=O)C2)cc2c1C(=O)N(C1CCC(=O)NC1=O)C2=O] | N-((1r,4r)-4-(4-cyano-3,5-dimethylphenoxy)cyclohexyl)-5-(4-((N-((1r,3r)-3-((2-(2,6-dioxopiperidin-3-yl)-7-methoxy-1,3-dioxoisoindolin-5-yl)oxy)cyclobutyl)acetamido)methyl)piperidin-1-yl)pyrazine-2-carboxamide | 1 and 4 |

TABLE 1B-continued

Exemplary heterobifunctional compounds of the present disclosure.

| Comp No. | Structure | Name | Scheme |
|---|---|---|---|
| 24 | 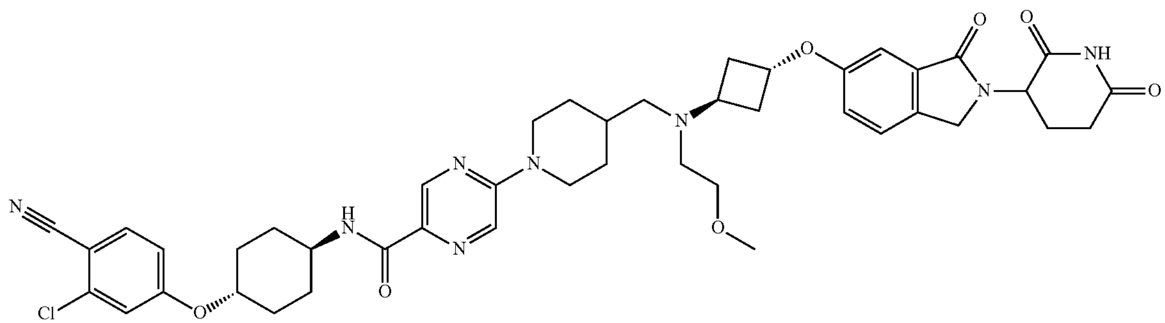 [SMILES: COCCN(CC1CCN(c2cnc(C(=O)N[C@H]3CC[C@H](Oc4ccc(C#N)c(Cl)c4)CC3)cn2)CC1)[C@H]1C[C@H](Oc2ccc3c(c2)C(=O)N(C2CCC(=O)NC2=O)C3)C1] | N-((1r,4r)-4-(3-chloro-4-cyanophenoxy)cyclohexyl)-5-(4-((((1r,3r)-3-((2-(2,6-dioxopiperidin-3-yl)-3-oxoisoindolin-5-yl)oxy)cyclobutyl)(2-methoxyethyl)amino)methyl)piperidin-1-yl)pyrazine-2-carboxamide | 3 and 4, and custom synthesis |
| 25 | 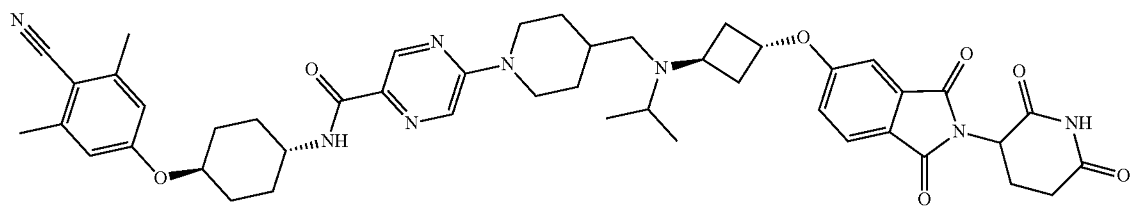 [SMILES: Cc1cc(O[C@H]2CC[C@H](NC(=O)c3cnc(N4CCC(CN(C(C)C)[C@H]5C[C@H](Oc6ccc7c(c6)C(=O)N(C6CCC(=O)NC6=O)C7=O)C5)CC4)cn3)CC2)cc(C)c1C#N] | N-((1r,4r)-4-(4-cyano-3,5-dimethylphenoxy)cyclohexyl)-5-(4-((((1r,3r)-3-((2-(2,6-dioxopiperidin-3-yl)-1,3-dioxoisoindolin-5-yl)oxy)cyclobutyl)(isopropyl)amino)methyl)piperidin-1-yl)pyrazine-2-carboxamide | 7 and 4 |
| 26 | 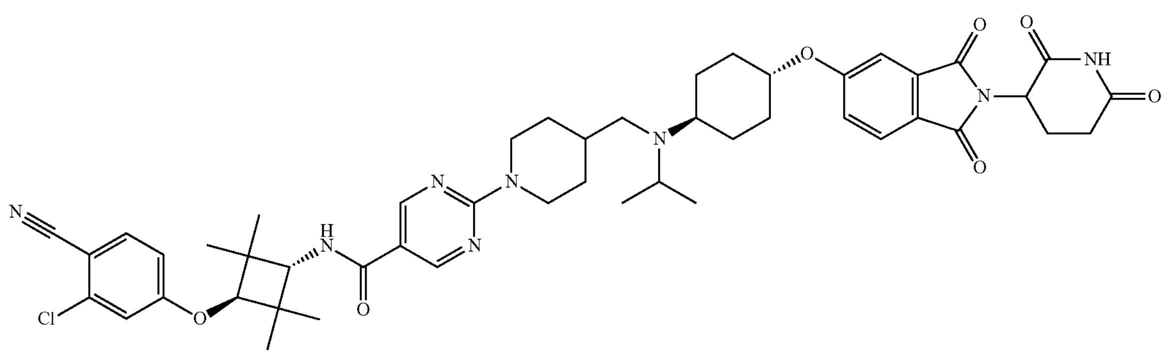 [SMILES: CC(C)N(CC1CCN(c2ncc(C(=O)N[C@H]3C(C)(C)[C@H](Oc4ccc(C#N)c(Cl)c4)C3(C)C)cn2)CC1)[C@H]1CC[C@H](Oc2ccc3c(c2)C(=O)N(C2CCC(=O)NC2=O)C3=O)CC1] | N-((1s,3r)-3-(3-chloro-4-cyanophenoxy)-2,2,4,4-tetramethylcyclobutyl)-2-(4-((((1r,4r)-4-((2-(2,6-dioxopiperidin-3-yl)-1,3-dioxoisoindolin-5-yl)oxy)cyclohexyl)(isopropyl)amino)methyl)piperidin-1-yl)pyrimidine-5-carboxamide | 7 |

TABLE 1B-continued

Exemplary heterobifunctional compounds of the present disclosure.

| Comp No. | Structure | Name | Scheme |
|---|---|---|---|
| 27 | 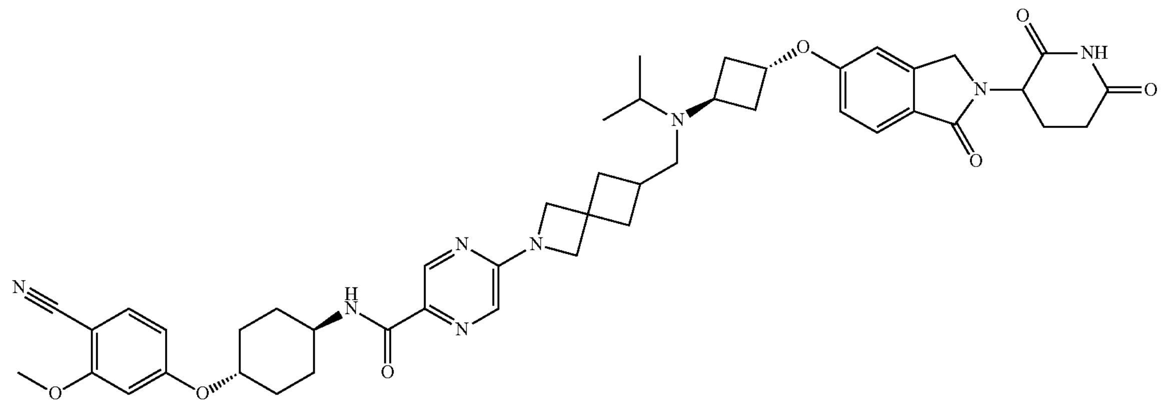 [SMILES: COc1cc(O[C@H]2CC[C@H](NC(=O)c3cnc(N4CC5(CC(CN(C(C)C)[C@H]6C[C@H](Oc7ccc8c(c7)CN(C7CCC(=O)NC7=O)C8=O)C6)C5)C4)cn3)CC2)ccc1C#N] | N-((1r,4r)-4-(4-cyano-3-methoxyphenoxy)cyclohexyl)-5-(6-((((1r,3r)-3-((2-(2,6-dioxopiperidin-3-yl)-1-oxoisoindolin-5-yl)oxy)cyclobutyl)(isopropyl)amino)methyl)-2-azaspiro[3.3]heptan-2-yl)pyrazine-2-carboxamide | 7 and 4 |
| 28 | 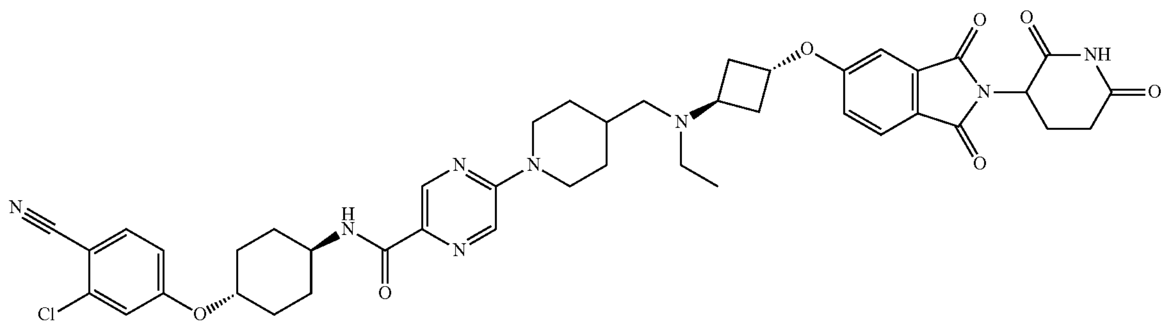 [SMILES: CCN(CC1CCN(c2cnc(C(=O)N[C@H]3CC[C@H](Oc4ccc(C#N)c(Cl)c4)CC3)cn2)CC1)[C@H]1C[C@H](Oc2ccc3c(c2)C(=O)N(C2CCC(=O)NC2=O)C3=O)C1] | N-((1r,4r)-4-(3-chloro-4-cyanophenoxy)cyclohexyl)-5-(4-(((1r,3r)-3-((2-(2,6-dioxopiperidin-3-yl)-1,3-dioxoisoindolin-5-yl)oxy)cyclobutyl)(ethyl)amino)methyl)piperidin-1-yl)pyrazine-2-carboxamide | 7 and 4 |

TABLE 1B-continued

Exemplary heterobifunctional compounds of the present disclosure.

| Comp No. | Structure | Name | Scheme |
|---|---|---|---|
| 29 | 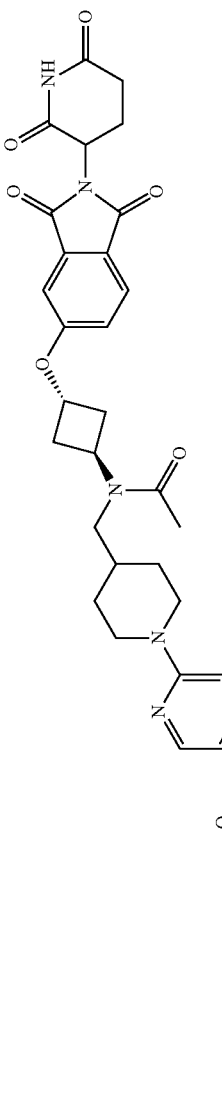 | N-((1r,4r)-4-(4-cyano-3-methoxyphenoxy)cyclohexyl)-5-(4-((N-(((1r,3r)-3-((2-(2,6-dioxopiperidin-3-yl)-1,3-dioxoisoindolin-5-yl)oxy)cyclobutyl)acetamido)methyl)piperidin-1-yl)pyrazine-2-carboxamide | 7 and 4 |
| 30 | 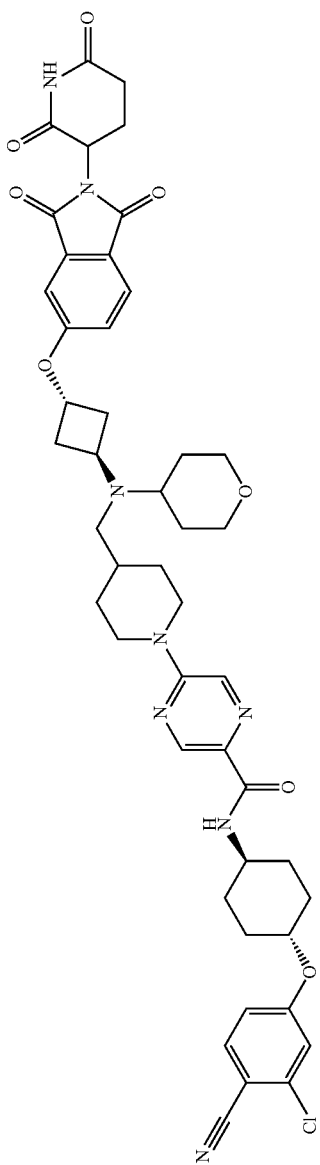 | N-((1r,4r)-4-(3-chloro-4-cyanophenoxy)cyclohexyl)-5-(4-((((1r,3r)-3-((2-(2,6-dioxopiperidin-3-yl)-1,3-dioxoisoindolin-5-yl)oxy)cyclobutyl)(tetrahydro-2H-pyran-4-yl)amino)methyl)piperidin-1-yl)pyrazine-2-carboxamide | 7 and 4 |

TABLE 1B-continued

Exemplary heterobifunctional compounds of the present disclosure.

| Comp. No. | Structure | Name | Scheme |
|---|---|---|---|
| 31 | 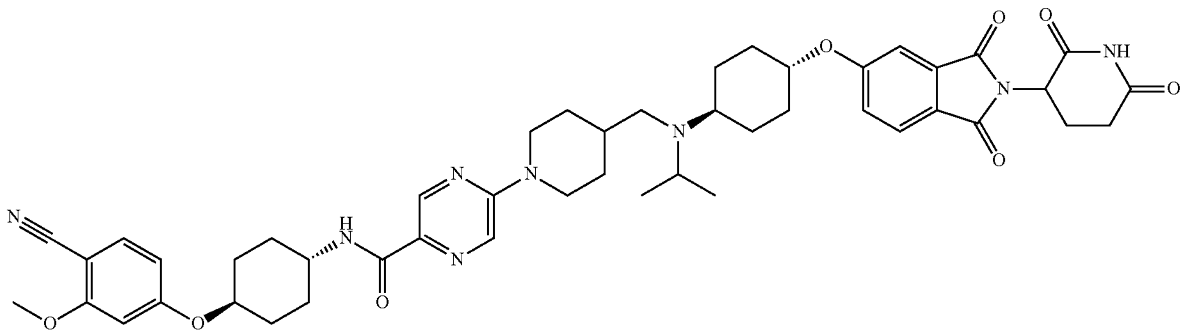 [SMILES: COc1cc(O[C@H]2CC[C@H](NC(=O)c3cnc(N4CCC(CN(C(C)C)[C@H]5CC[C@H](Oc6ccc7c(c6)C(=O)N(C6CCC(=O)NC6=O)C7=O)CC5)CC4)cn3)CC2)ccc1C#N] | N-((1r,4r)-4-(4-cyano-3-methoxyphenoxy)cyclohexyl)-5-(4-((((1r,4r)-4-((2-(2,6-dioxopiperidin-3-yl)-1,3-dioxoisoindolin-5-yl)oxy)cyclohexyl)(isopropyl)amino)methyl)piperidin-1-yl)pyrazine-2-carboxamide | 7 and 4 |
| 32 | 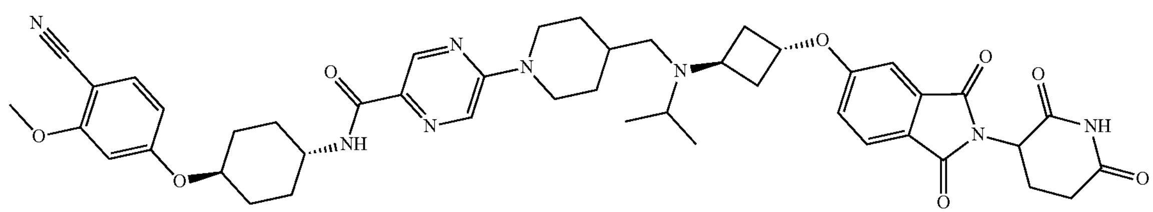 [SMILES: COc1cc(O[C@H]2CC[C@H](NC(=O)c3cnc(N4CCC(CN(C(C)C)[C@H]5C[C@H](Oc6ccc7c(c6)C(=O)N(C6CCC(=O)NC6=O)C7=O)C5)CC4)cn3)CC2)ccc1C#N] | N-((1r,4r)-4-(4-cyano-3-methoxyphenoxy)cyclohexyl)-5-(4-((((1r,3r)-3-((2-(2,6-dioxopiperidin-3-yl)-1,3-dioxoisoindolin-5-yl)oxy)cyclobutyl)(isopropyl)amino)methyl)piperidin-1-yl)pyrazine-2-carboxamide | 7 and 4 |
| 33 | 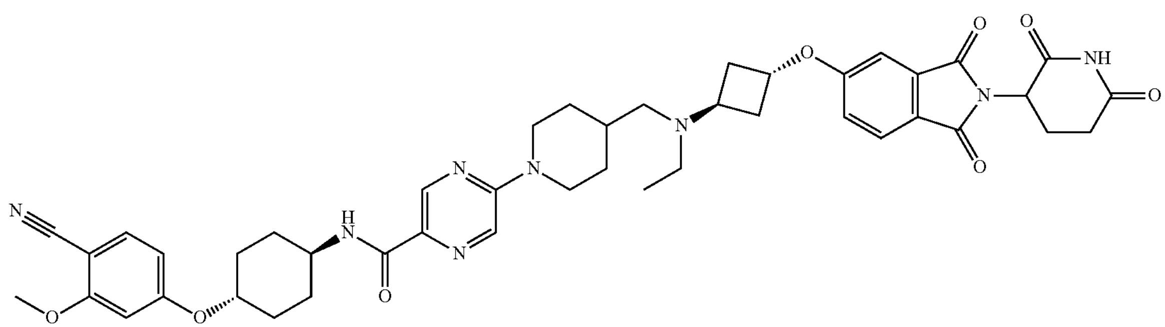 [SMILES: CCN(CC1CCN(c2cnc(C(=O)N[C@H]3CC[C@H](Oc4ccc(C#N)c(OC)c4)CC3)cn2)CC1)[C@H]1C[C@H](Oc2ccc3c(c2)C(=O)N(C2CCC(=O)NC2=O)C3=O)C1] | N-((1r,4r)-4-(4-cyano-3-methoxyphenoxy)cyclohexyl)-5-(4-((((1r,3r)-3-((2-(2,6-dioxopiperidin-3-yl)-1,3-dioxoisoindolin-5-yl)oxy)cyclobutyl)(ethyl)amino)methyl)piperidin-1-yl)pyrazine-2-carboxamide | 7 and 4 |

TABLE 1B-continued

Exemplary heterobifunctional compounds of the present disclosure.

| Comp No. | Structure | Name | Scheme |
|---|---|---|---|
| 34 | 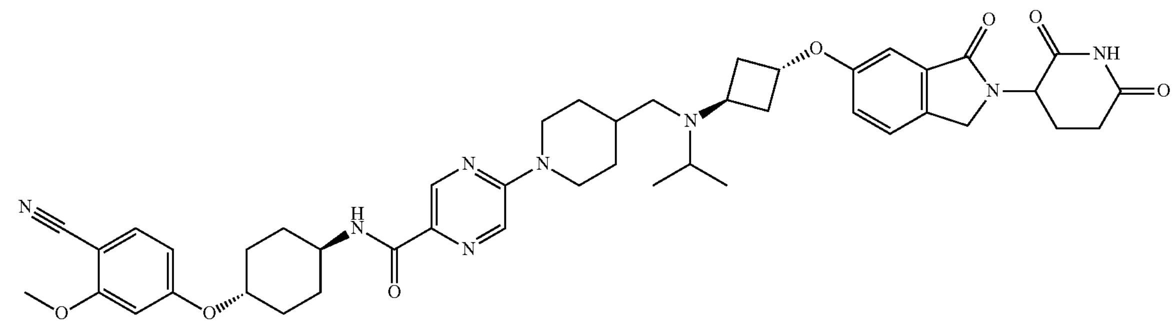 [SMILES: COc1cc(O[C@H]2CC[C@H](NC(=O)c3cnc(N4CCC(CN(C(C)C)[C@H]5C[C@H](Oc6ccc7c(c6)C(=O)N(C6CCC(=O)NC6=O)C7)C5)CC4)cn3)CC2)ccc1C#N] | N-((1r,4r)-4-(4-cyano-3-methoxyphenoxy)cyclohexyl)-5-(4-((((1r,3r)-3-((2-(2,6-dioxopiperidin-3-yl)-3-oxoisoindolin-5-yl)oxy)cyclobutyl)(isopropyl)amino)methyl)piperidin-1-yl)pyrazine-2-carboxamide | 3 and 4 |
| 35 | 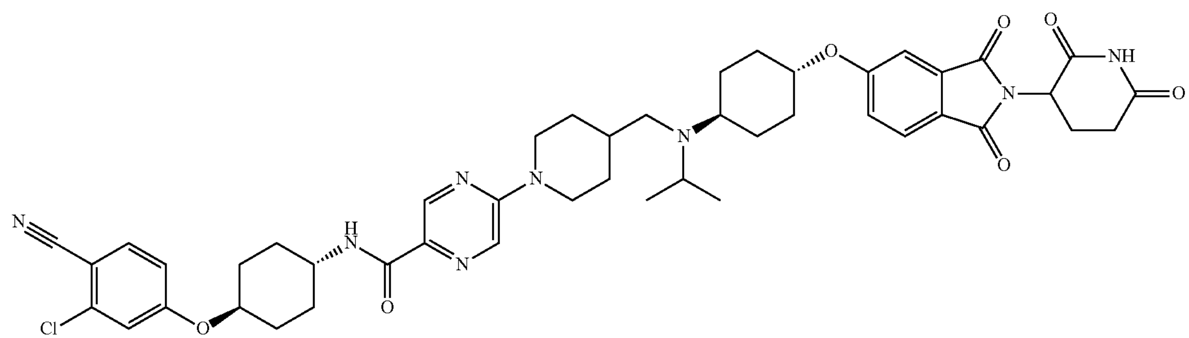 [SMILES: CC(C)N(CC1CCN(c2cnc(C(=O)N[C@H]3CC[C@H](Oc4ccc(C#N)c(Cl)c4)CC3)cn2)CC1)[C@H]1CC[C@H](Oc2ccc3c(c2)C(=O)N(C2CCC(=O)NC2=O)C3=O)CC1] | N-((1r,4r)-4-(3-chloro-4-cyanophenoxy)cyclohexyl)-5-(4-((((1r,4r)-4-((2-(2,6-dioxopiperidin-3-yl)-1,3-dioxoisoindolin-5-yl)oxy)cyclohexyl)(isopropyl)amino)methyl)piperidin-1-yl)pyrazine-2-carboxamide | 7 and 4 |

TABLE 1B-continued

Exemplary heterobifunctional compounds of the present disclosure.

| Comp No. | Structure | Name | Scheme |
|---|---|---|---|
| 36 | 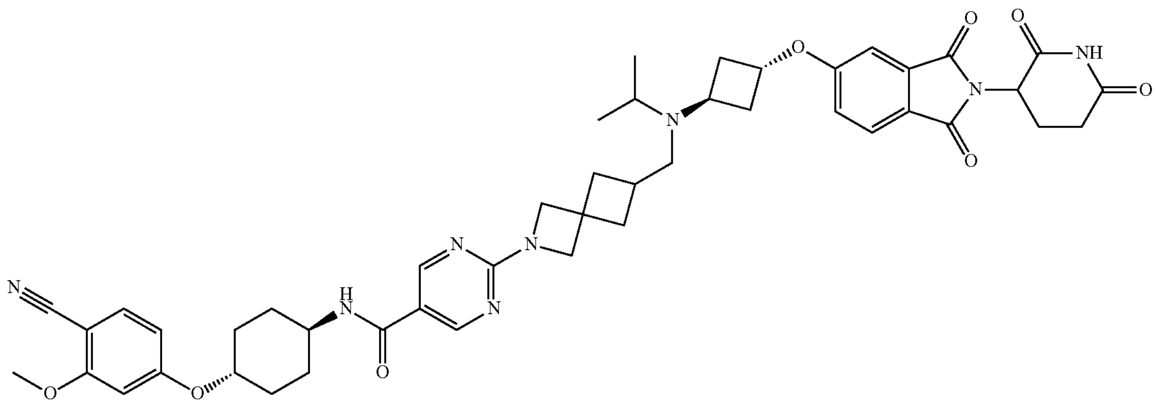 [SMILES: COc1cc(O[C@H]2CC[C@H](NC(=O)c3cnc(N4CC5(CC(CN(C(C)C)[C@H]6C[C@H](Oc7ccc8c(c7)C(=O)N(C7CCC(=O)NC7=O)C8=O)C6)C5)C4)nc3)CC2)ccc1C#N] | N-((1r,4r)-4-(4-cyano-3-methoxyphenoxy)cyclohexyl)-2-(6-((((1r,3r)-3-((2-(2,6-dioxopiperidin-3-yl)-1,3-dioxoisoindolin-5-yl)oxy)cyclobutyl)(isopropyl)amino)methyl)-2-azaspiro[3.3]heptan-2-yl)pyrimidine-5-carboxamide | 7 and 4 |
| 37 | 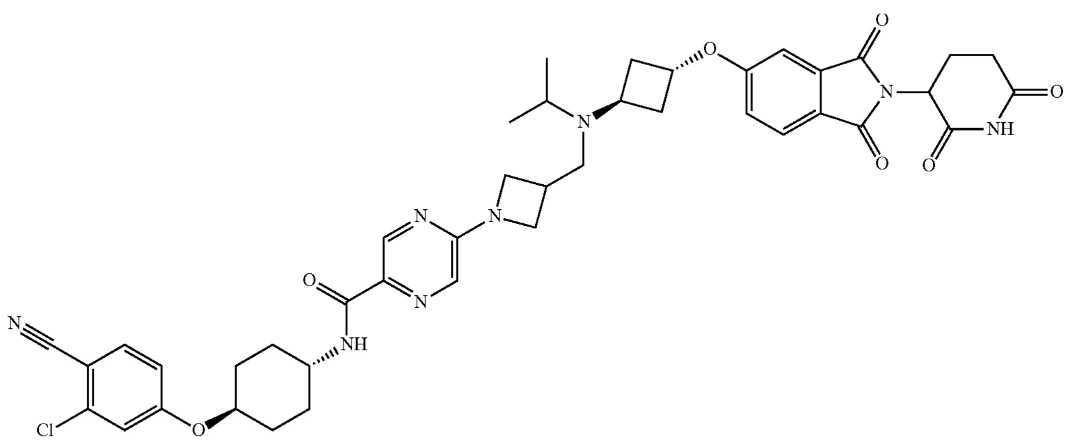 [SMILES: CC(C)N(CC1CN(c2cnc(C(=O)N[C@H]3CC[C@H](Oc4ccc(C#N)c(Cl)c4)CC3)cn2)C1)[C@H]1C[C@H](Oc2ccc3c(c2)C(=O)N(C2CCC(=O)NC2=O)C3=O)C1] | N-((1r,4r)-4-(3-chloro-4-cyanophenoxy)cyclohexyl)-5-(3-((((1r,3r)-3-((2-(2,6-dioxopiperidin-3-yl)-1,3-dioxoisoindolin-5-yl)oxy)cyclobutyl)(isopropyl)amino)methyl)azetidin-1-yl)pyrazine-2-carboxamide | 7 and 4 |

TABLE 1B-continued

Exemplary heterobifunctional compounds of the present disclosure.

| Comp No. | Structure | Name | Scheme |
|---|---|---|---|
| 38 | 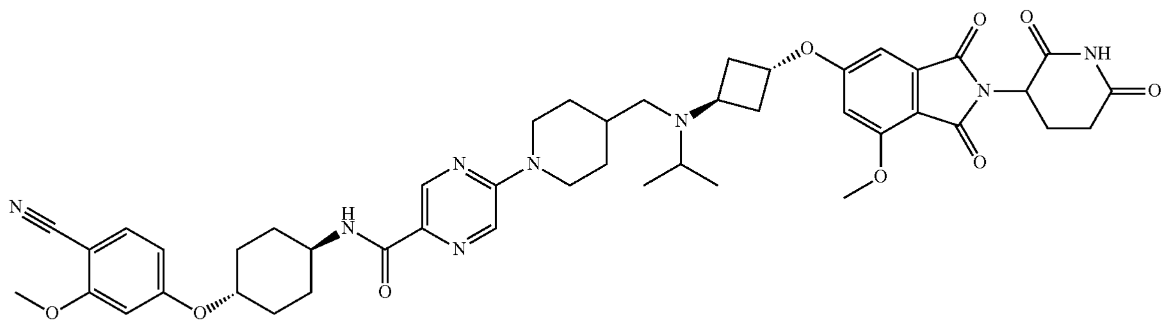 [SMILES: COc1cc(O[C@H]2CC[C@H](NC(=O)c3cnc(N4CCC(CN(C(C)C)[C@H]5C[C@H](Oc6cc(OC)c7c(c6)C(=O)N(C6CCC(=O)NC6=O)C7=O)C5)CC4)cn3)CC2)ccc1C#N] | N-((1r,4r)-4-(4-cyano-3-methoxyphenoxy)cyclohexyl)-5-(4-((((1r,3r)-3-((2-(2,6-dioxopiperidin-3-yl)-7-methoxy-1,3-dioxoisoindolin-5-yl)oxy)cyclobutyl)(isopropyl)amino)methyl)piperidin-1-yl)pyrazine-2-carboxamide | 1 and 4 |
| 39 | 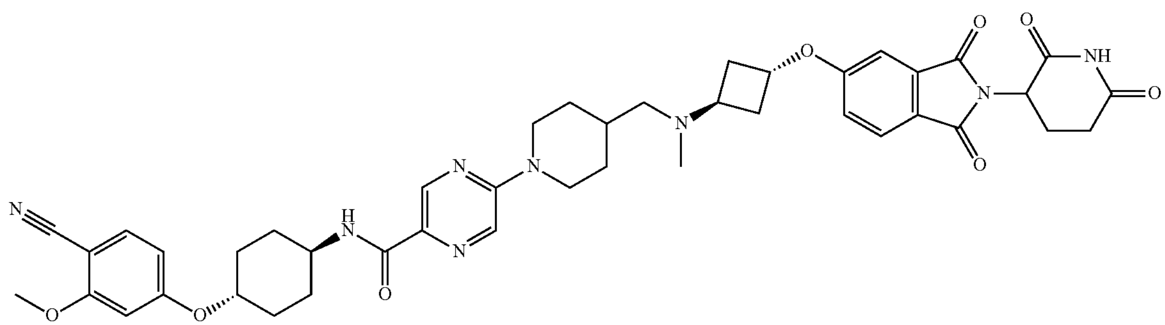 [SMILES: COc1cc(O[C@H]2CC[C@H](NC(=O)c3cnc(N4CCC(CN(C)[C@H]5C[C@H](Oc6ccc7c(c6)C(=O)N(C6CCC(=O)NC6=O)C7=O)C5)CC4)cn3)CC2)ccc1C#N] | N-((1r,4r)-4-(4-cyano-3-methoxyphenoxy)cyclohexyl)-5-(4-((((1r,3r)-3-((2-(2,6-dioxopiperidin-3-yl)-1,3-dioxoisoindolin-5-yl)oxy)cyclobutyl)(methyl)amino)methyl)piperidin-1-yl)pyrazine-2-carboxamide | 7 and 4 |
| 40 | 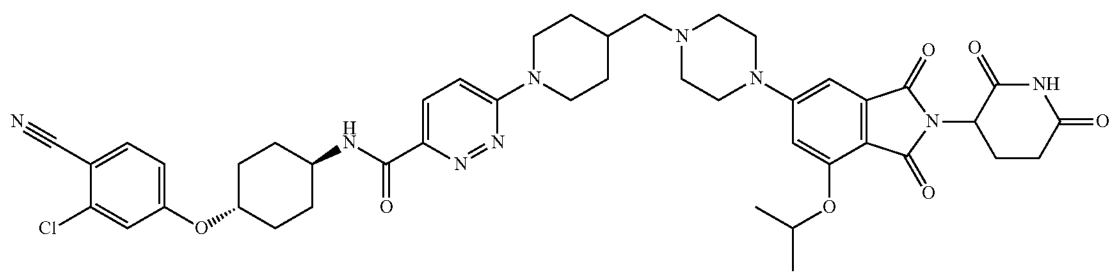 [SMILES: CC(C)Oc1cc(N2CCN(CC3CCN(c4ccc(C(=O)N[C@H]5CC[C@H](Oc6ccc(C#N)c(Cl)c6)CC5)nn4)CC3)CC2)cc2c1C(=O)N(C1CCC(=O)NC1=O)C2=O] | N-((1r,4r)-4-(3-chloro-4-cyanophenoxy)cyclohexyl)-6-(4-((4-(2-(2,6-dioxopiperidin-3-yl)-7-isopropoxy-1,3-dioxoisoindolin-5-yl)piperazin-1-yl)methyl)piperidin-1-yl)pyridazine-3-carboxamide | 8 and 6 |

TABLE 1B-continued

Exemplary heterobifunctional compounds of the present disclosure.

| Comp No. | Structure | Name | Scheme |
|---|---|---|---|
| 41 | 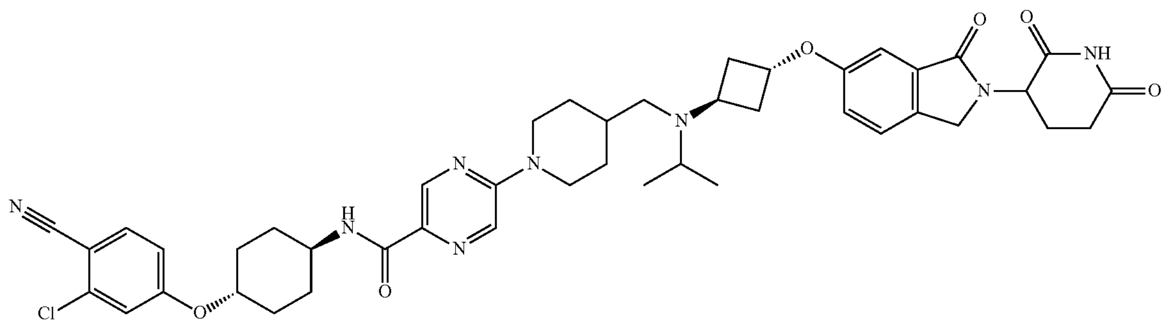 [SMILES: CC(C)N(CC1CCN(c2cnc(C(=O)N[C@H]3CC[C@H](Oc4ccc(C#N)c(Cl)c4)CC3)cn2)CC1)[C@H]1C[C@H](Oc2ccc3c(c2)C(=O)N(C2CCC(=O)NC2=O)C3)C1] | N-((1r,4r)-4-(3-chloro-4-cyanophenoxy)cyclohexyl)-5-(4-(((1r,3r)-3-((2-(2,6-dioxopiperidin-3-yl)-3-oxoisoindolin-5-yl)oxy)cyclobutyl)(isopropyl)amino)methyl)piperidin-1-yl)pyrazine-2-carboxamide | 3 and 4 |
| 42 | 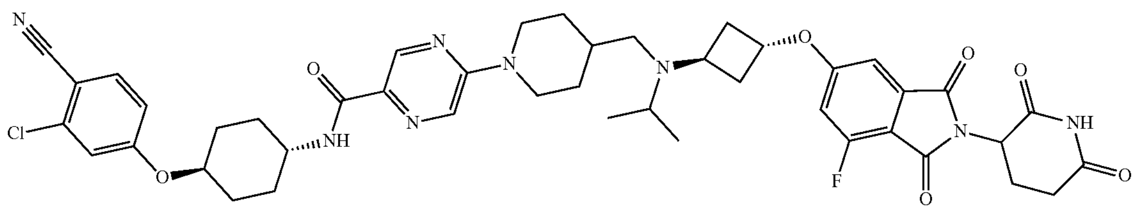 [SMILES: CC(C)N(CC1CCN(c2cnc(C(=O)N[C@H]3CC[C@H](Oc4ccc(C#N)c(Cl)c4)CC3)cn2)CC1)[C@H]1C[C@H](Oc2cc(F)c3c(c2)C(=O)N(C2CCC(=O)NC2=O)C3=O)C1] | N-((1r,4r)-4-(3-chloro-4-cyanophenoxy)cyclohexyl)-5-(4-(((1r,3r)-3-((2-(2,6-dioxopiperidin-3-yl)-7-fluoro-1,3-dioxoisoindolin-5-yl)oxy)cyclobutyl)(isopropyl)amino)methyl)piperidin-1-yl)pyrazine-2-carboxamide | 9 and 10 |

TABLE 1B-continued

Exemplary heterobifunctional compounds of the present disclosure.

| Comp. No. | Structure | Name | Scheme |
|---|---|---|---|
| 43 | 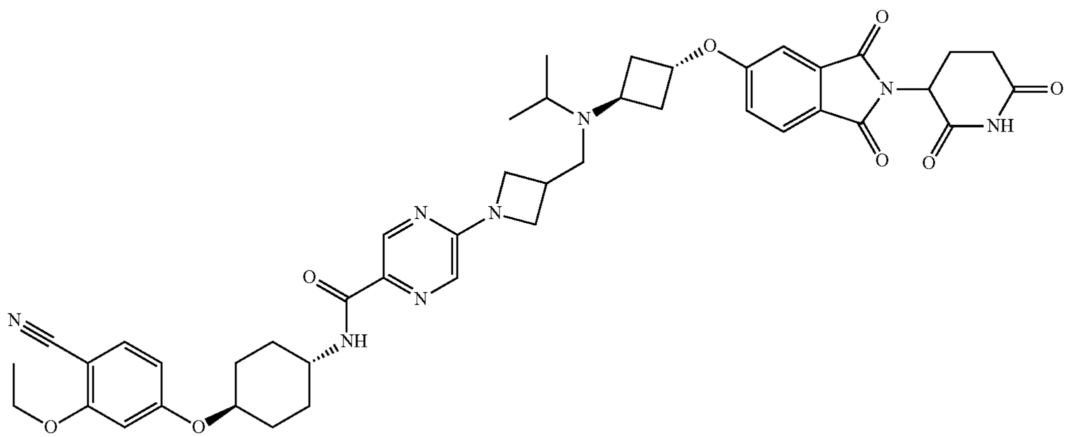 [SMILES: CCOc1cc(O[C@H]2CC[C@H](NC(=O)c3cnc(N4CC(CN(C(C)C)[C@H]5C[C@H](Oc6ccc7c(c6)C(=O)N(C6CCC(=O)NC6=O)C7=O)C5)C4)cn3)CC2)ccc1C#N] | N-((1r,4r)-4-(4-cyano-3-ethoxyphenoxy)cyclohexyl)-5-(3-(((1r,3r)-3-((2-(2,6-dioxopiperidin-3-yl)-1,3-dioxoisoindolin-5-yl)oxy)cyclobutyl)(isopropyl)amino)methyl)azetidin-1-yl)pyrazine-2-carboxamide | 7 and 4 |
| 44 | 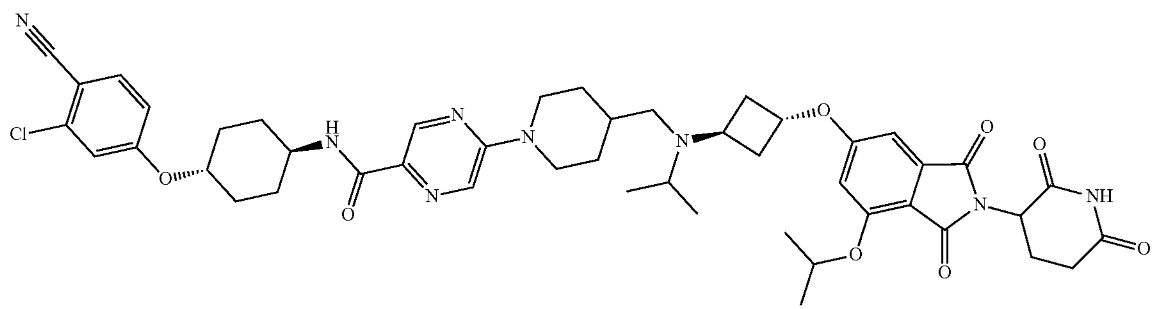 [SMILES: CC(C)Oc1cc(O[C@H]2C[C@H](N(CC3CCN(c4cnc(C(=O)N[C@H]5CC[C@H](Oc6ccc(C#N)c(Cl)c6)CC5)cn4)CC3)C(C)C)C2)cc2c1C(=O)N(C1CCC(=O)NC1=O)C2=O] | N-((1r,4r)-4-(3-chloro-4-cyanophenoxy)cyclohexyl)-5-(4-(((1r,3r)-3-((2-(2,6-dioxopiperidin-3-yl)-7-isopropoxy-1,3-dioxoisoindolin-5-yl)oxy)cyclobutyl)(isopropyl)amino)methyl)piperidin-1-yl)pyrazine-2-carboxamide | 1 and 4 |
| 45 | 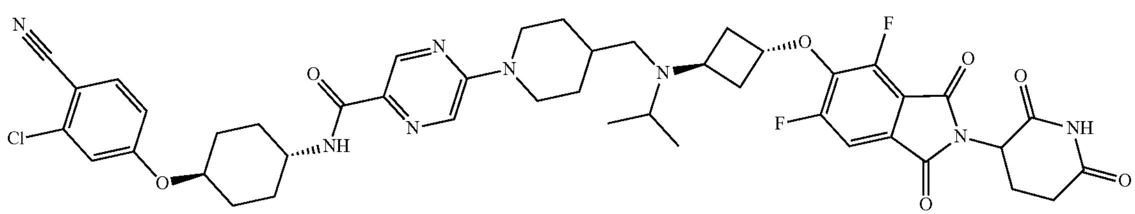 [SMILES: CC(C)N(CC1CCN(c2cnc(C(=O)N[C@H]3CC[C@H](Oc4ccc(C#N)c(Cl)c4)CC3)cn2)CC1)[C@H]1C[C@H](Oc2c(F)cc3c(c2F)C(=O)N(C2CCC(=O)NC2=O)C3=O)C1] | N-((1r,4r)-4-(3-chloro-4-cyanophenoxy)cyclohexyl)-5-(4-(((1r,3r)-3-((2-(2,6-dioxopiperidin-3-yl)-4,6-difluoro-1,3-dioxoisoindolin-5-yl)oxy)cyclobutyl)(isopropyl)amino)methyl)piperidin-1-yl)pyrazine-2-carboxamide | 10 |

TABLE 1B-continued

Exemplary heterobifunctional compounds of the present disclosure.

| Comp No. | Structure | Name | Scheme |
|---|---|---|---|
| 46 | 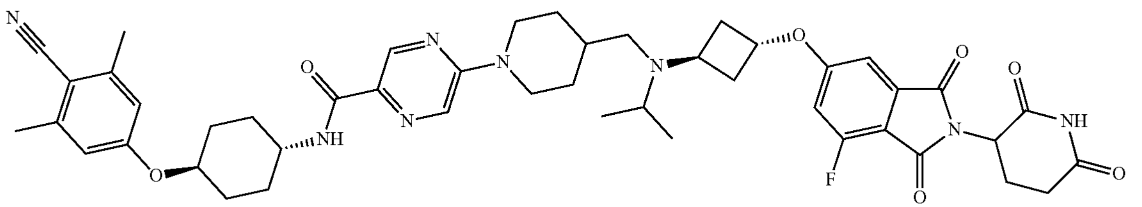 [SMILES: Cc1cc(O[C@H]2CC[C@H](NC(=O)c3cnc(N4CCC(CN(C(C)C)[C@H]5C[C@H](Oc6cc(F)c7c(c6)C(=O)N(C6CCC(=O)NC6=O)C7=O)C5)CC4)cn3)CC2)cc(C)c1C#N] | N-((1r,4r)-4-(4-cyano-3,5-dimethylphenoxy)cyclohexyl)-5-(4-(((1r,3r)-3-(2-(2,6-dioxopiperidin-3-yl)-7-fluoro-1,3-dioxoisoindolin-5-yl)oxy)cyclobutyl)(isopropyl)amino)methyl)piperidin-1-yl)pyrazine-2-carboxamide | 9 and 10 |
| 47 | 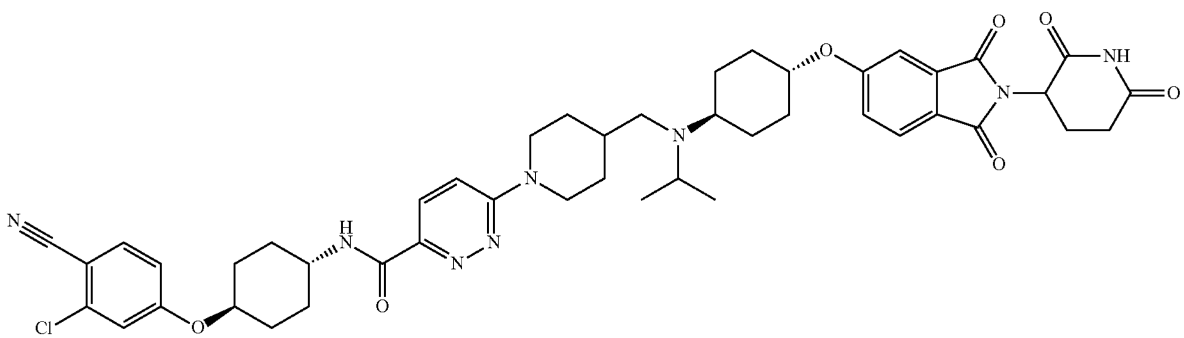 [SMILES: CC(C)N(CC1CCN(c2ccc(C(=O)N[C@H]3CC[C@H](Oc4ccc(C#N)c(Cl)c4)CC3)nn2)CC1)[C@H]1CC[C@H](Oc2ccc3c(c2)C(=O)N(C2CCC(=O)NC2=O)C3=O)CC1] | N-((1r,4r)-4-(3-chloro-4-cyanophenoxy)cyclohexyl)-6-(4-(((1r,4r)-4-((2-(2,6-dioxopiperidin-3-yl)-1,3-dioxoisoindolin-5-yl)oxy)cyclohexyl)(isopropyl)amino)methyl)piperidin-1-yl)pyridazine-3-carboxamide | 7 and 4 |
| 48 | 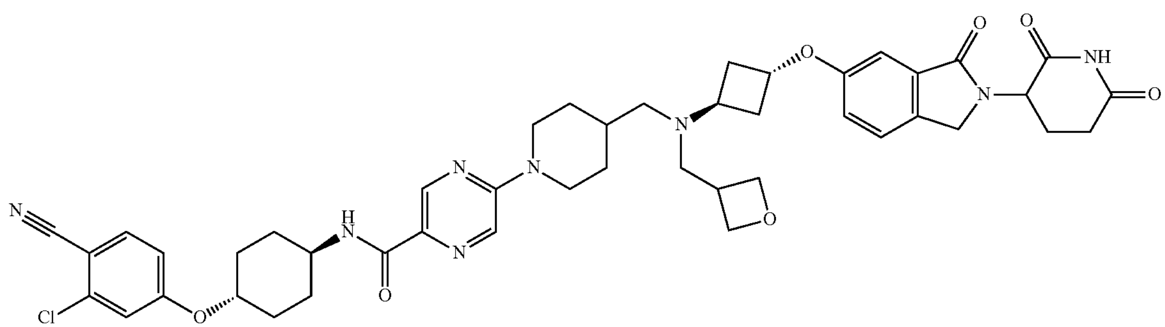 [SMILES: N#Cc1ccc(O[C@H]2CC[C@H](NC(=O)c3cnc(N4CCC(CN(CC5COC5)[C@H]5C[C@H](Oc6ccc7c(c6)C(=O)N(C6CCC(=O)NC6=O)C7)C5)CC4)cn3)CC2)cc1Cl] | N-((1r,4r)-4-(3-chloro-4-cyanophenoxy)cyclohexyl)-5-(4-(((1r,3r)-3-((2-(2,6-dioxopiperidin-3-yl)-3-oxoisoindolin-5-yl)oxy)cyclobutyl)(oxetan-3-yl)methyl)amino)methyl)piperidin-1-yl)pyrazine-2-carboxamide | 3 and 4 |

TABLE 1B-continued

Exemplary heterobifunctional compounds of the present disclosure.

| Comp No. | Structure | Name | Scheme |
| --- | --- | --- | --- |
| 49 | 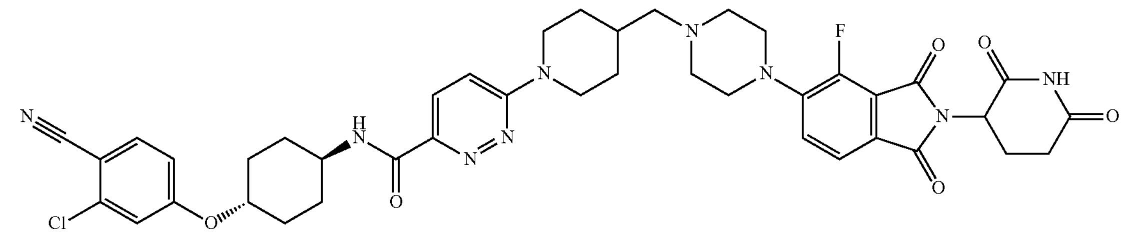 [SMILES: N#Cc1ccc(O[C@H]2CC[C@H](NC(=O)c3ccc(N4CCC(CN5CCN(c6ccc7c(c6F)C(=O)N(C6CCC(=O)NC6=O)C7=O)CC5)CC4)nn3)CC2)cc1Cl] | N-((1r,4r)-4-(3-chloro-4-cyanophenoxy)cyclohexyl)-6-(4-((4-(2-(2,6-dioxopiperidin-3-yl)-4-fluoro-1,3-dioxoisoindolin-5-yl)piperazin-1-yl)methyl)piperidin-1-yl)pyridazine-3-carboxamide | 11 and 12 |
| 50 | 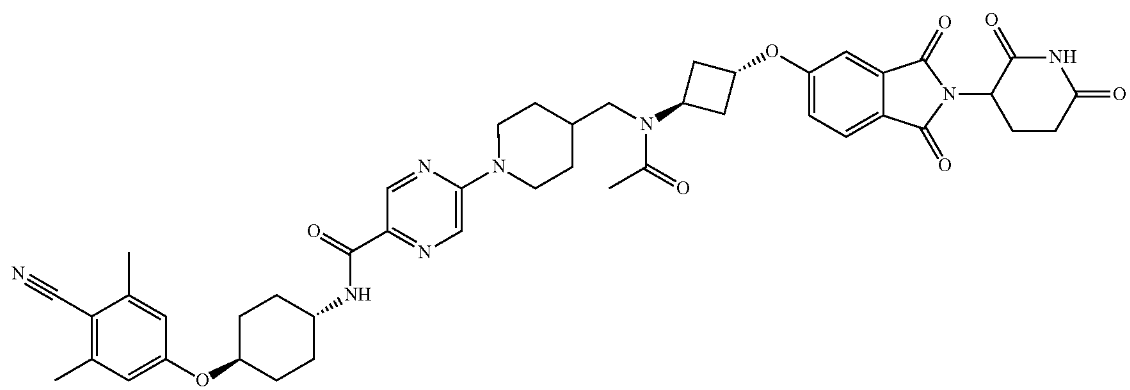 [SMILES: CC(=O)N(CC1CCN(c2cnc(C(=O)N[C@H]3CC[C@H](Oc4cc(C)c(C#N)c(C)c4)CC3)cn2)CC1)[C@H]1C[C@H](Oc2ccc3c(c2)C(=O)N(C2CCC(=O)NC2=O)C3=O)C1] | N-((1r,4r)-4-(4-cyano-3,5-dimethylphenoxy)cyclohexyl)-5-(4-(N-((1r,3r)-3-((2-(2,6-dioxopiperidin-3-yl)-1,3-dioxoisoindolin-5-yl)oxy)cyclobutyl)acetamido)methyl)piperidin-1-yl)pyrazine-2-carboxamide | 7 and 4 |
| 51 | 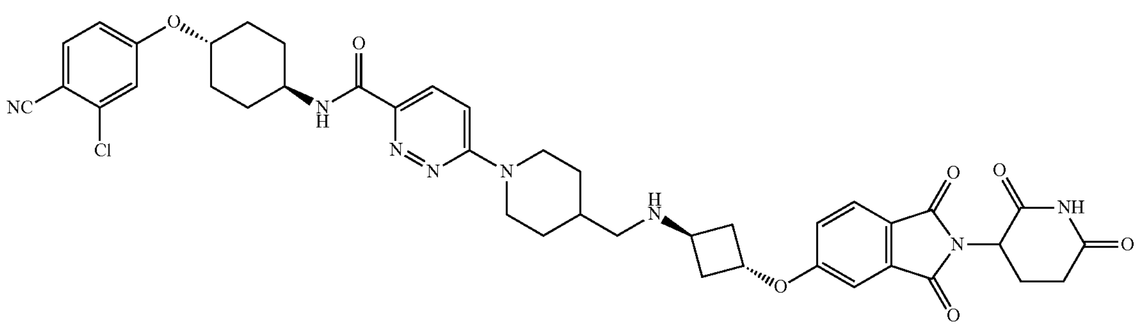 [SMILES: N#Cc1ccc(O[C@H]2CC[C@H](NC(=O)c3ccc(N4CCC(CN[C@H]5C[C@H](Oc6ccc7c(c6)C(=O)N(C6CCC(=O)NC6=O)C7=O)C5)CC4)nn3)CC2)cc1Cl] | rac-N-((1r,4r)-4-(3-chloro-4-cyanophenoxy)cyclohexyl)-6-(4-(((1r,3r)-3-((2-(2,6-dioxopiperidin-3-yl)-1,3-dioxoisoindolin-5-yl)oxy)cyclobutyl)amino)methyl)piperidin-1-yl)pyridazine-3-carboxamide | 7 and 4 |

TABLE 1B-continued

Exemplary heterobifunctional compounds of the present disclosure.

| Comp. No. | Structure | Name | Scheme |
|---|---|---|---|
| 52 | 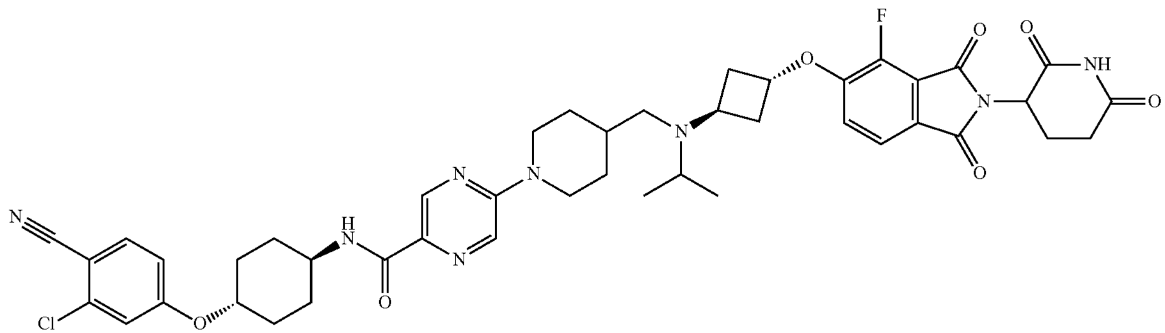 [SMILES: CC(C)N(CC1CCN(c2cnc(C(=O)N[C@H]3CC[C@H](Oc4ccc(C#N)c(Cl)c4)CC3)cn2)CC1)[C@H]1C[C@H](Oc2ccc3c(c2F)C(=O)N(C2CCC(=O)NC2=O)C3=O)C1] | N-((1r,4r)-4-(3-chloro-4-cyanophenoxy)cyclohexyl)-5-(4-((((1r,3r)-3-((2-(2,6-dioxopiperidin-3-yl)-4-fluoro-1,3-dioxoisoindolin-5-yl)oxy)cyclobutyl)(isopropyl)amino)methyl)piperidin-1-yl)pyrazine-2-carboxamide | 13 |
| 53 | 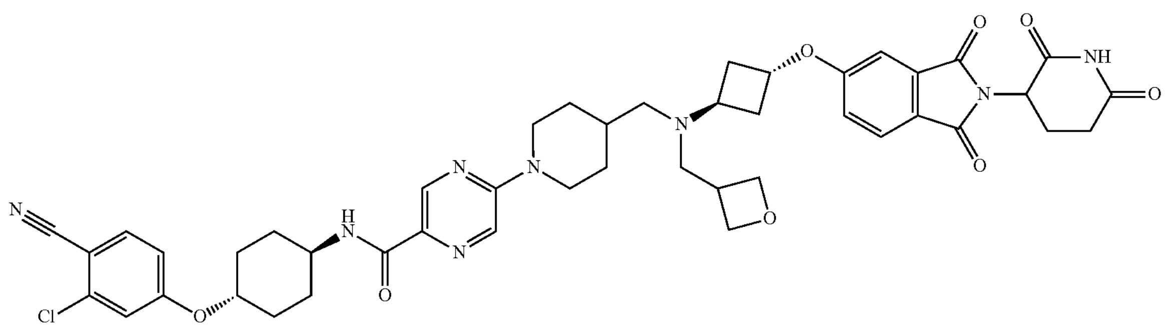 [SMILES: N#Cc1ccc(O[C@H]2CC[C@H](NC(=O)c3cnc(N4CCC(CN(CC5COC5)[C@H]5C[C@H](Oc6ccc7c(c6)C(=O)N(C6CCC(=O)NC6=O)C7=O)C5)CC4)cn3)CC2)cc1Cl] | N-((1r,4r)-4-(3-chloro-4-cyanophenoxy)cyclohexyl)-5-(4-((((1r,3r)-3-((2-(2,6-dioxopiperidin-3-yl)-1,3-dioxoisoindolin-5-yl)oxy)cyclobutyl)(oxetan-3-ylmethyl)amino)methyl)piperidin-1-yl)pyrazine-2-carboxamide | 7 and 4 |
| 54 | 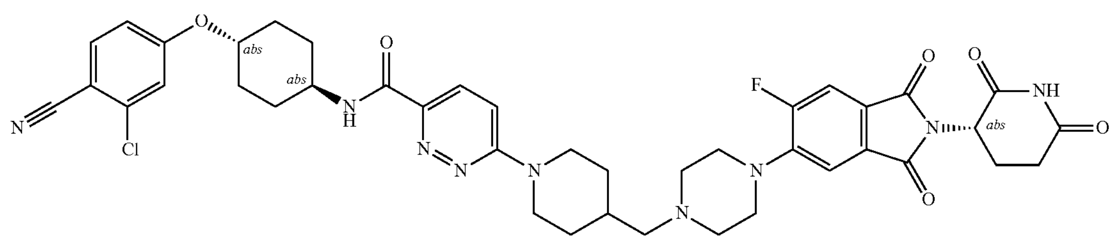 [SMILES: N#Cc1ccc(O[C@H]2CC[C@H](NC(=O)c3ccc(N4CCC(CN5CCN(c6cc7c(cc6F)C(=O)N([C@H]6CCC(=O)NC6=O)C7=O)CC5)CC4)nn3)CC2)cc1Cl] | N-((1r,4r)-4-(3-chloro-4-cyanophenoxy)cyclohexyl)-6-(4-(4-(2-((S)-2,6-dioxopiperidin-3-yl)-6-fluoro-1,3-dioxoisoindolin-5-yl)piperazin-1-yl)methyl)piperidin-1-yl)pyridazine-3-carboxamide | 12 with chiral SFC separation |

TABLE 1B-continued

Exemplary heterobifunctional compounds of the present disclosure.

| Comp. No. | Structure | Name | Scheme |
|---|---|---|---|
| 55 | 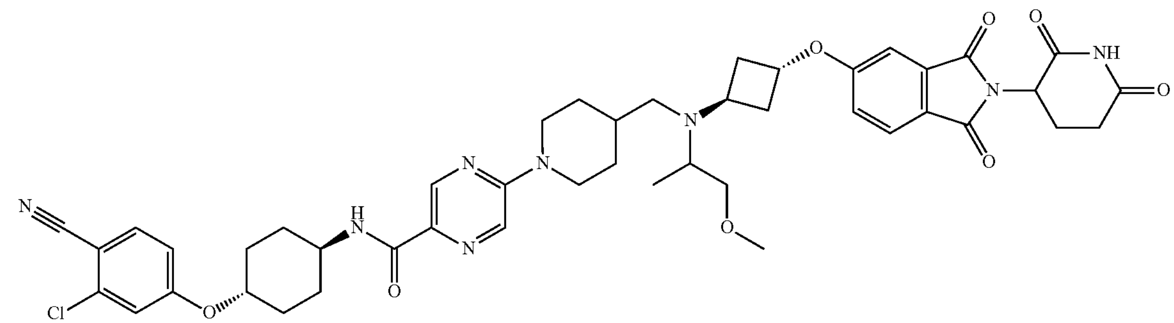 [SMILES: COCC(C)N(CC1CCN(c2cnc(C(=O)N[C@H]3CC[C@H](Oc4ccc(C#N)c(Cl)c4)CC3)cn2)CC1)[C@H]1C[C@H](Oc2ccc3c(c2)C(=O)N(C2CCC(=O)NC2=O)C3=O)C1] | N-((1r,4r)-4-(3-chloro-4-cyanophenoxy)cyclohexyl)-5-(4-((((1r,3r)-3-((2-(2,6-dioxopiperidin-3-yl)-1,3-dioxoisoindolin-5-yl)oxy)cyclobutyl)(1-methoxypropan-2-yl)amino)methyl)piperidin-1-yl)pyrazine-2-carboxamide | 7 and 4 |
| 56 | 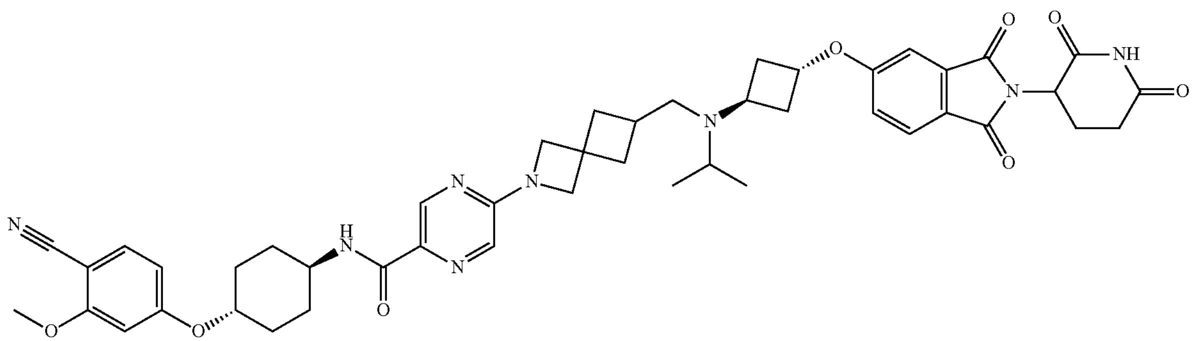 [SMILES: COc1cc(O[C@H]2CC[C@H](NC(=O)c3cnc(N4CC5(CC(CN(C(C)C)[C@H]6C[C@H](Oc7ccc8c(c7)C(=O)N(C7CCC(=O)NC7=O)C8=O)C6)C5)C4)cn3)CC2)ccc1C#N] | N-((1r,4r)-4-(4-cyano-3-methoxyphenoxy)cyclohexyl)-5-(6-((((1r,3r)-3-((2-(2,6-dioxopiperidin-3-yl)-1,3-dioxoisoindolin-5-yl)oxy)cyclobutyl)(isopropyl)amino)methyl)-2-azaspiro[3.3]heptan-2-yl)pyrazine-2-carboxamide | 7 and 4 |

TABLE 1B-continued

Exemplary heterobifunctional compounds of the present disclosure.

| Comp No. | Structure | Name | Scheme |
|---|---|---|---|
| 57 | 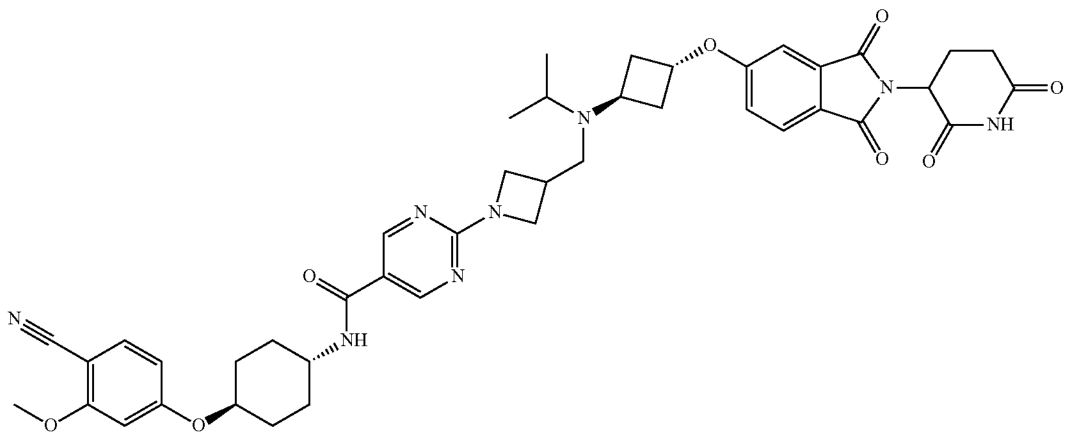 [SMILES: COc1cc(O[C@H]2CC[C@H](NC(=O)c3cnc(N4CC(CN(C(C)C)[C@H]5C[C@H](Oc6ccc7c(c6)C(=O)N(C6CCC(=O)NC6=O)C7=O)C5)C4)nc3)CC2)ccc1C#N] | N-((1r,4r)-4-(4-cyano-3-methoxyphenoxy)cyclohexyl)-2-(3-(((1r,3r)-3-((2-(2,6-dioxopiperidin-3-yl)-1,3-dioxoisoindolin-5-yl)oxy)cyclobutyl)(isopropyl)amino)methyl)azetidin-1-yl)pyrimidine-5-carboxamide | 7 and 4 |
| 58 | 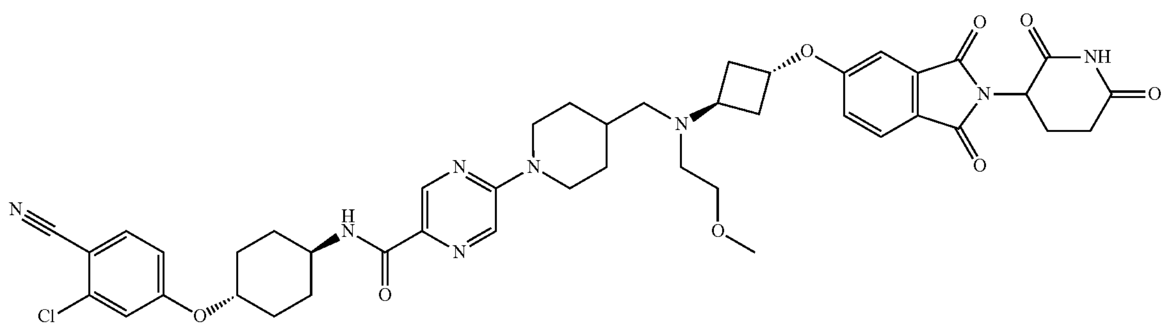 [SMILES: COCCN(CC1CCN(c2cnc(C(=O)N[C@H]3CC[C@H](Oc4ccc(C#N)c(Cl)c4)CC3)cn2)CC1)[C@H]1C[C@H](Oc2ccc3c(c2)C(=O)N(C2CCC(=O)NC2=O)C3=O)C1] | N-((1r,4r)-4-(3-chloro-4-cyanophenoxy)cyclohexyl)-5-(4-((((1r,3r)-3-((2-(2,6-dioxopiperidin-3-yl)-1,3-dioxoisoindolin-5-yl)oxy)cyclobutyl)(2-methoxyethyl)amino)methyl)piperidin-1-yl)pyrazine-2-carboxamide | 7 and 4 |

TABLE 1B-continued

Exemplary heterobifunctional compounds of the present disclosure.

| Comp. No. | Structure | Name | Scheme |
|---|---|---|---|
| 59 | 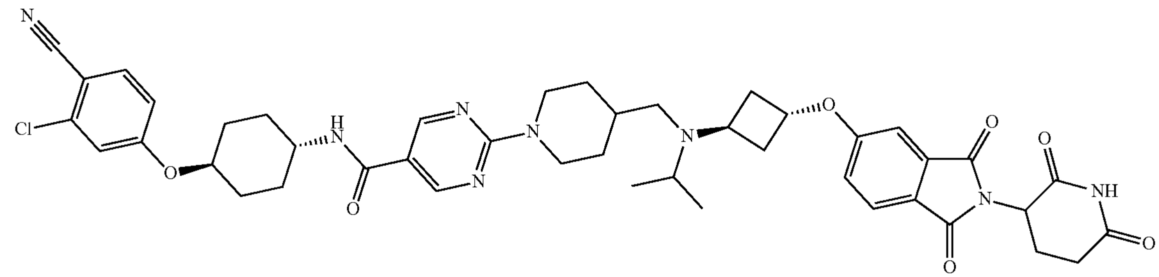 [SMILES: CC(C)N(CC1CCN(c2ncc(C(=O)N[C@H]3CC[C@H](Oc4ccc(C#N)c(Cl)c4)CC3)cn2)CC1)[C@H]1C[C@H](Oc2ccc3c(c2)C(=O)N(C2CCC(=O)NC2=O)C3=O)C1] | N-((1r,4r)-4-(3-chloro-4-cyanophenoxy)cyclohexyl)-2-(4-(((1r,4r)-4-((2-(2,6-dioxopiperidin-3-yl)-1,3-dioxoisoindolin-5-yl)oxy)cyclohexyl)(isopropyl)amino)methyl)piperidin-1-yl)pyrimidine-5-carboxamide | 7 and 4 |
| 60 | 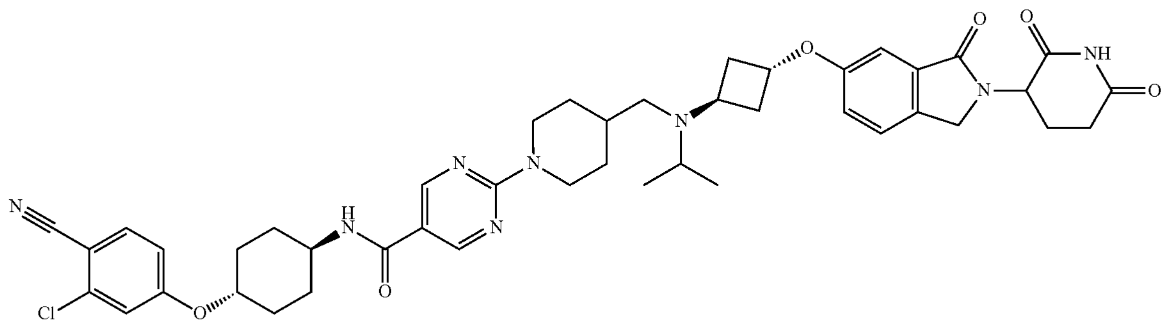 [SMILES: CC(C)N(CC1CCN(c2ncc(C(=O)N[C@H]3CC[C@H](Oc4ccc(C#N)c(Cl)c4)CC3)cn2)CC1)[C@H]1C[C@H](Oc2ccc3c(c2)C(=O)N(C2CCC(=O)NC2=O)C3)C1] | N-((1r,4r)-4-(3-chloro-4-cyanophenoxy)cyclohexyl)-2-(4-(((1r,3r)-3-((2-(2,6-dioxopiperidin-3-yl)-3-oxoisoindolin-5-yl)oxy)cyclobutyl)(isopropyl)amino)methyl)piperidin-1-yl)pyrimidine-5-carboxamide | 3 and 4 |
| 61 | 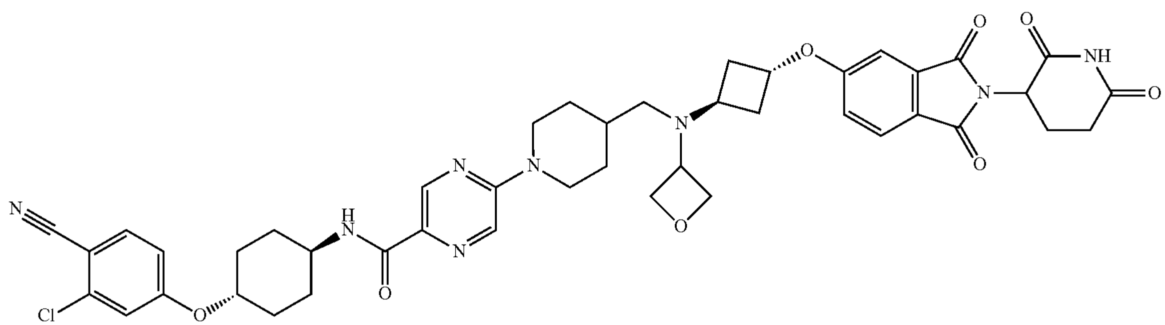 [SMILES: N#Cc1ccc(O[C@H]2CC[C@H](NC(=O)c3cnc(N4CCC(CN(C5COC5)[C@H]5C[C@H](Oc6ccc7c(c6)C(=O)N(C6CCC(=O)NC6=O)C7=O)C5)CC4)cn3)CC2)cc1Cl] | N-((1r,4r)-4-(3-chloro-4-cyanophenoxy)cyclohexyl)-5-(4-(((1r,3r)-3-((2-(2,6-dioxopiperidin-3-yl)-1,3-dioxoisoindolin-5-yl)oxy)cyclobutyl)(oxetan-3-yl)amino)methyl)piperidin-1-yl)pyrazine-2-carboxamide | 7 and 4 |

TABLE 1B-continued

Exemplary heterobifunctional compounds of the present disclosure.

| Comp No. | Structure | Name | Scheme |
|---|---|---|---|
| 62 | 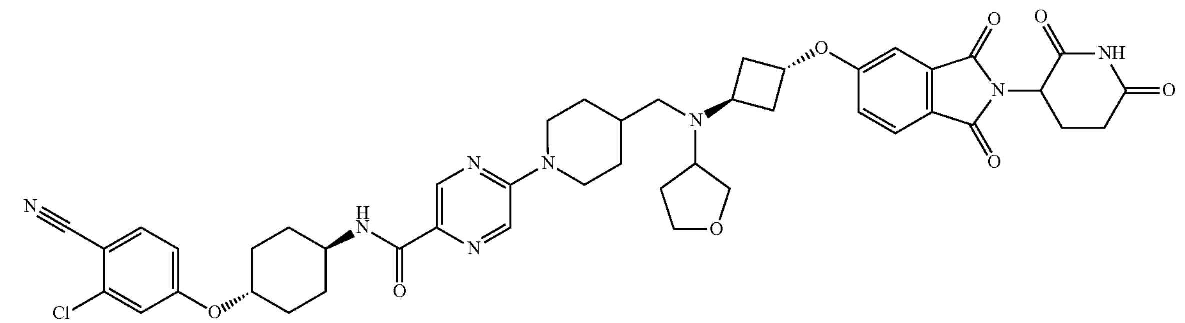 [SMILES: N#Cc1ccc(O[C@H]2CC[C@H](NC(=O)c3cnc(N4CCC(CN(C5CCOC5)[C@H]5C[C@H](Oc6ccc7c(c6)C(=O)N(C6CCC(=O)NC6=O)C7=O)C5)CC4)cn3)CC2)cc1Cl] | N-((1r,4r)-4-(3-chloro-4-cyanophenoxy)cyclohexyl)-5-(4-((((1r,3r)-3-((2-(2,6-dioxopiperidin-3-yl)-1,3-dioxoisoindolin-5-yl)oxy)cyclobutyl)(tetrahydrofuran-3-yl)amino)methyl)piperidin-1-yl)pyrazine-2-carboxamide | 7 and 4 |
| 63 | 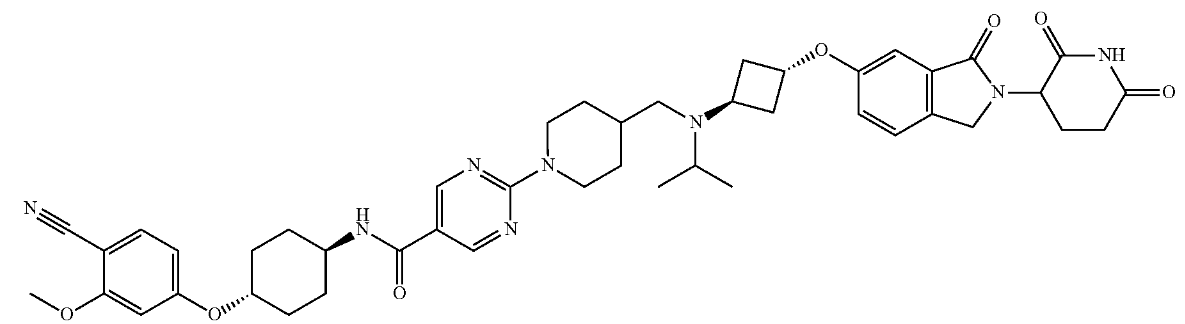 | N-((1r,4r)-4-(4-cyano-3-methoxyphenoxy)cyclohexyl)-2-(4-((((1r,3r)-3-((2-(2,6-dioxopiperidin-3-yl)-3-oxoisoindolin-5-yl)oxy)cyclobutyl)(isopropyl)amino)methyl)piperidin-1-yl)pyrimidine-5-carboxamide | 3 and 4 |
| 64 | 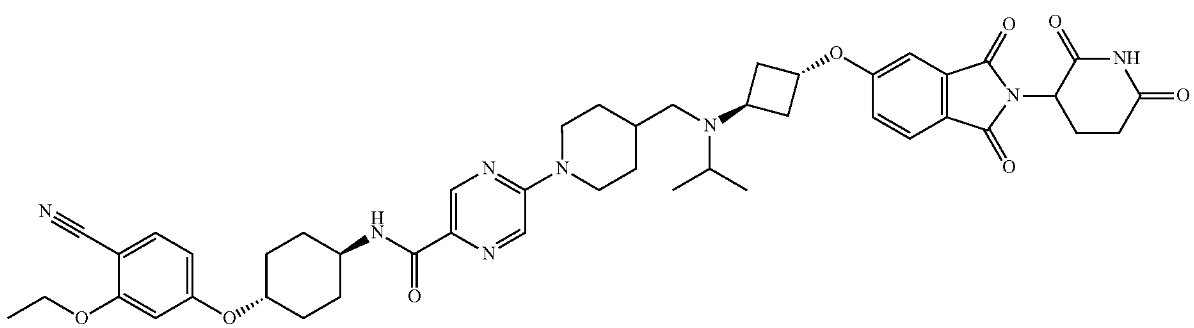 [SMILES: CCOc1cc(O[C@H]2CC[C@H](NC(=O)c3cnc(N4CCC(CN(C(C)C)[C@H]5C[C@H](Oc6ccc7c(c6)C(=O)N(C6CCC(=O)NC6=O)C7=O)C5)CC4)cn3)CC2)ccc1C#N] | N-((1r,4r)-4-(4-cyano-3-ethoxyphenoxy)cyclohexyl)-5-(4-((((1r,3r)-3-((2-(2,6-dioxopiperidin-3-yl)-1,3-dioxoisoindolin-5-yl)oxy)cyclobutyl)(isopropyl)amino)methyl)piperidin-1-yl)pyrazine-2-carboxamide | 7 and 4 |

TABLE 1B-continued

Exemplary heterobifunctional compounds of the present disclosure.

| Comp. No. | Structure | Name | Scheme |
|---|---|---|---|
| 65 | 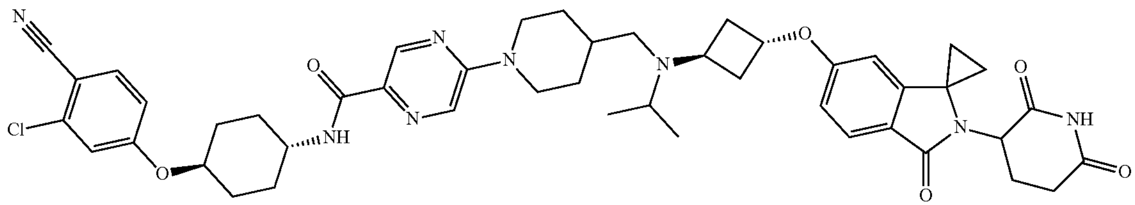 [SMILES: CC(C)N(CC1CCN(c2cnc(C(=O)N[C@H]3CC[C@H](Oc4ccc(C#N)c(Cl)c4)CC3)cn2)CC1)[C@H]1C[C@H](Oc2ccc3c(c2)C2(CC2)N(C2CCC(=O)NC2=O)C3=O)C1] | N-((1r,4r)-4-(3-chloro-4-cyanophenoxy)cyclohexyl)-5-(4-((((1r,3r)-3-((2'-(2,6-dioxopiperidin-3-yl)-3'-oxospiro[cyclopropane-1,1'-isoindolin]-6'-yl)oxy)cyclobutyl)(isopropyl)amino)methyl)piperidin-1-yl)pyrazine-2-carboxamide | 14 and 4 |
| 66 | 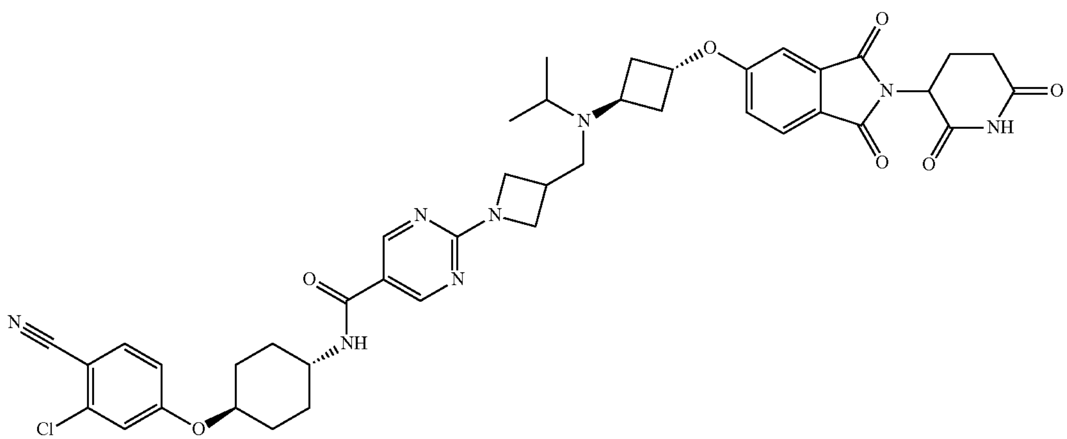 [SMILES: CC(C)N(CC1CN(c2ncc(C(=O)N[C@H]3CC[C@H](Oc4ccc(C#N)c(Cl)c4)CC3)cn2)C1)[C@H]1C[C@H](Oc2ccc3c(c2)C(=O)N(C2CCC(=O)NC2=O)C3=O)C1] | N-((1r,4r)-4-(3-chloro-4-cyanophenoxy)cyclohexyl)-2-(3-(((1r,3r)-3-((2-(2,6-dioxopiperidin-3-yl)-1,3-dioxoisoindolin-5-yl)oxy)cyclobutyl)(isopropyl)amino)methyl)azetidin-1-yl)pyrimidine-5-carboxamide | 7 and 4 |
| 67 | 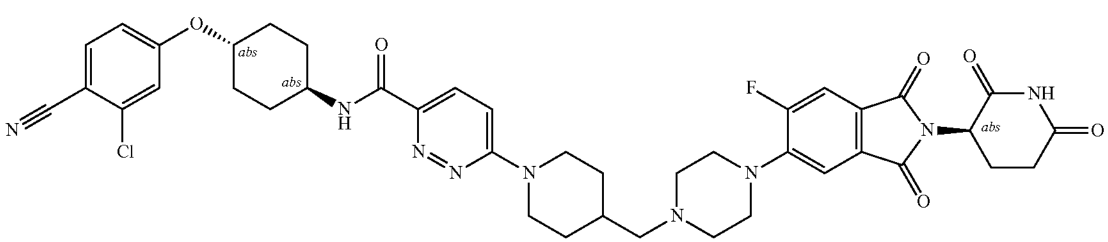 [SMILES: N#Cc1ccc(O[C@H]2CC[C@H](NC(=O)c3ccc(N4CCC(CN5CCN(c6cc7c(cc6F)C(=O)N([C@@H]6CCC(=O)NC6=O)C7=O)CC5)CC4)nn3)CC2)cc1Cl] | N-((1r,4r)-4-(3-chloro-4-cyanophenoxy)cyclohexyl)-6-(4-((4-(2-((R)-2,6-dioxopiperidin-3-yl)-6-fluoro-1,3-dioxoisoindolin-5-yl)piperazin-1-yl)methyl)piperidin-1-yl)pyridazine-3-carboxamide | 12 with chiral SFC separation |

TABLE 1B-continued

Exemplary heterobifunctional compounds of the present disclosure.

| Comp No. | Structure | Name | Scheme |
|---|---|---|---|
| 68 | 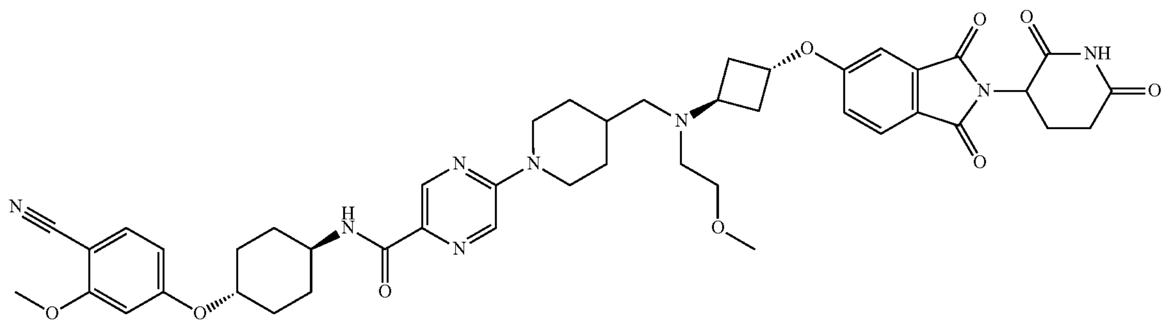 [SMILES: COCCN(CC1CCN(c2cnc(C(=O)N[C@H]3CC[C@H](Oc4ccc(C#N)c(OC)c4)CC3)cn2)CC1)[C@H]1C[C@H](Oc2ccc3c(c2)C(=O)N(C2CCC(=O)NC2=O)C3=O)C1] | N-((1r,4r)-4-(4-cyano-3-methoxyphenoxy)cyclohexyl)-5-(4-(((1r,3r)-3-(2-(2,6-dioxopiperidin-3-yl)-1,3-dioxoisoindolin-5-yl)oxy)cyclobutyl)(2-methoxyethyl)amino)methyl)piperidin-1-yl)pyrazine-2-carboxamide | 7 and 4 |
| 69 | 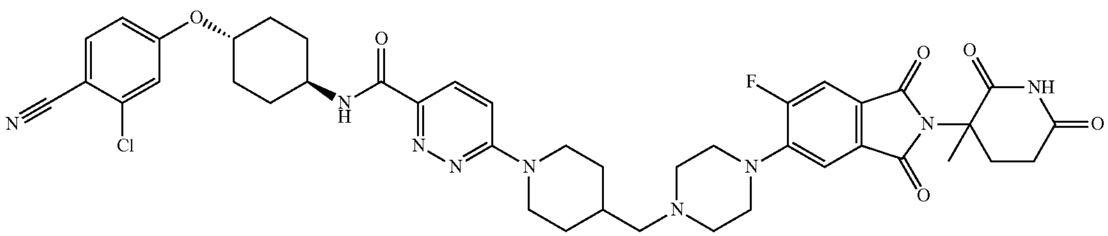 [SMILES: CC1(N2C(=O)c3cc(F)c(N4CCN(CC5CCN(c6ccc(C(=O)N[C@H]7CC[C@H](Oc8ccc(C#N)c(Cl)c8)CC7)nn6)CC5)CC4)cc3C2=O)CCC(=O)NC1=O] | N-((1r,4r)-4-(3-chloro-4-cyanophenoxy)cyclohexyl)-6-(4-((4-(6-fluoro-2-(3-methyl-2,6-dioxopiperidin-3-yl)-1,3-dioxoisoindolin-5-yl)piperazin-1-yl)methyl)piperidin-1-yl)pyridazine-3-carboxamide | 15 |
| 70 | 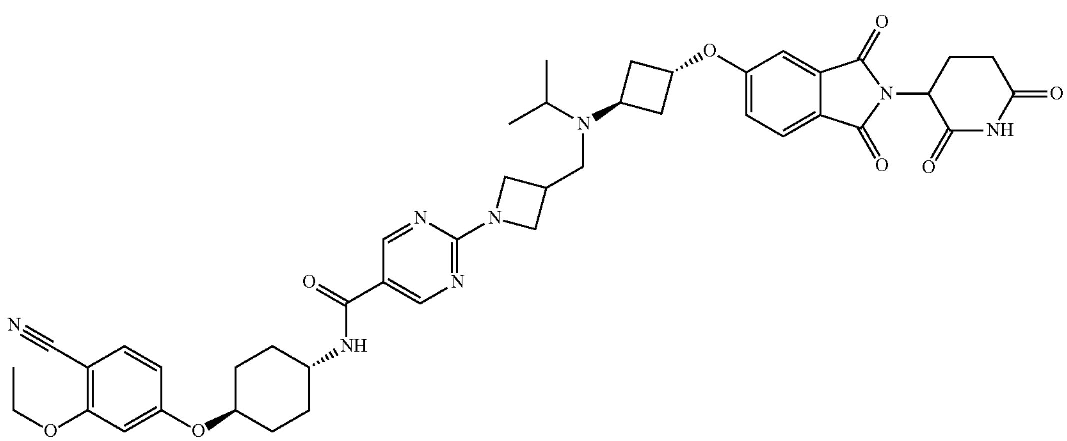 [SMILES: CCOc1cc(O[C@H]2CC[C@H](NC(=O)c3cnc(N4CC(CN(C(C)C)[C@H]5C[C@H](Oc6ccc7c(c6)C(=O)N(C6CCC(=O)NC6=O)C7=O)C5)C4)nc3)CC2)ccc1C#N] | N-((1r,4r)-4-(4-cyano-3-ethoxyphenoxy)cyclohexyl)-2-(3-(((1r,3r)-3-((2-(2,6-dioxopiperidin-3-yl)-1,3-dioxoisoindolin-5-yl)oxy)cyclobutyl)(isopropyl)amino)methyl)azetidin-1-yl)pyrimidine-5-carboxamide | 7 and 4 |

TABLE 1B-continued

Exemplary heterobifunctional compounds of the present disclosure.

| Comp. No. | Structure | Name | Scheme |
|---|---|---|---|
| 71 | 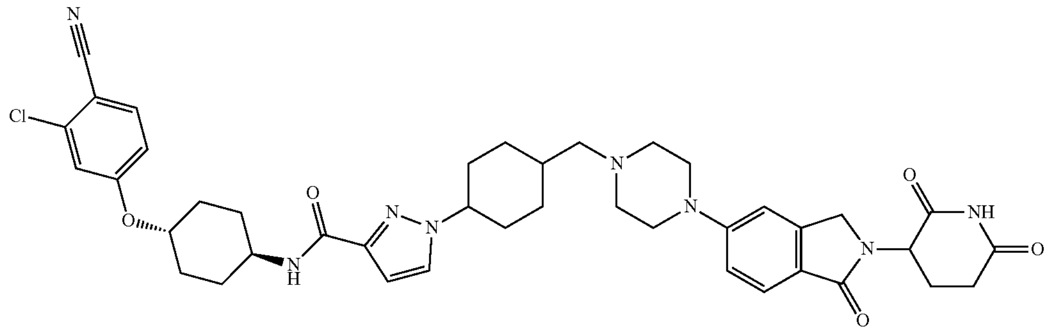 [SMILES: N#Cc1ccc(O[C@H]2CC[C@H](NC(=O)c3ccn(C4CCC(CN5CCN(c6ccc7c(c6)CN(C6CCC(=O)NC6=O)C7=O)CC5)CC4)n3)CC2)cc1Cl] | N-((1r,4r)-4-(3-chloro-4-cyanophenoxy)cyclohexyl)-1-(4-((4-(2-(2,6-dioxopiperidin-3-yl)-1-oxoisoindolin-5-yl)piperazin-1-yl)methyl)cyclohexyl)-1H-pyrazole-3-carboxamide | 16 |
| 72 | 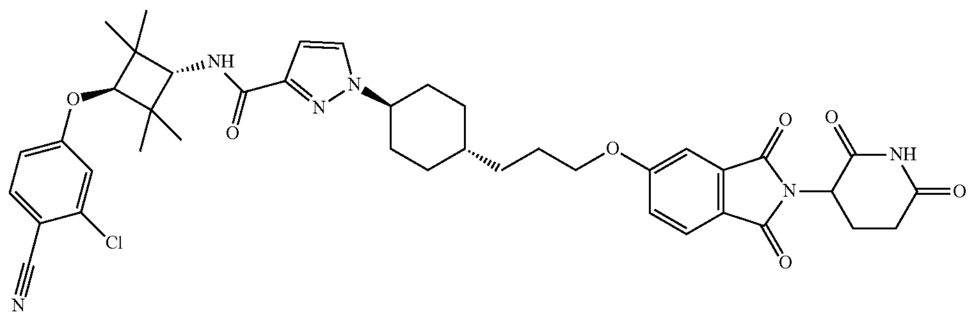 [SMILES: CC1(C)[C@H](NC(=O)c2ccn([C@H]3CC[C@H](CCCOc4ccc5c(c4)C(=O)N(C4CCC(=O)NC4=O)C5=O)CC3)n2)C(C)(C)[C@H]1Oc1ccc(C#N)c(Cl)c1] | N-((1r,3R)-3-(3-chloro-4-cyanophenoxy)-2,2,4,4-tetramethylcyclobutyl)-1-((1r,4R)-4-(3-(2-(2,6-dioxopiperidin-3-yl)-1,3-dioxoisoindolin-5-yl)oxy)propyl)cyclohexyl)-1H-pyrazole-3-carboxamide | 17 and 4 |
| 73 | 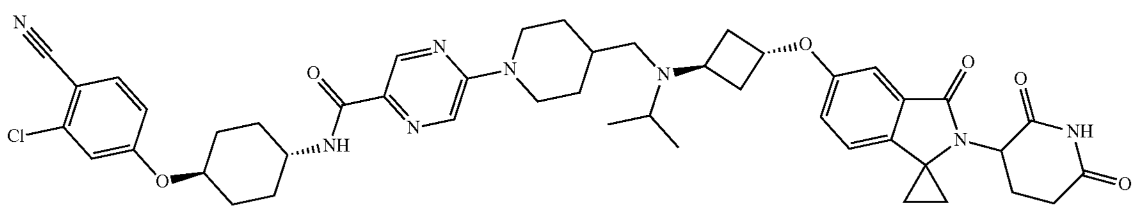 [SMILES: CC(C)N(CC1CCN(c2cnc(C(=O)N[C@H]3CC[C@H](Oc4ccc(C#N)c(Cl)c4)CC3)cn2)CC1)[C@H]1C[C@H](Oc2ccc3c(c2)C(=O)N(C2CCC(=O)NC2=O)C32CC2)C1] | N-((1r,4r)-4-(3-chloro-4-cyanophenoxy)cyclohexyl)-5-(4-(((1r,3r)-3-((2'-(2,6-dioxopiperidin-3-yl)-3'-oxospiro[cyclopropane-1,1'-isoindolin]-5'-yl)oxy)cyclobutyl)(isopropyl)amino)methyl)piperidin-1-yl)pyrazine-2-carboxamide | 4 and 18 |

TABLE 1B-continued

Exemplary heterobifunctional compounds of the present disclosure.

| Comp No. | Structure | Name | Scheme |
|---|---|---|---|
| 74 | 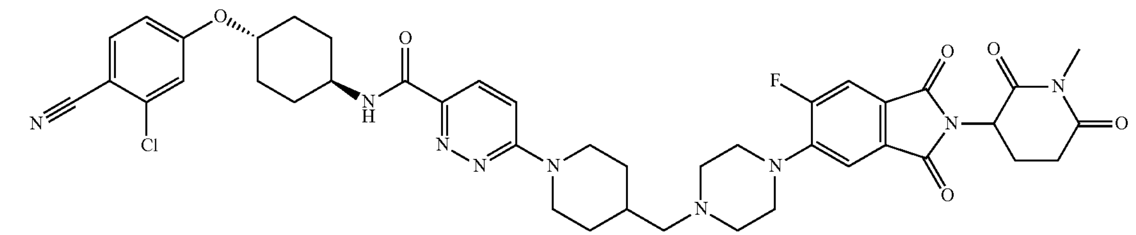 [SMILES: CN1C(=O)CCC(N2C(=O)c3cc(F)c(N4CCN(CC5CCN(c6ccc(C(=O)N[C@H]7CC[C@H](Oc8ccc(C#N)c(Cl)c8)CC7)nn6)CC5)CC4)cc3C2=O)C1=O] | N-((1r,4r)-4-(3-chloro-4-cyanophenoxy)cyclohexyl)-6-(4-((4-(6-fluoro-2-(1-methyl-2,6-dioxopiperidin-3-yl)-1,3-dioxoisoindolin-5-yl)piperazin-1-yl)methyl)piperidin-1-yl)pyridazine-3-carboxamide | 19 |
| 75 | 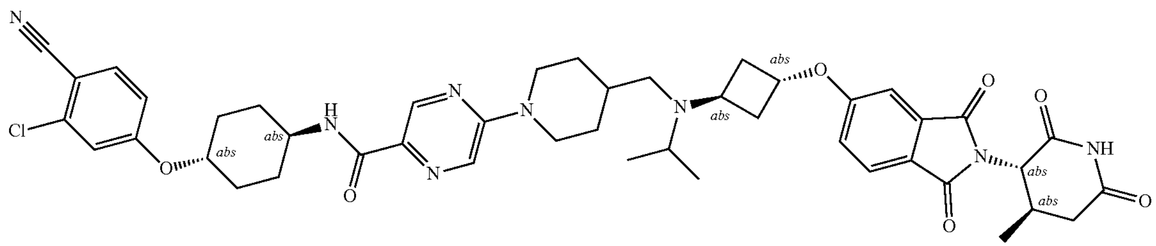 [SMILES: CC(C)N(CC1CCN(c2cnc(C(=O)N[C@H]3CC[C@H](Oc4ccc(C#N)c(Cl)c4)CC3)cn2)CC1)[C@H]1C[C@H](Oc2ccc3c(c2)C(=O)N([C@@H]2C(=O)NC(=O)C[C@H]2C)C3=O)C1] | N-((1r,4r)-4-(3-chloro-4-cyanophenoxy)cyclohexyl)-5-(4-(((isopropyl((1S,3r)-3-((2-((3S,4R)-4-methyl-2,6-dioxopiperidin-3-yl)-1,3-dioxoisoindolin-5-yl)oxy)cyclobutyl)amino)methyl)piperidin-1-yl)pyrazine-2-carboxamide | 20, 7, and 4 |
| 76 | 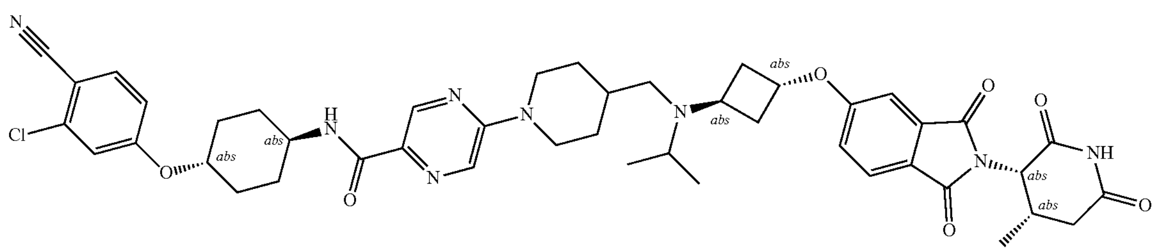 [SMILES: CC(C)N(CC1CCN(c2cnc(C(=O)N[C@H]3CC[C@H](Oc4ccc(C#N)c(Cl)c4)CC3)cn2)CC1)[C@H]1C[C@H](Oc2ccc3c(c2)C(=O)N([C@@H]2C(=O)NC(=O)C[C@@H]2C)C3=O)C1] | N-((1r,4r)-4-(3-chloro-4-cyanophenoxy)cyclohexyl)-5-(4-(((isopropyl((1S,3r)-3-((2-((3S,4S)-4-methyl-2,6-dioxopiperidin-3-yl)-1,3-dioxoisoindolin-5-yl)oxy)cyclobutyl)amino)methyl)piperidin-1-yl)pyrazine-2-carboxamide | 20, 7, and 4 |

TABLE 1B-continued

Exemplary heterobifunctional compounds of the present disclosure.

| Comp No. | Structure | Name | Scheme |
|---|---|---|---|
| 77 | 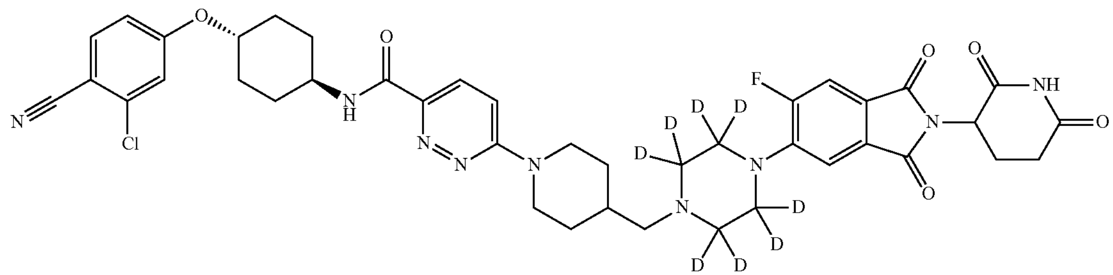 [SMILES: [2H]C1([2H])N(CC2CCN(c3ccc(C(=O)N[C@H]4CC[C@H](Oc5ccc(C#N)c(Cl)c5)CC4)nn3)CC2)C([2H])([2H])C([2H])([2H])N(c2cc3c(cc2F)C(=O)N(C2CCC(=O)NC2=O)C3=O)C1([2H])[2H]] | N-((1r,4r)-4-(3-chloro-4-cyanophenoxy)cyclohexyl)-6-(4-((4-(2-(2,6-dioxopiperidin-3-yl)-6-fluoro-1,3-dioxoisoindolin-5-yl)piperazin-1-yl-2,2,3,3,5,5,6,6-d8)methyl)piperidin-1-yl)pyridazine-3-carboxamide | 12 |
| 78 | 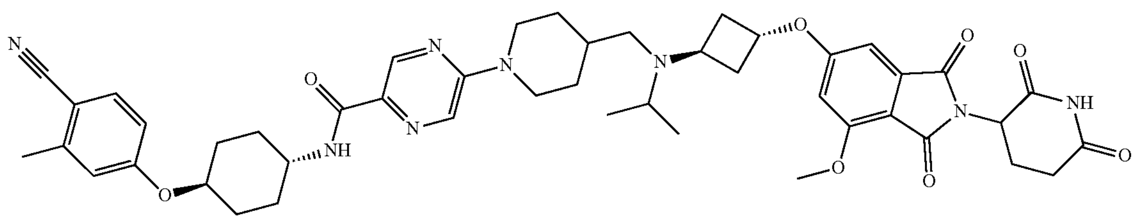 [SMILES: COc1cc(O[C@H]2C[C@H](N(CC3CCN(c4cnc(C(=O)N[C@H]5CC[C@H](Oc6ccc(C#N)c(C)c6)CC5)cn4)CC3)C(C)C)C2)cc2c1C(=O)N(C1CCC(=O)NC1=O)C2=O] | N-((1r,4r)-4-(4-cyano-3-methylphenoxy)cyclohexyl)-5-(4-((((1r,3r)-3-((2-(2,6-dioxopiperidin-3-yl)-7-methoxy-1,3-dioxoisoindolin-5-yl)oxy)cyclobutyl)(isopropyl)amino)methyl)piperidin-1-yl)pyrazine-2-carboxamide | 1 and 4 |

TABLE 1C

Exemplary heterobifunctional compounds of the present disclosure.

| Comp No. | Structure | Name | Scheme |
|---|---|---|---|
| 79 | 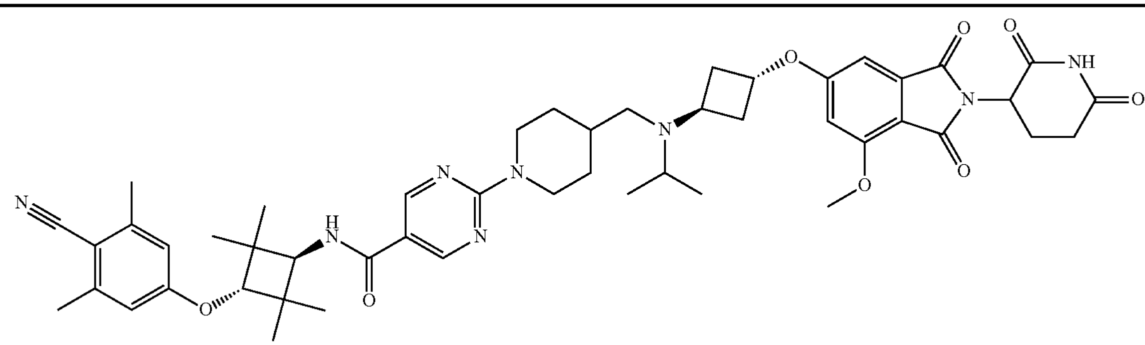 | N-((1r,3r)-3-(4-cyano-3,5-dimethylphenoxy)-2,2,4,4-tetramethylcyclobutyl)-2-(4-(((1r,3r)-3-((2-(2,6-dioxopiperidin-3-yl)-7-methoxy-1,3-dioxoisoindolin-5-yl)oxy)cyclobutyl)(isopropyl)amino)methyl)piperidin-1-yl)pyrimidine-5-carboxamide | 7 and 1 |
| 80 | 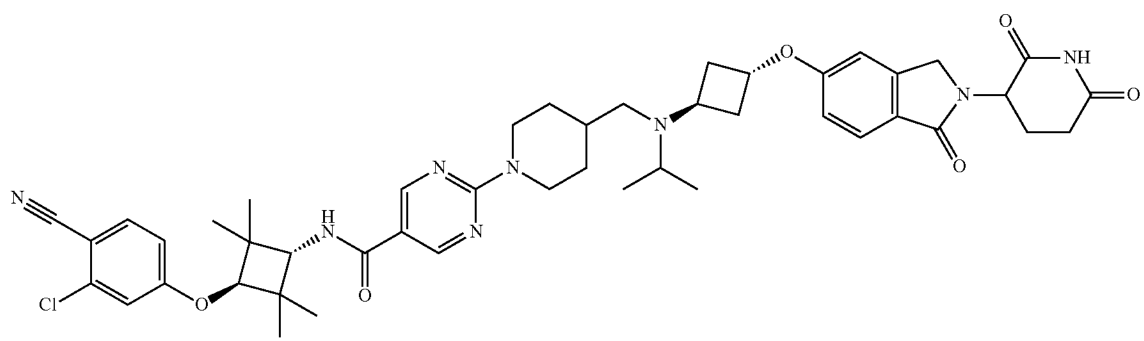 [SMILES: CC(C)N(CC1CCN(c2ncc(C(=O)N[C@H]3C(C)(C)[C@H](Oc4ccc(C#N)c(Cl)c4)C3(C)C)cn2)CC1)[C@H]1C[C@H](Oc2ccc3c(c2)CN(C2CCC(=O)NC2=O)C3=O)C1] | N-((1r,3r)-3-(3-chloro-4-cyanophenoxy)-2,2,4,4-tetramethylcyclobutyl)-2-(4-(((1r,3r)-3-((2-(2,6-dioxopiperidin-3-yl)-1-oxoisoindolin-5-yl)oxy)cyclobutyl)(isopropyl)amino)methyl)piperidin-1-yl)pyrimidine-5-carboxamide | 21 and 7 |

TABLE 1C-continued

Exemplary heterobifunctional compounds of the present disclosure.

| Comp No. | Structure | Name | Scheme |
|---|---|---|---|
| 81 | 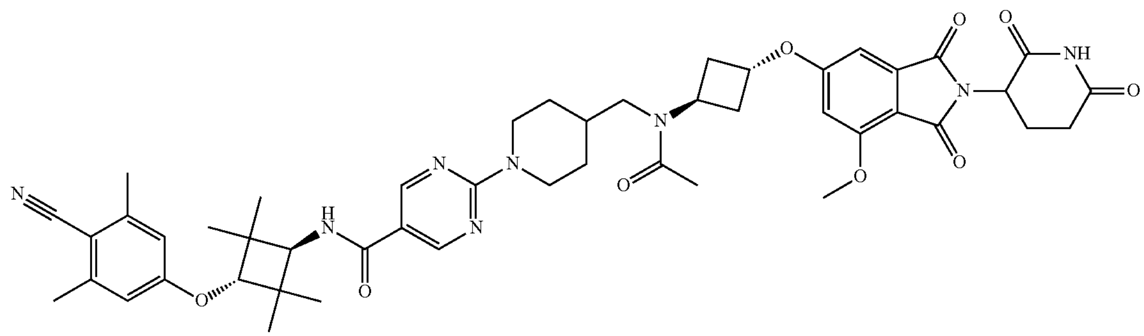 [SMILES: COc1cc(O[C@H]2C[C@H](N(CC3CCN(c4ncc(C(=O)N[C@H]5C(C)(C)[C@H](Oc6cc(C)c(C#N)c(C)c6)C5(C)C)cn4)CC3)C(C)=O)C2)cc2c1C(=O)N(C1CCC(=O)NC1=O)C2=O] | N-((1r,3r)-3-(4-cyano-3,5-dimethylphenoxy)-2,2,4,4-tetramethylcyclobutyl)-2-(4-((N-((1r,3r)-3-(2-(2,6-dioxopiperidin-3-yl)-7-methoxy-1,3-dioxoisoindolin-5-yl)oxy)cyclobutyl)acetamido)methyl)piperidin-1-yl)pyrimidine-5-carboxamide | 7 and 1 |
| 82 | 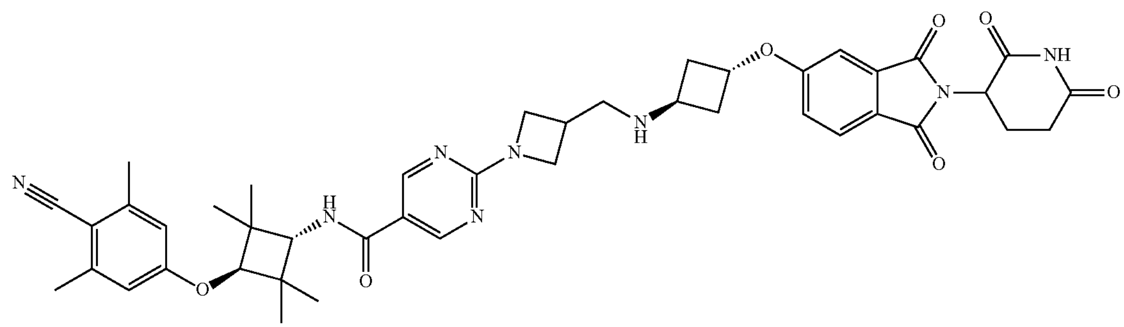 [SMILES: Cc1cc(O[C@H]2C(C)(C)[C@H](NC(=O)c3cnc(N4CC(CN[C@H]5C[C@H](Oc6ccc7c(c6)C(=O)N(C6CCC(=O)NC6=O)C7=O)C5)C4)nc3)C2(C)C)cc(C)c1C#N] | N-((1r,3r)-3-(4-cyano-3,5-dimethylphenoxy)-2,2,4,4-tetramethylcyclobutyl)-2-(3-(((1r,3r)-3-(2-(2,6-dioxopiperidin-3-yl)-1,3-dioxoisoindolin-5-yl)oxy)cyclobutyl)amino)methyl)azetidin-1-yl)pyrimidine-5-carboxamide | 7 |
| 83 | 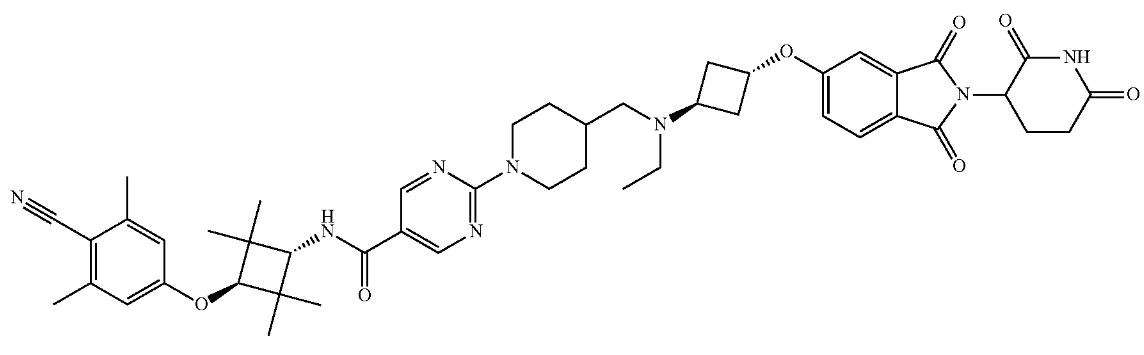 [SMILES: CCN(CC1CCN(c2ncc(C(=O)N[C@H]3C(C)(C)[C@H](Oc4cc(C)c(C#N)c(C)c4)C3(C)C)cn2)CC1)[C@H]1C[C@H](Oc2ccc3c(c2)C(=O)N(C2CCC(=O)NC2=O)C3=O)C1] | N-((1r,3r)-3-(4-cyano-3,5-dimethylphenoxy)-2,2,4,4-tetramethylcyclobutyl)-2-(4-((((1r,3r)-3-(2-(2,6-dioxopiperidin-3-yl)-1,3-dioxoisoindolin-5-yl)oxy)cyclobutyl)(ethyl)amino)methyl)piperidin-1-yl)pyrimidine-5-carboxamide | 7 |

TABLE 1C-continued

Exemplary heterobifunctional compounds of the present disclosure.

| Comp No. | Structure | Name | Scheme |
|---|---|---|---|
| 84 | 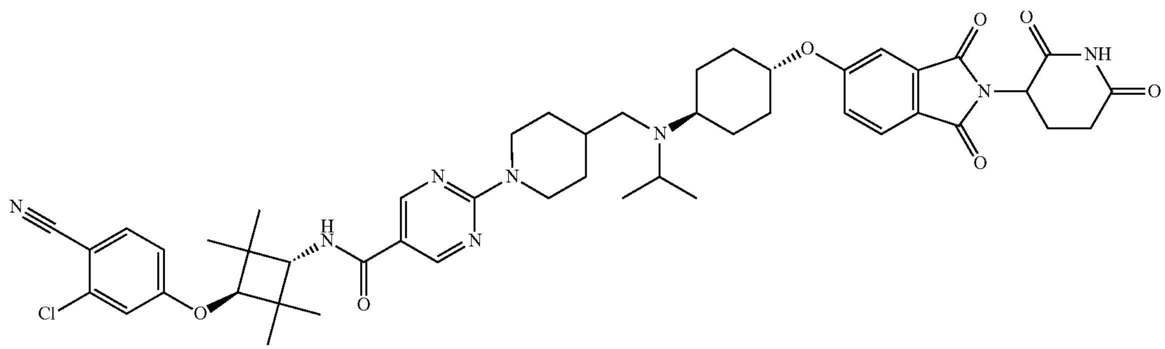 [SMILES: CC(C)N(CC1CCN(c2ncc(C(=O)N[C@H]3C(C)(C)[C@H](Oc4ccc(C#N)c(Cl)c4)C3(C)C)cn2)CC1)[C@H]1CC[C@H](Oc2ccc3c(c2)C(=O)N(C2CCC(=O)NC2=O)C3=O)CC1] | N-((1r,3r)-3-(3-chloro-4-cyanophenoxy)-2,2,4,4-tetramethylcyclobutyl)-2-(4-(((1r,4r)-4-((2-(2,6-dioxopiperidin-3-yl)-1,3-dioxoisoindolin-5-yl)oxy)cyclohexyl)(isopropyl)amino)methyl)piperidin-1-yl)pyrimidine-5-carboxamide | 7 using amino-cylohexanol in place of amino-cyclobutanol |
| 85 | 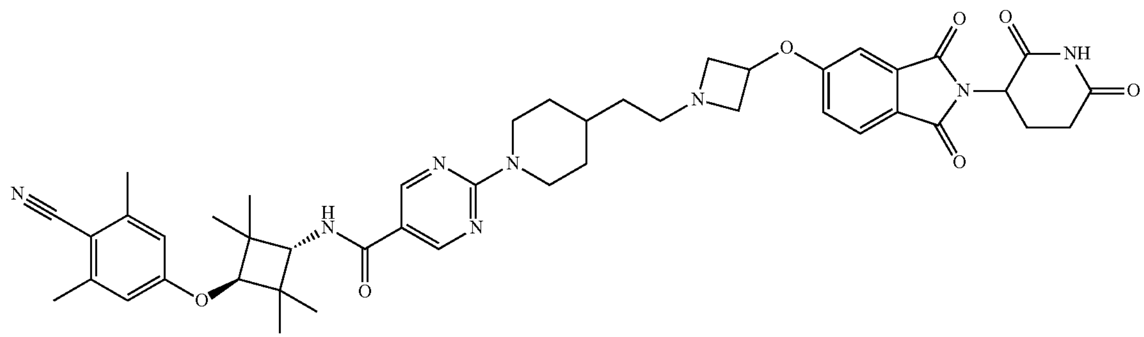 [SMILES: Cc1cc(O[C@H]2C(C)(C)[C@H](NC(=O)c3cnc(N4CCC(CCN5CC(Oc6ccc7c(c6)C(=O)N(C6CCC(=O)NC6=O)C7=O)C5)CC4)nc3)C2(C)C)cc(C)c1C#N] | N-((1r,3r)-3-(4-cyano-3,5-dimethylphenoxy)-2,2,4,4-tetramethylcyclobutyl)-2-(4-(2-(3-((2-(2,6-dioxopiperidin-3-yl)-1,3-dioxoisoindolin-5-yl)oxy)azetidin-1-yl)ethyl)piperidin-1-yl)pyrimidine-5-carboxamide | 22 |

TABLE 1C-continued

Exemplary heterobifunctional compounds of the present disclosure.

| Comp No. | Structure | Name | Scheme |
|---|---|---|---|
| 86 | 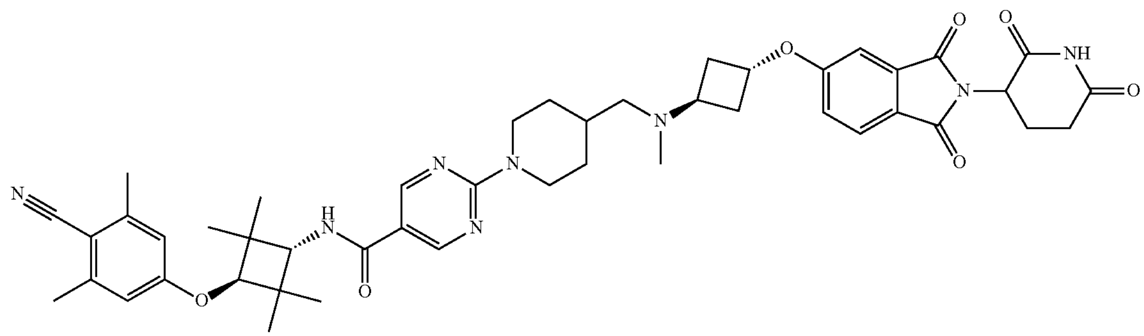 [SMILES: Cc1cc(O[C@H]2C(C)(C)[C@H](NC(=O)c3cnc(N4CCC(CN(C)[C@H]5C[C@H](Oc6ccc7c(c6)C(=O)N(C6CCC(=O)NC6=O)C7=O)C5)CC4)nc3)C2(C)C)cc(C)c1C#N] | N-((1r,3r)-3-(4-cyano-3,5-dimethylphenoxy)-2,2,4,4-tetramethylcyclobutyl)-2-(4-((((1r,3r)-3-((2-(2,6-dioxopiperidin-3-yl)-1,3-dioxoisoindolin-5-yl)oxy)cyclobutyl)(methyl)amino)methyl)piperidin-1-yl)pyrimidine-5-carboxamide | 7 |
| 87 | 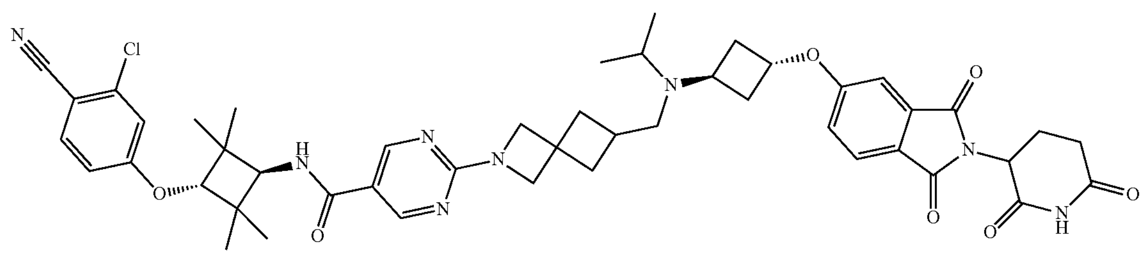 [SMILES: CC(C)N(CC1CC2(C1)CN(c1ncc(C(=O)N[C@H]3C(C)(C)[C@H](Oc4ccc(C#N)c(Cl)c4)C3(C)C)cn1)C2)[C@H]1C[C@H](Oc2ccc3c(c2)C(=O)N(C2CCC(=O)NC2=O)C3=O)C1] | N-((1r,3r)-3-(3-chloro-4-cyanophenoxy)-2,2,4,4-tetramethylcyclobutyl)-2-(6-((((1r,3r)-3-((2-(2,6-dioxopiperidin-3-yl)-1,3-dioxoisoindolin-5-yl)oxy)cyclobutyl)(isopropyl)amino)methyl)-2-azaspiro[3.3]heptan-2-yl)pyrimidine-5-carboxamide | 7 |

TABLE 1C-continued

Exemplary heterobifunctional compounds of the present disclosure.

| Comp No. | Structure | Name | Scheme |
|---|---|---|---|
| 88 | 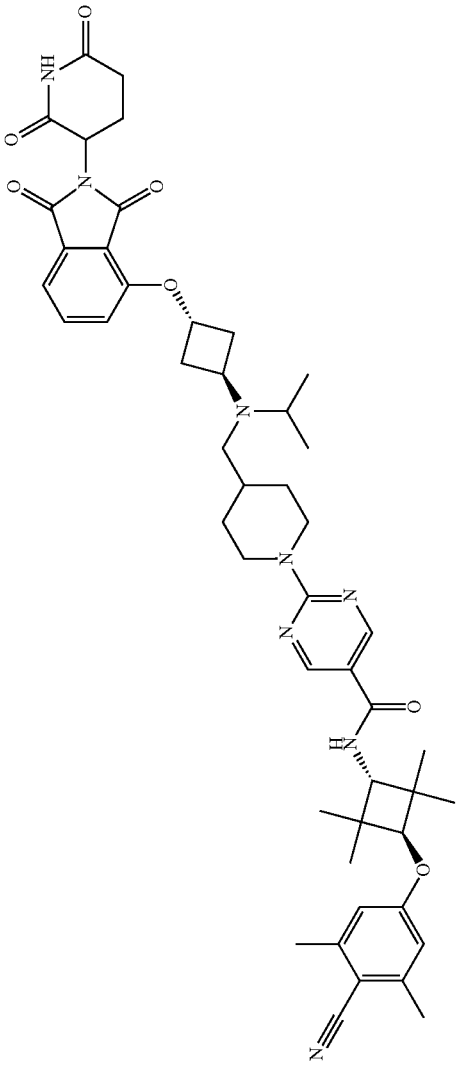 | N-((1r,3r)-3-(4-cyano-3,5-dimethylphenoxy)-2,2,4,4-tetramethylcyclobutyl)-2-(4-(((1r,3r)-3-((2-(2,6-dioxopiperidin-3-yl)-1,3-dioxoisoindolin-4-yl)oxy)cyclobutyl)(isopropyl)amino)methyl)piperidin-1-yl)pyrimidine-5-carboxamide | 7 |
| 89 | 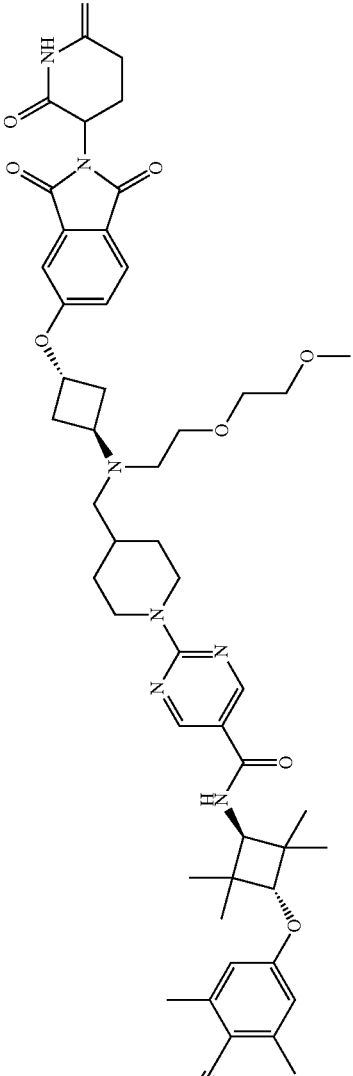 | N-((1r,3r)-3-(4-cyano-3,5-dimethylphenoxy)-2,2,4,4-tetramethylcyclobutyl)-2-(4-(((1r,3r)-3-((2-(2,6-dioxopiperidin-3-yl)-1,3-dioxoisoindolin-5-yl)oxy)cyclobutyl)(2-methoxyethoxy)ethyl)amino)methyl)piperidin-1-yl)pyrimidine-5-carboxamide | 7 |

TABLE 1C-continued

Exemplary heterobifunctional compounds of the present disclosure.

| Comp No. | Structure | Name | Scheme |
|---|---|---|---|
| 90 | 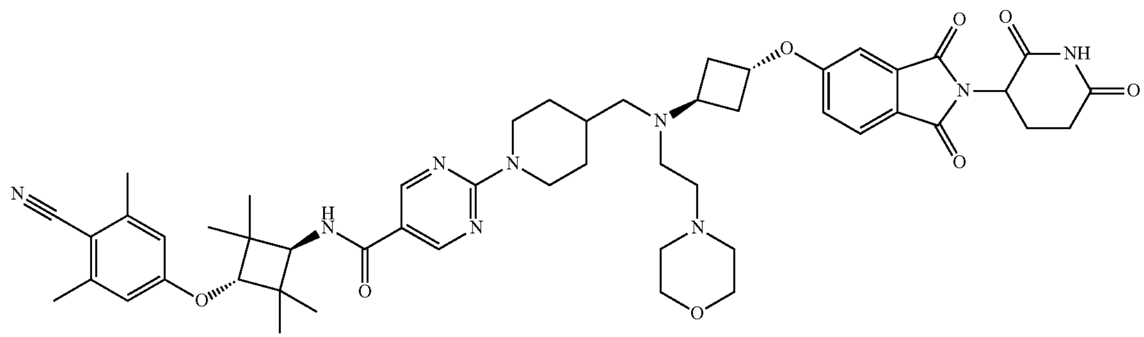 [SMILES: Cc1cc(O[C@H]2C(C)(C)[C@H](NC(=O)c3cnc(N4CCC(CN(CCN5CCOCC5)[C@H]5C[C@H](Oc6ccc7c(c6)C(=O)N(C6CCC(=O)NC6=O)C7=O)C5)CC4)nc3)C2(C)C)cc(C)c1C#N] | N-((1r,3r)-3-(4-cyano-3,5-dimethylphenoxy)-2,2,4,4-tetramethylcyclobutyl)-2-(4-(((1r,3r)-3-((2-(2,6-dioxopiperidin-3-yl)-1,3-dioxoisoindolin-5-yl)oxy)cyclobutyl)(2-morpholinoethyl)amino)methyl)piperidin-1-yl)pyrimidine-5-carboxamide | 7 |
| 91 | 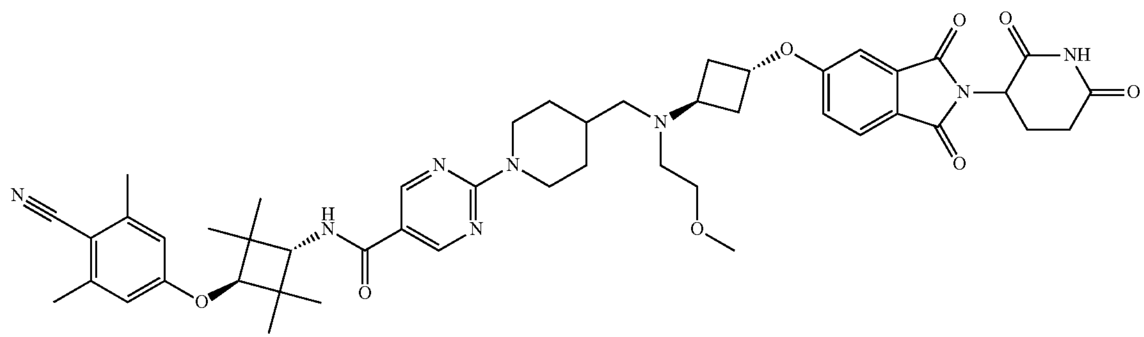 [SMILES: COCCN(CC1CCN(c2ncc(C(=O)N[C@H]3C(C)(C)[C@H](Oc4cc(C)c(C#N)c(C)c4)C3(C)C)cn2)CC1)[C@H]1C[C@H](Oc2ccc3c(c2)C(=O)N(C2CCC(=O)NC2=O)C3=O)C1] | N-((1r,3r)-3-(4-cyano-3,5-dimethylphenoxy)-2,2,4,4-tetramethylcyclobutyl)-2-(4-(((1r,3r)-3-((2-(2,6-dioxopiperidin-3-yl)-1,3-dioxoisoindolin-5-yl)oxy)cyclobutyl)(2-methoxyethyl)amino)methyl)piperidin-1-yl)pyrimidine-5-carboxamide | 7 |

TABLE 1C-continued

Exemplary heterobifunctional compounds of the present disclosure.

| Comp No. | Structure | Name | Scheme |
|---|---|---|---|
| 92 | 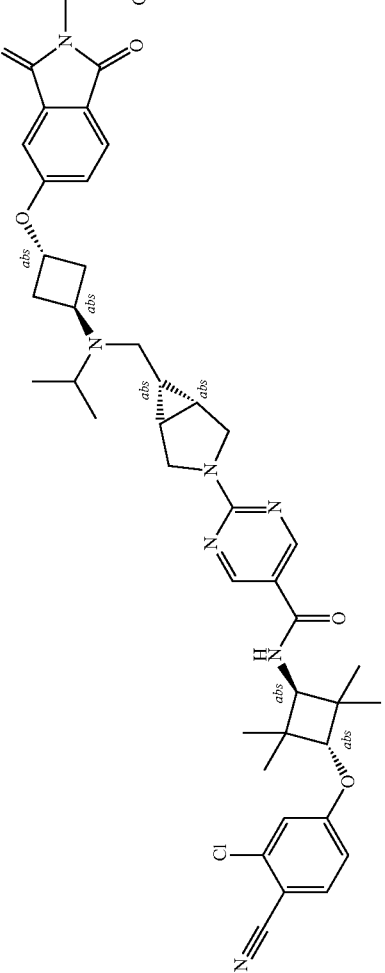 | N-((1r,3S)-3-(3-chloro-4-cyanophenoxy)-2,2,4,4-tetramethylcyclobutyl)-2-((1S,5S)-6-((((1r,3S)-3-((2-(2,6-dioxopiperidin-3-yl)-1,3-dioxoisoindolin-5-yl)oxy)cyclobutyl)(isopropyl)amino)methyl)-3-azabicyclo[3.1.0]hexan-3-yl)pyrimidine-5-carboxamide | 23 |
| 93 | 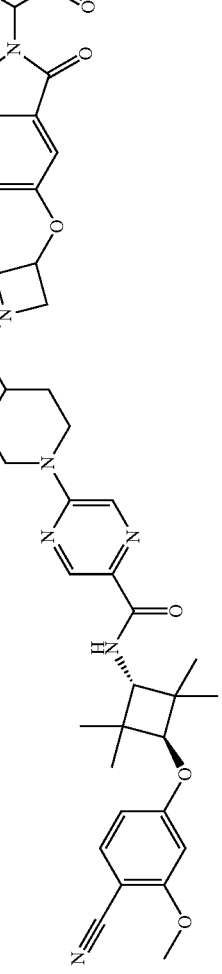 | N-((1r,3r)-3-(4-cyano-3-methoxyphenoxy)-2,2,4,4-tetramethylcyclobutyl)-5-(4-((3-((2-(2,6-dioxopiperidin-3-yl)-1,3-dioxoisoindolin-5-yl)oxy)azetidin-1-yl)methyl)piperidin-1-yl)pyrazine-2-carboxamide | 22 |

TABLE 1C-continued

Exemplary heterobifunctional compounds of the present disclosure.

| Comp No. | Structure | Name | Scheme |
|---|---|---|---|
| 94 | 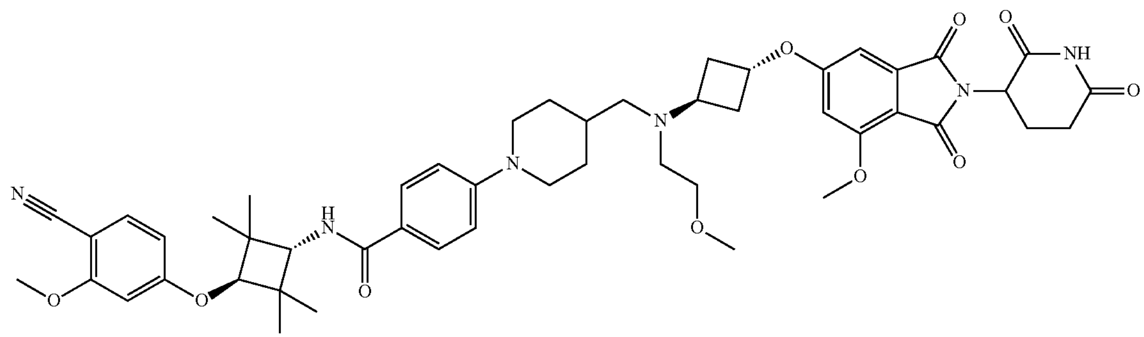 [SMILES: COCCN(CC1CCN(c2ccc(C(=O)N[C@H]3C(C)(C)[C@H](Oc4ccc(C#N)c(OC)c4)C3(C)C)cc2)CC1)[C@H]1C[C@H](Oc2cc(OC)c3c(c2)C(=O)N(C2CCC(=O)NC2=O)C3=O)C1] | N-((1r,3r)-3-(4-cyano-3-methoxyphenoxy)-2,2,4,4-tetramethylcyclobutyl)-4-(4-(((1r,3r)-3-((2-(2,6-dioxopiperidin-3-yl)-7-methoxy-1,3-dioxoisoindolin-5-yl)oxy)cyclobutyl)(2-methoxyethyl)amino)methyl)piperidin-1-yl)benzamide | 7 and 1 |
| 95 | 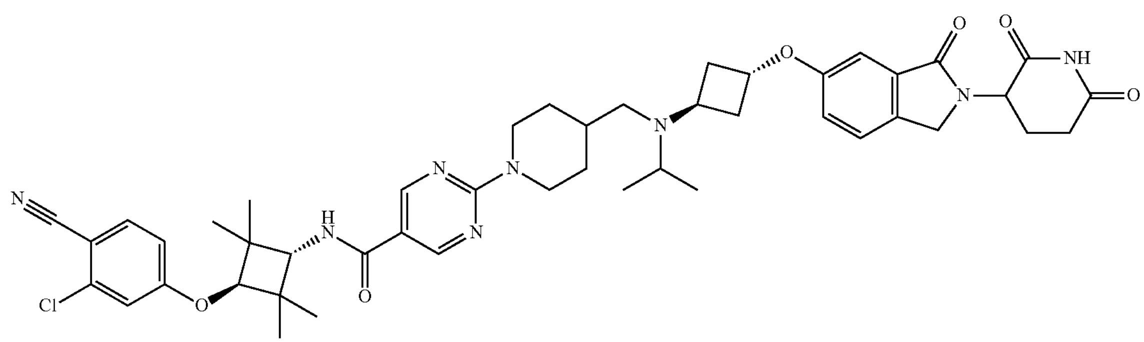 [SMILES: CC(C)N(CC1CCN(c2ncc(C(=O)N[C@H]3C(C)(C)[C@H](Oc4ccc(C#N)c(Cl)c4)C3(C)C)cn2)CC1)[C@H]1C[C@H](Oc2ccc3c(c2)C(=O)N(C2CCC(=O)NC2=O)C3)C1] | N-((1r,3r)-3-(3-chloro-4-cyanophenoxy)-2,2,4,4-tetramethylcyclobutyl)-2-(4-(((1r,3r)-3-((2-(2,6-dioxopiperidin-3-yl)-3-oxoisoindolin-5-yl)oxy)cyclobutyl)(isopropyl)amino)methyl)piperidin-1-yl)pyrimidine-5-carboxamide | 3 |
| 96 | 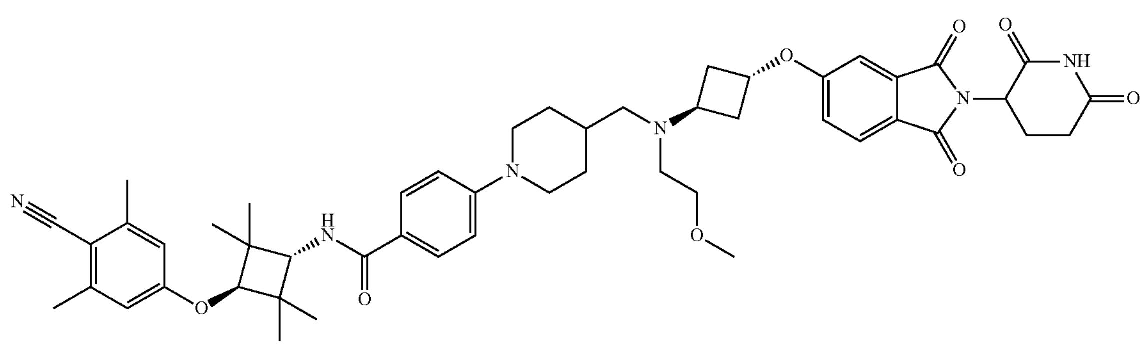 [SMILES: COCCN(CC1CCN(c2ccc(C(=O)N[C@H]3C(C)(C)[C@H](Oc4cc(C)c(C#N)c(C)c4)C3(C)C)cc2)CC1)[C@H]1C[C@H](Oc2ccc3c(c2)C(=O)N(C2CCC(=O)NC2=O)C3=O)C1] | N-((1r,3r)-3-(4-cyano-3,5-dimethylphenoxy)-2,2,4,4-tetramethylcyclobutyl)-4-(4-(((1r,3r)-3-((2-(2,6-dioxopiperidin-3-yl)-1,3-dioxoisoindolin-5-yl)oxy)cyclobutyl)(2-methoxyethyl)amino)methyl)piperidin-1-yl)benzamide | 7 |

TABLE 1C-continued

Exemplary heterobifunctional compounds of the present disclosure.

| Comp No. | Structure | Name | Scheme |
|---|---|---|---|
| 97 | 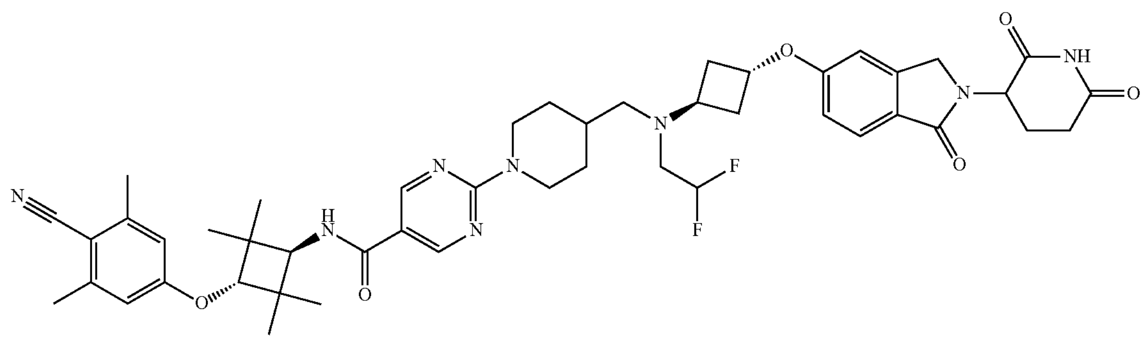 [SMILES: Cc1cc(O[C@H]2C(C)(C)[C@H](NC(=O)c3cnc(N4CCC(CN(CC(F)F)[C@H]5C[C@H](Oc6ccc7c(c6)CN(C6CCC(=O)NC6=O)C7=O)C5)CC4)nc3)C2(C)C)cc(C)c1C#N] | N-((1r,3r)-3-(4-cyano-3,5-dimethylphenoxy)-2,2,4,4-tetramethylcyclobutyl)-2-(4-(((1r,3r)-3-(2-(2,6-dioxopiperidin-3-yl)-1-oxoisoindolin-5-yl)oxy)cyclobutyl)amino)methyl)piperidin-1-yl)pyrimidine-5-carboxamide | 21 and 3 |
| 98 | 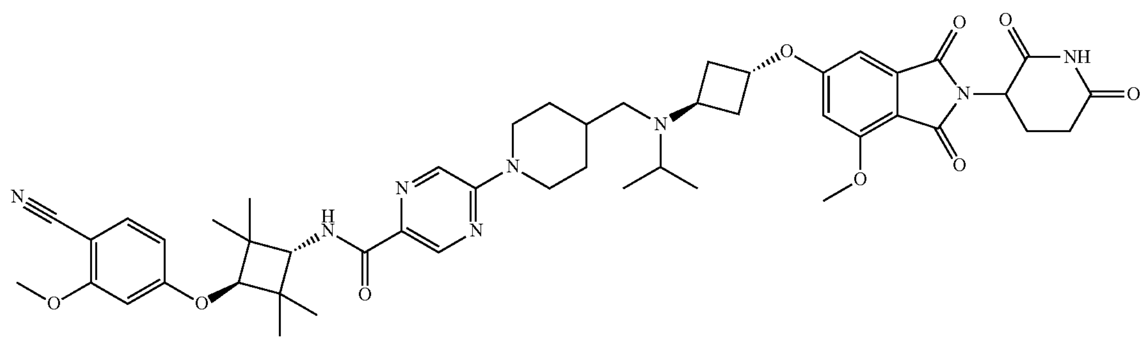 [SMILES: COc1cc(O[C@H]2C(C)(C)[C@H](NC(=O)c3cnc(N4CCC(CN(C(C)C)[C@H]5C[C@H](Oc6cc(OC)c7c(c6)C(=O)N(C6CCC(=O)NC6=O)C7=O)C5)CC4)cn3)C2(C)C)ccc1C#N] | N-((1r,3r)-3-(4-cyano-3-methoxyphenoxy)-2,2,4,4-tetramethylcyclobutyl)-5-(4-(((1r,3r)-3-(2-(2,6-dioxopiperidin-3-yl)-7-methoxy-1,3-dioxoisoindolin-5-yl)oxy)cyclobutyl)(isopropyl)amino)methyl)piperidin-1-yl)pyrazine-2-carboxamide | 7 and 1 |
| 99 | 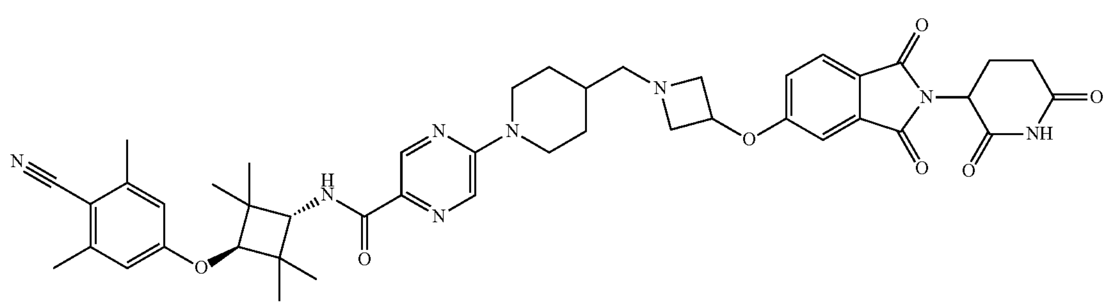 [SMILES: Cc1cc(O[C@H]2C(C)(C)[C@H](NC(=O)c3cnc(N4CCC(CN5CC(Oc6ccc7c(c6)C(=O)N(C6CCC(=O)NC6=O)C7=O)C5)CC4)cn3)C2(C)C)cc(C)c1C#N] | N-((1r,3r)-3-(4-cyano-3,5-dimethylphenoxy)-2,2,4,4-tetramethylcyclobutyl)-5-(4-((3-((2-(2,6-dioxopiperidin-3-yl)-1,3-dioxoisoindolin-5-yl)oxy)azetidin-1-yl)methyl)piperidin-1-yl)pyrazine-2-carboxamide | 22 |

TABLE 1C-continued

Exemplary heterobifunctional compounds of the present disclosure.

| Comp No. | Structure | Name | Scheme |
|---|---|---|---|
| 100 | 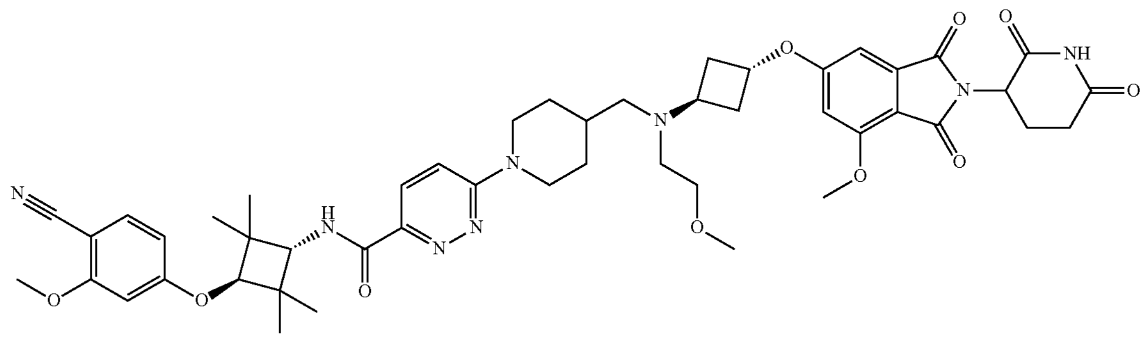 [SMILES: COCCN(CC1CCN(c2ccc(C(=O)N[C@H]3C(C)(C)[C@H](Oc4ccc(C#N)c(OC)c4)C3(C)C)nn2)CC1)[C@H]1C[C@H](Oc2cc(OC)c3c(c2)C(=O)N(C2CCC(=O)NC2=O)C3=O)C1] | N-((1r,3r)-3-(4-cyano-3-methoxyphenoxy)-2,2,4,4-tetramethylcyclobutyl)-6-(4-(((1r,3r)-3-((2-(2,6-dioxopiperidin-3-yl)-7-methoxy-1,3-dioxoisoindolin-5-yl)oxy)cyclobutyl)(2-methoxyethyl)amino)methyl)piperidin-1-yl)pyridazine-3-carboxamide | 7 and 1 |
| 101 | 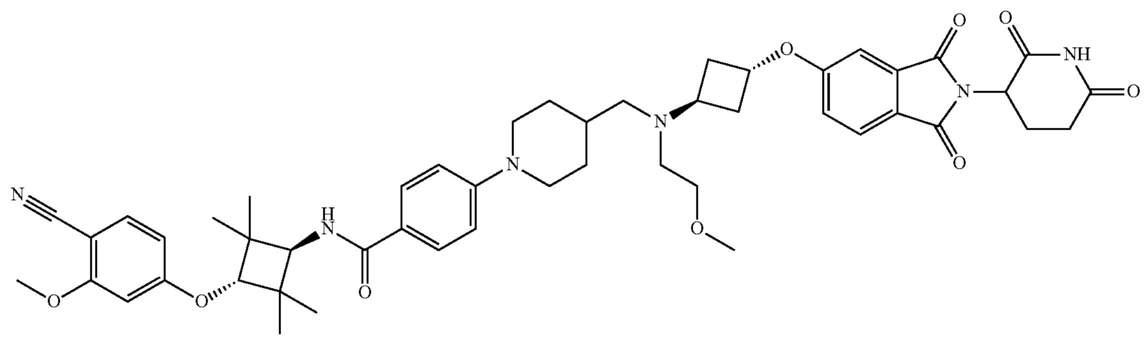 [SMILES: COCCN(CC1CCN(c2ccc(C(=O)N[C@H]3C(C)(C)[C@H](Oc4ccc(C#N)c(OC)c4)C3(C)C)cc2)CC1)[C@H]1C[C@H](Oc2ccc3c(c2)C(=O)N(C2CCC(=O)NC2=O)C3=O)C1] | N-((1r,3r)-3-(4-cyano-3-methoxyphenoxy)-2,2,4,4-tetramethylcyclobutyl)-4-(4-(((1r,3r)-3-((2-(2,6-dioxopiperidin-3-yl)-1,3-dioxoisoindolin-5-yl)oxy)cyclobutyl)(2-methoxyethyl)amino)methyl)piperidin-1-yl)benzamide | 7 |
| 102 | 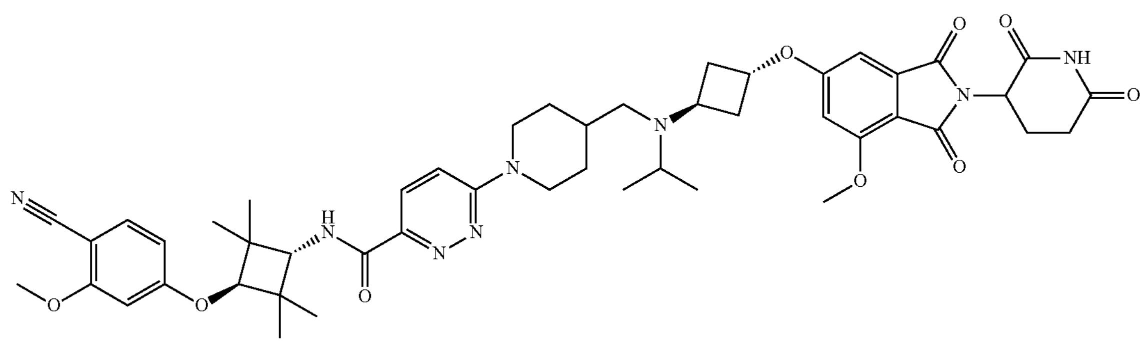 [SMILES: COc1cc(O[C@H]2C(C)(C)[C@H](NC(=O)c3ccc(N4CCC(CN(C(C)C)[C@H]5C[C@H](Oc6cc(OC)c7c(c6)C(=O)N(C6CCC(=O)NC6=O)C7=O)C5)CC4)nn3)C2(C)C)ccc1C#N] | N-((1r,3r)-3-(4-cyano-3-methoxyphenoxy)-2,2,4,4-tetramethylcyclobutyl)-6-(4-(((1r,3r)-3-((2-(2,6-dioxopiperidin-3-yl)-7-methoxy-1,3-dioxoisoindolin-5-yl)oxy)cyclobutyl)(isopropyl)amino)methyl)piperidin-1-yl)pyridazine-3-carboxamide | 7 and 1 |

TABLE 1C-continued

Exemplary heterobifunctional compounds of the present disclosure.

| Comp No. | Structure | Name | Scheme |
|---|---|---|---|
| 103 | 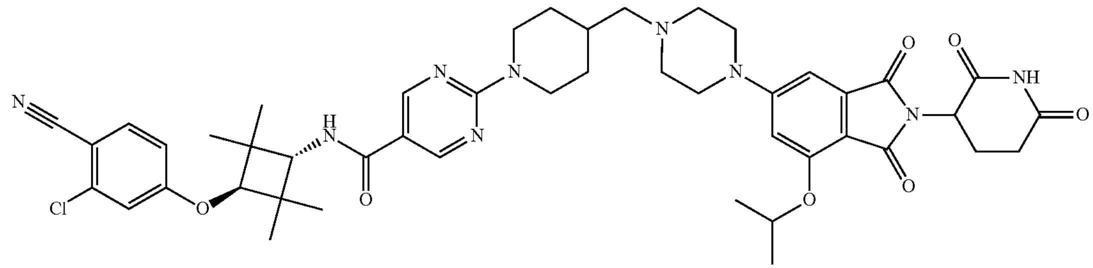 [SMILES: CC(C)Oc1cc(N2CCN(CC3CCN(c4ncc(C(=O)N[C@H]5C(C)(C)[C@H](Oc6ccc(C#N)c(Cl)c6)C5(C)C)cn4)CC3)CC2)cc2c1C(=O)N(C1CCC(=O)NC1=O)C2=O] | N-((1r,3r)-3-(3-chloro-4-cyanophenoxy)-2,2,4,4-tetramethylcyclobutyl)-2-(4-(2-(2,6-dioxopiperidin-3-yl)-1,3-dioxoisoindolin-5-yl)piperazin-1-yl)methyl)piperidin-1-yl)pyrimidine-5-carboxamide | 24 and 25 |
| 104 | 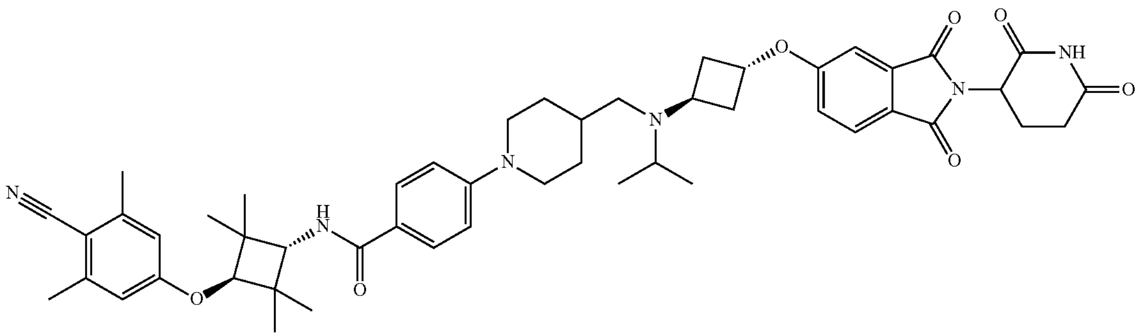 [SMILES: Cc1cc(O[C@H]2C(C)(C)[C@H](NC(=O)c3ccc(N4CCC(CN(C(C)C)[C@H]5C[C@H](Oc6ccc7c(c6)C(=O)N(C6CCC(=O)NC6=O)C7=O)C5)CC4)cc3)C2(C)C)cc(C)c1C#N] | N-((1r,3r)-3-(4-cyano-3,5-dimethylphenoxy)-2,2,4,4-tetramethylcyclobutyl)-4-(4-(((1r,3r)-3-((2-(2,6-dioxopiperidin-3-yl)-1,3-dioxoisoindolin-5-yl)oxy)cyclobutyl)(isopropyl)amino)methyl)piperidin-1-yl)benzamide | 7, and custom synthesis provided |
| 105 | 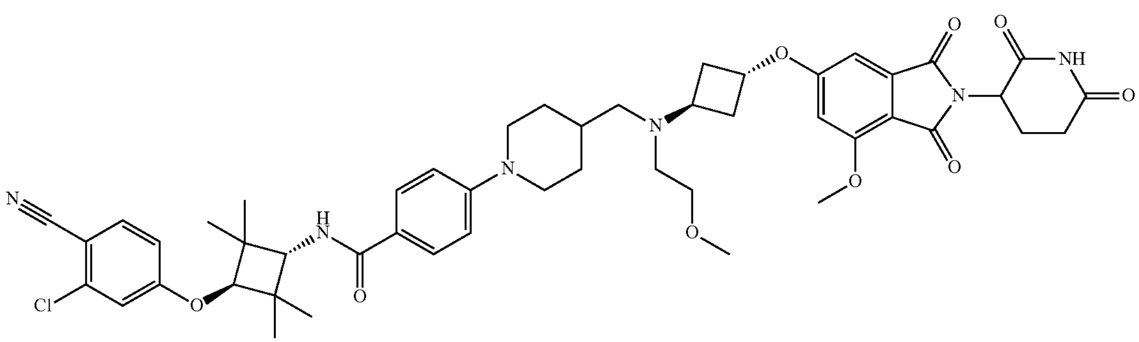 [SMILES: COCCN(CC1CCN(c2ccc(C(=O)N[C@H]3C(C)(C)[C@H](Oc4ccc(C#N)c(Cl)c4)C3(C)C)cc2)CC1)[C@H]1C[C@H](Oc2cc(OC)c3c(c2)C(=O)N(C2CCC(=O)NC2=O)C3=O)C1] | N-((1r,3r)-3-(3-chloro-4-cyanophenoxy)-2,2,4,4-tetramethylcyclobutyl)-4-(4-((((1r,3r)-3-((2-(2,6-dioxopiperidin-3-yl)-7-methoxy-1,3-dioxoisoindolin-5-yl)oxy)cyclobutyl)(2-methoxyethyl)amino)methyl)piperidin-1-yl)benzamide | 7 and 1 |

TABLE 1C-continued

Exemplary heterobifunctional compounds of the present disclosure.

| Comp No. | Structure | Name | Scheme |
|---|---|---|---|
| 106 | 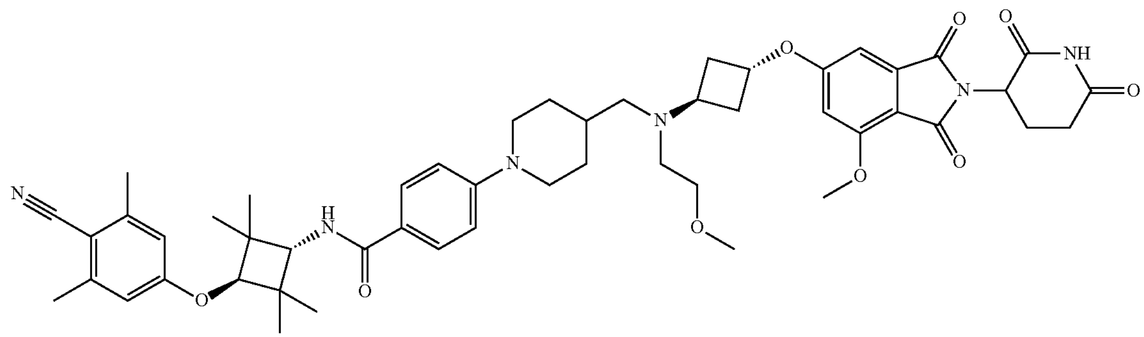 [SMILES: COCCN(CC1CCN(c2ccc(C(=O)N[C@H]3C(C)(C)[C@H](Oc4cc(C)c(C#N)c(C)c4)C3(C)C)cc2)CC1)[C@H]1C[C@H](Oc2cc(OC)c3c(c2)C(=O)N(C2CCC(=O)NC2=O)C3=O)C1] | N-((1r,3r)-3-(4-cyano-3,5-dimethylphenoxy)-2,2,4,4-tetramethylcyclobutyl)-4-(4-((((1r,3r)-3-((2-(2,6-dioxopiperidin-3-yl)-7-methoxy-1,3-dioxoisoindolin-5-yl)oxy)cyclobutyl)(2-methoxyethyl)amino)methyl)piperidin-1-yl)benzamide | 7 and 1 |
| 107 | 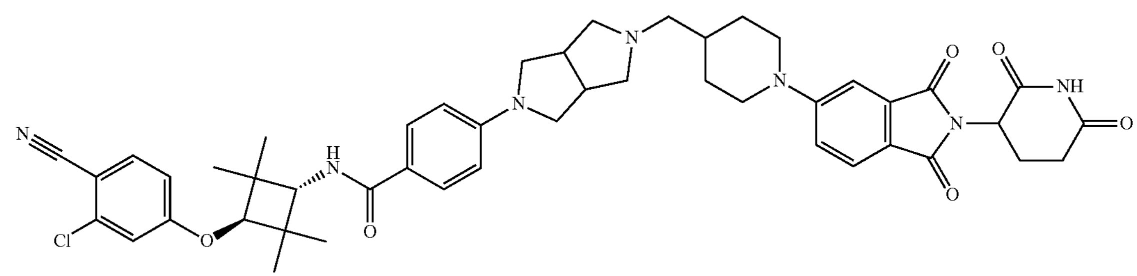 [SMILES: CC1(C)[C@H](NC(=O)c2ccc(N3CC4CN(CC5CCN(c6ccc7c(c6)C(=O)N(C6CCC(=O)NC6=O)C7=O)CC5)CC4C3)cc2)C(C)(C)[C@H]1Oc1ccc(C#N)c(Cl)c1] | N-((1r,3r)-3-(3-chloro-4-cyanophenoxy)-2,2,4,4-tetramethylcyclobutyl)-4-(5-((1-(2-(2,6-dioxopiperidin-3-yl)-1,3-dioxoisoindolin-5-yl)piperidin-4-yl)methyl)hexahydropyrrolo[3,4-c]pyrrol-2(1H)-yl)benzamide | 26 |
| 108 | 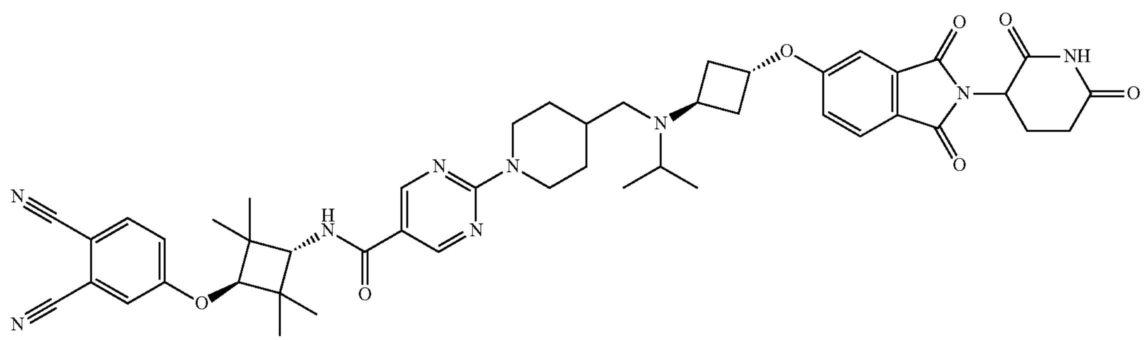 [SMILES: CC(C)N(CC1CCN(c2ncc(C(=O)N[C@H]3C(C)(C)[C@H](Oc4ccc(C#N)c(C#N)c4)C3(C)C)cn2)CC1)[C@H]1C[C@H](Oc2ccc3c(c2)C(=O)N(C2CCC(=O)NC2=O)C3=O)C1] | N-((1r,3r)-3-(3,4-dicyanophenoxy)-2,2,4,4-tetramethylcyclobutyl)-2-(4-((((1r,3r)-3-((2-(2,6-dioxopiperidin-3-yl)-1,3-dioxoisoindolin-5-yl)oxy)cyclobutyl)(isopropyl)amino)methyl)piperidin-1-yl)pyrimidine-5-carboxamide | 27 |

TABLE 1C-continued

Exemplary heterobifunctional compounds of the present disclosure.

| Comp No. | Structure | Name | Scheme |
|---|---|---|---|
| 109 | 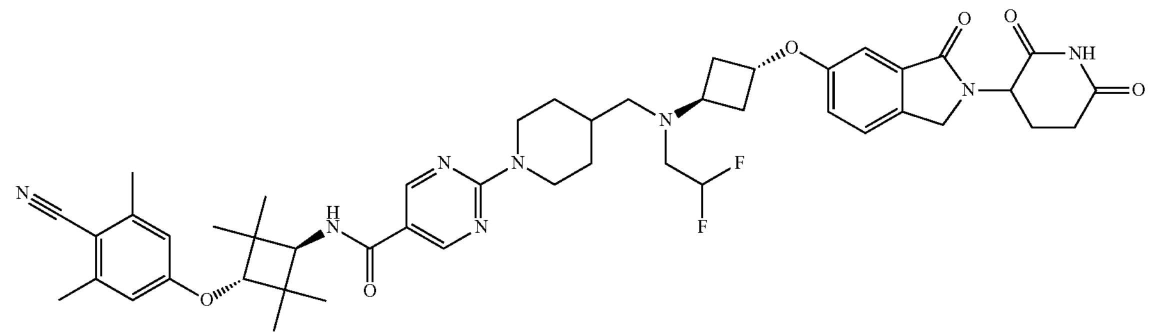 [SMILES: Cc1cc(O[C@H]2C(C)(C)[C@H](NC(=O)c3cnc(N4CCC(CN(CC(F)F)[C@H]5C[C@H](Oc6ccc7c(c6)C(=O)N(C6CCC(=O)NC6=O)C7)C5)CC4)nc3)C2(C)C)cc(C)c1C#N] | N-((1r,3r)-3-(4-cyano-3,5-dimethylphenoxy)-2,2,4,4-tetramethylcyclobutyl)-2-(4-(((2,2-difluoroethyl)((1r,3r)-3-((2-(2,6-dioxopiperidin-3-yl)-3-oxoisoindolin-5-yl)oxy)cyclobutyl)amino)methyl)piperidin-1-yl)pyrimidine-5-carboxamide | 3 |
| 110 | 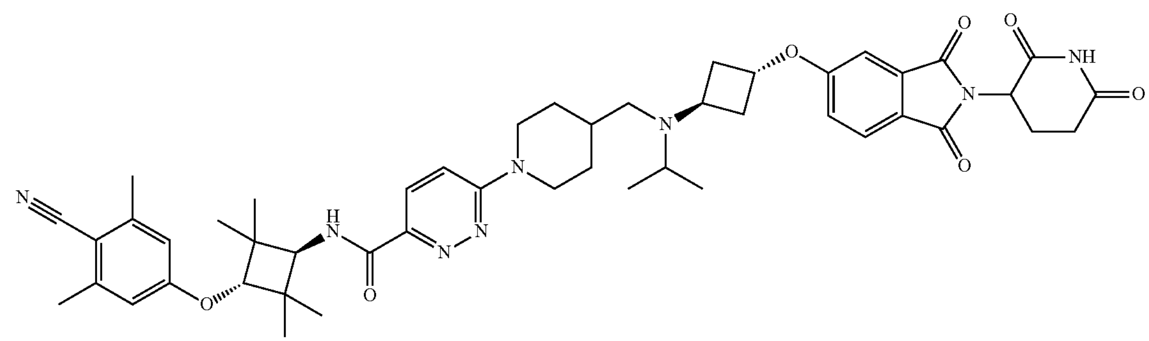 [SMILES: Cc1cc(O[C@H]2C(C)(C)[C@H](NC(=O)c3ccc(N4CCC(CN(C(C)C)[C@H]5C[C@H](Oc6ccc7c(c6)C(=O)N(C6CCC(=O)NC6=O)C7=O)C5)CC4)nn3)C2(C)C)cc(C)c1C#N] | N-((1r,3r)-3-(4-cyano-3,5-dimethylphenoxy)-2,2,4,4-tetramethylcyclobutyl)-6-(4-(((1r,3r)-3-((2-(2,6-dioxopiperidin-3-yl)-1,3-dioxoisoindolin-5-yl)oxy)cyclobutyl)(isopropyl)amino)methyl)piperidin-1-yl)pyridazine-3-carboxamide | 7 |
| 111 | 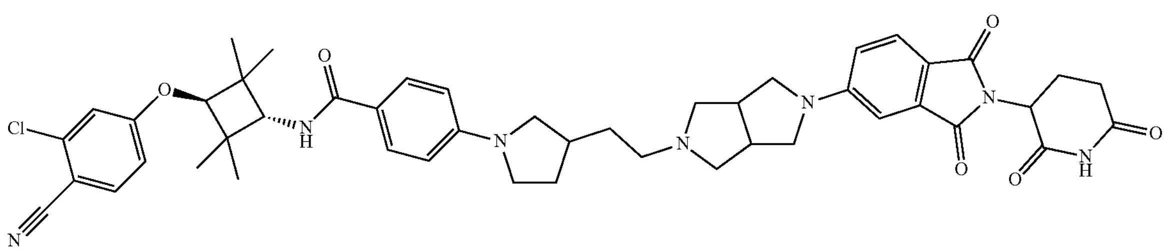 [SMILES: CC1(C)[C@H](NC(=O)c2ccc(N3CCC(CCN4CC5CN(c6ccc7c(c6)C(=O)N(C6CCC(=O)NC6=O)C7=O)CC5C4)C3)cc2)C(C)(C)[C@H]1Oc1ccc(C#N)c(Cl)c1] | N-((1r,3r)-3-(3-chloro-4-cyanophenoxy)-2,2,4,4-tetramethylcyclobutyl)-4-(3-(2-(5-(2-(2,6-dioxopiperidin-3-yl)-1,3-dioxoisoindolin-5-yl)hexahydropyrrolo[3,4-c]pyrrol-2(1H)-yl)ethyl)pyrrolidin-1-yl)benzamide | 25 |

TABLE 1C-continued

Exemplary heterobifunctional compounds of the present disclosure.

| Comp No. | Structure | Name | Scheme |
|---|---|---|---|
| 112 | 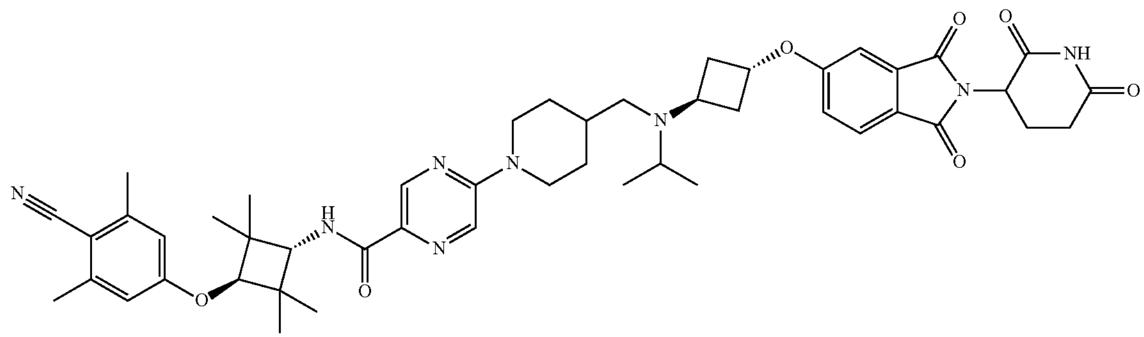 [SMILES: Cc1cc(O[C@H]2C(C)(C)[C@H](NC(=O)c3cnc(N4CCC(CN(C(C)C)[C@H]5C[C@H](Oc6ccc7c(c6)C(=O)N(C6CCC(=O)NC6=O)C7=O)C5)CC4)cn3)C2(C)C)cc(C)c1C#N] | N-((1r,3r)-3-(4-cyano-3,5-dimethylphenoxy)-2,2,4,4-tetramethylcyclobutyl)-5-(4-((((1r,3r)-3-((2-(2,6-dioxopiperidin-3-yl)-1,3-dioxoisoindolin-5-yl)oxy)cyclobutyl)(isopropyl)amino)methyl)piperidin-1-yl)pyrazine-2-carboxamide | 7 |
| 113 | 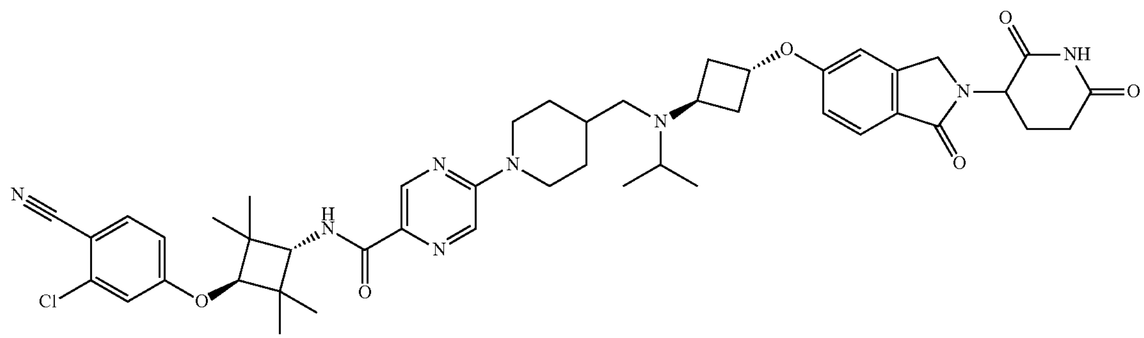 [SMILES: CC(C)N(CC1CCN(c2cnc(C(=O)N[C@H]3C(C)(C)[C@H](Oc4ccc(C#N)c(Cl)c4)C3(C)C)cn2)CC1)[C@H]1C[C@H](Oc2ccc3c(c2)CN(C2CCC(=O)NC2=O)C3=O)C1] | N-((1r,3r)-3-(3-chloro-4-cyanophenoxy)-2,2,4,4-tetramethylcyclobutyl)-5-(4-((((1r,3r)-3-((2-(2,6-dioxopiperidin-3-yl)-1-oxoisoindolin-5-yl)oxy)cyclobutyl)(isopropyl)amino)methyl)piperidin-1-yl)pyrazine-2-carboxamide | 21 and 7 |
| 114 | 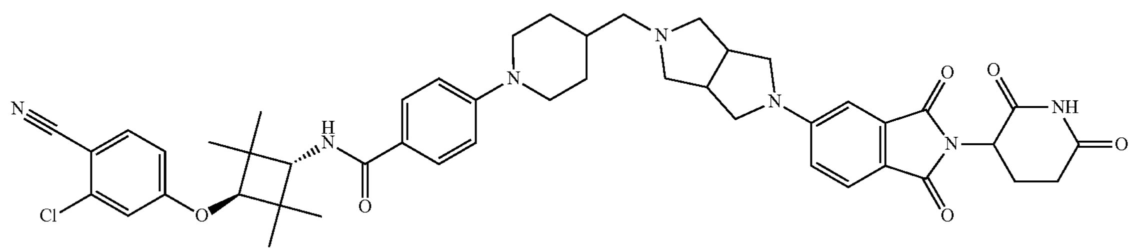 [SMILES: CC1(C)[C@H](NC(=O)c2ccc(N3CCC(CN4CC5CN(c6ccc7c(c6)C(=O)N(C6CCC(=O)NC6=O)C7=O)CC5C4)CC3)cc2)C(C)(C)[C@H]1Oc1ccc(C#N)c(Cl)c1] | N-((1r,3r)-3-(3-chloro-4-cyanophenoxy)-2,2,4,4-tetramethylcyclobutyl)-4-(4-(5-(2-(2,6-dioxopiperidin-3-yl)-1,3-dioxoisoindolin-5-yl)hexahydropyrrolo[3,4-c]pyrrol-2(1H)-yl)methyl)piperidin-1-yl)benzamide | 25 |

TABLE 1C-continued

Exemplary heterobifunctional compounds of the present disclosure.

| Comp No. | Structure | Name | Scheme |
|---|---|---|---|
| 115 | 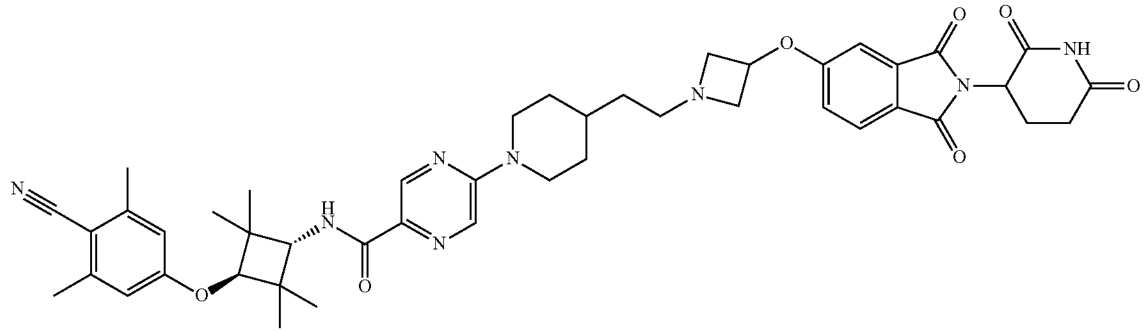 [SMILES: Cc1cc(O[C@H]2C(C)(C)[C@H](NC(=O)c3cnc(N4CCC(CCN5CC(Oc6ccc7c(c6)C(=O)N(C6CCC(=O)NC6=O)C7=O)C5)CC4)cn3)C2(C)C)cc(C)c1C#N] | N-((1r,3r)-3-(4-cyano-3,5-dimethylphenoxy)-2,2,4,4-tetramethylcyclobutyl)-5-(4-(2-(3-((2-(2,6-dioxopiperidin-3-yl)-1,3-dioxoisoindolin-5-yl)oxy)azetidin-1-yl)ethyl)piperidin-1-yl)pyrazine-2-carboxamide | 22 |
| 116 | 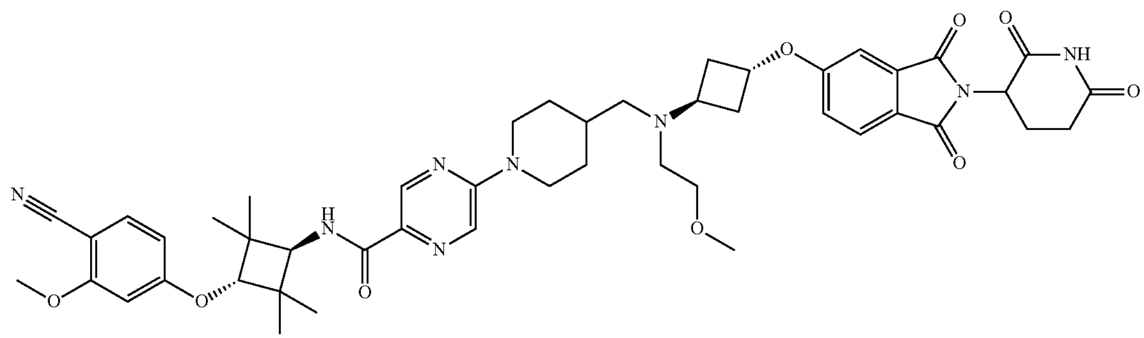 [SMILES: COCCN(CC1CCN(c2cnc(C(=O)N[C@H]3C(C)(C)[C@H](Oc4ccc(C#N)c(OC)c4)C3(C)C)cn2)CC1)[C@H]1C[C@H](Oc2ccc3c(c2)C(=O)N(C2CCC(=O)NC2=O)C3=O)C1] | N-((1r,3r)-3-(4-cyano-3-methoxyphenoxy)-2,2,4,4-tetramethylcyclobutyl)-5-(4-((((1r,3r)-3-((2-(2,6-dioxopiperidin-3-yl)-1,3-dioxoisoindolin-5-yl)oxy)cyclobutyl)(2-methoxyethyl)amino)methyl)piperidin-1-yl)pyrazine-2-carboxamide | 7 |
| 117 | 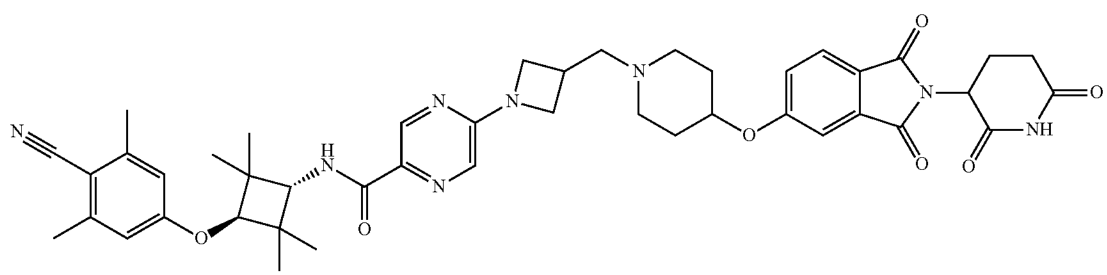 [SMILES: Cc1cc(O[C@H]2C(C)(C)[C@H](NC(=O)c3cnc(N4CC(CN5CCC(Oc6ccc7c(c6)C(=O)N(C6CCC(=O)NC6=O)C7=O)CC5)C4)cn3)C2(C)C)cc(C)c1C#N] | N-((1r,3r)-3-(4-cyano-3,5-dimethylphenoxy)-2,2,4,4-tetramethylcyclobutyl)-5-(3-((4-((2-(2,6-dioxopiperidin-3-yl)-1,3-dioxoisoindolin-5-yl)oxy)piperidin-1-yl)methyl)azetidin-1-yl)pyrazine-2-carboxamide | 28 and 22 |

TABLE 1C-continued

Exemplary heterobifunctional compounds of the present disclosure.

| Comp No. | Structure | Name | Scheme |
|---|---|---|---|
| 118 | 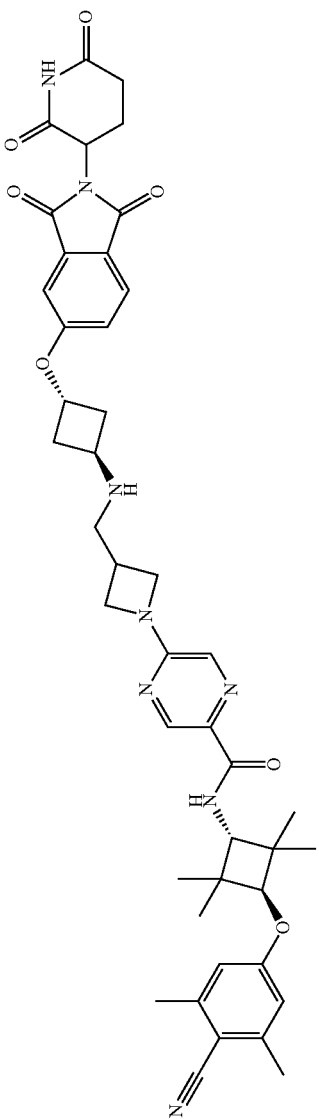 | N-((1r,3r)-3-(4-cyano-3,5-dimethylphenoxy)-2,2,4,4-tetramethylcyclobutyl)-5-(3-(((1r,3r)-3-((2-(2,6-dioxopiperidin-3-yl)-1,3-dioxoisoindolin-5-yl)oxy)cyclobutyl)amino)methyl)azetidin-1-yl)pyrazine-2-carboxamide | 7 |
| 119 | 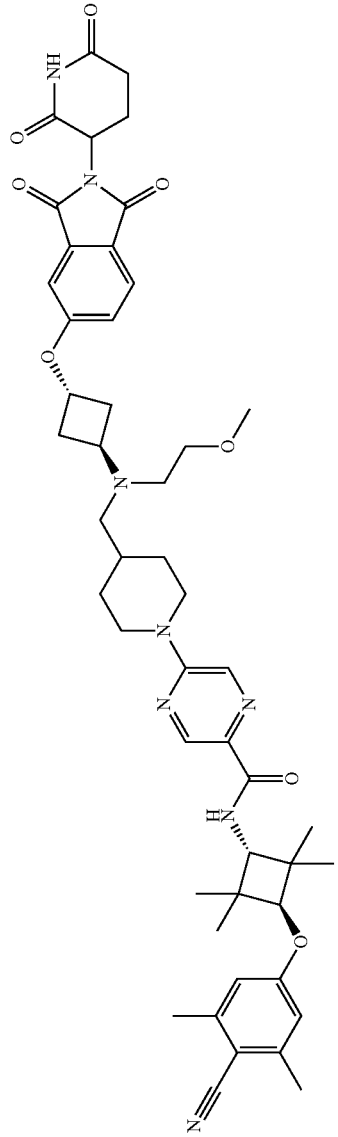 | N-((1r,3r)-3-(4-cyano-3,5-dimethylphenoxy)-2,2,4,4-tetramethylcyclobutyl)-5-(4-(((1r,3r)-3-((2-(2,6-dioxopiperidin-3-yl)-1,3-dioxoisoindolin-5-yl)oxy)cyclobutyl)(2-methoxyethyl)amino)methyl)piperidin-1-yl)pyrazine-2-carboxamide | 7 |

TABLE 1C-continued

Exemplary heterobifunctional compounds of the present disclosure.

| Comp No. | Structure | Name | Scheme |
|---|---|---|---|
| 120 | 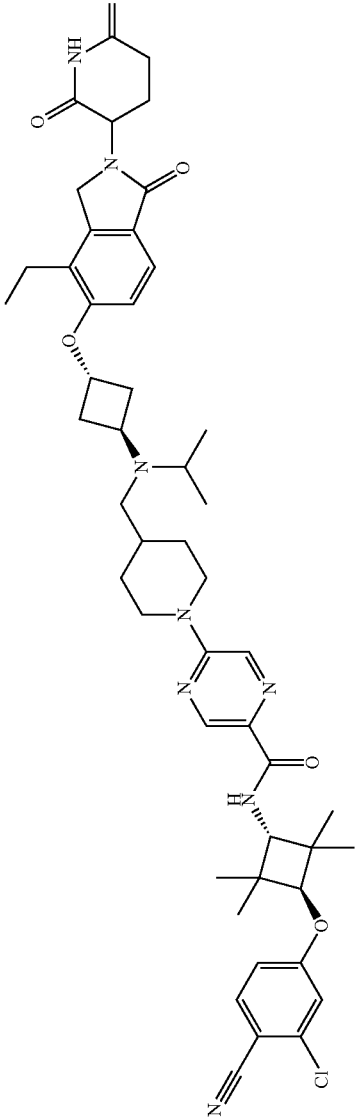 | N-((1r,3r)-3-(3-chloro-4-cyanophenoxy)-2,2,4,4-tetramethylcyclobutyl)-5-(4-(((1r,3r)-3-((2-(2,6-dioxopiperidin-3-yl)-4-ethyl-1-oxoisoindolin-5-yl)oxy)cyclobutyl)(isopropyl)amino)methyl)piperidin-1-yl)pyrazine-2-carboxamide | 29 and 3 |
| 121 | 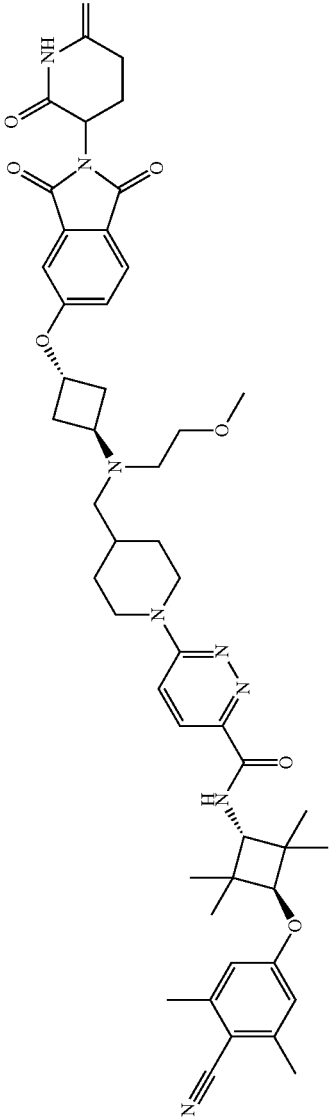 | N-((1r,3r)-3-(4-cyano-3,5-dimethylphenoxy)-2,2,4,4-tetramethylcyclobutyl)-6-(4-(((1r,3r)-3-((2-(2,6-dioxopiperidin-3-yl)-1,3-dioxoisoindolin-5-yl)oxy)cyclobutyl)(2-methoxyethyl)amino)methyl)piperidin-1-yl)pyridazine-3-carboxamide | 7 |

TABLE 1C-continued

Exemplary heterobifunctional compounds of the present disclosure.

| Comp No. | Structure | Name | Scheme |
|---|---|---|---|
| 122 | 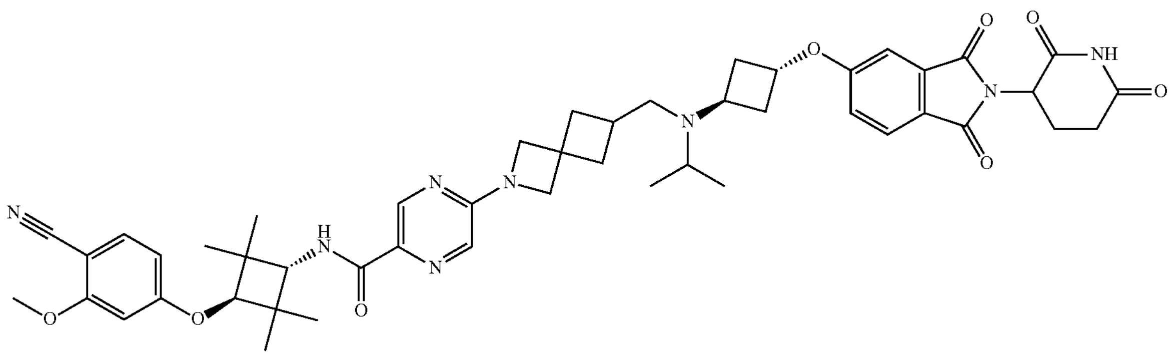 [SMILES: COc1cc(O[C@H]2C(C)(C)[C@H](NC(=O)c3cnc(N4CC5(CC(CN(C(C)C)[C@H]6C[C@H](Oc7ccc8c(c7)C(=O)N(C7CCC(=O)NC7=O)C8=O)C6)C5)C4)cn3)C2(C)C)ccc1C#N] | N-((1r,3r)-3-(4-cyano-3-methoxyphenoxy)-2,2,4,4-tetramethylcyclobutyl)-5-(6-((((1r,3r)-3-((2-(2,6-dioxopiperidin-3-yl)-1,3-dioxoisoindolin-5-yl)oxy)cyclobutyl)(isopropyl)amino)methyl)-2-azaspiro[3.3]heptan-2-yl)pyrazine-2-carboxamide | 23 |
| 123 | 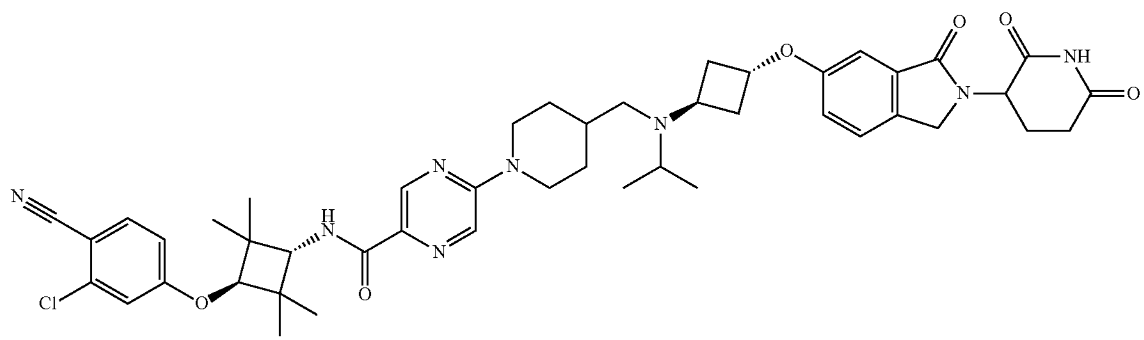 [SMILES: CC(C)N(CC1CCN(c2cnc(C(=O)N[C@H]3C(C)(C)[C@H](Oc4ccc(C#N)c(Cl)c4)C3(C)C)cn2)CC1)[C@H]1C[C@H](Oc2ccc3c(c2)C(=O)N(C2CCC(=O)NC2=O)C3)C1] | N-((1r,3r)-3-(3-chloro-4-cyanophenoxy)-2,2,4,4-tetramethylcyclobutyl)-5-(4-((((1r,3r)-3-((2-(2,6-dioxopiperidin-3-yl)-3-oxoisoindolin-5-yl)oxy)cyclobutyl)(isopropyl)amino)methyl)piperidin-1-yl)pyrazine-2-carboxamide | 3 |

TABLE 1C-continued

Exemplary heterobifunctional compounds of the present disclosure.

| Comp No. | Structure | Name | Scheme |
|---|---|---|---|
| 124 | 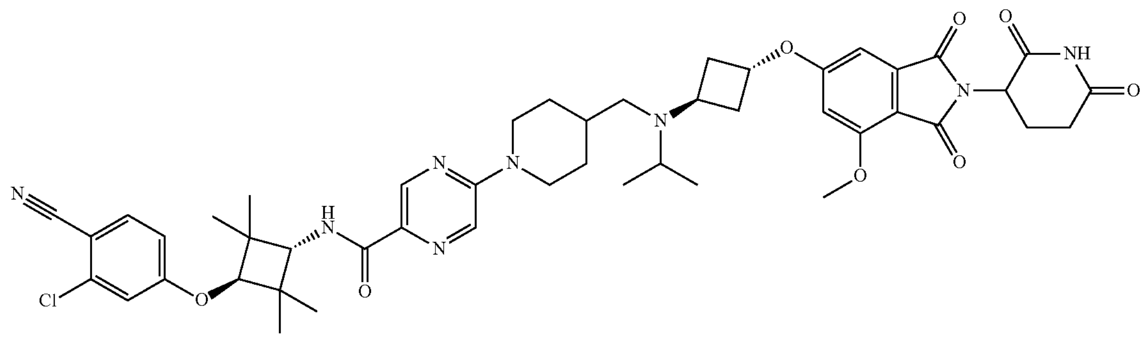 [SMILES: COc1cc(O[C@H]2C[C@H](N(CC3CCN(c4cnc(C(=O)N[C@H]5C(C)(C)[C@H](Oc6ccc(C#N)c(Cl)c6)C5(C)C)cn4)CC3)C(C)C)C2)cc2c1C(=O)N(C1CCC(=O)NC1=O)C2=O] | N-((1r,3r)-3-(3-chloro-4-cyanophenoxy)-2,2,4,4-tetramethylcyclobutyl)-5-(4-(((1r,3r)-3-((2-(2,6-dioxopiperidin-3-yl)-7-methoxy-1,3-dioxoisoindolin-5-yl)oxy)cyclobutyl)(isopropyl)amino)methyl)piperidin-1-yl)pyrazine-2-carboxamide | 1 and 7 |
| 125 | 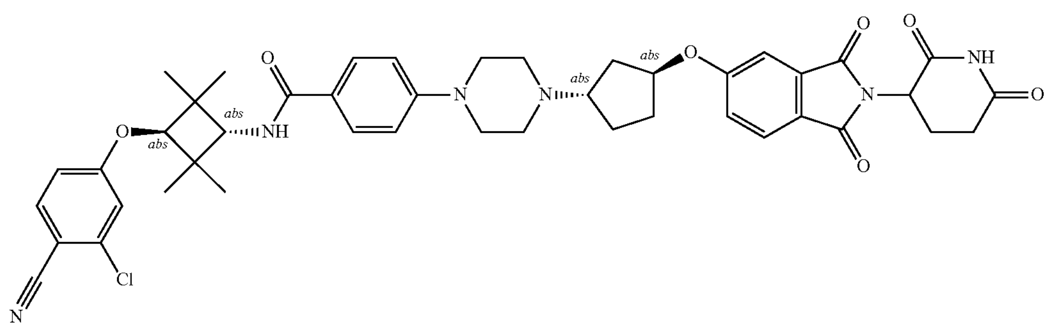 [SMILES: CC1(C)[C@H](NC(=O)c2ccc(N3CCN([C@H]4CC[C@H](Oc5ccc6c(c5)C(=O)N(C5CCC(=O)NC5=O)C6=O)C4)CC3)cc2)C(C)(C)[C@H]1Oc1ccc(C#N)c(Cl)c1] | N-((1r,3S)-3-(3-chloro-4-cyanophenoxy)-2,2,4,4-tetramethylcyclobutyl)-4-(4-((1S,3S)-3-((2-(2,6-dioxopiperidin-3-yl)-1,3-dioxoisoindolin-5-yl)oxy)cyclopentyl)piperazin-1-yl)benzamide | 30 |

TABLE 1C-continued

Exemplary heterobifunctional compounds of the present disclosure.

| Comp. No. | Structure | Name | Scheme |
|---|---|---|---|
| 126 | 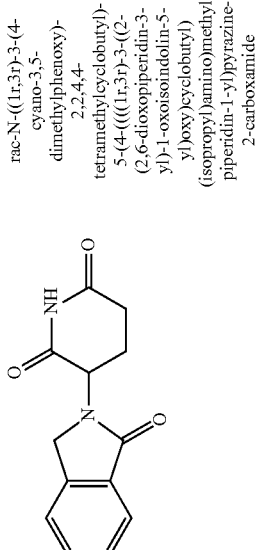 | rac-N-((1r,3r)-3-(4-cyano-3,5-dimethylphenoxy)-2,2,4,4-tetramethylcyclobutyl)-5-(4-((((1r,3r)-3-((2,6-dioxopiperidin-3-yl)-1-oxoisoindolin-5-yl)oxy)cyclobutyl)(isopropyl)amino)methyl)piperidin-1-yl)pyrazine-2-carboxamide | 21 and 7 |
| 127 | 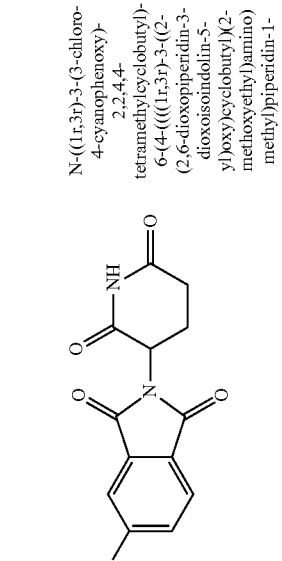 | N-((1r,3r)-3-(3-chloro-4-cyanophenoxy)-2,2,4,4-tetramethylcyclobutyl)-6-(4-((((1r,3r)-3-((2,6-dioxopiperidin-3-yl)dioxoisoindolin-5-yl)oxy)cyclobutyl)(2-methoxyethyl)amino)methyl)piperidin-1-yl)pyridazine-3-carboxamide | 7 |

TABLE 1C-continued

Exemplary heterobifunctional compounds of the present disclosure.

| Comp No. | Structure | Name | Scheme |
|---|---|---|---|
| 128 | 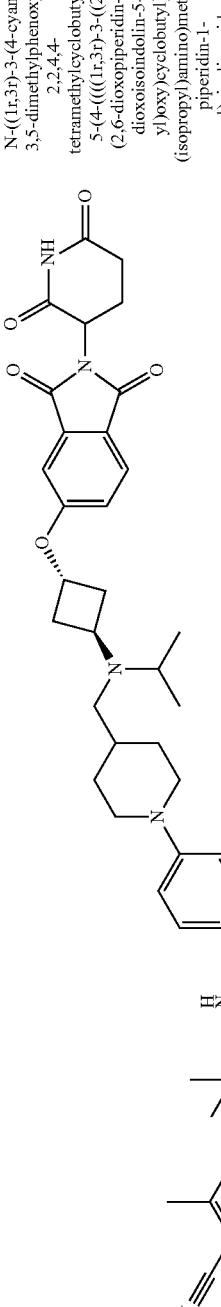 | N-((1r,3r)-3-(4-cyano-3,5-dimethylphenoxy)-2,2,4,4-tetramethylcyclobutyl)-5-(4-(((1r,3r)-3-((2-(2,6-dioxopiperidin-3-yl)-1,3-dioxoisoindolin-5-yl)oxy)cyclobutyl)(isopropyl)amino)methyl)piperidin-1-yl)picolinamide | 7 |
| 129 | 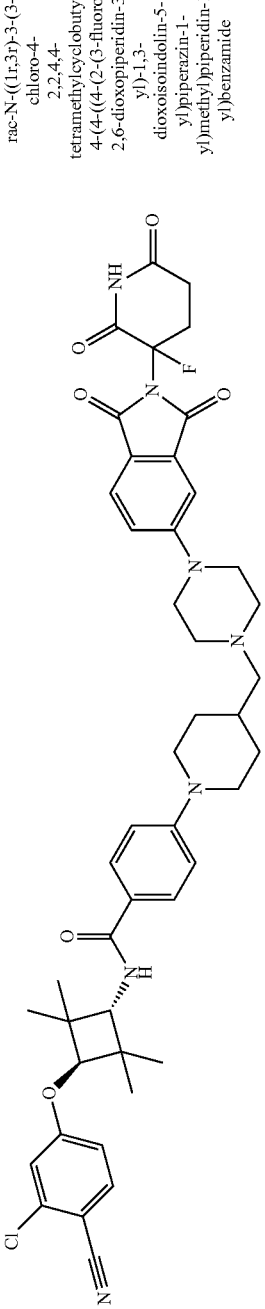 | rac-N-((1r,3r)-3-(3-chloro-4-2,2,4,4-tetramethylcyclobutyl)-4-(4-((4-(2-(3-fluoro-2,6-dioxopiperidin-3-yl)-1,3-dioxoisoindolin-5-yl)piperazin-1-yl)methyl)piperidin-1-yl)benzamide | 5 and 25, and custom synthesis provided |

TABLE 1C-continued

Exemplary heterobifunctional compounds of the present disclosure.

| Comp No. | Structure | Name | Scheme |
|---|---|---|---|
| 130 | 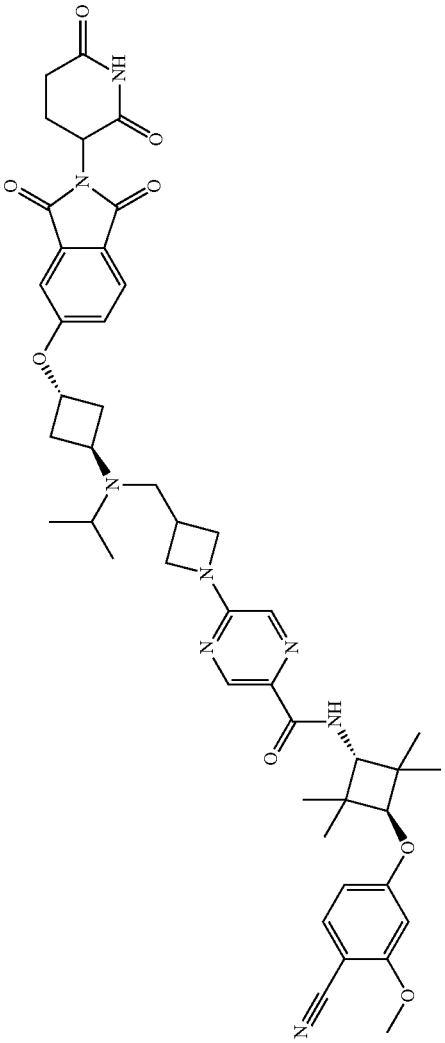 | N-((1r,3r)-3-(4-cyano-3-methoxyphenoxy)-2,2,4,4-tetramethylcyclobutyl)-5-(3-(((1r,3r)-3-((2-(2,6-dioxopiperidin-3-yl)-1,3-dioxoisoindolin-5-yl)oxy)cyclobutyl)(isopropyl)amino)methyl)azetidin-1-yl)pyrazine-2-carboxamide | 7 |
| 131 | 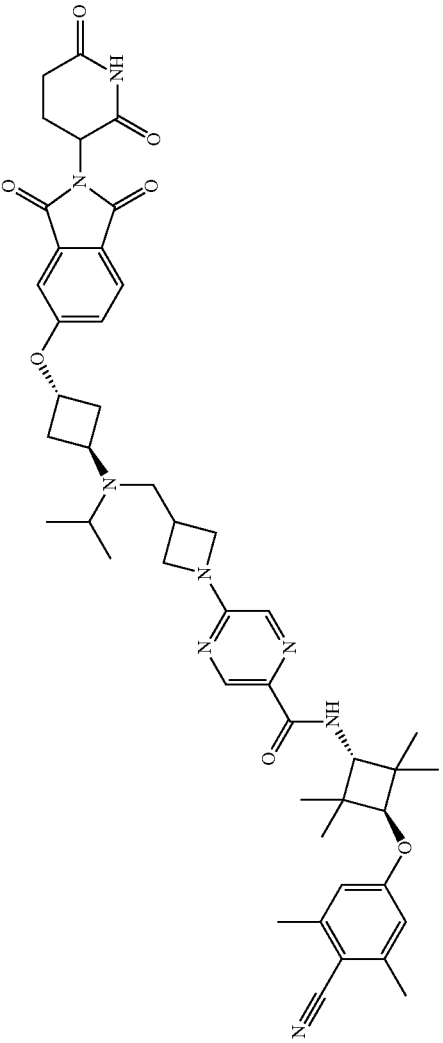 | N-((1r,3r)-3-(4-cyano-3,5-dimethylphenoxy)-2,2,4,4-tetramethylcyclobutyl)-5-(3-(((1r,3r)-3-((2-(2,6-dioxopiperidin-3-yl)-1,3-dioxoisoindolin-5-yl)oxy)cyclobutyl)(isopropyl)amino)methyl)azetidin-1-yl)pyrazine-2-carboxamide | 7 |

TABLE 1C-continued

Exemplary heterobifunctional compounds of the present disclosure.

| Comp No. | Structure | Name | Scheme |
|---|---|---|---|
| 132 | 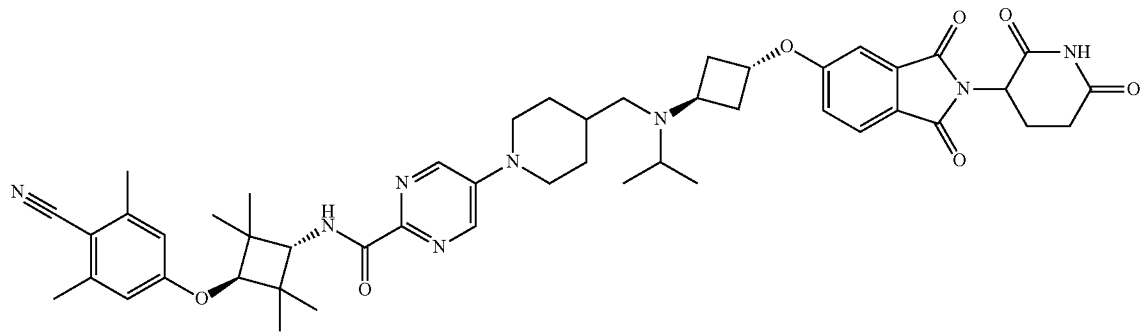 [SMILES: Cc1cc(O[C@H]2C(C)(C)[C@H](NC(=O)c3ncc(N4CCC(CN(C(C)C)[C@H]5C[C@H](Oc6ccc7c(c6)C(=O)N(C6CCC(=O)NC6=O)C7=O)C5)CC4)cn3)C2(C)C)cc(C)c1C#N] | N-((1r,3r)-3-(4-cyano-3,5-dimethylphenoxy)-2,2,4,4-tetramethylcyclobutyl)-5-(4-(((1r,3r)-3-((2-(2,6-dioxopiperidin-3-yl)-1,3-dioxoisoindolin-5-yl)oxy)cyclobutyl)(isopropyl)amino)methyl)piperidin-1-yl)pyrimidine-2-carboxamide | 7 |
| 133 | 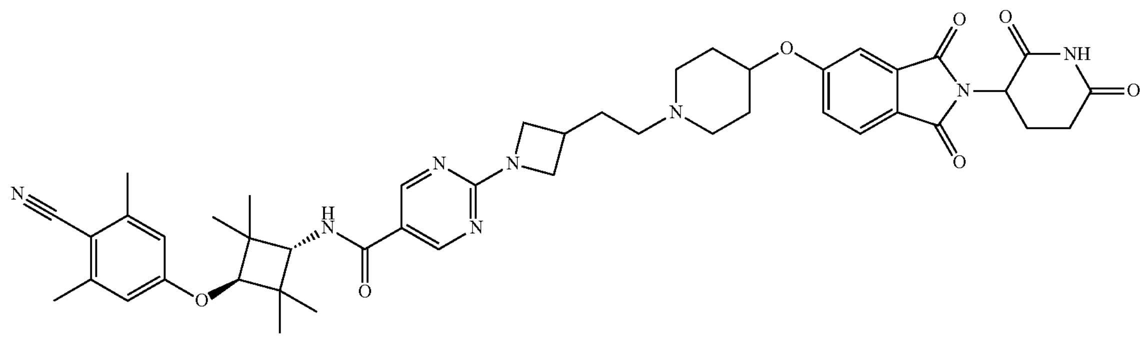 [SMILES: Cc1cc(O[C@H]2C(C)(C)[C@H](NC(=O)c3cnc(N4CC(CCN5CCC(Oc6ccc7c(c6)C(=O)N(C6CCC(=O)NC6=O)C7=O)CC5)C4)nc3)C2(C)C)cc(C)c1C#N] | N-((1r,3r)-3-(4-cyano-3,5-dimethylphenoxy)-2,2,4,4-tetramethylcyclobutyl)-2-(3-(2-(4-(2-(2,6-dioxopiperidin-3-yl)-1,3-dioxoisoindolin-5-yl)oxy)piperidin-1-yl)ethyl)azetidin-1-yl)pyrimidine-5-carboxamide | 22 |

TABLE 1C-continued

Exemplary heterobifunctional compounds of the present disclosure.

| Comp No. | Structure | Name | Scheme |
|---|---|---|---|
| 134 | 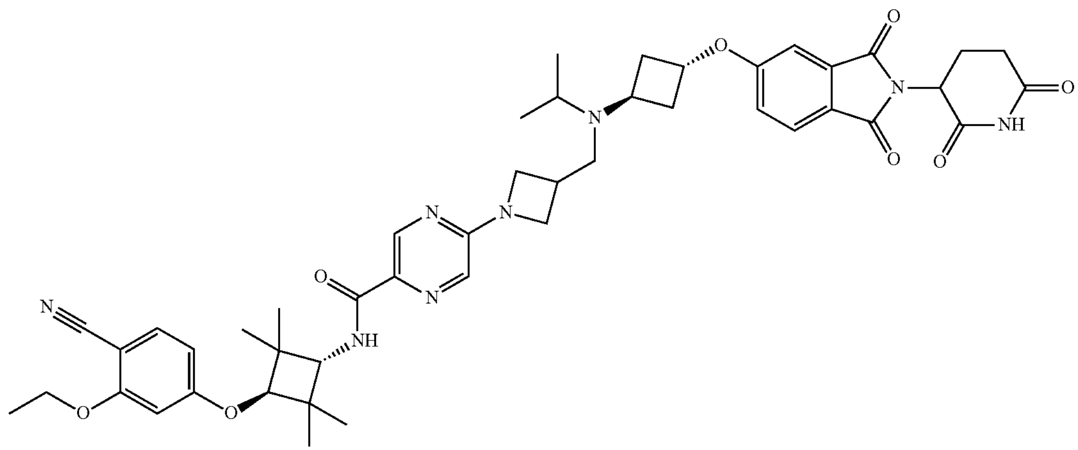 [SMILES: CCOc1cc(O[C@H]2C(C)(C)[C@H](NC(=O)c3cnc(N4CC(CN(C(C)C)[C@H]5C[C@H](Oc6ccc7c(c6)C(=O)N(C6CCC(=O)NC6=O)C7=O)C5)C4)cn3)C2(C)C)ccc1C#N] | N-((1r,3r)-3-(4-cyano-3-ethoxyphenoxy)-2,2,4,4-tetramethylcyclobutyl)-5-(3-(((1r,3r)-3-((2-(2,6-dioxopiperidin-3-yl)-1,3-dioxoisoindolin-5-yl)oxy)cyclobutyl)(isopropyl)amino)methyl)azetidin-1-yl)pyrazine-2-carboxamide | 7 |
| 135 | 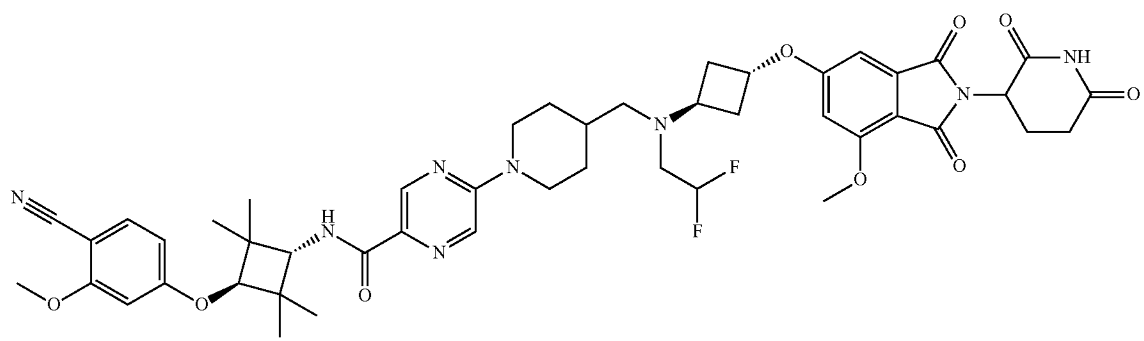 [SMILES: COc1cc(O[C@H]2C(C)(C)[C@H](NC(=O)c3cnc(N4CCC(CN(CC(F)F)[C@H]5C[C@H](Oc6cc(OC)c7c(c6)C(=O)N(C6CCC(=O)NC6=O)C7=O)C5)CC4)cn3)C2(C)C)ccc1C#N] | N-((1r,3r)-3-(4-cyano-3-methoxyphenoxy)-2,2,4,4-tetramethylcyclobutyl)-5-(4-(((2,2-difluoroethyl)((1r,3r)-3-((2-(2,6-dioxopiperidin-3-yl)-7-methoxy-1,3-dioxoisoindolin-5-yl)oxy)cyclobutyl)amino)methyl)piperidin-1-yl)pyrazine-2-carboxamide | 7 and 1 |

TABLE 1C-continued

Exemplary heterobifunctional compounds of the present disclosure.

| Comp No. | Structure | Name | Scheme |
|---|---|---|---|
| 136 | 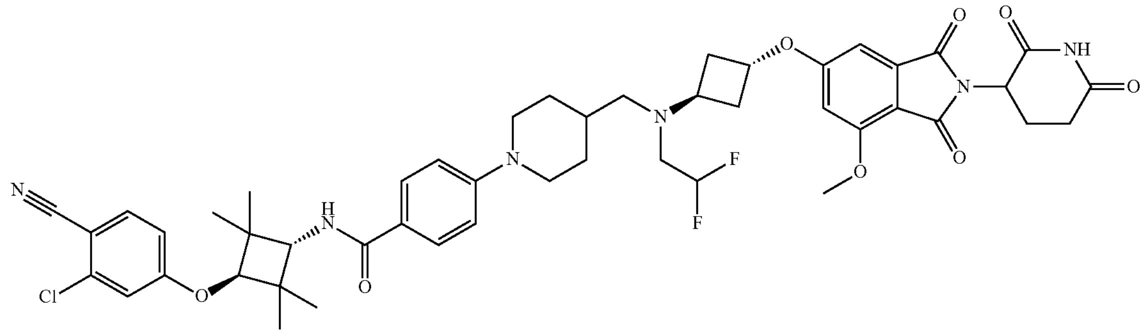 [SMILES: COc1cc(O[C@H]2C[C@H](N(CC(F)F)CC3CCN(c4ccc(C(=O)N[C@H]5C(C)(C)[C@H](Oc6ccc(C#N)c(Cl)c6)C5(C)C)cc4)CC3)C2)cc2c1C(=O)N(C1CCC(=O)NC1=O)C2=O] | N-((1r,3r)-3-(3-chloro-4-cyanophenoxy)-2,2,4,4-tetramethylcyclobutyl)-4-(4-(((1r,3r)-3-(2-(2,6-dioxopiperidin-3-yl)-7-methoxy-1,3-dioxoisoindolin-5-yl)oxy)cyclobutyl)amino)methyl)piperidin-1-yl)benzamide | 7 and 1 |
| 137 | 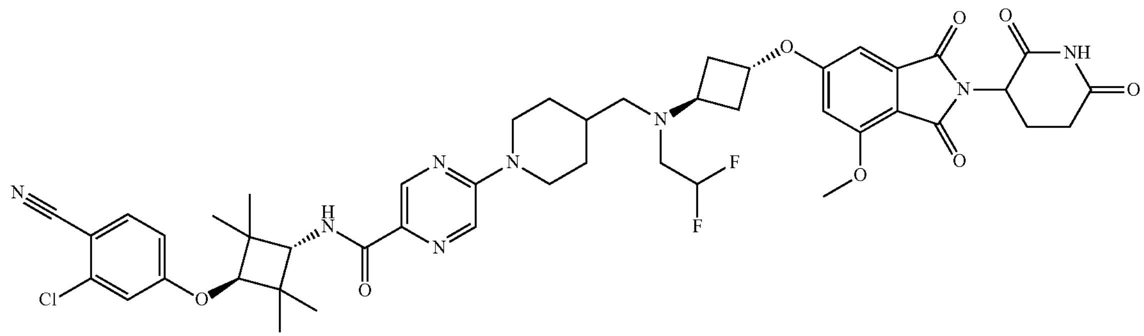 [SMILES: COc1cc(O[C@H]2C[C@H](N(CC(F)F)CC3CCN(c4cnc(C(=O)N[C@H]5C(C)(C)[C@H](Oc6ccc(C#N)c(Cl)c6)C5(C)C)cn4)CC3)C2)cc2c1C(=O)N(C1CCC(=O)NC1=O)C2=O] | N-((1r,3r)-3-(3-chloro-4-cyanophenoxy)-2,2,4,4-tetramethylcyclobutyl)-5-(4-(((2,2-difluoroethyl)((1r,3r)-3-(2-(2,6-dioxopiperidin-3-yl)-7-methoxy-1,3-dioxoisoindolin-5-yl)oxy)cyclobutyl)amino)methyl)piperidin-1-yl)pyrazine-2-carboxamide | 7 and 1 |
| 138 | 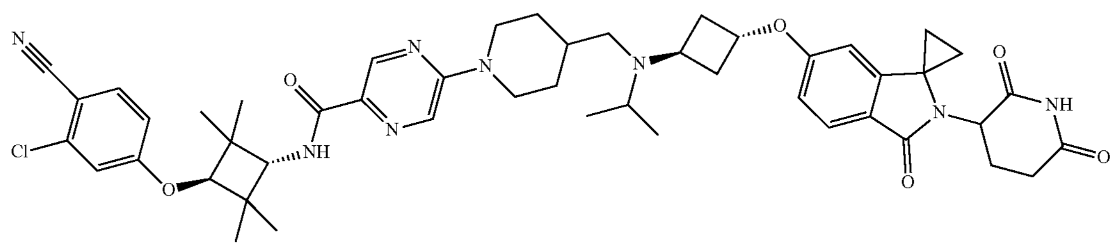 [SMILES: CC(C)N(CC1CCN(c2cnc(C(=O)N[C@H]3C(C)(C)[C@H](Oc4ccc(C#N)c(Cl)c4)C3(C)C)cn2)CC1)[C@H]1C[C@H](Oc2ccc3c(c2)C2(CC2)N(C2CCC(=O)NC2=O)C3=O)C1] | N-((1r,3r)-3-(3-chloro-4-cyanophenoxy)-2,2,4,4-tetramethylcyclobutyl)-5-(4-((((1r,3r)-3-((2'-(2,6-dioxopiperidin-3-oxospiro[cyclopropane-1,1'-isoindolin]-6-yl)oxy)cyclobutyl)(isopropyl)amino)methyl)piperidin-1-yl)pyrazine-2-carboxamide | 14 |

TABLE 1C-continued

Exemplary heterobifunctional compounds of the present disclosure.

| Comp. No. | Structure | Name | Scheme |
|---|---|---|---|
| 139 | 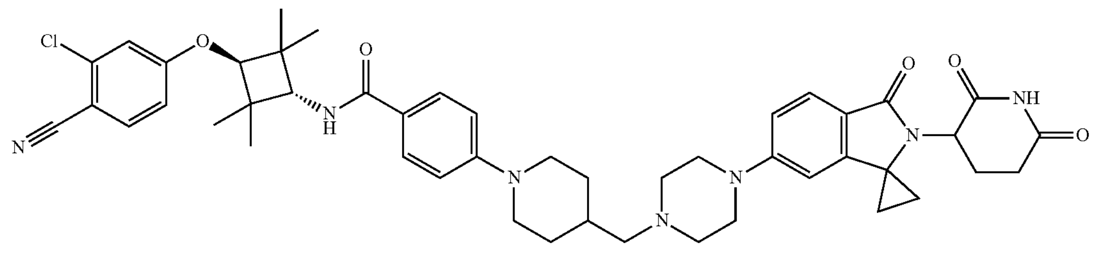 [SMILES: CC1(C)[C@H](NC(=O)c2ccc(N3CCC(CN4CCN(c5ccc6c(c5)C5(CC5)N(C5CCC(=O)NC5=O)C6=O)CC4)CC3)cc2)C(C)(C)[C@H]1Oc1ccc(C#N)c(Cl)c1] | N-((1r,3r)-3-(3-chloro-4-cyanophenoxy)-2,2,4,4-tetramethylcyclobutyl)-4-(4-(4-(2'-(2,6-dioxopiperidin-3-yl)-3'-oxospiro[cyclopropane-1,1'-isoindolin]-6'-yl)piperazin-1-yl)methyl)piperidin-1-yl)benzamide | 31 and 25 |
| 140 | 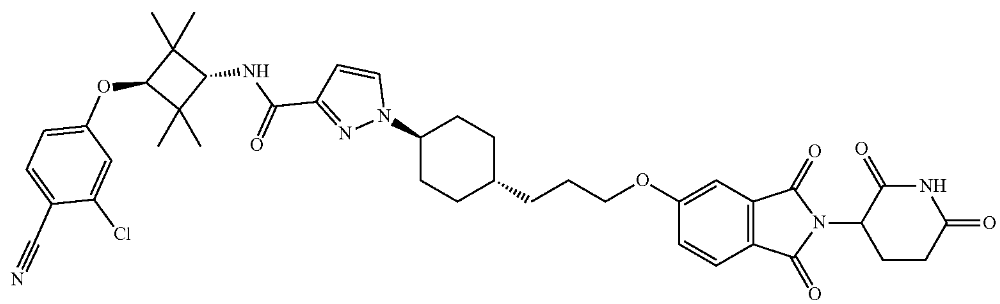 [SMILES: CC1(C)[C@H](NC(=O)c2ccn([C@H]3CC[C@H](CCCOc4ccc5c(c4)C(=O)N(C4CCC(=O)NC4=O)C5=O)CC3)n2)C(C)(C)[C@H]1Oc1ccc(C#N)c(Cl)c1] | N-((1r,3R)-3-(3-chloro-4-cyanophenoxy)-2,2,4,4-tetramethylcyclobutyl)-1-((1r,4R)-4-(3-((2-(2,6-dioxopiperidin-3-yl)-1,3-dioxoisoindolin-5-yl)oxy)propyl)cyclohexyl)-1H-pyrazole-3-carboxamide | 17, and custom synthesis provided |
| 141 | 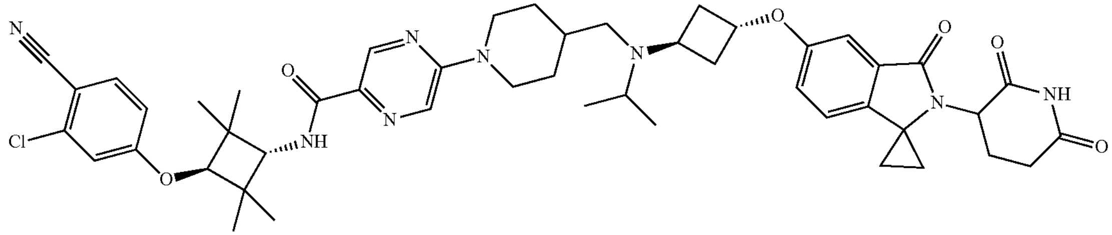 [SMILES: CC(C)N(CC1CCN(c2cnc(C(=O)N[C@H]3C(C)(C)[C@H](Oc4ccc(C#N)c(Cl)c4)C3(C)C)cn2)CC1)[C@H]1C[C@H](Oc2ccc3c(c2)C(=O)N(C2CCC(=O)NC2=O)C32CC2)C1] | N-((1r,3r)-3-(3-chloro-4-cyanophenoxy)-2,2,4,4-tetramethylcyclobutyl)-5-(4-(((1r,3r)-3-((2'-(2,6-dioxopiperidin-3-yl)-3'-oxospiro[cyclopropane-1,1'-isoindolin]-5'-yl)oxy)cyclobutyl)(isopropyl)amino)methyl)piperidin-1-yl)pyrazine-2-carboxamide | 18 |

TABLE 1C-continued

Exemplary heterobifunctional compounds of the present disclosure.

| Comp No. | Structure | Name | Scheme |
|---|---|---|---|
| 142 | 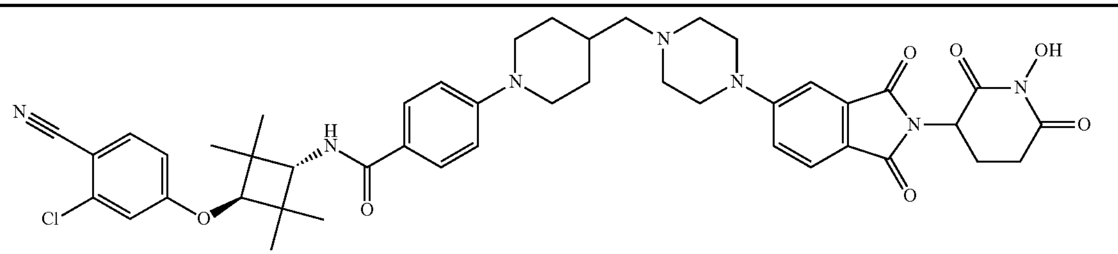 | N-((1r,3r)-3-(3-chloro-4-cyanophenoxy)-2,2,4,4-tetramethylcyclobutyl)-4-(4-((4-(2-(1-hydroxy-2,6-dioxopiperidin-3-yl)-1,3-dioxoisoindolin-5-yl)piperazin-1-yl)methyl)piperidin-1-yl)benzamide | 32 and 33 |
| 143 | 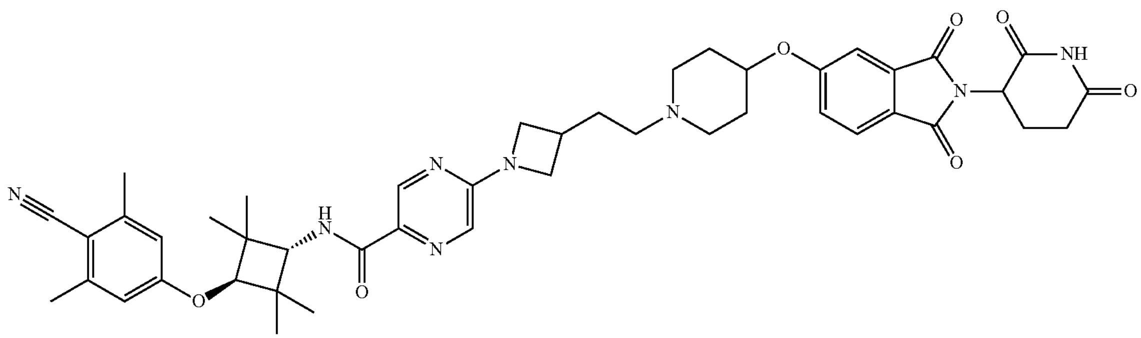 | N-((1r,3r)-3-(4-cyano-3,5-dimethylphenoxy)-2,2,4,4-tetramethylcyclobutyl)-5-(3-(2-(4-(2-(2,6-dioxopiperidin-3-yl)-1,3-dioxoisoindolin-5-yl)oxy)piperidin-1-yl)ethyl)azetidin-1-yl)pyrazine-2-carboxamide | 22 |

TABLE 1C-continued

Exemplary heterobifunctional compounds of the present disclosure.

| Comp No. | Structure | Name | Scheme |
|---|---|---|---|
| 144 | 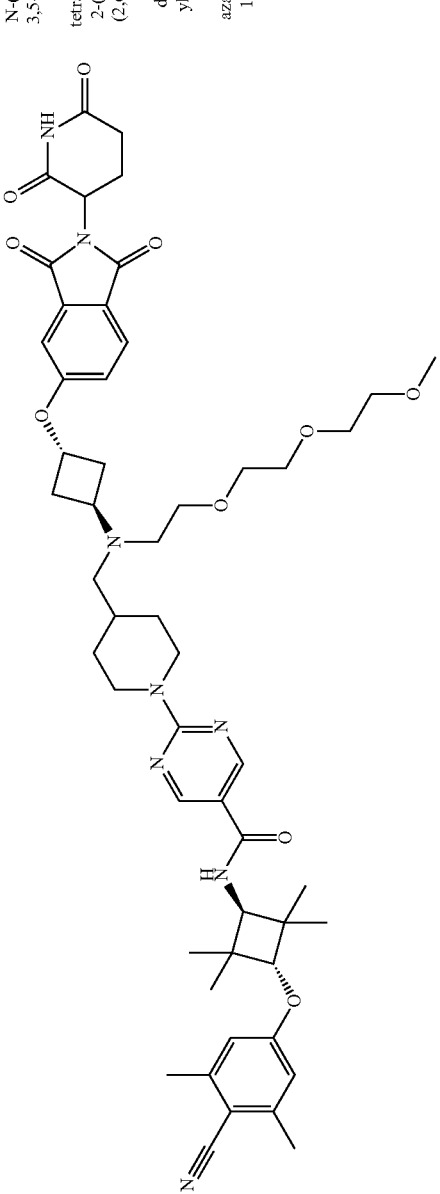 | N-((1r,3r)-3-(4-cyano-3,5-dimethylphenoxy)-2,2,4,4-tetramethylcyclobutyl)-2-(4-(2-((1r,3r)-3-((2-(2,6-dioxopiperidin-3-yl)-1,3-dioxoisoindolin-5-yl)oxy)cyclobutyl)-5,8,11-trioxa-2-azadodecyl)piperidin-1-yl)pyrimidine-5-carboxamide | 7 |
| 145 | 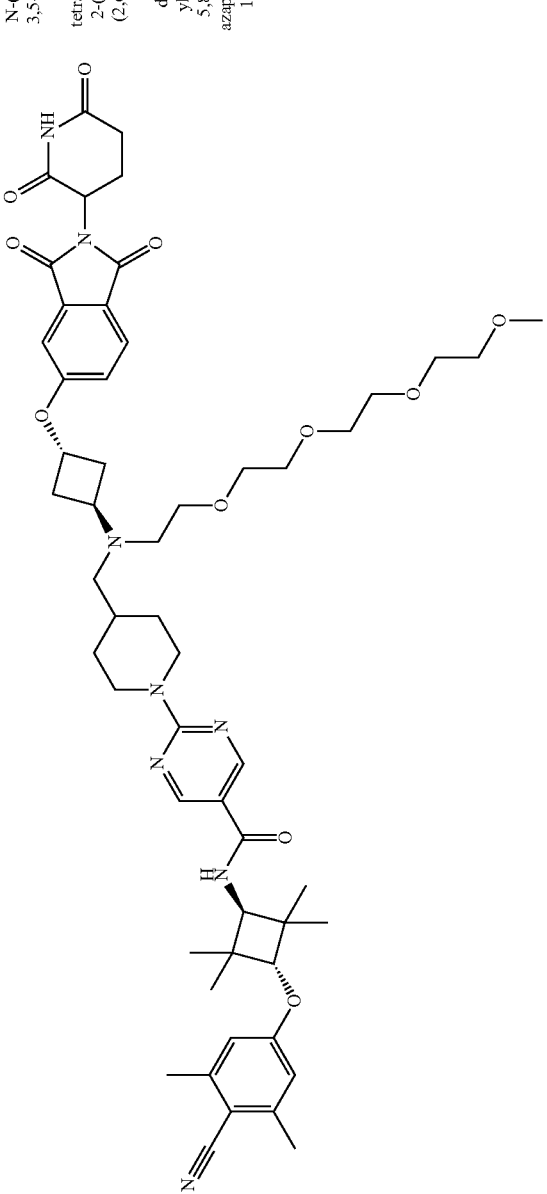 | N-((1r,3r)-3-(4-cyano-3,5-dimethylphenoxy)-2,2,4,4-tetramethylcyclobutyl)-2-(4-(2-((1r,3r)-3-((2-(2,6-dioxopiperidin-3-yl)-1,3-dioxoisoindolin-5-yl)oxy)cyclobutyl)-5,8,11,14-tetraoxa-2-azapentadecyl)piperidin-1-yl)pyrimidine-5-carboxamide | 7 |

TABLE 1C-continued

Exemplary heterobifunctional compounds of the present disclosure.

| Comp No. | Structure | Name | Scheme |
|---|---|---|---|
| 146 | 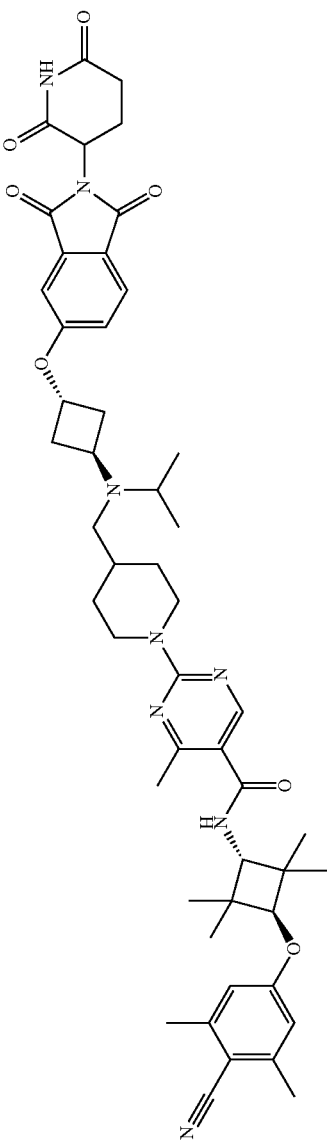 | rac-N-((1r,3r)-3-(4-cyano-3,5-dimethylphenoxy)-2,2,4,4-tetramethylcyclobutyl)-2-(4-(((1r,3r)-3-((2-(2,6-dioxopiperidin-3-yl)-1,3-dioxoisoindolin-5-yl)oxy)cyclobutyl)(isopropyl)amino)methyl)piperidin-1-yl)-4-methylpyrimidine-5-carboxamide | 7 |
| 147 | 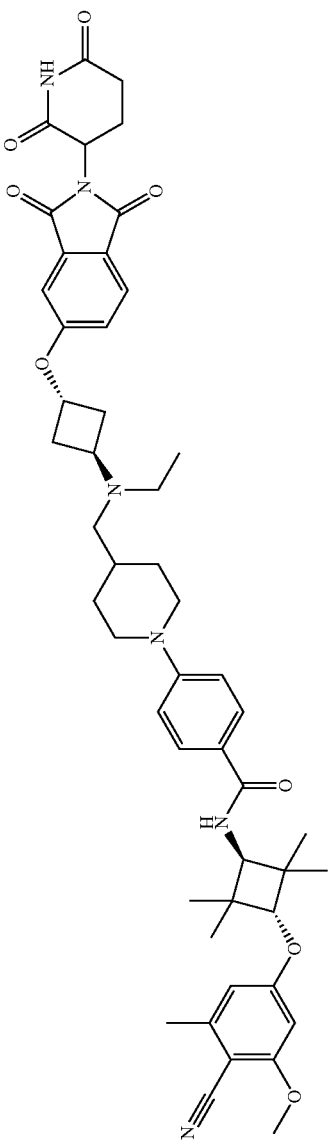 | N-((1r,3r)-3-(4-cyano-3-methoxyphenoxy)-2,2,4,4-tetramethylcyclobutyl)-4-(4-(((1r,3r)-3-((2-(2,6-dioxopiperidin-3-yl)-1,3-dioxoisoindolin-5-yl)oxy)cyclobutyl)(ethyl)amino)methyl)piperidin-1-yl)benzamide | 7 and custom synthesis provided |

TABLE 1C-continued

Exemplary heterobifunctional compounds of the present disclosure.

| Comp No. | Structure | Name | Scheme |
|---|---|---|---|
| 148 | 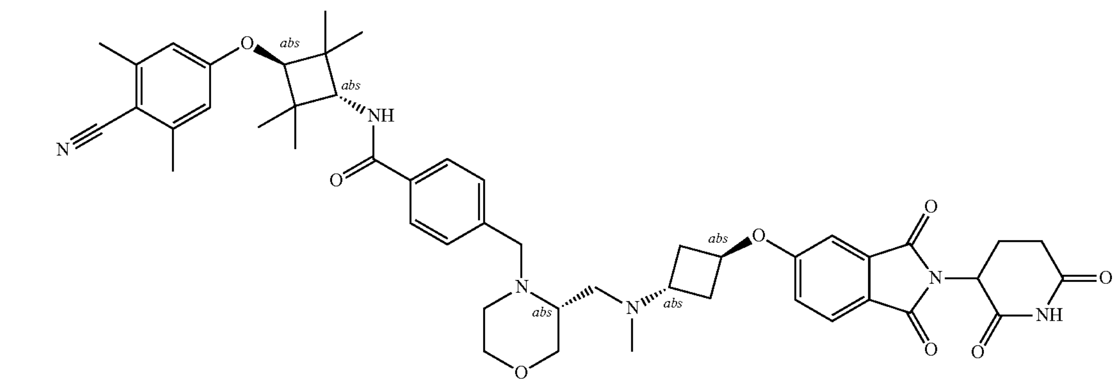 [SMILES: Cc1cc(O[C@H]2C(C)(C)[C@H](NC(=O)c3ccc(CN4CCOC[C@H]4CN(C)[C@H]4C[C@H](Oc5ccc6c(c5)C(=O)N(C5CCC(=O)NC5=O)C6=O)C4)cc3)C2(C)C)cc(C)c1C#N] | N-((1r,3R)-3-(4-cyano-3,5-dimethylphenoxy)-2,2,4,4-tetramethylcyclobutyl)-4-(((3R)-3-((((1r,3R)-3-(2-(2,6-dioxopiperidin-3-yl)-1,3-dioxoisoindolin-5-yl)oxy)cyclobutyl)(methyl)amino)methyl)morpholino)methyl)benzamide | 7 |
| 149 | 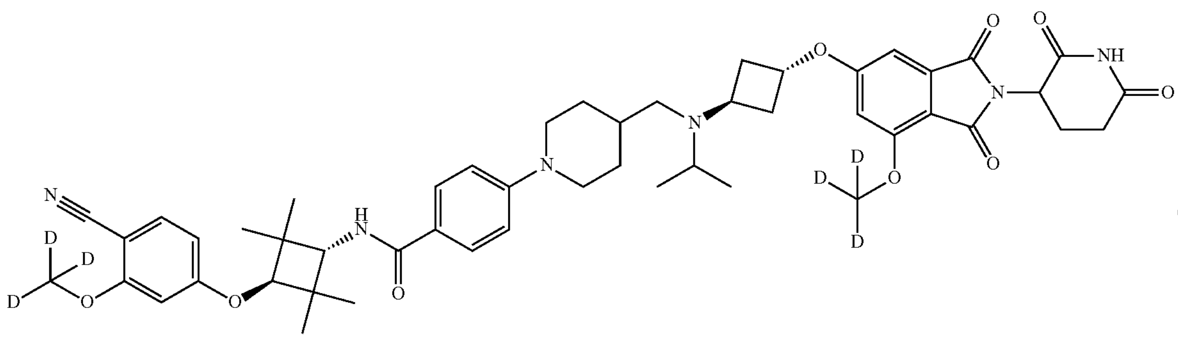 | rac-N-((1r,3r)-3-(4-cyano-3-(methoxy-d3)phenoxy)-2,2,4,4-tetramethylcyclobutyl)-4-(((1r,3r)-3-((2-(2,6-dioxopiperidin-3-yl)-7-(methoxy-d3)-1,3-dioxoisoindolin-5-yl)oxy)cyclobutyl)(isopropyl)amino)methyl)piperidin-1-yl)benzamide | 34 |
| 150 | 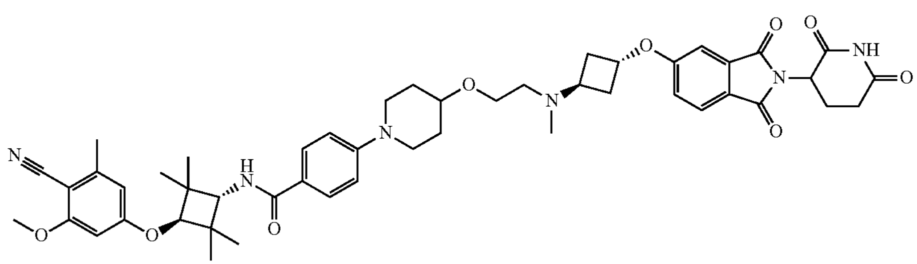 [SMILES: COc1cc(O[C@H]2C(C)(C)[C@H](NC(=O)c3ccc(N4CCC(OCCN(C)[C@H]5C[C@H](Oc6ccc7c(c6)C(=O)N(C6CCC(=O)NC6=O)C7=O)C5)CC4)cc3)C2(C)C)cc(C)c1C#N] | rac-N-((1r,3r)-3-(4-cyano-3,5-dimethylphenoxy)-2,2,4,4-tetramethylcyclobutyl)-4-(4-(2-(((1r,3r)-3-((2-(2,6-dioxopiperidin-3-yl)-1,3-dioxoisoindolin-5-yl)oxy)cyclobutyl)(methyl)amino)ethoxy)piperidin-1-yl)benzamide | 54 and 7 |

TABLE 1C-continued

Exemplary heterobifunctional compounds of the present disclosure.

| Comp. No. | Structure | Name | Scheme |
|---|---|---|---|
| 151 | 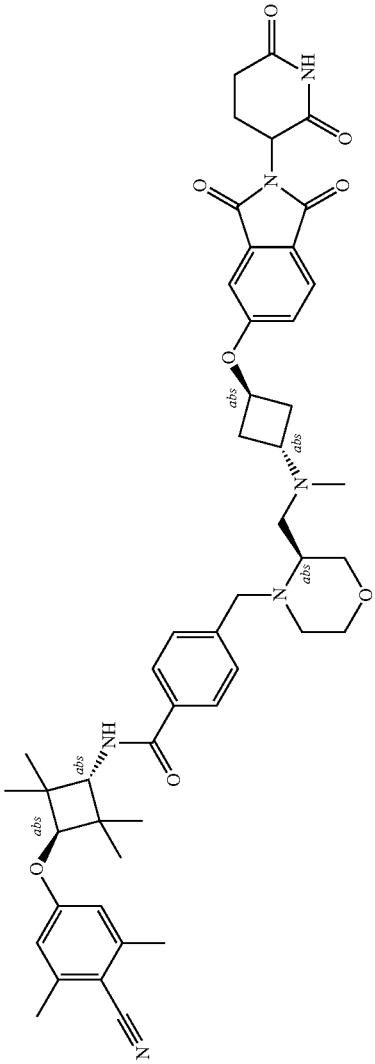 | N-((1r,3S)-3-(4-cyano-3,5-dimethylphenoxy)-2,2,4,4-tetramethylcyclobutyl)-4-(((3S)-3-((((1r,3S)-3-((2-(2,6-dioxopiperidin-3-yl)-1,3-dioxoisoindolin-5-yl)oxy)cyclobutyl)(methyl)amino)methyl)morpholino)methyl)benzamide | 7 |
| 152 | 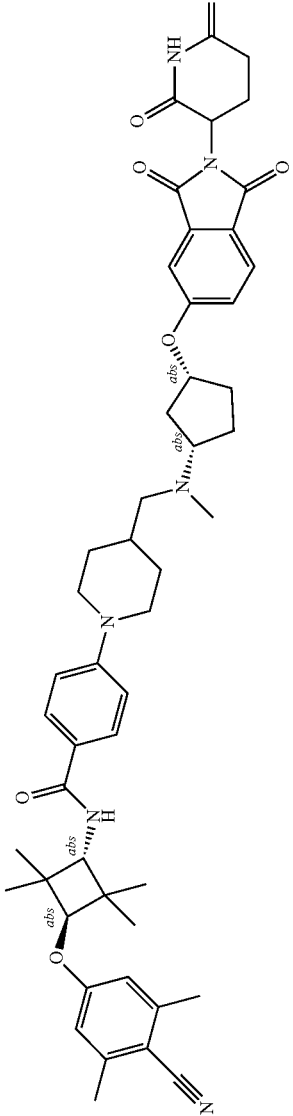 | N-((1r,3S)-3-(4-cyano-3,5-dimethylphenoxy)-2,2,4,4-tetramethylcyclobutyl)-4-(4-((((1S,3R)-3-((2-(2,6-dioxopiperidin-3-yl)-1,3-dioxoisoindolin-5-yl)oxy)cyclopentyl)(methyl)amino)methyl)piperidin-1-yl)benzamide | 7 |

TABLE 1C-continued

Exemplary heterobifunctional compounds of the present disclosure.

| Comp No. | Structure | Name | Scheme |
|---|---|---|---|
| 153 | 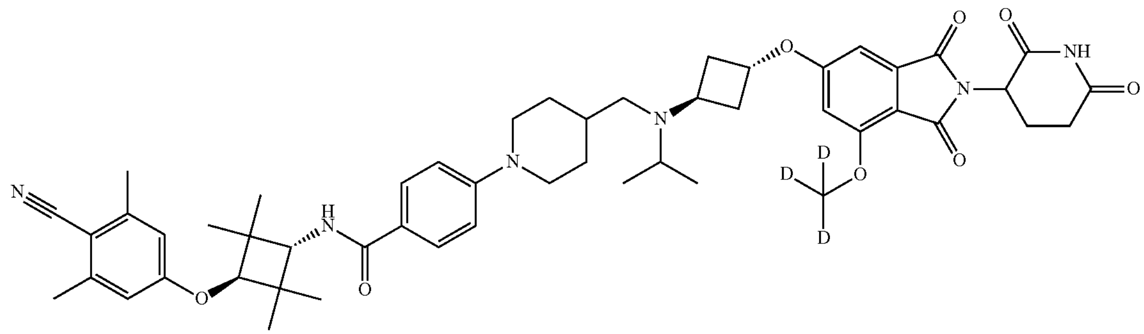 [SMILES: [2H]C([2H])([2H])Oc1cc(O[C@H]2C[C@H](N(CC3CCN(c4ccc(C(=O)N[C@H]5C(C)(C)[C@H](Oc6cc(C)c(C#N)c(C)c6)C5(C)C)cc4)CC3)C(C)C)C2)cc2c1C(=O)N(C1CCC(=O)NC1=O)C2=O] | rac-N-((1r,3r)-3-(4-cyano-3,5-dimethylphenoxy)-2,2,4,4-tetramethylcyclobutyl)-4-(4-(((1r,3r)-3-((2-(2,6-dioxopiperidin-3-yl)-7-(methoxy-d3)-1,3-dioxoisoindolin-5-yl)oxy)cyclobutyl)(isopropyl)amino)methyl)piperidin-1-yl)benzamide | 34 |
| 154 | 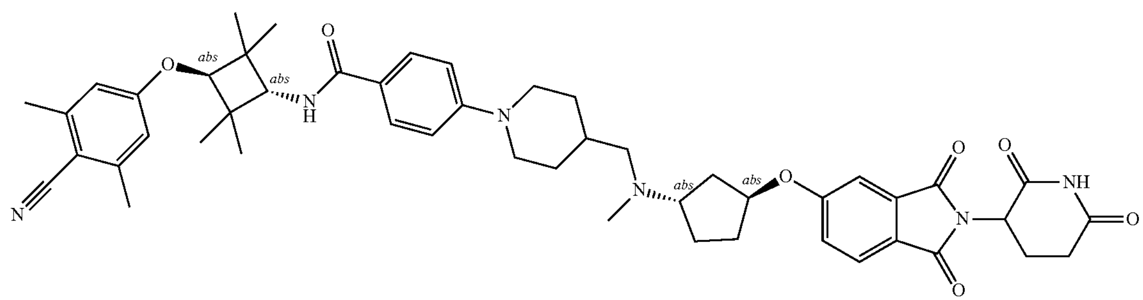 [SMILES: Cc1cc(O[C@H]2C(C)(C)[C@H](NC(=O)c3ccc(N4CCC(CN(C)[C@H]5CC[C@H](Oc6ccc7c(c6)C(=O)N(C6CCC(=O)NC6=O)C7=O)C5)CC4)cc3)C2(C)C)cc(C)c1C#N] | N-((1r,3S)-3-(4-cyano-3,5-dimethylphenoxy)-2,2,4,4-tetramethylcyclobutyl)-4-(4-(((1S,3S)-3-((2-(2,6-dioxopiperidin-3-yl)-1,3-dioxoisoindolin-5-yl)oxy)cyclopentyl)(methyl)amino)methyl)piperidin-1-yl)benzamide | 7 |

TABLE 1C-continued

Exemplary heterobifunctional compounds of the present disclosure.

| Comp No. | Structure | Name | Scheme |
|---|---|---|---|
| 155 | 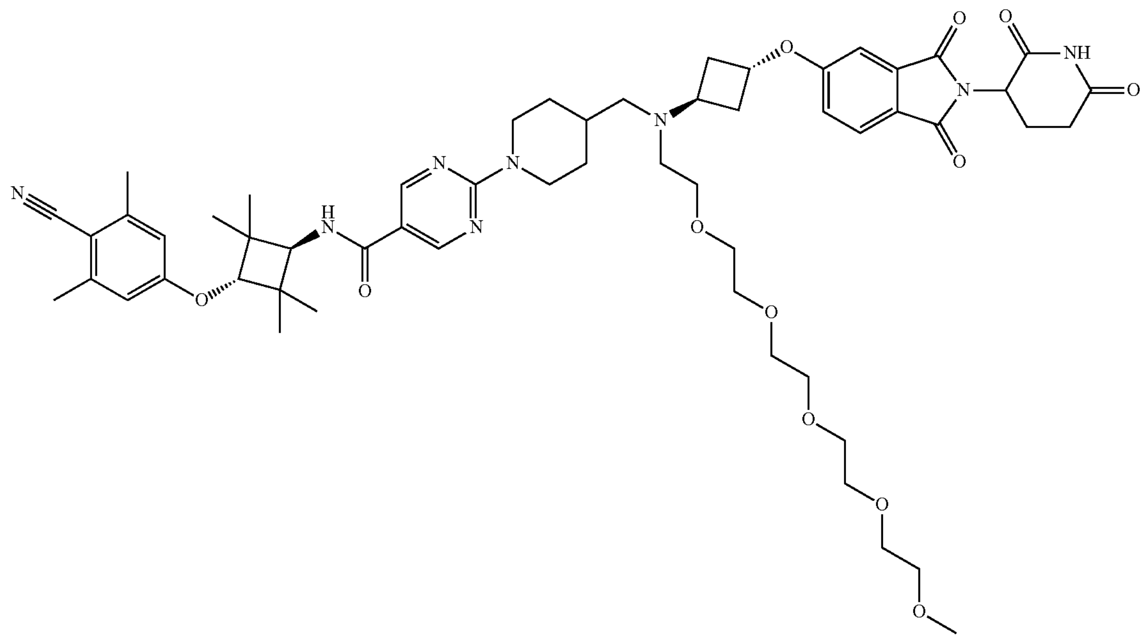 [SMILES: COCCOCCOCCOCCOCCN(CC1CCN(c2ncc(C(=O)N[C@H]3C(C)(C)[C@H](Oc4cc(C)c(C#N)c(C)c4)C3(C)C)cn2)CC1)[C@H]1C[C@H](Oc2ccc3c(c2)C(=O)N(C2CCC(=O)NC2=O)C3=O)C1] | N-((1r,3r)-3-(4-cyano-3,5-dimethylphenoxy)-2,2,4,4-tetramethylcyclobutyl)-2-(4-(2-((1r,3r)-3-((2-(2,6-dioxopiperidin-3-yl)-1,3-dioxoisoindolin-5-yl)oxy)cyclobutyl)-5,8,11,14,17-pentaoxa-2-azaoctadecyl)piperidin-1-yl)pyrimidine-5-carboxamide | 7 |
| 156 | 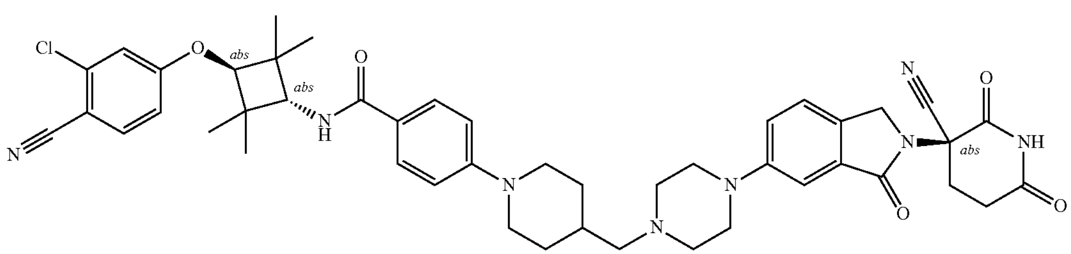 [SMILES: CC1(C)[C@H](NC(=O)c2ccc(N3CCC(CN4CCN(c5ccc6c(c5)C(=O)N([C@]5(C#N)CCC(=O)NC5=O)C6)CC4)CC3)cc2)C(C)(C)[C@H]1Oc1ccc(C#N)c(Cl)c1] | N-((1r,3r)-3-(3-chloro-4-cyanophenoxy)-2,2,4,4-tetramethylcyclobutyl)-4-(4-((2-(S)-3-cyano-2,6-dioxopiperidin-3-yl)-3-oxoisoindolin-5-yl)piperazin-1-yl)methyl)piperidin-1-yl)benzamide | 49 and 25 |

TABLE 1C-continued

Exemplary heterobifunctional compounds of the present disclosure.

| Comp No. | Structure | Name | Scheme |
|---|---|---|---|
| 157 | 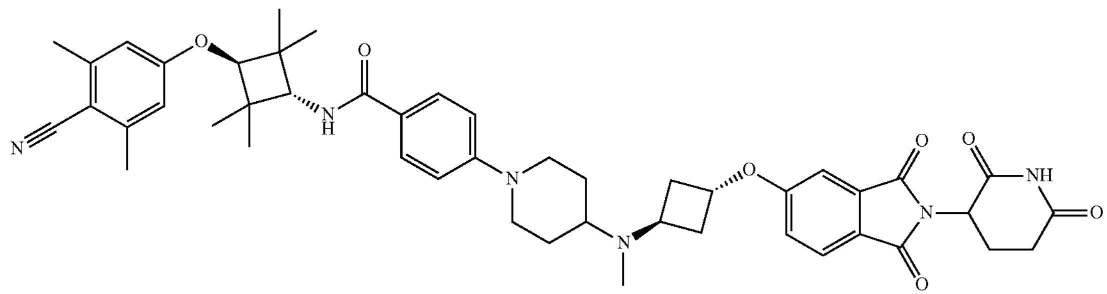 [SMILES: Cc1cc(O[C@H]2C(C)(C)[C@H](NC(=O)c3ccc(N4CCC(N(C)[C@H]5C[C@H](Oc6ccc7c(c6)C(=O)N(C6CCC(=O)NC6=O)C7=O)C5)CC4)cc3)C2(C)C)cc(C)c1C#N] | rac-N-((1r,3r)-3-(4-cyano-3,5-dimethylphenoxy)-2,2,4,4-tetramethylcyclobutyl)-4-(4-(((1r,3r)-3-((2-(2,6-dioxopiperidin-3-yl)-1,3-dioxoisoindolin-5-yl)oxy)cyclobutyl)(methyl)amino)piperidin-1-yl)benzamide | 7 |
| 158 | 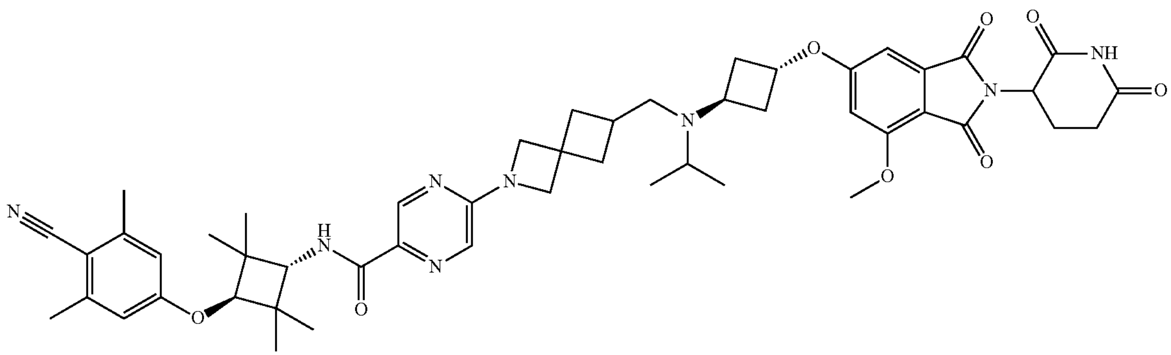 [SMILES: COc1cc(O[C@H]2C[C@H](N(CC3CC4(C3)CN(c3cnc(C(=O)N[C@H]5C(C)(C)[C@H](Oc6cc(C)c(C#N)c(C)c6)C5(C)C)cn3)C4)C(C)C)C2)cc2c1C(=O)N(C1CCC(=O)NC1=O)C2=O] | N-((1r,3r)-3-(4-cyano-3,5-dimethylphenoxy)-2,2,4,4-tetramethylcyclobutyl)-5-(6-(((1r,3r)-3-((2-(2,6-dioxopiperidin-3-yl)-7-methoxy-1,3-dioxoisoindolin-5-yl)oxy)cyclobutyl)(isopropyl)amino)methyl)-2-azaspiro[3.3]heptan-2-yl)pyrazine-2-carboxamide | 7 and 1 |
| 159 | 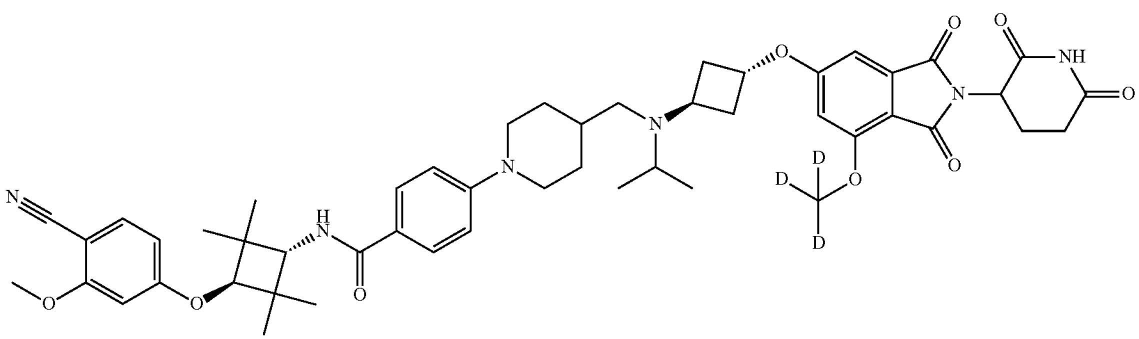 | rac-N-((1r,3r)-3-(4-cyano-3-methoxyphenoxy)-2,2,4,4-tetramethylcyclobutyl)-4-(4-(((1r,3r)-3-((2-(2,6-dioxopiperidin-3-yl)-7-(methoxy-d3)-1,3-dioxoisoindolin-5-yl)oxy)cyclobutyl)(isopropyl)amino)methyl)piperidin-1-yl)benzamide | 34 |

TABLE 1C-continued

Exemplary heterobifunctional compounds of the present disclosure.

| Comp No. | Structure | Name | Scheme |
|---|---|---|---|
| 160 | 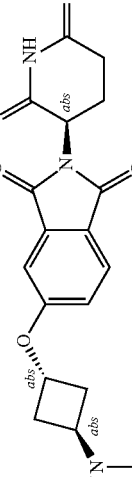 | N-((1r,3r)-3-(4-cyano-3,5-dimethylphenoxy)-2,2,4,4-tetramethylcyclobutyl)-4-(4-(((1R,3r)-3-((2-((R)-2,6-dioxopiperidin-3-yl)-1,3-dioxoisoindolin-5-yl)oxy)cyclobutyl)(isopropyl)amino)methyl)piperidin-1-yl)benzamide | 7 |
| 161 | 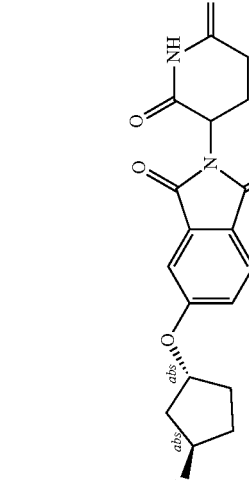 | N-((1r,3R)-3-(4-cyano-3,5-dimethylphenoxy)-2,2,4,4-tetramethylcyclobutyl)-4-(4-(((1R,3R)-3-((2-(2,6-dioxopiperidin-3-yl)-1,3-dioxoisoindolin-5-yl)oxy)cyclopentyl)(methyl)amino)methyl)piperidin-1-yl)benzamide | 7 |

TABLE 1C-continued

Exemplary heterobifunctional compounds of the present disclosure.

| Comp No. | Structure | Name | Scheme |
|---|---|---|---|
| 162 | 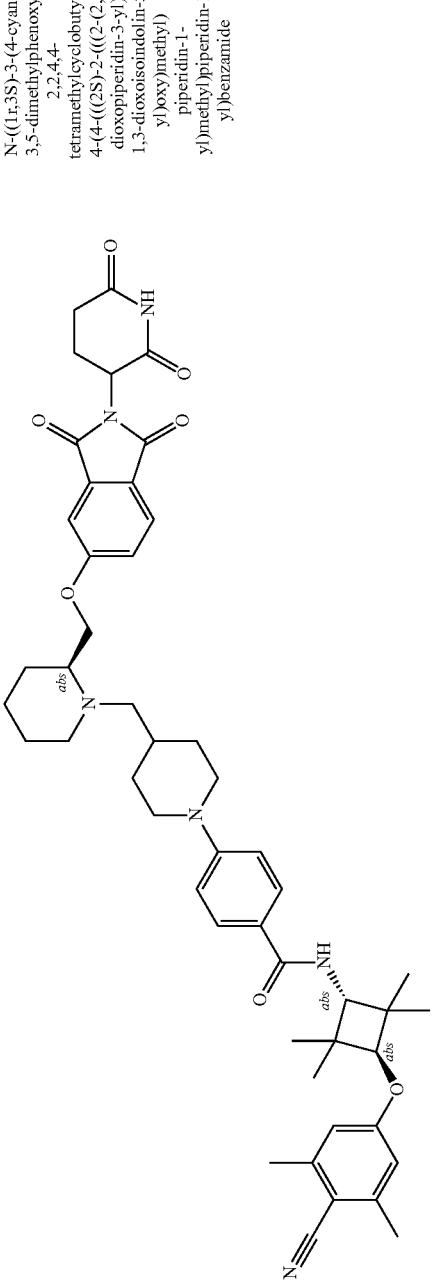 | N-((1s,3S)-3-(4-cyano-3,5-dimethylphenoxy)-2,2,4,4-tetramethylcyclobutyl)-4-(4-(((2S)-2-(((2-(2,6-dioxopiperidin-3-yl)-1,3-dioxoisoindolin-5-yl)oxy)methyl)piperidin-1-yl)methyl)piperidin-1-yl)benzamide | 36 and 7 |
| 163 | 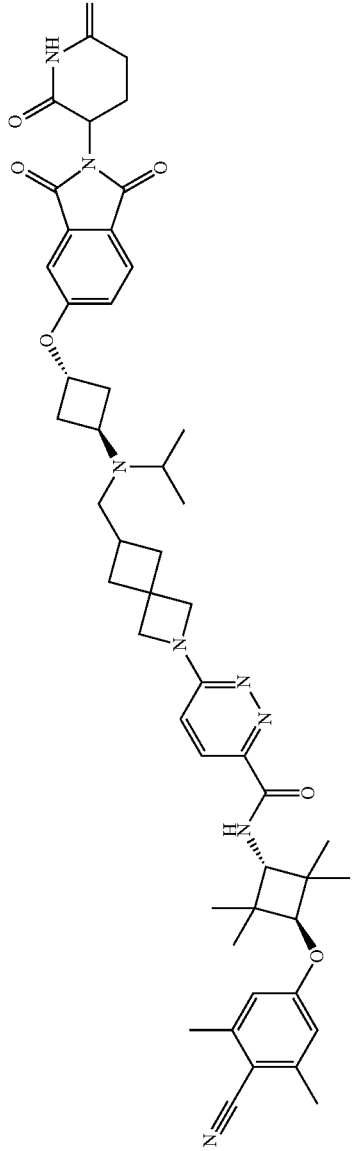 | N-((1r,3r)-3-(4-cyano-3,5-dimethylphenoxy)-2,2,4,4-tetramethylcyclobutyl)-6-(6-((((1r,3r)-3-((2-(2,6-dioxopiperidin-3-yl)-1,3-dioxoisoindolin-5-yl)oxy)cyclobutyl)(isopropyl)amino)methyl)-2-azaspiro[3.3]heptan-2-yl)pyridazine-3-carboxamide | 7 |

TABLE 1C-continued

Exemplary heterobifunctional compounds of the present disclosure.

| Comp No. | Structure | Name | Scheme |
|---|---|---|---|
| 164 | 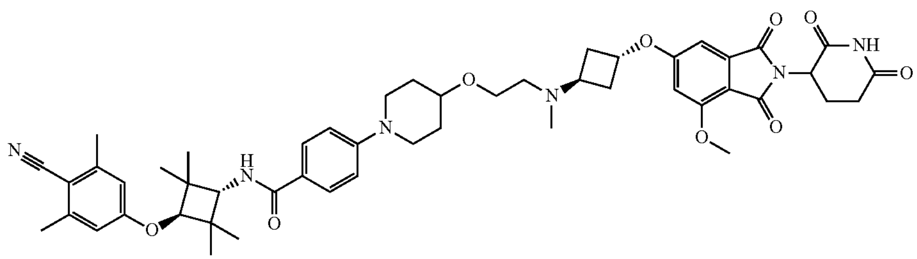 [SMILES: COc1cc(O[C@H]2C[C@H](N(C)CCOC3CCN(c4ccc(C(=O)N[C@H]5C(C)(C)[C@H](Oc6cc(C)c(C#N)c(C)c6)C5(C)C)cc4)CC3)C2)cc2c1C(=O)N(C1CCC(=O)NC1=O)C2=O] | N-((1r,3r)-3-(4-cyano-3,5-dimethylphenoxy)-2,2,4,4-tetramethylcyclobutyl)-4-(4-(2-(((1r,3r)-3-((2-(2,6-dioxopiperidin-3-yl)-7-methoxy-1,3-dioxoisoindolin-5-yl)oxy)cyclobutyl)(methyl)amino)ethoxy)piperidin-1-yl)benzamide | 34 and 7 |
| 165 | 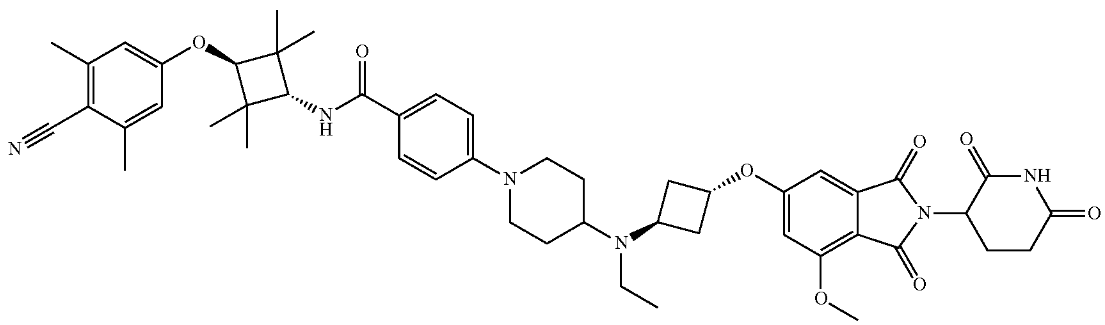 [SMILES: CCN(C1CCN(c2ccc(C(=O)N[C@H]3C(C)(C)[C@H](Oc4cc(C)c(C#N)c(C)c4)C3(C)C)cc2)CC1)[C@H]1C[C@H](Oc2cc(OC)c3c(c2)C(=O)N(C2CCC(=O)NC2=O)C3=O)C1] | rac-N-((1r,3r)-3-(4-cyano-3,5-dimethylphenoxy)-2,2,4,4-tetramethylcyclobutyl)-4-(4-(((1r,3r)-3-((2-(2,6-dioxopiperidin-3-yl)-7-methoxy-1,3-dioxoisoindolin-5-yl)oxy)cyclobutyl)(ethyl)amino)piperidin-1-yl)benzamide | 34 |
| 166 | 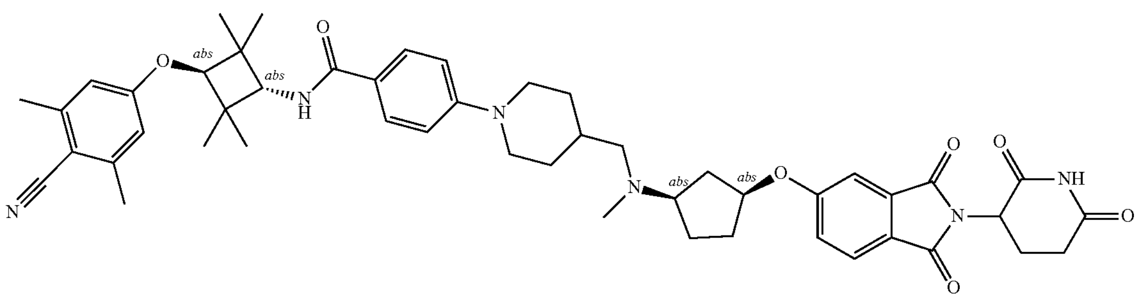 [SMILES: Cc1cc(O[C@H]2C(C)(C)[C@H](NC(=O)c3ccc(N4CCC(CN(C)[C@@H]5CC[C@H](Oc6ccc7c(c6)C(=O)N(C6CCC(=O)NC6=O)C7=O)C5)CC4)cc3)C2(C)C)cc(C)c1C#N] | N-((1r,3R)-3-(4-cyano-3,5-dimethylphenoxy)-2,2,4,4-tetramethylcyclobutyl)-4-(4-(((1R,3S)-3-((2-(2,6-dioxopiperidin-3-yl)-1,3-dioxoisoindolin-5-yl)oxy)cyclopentyl)(methyl)amino)methyl)piperidin-1-yl)benzamide | 7 |

TABLE 1C-continued

Exemplary heterobifunctional compounds of the present disclosure.

| Comp No. | Structure | Name | Scheme |
|---|---|---|---|
| 167 | 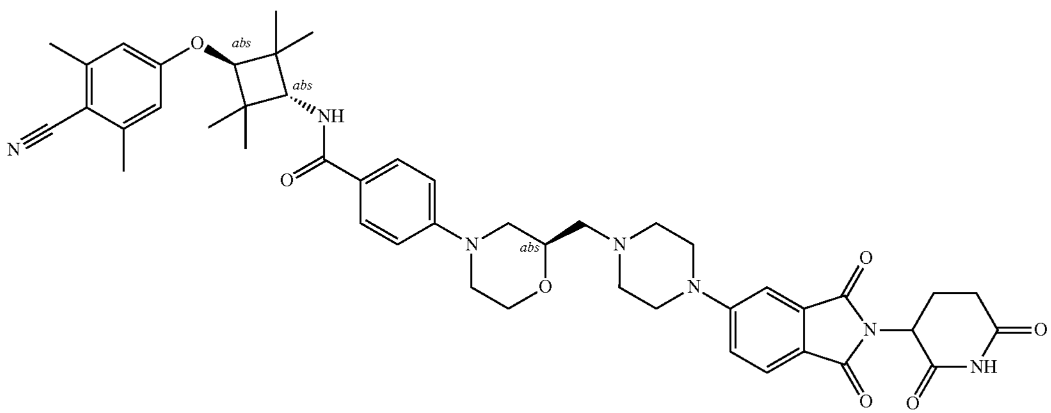 [SMILES: Cc1cc(O[C@H]2C(C)(C)[C@H](NC(=O)c3ccc(N4CCO[C@H](CN5CCN(c6ccc7c(c6)C(=O)N(C6CCC(=O)NC6=O)C7=O)CC5)C4)cc3)C2(C)C)cc(C)c1C#N] | N-((1r,3R)-3-(4-cyano-3,5-dimethylphenoxy)-2,2,4,4-tetramethylcyclobutyl)-4-((2R)-2-((4-(2-(2,6-dioxopiperidin-3-yl)-1,3-dioxoisoindolin-5-yl)piperazin-1-yl)methyl)morpholino)benzamide | 38 and 3 |
| 168 | 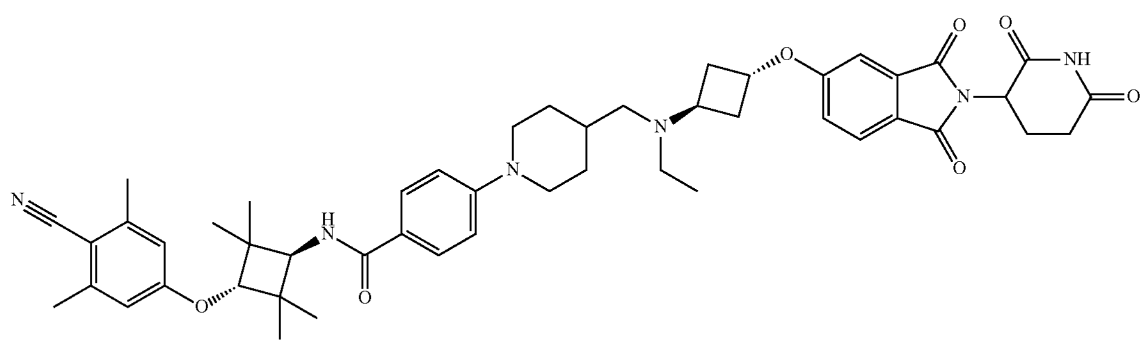 [SMILES: CCN(CC1CCN(c2ccc(C(=O)N[C@H]3C(C)(C)[C@H](Oc4cc(C)c(C#N)c(C)c4)C3(C)C)cc2)CC1)[C@H]1C[C@H](Oc2ccc3c(c2)C(=O)N(C2CCC(=O)NC2=O)C3=O)C1] | N-((1r,3r)-3-(4-cyano-3,5-dimethylphenoxy)-2,2,4,4-tetramethylcyclobutyl)-4-(4-(((1r,3r)-3-((2-(2,6-dioxopiperidin-3-yl)-1,3-dioxoisoindolin-5-yl)oxy)cyclobutyl)(ethyl)amino)methyl)piperidin-1-yl)benzamide | 7 |

TABLE 1C-continued

Exemplary heterobifunctional compounds of the present disclosure.

| Comp No. | Structure | Name | Scheme |
|---|---|---|---|
| 169 | 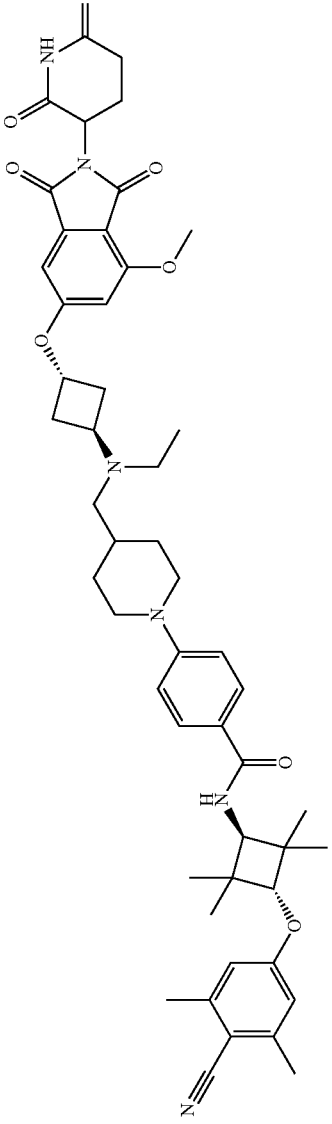 | rac-N-((1r,3r)-3-(4-cyano-3,5-dimethylphenoxy)-2,2,4,4-tetramethylcyclobutyl)-4-(4-(((1r,3r)-3-((2-(2,6-dioxopiperidin-3-yl)-7-methoxy-1,3-dioxoisoindolin-5-yl)oxy)cyclobutyl)(ethyl)amino)methyl)piperidin-1-yl)benzamide | 7 and 1 |
| 170 | 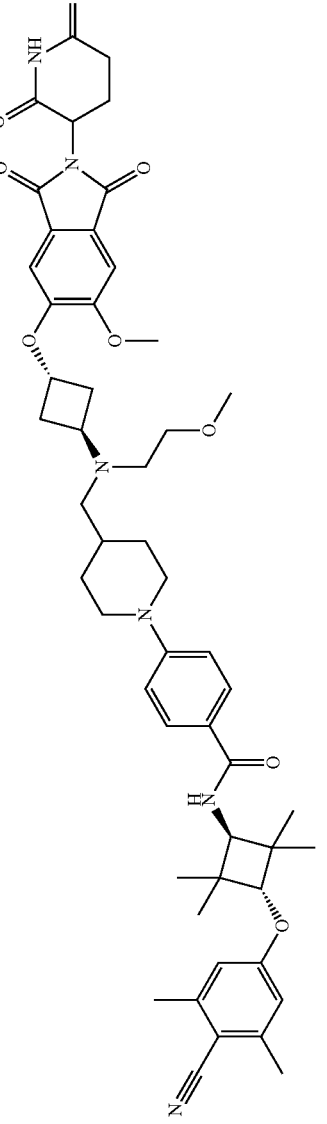 | rac-N-((1r,3r)-3-(4-cyano-3,5-dimethylphenoxy)-2,2,4,4-tetramethylcyclobutyl)-4-(4-(((1r,3r)-3-((2-(2,6-dioxopiperidin-3-yl)-6-methoxy-1,3-dioxoisoindolin-5-yl)oxy)cyclobutyl)(2-methoxyethyl)amino)methyl)piperidin-1-yl)benzamide | 39 and 7 |

TABLE 1C-continued

Exemplary heterobifunctional compounds of the present disclosure.

| Comp No. | Structure | Name | Scheme |
|---|---|---|---|
| 171 | 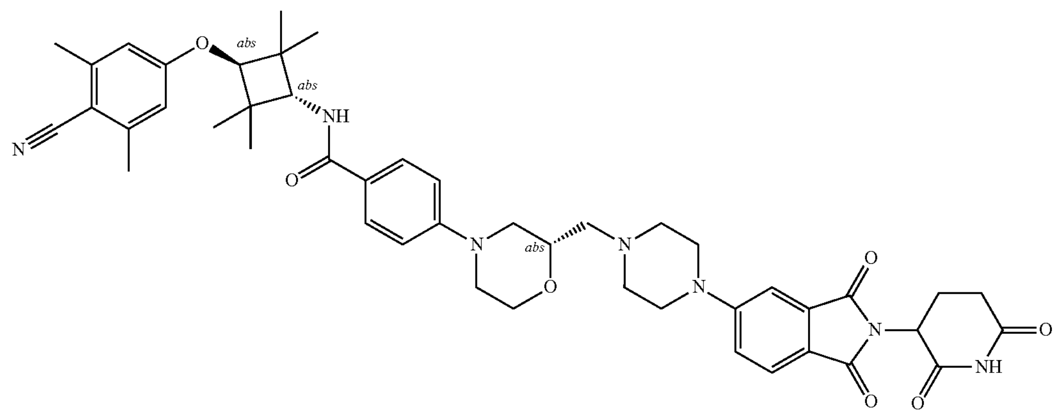 [SMILES: Cc1cc(O[C@H]2C(C)(C)[C@H](NC(=O)c3ccc(N4CCO[C@@H](CN5CCN(c6ccc7c(c6)C(=O)N(C6CCC(=O)NC6=O)C7=O)CC5)C4)cc3)C2(C)C)cc(C)c1C#N] | N-((1r,3S)-3-(4-cyano-3,5-dimethylphenoxy)-2,2,4,4-tetramethylcyclobutyl)-4-((2S)-2-((4-(2-(2,6-dioxopiperidin-3-yl)-1,3-dioxoisoindolin-5-yl)piperazin-1-yl)methyl)morpholino)benzamide | 38 and 3 |
| 172 | 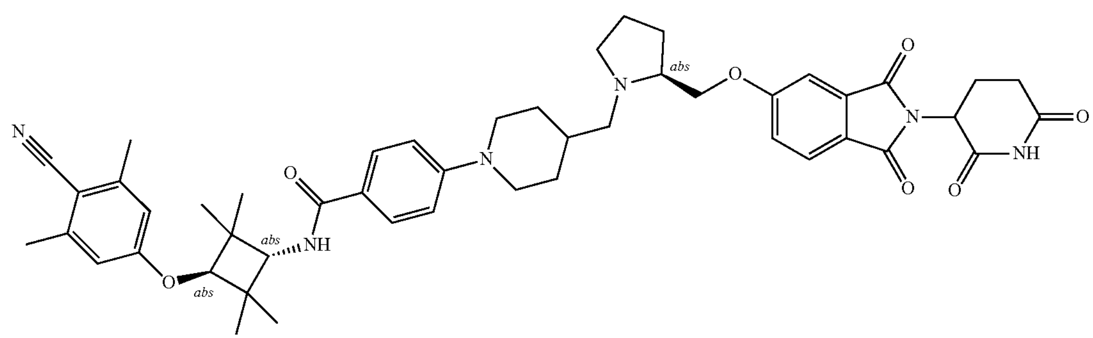 [SMILES: Cc1cc(O[C@H]2C(C)(C)[C@H](NC(=O)c3ccc(N4CCC(CN5CCC[C@H]5COc5ccc6c(c5)C(=O)N(C5CCC(=O)NC5=O)C6=O)CC4)cc3)C2(C)C)cc(C)c1C#N] | N-((1r,3S)-3-(4-cyano-3,5-dimethylphenoxy)-2,2,4,4-tetramethylcyclobutyl)-4-(4-(((2S)-2-(((2-(2,6-dioxopiperidin-3-yl)-1,3-dioxoisoindolin-5-yl)oxy)methyl)pyrrolidin-1-yl)methyl)piperidin-1-yl)benzamide | 36 and 7 |

TABLE 1C-continued

Exemplary heterobifunctional compounds of the present disclosure.

| Comp No. | Structure | Name | Scheme |
|---|---|---|---|
| 173 | 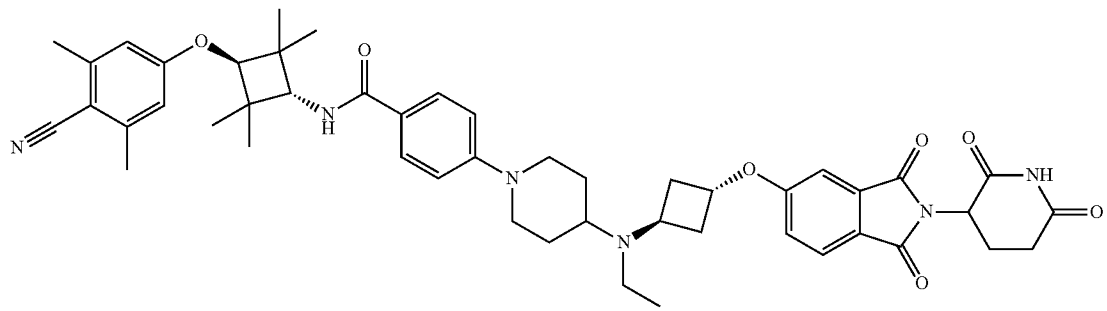 [SMILES: CCN(C1CCN(c2ccc(C(=O)N[C@H]3C(C)(C)[C@H](Oc4cc(C)c(C#N)c(C)c4)C3(C)C)cc2)CC1)[C@H]1C[C@H](Oc2ccc3c(c2)C(=O)N(C2CCC(=O)NC2=O)C3=O)C1] | rac-N-((1r,3r)-3-(4-cyano-3,5-dimethylphenoxy)-2,2,4,4-tetramethylcyclobutyl)-4-(4-(((1r,3r)-3-((2-(2,6-dioxopiperidin-3-yl)-1,3-dioxoisoindolin-5-yl)oxy)cyclobutyl)(ethyl)amino)piperidin-1-yl)benzamide | 7 |
| 174 | 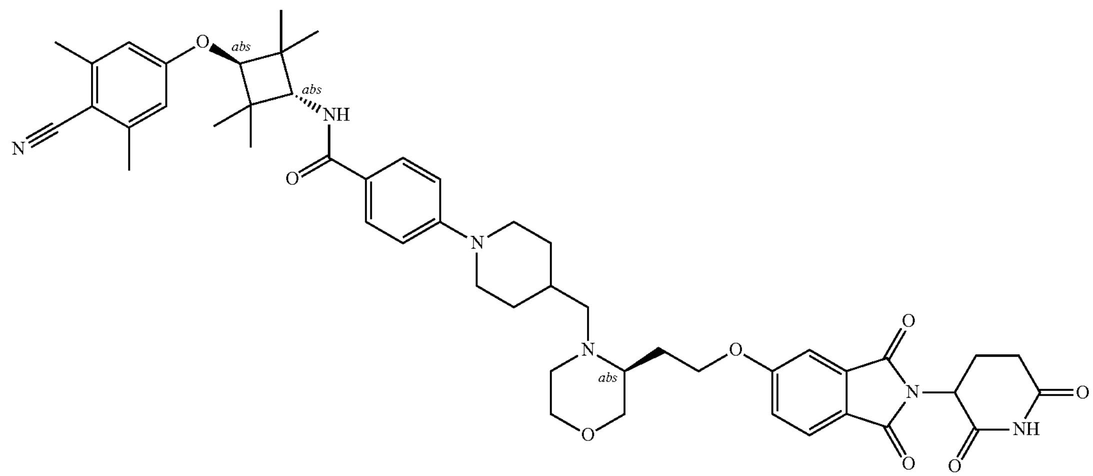 [SMILES: Cc1cc(O[C@H]2C(C)(C)[C@H](NC(=O)c3ccc(N4CCC(CN5CCOC[C@@H]5CCOc5ccc6c(c5)C(=O)N(C5CCC(=O)NC5=O)C6=O)CC4)cc3)C2(C)C)cc(C)c1C#N] | N-((1r,3S)-3-(4-cyano-3,5-dimethylphenoxy)-2,2,4,4-tetramethylcyclobutyl)-4-(4-(((3S)-3-(2-((2-(2,6-dioxopiperidin-3-yl)-1,3-dioxoisoindolin-5-yl)oxy)ethyl)morpholino)methyl)piperidin-1-yl)benzamide | 36 and 7 |

TABLE 1C-continued

Exemplary heterobifunctional compounds of the present disclosure.

| Comp No. | Structure | Name | Scheme |
|---|---|---|---|
| 175 | 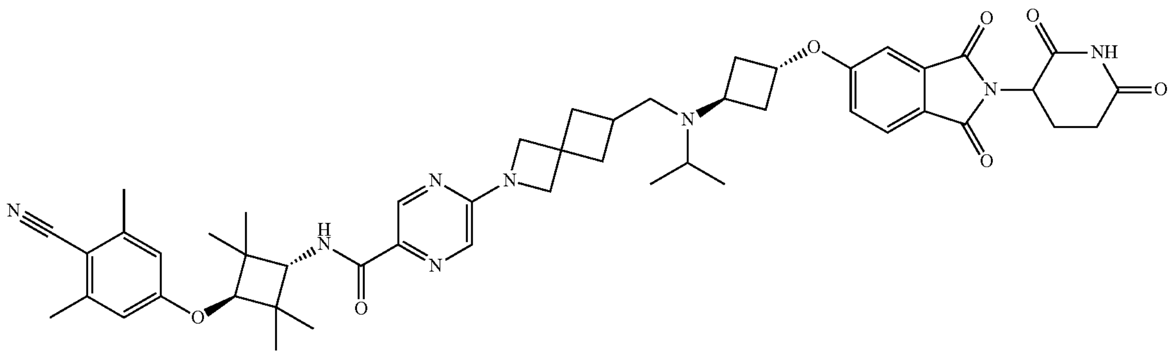 [SMILES: Cc1cc(O[C@H]2C(C)(C)[C@H](NC(=O)c3cnc(N4CC5(CC(CN(C(C)C)[C@H]6C[C@H](Oc7ccc8c(c7)C(=O)N(C7CCC(=O)NC7=O)C8=O)C6)C5)C4)cn3)C2(C)C)cc(C)c1C#N] | N-((1r,3r)-3-(4-cyano-3,5-dimethylphenoxy)-2,2,4,4-tetramethylcyclobutyl)-5-(6-(((1r,3r)-3-((2-(2,6-dioxopiperidin-3-yl)-1,3-dioxoisoindolin-5-yl)oxy)cyclobutyl)(isopropyl)amino)methyl)-2-azaspiro[3.3]heptan-2-yl)pyrazine-2-carboxamide | 7 |
| 176 | 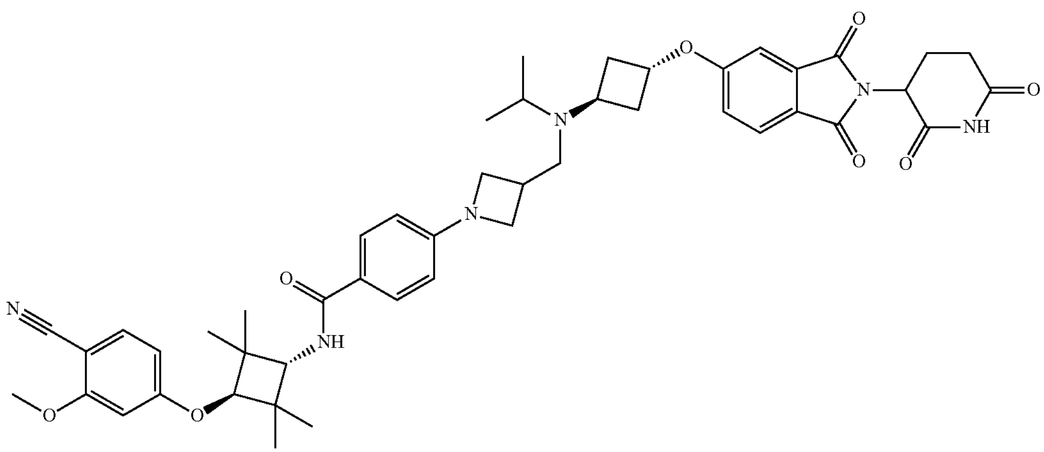 [SMILES: COc1cc(O[C@H]2C(C)(C)[C@H](NC(=O)c3ccc(N4CC(CN(C(C)C)[C@H]5C[C@H](Oc6ccc7c(c6)C(=O)N(C6CCC(=O)NC6=O)C7=O)C5)C4)cc3)C2(C)C)ccc1C#N] | rac-N-((1r,3r)-3-(4-cyano-3-methoxyphenoxy)-2,2,4,4-tetramethylcyclobutyl)-4-(3-(((1r,3r)-3-((2-(2,6-dioxopiperidin-3-yl)-1,3-dioxoisoindolin-5-yl)oxy)cyclobutyl)(isopropyl)amino)methyl)azetidin-1-yl)benzamide | 7 |

TABLE 1C-continued

Exemplary heterobifunctional compounds of the present disclosure.

| Comp No. | Structure | Name | Scheme |
|---|---|---|---|
| 177 | 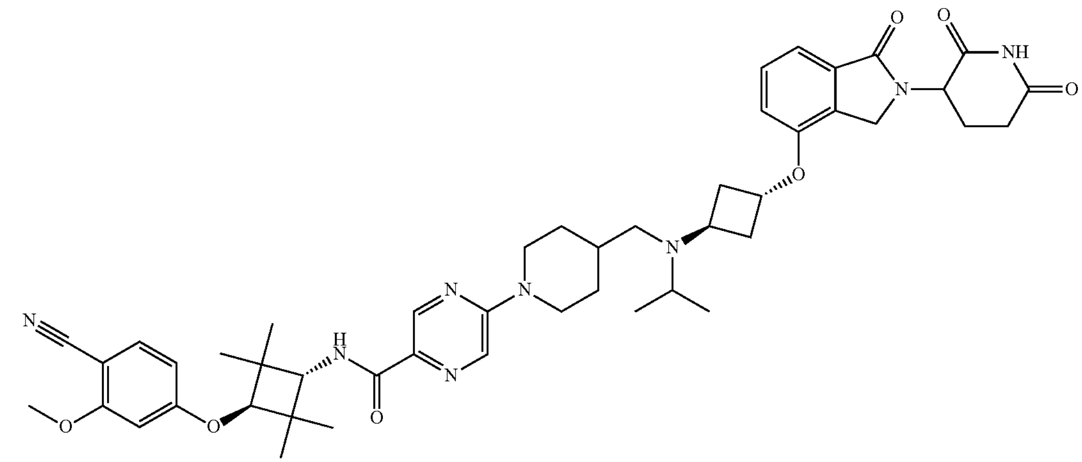 [SMILES: COc1cc(O[C@H]2C(C)(C)[C@H](NC(=O)c3cnc(N4CCC(CN(C(C)C)[C@H]5C[C@H](Oc6cccc7c6CN(C6CCC(=O)NC6=O)C7=O)C5)CC4)cn3)C2(C)C)ccc1C#N] | rac-N-((1r,3r)-3-(4-cyano-3-methoxyphenoxy)-2,2,4,4-tetramethylcyclobutyl)-5-(4-(((1r,3r)-3-((2-(2,6-dioxopiperidin-3-yl)-1-oxoisoindolin-4-yl)oxy)cyclobutyl)(isopropyl)amino)methyl)piperidin-1-yl)pyrazine-2-carboxamide | 7 with 3-(4-hydroxy-1-oxoisoindolin-2-yl)piperidine-2,6-dione |
| 178 | 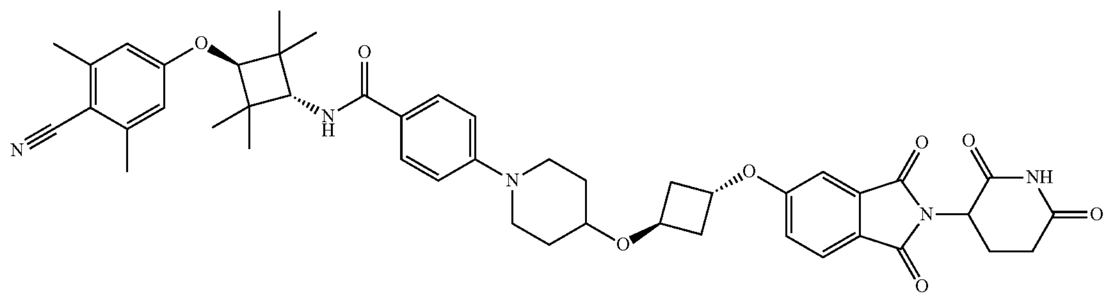 [SMILES: Cc1cc(O[C@H]2C(C)(C)[C@H](NC(=O)c3ccc(N4CCC(O[C@H]5C[C@H](Oc6ccc7c(c6)C(=O)N(C6CCC(=O)NC6=O)C7=O)C5)CC4)cc3)C2(C)C)cc(C)c1C#N] | rac-N-((1r,3r)-3-(4-cyano-3,5-dimethylphenoxy)-2,2,4,4-tetramethylcyclobutyl)-4-(4-((1r,3r)-3-((2-(2,6-dioxopiperidin-3-yl)-1,3-dioxoisoindolin-5-yl)oxy)cyclobutoxy)piperidin-1-yl)benzamide | 40 and custom synthesis provided |

TABLE 1C-continued

Exemplary heterobifunctional compounds of the present disclosure.

| Comp. No. | Structure | Name | Scheme |
|---|---|---|---|
| 179 | 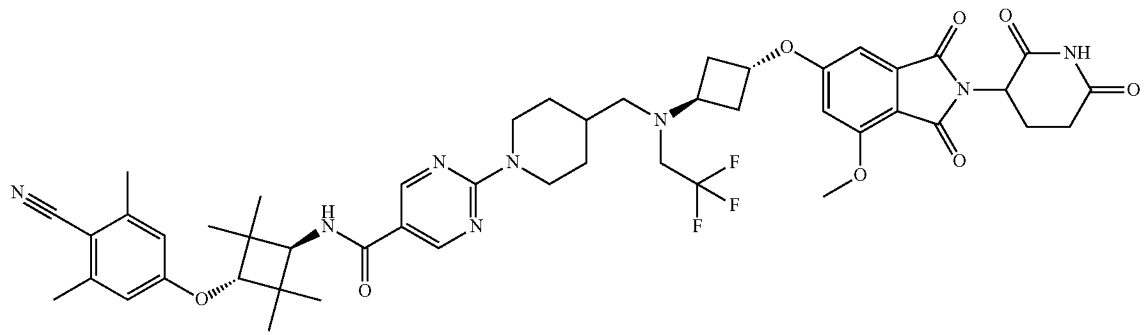 [SMILES: COc1cc(O[C@H]2C[C@H](N(CC3CCN(c4ncc(C(=O)N[C@H]5C(C)(C)[C@H](Oc6cc(C)c(C#N)c(C)c6)C5(C)C)cn4)CC3)CC(F)(F)F)C2)cc2c1C(=O)N(C1CCC(=O)NC1=O)C2=O] | N-((1r,3r)-3-(4-cyano-3,5-dimethylphenoxy)-2,2,4,4-tetramethylcyclobutyl)-2-(4-(((1r,3r)-3-((2-(2,6-dioxopiperidin-3-yl)-7-methoxy-1,3-dioxoisoindolin-5-yl)oxy)cyclobutyl)(2,2,2-trifluoroethyl)amino)methyl)piperidin-1-yl)pyrimidine-5-carboxamide | 7 and 1 |
| 180 | 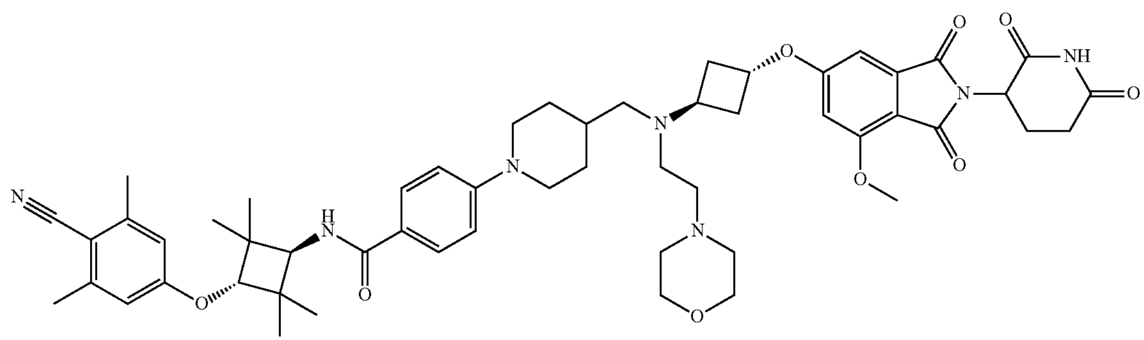 | N-((1r,3r)-3-(4-cyano-3,5-dimethylphenoxy)-2,2,4,4-tetramethylcyclobutyl)-4-(4-(((1r,3r)-3-((2-(2,6-dioxopiperidin-3-yl)-7-methoxy-1,3-dioxoisoindolin-5-yl)oxy)cyclobutyl)(2-morpholinoethyl)amino)methyl)piperidin-1-yl)benzamide | 7 and 1 |
| 181 | 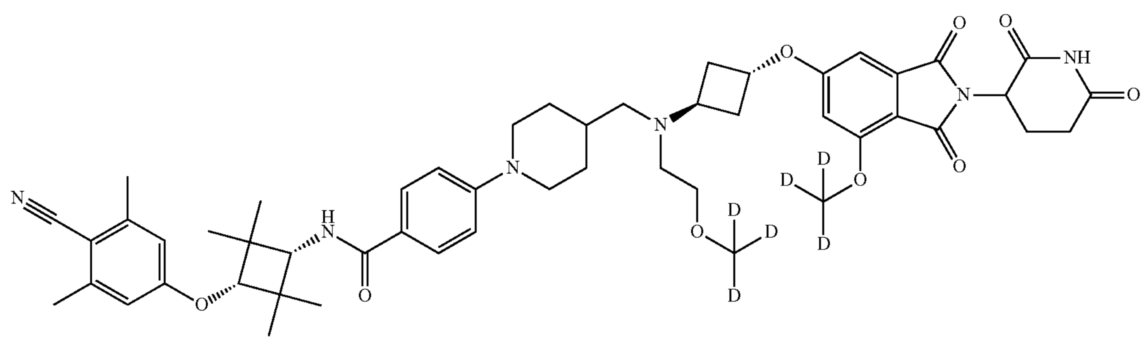 [SMILES: [2H]C([2H])([2H])OCCN(CC1CCN(c2ccc(C(=O)N[C@H]3C(C)(C)[C@@H](Oc4cc(C)c(C#N)c(C)c4)C3(C)C)cc2)CC1)[C@H]1C[C@H](Oc2cc(OC([2H])([2H])[2H])c3c(c2)C(=O)N(C2CCC(=O)NC2=O)C3=O)C1] | rac-N-((1r,3r)-3-(4-cyano-3,5-dimethylphenoxy)-2,2,4,4-tetramethylcyclobutyl)-4-(4-(((1r,3r)-3-((2-(2,6-dioxopiperidin-3-yl)-7-(methoxy-d3)-1,3-dioxoisoindolin-5-yl)oxy)cyclobutyl)(2-(methoxy-d3)ethyl)amino)methyl)piperidin-1-yl)benzamide | 34 |

TABLE 1C-continued

Exemplary heterobifunctional compounds of the present disclosure.

| Comp No. | Structure | Name | Scheme |
|---|---|---|---|
| 182 | 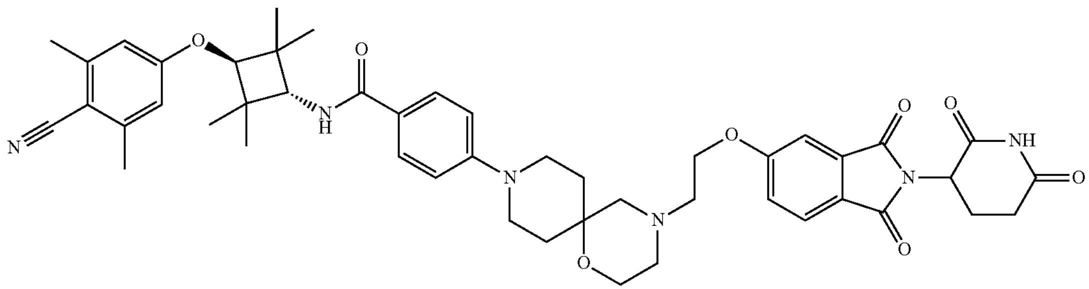 [SMILES: Cc1cc(O[C@H]2C(C)(C)[C@H](NC(=O)c3ccc(N4CCC5(CC4)CN(CCOc4ccc6c(c4)C(=O)N(C4CCC(=O)NC4=O)C6=O)CCO5)cc3)C2(C)C)cc(C)c1C#N] | rac-N-((1r,3r)-3-(4-cyano-3,5-dimethylphenoxy)-2,2,4,4-tetramethylcyclobutyl)-4-(4-(2-((2-(2,6-dioxopiperidin-3-yl)-1,3-dioxoisoindolin-5-yl)oxy)ethyl)-1-oxa-4,9-diazaspiro[5.5]undecan-9-yl)benzamide | 41 |
| 183 | 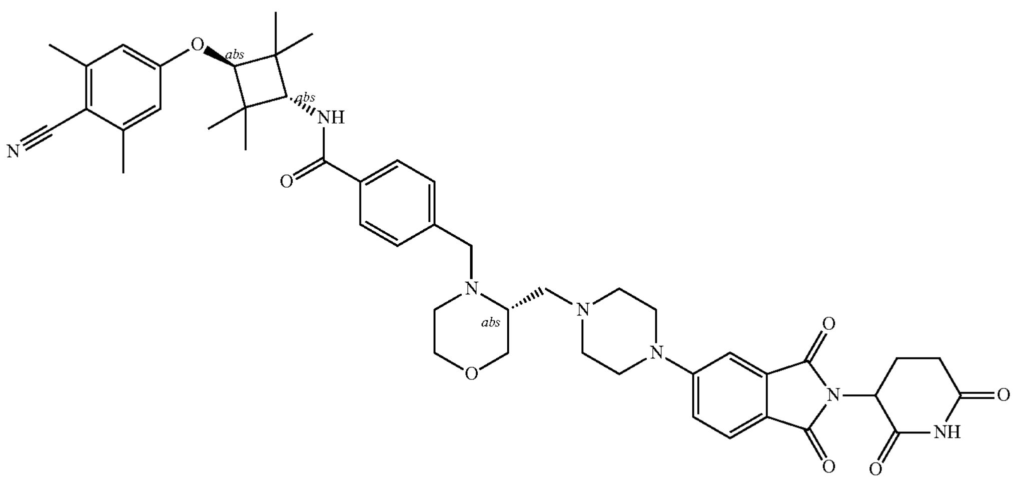 [SMILES: Cc1cc(O[C@H]2C(C)(C)[C@H](NC(=O)c3ccc(CN4CCOC[C@H]4CN4CCN(c5ccc6c(c5)C(=O)N(C5CCC(=O)NC5=O)C6=O)CC4)cc3)C2(C)C)cc(C)c1C#N] | N-((1r,3R)-3-(4-cyano-3,5-dimethylphenoxy)-2,2,4,4-tetramethylcyclobutyl)-4-(((3R)-3-((4-(2-(2,6-dioxopiperidin-3-yl)-1,3-dioxoisoindolin-5-yl)piperazin-1-yl)methyl)morpholino)methyl)benzamide | 38 and 3 |

TABLE 1C-continued

Exemplary heterobifunctional compounds of the present disclosure.

| Comp No. | Structure | Name | Scheme |
|---|---|---|---|
| 184 | 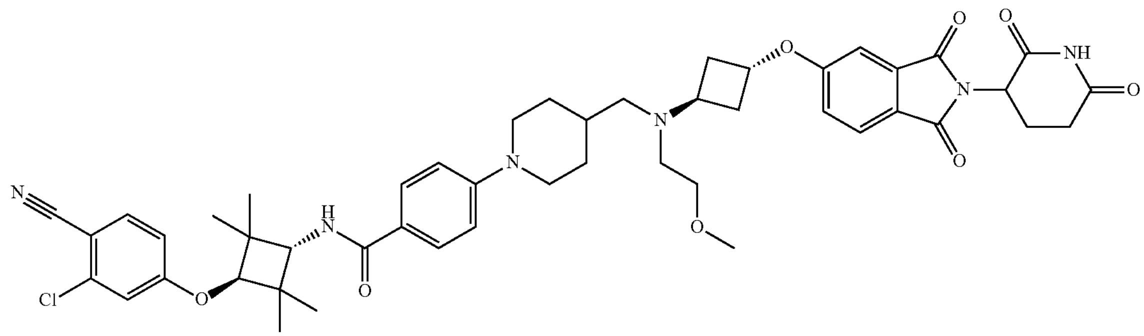 | N-((1r,3r)-3-(3-chloro-4-cyanophenoxy)-2,2,4,4-tetramethylcyclobutyl)-4-(4-(((1r,3r)-3-((2-(2,6-dioxopiperidin-3-yl)-1,3-dioxoisoindolin-5-yl)oxy)cyclobutyl)(2-methoxyethyl)amino)methyl)piperidin-1-yl)benzamide | 7 |
| 185 | 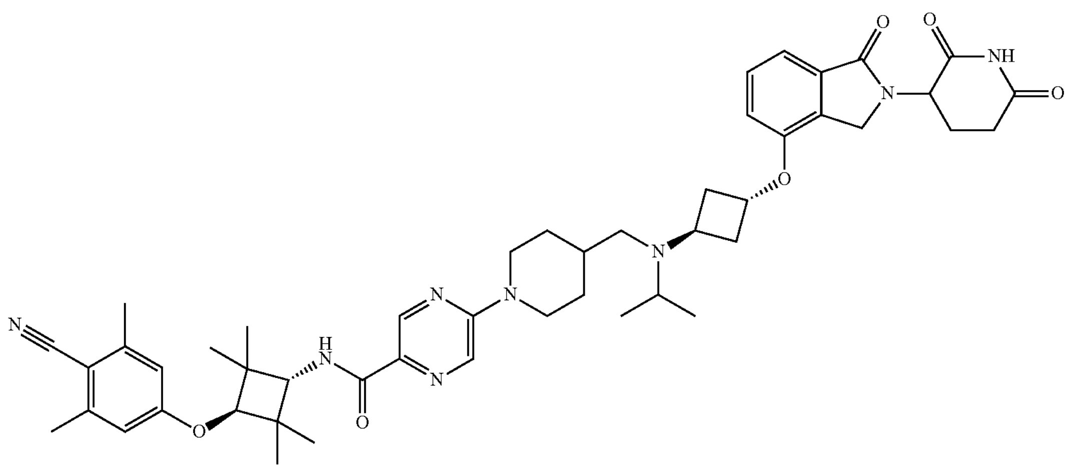 [SMILES: Cc1cc(O[C@H]2C(C)(C)[C@H](NC(=O)c3cnc(N4CCC(CN(C(C)C)[C@H]5C[C@H](Oc6cccc7c6CN(C6CCC(=O)NC6=O)C7=O)C5)CC4)cn3)C2(C)C)cc(C)c1C#N] | rac-N-((1r,3r)-3-(4-cyano-3,5-dimethylphenoxy)-2,2,4,4-tetramethylcyclobutyl)-5-(4-(((1r,3r)-3-((2-(2,6-dioxopiperidin-3-yl)-1-oxoisoindolin-4-yl)oxy)cyclobutyl)(isopropyl)amino)methyl)piperidin-1-yl)pyrazine-2-carboxamide | 7 with 3-(4-hydroxy-1-oxoisoindolin-2-yl)piperidine-2,6-dione |

TABLE 1C-continued

Exemplary heterobifunctional compounds of the present disclosure.

| Comp No. | Structure | Name | Scheme |
|---|---|---|---|
| 186 | 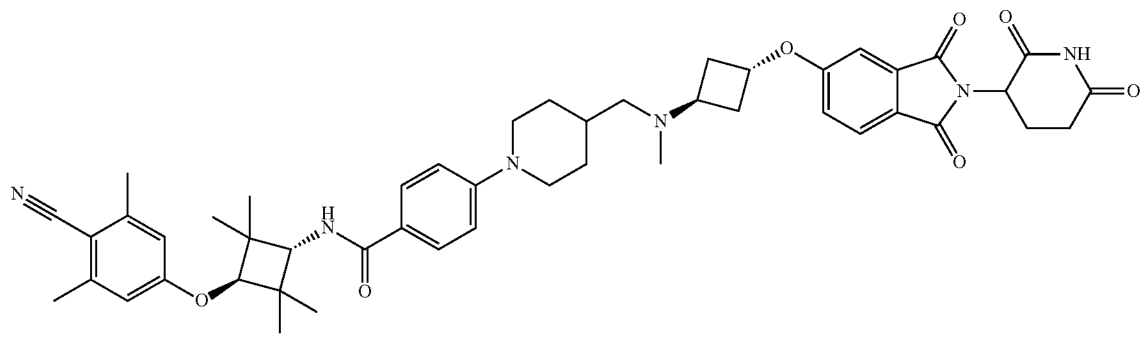 [SMILES: Cc1cc(O[C@H]2C(C)(C)[C@H](NC(=O)c3ccc(N4CCC(CN(C)[C@H]5C[C@H](Oc6ccc7c(c6)C(=O)N(C6CCC(=O)NC6=O)C7=O)C5)CC4)cc3)C2(C)C)cc(C)c1C#N] | rac-N-((1r,3r)-3-(4-cyano-3,5-dimethylphenoxy)-2,2,4,4-tetramethylcyclobutyl)-4-(4-((((1r,3r)-3-((2-(2,6-dioxopiperidin-3-yl)-1,3-dioxoisoindolin-5-yl)oxy)cyclobutyl)(methyl)amino)methyl)piperidin-1-yl)benzamide | 7 |
| 187 | 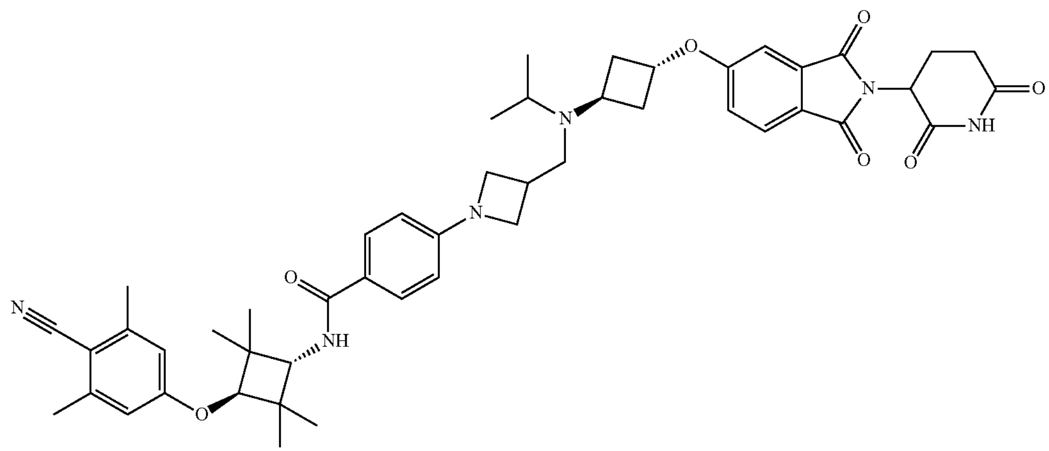 [SMILES: Cc1cc(O[C@H]2C(C)(C)[C@H](NC(=O)c3ccc(N4CC(CN(C(C)C)[C@H]5C[C@H](Oc6ccc7c(c6)C(=O)N(C6CCC(=O)NC6=O)C7=O)C5)C4)cc3)C2(C)C)cc(C)c1C#N] | N-((1r,3r)-3-(4-cyano-3,5-dimethylphenoxy)-2,2,4,4-tetramethylcyclobutyl)-4-(3-((((1r,3r)-3-((2-(2,6-dioxopiperidin-3-yl)-1,3-dioxoisoindolin-5-yl)oxy)cyclobutyl)(isopropyl)amino)methyl)azetidin-1-yl)benzamide | 7 |

TABLE 1C-continued

Exemplary heterobifunctional compounds of the present disclosure.

| Comp No. | Structure | Name | Scheme |
|---|---|---|---|
| 188 | 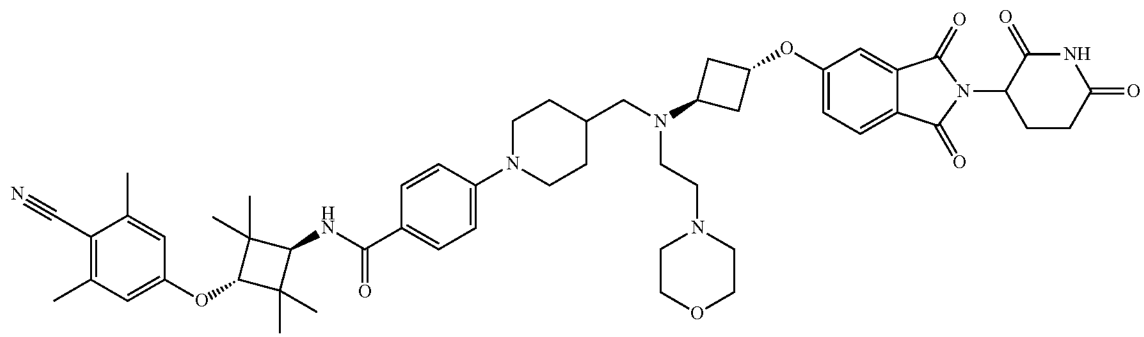 | rac-N-((1r,3r)-3-(4-cyano-3,5-dimethylphenoxy)-2,2,4,4-tetramethylcyclobutyl)-4-(4-(((1r,3r)-3-((2-(2,6-dioxopiperidin-3-yl)-1,3-dioxoisoindolin-5-yl)oxy)cyclobutyl)(2-morpholinoethyl)amino)methyl)piperidin-1-yl)benzamide | 7 |
| 189 | 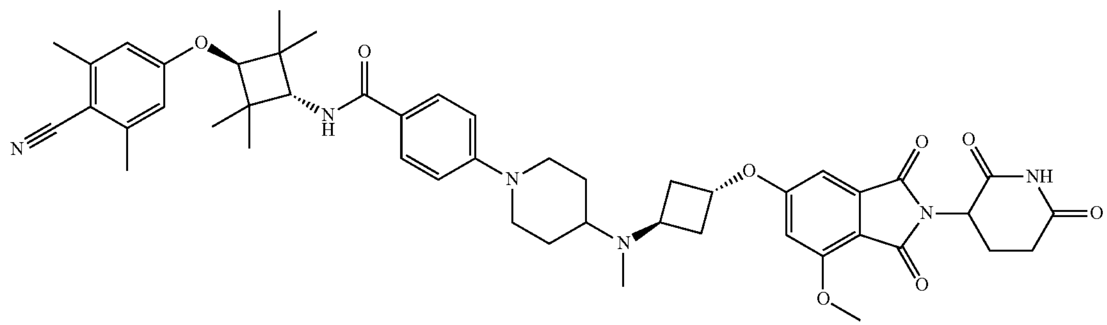 [SMILES: COc1cc(O[C@H]2C[C@H](N(C)C3CCN(c4ccc(C(=O)N[C@H]5C(C)(C)[C@H](Oc6cc(C)c(C#N)c(C)c6)C5(C)C)cc4)CC3)C2)cc2c1C(=O)N(C1CCC(=O)NC1=O)C2=O] | rac-N-((1r,3r)-3-(4-cyano-3,5-dimethylphenoxy)-2,2,4,4-tetramethylcyclobutyl)-4-(4-(((1r,3r)-3-((2-(2,6-dioxopiperidin-3-yl)-7-methoxy-1,3-dioxoisoindolin-5-yl)oxy)cyclobutyl)(methyl)amino)piperidin-1-yl)benzamide | 34 |

TABLE 1C-continued

Exemplary heterobifunctional compounds of the present disclosure.

| Comp No. | Structure | Name | Scheme |
|---|---|---|---|
| 190 | 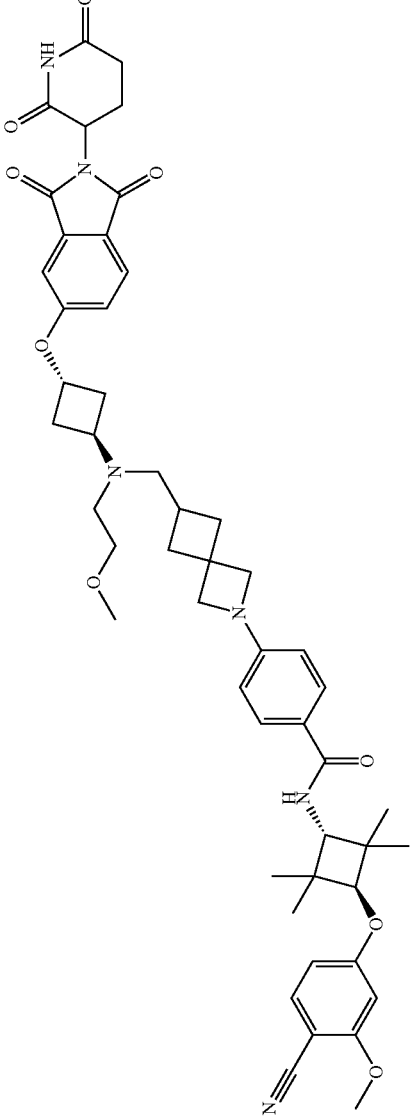 | rac-N-((1r,3r)-3-(4-cyano-3-methoxyphenoxy)-2,2,4,4-tetramethylcyclobutyl)-4-(6-(((1r,3r)-3-((2-(2,6-dioxopiperidin-3-yl)-1,3-dioxoisoindolin-5-yl)oxy)cyclobutyl)(2-methoxyethyl)amino)methyl)-2-azaspiro[3.3]heptan-2-yl)benzamide | 7 |
| 191 | 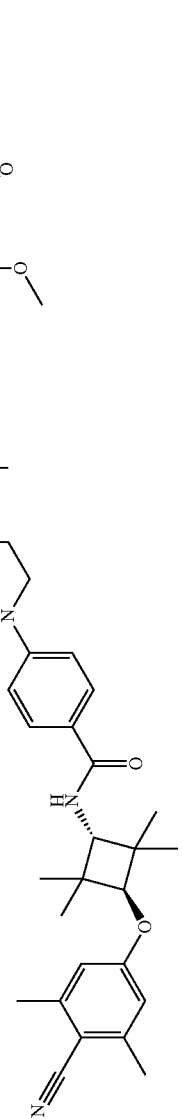 | rac-N-((1r,3r)-3-(4-cyano-3,5-dimethylphenoxy)-2,2,4,4-tetramethylcyclobutyl)-4-(4-(((1r,3r)-3-((2-(2,6-dioxopiperidin-3-yl)-7-methoxy-1,3-dioxoisoindolin-5-yl)oxy)cyclobutyl)(methyl)amino)methyl)piperidin-1-yl)benzamide | 34 |

TABLE 1C-continued

Exemplary heterobifunctional compounds of the present disclosure.

| Comp No. | Structure | Name | Scheme |
|---|---|---|---|
| 192 | 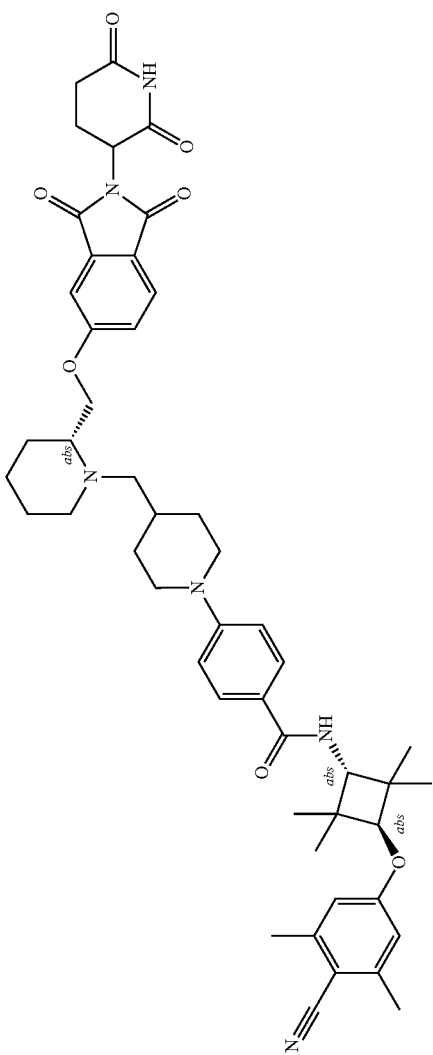 | N-((1r,3R)-3-(4-cyano-3,5-dimethylphenoxy)-2,2,4,4-tetramethylcyclobutyl)-4-(4-(((2R)-2-(((2-(2,6-dioxopiperidin-3-yl)-1,3-dioxoisoindolin-5-yl)oxy)methyl)piperidin-1-yl)methyl)piperidin-1-yl)benzamide | 36 and 7 |
| 193 | 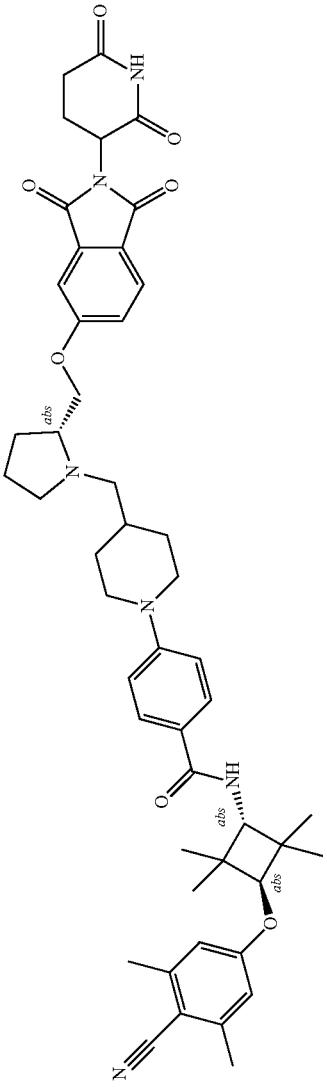 | N-((1r,3R)-3-(4-cyano-3,5-dimethylphenoxy)-2,2,4,4-tetramethylcyclobutyl)-4-(4-(((2R)-2-(((2-(2,6-dioxopiperidin-3-yl)-1,3-dioxoisoindolin-5-yl)oxy)methyl)pyrrolidin-1-yl)methyl)piperidin-1-yl)benzamide | 36 and 7 |

TABLE 1C-continued

Exemplary heterobifunctional compounds of the present disclosure.

| Comp No. | Structure | Name | Scheme |
|---|---|---|---|
| 194 | 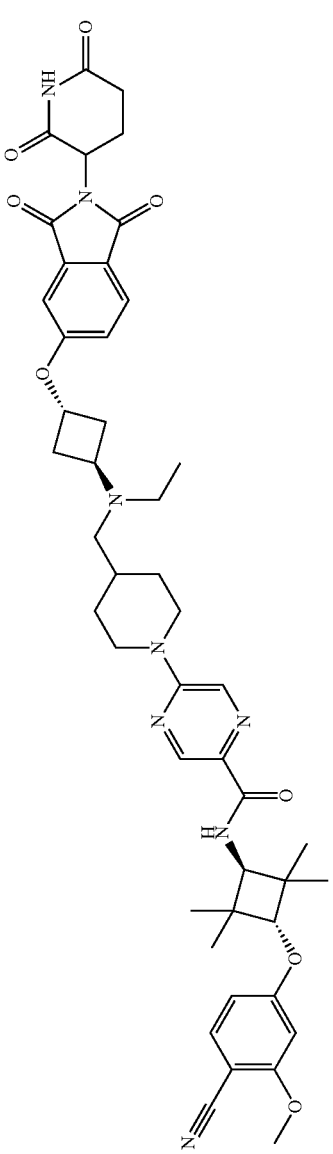 | N-((1r,3r)-3-(4-cyano-3-methoxyphenoxy)-2,2,4,4-tetramethylcyclobutyl)-5-(4-((((1r,3r)-3-((2-(2,6-dioxopiperidin-3-yl)-1,3-dioxoisoindolin-5-yl)oxy)cyclobutyl)(ethyl)amino)methyl)piperidin-1-yl)pyrazine-2-carboxamide | 7 |
| 195 | 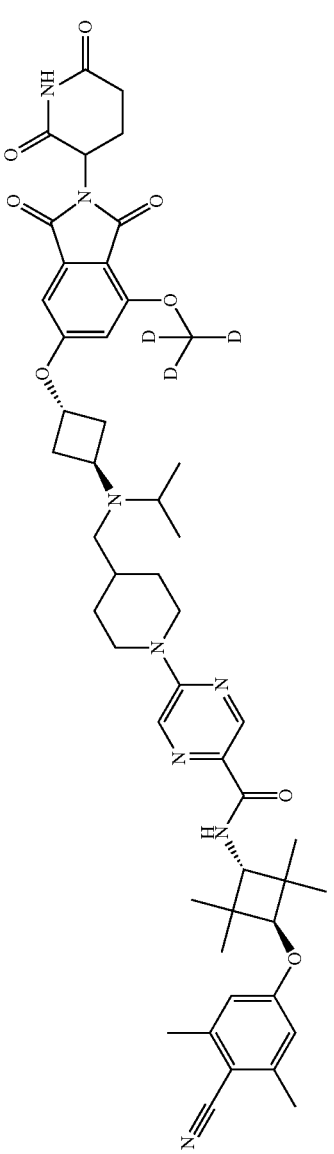 | rac-N-((1r,3r)-3-(4-cyano-3,5-dimethylphenoxy)-2,2,4,4-tetramethylcyclobutyl)-5-(4-((((1r,3r)-3-((2-(2,6-dioxopiperidin-3-yl)-7-(methoxy-d3)-1,3-dioxoisoindolin-5-yl)oxy)cyclobutyl)(isopropyl)amino)methyl)piperidin-1-yl)pyrazine-2-carboxamide | 34 |

TABLE 1C-continued

Exemplary heterobifunctional compounds of the present disclosure.

| Comp No. | Structure | Name | Scheme |
|---|---|---|---|
| 196 | 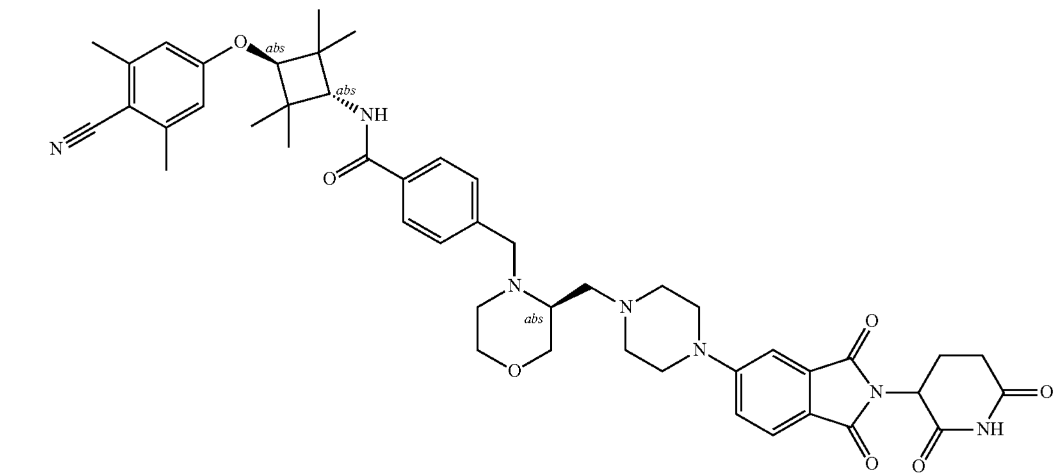 [SMILES: Cc1cc(O[C@H]2C(C)(C)[C@H](NC(=O)c3ccc(CN4CCOC[C@@H]4CN4CCN(c5ccc6c(c5)C(=O)N(C5CCC(=O)NC5=O)C6=O)CC4)cc3)C2(C)C)cc(C)c1C#N] | N-((1r,3S)-3-(4-cyano-3,5-dimethylphenoxy)-2,2,4,4-tetramethylcyclobutyl)-4-(((3S)-3-((4-(2-(2,6-dioxopiperidin-3-yl)-1,3-dioxoisoindolin-5-yl)piperazin-1-yl)methyl)morpholino)methyl)benzamide | 38 and 3 |
| 197 | 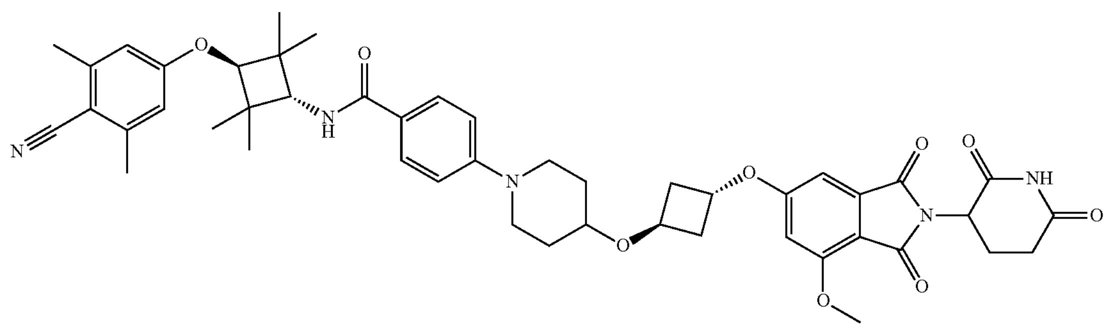 [SMILES: COc1cc(O[C@H]2C[C@H](OC3CCN(c4ccc(C(=O)N[C@H]5C(C)(C)[C@H](Oc6cc(C)c(C#N)c(C)c6)C5(C)C)cc4)CC3)C2)cc2c1C(=O)N(C1CCC(=O)NC1=O)C2=O] | rac-N-((1r,3r)-3-(4-cyano-3,5-dimethylphenoxy)-2,2,4,4-tetramethylcyclobutyl)-4-(4-((1r,3r)-3-((2-(2,6-dioxopiperidin-3-yl)-7-methoxy-1,3-dioxoisoindolin-5-yl)oxy)cyclobutoxy)piperidin-1-yl)benzamide | 1 and 40 |

TABLE 1C-continued

Exemplary heterobifunctional compounds of the present disclosure.

| Comp No. | Structure | Name | Scheme |
|---|---|---|---|
| 198 | 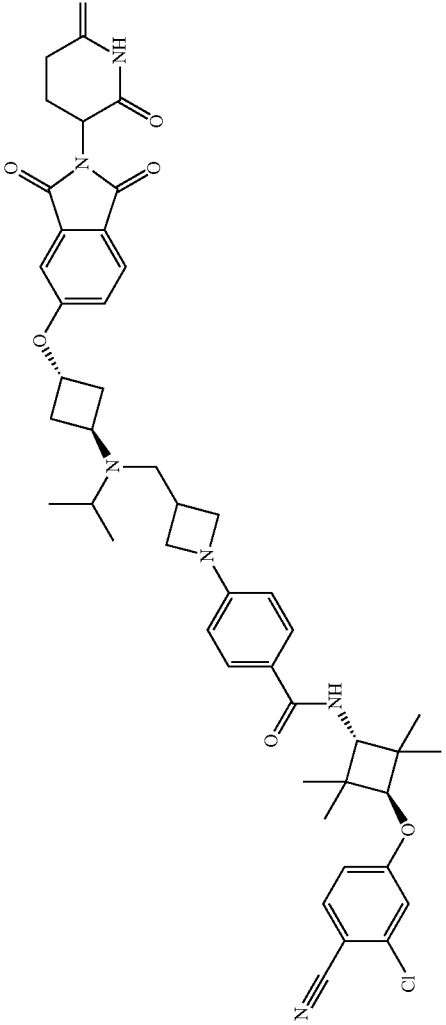 | rac-N-((1r,3r)-3-(3-chloro-4-cyanophenoxy)-2,2,4,4-tetramethylcyclobutyl)-4-(3-(((1r,3r)-3-((2-(2,6-dioxopiperidin-3-yl)-1,3-dioxoisoindolin-5-yl)oxy)cyclobutyl)(isopropyl)amino)methyl)azetidin-1-yl)benzamide | 7 |
| 199 | 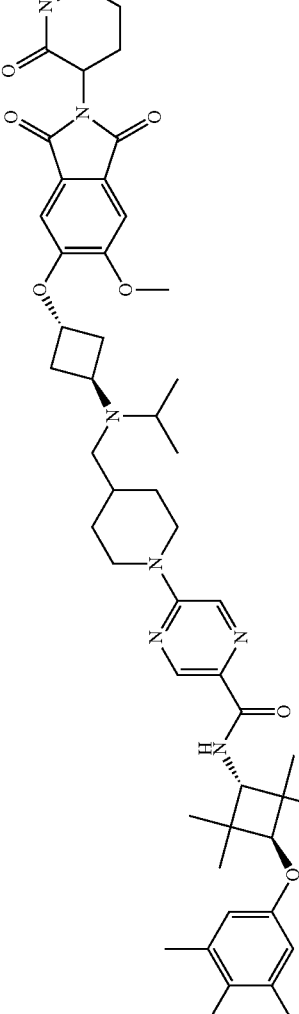 | rac-N-((1r,3r)-3-(4-cyano-3,5-dimethylphenoxy)-2,2,4,4-tetramethylcyclobutyl)-5-(4-(((1r,3r)-3-((2-(2,6-dioxopiperidin-3-yl)-6-methoxy-1,3-dioxoisoindolin-5-yl)oxy)cyclobutyl)(isopropyl)amino)methyl)piperidin-1-yl)pyrazine-2-carboxamide | 39 and 7, and custom synthesis intermediate and compound |

TABLE 1C-continued

Exemplary heterobifunctional compounds of the present disclosure.

| Comp No. | Structure | Name | Scheme |
|---|---|---|---|
| 200 | 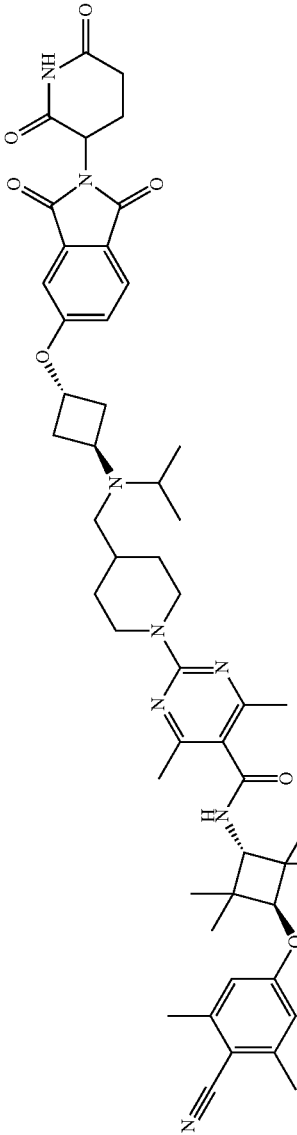 | rac-N-((1r,3r)-3-(4-cyano-3,5-dimethylphenoxy)-2,2,4,4-tetramethylcyclobutyl)-2-(4-(((1r,3r)-3-((2-(2,6-dioxopiperidin-3-yl)-1,3-dioxoisoindolin-5-yl)oxy)cyclobutyl)(isopropyl)amino)methyl)piperidin-1-yl)-4,6-dimethylpyrimidine-5-carboxamide | 42 and 7 |
| 201 | 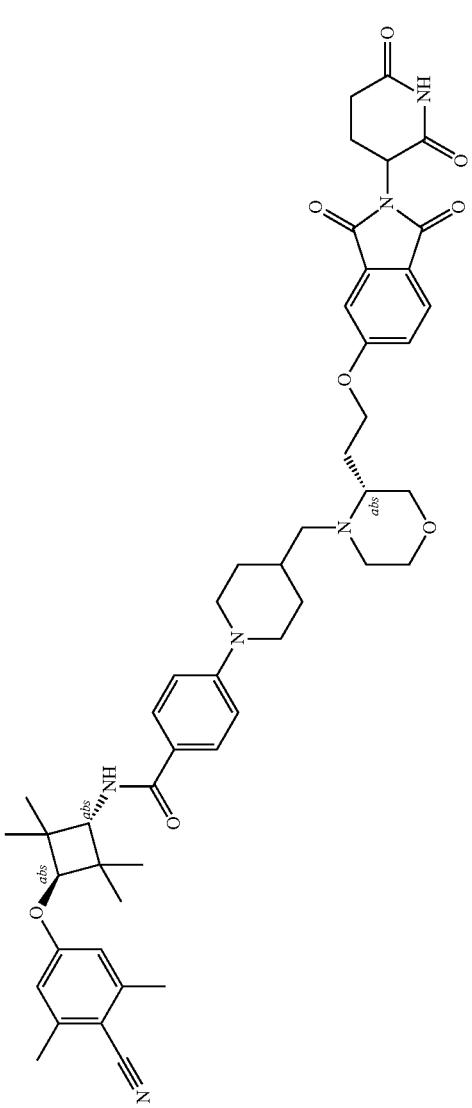 | N-((1r,3R)-3-(4-cyano-3,5-dimethylphenoxy)-2,2,4,4-tetramethylcyclobutyl)-4-(4-((3R)-3-(2-((2-(2,6-dioxopiperidin-3-yl)-1,3-dioxoisoindolin-5-yl)oxy)ethyl)morpholino)methyl)piperidin-1-yl)benzamide | 36 and 7 |

TABLE 1C-continued

Exemplary heterobifunctional compounds of the present disclosure.

| Comp. No. | Structure | Name | Scheme |
|---|---|---|---|
| 202 | 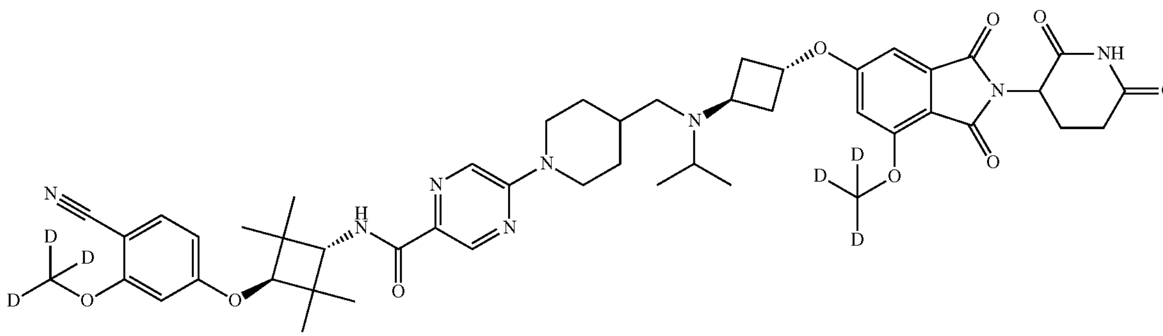 | rac-N-((1r,3r)-3-(4-cyano-3-(methoxy-d3)phenoxy)-2,2,4,4-tetramethylcyclobutyl)-5-(4-((((1r,3r)-3-(2-(2,6-dioxopiperidin-3-yl)-7-(methoxy-d3)-1,3-dioxoisoindolin-5-yl)oxy)cyclobutyl)(isopropyl)amino)methyl)piperidin-1-yl)pyrazine-2-carboxamide | 34 |
| 203 | 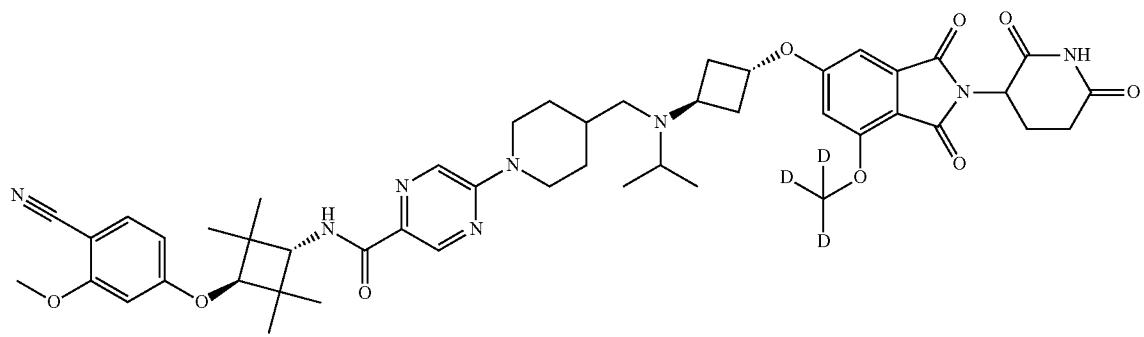 [SMILES: [2H]C([2H])([2H])Oc1cc(O[C@H]2C[C@H](N(CC3CCN(c4cnc(C(=O)N[C@H]5C(C)(C)[C@H](Oc6ccc(C#N)c(OC)c6)C5(C)C)cn4)CC3)C(C)C)C2)cc2c1C(=O)N(C1CCC(=O)NC1=O)C2=O] | rac-N-((1r,3r)-3-(4-cyano-3-methoxyphenoxy)-2,2,4,4-tetramethylcyclobutyl)-5-(4-((((1r,3r)-3-(2-(2,6-dioxopiperidin-3-yl)-7-(methoxy-d3)-1,3-dioxoisoindolin-5-yl)oxy)cyclobutyl)(isopropyl)amino)methyl)piperidin-1-yl)pyrazine-2-carboxamide | 34 |
| 204 | 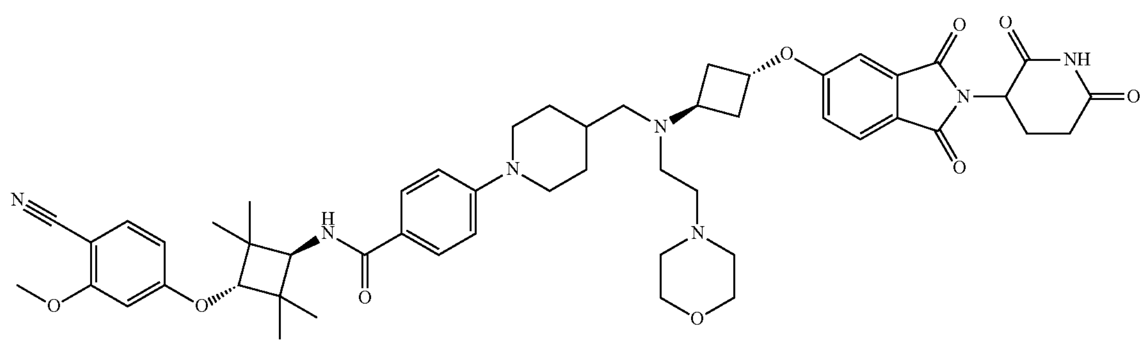 [SMILES: COc1cc(O[C@H]2C(C)(C)[C@H](NC(=O)c3ccc(N4CCC(CN(CCN5CCOCC5)[C@H]5C[C@H](Oc6ccc7c(c6)C(=O)N(C6CCC(=O)NC6=O)C7=O)C5)CC4)cc3)C2(C)C)ccc1C#N] | N-((1r,3r)-3-(4-cyano-3-methoxyphenoxy)-2,2,4,4-tetramethylcyclobutyl)-4-(4-((((1r,3r)-3-(2-(2,6-dioxopiperidin-3-yl)-1,3-dioxoisoindolin-5-yl)oxy)cyclobutyl)(2-morpholinoethyl)amino)methyl)piperidin-1-yl)benzamide | 7 |

TABLE 1C-continued

Exemplary heterobifunctional compounds of the present disclosure.

| Comp No. | Structure | Name | Scheme |
|---|---|---|---|
| 205 | 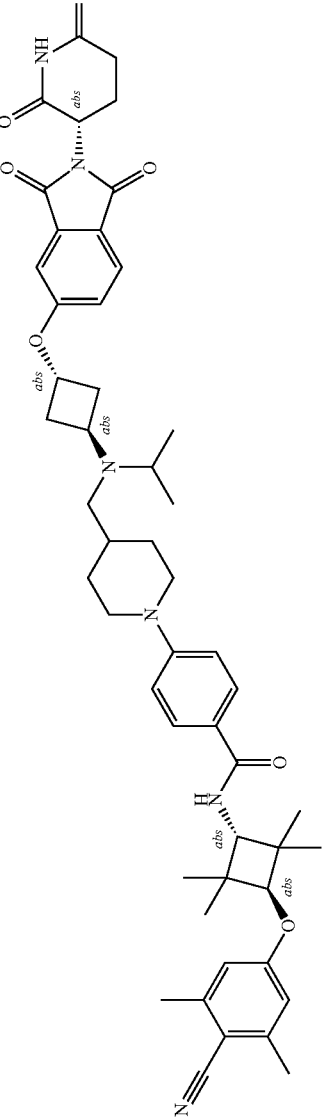 | N-((1r,3r)-3-(4-cyano-3,5-dimethylphenoxy)-2,2,4,4-tetramethylcyclobutyl)-4-(4-(((1S,3r)-3-((2-((S)-2,6-dioxopiperidin-3-yl)-1,3-dioxoisoindolin-5-yl)oxy)cyclobutyl)(isopropyl)amino)methyl)piperidin-1-yl)benzamide | 7 |
| 206 | 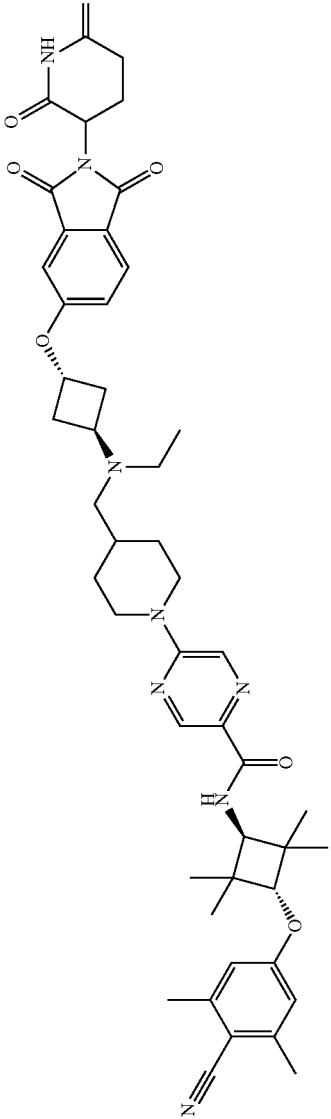 | N-((1r,3r)-3-(4-cyano-3,5-dimethylphenoxy)-2,2,4,4-tetramethylcyclobutyl)-5-(4-(((1r,3r)-3-((2-(2,6-dioxopiperidin-3-yl)-1,3-dioxoisoindolin-5-yl)oxy)cyclobutyl)(ethyl)amino)methyl)piperidin-1-yl)pyrazine-2-carboxamide | 7 |

TABLE 1C-continued

Exemplary heterobifunctional compounds of the present disclosure.

| Comp. No. | Structure | Name | Scheme |
|---|---|---|---|
| 207 | 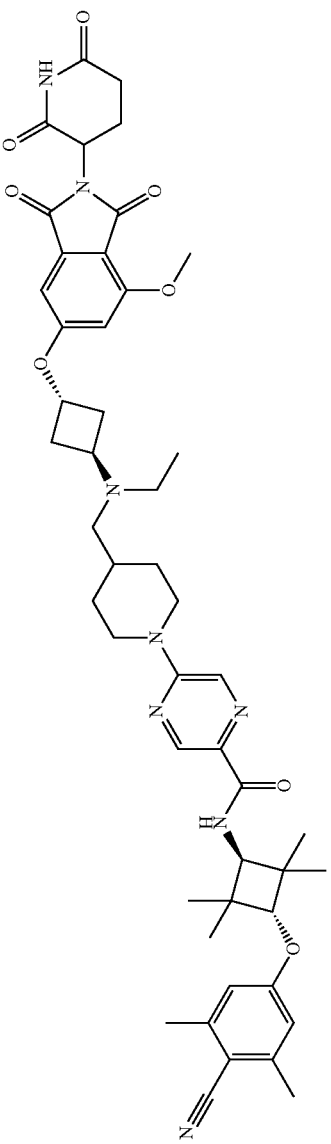 | N-((1r,3r)-3-(4-cyano-3,5-dimethylphenoxy)-2,2,4,4-tetramethylcyclobutyl)-5-(4-((((1r,3r)-3-((2-(2,6-dioxopiperidin-3-yl)-7-methoxy-1,3-dioxoisoindolin-5-yl)oxy)cyclobutyl)(ethyl)amino)methyl)piperidin-1-yl)pyrazine-2-carboxamide | 7 and 1, and custom synthesis provided |
| 208 | 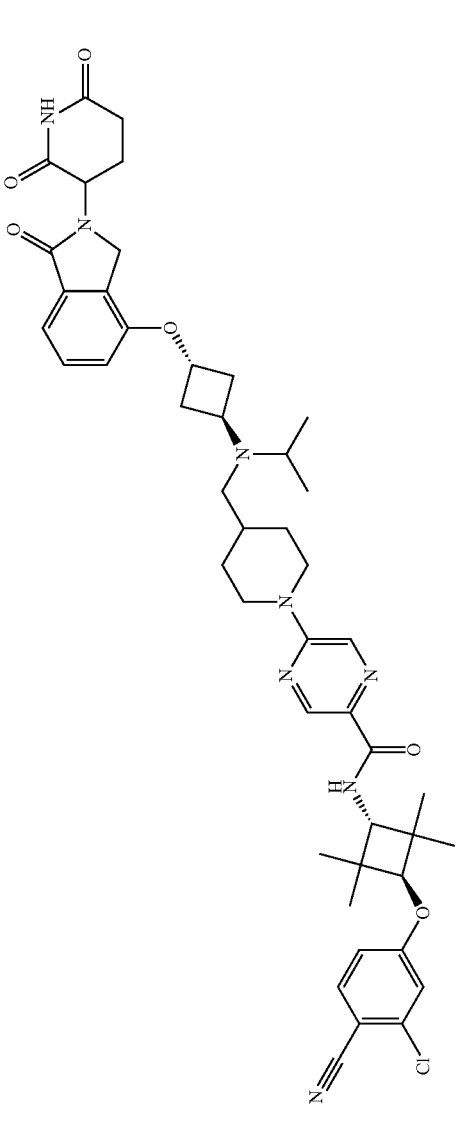 | rac-N-((1r,3r)-3-(3-chloro-4-cyanophenoxy)-2,2,4,4-tetramethylcyclobutyl)-5-(4-((((1r,3r)-3-((2-(2,6-dioxopiperidin-3-yl)-1-oxoisoindolin-4-yl)oxy)cyclobutyl)(isopropyl)amino)methyl)piperidin-1-yl)pyrazine-2-carboxamide | 7 with 3-(4-hydroxy-1-oxoisoindolin-2-yl)piperidine-2,6-dione |

TABLE 1C-continued

Exemplary heterobifunctional compounds of the present disclosure.

| Comp No. | Structure | Name | Scheme |
|---|---|---|---|
| 209 | 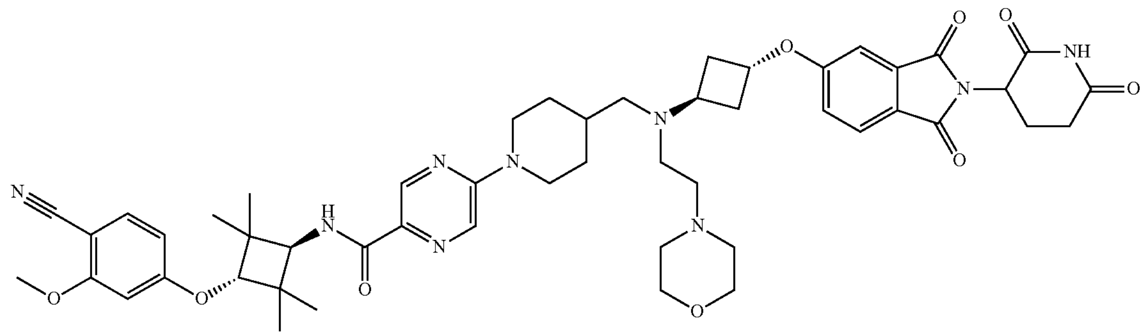 [SMILES: COc1cc(O[C@H]2C(C)(C)[C@H](NC(=O)c3cnc(N4CCC(CN(CCN5CCOCC5)[C@H]5C[C@H](Oc6ccc7c(c6)C(=O)N(C6CCC(=O)NC6=O)C7=O)C5)CC4)cn3)C2(C)C)ccc1C#N] | N-((1r,3r)-3-(4-cyano-3-methoxyphenoxy)-2,2,4,4-tetramethylcyclobutyl)-5-(4-((((1r,3r)-3-((2-(2,6-dioxopiperidin-3-yl)-1,3-dioxoisoindolin-5-yl)oxy)cyclobutyl)(2-morpholinoethyl)amino)methyl)piperidin-1-yl)pyrazine-2-carboxamide | 7 |
| 210 | 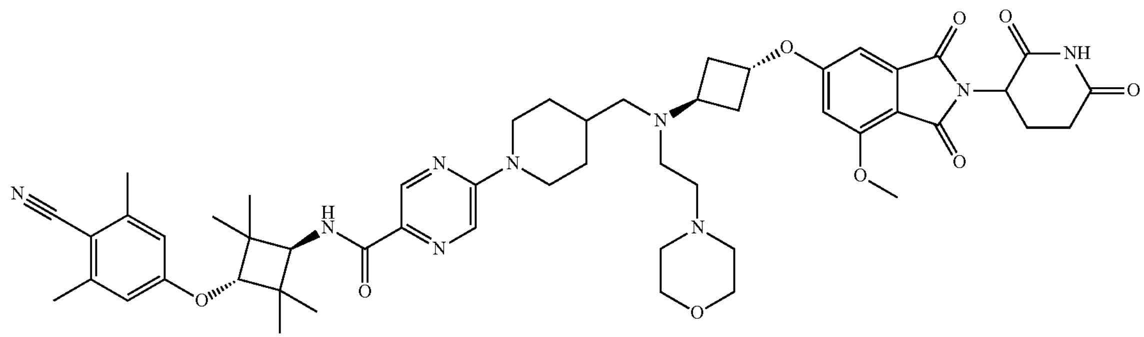 [SMILES: COc1cc(O[C@H]2C[C@H](N(CCN3CCOCC3)CC3CCN(c4cnc(C(=O)N[C@H]5C(C)(C)[C@H](Oc6cc(C)c(C#N)c(C)c6)C5(C)C)cn4)CC3)C2)cc2c1C(=O)N(C1CCC(=O)NC1=O)C2=O] | N-((1r,3r)-3-(4-cyano-3,5-dimethylphenoxy)-2,2,4,4-tetramethylcyclobutyl)-5-(4-((((1r,3r)-3-((2-(2,6-dioxopiperidin-3-yl)-7-methoxy-1,3-dioxoisoindolin-5-yl)oxy)cyclobutyl)(2-morpholinoethyl)amino)methyl)piperidin-1-yl)pyrazine-2-carboxamide | 7 and 1 |
| 211 | 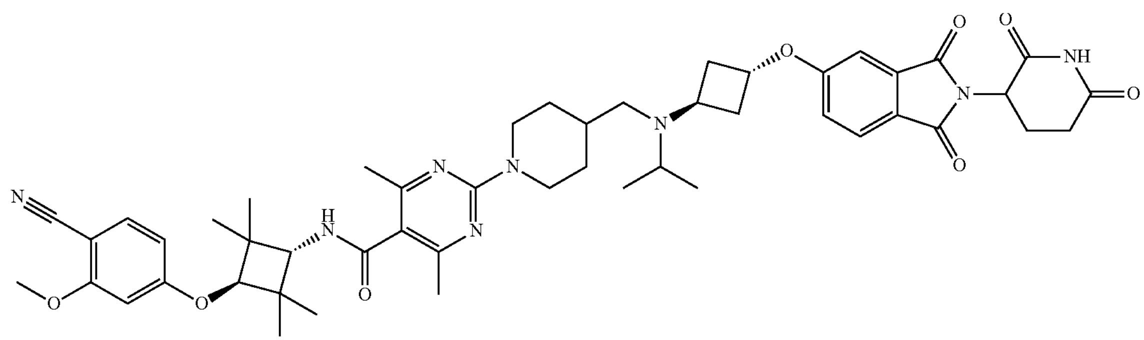 [SMILES: COc1cc(O[C@H]2C(C)(C)[C@H](NC(=O)c3c(C)nc(N4CCC(CN(C(C)C)[C@H]5C[C@H](Oc6ccc7c(c6)C(=O)N(C6CCC(=O)NC6=O)C7=O)C5)CC4)nc3C)C2(C)C)ccc1C#N] | rac-N-((1r,3r)-3-(4-cyano-3-methoxyphenoxy)-2,2,4,4-tetramethylcyclobutyl)-2-(4-((((1r,3r)-3-((2-(2,6-dioxopiperidin-3-yl)-1,3-dioxoisoindolin-5-yl)oxy)cyclobutyl)(isopropyl)amino)methyl)piperidin-1-yl)-4,6-dimethylpyrimidine-5-carboxamide | 42 and 7 |

TABLE 1C-continued

Exemplary heterobifunctional compounds of the present disclosure.

| Comp No. | Structure | Name | Scheme |
|---|---|---|---|
| 212 | 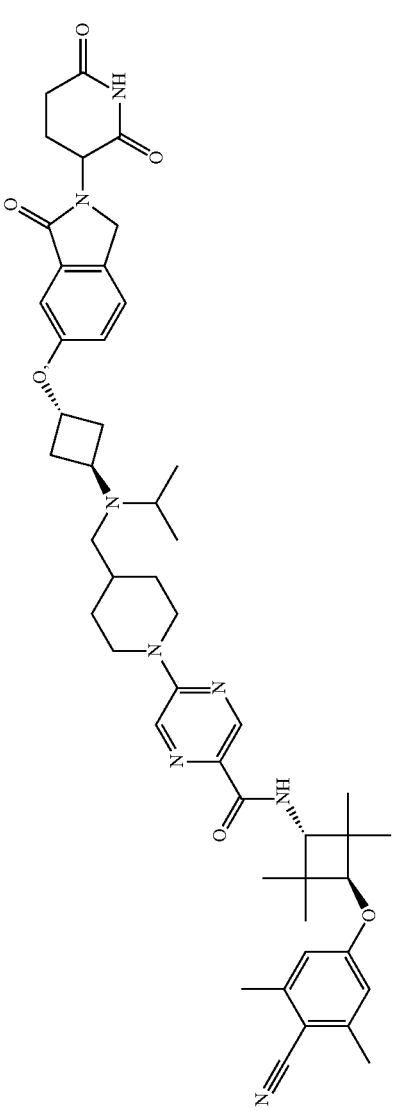 | rac-N-((1r,3r)-3-(4-cyano-3,5-dimethylphenoxy)-2,2,4,4-tetramethylcyclobutyl)-5-(4-(((1r,3r)-3-((2-(2,6-dioxopiperidin-3-yl)-3-oxoisoindolin-5-yl)oxy)cyclobutyl)(isopropyl)amino)methyl)piperidin-1-yl)pyrazine-2-carboxamide | 3 |
| 213 | 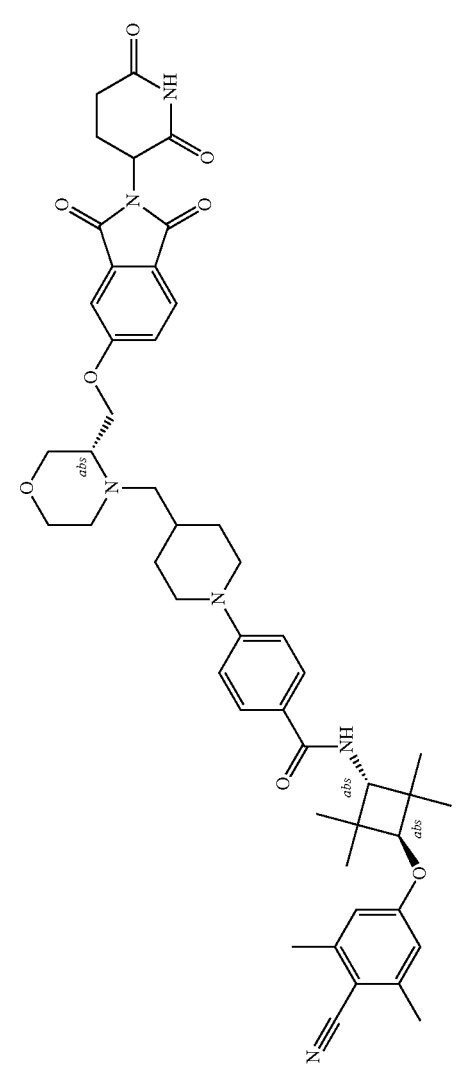 | N-((1r,3R)-3-(4-cyano-3,5-dimethylphenoxy)-2,2,4,4-tetramethylcyclobutyl)-4-(4-(((3R)-3-((2-(2,6-dioxopiperidin-3-yl)-1,3-dioxoisoindolin-5-yl)oxy)methyl)morpholino)methyl)piperidin-1-yl)benzamide | 43 |

TABLE 1C-continued

Exemplary heterobifunctional compounds of the present disclosure.

| Comp No. | Structure | Name | Scheme |
|---|---|---|---|
| 214 | 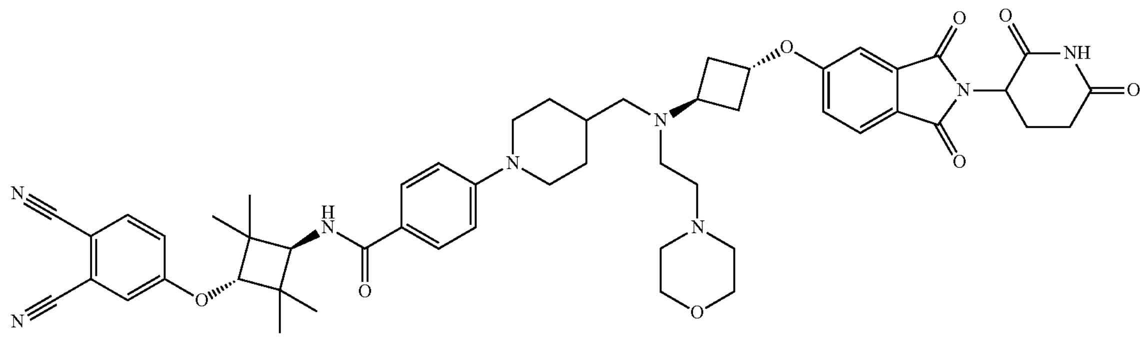 | N-((1r,3r)-3-(3,4-dicyanophenoxy)-2,2,4,4-tetramethylcyclobutyl)-4-(4-(((1r,3r)-3-((2-(2,6-dioxopiperidin-3-yl)-1,3-dioxoisoindolin-5-yl)oxy)cyclobutyl)(2-morpholinoethyl)amino)methyl)piperidin-1-yl)benzamide | 7 |
| 215 | 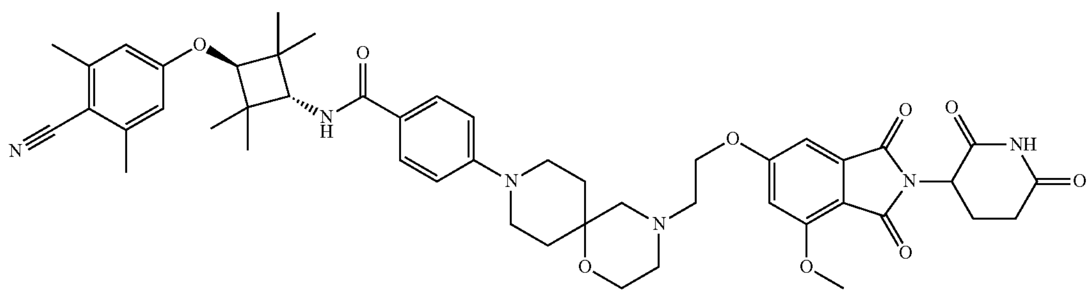 [SMILES: COc1cc(OCCN2CCOC3(CCN(c4ccc(C(=O)N[C@H]5C(C)(C)[C@H](Oc6cc(C)c(C#N)c(C)c6)C5(C)C)cc4)CC3)C2)cc2c1C(=O)N(C1CCC(=O)NC1=O)C2=O] | N-((1r,3r)-3-(4-cyano-3,5-dimethylphenoxy)-2,2,4,4-tetramethylcyclobutyl)-4-(4-(2-((2-(2,6-dioxopiperidin-3-yl)-7-methoxy-1,3-dioxoisoindolin-5-yl)oxy)ethyl)-1-oxa-4,9-diazaspiro[5.5]undecan-9-yl)benzamide | 34 and 45 |

TABLE 1C-continued

Exemplary heterobifunctional compounds of the present disclosure.

| Comp No. | Structure | Name | Scheme |
|---|---|---|---|
| 216 | 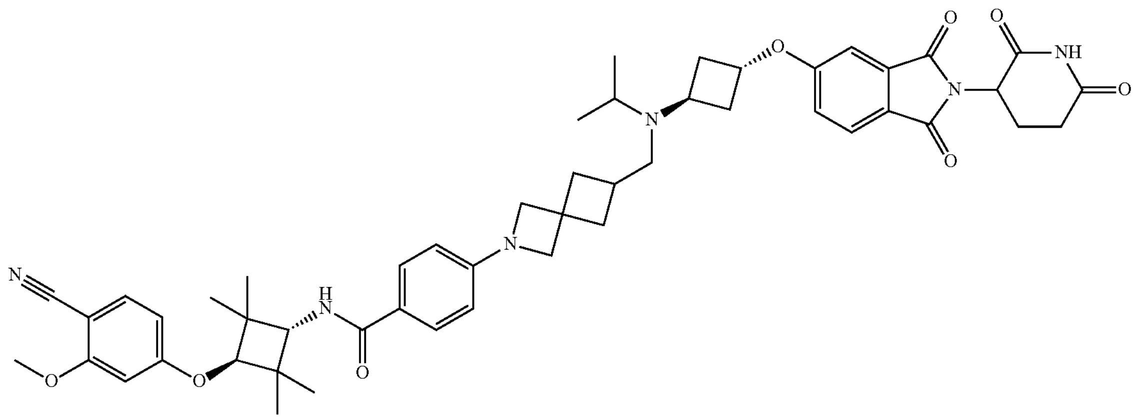 [SMILES: COc1cc(O[C@H]2C(C)(C)[C@H](NC(=O)c3ccc(N4CC5(CC(CN(C(C)C)[C@H]6C[C@H](Oc7ccc8c(c7)C(=O)N(C7CCC(=O)NC7=O)C8=O)C6)C5)C4)cc3)C2(C)C)ccc1C#N] | rac-N-((1r,3r)-3-(4-cyano-3-methoxyphenoxy)-2,2,4,4-tetramethylcyclobutyl)-4-(6-(((1r,3r)-3-((2-(2,6-dioxopiperidin-3-yl)-1,3-dioxoisoindolin-5-yl)oxy)cyclobutyl)(isopropyl)amino)methyl)-2-azaspiro[3.3]heptan-2-yl)benzamide | 7 |
| 217 | 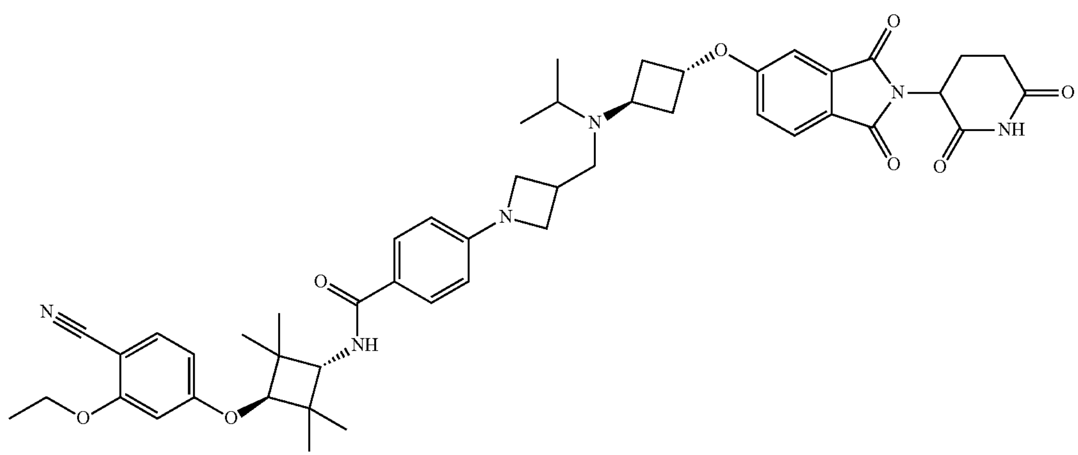 [SMILES: CCOc1cc(O[C@H]2C(C)(C)[C@H](NC(=O)c3ccc(N4CC(CN(C(C)C)[C@H]5C[C@H](Oc6ccc7c(c6)C(=O)N(C6CCC(=O)NC6=O)C7=O)C5)C4)cc3)C2(C)C)ccc1C#N] | N-((1r,3r)-3-(4-cyano-3-ethoxyphenoxy)-2,2,4,4-tetramethylcyclobutyl)-4-(3-(((1r,3r)-3-((2-(2,6-dioxopiperidin-3-yl)-1,3-dioxoisoindolin-5-yl)oxy)cyclobutyl)(isopropyl)amino)methyl)azetidin-1-yl)benzamide | 7 |

TABLE 1C-continued

Exemplary heterobifunctional compounds of the present disclosure.

| Comp No. | Structure | Name | Scheme |
|---|---|---|---|
| 218 | 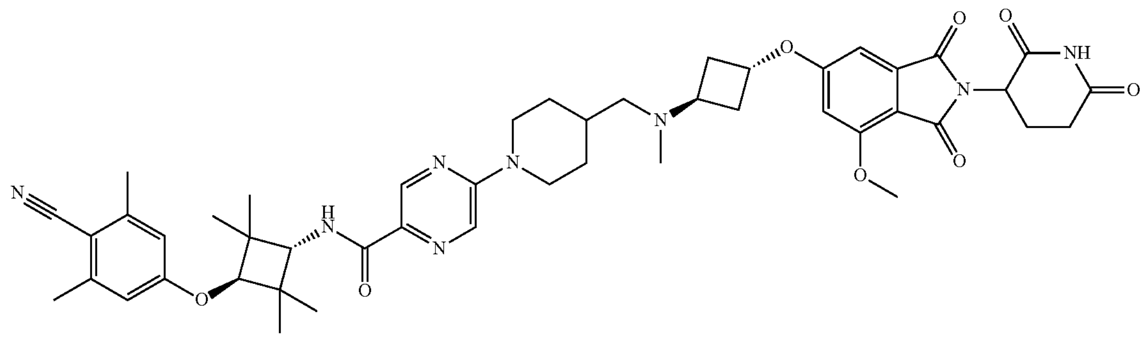 [SMILES: COc1cc(O[C@H]2C[C@H](N(C)CC3CCN(c4cnc(C(=O)N[C@H]5C(C)(C)[C@H](Oc6cc(C)c(C#N)c(C)c6)C5(C)C)cn4)CC3)C2)cc2c1C(=O)N(C1CCC(=O)NC1=O)C2=O] | rac-N-((1r,3r)-3-(4-cyano-3,5-dimethylphenoxy)-2,2,4,4-tetramethylcyclobutyl)-5-(4-(((1r,3r)-3-((2-(2,6-dioxopiperidin-3-yl)-7-methoxy-1,3-dioxoisoindolin-5-yl)oxy)cyclobutyl)(methyl)amino)methyl)piperidin-1-yl)pyrazine-2-carboxamide | 34 |
| 219 | 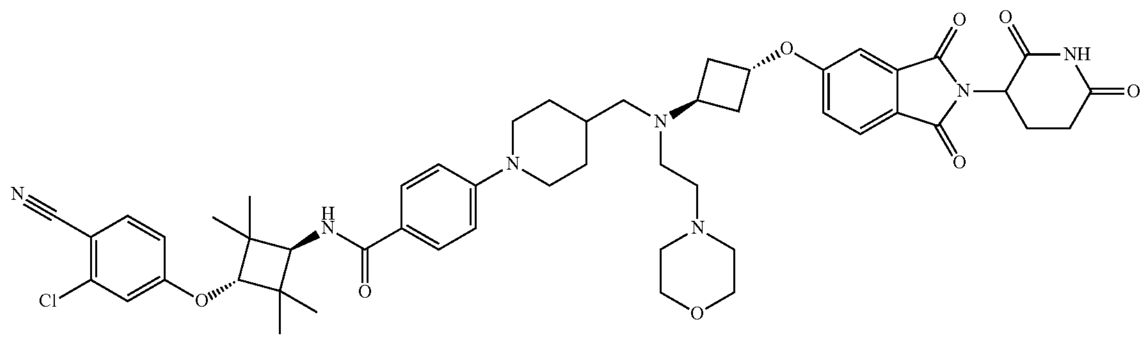 [SMILES: CC1(C)[C@H](NC(=O)c2ccc(N3CCC(CN(CCN4CCOCC4)[C@H]4C[C@H](Oc5ccc6c(c5)C(=O)N(C5CCC(=O)NC5=O)C6=O)C4)CC3)cc2)C(C)(C)[C@H]1Oc1ccc(C#N)c(Cl)c1] | N-((1r,3r)-3-(3-chloro-4-cyanophenoxy)-2,2,4,4-tetramethylcyclobutyl)-4-(4-(((1r,3r)-3-((2-(2,6-dioxopiperidin-3-yl)-1,3-dioxoisoindolin-5-yl)oxy)cyclobutyl)(2-morpholinoethyl)amino)methyl)piperidin-1-yl)benzamide | 7 |
| 220 | 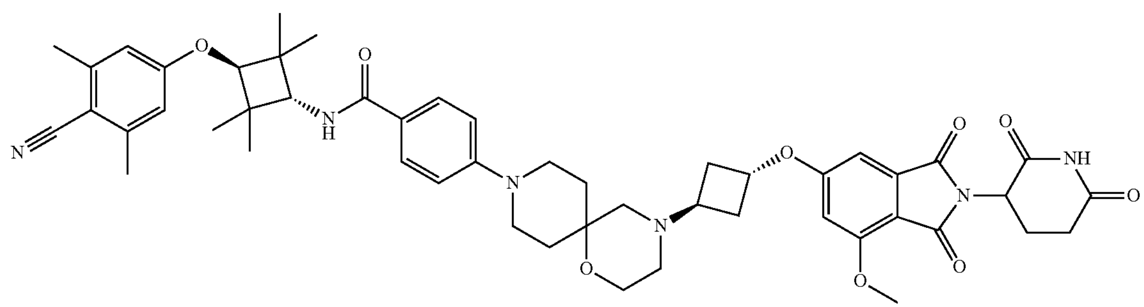 [SMILES: COc1cc(O[C@H]2C[C@H](N3CCOC4(CCN(c5ccc(C(=O)N[C@H]6C(C)(C)[C@H](Oc7cc(C)c(C#N)c(C)c7)C6(C)C)cc5)CC4)C3)C2)cc2c1C(=O)N(C1CCC(=O)NC1=O)C2=O] | rac-N-((1r,3r)-3-(4-cyano-3,5-dimethylphenoxy)-2,2,4,4-tetramethylcyclobutyl)-4-(4-(((1r,3r)-3-((2-(2,6-dioxopiperidin-3-yl)-7-methoxy-1,3-dioxoisoindolin-5-yl)oxy)cyclobutyl)-1-oxa-4,9-diazaspiro[5.5]undecan-9-yl)benzamide | 45 and 34 |

TABLE 1C-continued

Exemplary heterobifunctional compounds of the present disclosure.

| Comp No. | Structure | Name | Scheme |
|---|---|---|---|
| 221 | 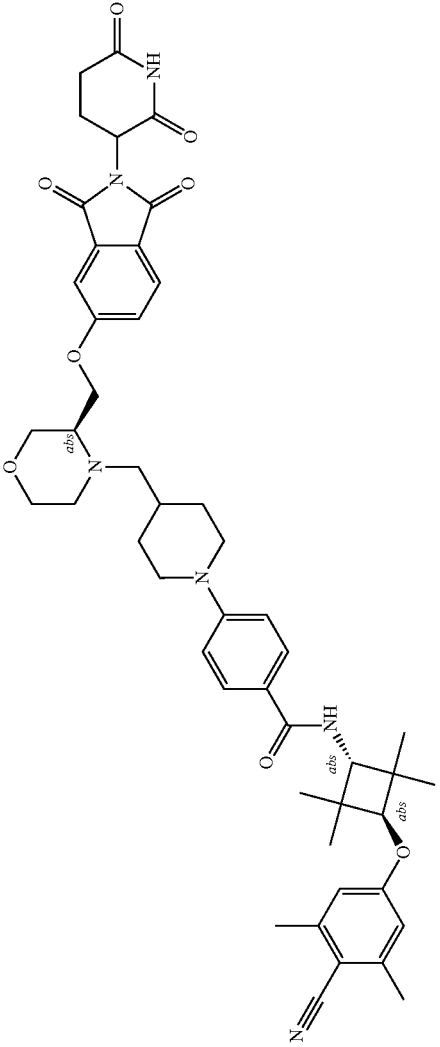 | N-((1r,3S)-3-(4-cyano-3,5-dimethylphenoxy)-2,2,4,4-tetramethylcyclobutyl)-4-(4-(((3S)-3-(((2-(2,6-dioxopiperidin-3-yl)-1,3-dioxoisoindolin-5-yl)oxy)methyl)morpholino)methyl)piperidin-1-yl)benzamide | 43 |
| 222 | 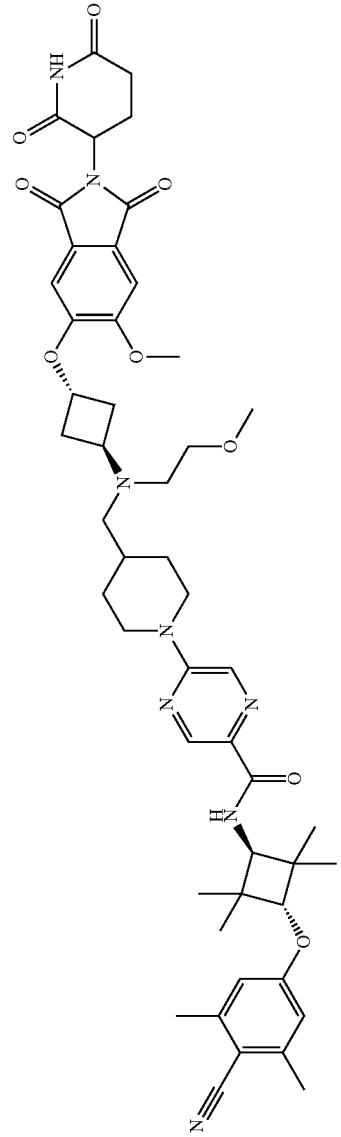 | rac-N-((1r,3r)-3-(4-cyano-3,5-dimethylphenoxy)-2,2,4,4-tetramethylcyclobutyl)-5-(4-((((1r,3r)-3-((2-(2,6-dioxopiperidin-3-yl)-6-methoxy-1,3-dioxoisoindolin-5-yl)oxy)cyclobutyl)(2-methoxyethyl)amino)methyl)piperidin-1-yl)pyrazine-2-carboxamide | 39 and 7 |

TABLE 1C-continued

Exemplary heterobifunctional compounds of the present disclosure.

| Comp No. | Structure | Name | Scheme |
|---|---|---|---|
| 223 | 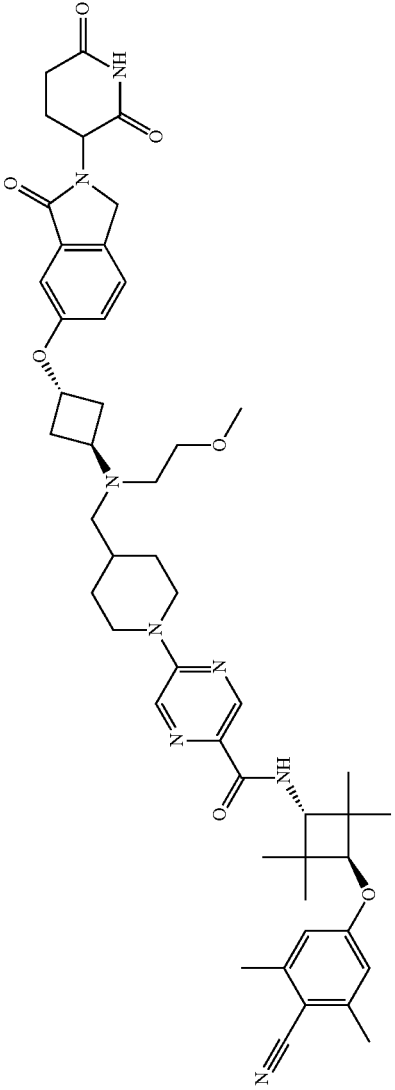 | rac-N-((1r,3r)-3-(4-cyano-3,5-dimethylphenoxy)-2,2,4,4-tetramethylcyclobutyl)-5-(4-((((1r,3r)-3-((2-(2,6-dioxopiperidin-3-yl)-3-oxoisoindolin-5-yl)oxy)cyclobutyl)(2-methoxyethyl)amino)methyl)piperidin-1-yl)pyrazine-2-carboxamide | 3 |
| 224 | 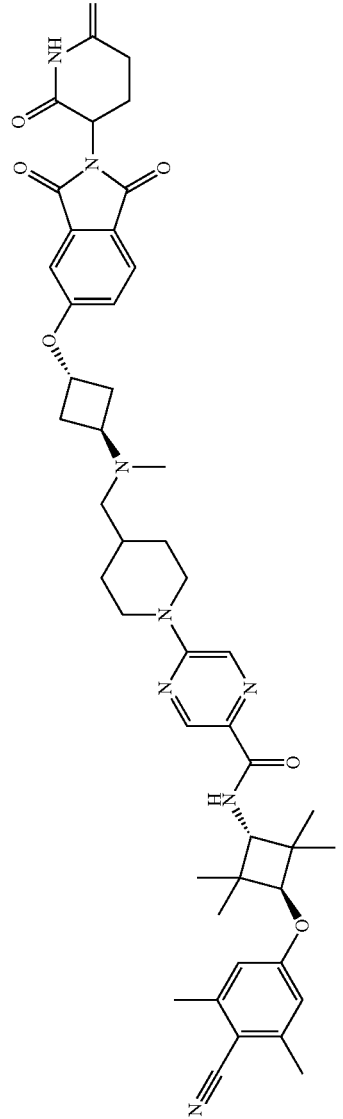 | rac-N-((1r,3r)-3-(4-cyano-3,5-dimethylphenoxy)-2,2,4,4-tetramethylcyclobutyl)-5-(4-((((1r,3r)-3-((2-(2,6-dioxopiperidin-3-yl)-1,3-dioxoisoindolin-5-yl)oxy)cyclobutyl)(methyl)amino)methyl)piperidin-1-yl)pyrazine-2-carboxamide | 7 |

TABLE 1C-continued

Exemplary heterobifunctional compounds of the present disclosure.

| Comp No. | Structure | Name | Scheme |
|---|---|---|---|
| 225 | 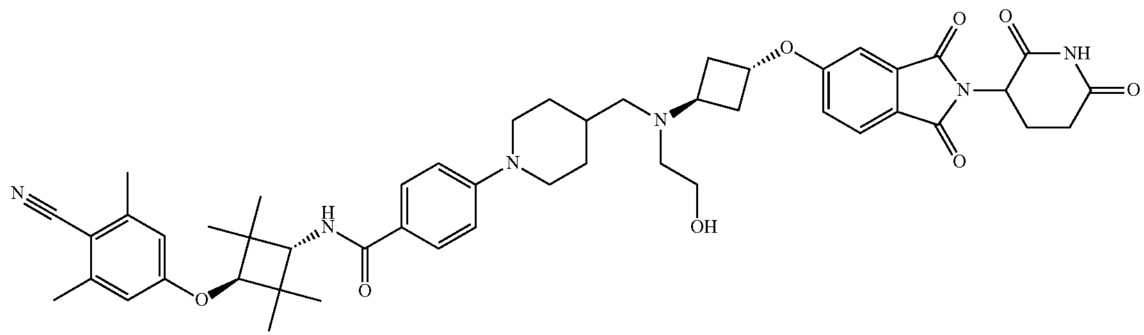 [SMILES: Cc1cc(O[C@H]2C(C)(C)[C@H](NC(=O)c3ccc(N4CCC(CN(CCO)[C@H]5C[C@H](Oc6ccc7c(c6)C(=O)N(C6CCC(=O)NC6=O)C7=O)C5)CC4)cc3)C2(C)C)cc(C)c1C#N] | rac-N-((1r,3r)-3-(4-cyano-3,5-dimethylphenoxy)-2,2,4,4-tetramethylcyclobutyl)-4-(((1r,3r)-3-((2-(2,6-dioxopiperidin-3-yl)-1,3-dioxoisoindolin-5-yl)oxy)cyclobutyl)(2-hydroxyethyl)amino)methyl)piperidin-1-yl)benzamide | 7 |
| 226 | 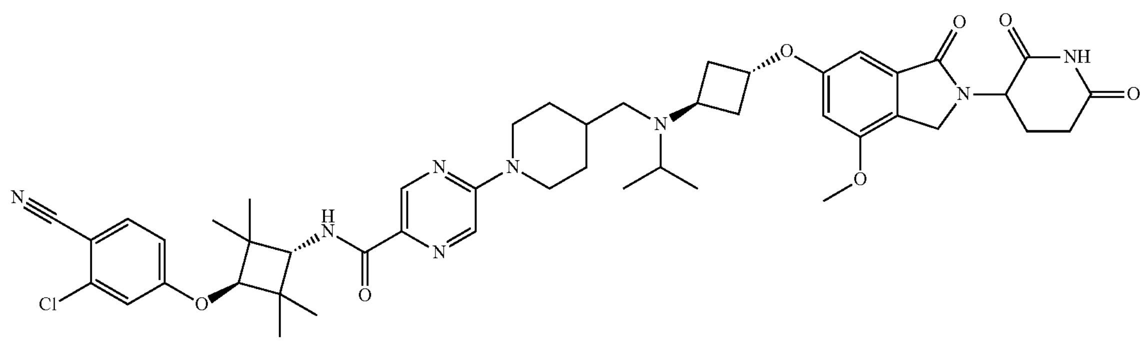 [SMILES: COc1cc(O[C@H]2C[C@H](N(CC3CCN(c4cnc(C(=O)N[C@H]5C(C)(C)[C@H](Oc6ccc(C#N)c(Cl)c6)C5(C)C)cn4)CC3)C(C)C)C2)cc2c1CN(C1CCC(=O)NC1=O)C2=O] | rac-N-((1r,3r)-3-(3-chloro-4-cyanophenoxy)-2,2,4,4-tetramethylcyclobutyl)-5-(4-(((1r,3r)-3-((2-(2,6-dioxopiperidin-3-yl)-7-methoxy-3-oxoisoindolin-5-yl)oxy)cyclobutyl)(isopropyl)amino)methyl)piperidin-1-yl)pyrazine-2-carboxamide | 46 and 7 |

TABLE 1C-continued

Exemplary heterobifunctional compounds of the present disclosure.

| Comp No. | Structure | Name | Scheme |
|---|---|---|---|
| 227 | 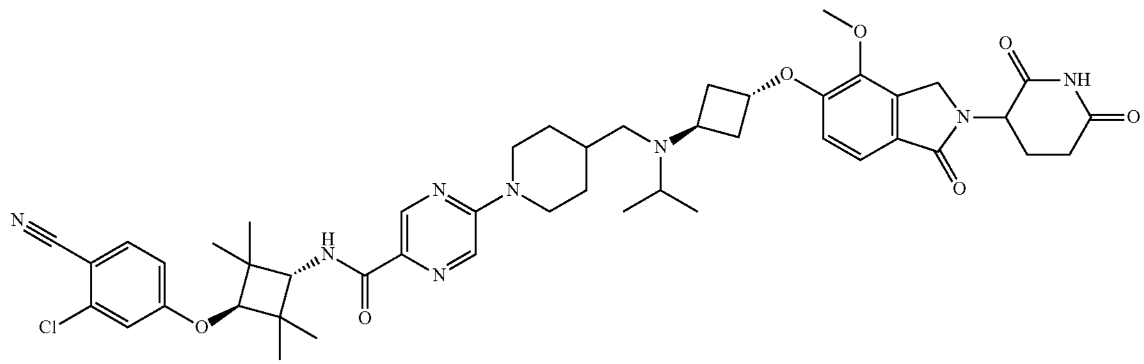 [SMILES: COc1c(O[C@H]2C[C@H](N(CC3CCN(c4cnc(C(=O)N[C@H]5C(C)(C)[C@H](Oc6ccc(C#N)c(Cl)c6)C5(C)C)cn4)CC3)C(C)C)C2)ccc2c1CN(C1CCC(=O)NC1=O)C2=O] | rac-N-((1r,3r)-3-(3-chloro-4-cyanophenoxy)-2,2,4,4-tetramethylcyclobutyl)-5-(4-((((1r,3r)-3-((2-(2,6-dioxopiperidin-3-yl)-4-methoxy-1-oxoisoindolin-5-yl)oxy)cyclobutyl)(isopropyl)amino)methyl)piperidin-1-yl)pyrazine-2-carboxamide | 47 and custom synthesis provided |
| 228 | 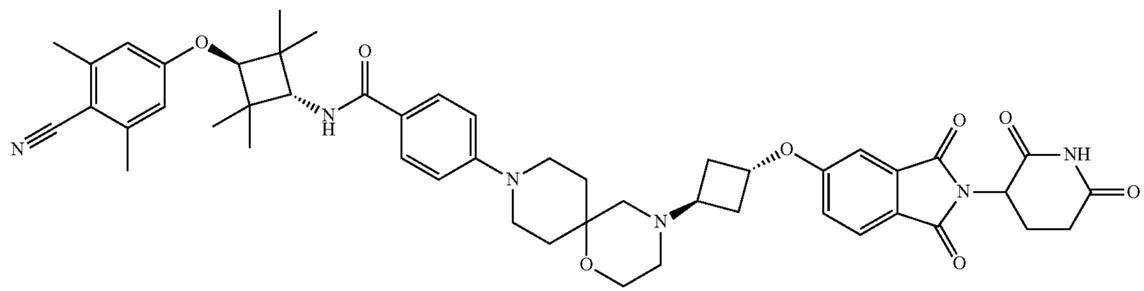 [SMILES: Cc1cc(O[C@H]2C(C)(C)[C@H](NC(=O)c3ccc(N4CCC5(CC4)CN([C@H]4C[C@H](Oc6ccc7c(c6)C(=O)N(C6CCC(=O)NC6=O)C7=O)C4)CCO5)cc3)C2(C)C)cc(C)c1C#N] | rac-N-((1r,3r)-3-(4-cyano-3,5-dimethylphenoxy)-2,2,4,4-tetramethylcyclobutyl)-4-(4-((1r,3r)-3-((2-(2,6-dioxopiperidin-3-yl)-1,3-dioxoisoindolin-5-yl)oxy)cyclobutyl)-1-oxa-4,9-diazaspiro[5.5]undecan-9-yl)benzamide | 45 |
| 229 | 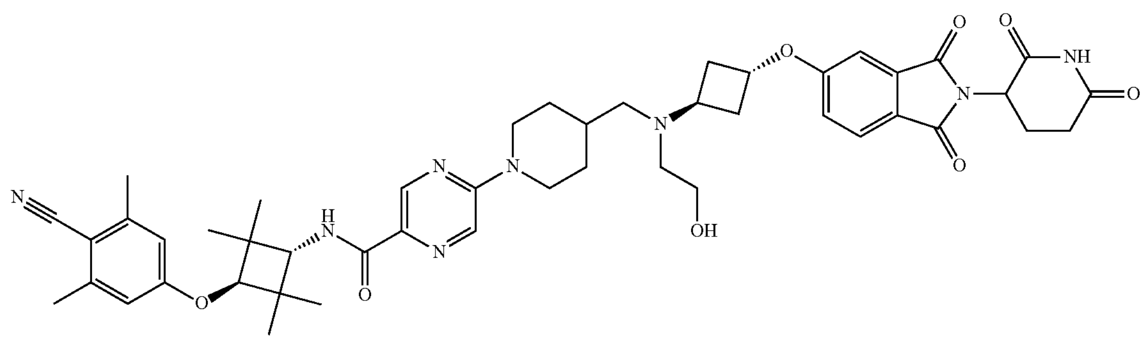 [SMILES: Cc1cc(O[C@H]2C(C)(C)[C@H](NC(=O)c3cnc(N4CCC(CN(CCO)[C@H]5C[C@H](Oc6ccc7c(c6)C(=O)N(C6CCC(=O)NC6=O)C7=O)C5)CC4)cn3)C2(C)C)cc(C)c1C#N] | rac-N-((1r,3r)-3-(4-cyano-3,5-dimethylphenoxy)-2,2,4,4-tetramethylcyclobutyl)-5-(4-((((1r,3r)-3-((2-(2,6-dioxopiperidin-3-yl)-1,3-dioxoisoindolin-5-yl)oxy)cyclobutyl)(2-hydroxyethyl)amino)methyl)piperidin-1-yl)pyrazine-2-carboxamide | 7 |

TABLE 1C-continued

Exemplary heterobifunctional compounds of the present disclosure.

| Comp No. | Structure | Name | Scheme |
|---|---|---|---|
| 230 | 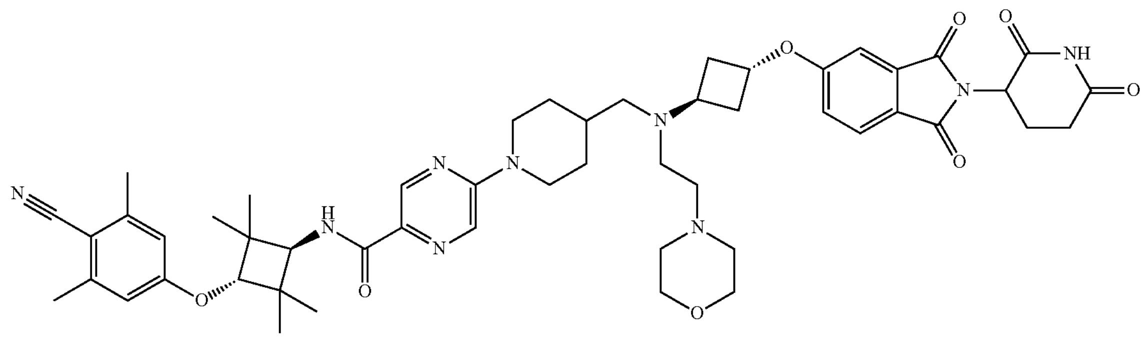 [SMILES: Cc1cc(O[C@H]2C(C)(C)[C@H](NC(=O)c3cnc(N4CCC(CN(CCN5CCOCC5)[C@H]5C[C@H](Oc6ccc7c(c6)C(=O)N(C6CCC(=O)NC6=O)C7=O)C5)CC4)cn3)C2(C)C)cc(C)c1C#N] | N-((1r,3r)-3-(4-cyano-3,5-dimethylphenoxy)-2,2,4,4-tetramethylcyclobutyl)-5-(4-(((1r,3r)-3-((2-(2,6-dioxopiperidin-3-yl)-1,3-dioxoisoindolin-5-yl)oxy)cyclobutyl)(2-morpholinoethyl)amino)methyl)piperidin-1-yl)pyrazine-2-carboxamide | 7 |
| 231 | 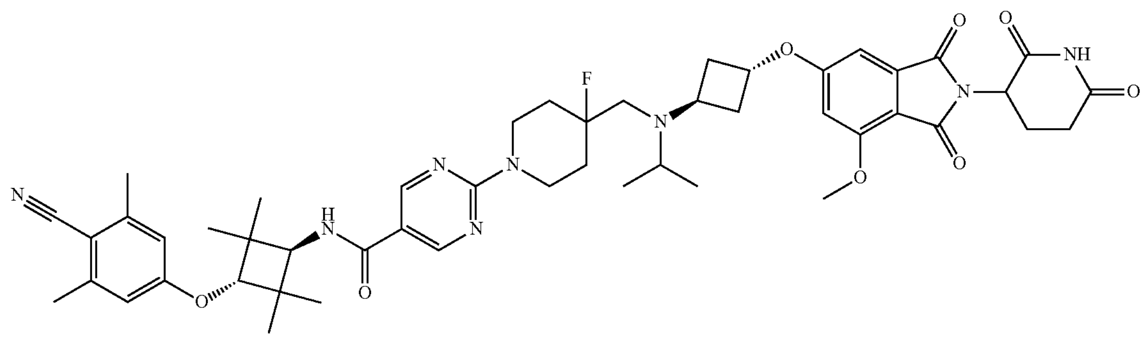 [SMILES: COc1cc(O[C@H]2C[C@H](N(CC3(F)CCN(c4ncc(C(=O)N[C@H]5C(C)(C)[C@H](Oc6cc(C)c(C#N)c(C)c6)C5(C)C)cn4)CC3)C(C)C)C2)cc2c1C(=O)N(C1CCC(=O)NC1=O)C2=O] | N-((1r,3r)-3-(4-cyano-3,5-dimethylphenoxy)-2,2,4,4-tetramethylcyclobutyl)-2-(4-(((1r,3r)-3-((2-(2,6-dioxopiperidin-3-yl)-7-methoxy-1,3-dioxoisoindolin-5-yl)oxy)cyclobutyl)(isopropyl)amino)methyl)-4-fluoropiperidin-1-yl)pyrimidine-5-carboxamide | 7, 1, and 48 |
| 232 | 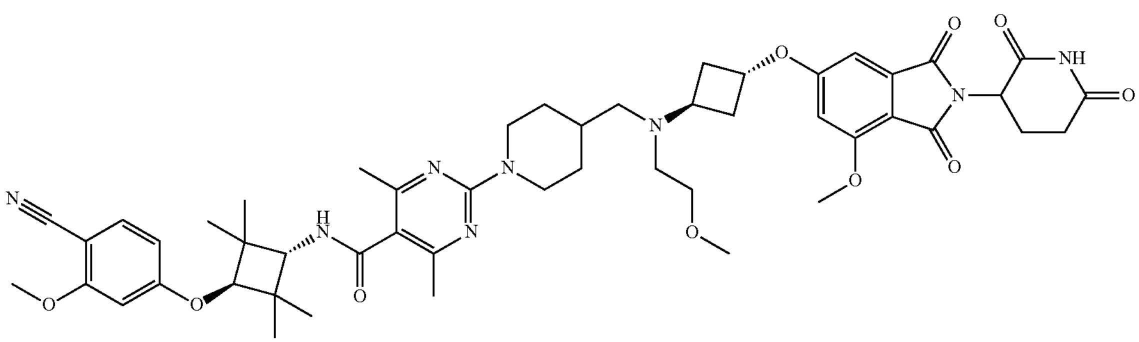 [SMILES: COCCN(CC1CCN(c2nc(C)c(C(=O)N[C@H]3C(C)(C)[C@H](Oc4ccc(C#N)c(OC)c4)C3(C)C)c(C)n2)CC1)[C@H]1C[C@H](Oc2cc(OC)c3c(c2)C(=O)N(C2CCC(=O)NC2=O)C3=O)C1] | rac-N-((1r,3r)-3-(4-cyano-3-methoxyphenoxy)-2,2,4,4-tetramethylcyclobutyl)-2-(4-(((1r,3r)-3-((2-(2,6-dioxopiperidin-3-yl)-7-methoxy-1,3-dioxoisoindolin-5-yl)oxy)cyclobutyl)(2-methoxyethyl)amino)methyl)piperidin-1-yl)-4,6-dimethylpyrimidine-5-carboxamide | 42 and 7 |

TABLE 1C-continued

Exemplary heterobifunctional compounds of the present disclosure.

| Comp No. | Structure | Name | Scheme |
|---|---|---|---|
| 233 | 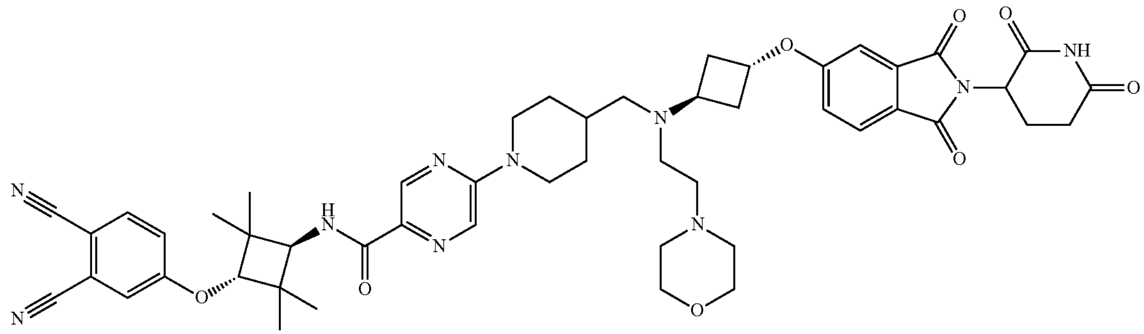 [SMILES: CC1(C)[C@H](NC(=O)c2cnc(N3CCC(CN(CCN4CCOCC4)[C@H]4C[C@H](Oc5ccc6c(c5)C(=O)N(C5CCC(=O)NC5=O)C6=O)C4)CC3)cn2)C(C)(C)[C@H]1Oc1ccc(C#N)c(C#N)c1] | N-((1r,3r)-3-(3,4-dicyanophenoxy)-2,2,4,4-tetramethylcyclobutyl)-5-(4-(((1r,3r)-3-((2-(2,6-dioxopiperidin-3-yl)-1,3-dioxoisoindolin-5-yl)oxy)cyclobutyl)(2-morpholinoethyl)amino)methyl)piperidin-1-yl)pyrazine-2-carboxamide | 7 and 1 |
| 234 | 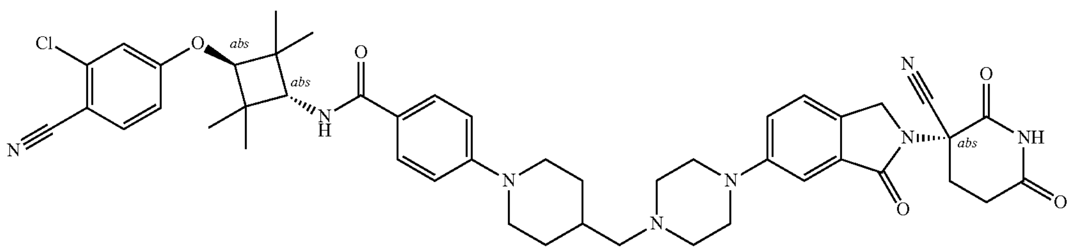 [SMILES: CC1(C)[C@H](NC(=O)c2ccc(N3CCC(CN4CCN(c5ccc6c(c5)C(=O)N([C@@]5(C#N)CCC(=O)NC5=O)C6)CC4)CC3)cc2)C(C)(C)[C@H]1Oc1ccc(C#N)c(Cl)c1] | N-((1r,3r)-3-(3-chloro-4-cyanophenoxy)-2,2,4,4-tetramethylcyclobutyl)-4-(4-((4-(2-(R)-3-cyano-2,6-dioxopiperidin-3-yl)-3-oxoisoindolin-5-yl)piperazin-1-yl)methyl)piperidin-1-yl)benzamide | 49 and 25 |
| 235 | 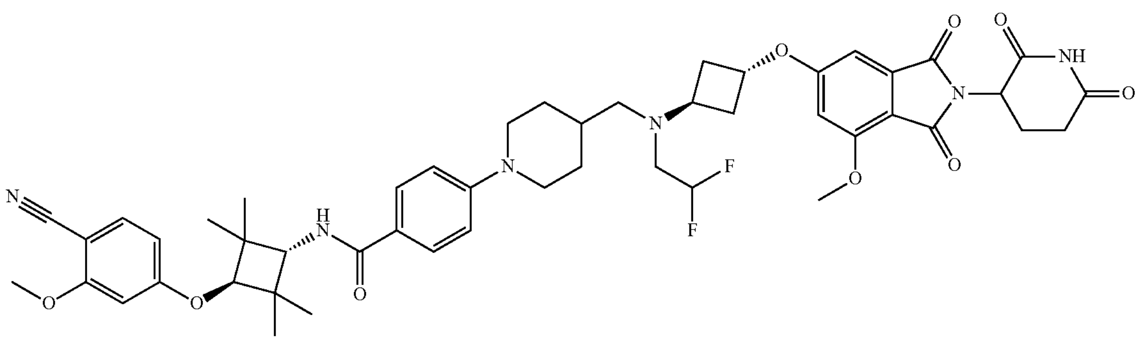 [SMILES: COc1cc(O[C@H]2C(C)(C)[C@H](NC(=O)c3ccc(N4CCC(CN(CC(F)F)[C@H]5C[C@H](Oc6cc(OC)c7c(c6)C(=O)N(C6CCC(=O)NC6=O)C7=O)C5)CC4)cc3)C2(C)C)ccc1C#N] | N-((1r,3r)-3-(4-cyano-3-methoxyphenoxy)-2,2,4,4-tetramethylcyclobutyl)-4-(4-(((1r,3r)-3-(2,2-difluoroethyl)((1r,3r)-3-((2-(2,6-dioxopiperidin-3-yl)-7-methoxy-1,3-dioxoisoindolin-5-yl)oxy)cyclobutyl)amino)methyl)piperidin-1-yl)benzamide | 7 and 1 |

TABLE 1C-continued

Exemplary heterobifunctional compounds of the present disclosure.

| Comp No. | Structure | Name | Scheme |
|---|---|---|---|
| 236 | 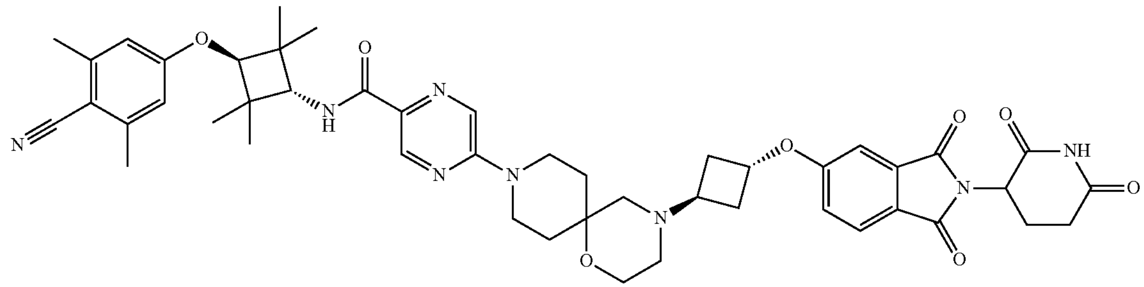 [SMILES: Cc1cc(O[C@H]2C(C)(C)[C@H](NC(=O)c3cnc(N4CCC5(CC4)CN([C@H]4C[C@H](Oc6ccc7c(c6)C(=O)N(C6CCC(=O)NC6=O)C7=O)C4)CCO5)cn3)C2(C)C)cc(C)c1C#N] | rac-N-((1r,3r)-3-(4-cyano-3,5-dimethylphenoxy)-2,2,4,4-tetramethylcyclobutyl)-5-(4-((1r,3r)-3-((2-(2,6-dioxopiperidin-3-yl)-1,3-dioxoisoindolin-5-yl)oxy)cyclobutyl)-1-oxa-4,9-diazaspiro[5.5]undecan-9-yl)pyrazine-2-carboxamide | 45 |
| 237 | 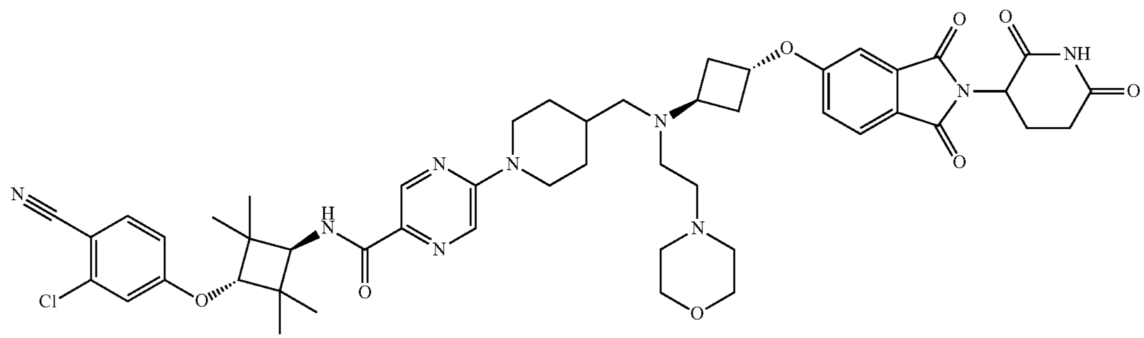 [SMILES: CC1(C)[C@H](NC(=O)c2cnc(N3CCC(CN(CCN4CCOCC4)[C@H]4C[C@H](Oc5ccc6c(c5)C(=O)N(C5CCC(=O)NC5=O)C6=O)C4)CC3)cn2)C(C)(C)[C@H]1Oc1ccc(C#N)c(Cl)c1] | N-((1r,3r)-3-(3-chloro-4-cyanophenoxy)-2,2,4,4-tetramethylcyclobutyl)-5-(4-(((1r,3r)-3-((2-(2,6-dioxopiperidin-3-yl)-1,3-dioxoisoindolin-5-yl)oxy)cyclobutyl)(2-morpholinoethyl)amino)methyl)piperidin-1-yl)pyrazine-2-carboxamide | 7 |
| 238 | 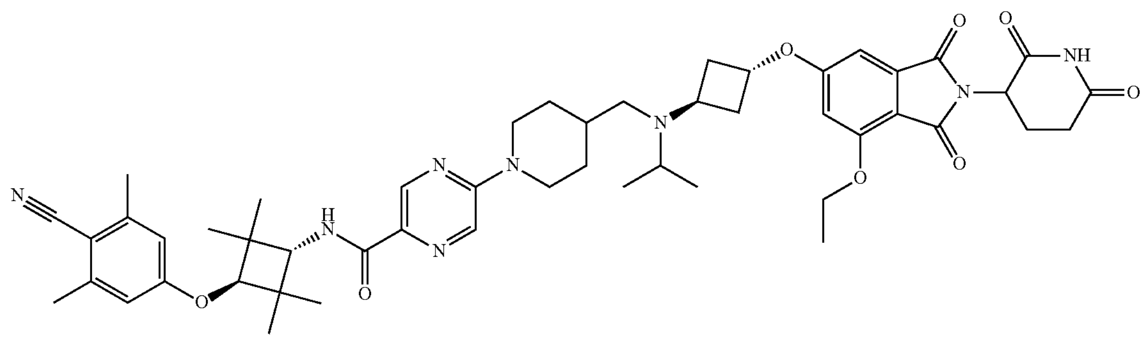 [SMILES: CCOc1cc(O[C@H]2C[C@H](N(CC3CCN(c4cnc(C(=O)N[C@H]5C(C)(C)[C@H](Oc6cc(C)c(C#N)c(C)c6)C5(C)C)cn4)CC3)C(C)C)C2)cc2c1C(=O)N(C1CCC(=O)NC1=O)C2=O] | rac-N-((1r,3r)-3-(4-cyano-3,5-dimethylphenoxy)-2,2,4,4-tetramethylcyclobutyl)-5-(4-(((1r,3r)-3-((2-(2,6-dioxopiperidin-3-yl)-7-ethoxy-1,3-dioxoisoindolin-5-yl)oxy)cyclobutyl)(isopropyl)amino)methyl)piperidin-1-yl)pyrazine-2-carboxamide | 34 |

TABLE 1C-continued

Exemplary heterobifunctional compounds of the present disclosure.

| Comp No. | Structure | Name | Scheme |
|---|---|---|---|
| 239 | 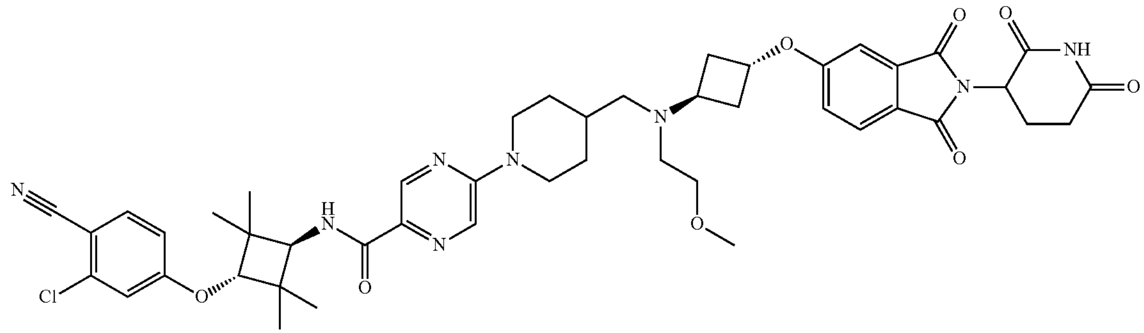 [SMILES: COCCN(CC1CCN(c2cnc(C(=O)N[C@H]3C(C)(C)[C@H](Oc4ccc(C#N)c(Cl)c4)C3(C)C)cn2)CC1)[C@H]1C[C@H](Oc2ccc3c(c2)C(=O)N(C2CCC(=O)NC2=O)C3=O)C1] | N-((1r,3r)-3-(3-chloro-4-cyanophenoxy)-2,2,4,4-tetramethylcyclobutyl)-5-(4-(((1r,3r)-3-((2-(2,6-dioxopiperidin-3-yl)-1,3-dioxoisoindolin-5-yl)oxy)cyclobutyl)(2-methoxyethyl)amino)methyl)piperidin-1-yl)pyrazine-2-carboxamide | 7 |
| 240 | 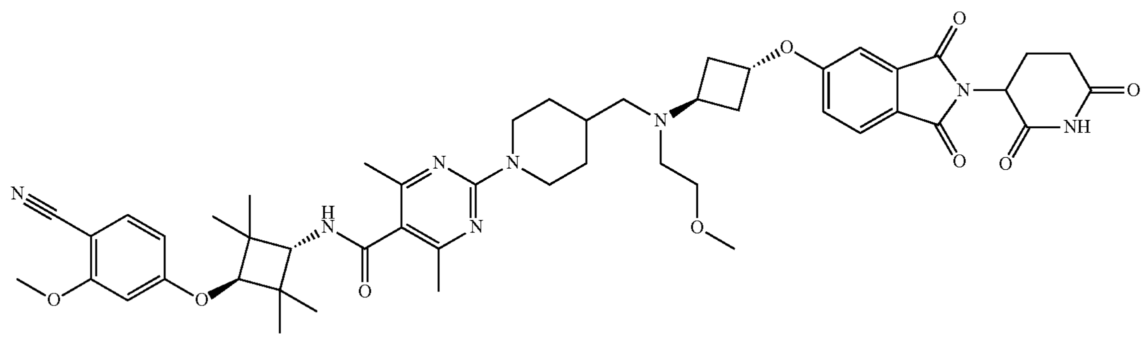 [SMILES: COCCN(CC1CCN(c2nc(C)c(C(=O)N[C@H]3C(C)(C)[C@H](Oc4ccc(C#N)c(OC)c4)C3(C)C)c(C)n2)CC1)[C@H]1C[C@H](Oc2ccc3c(c2)C(=O)N(C2CCC(=O)NC2=O)C3=O)C1] | rac-N-((1r,3r)-3-(4-cyano-3-methoxyphenoxy)-2,2,4,4-tetramethylcyclobutyl)-2-(4-(((1r,3r)-3-((2-(2,6-dioxopiperidin-3-yl)-1,3-dioxoisoindolin-5-yl)oxy)cyclobutyl)(2-methoxyethyl)amino)methyl)piperidin-1-yl)-4,6-dimethylpyrimidine-5-carboxamide | 42 and 7 |
| 241 | 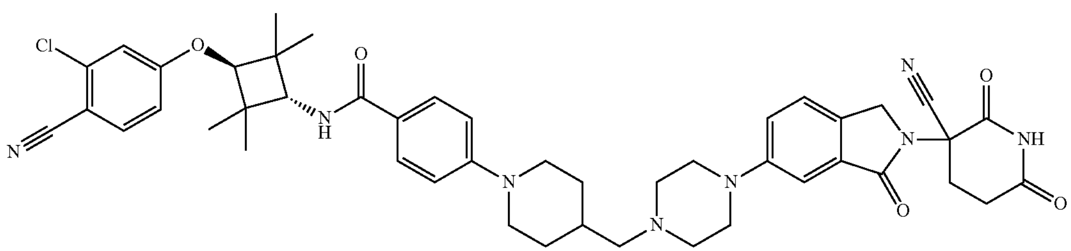 [SMILES: CC1(C)[C@H](NC(=O)c2ccc(N3CCC(CN4CCN(c5ccc6c(c5)C(=O)N(C5(C#N)CCC(=O)NC5=O)C6)CC4)CC3)cc2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-4-(4-((4-(2-(3-cyano-2,6-dioxopiperidin-3-yl)-3-oxoisoindolin-5-yl)piperazin-1-yl)methyl)piperidin-1-yl)benzamide | 49 and 25 |

TABLE 1C-continued

Exemplary heterobifunctional compounds of the present disclosure.

| Comp No. | Structure | Name | Scheme |
|---|---|---|---|
| 242 | 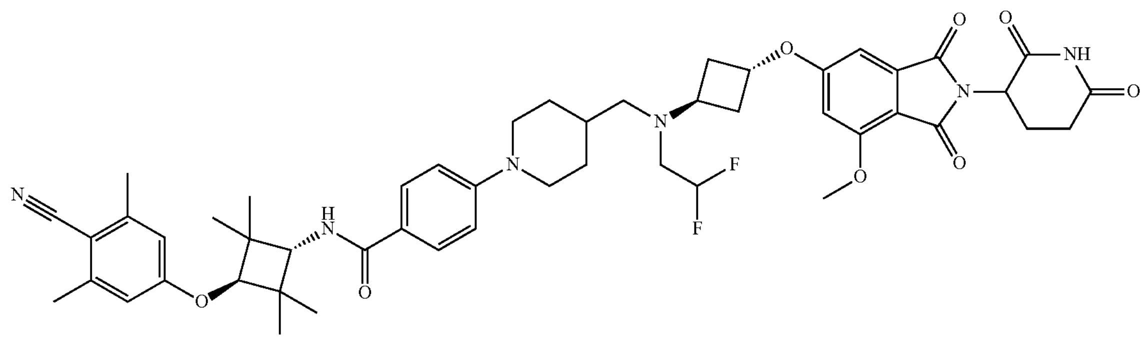 [SMILES: COc1cc(O[C@H]2C[C@H](N(CC(F)F)CC3CCN(c4ccc(C(=O)N[C@H]5C(C)(C)[C@H](Oc6cc(C)c(C#N)c(C)c6)C5(C)C)cc4)CC3)C2)cc2c1C(=O)N(C1CCC(=O)NC1=O)C2=O] | N-((1r,3r)-3-(4-cyano-3,5-dimethylphenoxy)-2,2,4,4-tetramethylcyclobutyl)-4-(4-(((2,2-difluoroethyl)((1r,3r)-3-((2-(2,6-dioxopiperidin-3-yl)-7-methoxy-1,3-dioxoisoindolin-5-yl)oxy)cyclobutyl)amino)methyl)piperidin-1-yl)benzamide | 7 and 1 |
| 243 | 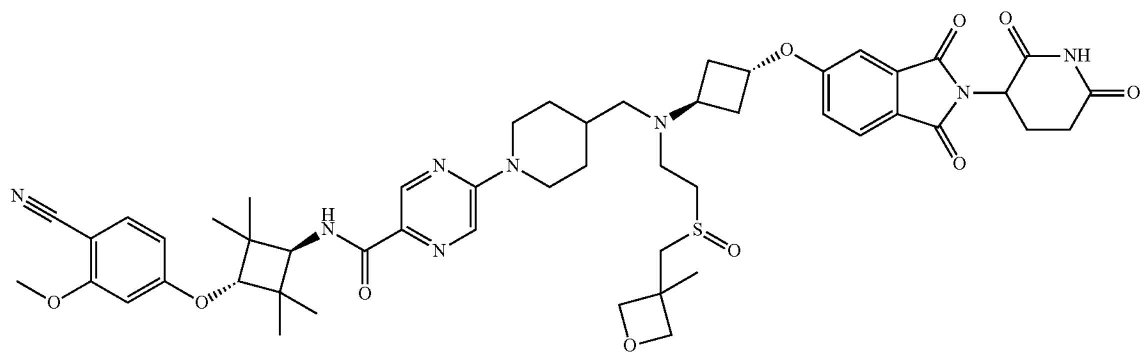 [SMILES: COc1cc(O[C@H]2C(C)(C)[C@H](NC(=O)c3cnc(N4CCC(CN(CCS(=O)CC5(C)COC5)[C@H]5C[C@H](Oc6ccc7c(c6)C(=O)N(C6CCC(=O)NC6=O)C7=O)C5)CC4)cn3)C2(C)C)ccc1C#N] | rac-N-((1r,3r)-3-(4-cyano-3-methoxyphenoxy)-2,2,4,4-tetramethylcyclobutyl)-5-(4-((((1r,3r)-3-((2-(2,6-dioxopiperidin-3-yl)-1,3-dioxoisoindolin-5-yl)oxy)cyclobutyl)(2-((3-methyloxetan-3-yl)methyl)sulfinyl)ethyl)amino)methyl)piperidin-1-yl)pyrazine-2-carboxamide | 50 and 7 |

TABLE 1C-continued

Exemplary heterobifunctional compounds of the present disclosure.

| Comp No. | Structure | Name | Scheme |
|---|---|---|---|
| 244 | 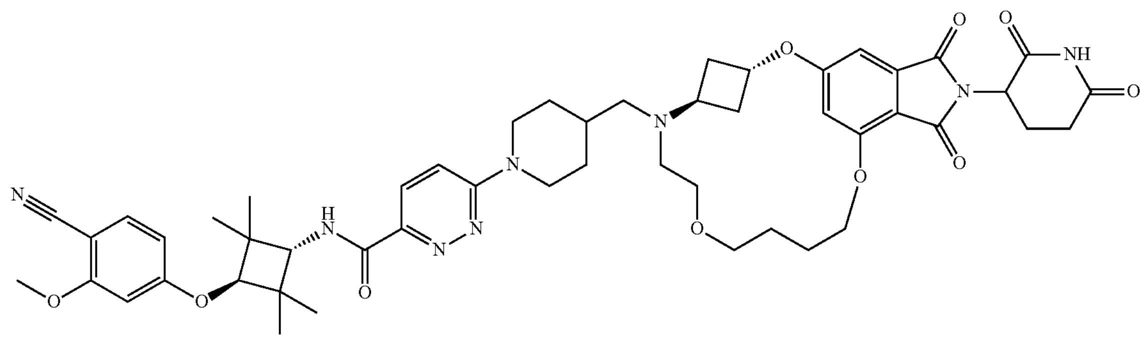 [SMILES: COc1cc(O[C@H]2C(C)(C)[C@H](NC(=O)c3ccc(N4CCC(CN5CCOCCCCOc6cc(cc7c6C(=O)N(C6CCC(=O)NC6=O)C7=O)O[C@H]6C[C@H]5C6)CC4)nn3)C2(C)C)ccc1C#N] | N-((1r,3r)-3-(3-chloro-4-cyanophenoxy)-2,2,4,4-tetramethylcyclobutyl)-4-(4-(((1r,3r)-3-((2-(2,6-dioxopiperidin-3-yl))-1,3-dioxoisoindolin-5-yl)oxy)cyclobutoxy)methyl)piperidin-1-yl)benzamide | 51 |
| 245 | 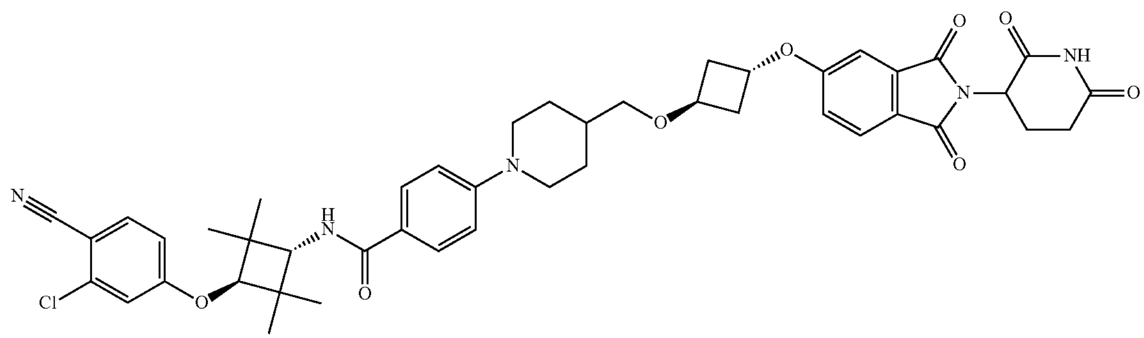 [SMILES: CC1(C)[C@H](NC(=O)c2ccc(N3CCC(CO[C@H]4C[C@H](Oc5ccc6c(c5)C(=O)N(C5CCC(=O)NC5=O)C6=O)C4)CC3)cc2)C(C)(C)[C@H]1Oc1ccc(C#N)c(Cl)c1] | N-((1r,3r)-3-(4-cyano-3,5-dimethylphenoxy)-2,2,4,4-tetramethylcyclobutyl)-5-(4-(((2,2-difluoroethyl)(1r,3r)-3-((2-(2,6-dioxopiperidin-3-yl)-7-methoxy-1,3-dioxoisoindolin-5-yl)oxy)cyclobutyl)amino)methyl)piperidin-1-yl)pyrazine-2-carboxamide | 7 and 1 |
| 246 | 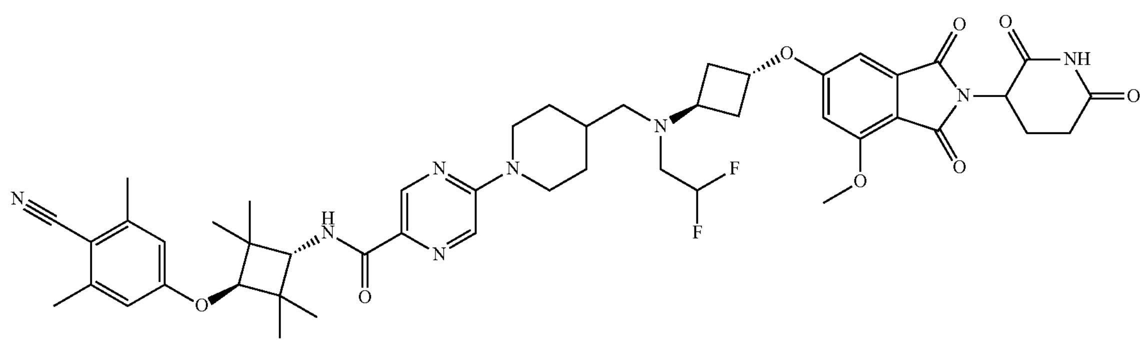 [SMILES: COc1cc(O[C@H]2C[C@H](N(CC(F)F)CC3CCN(c4cnc(C(=O)N[C@H]5C(C)(C)[C@H](Oc6cc(C)c(C#N)c(C)c6)C5(C)C)cn4)CC3)C2)cc2c1C(=O)N(C1CCC(=O)NC1=O)C2=O] | N-((1r,3r)-3-(4-cyano-3,5-dimethylphenoxy)-2,2,4,4-tetramethylcyclobutyl)-5-(4-(((2,2-difluoroethyl)(1r,3r)-3-((2-(2,6-dioxopiperidin-3-yl)-7-methoxy-1,3-dioxoisoindolin-5-yl)oxy)cyclobutyl)amino)methyl)piperidin-1-yl)pyrazine-2-carboxamide | 7 and 1 |

TABLE 1C-continued
Exemplary heterobifunctional compounds of the present disclosure.
| Comp No. | Structure | Name | Scheme |
|---|---|---|---|
| 247 | 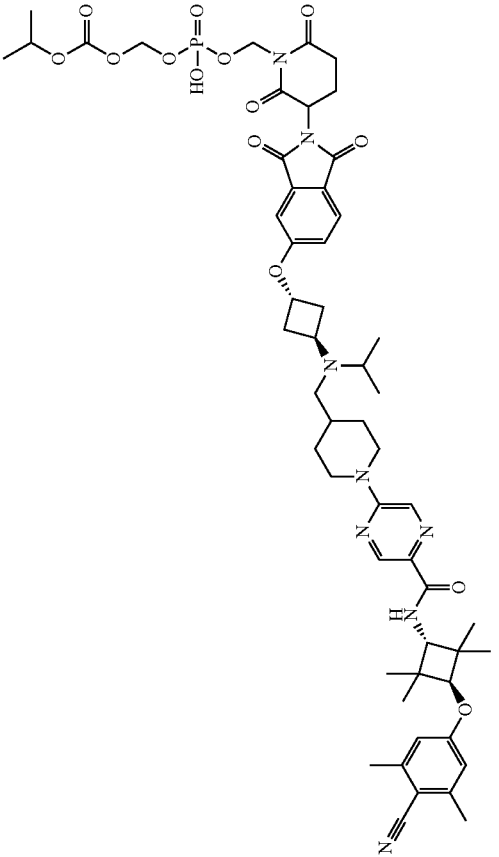 | rac-((((3-(5-((1r,3r)-3-(((1-(5-(((1r,3r)-3-(4-cyano-3,5-dimethylphenoxy)-2,2,4,4-tetramethylcyclobutyl)carbamoyl)pyrazin-2-yl)piperidin-4-yl)methyl)(isopropyl)amino)cyclobutoxy)-1,3-dioxoisoindolin-2-yl)-2,6-dioxopiperidin-1-yl)methoxy)(hydroxy)phosphoryl)oxy)methyl isopropyl carbonate | 7 and 52 |

TABLE 2A

Degradation of AR proteins by exemplary heterobifunctional compounds of the present disclosure.

| Comp No. | Exact Mass | Observed Mass | DC50 Code* | NMR |
|---|---|---|---|---|
| 1 | 872.42 | 873.75 | B | ¹H NMR (400 MHz, DMSO-$d_6$) δ 11.07 (s, 1H), 8.72 (s, 2H), 8.39 (d, J = 6.4 Hz, 1H), 8.16 (s, 1H), 6.82 (d, J = 16.8 Hz, 2H), 6.72 (s, 2H), 5.04 (d, J = 8.0 Hz, 1H), 4.90 (s, 1H), 4.63-4.80 (m, 3H), 4.30 (d, J = 7.2 Hz, 1H), 3.92 (s, 3H), 2.60-2.96 (m, 7H), 2.40 (s, 8H), 1.95-2.32 (m, 12H), 1.83 (d, J = 10.4 Hz, 3H), 1.67 (s, 1H), 0.84-1.01 (m, 8H). |
| 2 | 886.44 | 887.77 | D | ¹H NMR (400 MHz, DMSO-$d_6$) δ 11.09 (s, 1H), 8.73 (s, 2H), 8.18 (s, 1H), 6.89-6.74 (m, 4H), 5.10-4.97 (m, 2H), 4.91 (br s, 1H), 4.76 (br d, J = 12.4 Hz, 2H), 4.17 (br d, J = 7.2 Hz, 1H), 3.93 (s, 3H), 3.66 (br t, J = 8.0 Hz, 2H), 3.00-2.81 (m, 6H), 2.41 (s, 8H), 2.29-2.13 (m, 6H), 2.12-1.88 (m, 4H), 1.83 (br s, 4H), 1.69 (br s, 1H), 1.38-1.23 (m, 2H), 1.07-0.89 (m, 8H). |
| 3 | 885.45 | 886.78 | D | ¹H NMR (400 MHz, DMSO-$d_6$) δ 11.06 (s, 1H), 8.67-8.73 (m, 2H), 8.40 (d, J = 8.0 Hz, 1H), 8.28 (s, 1H), 7.16 (s, 2H), 6.77-6.88 (m, 2H), 5.04 (dd, J = 12.8, 5.6 Hz, 1H), 4.87-4.96 (m, 1H), 4.74 (br d, J = 13.6 Hz, 2H), 4.08-4.18 (m, 1H), 3.93 (s, 3H), 3.66 (t, J = 8.0 Hz, 2H), 3.58 (s, 2H), 2.82-2.97 (m, 5H), 2.54-2.63 (m, 4H), 2.45-2.47 (m, 1H), 2.41 (s, 6H), 2.35-2.40 (m, 1H), 2.14-2.26 (m, 6H), 2.06-2.14 (m, 2H), 1.95-2.03 (m, 1H), 1.83 (d, J = 10.4 Hz, 2H), 1.68 (s, 1H), 1.34-1.44 (m, 2H), 0.94-1.04 (m, 2H), 0.93 (s, 3H), 0.91 (s, 3H). |
| 4 | 846.41 | 847.74 | D | ¹H NMR (400 MHz, DMSO-$d_6$) δ 11.09 (s, 1H), 8.73 (s, 2H), 8.25 (m, 1H), 6.86-6.80 (m, 4H), 5.05 (m, 1H), 4.89 (m, 2H), 4.75 (m, 2H), 4.25 (m, 1H), 3.93 (s, 3H), 3.65 (m, 1H), 2.91 (m, 4H), 2.51-2.50 (m, 2H), 2.41 (m, 4H), 2.18 (m, 4H), 1.99-1.98 (m, 3H), 1.98 (s, 3H), 1.86 (m, 3H), 1.72-1.59 (m, 3H), 1.23 (m, 4H), 0.93-0.91 (m, 6H). |
| 5 | 846.41 | 847.74 | D | ¹H NMR (400 MHz, Methanol-$d_4$) δ 8.72 (s, 1H), 6.87 (d, 1H), 6.79 (d, 1H), 6.73 (s, 2H), 5.08-5.06 (m, 1H), 5.05 (m, 1H), 4.54 (m, 1H), 3.98 (s, 3H), 3.87 (m, 1H), 3.65 (m, 1H), 3.37 (m, 1H), 3.15-3.04 (m, 1H), 2.99-2.95 (m, 2H), 2.86 (m, 1H), 2.75-2.71 (m, 2H), 2.59-2.49 (m, 2H), 2.46-2.42 (m, 2H), 2.34-2.23 (m, 4H), 2.04-2.01 (m, 2H), 2.00-1.95 (m, 1H), 1.92-1.87 (m, 3H), 1.82-1.71 (m, 2H), 1.67-1.53 (m, 4H), 1.29-1.22 (m, 9H), 1.10-1.04 (m, 6H). |
| 6 | 818.38 | 819.70 | D | |
| 7 | 818.38 | 819.70 | D | ¹H NMR (400 MHz, Chloroform-d) δ 8.82 (s, 1H), 7.95 (s, 2H), 7.79 (m, , 1H), 7.45 (d, J = 8.3 Hz, 2H), 7.24-7.09 (m, 2H), 6.45 (d, J = 8.9 Hz, 2H), 5.00-4.91 (m, 1H), 4.91 (s, 1H), 4.75 (s, 1H), 4.65 (q, J = 7.3 Hz, 1H), 4.49 (d, J = 12.9 Hz, 2H), 3.89 (s, 3H), 3.76-3.68 (m, 1H), 2.97 (d, J = 12.2 Hz, 1H), 2.91 (d, J = 14.1 Hz, 2H), 2.84-2.71 (m, 1H), 2.46-2.25 (m, 6H), 2.25 (d, J = 7.4 Hz, 2H), 2.14 (d, J = 9.9 Hz, 1H), 1.95 (m, 3H), 1.73-1.62 (m, 2H), 1.31 (d, J = 5.7 Hz, 3H), 1.25 (s, 6H), 1.12 (d, J = 12.4 Hz, 1H), 0.85 (s, 3H). |
| 8 | 846.41 | 847.73 | D | ¹H NMR (300 MHz, DMSO-$d_6$) δ 11.07 (s, 1H), 8.72-8.67 (s, 2H), 8.22 (s, 1H), 6.84-6.75(m, 4H), 5.04-4.90 (m, 3H), 4.74 (m, 3H), 4.76-4.73 (m, 2H), 4.56-4.51 (m, 1H), 3.92 (m, 3H), 3.65 (s, 1H), 2.91 (m, 6H), 2.41 (m, 7H), 2.24-1.60 (m, 9H), 1.23-1.67 (m, 2H), 0.92 (m, 9H). |
| 9 | 846.41 | 847.73 | D | ¹H NMR (300 MHz, DMSO-$d_6$) δ 11.06 (s, 1H), 8.71 (m, 2H), 8.23-8.21 (m, 1H), 6.84 (m, 1H), 6.78 (m, 3H), 5.02 (m, 1H), 4.89-4.87 (m, 2H), 4.76-4.71 (m, 2H), 4.24-4.16 (m, 1H), 3.91 (s, 3H), 3.65 (m, 1H), 2.93-2.86 (m, 4H), 2.59-2.56 (m, 2H), 2.39 (m, 9H), 2.23-2.16 (m, 4H), 1.98-1.96 (m, 3H), 1.84-1.80 (m, 3H), 1.72-1.67 (m, 3H), 0.99-0.90 (m, 8H). |
| 10 | 818.38 | 819.69 | D | ¹H NMR (400 MHz, Methanol-$d_4$) δ 8.66 (d, J = 1.3 Hz, 1H), 8.22 (s, 1H), 7.82 (d, J = 8.3 Hz, 1H), 7.53 (d, J = 8.5 Hz, 1H), 7.30-7.22 (m, 1H), 6.69-6.60 (m, 2H), 4.64-4.55 (m, 3H), 3.94 (s, 3H), 3.02 (s, 2H), 2.77 (d, J = 12.2 Hz, 1H), 1.41 (d, J = 12.1 Hz, 1H), 1.31 (s, 6H), 1.03 (d, J = 6.6 Hz, 6H), 0.92 (s, 1H), 0.90 (s, 3H), 0.63 (s, 0H), 0.12 (s, 8H). |
| 11 | 818.38 | 819.69 | D | ¹H NMR (400 MHz, Methanol-$d_4$) δ 8.65 (d, J = 1.4 Hz, 1H), 8.22 (s, 1H), 7.82 (d, J = 8.2 Hz, 1H), 7.54 (d, J = 8.9 Hz, 1H), 7.31-7.22 (m, 2H), 6.69 (d, J = 7.7 Hz, 2H), 4.59 (d, J = 15.5 Hz, 4H), 3.94 (s, 3H), 3.02 (t, J = 12.6 Hz, 3H), 2.77 (d, J = 14.9 Hz, 1H), 2.50 (s, 2H), 2.36 (d, J = 6.4 Hz, 1H), 2.15 (d, J = 7.8 Hz, 1H), 1.98 (s, 2H), 1.41 (d, J = 12.1 Hz, 1H), 1.31 (s, 6H), 1.03 (d, J = 6.6 Hz, 6H), 0.92 (s, 0H), 0.90 (s, 3H), 0.12 (s, 5H), 0.11 (s, 2H). |
| 12 | 871.44 | 872.77 | D | ¹H NMR (400 MHz, DMSO-$d_6$) δ 11.08 (s, 1H), 10.33 (s, 1H), 8.84-8.98 (m, 1H), 8.73 (s, 2H), 8.45 (d, J = 7.2 Hz, 1H), 7.32-7.37 (m, 2H), 6.90 (dd, J = 11.2, 1.6 Hz, 2H), 5.08 (m, 2H), 4.71-4.81 (m, 2H), 4.34 (s, 2H), 4.10-4.30 (m, 6H), 4.01 (s, 1H), 3.95 (s, 3H), 2.76-3.13 (m, 8H), 2.56-2.69 (m, 4H), 2.50 (s, 6H), 2.21-2.35 (m, 2H), 1.94-2.06 (m, 3H), 1.86 (d, J = 12.0 Hz, 1H), 1.28 (d, J = 6.4 Hz, 3H), 1.04-1.25 (m, 6H). |

TABLE 2B

Degradation of AR proteins by exemplary heterobifunctional compounds of the present disclosure.

| Comp No. | Exact Mass | Observed Mass | DC50 Code* | NMR |
|---|---|---|---|---|
| 13 | 850.3569 | 851.69 | A | ¹H NMR (300 MHz, DMSO-$d_6$) δ 10.97 (s, 1H), 8.59 (s, 1H), 8.25 (s, 1H), 8.08-8.05 (m, 1H), 7.88-7.85 (d, 1H), 7.63-7.61 (d, 1H), 7.38-7.37 (s, 1H), 7.14-7.11 (m, 1H), 7.01 (m, 1H), 6.96-6.94 (m, 1H), 5.09 (m, 1H), 4.81 (m, 1H), 4.64-4.60 (m, 2H), 4.50-4.45 (m, 3H), 4.35 (m, 1H), 4.28-4.22 (m, 3H), 3.87 (m, 1H), 3.18-2.89 (m, 3H), 2.72-2.70 (m, 2H), 2.38-2.20 (m, 3H), 2.15-2.12 (m, 5H), 2.07 (s, 2H), 1.97-1.86 (m, 4H), 1.80-1.71 (m, 3H), 1.63-1.48 (m, 4H), 1.23 (m, 6H), 1.05-1.03 (m, 2H). |
| 14 | 866.3518 | 867.68 | A | ¹H NMR (400 MHz, DMSO-$d_6$) δ 11.06 (s, 1H), 8.59 (s, 1H), 8.25 (s, 1H), 8.17 (s, 1H), 8.03 (s, 1H), 7.37-7.36 (d, J = 4 Hz 1H), 7.12-7.11 (d, J = 4 Hz 1H), 6.91-6.81 (m, 4H), 5.05 (dd, J = 5.2, 15.2 Hz, 2H), 4.46 (s, 1H), 4.42-4.32 (m, 3H), 3.93 (s, 3H), 3.34 (s, 1H), 3.26-3.24 (m, 3H), 2.92-2.88 (m, 3H), 2.53-2.50 (m, 1H), 2.40 (s, 6H), 2.07-2.05 (d, J = 8 Hz 1H), 2.01 (s, 3H) 1.64(m, 2H), 1.09 (s, 2H), 0.97 (s, 6H). |

TABLE 2B-continued

Degradation of AR proteins by exemplary heterobifunctional compounds of the present disclosure.

| Comp No. | Exact Mass | Observed Mass | DC50 Code* | NMR |
|---|---|---|---|---|
| 15 | 836.3413 | 837.68 | A | $^1$H NMR (300 MHz, DMSO-d$_6$) δ 10.99 (s, 1H), 8.60 (s, 1H), 8.26 (s, 1H), 8.10-8.07 (m, 1H), 7.89-7.86 (m, 1H), 7.53-7.51 (m, 1H), 7.38 (s, 1H), 7.16-7.13 (m, 2H), 7.03 (s, 1H), 5.15-5.08 (m, 1H), 4.80 (m, 1H), 4.54-4.41 (m, 7H), 4.36-4.22 (m, 2H), 4.01-3.97 (m, 1H), 3.85-3.82 (m, 1H), 3.60-3.55 (m, 1H), 3.02-2.90 (m, 3H), 2.64-2.58 (m, 1H), 2.46-2.29 (m, 5H), 2.17-1.93 (m, 5H), 1.92-1.75 (m, 4H), 1.72-1.47 (m, 5H), 1.09-0.93 (m, 2H). |
| 16 | 838.3569 | 839.69 | A | $^1$H NMR (300 MHz, DMSO-d$_6$) δ 10.95 (s, 1H), 8.52 (s, 1H), 8.18 (s, 1H), 8.01-8.00 (d, 1H), 7.81-7.78 (d, 1H), 7.56-7.54 (d, 1H), 7.31-7.30 (m, 1H), 7.08-7.04 (m, 1H), 6.93 (m, 1H), 6.89-6.86 (m, 1H), 5.05-4.96 (m, 1H), 4.78-4.67 (m, 1H), 4.42-4.34 (m, 3H), 4.28-4.21 (m, 2H), 3.81-3.67 (m, 1H), 3.40-3.31 (m, 2H), 3.17 (m, 3H), 2.91-2.75 (m, 3H), 2.55-2.47 (m, 3H), 2.43-2.01 (m, 10H), 1.91-1.74 (m, 6H), 1.56-1.41 (m, 4H), 0.98 (m, 2H). |
| 17 | 860.4221 | 861.65 | A | $^1$H NMR (300 MHz, DMSO-d$_6$) δ 11.10 (s, 1H), 8.60 (s, 1H), 8.25 (s, 1H), 8.05 (d, J = 6.6 Hz, 1H), 7.95-7.80 (m, 4H), 5.10-5.00 (m, 1H), 4.95-4.85 (m, 1H), 4.60-4.35 (m, 3H), 4.00-3.80 (m, 4H), 3.79-3.60 (m, 1H), 3.05-2.80 (m, 4H), 2.60-2.55 (m, 1H), 2.48-2.32 (m, 9H), 2.30-2.00 (m, 7H), 1.85 (s, 4H), 1.80-1.40 (m, 5H), 1.20-0.90 (m, 8H). |
| 18 | 811.3009 | 812.6276 | A | $^1$H NMR (400 Hz, DMSO-d$_6$) δ ppm 11.39 (s, 1H), 8.57 (d, J = 8 Hz, 1H), 7.84-7.76 (m, 2H), 7.67-7.65 (m, 1H), 7.36-7.27 (m, 3H), 7.10 (d, J = 12 Hz, 2H), 4.47 (m, 3H), 3.82 (m, 2H), 3.43 (m, 3H), 3.25 (m, 2H), 2.99 (m, 2H), 2.73-2.42 (m, 6H), 2.30-2.05 (m, 5H), 1.85 (m, 4H), 1.65-1.46 (m, 4H), 1.11 (m, 2H). |
| 19 | 846.4428 | 847.785 | A | $^1$H NMR (300 MHz, DMSO-d$_6$, ppm) δ 8.61 (s, 1H), 8.29 (s, 1H), 7.66-7.60 (m, 2H), 7.17 (s, 1H), 7.08-7.05 (d, J = 8.4 Hz, 1H), 6.72-6.70 (m, 2H), 5.07-5.03 (m, 1H), 4.55-4.24 (m, 6H), 3.89-3.71 (m, 5H), 3.42-3.32 (m, 1H), 3.04-2.91 (m, 5H), 2.64-2.63 (m, 1H), 2.41-2.35 (m, 1H), 2.24-2.10 (m, 6H), 1.97-1.87 (m, 6H), 1.79-1.49 (m, 8H), 1.34-1.27 (m, 8H). |
| 20 | 804.3595 | 805.69 | A | $^1$H NMR (400 MHz, DMSO-d$_6$) δ 11.11 (s, 1H), 8.57 (d, J = 1.2 Hz, 1H), 8.16 (s, 1H), 8.10 (d, J = 8.4 Hz, 1H), 7.86-7.78 (m, 2H), 7.61 (d, J = 9.2 Hz, 1H), 7.29-7.23 (m, 2H), 6.71 (dd, J = 2.4, 4.8 Hz, 2H), 5.11 (dd, J = 5.6, 12.8 Hz, 1H), 4.92 (s, 1H), 4.47 (s, 1H), 4.16 (t, J = 8.4 Hz, 2H), 3.88 (s, 3H), 3.82 (d, J = 4.8 Hz, 1H), 3.77 (dd, J = 5.2, 8.8 Hz, 2H), 3.69-3.58 (m, 1H), 2.99-2.81 (m, 3H), 2.68 (s, 1H), 2.64-2.53 (m, 2H), 2.42 (s, 2H), 2.36-2.34 (m, 1H), 2.24 (d, J = 9.6 Hz, 2H), 2.15-1.99 (m, 3H), 1.88 (d, J = 9.6 Hz, 2H), 1.67-1.41 (m, 4H), 0.94 (d, J = 6.4 Hz, 6H). |
| 21 | 836.3413 | 837.68 | A | $^1$H NMR (300 MHz, DMSO-d$_6$) δ 10.96 (s, 1H), 8.59-8.58 (s, 1H), 8.25 (s, 1H), 8.08-8.05 (d, 1H), 7.87-7.85 (m, 1H), 7.64-7.61 (d, 1H), 7.38-7.37 (s, 1H), 7.14-7.11 (m, 1H), 7.00-6.93 (m, 1H), 5.13-5.02 (m, 1H), 4.78 (m, 1H), 4.53-4.48 (m, 7H), 4.41-4.35 (m, 1H), 4.28-4.21 (m, 2H), 3.98 (m, 1H), 3.92-3.75 (m, 1H), 3.62-3.47 (m, 1H), 2.96-2.94 (m, 3H), 2.60-2.54 (m, 1H), 2.39-2.27 (m, 5H), 2.20-2.11 (m, 4H), 2.08-1.83 (m, 5H), 1.65-1.48 (m, 5H), 1.24 (m, 1H), 1.06 (d, 2H). |
| 22 | 832.3908 | 833.6 | A | $^1$H NMR (400 MHz, DMSO-d$_6$) δ 11.09 (s, 1H), 8.59 (d, J = 1.2 Hz, 1H), 8.20 (s, 1H), 8.07 (d, J = 8.4 Hz, 1H), 7.83-7.77 (m, 2H), 7.62 (d, J = 9.2 Hz, 1H), 7.45 (d, J = 2.0 Hz, 1H), 7.33 (m, 1H), 6.74-6.67 (m, 2H), 5.16-5.07 (m, 1H), 4.64-4.42 (m, 2H), 4.16 (m, 2H), 3.89 (s, 3H), 3.76 (m, 4H), 3.04-2.87 (m, 3H), 2.77 (d, J = 7.6 Hz, 2H), 2.65-2.56 (m, 2H), 2.16-2.03 (m, 5H), 1.94-1.85 (m, 2H), 1.72-1.40 (m, 10H), 1.01 (d, J = 6.4 Hz, 6H). |
| 23 | 860.3857 | 861.72 | A | $^1$H NMR (400 MHz, DMSO-d$_6$) δ 11.10 (s, 1H), 8.58 (s, 1H), 8.25 (s, 1H), 8.11-8.09 (d, J = 4 Hz 1H), 6.91-6.81 (m, 4H), 5.05 (dd, J = 5.2, 15.2 Hz, 2H), 4.46 (s, 1H), 4.42-4.32 (m, 3H), 3.93 (s, 3H), 3.34 (s, 1H), 3.26-3.24 (m, 3H), 2.92-2.88 (m, 3H), 2.53-2.50 (m, 1H), 2.40 (s, 6H), 2.07-2.05 (d, J = 8 Hz 1H), 2.01 (s, 3H) 1.64(m, 2H), 1.48 (s, 2H), 1.16 (s, 3H). |
| 24 | 838.3569 | 839.69 | A | $^1$H NMR (300 MHz, DMSO-d$_6$) δ 10.97 (s, 1H), 8.59 (s, 1H), 8.25 (s, 1H), 8.08-8.06 (d, 1H), 7.87-7.84 (d, 1H), 7.52-7.49 (d, 1H), 7.38-7.37 (m, 1H), 7.14-7.11 (m, 2H), 7.01-7.00 (m, 1H), 5.09 (m, 1H), 4.80 (m, 1H), 4.49-4.40 (m, 3H), 4.34-4.26 (m, 2H), 3.87-3.75 (m, 1H), 3.48-3.38 (m, 3H), 3.24 (s, 3H), 3.02-2.91 (m, 3H), 2.62-2.51 (m, 2H), 2.40-2.00 (m, 10H), 1.86-1.82 (m, 5H), 1.63-1.48 (m, 4H), 1.24 (m, 1H), 1.10-1.06 (m, 2H). |
| 25 | 830.4115 | 831.625 | A | $^1$H NMR (400 MHz, DMSO-d$_6$) δ 11.12 (br s, 1H), 8.59 (d, J = 1.2 Hz, 1H), 8.33 (br s, 1H), 8.25 (s, 1H), 8.07 (d, J = 8.4 Hz, 1H), 7.83 (d, J = 8.4 Hz, 1H), 7.29-7.20 (m, 2H), 6.85 (s, 2H), 5.11 (dd, J = 5.2, 12.8 Hz, 1H), 4.90 (br s, 1H), 4.54-4.37 (m, 3H), 3.82 (br d, J = 8.8 Hz, 1H), 3.72-3.60 (m, 1H), 3.01-2.85 (m, 5H), 2.65-2.54 (m, 3H), 2.53 (d, J = 2.0 Hz, 3H), 2.41 (s, 6H), 2.28-2.16 (m, 4H), 2.11-2.02 (m, 3H), 1.87 (br s, 4H), 1.65-1.46 (m, 4H), 1.11-1.00 (m, 2H), 0.92 (d, J = 6.8 Hz, 6H). |
| 26 | 892.4039 | 893.645 | A | $^1$H NMR (400 MHz, DMSO-d$_6$) δ 11.06 (s, 1H), 8.75 (s, 2H), 7.90 (d, J = 8.8 Hz, 1H), 7.80 (d, J = 8.4 Hz, 1H), 7.77 (d, J = 8.8 Hz, 1H), 7.44 (s, 1H), 7.32 (d, J = 8.8 Hz, 1H), 7.22 (s, 1H), 6.99 (d, J = 8.8 Hz, 1H), 5.10-5.08 (m, 1H), 4.77-4.74 (m, 2H), 4.65 (b, 1H), 4.29 (s, 1H), 4.03 (d, J = 8.4 Hz, 1H), 3.02-2.92 (m, 6H), 2.51-2.50 (m, 3H), 2.20-2.01 (m, 4H), 1.85-1.82 (m, 2H), 1.69-1.66 (m, 3H), 1.48-1.43 (m, 4H), 1.21 (s, 6H), 1.11 (s, 6H), 0.98-0.96 (m, 7H). |
| 27 | 830.4115 | 831.74 | A | $^1$H NMR (400 MHz, DMSO-d$_6$) δ 10.94 (s, 1H), 8.56 (s, 1H), 8.18 (s, 1H), 8.05 (s, 1H), 8.03 (s, 1H), 7.63-7.59 (m, 2H), 7.0(s, 1H), 6.96-6.94 (m, 1H), 6.70-6.68 (m, 2H), 5.08-5.07 (m, 1H), 4.79-4.77 (m, 1H), 4.40 (s, 1H), 4.36-4.27(m, 2H), 4.23-4.14 (m, 2H), 4.04 (s, 2H), 3.59-3.57 (m, 3H), 2.90-2.88 (m, 1H), 2.39-2.37 (m, 1H), 2.33-2.32 (m, 2H), 2.28-2.26 (m, 1H), 2.18-1.89 (m, 6H), 1.86-1.51 (m, 2H), 1.99-1.94 (m, 2H), 1.82 (m, 2H), 1.22 (m, 1H), 1.57 (m, 4H), 1.51(m, 4H), 0.92-0.91 (m, 6H). |
| 28 | 822.3256 | 823.5367 | A | $^1$H NMR (400 MHz, DMSO-d$_6$) δ 8.59 (s, 1H), 8.25 (s, 1H), 8.08-8.06 (d, J = 7.6 Hz, 1H), 7.87-7.83 (m, 2H), 7.37 (s, 1H), 7.28-7.25 (d, J = 12 Hz, 2H), 7.14-7.11 (d, J = 8.4 Hz, 1H), 5.13-5.10 (m, 1H), 4.93 (s, 1H), 4.52-4.45 (m, 3H), 4.00 (s, 1H), 2.99-2.96 (d, J = 11.2 Hz, 3H), 2.62-2.55 (m, 2H), 2.37 (s, 3H), 2.20-2.18 (d, J = 7.2 Hz, 4H), 2.11-2.07 (d, J = 13.2 Hz, 4H), 1.86-1.83 (d, J = 13.2 Hz, 4H), 1.62-1.49 (m, 6H), 1.24 (s, 1H), 1.10-1.07 (d, J = 12.8 Hz, 2H), 1.03-1.00 (m, 3H). |
| 29 | 832.3544 | 833.56 | A | $^1$H NMR (400 MHz, DMSO-d$_6$) δ 11.10 (s, 1H), 8.59 (d, J = 1.2 Hz, 1H), 8.29-8.21 (m, 1H), 8.04 (d, J = 8.3 Hz, 1H), 7.85 (d, J = 8.0 Hz, 1H), 7.61 (d, J = 9.2 Hz, 1H), 7.35-7.22 (m, 2H), 6.76-6.65 (m, 2H), 5.20-4.91 (m, 2H), 4.74-4.32 (m, 4H), 3.95-3.76 (m, 4H), 3.25 (s, 3H), 3.03-2.79 (m, 4H), 2.74-2.52 (m, 3H), 2.41 (d, J = 12.0 Hz, 2H), 2.15-2.05 (m, 3H), 2.02 (s, 3H), 1.89 (d, J = 10.0 Hz, 3H), 1.73-1.48 (m, 6H), 1.17 (d, J = 11.2 Hz, 2H). |

TABLE 2B-continued

Degradation of AR proteins by exemplary heterobifunctional compounds of the present disclosure.

| Comp No. | Exact Mass | Observed Mass | DC50 Code* | NMR |
|---|---|---|---|---|
| 30 | 878.3518 | 879.59 | A | $^1$H NMR (300 MHz, CDCl$_3$) δ 8.84 (s, 1H), 8.83 (s, 2H), 7.97-7.97 (d, J = 1.2 Hz, 1H), 7.79-7.77 (d, J = 8.1 Hz, 1H), 7.57-7.55 (d, J = 8.7 Hz, 1H), 7.17-7.11 (m, 2H), 7.10 (s, 1H), 7.00-6.83 (m, 1H), 4.80-4.67 (m, 1H), 4.53-4.48 (d, J = 13.5 Hz, 1H), 4.29 (s, 2H), 4.03-4.00 (d, J = 10.5 Hz, 1H), 3.63-3.42 (m, 4H), 3.35-3.34 (d, J = 2.7 Hz, 2H), 2.96-2.78 (m, 6H), 2.40-2.33 (m, 5H), 2.20-2.14 (m, 5H), 1.98-1.93 (m, 2H), 1.71-1.44 (m, 10H), 1.15-1.12 (m, 2H). |
| 31 | 860.4221 | 861.63 | A | $^1$H NMR (400 MHz, DMSO-d$_6$) δ 11.09 (s, 1H), 8.60 (s, 1H), 8.26 (s, 1H), 8.05 (d, J = 8.8 Hz, 1H), 7.81 (d, J = 8.0 Hz, 1H), 7.66-7.57 (m, 1H), 7.44 (d, J = 2.0 Hz, 1H), 7.33 (m, 1H), 6.83-6.54 (m, 2H), 5.11 (m, 1H), 4.59-4.45 (m, 4H), 3.92-3.83 (m, 4H), 3.03-2.84 (m, 4H), 2.66-2.55 (m, 5H), 2.18-1.95 (m, 6H), 1.93-1.79 (m, 4H), 1.69-1.45 (m, 10H), 1.09-0.96 (m, 8H). |
| 32 | 832.3908 | 833.605 | A | $^1$H NMR (400 MHz, DMSO-d$_6$) δ 11.10 (s, 1H), 8.59 (s, 1H), 8.22 (d, J = 20 Hz, 2H), 8.04 (d, J = 8.4 Hz, 1H), 7.83 (d, J = 8.4 Hz, 1H), 7.65-7.56 (m, 1H), 7.32-7.17 (m, 2H), 6.80-6.59 (m, 2H), 5.11 (dd, J = 5.4, 12.8 Hz, 1H), 4.89 (s, 1H), 4.49 (d, J = 12.8 Hz, 3H), 3.88 (s, 3H), 3.86-3.75 (m, 2H), 3.68 (s, 1H), 3.05-2.81 (m, 4H), 2.64-2.56 (m, 2H), 2.44-2.43 (m, 1H), 2.41 (s, 2H), 2.25 (d, J = 6.8 Hz, 2H), 2.22-2.15 (m, 2H), 2.13-2.02 (m, 3H), 1.92-1.82 (m, 4H), 1.72-1.47 (m, 5H), 1.13-1.01 (m, 2H), 0.92 (d, J = 6.4 Hz, 6H). |
| 33 | 818.3752 | 819.585 | A | $^1$H NMR (400 MHz, d-DMSO ) δ 11.10 (s, 1H), 8.59 (s, 1H), 8.25 (s, 1H), 8.06-8.04 (d, J = 8.0 Hz, 1H), 7.84-7.82 (d, J = 8.0 Hz, 1H), 7.62-7.60 (d, J = 8.8 Hz, 1H), 7.27-7.24 (d, J = 8.8 Hz, 2H), 6.71 (s, 2H), 5.13-4.94 (m, 2H), 4.49-4.46 (d, J = 12.0 Hz, 3H), 3.84 (s, 4H), 3.45-3.41 (m, 1H), 3.17-2.86 (m, 3H), 2.57-2.35 (m, 4H), 2.29-2.12 (m, 4H), 2.09-2.03 (m, 4H), 1.84-1.76 (m, 6H), 1.65-1.47 (m, 4H), 1.10-1.07 (d, J = 10.4 Hz, 2H), 0.94-0.90 (m, 3H). |
| 34 | 818.4115 | 819.61 | A | $^1$H NMR (300 MHz, DMSO-d$_6$) δ 10.93 (s, 1H), 8.56 (s, 1H), 8.22 (s, 1H), 8.00 (d, J = 8.4 Hz, 1H), 7.58 (d, J = 9.3 Hz, 1H), 7.47 (d, J = 8.1 Hz, 1H), 7.13-7.09 (m, 1H), 6.99 (s, 1H), 6.68 (d, J = 5.7 Hz, 2H), 5.10-5.04 (m, 1H), 4.75-4.74 (m, 1H), 4.48-4.45 (m, 3H), 4.38-4.19 (m, 2H), 3.86-3.82 (m, 4H), 3.63-3.60 (m, 1H), 2.98-2.84 (m, 4H), 2.60-2.58 (m, 2H), 2.39-2.33 (m, 3H), 2.24-2.22 (m, 2H), 2.17-2.10 (m, 4H), 1.99-1.82 (m, 5H), 1.65-1.46 (m, 5H), 1.06-1.02 (m, 2H), 0.91-0.89 (m, 6H). |
| 35 | 864.3726 | 865.51 | A | $^1$H NMR (400 MHz, DMSO-d$_6$) δ 11.09 (s, 1H), 8.59 (s, 1H), 8.24 (d, J = 11.2 Hz, 2H), 8.05 (d, J = 8.4 Hz, 1H), 7.86 (d, J = 8.8 Hz, 1H), 7.80 (d, J = 8.4 Hz, 1H), 7.44 (d, J = 2.4 Hz, 1H), 7.37 (d, J = 2.4 Hz, 1H), 7.32 (dd, J = 2.0, 8.4 Hz, 1H), 7.13 (dd, J = 2.4, 8.8 Hz, 1H), 5.11 (dd, J = 5.6, 12.8 Hz, 1H), 4.61-4.43 (m, 4H), 3.82 (s, 2H), 3.05-2.82 (m, 5H), 2.60 (d, J = 17.6 Hz, 2H), 2.53 (s, 3H), 2.14-2.00 (m, 5H), 1.93-1.79 (m, 4H), 1.66 (s, 3H), 1.64-1.38 (m, 8H), 0.98 (d, J = 6.4 Hz, 6H). |
| 36 | 844.3908 | 845.6 | A | $^1$H NMR (400 MHz, DMSO-d$_6$) δ 11.09 (s, 1H), 8.71 (s, 2H), 8.23 (s, 1H), 8.11 (d, J = 7.6 Hz, 1H), 7.84 (d, J = 8.4 Hz, 1H), 7.61 (d, J = 8.4 Hz, 1H), 7.32-7.22 (m, 2H), 6.76-6.67 (m, 2H), 5.11 (dd, J = 5.6, 12.8 Hz, 1H), 4.91 (t, J = 6.4 Hz, 1H), 4.49 (s, 1H), 4.11 (s, 2H), 4.01 (s, 2H), 3.89 (s, 3H), 3.79 (s, 2H), 3.61 (td, J = 8.0, 16.0 Hz, 1H), 2.93-2.83 (m, 2H), 2.64-2.52 (m, 2H), 2.38 (d, J = 4.8 Hz, 4H), 2.30-2.17 (m, 5H), 2.14-2.01 (m, 3H), 1.96-1.78 (m, 4H), 1.57-1.42 (m, 4H), 0.92 (d, J = 6.4 Hz, 6H). |
| 37 | 808.31 | 809.51 | A | $^1$H NMR (400 MHz, DMSO-d$_6$) δ 11.09 (s, 1H), 8.57 (d, J = 1.3 Hz, 1H), 8.15 (s, 1H), 8.08 (d, J = 8.0 Hz, 1H), 7.89-7.77 (m, 3H), 7.37 (d, J = 2.4 Hz, 1H), 7.29-7.23 (m, 2H), 7.12 (dd, J = 2.4, 8.8 Hz, 1H), 5.11 (dd, J = 5.2, 12.8 Hz, 1H), 4.92 (s, 1H), 4.51 (s, 1H), 4.16 (t, J = 8.4 Hz, 1H), 3.80-3.72 (m, 3H), 3.69-3.61 (m, 1H), 2.99-2.82 (m, 4H), 2.61 (s, 2H), 2.44 (s, 3H), 2.23 (s, 2H), 2.13-2.00 (m, 3H), 1.88 (d, J = 9.2 Hz, 2H), 1.68-1.40 (m, 4H), 0.94 (d, J = 6.4 Hz, 6H). |
| 38 | 862.4014 | 863.63 | A | $^1$H NMR (300 MHz, DMSO-d$_6$) δ 11.09 (s, 1H), 8.60 (s, 1H), 8.26 (s, 1H), 8.06 (d, J = 8.1 Hz, 1H), 7.62 (d, J = 9.3 Hz, 1H), 6.86-6.71 (m, 4H), 5.05-4.92 (m, 2H), 4.52-4.48 (m, 3H), 3.94-3.67 (m, 8H), 3.00-2.89 (m, 4H), 2.61-2.42 (m, 3H), 2.27-1.88 (m, 11H), 1.67-1.50 (m, 5H), 1.17 (s, 1H), 1.24-1.08 (m, 8H). |
| 39 | 804.3595 | 805.57 | A | $^1$H NMR (400 MHz, d-DMSO ) δ 11.10 (s, 1H), 8.59 (s, 1H), 8.25 (s, 1H), 8.06-8.04 (d, J = 8.0 Hz, 1H), 7.84-7.82 (d, J = 8.0 Hz, 1H), 7.62-7.60 (d, J = 8.8 Hz, 1H), 7.27-7.24 (d, J = 8.8 Hz, 2H), 6.71 (s, 2H), 5.13-5.09 (m, 1H), 4.95 (s, 1H), 4.48-4.45 (d, J = 12.0 Hz, 3H), 3.89-3.82 (m, 4H), 3.00-2.62 (m, 4H), 2.57-2.50 (m, 2H), 2.38-2.33 (m, 2H), 2.19-2.05 (m, 2H), 1.97-1.87 (m, 8H), 1.84-1.75 (m, 5H), 1.65-1.39 (m, 4H), 1.15-1.09 (m, 2H). |
| 40 | 851.3522 | 852.57 | A | $^1$H NMR (300 MHz, DMSO-d$_6$) δ 11.10 (s, 1H), 8.60 (d, J = 6.0 Hz, 1H), 7.88-7.80 (m, 2H), 7.40-7.39 (m, 2H), 7.18-7.10 (m, 1H), 6.98 (s, 1H), 6.70 (s, 1H), 5.05-4.85 (m, 2H), 4.65-4.40 (m, 3H), 3.98-3.80 (m, 1H), 3.46 (s, 4H), 3.35-3.30 (m, 3H), 3.05-2.80 (m, 3H), 2.52 (s, 2H), 2.45 (s, 2H), 2.25-2.10 (m, 4H), 2.08-1.80 (m, 6H), 1.78-1.45 (m, 4H), 1.35-1.05 (m, 9H). |
| 41 | 822.362 | 823.565 | A | $^1$H NMR (300 MHz, DMSO-d$_6$) δ 10.79 (s, 1H), 8.56 (s, 1H), 8.22 (s, 1H), 8.02 (d, J = 8.7 Hz, 1H), 7.83 (d, J = 8.7 Hz, 1H), 7.47 (d, J = 8.4 Hz, 1H), 7.35 (d, J = 1.8 Hz, 1H), 7.10 (d, J = 8.1 Hz, 2H), 6.99 (s, 1H), 5.10-5.04 (m, 1H), 4.74-4.71 (m, 1H), 4.49-4.45 (m, 3H), 4.38-4.32 (m, 1H), 4.24-4.18 (m, 1H), 3.80-3.78 (m, 1H), 3.66-3.57 (m, 1H), 2.98-2.85 (m, 4H), 2.60-2.54 (m, 1H), 2.34-2.31 (m, 2H), 2.24-2.22 (m, 2H), 2.17-1.95 (m, 6H), 1.85-1.82 (m, 4H), 1.64-1.42 (m, 5H), 1.09-1.02 (m, 2H), 0.91-0.89 (m, 6H). |
| 42 | 854.3319 | 855.54 | A | $^1$H NMR (400 MHz, DMSO-d$_6$) δ 11.11 (s, 1H), 8.58 (s, 1H), 8.24 (s, 1H), 8.06 (s, 1H), 7.86-7.84 (d, J = 8 Hz 1H), 7.37 (s, 1H) 7.17-7.10 (m, 3H), 5.12 (dd, J = 5.2, 15.2 Hz, 1H), 4.92 (s, 1H), 4.50-4.47 (m, 3H), 3.81 (s, 1H), 3.68-3.64 (m, 3H), 2.95-2.92 (m, 3H), 2.53-2.52 (m, 2H), 2.50-2.49 (m, 2H), 2.25-2.24 (m, 2H), 2.07-1.86 (m, 2H), 1.83-1.82 (m, 5H), 1.58-1.52(m, 5H), 1.07 (s, 2H), 0.93-0.92 (d, J = 4 Hz 1H). |
| 43 | 818.3752 | 819.56 | A | $^1$H NMR (400 MHz, DMSO-d$_6$) δ 11.11 (s, 1H), 8.73 (s, 2H), 8.17 (s, 1H), 8.12 (d, J = 7.6 Hz, 1H), 7.83 (d, J = 8.4 Hz, 1H), 7.60 (d, J = 8.4 Hz, 1H), 7.29-7.24 (m, 2H), 6.74-6.68 (m, 2H), 5.11 (dd, J = 5.6, 12.8 Hz, 1H), 4.92 (t, J = 6.4 Hz, 1H), 4.49 (s, 1H), 4.20-4.08 (m, 4H), 3.79 (s, 1H), 3.72 (dd, J = 5.2, 9.0 Hz, 2H), 3.64 (t, J = 8.0 Hz, 1H), 3.02-2.76 (m, 3H), 2.64 (s, 1H), 2.63-2.53 (m, 2H), 2.41 (s, 3H), 2.27-2.16 (m, 3H), 2.14-2.00 (m, 3H), 1.91 (s, 2H), 1.59-1.42 (m, 4H), 1.35 (t, J = 7.2 Hz, 3H), 0.94 (d, J = 6.4 Hz, 6H). |
| 44 | 894.3831 | 895.72 | A | $^1$H NMR (400 MHz, DMSO-d$_6$) δ 11.08 (s, 1H), 8.59 (s, 1H), 8.26 (s, 1H), 8.20 (s, 1H), 8.11-8.09 (d, J = 4 Hz 1H), 6.91-6.81 (m, 4H), 5.05 (dd, J = 5.2, 15.2 Hz, 2H), 4.46 (s, 1H), 4.42-4.32 (m, 3H), 3.93 (s, 3H), 3.34 (s, 1H), 3.26-3.24 (m, 3H), 2.92-2.88 (m, 3H), 2.53-2.50 (m, 1H), 2.40 (s, 6H), 2.07-2.05 (d, J = 8 Hz 1H), 2.01 (s, 3H) 1.64 (m, 2H), 1.48 (s, 2H), 1.32-1.30 (d, J = 8 Hz 6H) 1.16 (s, 2H). |

TABLE 2B-continued

Degradation of AR proteins by exemplary heterobifunctional compounds of the present disclosure.

| Comp No. | Exact Mass | Observed Mass | DC50 Code* | NMR |
|---|---|---|---|---|
| 45 | 872.3224 | 873.55 | A | $^1$H NMR (400 MHz, DMSO-d$_6$) δ 11.23-11.03 (m, 1H), 8.57 (s, 1H), 8.38 (s, 1H), 8.24 (s, 1H), 8.07 (d, J = 8.0 Hz, 1H), 7.91-7.82 (m, 2H), 7.37 (d, J = 2.0 Hz, 1H), 7.12 (dd, J = 2.4, 8.8 Hz, 1H), 5.14 (dd, J = 5.6, 13.2 Hz, 1H), 4.96 (s, 1H), 4.56-4.41 (m, 3H), 3.88-3.68 (m, 3H), 2.95-2.88 (m, 3H), 2.64-2.56 (m, 2H), 2.22 (d, J = 7.2 Hz, 5H), 2.13-2.00 (m, 3H), 1.88-1.76 (m, 4H), 1.69-1.57 (m, 3H), 1.56-1.43 (m, 3H), 1.11-0.99 (m, 2H), 0.93 (d, J = 6.4 Hz, 6H). |
| 46 | 848.4021 | 849.61 | A | $^1$H NMR (400 MHz, DMSO-d$_6$) δ 11.11 (s, 1H), 8.58 (s, 1H), 8.24 (s, 1H), 8.06 (s, 1H), 7.86-7.84 (d, J = 8 Hz 1H), 7.37 (s, 1H) 7.17-7.10 (m, 3H), 6.85 (s, 2H) 5.12 (dd, J = 5.2, 15.2 Hz, 1H), 4.92 (s, 1H), 4.50-4.47 (m, 3H), 3.81 (s, 1H), 3.68-3.64 (m, 3H), 2.95-2.92 (m, 3H), 2.53-2.52 (m, 3H), 2.50-2.49 (m, 2H), 2.25-2.24 (m, 2H), 2.07-1.86 (m, 2H), 1.83-1.82 (m, 5H), 1.58-1.52(m, 5H), 1.07 (s, 3H), 0.93-0.92 (d, J = 4 Hz 1H). |
| 47 | 864.3726 | 865.59 | A | $^1$H NMR (400 MHz, DMSO-d$_6$) δ 11.09 (s, 1H), 8.57 (d, J = 8.4 Hz, 1H), 7.92-7.75 (m, 3H), 7.46-7.30 (m, 4H), 7.14 (m, 1H), 5.11 (m, 1H), 4.69-4.42 (m, 4H), 3.87 (d, J = 7.6 Hz, 1H), 3.09-2.88 (m, 4H), 2.65-2.57 (m, 3H), 2.34 (d, J = 1.6 Hz, 2H), 2.09 (d, J = 5.6 Hz, 5H), 1.97-1.83 (m, 4H), 1.71-1.43 (m, 10H), 1.37-1.26 (m, 1H), 1.18-0.76 (m, 8H). |
| 48 | 850.3569 | 851.7 | A | $^1$H NMR (300 MHz, DMSO-d$_6$) δ 11.01 (s, 1H), 8.59 (s, 1H), 8.25 (s, 1H), 8.18 (d, J = 8.1 Hz, 1H), 7.86 (d, J = 8.7 Hz, 1H), 7.51 (d, J = 8.4 Hz, 1H), 7.39 (d, J = 2.4 Hz, 1H), 7.15-7.11 (m, 2H), 7.03-(d, J = 2.1 Hz, 1H), 5.14-5.07 (m, 1H), 4.78 (s, 1H), 4.70-4.60 (m, 2H), 4.50-4.35 (m, 4H), 4.27-4.21 (m, 3H), 3.82 (s, 1H), 3.34-3.31 (m, 1H), 3.21-3.08 (m, 1H), 3.01-2.82 (m, 3H), 2.73-2.70 (m, 2H), 2.60 (s, 1H), 2.37-2.31 (m, 4H), 2.22-2.12 (m, 6H), 1.90-1.87 (m, 2H), 1.81-1.77 (m, 3H), 1.63-1.53 (m, 4H), 1.12-1.07 (m, 2H). |
| 49 | 811.3009 | 812.52 | A | $^1$H NMR (400 MHz, DMSO-d$_6$) δ 8.18(s, 1H), 7.80 (dd, J = 9.1, 6.9 Hz, 2H), 7.62 (d, J = 8.0 Hz, 1H), 7.41--7.26 (m, 3H), 7.09 (dd, J = 8.8, 2.4 Hz, 1H), 5.05 (dd, J = 12.8, 5.5 Hz, 1H), 4.71-4.44 (m, 3H), 3.91-3.80 (m, 2H), 3.30-3.20 (m, 4H), 3.00 (t, J = 12.5 Hz, 2H), 2.91-2.77 (m, 1H), 2.71-2.55 (m, 5H), 2.22 (d, J = 7.1 Hz, 2H), 2.10-2.00 (m, 3H), 1.95-1.75 (m, 5H), 1.65-1.45 (m, 4H), 1.20-1.00 (m, 2H). |
| 50 | 830.3752 | 831.58 | A | $^1$H NMR (400 MHz, DMSO-d$_6$) δ 11.10 (s, 1H), 8.59 (d, J = 1.2 Hz), 8.39 (s, 1H), 8.26 (s, 1H), 8.06 (d, J = 8.0 Hz, 1H), 7.86 (d, J = 8.0 Hz, 1H), 7.38-7.20 (m, 2H), 6.86 (s, 2H), 5.18-4.95 (m, 2H), 4.77-4.34 (m, 4H), 3.91-3.75 (m, 1H), 3.44-3.18 (m, 5H), 3.01-2.78 (m, 4H), 2.76-2.53 (m, 3H), 2.42 (s, 7H), 2.14-2.03 (m, 4H), 1.88 (d, J = 10.4 Hz, 3H), 1.73-1.45 (m, 6H), 1.18 (d, J = 10.4 Hz, 2H). |
| 51 | 794.2943 | 795.6328 | A | $^1$H NMR (400 Hz, DMSO-d$_6$) δ ppm 11.08 (s, 1H), 8.56 (d, J = 8 Hz, 1H), 7.81 (m, 2H), 7.36 (s, 1H), 7.31 (d, J = 12 Hz, 1H), 7.20 (m, 2H), 7.11 (d, J = 12 Hz, 1H), 5.10-4.99 (m, 2H), 4.47 (m, 3H), 3.82 (m, 1H), 3.33 (m, 2H), 2.99-2.82 (m, 3H), 2.58 (m, 3H), 2.32-2.23 (m, 5H), 2.05 (m, 3H), 1.87-1.46 (m, 8H), 1.12 (m, 2H). |
| 52 | 854.3319 | 855.56 | A | $^1$H NMR (400 MHz, Chloroform-d) δ 8.85 (s, 1H), 7.97 (s, 1H), 7.63-7.60 (m, 2H), 7.38 (d, J = 8.2 Hz, 1H), 7.01 (d, J = 2.6 Hz, 2H), 6.86 (dd, J = 8.6, 2.5 Hz, 1H), 4.97 (dd, J = 12.3, 5.3 Hz, 1H), 4.82-4.78 (m, 1H), 4.52-4.48 (m, 2H), 4.34-4.31 (m, 1H), 4.05-4.01 (m, 1H), 3.80-3.78 (m, 1H), 3.03-2.80 (m, 3H), 2.88-2.73 (m, 1H), 2.40-2.37 (m, 3H), 2.29-2.26 (m, 6H), 1.97-1.89 (m, 2H), 1.78-1.68 (m, 3H), 1.55-1.41 (m, 3H), 1.39-1.22 (m, 3H), 1.21-1.05 (m, 2H), 1.00 (d, J = 6.6 Hz, 6H). |
| 53 | 864.3362 | 865.565 | A | $^1$H NMR (300 MHz, DMSO-d$_6$) δ 11.10 (s, 1H), 8.57-8.56 (d, J = 0.9 Hz, 1H), 8.23 (s, 1H), 8.07-8.04 (d, J = 8.4 Hz, 1H), 7.85-7.80 (m, 2H), 7.36-7.35 (d, J = 2.4 Hz, 1H), 7.26-7.23 (m, 2H), 7.12-7.09 (m, 1H), 5.13-5.07 (m, 1H), 4.91 (s, 1H), 4.62-4.58 (m, 2H), 4.48-4.43 (d, J = 13.5 Hz, 3H), 4.24-4.20 (m, 2H), 4.00 (s, 1H), 3.36 (s, 1H), 3.24 (s, 1H), 3.00-2.92 (m, 3H), 2.70-2.48 (m, 3H), 2.48 (s, 1H), 2.35-2.33 (d, J = 5.7 Hz, 2H), 2.23-2.06 (m, 8H), 1.84-1.74 (m, 5H), 1.61-1.46 (m, 4H), 1.01 (s, 2H). |
| 54 | 811.3009 | 812.5 | A | |
| 55 | 866.3518 | 867.58 | A | $^1$H NMR (400 MHz, DMSO-d$_6$) δ 8.60 (s, 1H), 8.28 (s, 1H), 8.08 (d, J = 8.4 Hz, 1H), 7.86 (d, J = 8.8 Hz, 2H), 7.37-7.32 (m, 3H), 7.13-7.11 (m, 1H), 5.14-5.10 (m, 2H), 4.52-4.49 (m, 4H), 3.83 (d, J = 8.4 Hz, 1H), 3.57 (s, 3H), 3.41 (s, 1H), 3.34-2.92 (m, 4H), 2.89-2.85 (m, 3H), 2.63-2.50 (m, 2H), 2.41-2.33 (m, 1H), 2.10-2.04 (m, 5H), 1.88 (d, J = 9.6 Hz, 3H), 1.65-1.49 (m, 5H), 1.26-0.92 (m, 6H). |
| 56 | 844.3908 | 845.6 | A | $^1$H NMR (400 MHz, DMSO-d$_6$) δ 11.10 (s, 1H), 8.56 (d, J = 12.8 Hz, 1H), 8.19 (s, 1H), 8.05 (d, J = 8.4 Hz, 1H), 7.84 (d, J = 8.4 Hz, 1H), 7.75 (d, J = 1.2 Hz, 1H), 7.61 (d, J = 9.2 Hz, 1H), 7.31-7.22 (m, 2H), 6.76- 6.66 (m, 2H), 5.11 (dd, J = 5.2, 12.8 Hz, 1H), 4.92 (t, J = 6.0 Hz, 1H), 4.55-4.41 (m, 1H), 4.16 (m, 2H), 4.08- 4.01 (m, 2H), 3.88 (s, 3H), 3.86-3.81 (m, 1H), 3.61 (td, J = 8.0, 16.0 Hz, 1H), 2.94-2.86 (m, 2H), 2.64- 2.53 (m, 2H), 2.39 (d, J = 5.6 Hz, 4H), 2.31-2.16 (m, 5H), 2.14-2.02 (m, 3H), 1.88 (d, J = 10.4 Hz, 4H), 1.67-1.42 (m, 4H), 0.92 (d, J = 6.8 Hz, 6H). |
| 57 | 804.3595 | 805.56 | A | $^1$H NMR (400 MHz, DMSO-d$_6$) δ 11.09 (s, 1H), 8.73 (s, 2H), 8.15 (s, 1H), 8.11 (d, J = 7.2 Hz, 1H), 7.83 (d, J = 8.4 Hz, 1H), 7.61 (d, J = 8.8 Hz, 1H), 7.29-7.23 (m, 2H), 6.76-6.69 (m, 2H), 5.11 (dd, J = 5.2, 12.8 Hz, 1H), 4.92 (s, 1H), 4.50 (s, 1H), 4.12 (t, J = 8.8 Hz, 2H), 3.89 (s, 3H), 3.79 (s, 2H), 3.73 (dd, J = 5.2, 8.8 Hz, 3H), 3.68-3.59 (m, 3H), 2.94-2.80 (m, 2H), 2.24 (d, J = 8.0 Hz, 3H), 2.12 (s, 2H), 2.07-2.01 (m, 1H), 1.92 (s, 3H), 1.56-1.46 (m, 4H), 0.94 (d, J = 6.4 Hz, 6H). |
| 58 | 852.3362 | 853.56 | A | $^1$H NMR (300 MHz, DMSO-d$_6$, ppm) δ 11.12 (br, 1H), 8.59 (s, 1H), 8.25 (br, 1H), 8.09-8.06 (d, J = 9 Hz, 1H), 7.88-7.82 (m, 2H), 7.38-7.37 (d, J = 3 Hz, 1H), 7.28-7.24 (m, 2H), 7.15-7.11 (m, 1H), 5.15-5.10 (m, 1H), 4.96-4.90 (m, 1H), 4.50-4.45 (m, 3H), 3.88-3.79 (m, 1H), 3.52-3.47 (m, 1H), 3.40-3.36 (m, 2H), 3.24 (s, 3H), 2.98-2.94 (m, 3H), 2.64-2.51 (m, 3H), 2.49-2.34 (m, 3H), 2.27-2.20 (m, 4H), 2.11-2.08 (m, 3H), 1.89-1.81 (m, 5H), 1.62-1.48 (m, 4H), 1.09-1.05(m, 2H). |
| 59 | 864.3726 | 865.59 | A | $^1$H NMR (400 MHz, DMSO-d$_6$) δ 11.10 (s, 1H), 8.77 (s, 2H), 8.24 (br s, 1H), 8.13 (br d, J = 7.2 Hz, 1H), 7.85 (t, J = 8.0 Hz, 2H), 7.46 (s, 1H), 7.41-7.32 (m, 2H), 7.14 (dd, J = 2.4, 8.8 Hz, 1H), 5.12 (dd, J = 5.2, 13.2 Hz, 1H), 4.79 (br d, J = 10.8 Hz, 2H), 4.66-4.48 (m, 2H), 3.79 (br s, 1H), 3.07-2.82 (m, 5H), 2.60 (br d, J = 16.8 Hz, 1H), 2.20 (br d, J = 14.8 Hz, 5H), 1.94 (br d, J = 14.4 Hz, 5H), 1.84- 1.70 (m, 2H), 1.51 (br s, 7H), 1.35-1.14 (m, 9H), 1.06 (t, J = 7.2 Hz, 1H). |
| 60 | 822.362 | 823.585 | A | $^1$H NMR (300 MHz, DMSO-d$_6$) δ 10.99 (s, 1H), 8.77-8.46 (m, 2H), 8.15-8.09 (m, 1H), 7.89-7.83 (m, 1H), 7.41-7.36 (m, 2H), 7.19-6.89 (m, 3H), 5.17-5.03 (m, 1H), 5.02-4.88 (m, 1H), 4.87-4.66 (m, 2H), 4.65-4.48 (m, 1H), 4.47-4.13 (m, 2H), 3.93-3.46 (m, 2H), 3.21-2.72 (m, 5H), 2.71-2.58 (m, 1H), 2.48-1.63 (m, 12H), 1.62-1.40 (m, 4H), 1.39-0.73 (m, 10H). |

TABLE 2B-continued

Degradation of AR proteins by exemplary heterobifunctional compounds of the present disclosure.

| Comp No. | Exact Mass | Observed Mass | DC50 Code* | NMR |
|---|---|---|---|---|
| 61 | 850.3205 | 851.55 | A | $^1$H NMR (300 MHz, DMSO-d$_6$) δ 11.09 (s, 1H), 8.57 (s, 1H), 8.23 (s, 1H), 8.07-8.04 (d, J = 8.4 Hz, 1H), 7.85-7.80 (m, 2H), 7.36-7.35 (d, J = 2.1 Hz, 1H), 7.25-7.23 (d, J = 7.5 Hz, 2H), 7.12-7.09 (m, 1H), 5.13-5.07 (m, 1H), 4.90 (s, 1H), 4.51-4.48 (d, J = 6.3 Hz, 7H), 3.99-3.94 (m, 1H), 3.82-3.80 (d, J = 5.7 Hz, 1H), 3.59-3.53 (m, 1H), 2.98-2.83 (s, 3H), 2.60 (s, 1H), 2.49-2.48 (m, 2H), 2.36-2.34 (d, J = 6.0 Hz, 2H), 2.28-2.06 (m, 10H), 1.84-1.61 (m, 5H), 1.06 (s, 2H). |
| 62 | 864.3362 | 865.57 | A | $^1$H NMR (300 MHz, CDCl$_3$) δ 8.76 (s, 1H), 8.03-8.02 (d, J = 3.6 Hz, 1H), 7.89-7.86 (d, J = 10.8 Hz, 1H), 7.73-7.70 (d, J = 8.4 Hz, 1H), 7.50-7.47 (d, J = 9.0 Hz, 1H), 7.32-7.30 (d, J = 7.8 Hz, 1H), 7.10-7.04 (m, 2H), 6.92 (s, 1H), 6.79-6.76 (m, 1H), 4.90-4.69 (m, 2H), 4.43-4.35 (m, 2H), 4.24 (s, 1H), 3.98-3.89 (m, 2H), 3.63-3.58 (m, 3H), 3.49-3.44 (m, 1H), 2.93-2.67 (m, 5H), 2.45-2.11 (m, 12H), 1.97-1.87 (m, 3H), 1.64 (s, 2H), 1.45-1.38 (m, 3H), 1.19-1.00 (m, 8H). |
| 63 | 818.4115 | 819.61 | A | $^1$H NMR (300 MHz, DMSO-d$_6$) δ 10.93 (s, 1H), 8.71 (s, 2H), 8.05 (d, J = 7.2 Hz, 1H), 7.58 (d, J = 8.4 Hz, 1H), 7.47 (d, J = 8.1 Hz, 1H), 7.12 (d, J = 8.1 Hz, 1H), 6.99 (s, 1H), 6.71 (d, J = 8.7 Hz, 2H), 5.10-5.04 (m, 1H), 4.74-4.71 (m, 3H), 4.49-4.19 (m, 3H), 3.86-3.84 (m, 3H), 3.78-3.60 (m, 2H), 2.94-2.87 (m, 4H), 2.60 (s, 1H), 2.39-2.12 (m, 5H), 2.12-2.10 (m, 4H), 1.98-1.80 (m, 5H), 1.73-1.65 (m, 1H), 1.48-145 (m, 4H), 1.06-0.85 (m, 8H). |
| 64 | 846.4065 | 847.62 | A | $^1$H NMR (300 MHz, DMSO-d$_6$) δ 11.03 (s, 1H), 8.59 (s, 1H), 8.25 (s, 1H), 8.04 (d, J = 7.8 Hz, 1H), 7.82 (d, J = 7.8 Hz, 1H), 7.60 (d, J = 8.1 Hz, 1H), 7.27-7.24 (m, 2H), 6.69 (s, 2H), 5.13-5.10 (m, 1H), 4.89-4.88 (m, 1H), 4.50-4.47 (m, 3H), 4.17-4.15 (m, 2H), 3.83-3.64 (m, 2H), 2.95-2.91 (m, 4H), 2.61-2.50 (m, 2H), 2.42-2.40 (m, 2H), 2.24-2.07 (m, 7H), 2.01-1.84 (m, 4H), 1.67-1.23 (m, 8H), 1.07-1.04 (m, 8H. |
| 65 | 848.3777 | 849.6 | A | $^1$H NMR (400 MHz, DMSO-d$_6$) δ 10.90 (s, 1H), 8.59 (d, J = 1.2 Hz, 1H), 8.34-8.24 (m, 2H), 8.07 (d, J = 8.4 Hz, 1H), 7.87 (d, J = 8.4 Hz, 1H), 7.58 (d, J = 8.4 Hz, 1H), 7.38 (d, J = 2.4 Hz, 1H), 7.16-7.10 (m, 1H), 6.88 (br d, J = 8.4 Hz, 2H), 6.71 (s, 1H), 4.77 (s, 1H), 4.52 (br s, 3H), 4.01-3.80 (m, 3H), 2.95 (br d, J = 11.4 Hz, 4H), 2.67-2.63 (m, 3H), 2.58-2.56 (m, 2H), 2.47-2.42 (m, 3H), 2.26-2.24 (m, 2H), 2.25 (br d, J = 7.0 Hz, 2H), 2.12 (br s, 5H), 1.88 (br s, 6H), 1.64-1.49 (m, 7H), 0.93 (d, J = 6.5 Hz, 6H). |
| 66 | 808.31 | 809.5 | A | $^1$H NMR (400 MHz, DMSO-d$_6$) δ 11.09 (s, 1H), 8.73 (s, 2H), 8.15-8.09 (m, 2H), 7.87-7.81 (m, 2H), 7.38 (d, J = 2.4 Hz, 1H), 7.29-7.24 (m, 2H), 7.14 (dd, J = 2.4, 8.8 Hz, 1H), 5.11 (dd, J = 5.2, 12.7 Hz, 1H), 4.95-4.88 (m, 1H), 4.55 (s, 1H), 4.12 (t, J = 8.4 Hz, 2H), 3.78 (s, 1H), 3.73 (dd, J = 5.2, 8.8 Hz, 2H), 3.65 (t, J = 8.8 Hz, 1H), 2.98-2.77 (m, 3H), 2.69-2.60 (m, 4H), 2.41 (s, 3H), 2.24 (d, J = 10.0 Hz, 2H), 2.15-2.00 (m, 4H), 1.91 (s, 2H), 1.50 (s, 4H), 0.94 (d, J = 6.4 Hz, 6H). |
| 67 | 811.3009 | 812.5 | A | |
| 68 | 848.3857 | 849.59 | A | |
| 69 | 825.3165 | 826.53 | A | $^1$H NMR (300 MHz, DMSO-d$_6$) δ 11.00 (s, 1H), 8.59-8.56 (m, 1H), 7.86-7.82 (m, 2H), 7.78-7.61 (m, 1H), 7.38-7.31(m, 3H), 7.15-7.11 (m, 1H), 4.53-4.46 (m, 3H), 3.91-3.84 (m, 1H), 3.32-3.23 (m, 4H), 3.05-2.97 (m, 2H), 2.80-2.69 (m, 1H), 2.68-2.63 (m, 3H), 2.22-2.12 (m, 2H), 2.07-2.00 (m, 4H), 1.90-1.80 (m, 9H), 1.70-1.49 (m, 5H), 1.25-1.05 (m, 2H). |
| 70 | 818.3752 | 819.56 | B | $^1$H NMR (400 MHz, DMSO-d$_6$) δ 11.11 (s, 1H), 8.73 (s, 2H), 8.17 (s, 1H), 8.12 (d, J = 7.6 Hz, 1H), 7.83 (d, J = 8.4 Hz, 1H), 7.60 (d, J = 8.4 Hz, 1H), 7.29-7.24 (m, 2H), 6.74-6.68 (m, 2H), 5.11 (dd, J = 5.6, 12.8 Hz, 1H), 4.92 (t, J = 6.4 Hz, 1H), 4.49 (s, 1H), 4.20-4.08 (m, 4H), 3.79 (s, 1H), 3.72 (dd, J = 5.2, 9.2 Hz, 2H), 3.64 (t, J = 8.0 Hz, 1H), 3.02-2.76 (m, 3H), 2.64 (s, 1H), 2.63-2.53 (m, 2H), 2.41 (s, 3H), 2.27-2.16 (m, 2H), 2.14-2.00 (m, 3H), 1.91 (s, 2H), 1.59-1.42 (m, 4H), 1.35 (t, J = 7.2 Hz, 3H), 0.94 (d, J = 6.4 Hz, 6H). |
| 71 | 766.3358 | 767.595 | B | |
| 72 | 768.3038 | 769.515 | D | $^1$H NMR (300 MHz, DMSO-d$_6$) δ 1.05-1.08 (m, 7H), 1.13 (s, 6H), 1.25-1.90 (m, 10H), 1.92-2.18 (m, 3H), 2.46-2.65 (m, 2H), 2.75-2.96 (m, 1H), 3.80-3.96 (m, 1H), 4.02-4.34 (m, 3H), 4.36-4.48 (m, 1H), 4.95-5.18 (m, 1H), 6.59-6.61 (m, 1H), 6.94-6.97 (m, 1H), 7.15-7.21 (m, 1H), 7.24-7.28 (m, 1H), 7.30-7.34 (m, 1H), 7.35-7.37 (m, 1H), 7.75-7.88 (m, 3H), 11.05 (s, 1H). |
| 73 | 848.3777 | 849.6 | D | $^1$H NMR (400 MHz, DMSO-d$_6$) δ 10.92 (s, 1H), 8.58 (d, J = 1.2 Hz, 1H), 8.25 (s, 1H), 8.13 (s, 1H), 8.06 (d, J = 8.4 Hz, 1H), 7.86 (d, J = 8.8 Hz, 1H), 7.59 (d, J = 2.0, 7.6 Hz, 1H), 7.37 (d, J = 2.4 Hz, 1H), 7.34-7.28 (m, 1H), 7.23 (d, J = 8.4 Hz, 1H), 7.12 (dd, J = 2.4, 8.8 Hz, 2H), 6.97 (s, 1H), 4.79 (s, 1H), 4.55-4.45 (m, 3H), 4.05-3.95 (m, 1H), 3.90-3.75 (m, 1H), 3.75-3.60 (m, 1H), 2.96 (br t, J = 12.4 Hz, 2H), 2.77-2.68 (m, 1H), 2.58-2.52 (m, 4H), 2.12-2.04 (m, 2H), 1.93-1.81 (m, 6H), 1.68-1.45 (m, 8H), 1.44-1.29 (m, 8H), 1.18-0.84 (m, 10H). |
| 74 | 825.3165 | 826.53 | D | $^1$H NMR (300 MHz, DMSO-d$_6$) δ 8.59-8.57 (m, 1H), 7.87-7.71 (m, 3H), 7.47-7.31 (m, 3H), 7.15-7.11 (m, 1H), 5.21-5.11(m, 1H), 4.53-4.46 (m, 3H), 3.89-3.80 (m, 1H), 3.32-3.26 (m, 4H), 3.06-2.90 (m, 6H), 2.88-2.70 (m, 1H), 2.55-2.50 (m, 4H), 2.24-2.07 (m, 5H), 1.91-1.82 (m, 5H), 1.66-1.49 (m, 4H), 1.21-1.11 (m, 2H). |
| 75 | 850.3569 | 851.57 | D | $^1$H NMR (400 MHz, DMSO-d$_6$) δ 11.16 (s, 1H), 8.59 (d, J = 1.1 Hz, 1H), 8.26 (s, 1H), 8.07 (d, J = 8.4 Hz, 1H), 7.93-7.77 (m, 2H), 7.38 (d, J = 2.4 Hz, 1H), 7.31-7.24 (m, 2H), 7.13 (m, 1H), 5.02-4.78 (m, 2H), 4.61-4.40 (m, 3H), 3.84 (s, 1H), 3.71-3.62 (m, 1H), 3.03-2.75 (m, 4H), 2.44-2.35 (m, 3H), 2.27-2.08 (m, 6H), 1.94-1.83 (m, 4H), 1.67-1.44 (m, 5H), 1.24-1.01 (m, 3H), 0.97-0.86 (m, 9H). |
| 76 | 850.3569 | 851.57 | D | $^1$H NMR (400 MHz, DMSO-d$_6$) δ 11.13 (s, 1H), 8.57 (d, J = 1.2 Hz, 1H), 8.63-8.53 (m, 1H), 8.23 (s, 1H), 8.05 (d, J = 8.8 Hz, 1H), 7.87-7.79 (m, 1H), 7.88-7.78 (m, 1H), 7.35 (d, J = 2.4 Hz, 1H), 7.29-7.20 (m, 2H), 7.11 (m, 1H), 4.94-4.77 (m, 2H), 4.58-4.38 (m, 3H), 3.92-3.59 (m, 2H), 3.05-2.75 (m, 4H), 2.43-2.35 (m, 3H), 2.26-2.05 (m, 6H), 1.88-1.77 (m, 4H), 1.66-1.40 (m, 5H), 1.21-0.97 (m, 3H), 0.95-0.78 (m, 9H). |
| 77 | 819.3511 | 820.58 | | $^1$H NMR (400 Hz, DMSO-d$_6$) δ ppm 11.08 (s, 1H), 8.56 (d, J = 8 Hz, 1H), 7.83-7.76 (m, 2H), 7.70 (d, J = 12 Hz, 1H), 7.42 (d, J = 8 Hz, 1H), 7.36 (s, 1H), 7.31-7.29 (d, J = 8 Hz, 1H), 7.12-7.09 (d, J = 12 Hz, 1H), 5.07 (m, 1H), 4.53-4.43 (m, 3H), 3.82 (m, 1H), 3.02-2.82 (m, 2H), 2.54 (m, 2H), 2.19 (m, 2H), 2.08-1.79 (m, 8H), 1.67-1.46 (m, 4H), 1.11 (m, 1H). |
| 78 | 846.4065 | 847.74 | A | $^1$H NMR (400 MHz, DMSO-d$_6$) δ 11.06 (s, 1H), 8.59 (s, 1H), 8.25 (s, 1H), 8.14 (s, 1H), 8.05-8.03 (d, J = 8 Hz 1H), 6.91-6.81 (m, 4H), 5.05 (dd, J = 5.2, 15.2 Hz, 2H), 4.46 (s, 1H), 4.42-4.32 (m, 3H), 3.93 (s, 3H), 3.34 (s, 1H), 3.26-3.24 (m, 3H), 2.92-2.88 (m, 3H), 2.53-2.50 (m, 1H), 2.40 (s, 6H), 2.07-2.05 (d, J = 8 Hz 1H), 2.01 (s, 3H) 1.64(m, 2H), 1.09 (s, 2H), 0.97 (s, 6H). |

TABLE 2C

Degradation of AR proteins by exemplary heterobifunctional compounds of the present disclosure.

| Comp No. | Exact Mass | Observed Mass | DC50 Code* | NMR |
|---|---|---|---|---|
| 79 | 888.45 | 889.79 | A | $^1$H NMR (400 MHz, DMSO-d$_6$) δ 11.09 (s, 1H), 8.76 (s, 2H), 7.71-7.69 (m, 1H), 6.86-6.81 (d, 2H), 6.73 (s, 2H), 5.06-5.04 (m, 1H), 4.91 (m, 1H), 4.79-4.76 (m, 2H), 4.19 (s, 1H), 4.03-4.01 (m, 1H), 3.93 (s, 3H), 3.66-3.64 (m, 1H), 2.94-2.91 (m, 4H), 2.60 (m, 1H), 2.43 (m, 6H), 2.24-2.19 (m, 4H), 2.00-1.69 (m, 4H), 1.22 (m, 8H), 1.11-1.00 (m, 6H), 0.93 (m, 9H). |
| 80 | 850.39 | 851.62 | A | $^1$H NMR (400 MHz, CDCl$_3$, ppm) δ 8.71 (s, 2H), 8.00 (s, 1H), 7.81 (d, J = 8.4 Hz, 1H), 7.60 (d, J = 8.8 Hz, 1H), 6.98-6.97 (m, 1H), 6.94-6.91 (m, 1H), 6.83-6.80 (m, 2H), 5.96 (d, J = 8.0 Hz, 1H), 5.24-5.19 (m, 1H), 4.98-4.90 (m, 2H), 4.89-4.80 (m, 1H), 4.47-4.43 (m, 1H), 4.33-4.29 (m, 1H), 4.14 (d, J = 8.4 Hz, 1H), 4.06 (s, 1H), 3.91-3.89 (m, 1H), 3.00-2.80 (m, 5H), 3.54-3.30 (m, 5H), 2.28-2.19 (m, 1H), 2.15-2.00 (m, 2H), 2.00-1.69 (m, 5H), 1.26 (s, 6H), 1.23 (s, 6H), 1.20-1.15 (m, 6H) |
| 81 | 888.42 | 889.76 | A | $^1$H NMR (300 MHz, DMSO-d$_6$) δ 11.18-11.09 (s, 1H), 8.76 (s, 2H), 7.73-7.70 (m, 1H), 6.90-6.87 (m, 2H), 6.73 (s, 2H), 5.12-5.02 (m, 2H), 4.82-4.38 (m, 3H), 4.19 (s, 1H), 4.04 (m, 1H), 3.94 (s, 3H), 3.29 (m, 3H), 2.96-2.68 (m, 5H), 2.51 (m, 1H), 2.43 (m, 7H), 2.01-1.93 (m, 4H), 1.90-1.73 (m, 2H), 1.68-1.59 (m, 2H), 1.23 (m, 7H), 1.08 (m, 8H). |
| 82 | 788.36 | 789.68 | A | $^1$H NMR (300 MHz, DMSO-d$_6$) δ 11.10 (s, 1H), 8.72 (s, 2H), 7.84-7.69 (m, 2H), 7.25-7.23 (m, 2H), 6.72 (s, 2H), 5.13-5.04 (m, 2H), 4.17-4.12 (m, 3H), 4.02-3.99 (m, 1H), 3.82-3.77 (m, 2H), 2.88-2.76 (m, 2H), 2.71-2.96 (m, 2H), 2.61 (m, 3H), 2.49-2.41 (m, 6H), 2.28 (m, 4H), 2.06-2.00 (m, 1H), 1.28 (m, 7H), 1.20 (s, 6H). |
| 83 | 844.43 | 845.76 | A | $^1$H NMR (300 MHz, CDCl$_3$) δ 8.70 (s, 2H), 7.96 (m, 1H), 7.79-7.77 (m, 1H), 7.19 (m, 1H), 6.57 (s, 2H), 5.94 (m, 1H), 4.98-4.86 (m, 4H), 4.12-4.09 (d, 1H), 4.02 (s, 1H), 3.49 (m, 1H), 3.26-3.12 (m, 1H), 2.99-2.74 (m, 6H), 2.61-2.58 (m, 6H), 2.49-2.13 (m, 4H), 1.94-1.90 (m, 2H), 1.56-1.40 (m, 6H), 1.37 (m, 2H), 1.25-1.07 (m, 12H), 1.00-0.96 (m, 2H). |
| 84 | 892.40 | 893.65 | A | $^1$H NMR (400 MHz, DMSO-d$_6$) δ 11.06 (s, 1H), 8.75 (s, 2H), 7.90 (d, J = 8.8 Hz, 1H), 7.80 (d, J = 8.4 Hz, 1H), 7.77 (d, J = 8.8 Hz, 1H), 7.44 (s, 1H), 7.32 (d, J = 8.8 Hz, 1H), 7.22 (s, 1H), 6.99 (d, J = 8.8 Hz, 1H), 5.10-5.08 (m, 1H), 4.77-4.74 (m, 2H), 4.65 (b, 1H), 4.29 (s, 1H), 4.03 (d, J = 8.4 Hz, 1H), 3.02-2.92 (m, 6H), 2.51-2.50 (m, 3H), 2.20-2.01 (m, 4H), 1.85-1.82 (m, 2H), 1.69-1.66 (m, 3H), 1.48-1.43 (m, 4H), 1.21 (s, 6H), 1.11 (s, 6H), 0.98-0.96 (m, 7H) |
| 85 | 816.40 | 817.71 | A | $^1$H NMR (400 MHz, DMSO-d$_6$) δ 11.14 (s, 1H), 10.07-10.51 (m, 1H), 8.76 (s, 2H), 7.92 (d, J = 8.0 Hz, 1H), 7.73 (d, J = 8.8 Hz, 1H), 7.34-7.42 (m, 2H), 6.73 (s, 2H), 5.25-5.45 (m, 1H), 5.14 (dd, J = 12.8, 4.8 Hz, 1H), 4.68-4.80 (m, 3H), 4.53 (s, 1H), 4.32 (s, 1H), 4.12-4.25 (m, 2H), 4.02 (d, J = 9.2 Hz, 1H), 3.21-3.45 (m, 2H), 2.86-2.99 (m, 3H), 2.55-2.64 (m, 2H), 2.43 (s, 6H), 2.03-2.10 (m, 1H), 1.64-1.78 (m, 3H), 1.47 (s, 2H), 1.21 (s, 6H), 1.11 (s, 6H), 1.02-1.09 (m, 2H). |
| 86 | 830.41 | 831.74 | A | $^1$H NMR (300 MHz, CDCl$_3$) δ 8.70 (s, 2H), 8.04 (s, 1H), 7.79-7.76 (d, 1H), 7.19 (s, 1H), 7.11-7.07 (m, 1H), 6.57 (s, 2H), 6.02-5.89 (m, 1H), 4.98-4.87 (m, 4H), 4.12-4.09 (m, 1H), 4.02 (s, 1H), 3.01-2.72 (m, 6H), 2.48 (m, 6H), 2.34-2.19 (m, 3H), 2.16-2.00 (m, 4H), 1.93-1.89 (m, 2H), 1.25-1.06 (m, 18H). |
| 87 | 876.37 | 877.60 | A | $^1$H NMR (400 MHz, DMSO-d$_6$) δ 11.12 (s, 1H), 8.81-8.61 (m, 2H), 8.17 (s, 2H), 7.90 (d, J = 8.7 Hz, 1H), 7.84 (d, J = 8.2 Hz, 1H), 7.74 (d, J = 9.2 Hz, 1H), 7.33-7.24 (m, 2H), 7.21 (d, J = 2.3 Hz, 1H), 7.00 (dd, J = 2.4, 8.8 Hz, 1H), 5.12 (dd, J = 5.4, 12.9 Hz, 1H), 4.98-4.86 (m, 1H), 4.29 (s, 1H), 4.15-4.10 (m, 2H), 4.06-4.00 (m, 3H), 3.79-3.71 (m, 2H), 2.96-2.86 (m, 2H), 2.60 (d, J = 17.7 Hz, 1H), 2.41 (br s, 4H), 2.30-2.16 (m, 5H), 2.07-2.01 (m, 1H), 1.87 (br d, J = 4.5 Hz, 2H), 1.21 (s, 6H), 1.11 (s, 5H), 1.14-1.06 (m, 1H), 0.96-0.89 (m, 6H) |
| 88 | 858.44 | 859.78 | A | $^1$H NMR (400 MHz, DMSO-d$_6$) δ 11.11 (s, 1H), 8.73 (s, 2H), 7.80-7.76 (m, 1H), 7.69-7.68 (d, 1H), 7.45-7.44 (m, 1H), 7.38-7.36 (m, 1H), 6.73 (s, 2H), 5.10-5.08 (m, 1H), 4.77-4.74 (m, 2H), 4.64 (m, 1H), 4.18 (s, 1H), 4.02-4.00 (d, 1H), 2.98-2.89 (m, 5H), 2.71-2.67 (m, 2H), 2.56 (m, 1H), 2.43 (s, 6H), 2.22-2.20 (m, 2H), 2.02-1.84 (m, 6H), 1.68 (m, 1H), 1.21 (s, 6H), 1.10 (s, 6H), 0.94 (m, 8H). |
| 89 | 918.46 | 919.81 | A | $^1$H NMR (400 MHz, DMSO-d$_6$) δ 11.12 (s, 1H), 8.75 (s, 2H), 7.83 (d, J = 8.8 Hz, 1H), 7.69 (d, J = 9.2 Hz, 1H), 7.23-7.29 (m, 2H), 6.73 (s, 2H), 5.11 (dd, J = 12.8, 5.2 Hz, 1H), 4.94 (s, 1H), 4.75 (d, J = 12.4 Hz, 2H), 4.18 (s, 1H), 4.02 (d, J = 8.8 Hz, 1H), 3.40-3.54 (m, 6H), 3.29-3.31 (m, 1H), 3.22 (s, 3H), 2.90-3.05 (m, 3H), 2.83-2.90 (m, 1H), 2.59-2.65 (m, 2H), 2.52-2.58 (m, 2H), 2.43 (s, 6H), 2.35-2.39 (m, 1H), 2.15-2.31 (m, 4H), 1.99-2.09 (m, 1H), 1.74-1.88 (m, 3H), 1.21 (s, 6H), 1.10 (s, 6H), 0.96-1.06 (m, 2H). |
| 90 | 929.48 | 930.83 | A | $^1$H NMR (400 MHz, DMSO-d$_6$) δ 11.12 (s, 1H), 8.76 (s, 2H), 8.17 (s, 1H), 7.84 (d, J = 8.0 Hz, 1H), 7.70 (d, J = 9.2 Hz, 1H), 7.19-7.34 (m, 2H), 6.74 (s, 2H), 5.12 (dd, J = 12.4, 5.2 Hz, 1H), 4.94 (s, 1H), 4.75 (d, J = 12.4 Hz, 2H), 4.19 (s, 1H), 4.02 (d, J = 9.2 Hz, 1H), 3.53-3.59 (m, 7H), 2.84-3.04 (m, 3H), 2.53-2.64 (m, 4H), 2.43 (s, 6H), 2.35-2.40 (m, 6H), 2.18-2.28 (m, 4H), 2.00-2.10 (m, 1H), 1.75-1.89 (m, 3H), 1.22 (s, 6H), 1.11 (s, 6H), 0.94-1.06 (m, 2H). |
| 91 | 874.44 | 875.77 | A | $^1$H NMR (300 MHz, DMSO-d$_6$) δ 11.12 (s, 1H), 8.76 (s, 2H), 7.85-7.82 (m, 1H), 7.71-7.68 (m, 1H), 7.28-7.25 (m, 2H), 6.79-6.74 (s, 2H), 5.15-5.11 (m, 1H), 5.09-4.94 (m, 1H), 4.77-4.73 (m, 2H), 4.19 (s, 1H), 4.04-4.00 (m, 1H), 3.51-3.48 (m, 1H), 3.42-3.85 (m, 2H), 3.25 (m, 3H), 3.01-2.94 (m, 3H), 2.73-2.62 (m, 3H), 2.43 (m, 6H), 2.39-2.32 (m, 2H), 2.27-2.22 (m, 5H), 2.16-1.94 (m, 1H), 1.90-1.75 (m, 3H), 1.22 (s, 6H), 1.08 (s, 6H), 1.05-0.92 (m, 2H). |
| 92 | 862.36 | 863.58 | A | $^1$H NMR (400 MHz, DMSO-d$_6$) δ 11.13 (s, 1H), 8.74 (s, 2H), 8.38 (s, 1H), 8.43-8.30 (m, 1H), 7.90 (d, J = 8.8 Hz, 1H), 7.84 (d, J = 8.4 Hz, 1H), 7.72 (d, J = 9.2 Hz, 1H), 7.32-7.19 (m, 3H), 7.01 (m, 1H), 5.12 (m, 1H), 4.92 (s, 1H), 4.29 (s, 1H), 4.03 (d, J = 9.2 Hz, 1H), 3.83 (d, J = 11.6 Hz, 2H), 3.66-3.54 (m, 2H), 3.04-2.87 (m, 2H), 2.70-2.55 (m, 4H), 2.47-2.34 (m, 3H), 2.28-2.17 (m, 2H), 2.03 (d, J = 5.6 Hz, 1H), 1.57 (s, 2H), 1.21 (s, 6H), 1.11 (s, 6H), 0.94 (d, J = 6.8 Hz, 6H), 0.69-0.58 (m, 1H). |

TABLE 2C-continued

Degradation of AR proteins by exemplary heterobifunctional compounds of the present disclosure.

| Comp No. | Exact Mass | Observed Mass | DC50 Code* | NMR |
|---|---|---|---|---|
| 93 | 804.36 | 805.67 | A | $^1$H NMR (400 MHz, DMSO-d$_6$) δ 11.11 (s, 1H), 8.59 (s, 1H), 8.31 (s, 1H), 7.79-7.86 (m, 2H), 7.63 (d, J = 8.8 Hz, 1H), 7.26-7.30 (m, 2H), 6.66 (d, J = 2.0 Hz, 1H), 6.56 (dd, J = 8.8, 2.0 Hz, 1H), 5.11 (dd, J = 12.8, 5.2 Hz, 1H), 5.05 (q, J = 5.2 Hz, 1H), 4.46 (d, J = 13.2 Hz, 2H), 4.36 (s, 1H), 3.95 (d, J = 9.2 Hz, 2H), 3.90 (s, 3H), 3.77 (t, J = 6.8 Hz, 2H), 3.04-3.08 (m, 2H), 2.97 (t, J = 12.0 Hz, 2H), 2.89 (dd, J = 5.2, 3.2 Hz, 1H), 2.61 (d, J = 2.8 Hz, 1H), 2.56 (d, J = 12.0 Hz, 2H), 2.32-2.40 (m, 2H), 2.05 (dd, J = 11.2, 5.6 Hz, 1H), 1.77 (d, J = 11.2 Hz, 2H), 1.66 (d, J = 3.2 Hz, 1H), 1.19 (s, 6H), 1.14 (s, 6H). |
| 94 | 904.44 | 905.78 | A | $^1$H NMR (400 MHz, DMSO-d$_6$) δ 11.07 (s, 1H), 8.16 (s, 1H), 7.74 (br d, J = 8.8 Hz, 2H), 7.65 (d, J = 8.8 Hz, 1H), 7.48 (br d, J = 9.2 Hz, 1H), 6.96 (br d, J = 9.2 Hz, 2H), 6.84 (br d, J = 8.8 Hz, 2H), 6.64 (d, J = 2.0 Hz, 1H), 6.54 (dd, J = 8.8, 2.0 Hz, 1H), 5.09-4.91 (m, 2H), 4.27 (s, 1H), 4.06 (s, 1H), 3.94 (s, 3H), 3.91 (s, 3H), 3.87 (br d, J = 12.4 Hz, 2H), 3.55-3.53 (m, 1H), 3.44-3.43 (m, 2H), 3.29-3.28 (m, 3H), 2.86-2.76 (m, 3H), 2.66-2.58 (m, 4H), 2.38 (br d, J = 6.4 Hz, 2H), 2.31-2.21 (m, 4H), 2.00 (br d, J = 4.4 Hz, 1H), 1.82 (br d, J = 11.6 Hz, 3H), 1.33-1.27 (m, 2H), 1.23 (s, 6H), 1.15 (s, 6H). |
| 95 | 850.39 | 851.62 | A | $^1$H NMR (300 MHz, DMSO-d$_6$) δ 10.96 (s, 1H), 8.75 (m, 3H), 7.88 (d, J = 8.8 Hz, 1H), 7.70 (d, J = 9.1 Hz, 1H), 7.53 (d, J = 8.4 Hz, 1H), 7.29-7.05 (m, 2H), 7.04-6.88 (m, 1H), 5.09 (dd, J = 13.1, 4.9 Hz, 1H), 4.94 (s, 1H), 4.76 (d, J = 12.8 Hz, 2H), 4.38 (d, J = 17.1 Hz, 1H), 4.31-4.17 (m, 3H), 4.02 (d, J = 9.1 Hz, 1H), 3.63-3.52 (m, 1H), 3.04-2.82 (m, 7H), 2.63 (m, 1H), 2.38 (m, 1H), 2.13-1.80 (m, 4H), 1.28 (d, J = 6.4 Hz, 3H), 1.25-1.06 (m, 19H). |
| 96 | 872.45 | 873.78 | A | $^1$H NMR (400 MHz, DMSO-d$_6$) δ 11.10 (br s, 1H), 8.27 (br s, 1H), 7.83 (d, J = 8.0 Hz, 1H), 7.73 (br d, J = 8.8 Hz, 2H), 7.46 (br d, J = 9.2 Hz, 1H), 7.29-7.21 (m, 2H), 6.95 (br d, J = 8.8 Hz, 2H), 6.73 (s, 2H), 5.11 (dd, J = 12.8, 5.4 Hz, 1H), 4.93 (br s, 1H), 4.22 (s, 1H), 4.03 (d, J = 9.2 Hz, 1H), 3.86 (br d, J = 12.0 Hz, 2H), 3.23 (s, 3H), 2.94-2.82 (m, 2H), 2.77 (br t, J = 11.6 Hz, 3H), 2.65-2.52 (m, 5H), 2.42 (s, 6H), 2.35 (br dd, J = 13.2, 6.8 Hz, 3H), 2.29-2.16 (m, 4H), 2.08-2.00 (m, 1H), 1.80 (br d, J = 11.6 Hz, 2H), 1.64 (br s, 1H), 1.21 (s, 6H), 1.15 (br s, 1H), 1.11 (s, 6H). |
| 97 | 866.43 | 867.65 | A | $^1$H NMR (400 MHz, DMSO-d$_6$) δ 10.96 (s, 1H), 8.75 (s, 2H), 7.69-7.61 (m, 2H), 7.01 (m, 1H), 6.96-6.94 (m, 1H), 6.73 (s, 2H), 5.09-5.05 (m, 1H), 4.81-4.73 (m, 3H), 4.40-4.03 (m, 4H), 3.59-3.55 (m, 1H), 3.00-2.81 (m, 5H), 2.67-2.61 (m, 1H), 2.43-2.34 (m, 11H), 2.24-2.22 (m, 2H), 1.99-1.96 (m, 1H), 1.84-1.81 (m, 3H), 1.21-1.00 (m, 15H). |
| 98 | 890.43 | 891.77 | A | $^1$H NMR (400 MHz, DMSO-d$_6$) δ 11.08 (s, 1H), 8.51-8.64 (m, 1H), 8.33 (s, 1H), 8.23 (s, 1H), 7.81 (d, J = 8.8 Hz, 1H), 7.64 (d, J = 8.8 Hz, 1H), 6.73-6.87 (m, 2H), 6.66 (d, J = 2.0 Hz, 1H), 6.56 (dd, J = 8.8, 2.0 Hz, 1H), 5.04 (dd, J = 12.8, 5.6 Hz, 1H), 4.91 (s, 1H), 4.51 (d, J = 12.4 Hz, 2H), 4.37 (s, 1H), 3.83-3.98 (m, 8H), 3.66 (dt, J = 16.8, 8.4 Hz, 1H), 2.78-3.04 (m, 4H), 2.53-2.62 (m, 2H), 2.43 (d, J = 14.4 Hz, 3H), 2.13-2.28 (m, 4H), 1.95-2.04 (m, 1H), 1.85 (d, J = 10.0 Hz, 1H), 1.70 (s, 1H), 1.19 (s, 6H), 1.14 (s, 6H), 1.05 (d, J = 11.2 Hz, 2H), 0.92 (d, J = 6.4 Hz, 6H). |
| 99 | 802.38 | 803.70 | A | $^1$H NMR (400 MHz, DMSO-d$_6$) δ 11.14 (s, 1H), 9.99-10.75 (m, 1H), 8.62 (s, 1H), 8.36 (s, 1H), 7.91 (d, J = 8.0 Hz, 1H), 7.81 (d, J = 9.2 Hz, 1H), 7.32-7.42 (m, 2H), 6.76 (s, 2H), 5.26-5.44 (m, 1H), 5.09-5.21 (m, 1H), 4.85 (s, 1H), 4.60 (s, 1H), 4.50 (d, J = 13.2 Hz, 2H), 4.42 (s, 1H), 4.20-4.33 (s, 2H), 3.94 (d, J = 8.8 Hz, 1H), 3.24 (s, 2H), 2.85-3.06 (m, 3H), 2.54-2.65 (m, 2H), 2.43 (s, 6H), 1.96-2.11 (m, 2H), 1.79 (d, J = 11.6 Hz, 2H), 1.21-1.29 (m, 1H), 1.19 (s, 6H), 1.12 (s, 6H). |
| 100 | 906.43 | 907.77 | A | $^1$H NMR (400 MHz, DMSO-d$_6$) δ 11.09 (s, 1H), 8.25 (d, J = 9.2 Hz, 1H), 7.82 (d, J = 9.6 Hz, 1H), 7.65 (d, J = 8.8 Hz, 1H), 7.37 (d, J = 9.6 Hz, 1H), 6.79-6.88 (m, 2H), 6.67 (d, J = 2.4 Hz, 1H), 6.57 (dd, J = 8.8, 2.0 Hz, 1H), 5.05 (dd, J = 12.8, 5.4 Hz, 1H), 4.95 (s, 1H), 4.51 (d, J = 12.8 Hz, 2H), 4.41 (s, 1H), 4.01 (d, J = 9.2 Hz, 1H), 3.93 (s, 3H), 3.92 (s, 3H), 3.50 (t, J = 7.6 Hz, 1H), 3.39-3.41 (m, 2H), 3.25 (s, 3H), 3.03 (t, J = 12.8 Hz, 2H), 2.82-2.94 (m, 1H), 2.53-2.66 (m, 4H), 2.32-2.41 (m, 2H), 2.16-2.29 (m, 4H), 1.95-2.05 (m, 1H), 1.71-1.90 (m, 3H), 1.24 (s, 6H), 1.16 (s, 6H), 1.02-1.13 (m, 2H). |
| 101 | 874.43 | 875.76 | A | $^1$H NMR (400 MHz, DMSO-d$_6$) δ 11.11 (s, 1H), 8.16 (s, 1H), 7.83 (d, J = 8.0 Hz, 1H), 7.73 (br d, J = 8.8 Hz, 2H), 7.65 (d, J = 8.8 Hz, 1H), 7.49 (br d, J = 9.2 Hz, 1H), 7.29-7.22 (m, 2H), 6.95 (br d, J = 8.8 Hz, 2H), 6.64 (d, J = 1.6 Hz, 1H), 6.53 (dd, J = 8.4, 1.6 Hz, 1H), 5.11 (dd, J = 13.2, 5.2 Hz, 1H), 4.93 (br s, 1H), 4.27 (s, 1H), 4.05 (br d, J = 9.2 Hz, 1H), 3.90 (s, 3H), 3.86 (br d, J = 12.8 Hz, 2H), 3.53-3.46 (m, 1H), 3.38 (br t, J = 6.0 Hz, 4H), 3.24 (s, 3H), 2.77 (br t, J = 11.6 Hz, 2H), 2.61 (br s, 3H), 2.57 (br s, 1H), 2.36 (br dd, J = 13.2, 6.4 Hz, 3H), 2.28-2.17 (m, 4H), 2.08-2.00 (m, 1H), 1.80 (br d, J = 11.6 Hz, 2H), 1.64 (br s, 1H), 1.22 (s, 6H), 1.14 (s, 6H). |
| 102 | 890.43 | 891.77 | A | $^1$H NMR (400 MHz, DMSO-d$_6$) δ 11.08 (s, 1 H), 8.24 (d, J = 8.8 Hz, 1 H), 8.13 (s, 1 H), 7.82 (d, J = 9.2 Hz, 1 H), 7.64 (d, J = 8.4 Hz, 1 H), 7.37 (d, J = 9.6 Hz, 1 H), 6.84 (d, J = 17.8 Hz, 2 H), 6.66 (s, 1 H), 6.56 (d, J = 8.8 Hz, 1 H), 4.99-5.12 (m, 1 H), 4.93 (s, 1 H), 4.53 (d, J = 12.4 Hz, 2 H), 4.40 (s, 1 H), 3.83-4.06 (m, 8 H), 3.72 (s, 1 H), 3.15-3.15 (m, 1 H), 2.76-3.18 (m, 3 H), 2.59 (s, 2 H), 2.17-2.46 (m, 7 H), 1.69-2.10 (m, 4 H), 1.23 (s, 6 H), 1.16 (s, 6 H), 1.09 (d, J = 13.6 Hz, 2 H), 0.96 (s, 6 H). |
| 103 | 879.38 | 880.62 | A | $^1$H NMR (300 MHz, DMSO-d$_6$) δ 11.06 (s, 1H), 8.77 (s, 2H), 7.91 (d, J = 8.7 Hz, 1H), 7.71 (d, J = 9.0 Hz, 1H), 7.22 (s, 1H), 7.04-6.98 (m, 2H), 6.68 (s, 1H), 5.03-4.90 (m, 2H), 4.77-4.73 (m, 2H), 4.30 (s, 1H), 4.06-4.03 (m, 1H), 3.46 (s, 4H), 3.04-2.88 (m, 4H), 2.52 (s, 1H), 2.23-2.21 (m, 2H), 2.00-1.82 (m, 5H), 1.33-1.00 (m, 23H). |
| 104 | 856.45 | 857.73 | A | $^1$H NMR (400 MHz, DMSO-d$_6$) δ 11.12 (brs, 1H), 8.26 (s, 1H), 7.84 (d, J = 8.0 Hz, 1H), 7.74 (d, J = 8.8 Hz, 2H), 7.48 (d, J = 9.6 Hz, 1H), 7.30-7.24 (m, 2H), 6.96 (d, J = 8.8 Hz, 2H), 6.74 (s, 2H), 5.12 (dd, J = 12.8, 5.6 Hz, 1H), 4.91 (br s, 1H), 4.23 (s, 1H), 4.04 (d, J = 9.2 Hz, 1H), 3.89 (br d, J = 12.0 Hz, 2H), 3.72-3.62 (m, 1H), 2.95-2.83 (m, 3H), 2.76 (br t, J = 12.0 Hz, 2H), 2.68 (br s, 1H), 2.61 (br s, 1H), 2.44 (s, 7H), 2.26 (br d, J = 6.8 Hz, 2H), 2.21 (br d, J = 8.0 Hz, 2H), 2.10-1.99 (m, 1H), 1.83 (br d, J = 12.4 Hz, 2H), 1.57 (br s, 1H), 1.22 (s, 6H), 1.18 (br s, 2H), 1.12 (s, 6H), 0.93 (d, J = 6.4 Hz, 6H). |

TABLE 2C-continued

Degradation of AR proteins by exemplary heterobifunctional compounds of the present disclosure.

| Comp No. | Exact Mass | Observed Mass | DC50 Code* | NMR |
|---|---|---|---|---|
| 105 | 908.39 | 909.73 | A | $^1$H NMR (400 MHz, DMSO-d$_6$) δ 11.08 (s, 1H), 8.20 (s, 1H), 7.91 (d, J = 8.8 Hz, 1H), 7.73 (br d, J = 9.2 Hz, 2H), 7.49 (d, J = 9.6 Hz, 1H), 7.21 (d, J = 2.0 Hz, 1H), 7.04-6.92 (m, 3H), 6.84 (d, J = 9.6 Hz, 2H), 5.11-4.91 (m, 2H), 4.32 (s, 1H), 4.05 (d, J = 8.8 Hz, 1H), 3.94 (s, 3H), 3.87 (br d, J = 12.0 Hz, 2H), 3.58-3.48 (m, 1H), 3.41-3.41 (m, 2H), 3.29-3.28 (m, 3H), 2.80 (br d, J = 11.2 Hz, 3H), 2.62 (br d, J = 6.4 Hz, 4H), 2.43-2.35 (m, 2H), 2.23 (br d, J = 18.0 Hz, 4H), 2.09-1.91 (m, 2H), 1.83 (br s, 2H), 1.64 (s, 1H), 1.22 (s, 6H), 1.13 (s, 7H). |
| 106 | 902.46 | 903.70 | A | $^1$H NMR (400 MHz, DMSO-d$_6$) δ 11.07 (s, 1H), 7.74 (d, J = 8.8 Hz, 2H), 7.46 (d, J = 9.2 Hz, 1H), 6.96 (br d, J = 8.8 Hz, 2H), 6.84 (d, J = 8.8 Hz, 2H), 6.74 (s, 2H), 5.05 (dd, J = 12.8, 5.6 Hz, 1H), 4.96 (br s, 1H), 4.23 (s, 1H), 4.04 (d, J = 9.2 Hz, 1H), 3.94 (s, 3H), 3.92-3.92 (m, 1H), 3.87 (br d, J = 12.0 Hz, 2H), 3.48-3.45 (m, 1H), 3.41-3.40 (m, 2H), 3.30-3.29 (m, 3H), 2.90 (s, 1H), 2.83-2.73 (m, 2H), 2.65-2.59 (m, 2H), 2.55 (br s, 2H), 2.44 (s, 6H), 2.40-2.35 (m, 2H), 2.31-2.15 (m, 4H), 2.00 (br d, J = 4.0 Hz, 1H), 1.81 (br d, J = 11.6 Hz, 2H), 1.65 (br s, 1H), 1.22 (s, 6H), 1.16 (br s, 1H), 1.12 (s, 5H), 0.98 (br s, 1H). |
| 107 | 845.37 | 846.59 | A | $^1$H NMR (400 MHz, DMSO) δ 8.27 (brs, 1H), 7.84 (d, J = 8.8 Hz, 1H), 7.70 (d, J = 8.6 Hz, 2H), 7.63 (d, J = 8.6 Hz, 1H), 7.46 (d, J = 9.2 Hz, 1H), 7.25-7.24 (m, 1H), 7.22-7.14 (m, 2H), 7.00-6.95 (m, 1H), 6.64 (d, J = 8.7 Hz, 2H), 4.99 (dd, J = 12.8, 5.6 Hz, 1H), 4.31 (s, 1H), 3.75-4.04(m, 5H), 3.44-3.41 ($_m$, 2H), 3.19-3.17 (m, J = 9.9 Hz, 2H), 2.93-2.72 (m, 7H), 2.68-2.55 (m, 2H), 2.46-2.41 (m, 2H), 2.03-1.95 (m, 1H), 1.81-1.76 (m, 3H), 1.17 (d, J = 28.2 Hz, 7H), 1.10 (d, J = 28.2 Hz, 7H). |
| 108 | 855.41 | 856.63 | A | $^1$H NMR (400 MHz, CDCl$_3$) δ 8.70 (s, 2H), 8.16 (s, 1H), 7.79 (s, 1H), 7.77(s, 1H), 7.72-7.11 (m, 4H), 5.97-5.95 (d, J = 8.0 Hz, 1H), 4.98-4.88 (m, 3H), 4.74 (s, 1H), 4.16-4.14 (d, J = 8.0 Hz, 1H), 4.08 (s, 1H), 3.72 (s, 1H), 2.96-2.73 (m, 6H), 2.38-2.01 (m, 6H), 1.94-1.92 (m, 2H), 1.66 (s, 3H), 1.42-1.43 (m, 19H). |
| 109 | 866.43 | 867.65 | A | $^1$H NMR(300 MHz, DMSO-d$_6$) δ 10.99 (s, 1H), 8.75 (s, 2H), 7.71-7.68 (d, 1H), 7.52-7.49 (d, 1H), 7.15-7.12 (m, 1H), 7.02 (s, 1H), 6.72 (s, 2H), 5.13-5.08 (m, 1H), 4.82-4.73 (m, 3H), 4.40-4.19 (m, 3H), 4.04-4.00 (m, 1H), 3.61-3.56 (m, 1H), 3.00-2.73 (m, 5H), 2.62-2.51 (m, 2H), 2.43-2.22 (m, 12H), 2.08-1.72 (m, 4H), 1.31-0.81 (s, 15H). |
| 110 | 858.44 | 859.77 | A | $^1$H NMR (400 MHz, DMSO-d$_6$) δ 11.12 (s, 1H), 8.23 (d, J = 9.2 Hz, 1H), 7.91-7.75 (m, 2H), 7.38 (d, J = 9.6 Hz, 1H), 7.31-7.20 (m, 2H), 6.77 (s, 2H), 5.12 (dd, J = 12.8, 5.6 Hz, 1H), 4.92 (br s, 1H), 4.54 (br d, J = 12.0 Hz, 2H), 4.33 (s, 1H), 4.00 (d, J = 8.8 Hz, 1H), 3.69 (br s, 1H), 3.01-3.07 (m, 4H), 2.64-2.53 (m, 4H), 2.44 (s, 6H), 2.32-2.15 (m, 4H), 2.11-1.98 (m, 1H), 1.87 (br d, J = 10.8 Hz, 2H), 1.73 (br s, 1H), 1.23 (s, 6H), 1.14 (s, 6H), 1.09 (br d, J = 11.6 Hz, 2H), 0.94 (br d, J = 5.2 Hz, 6H). |
| 111 | 845.37 | 846.59 | A | $^1$H NMR (300 MHz, DMSO-d$_6$) δ 11.08 (s, 1H), 8.05 (s, 1H), 7.79-7.62 (m, 3H), 7.37 (d, J = 9.1 Hz, 1H), 7.22 (d, J = 2.4 Hz, 1H), 7.07-6.95 (m, 2H), 6.94-6.83 (m, 1H), 6.50 (d, J = 8.6 Hz, 2H), 5.07 (dd, J = 12.5, 5.3 Hz, 1H), 4.33 (s, 1H), 4.06 (d, J = 9.1 Hz, 1H), 3.78-3.61 (m, 2H), 3.48-3.32 (m, 2H), 3.24-3.12 (m, 2H), 3.04-2.98 (m, 2H), 2.89-2.81 (m, 2H), 2.76-2.70 (m, 4H), 2.69-2.59 (m, 4H), 2.58-2.47 (m, 1H), 2.41-2.20 (m, 1H), 2.07-1.97 (m, 2H), 1.75-1.55 (m, 3H), 1.22 (s, 6H), 1.13 (s, 6H). |
| 112 | 858.44 | 859.75 | A | $^1$H NMR (400 MHz, DMSO-d$_6$) δ 11.11 (s, 1H), 8.61 (s, 1H), 8.33 (m, 1H), 7.85-7.79 (m, 2H), 7.28-7.25 (m, 2H), 6.76 (s, 2H), 5.14-5.09 (m, 1H), 4.90 (m, 1H), 4.53-4.50 (m, 2H), 4.30 (s, 1H), 3.94 (d, 1H), 3.00-2.90 (m, 4H), 2.43 (m, 8H), 2.26-2.21 (m, 3H), 2.19-2.16 (m, 3H), 1.89-1.79 (m, 2H), 1.25-0.97 (m, 16H), 0.96-0.75 (m, 7H). |
| 113 | 850.39 | 851.62 | A | $^1$H NMR (400 MHz, CDCl$_3$, ppm) δ 8.83 (s, 1H), 8.02 (s, 1H), 7.93 (s, 1H), 7.81-7.76 (m, 2H), 7.58 (d, J = 8.8 Hz, 1H), 7.00-6.98 (m, 1H), 6.92-6.90 (m, 1H), 6.85-6.80 (m, 2H), 5.24-5.19 (m, 1H), 4.75-4.69 (m, 1H), 4.57-4.47 (m, 2H), 4.43 (s, 1H), 4.32-4.28 (m, 1H), 4.16 (d, J = 8.8 Hz, 1H), 4.08 (s, 1H), 3.80-3.69 (m, 1H), 3.01-2.85 (m, 4H), 2.41-2.19 (m, 7H), 2.01-1.93 (m, 2H), 1.76-1.65 (m, 1H), 1.62-1.50 (m, 4H), 1.28 (s, 6H), 1.23 (s, 6H), 1.20-1.08 (m, 1H), 1.00-0.98 (m, 5H). |
| 114 | 845.37 | 846.58 | A | $^1$H NMR (400 MHz, DMSO) δ 7.87 (d, J = 8.8 Hz, 1H), 7.72-7.66 (m, 3H), 7.48 (d, J = 9.2 Hz, 1H), 7.18 (d, J = 2.4 Hz, 1H), 7.03-6.84 (m, 5H), 5.04 (dd, J = 12.8, 5.4 Hz, 1H), 4.31 (s, 1H), 4.02 (d, J = 9.3 Hz, 1H), 3.82 (d, J = 12.6 Hz, 2H), 3.67-3.61 (m, 3H), 3.35-3.32 (m, 2H), 3.03 (s, 2H), 2.95-2.63 (m, 6H), 2.65-2.56 (m, 4H), 2.54 (s, 2H), 2.05-1.97 (m, 1H), 1.79-1.76 (m, 3H), 1.17 (d, J = 31.2 Hz, 6H), 1.13(d, J = 31.2 Hz, 6H). |
| 115 | 816.40 | 817.71 | A | $^1$H NMR (400 MHz, DMSO-d$_6$) δ 11.11 (s, 1H), 8.59 (d, J = 1.2 Hz, 1H), 8.29-8.32 (m, 1H), 7.76-7.87 (m, 2H), 7.25-7.31 (m, 2H), 6.75 (s, 2H), 5.11 (dd, J = 12.8, 5.2 Hz, 1H), 5.04 (q, J = 5.2 Hz, 1H), 4.46 (d, J = 13.2 Hz, 2H), 4.29 (s, 1H), 3.93 (d, J = 9.2 Hz, 1H), 3.72-3.78 (m, 2H), 3.01 (dd, J = 8.0, 5.2 Hz, 3H), 2.91-2.98 (m, 2H), 2.82-2.90 (m, 1H), 2.59-2.63 (m, 1H), 2.56-2.59 (m, 1H), 2.54 (s, 1H), 2.42 (s, 6H), 2.00-2.08 (m, 1H), 1.75 (d, J = 12.0 Hz, 2H), 1.61-1.70 (m, 1H), 1.25 (q, J = 6.6 Hz, 2H), 1.19 (s, 6H), 1.15 (d, J = 6.8 Hz, 1H), 1.11 (s, 6H), 1.03-1.08 (m, 1H). |
| 116 | 876.42 | 877.75 | A | $^1$H NMR (400 MHz, DMSO-d$_6$) δ 11.11 (s, 1H), 8.61 (s, 1H), 8.32 (s, 1H), 7.82 (t, J = 7.6 Hz, 2H), 7.64 (s, 1H), 7.49 (d, J = 8.8 Hz, 1H), 7.18-7.31 (m, 2H), 6.67 (s, 1H), 6.57 (d, J = 8.4 Hz, 1H), 5.11 (dd, J = 13.2, 12.8 Hz, 1H), 4.93 (s, 1H), 4.49 (d, J = 12.8 Hz, 2H), 4.37 (s, 1H), 3.82-4.03 (m, 4H), 3.26-3.32 (m, 3H), 2.83-3.03 (m, 4H), 2.57-2.67 (m, 4H), 2.36 (d, J = 5.2 Hz, 3H), 2.16-2.28 (m, 4H), 1.99-2.10 (m, 1H), 1.84 (d, J = 12.4 Hz, 4H), 1.15 (s, 6H), 1.20 (s, 6H), 1.08 (d, J = 7.6 Hz, 2H). |
| 117 | 802.38 | 803.69 | A | $^1$H NMR (400 MHz, DMSO-d$_6$) δ 11.11 (s, 1H), 8.59 (d, J = 1.2 Hz, 1H), 8.30 (s, 1H), 7.78-7.94 (m, 3H), 7.47 (d, J = 2.0 Hz, 1H), 7.38 (dd, J = 8.4, 2.0 Hz, 1H), 6.76 (s, 2H), 5.12 (dd, J = 12.8, 5.4 Hz, 1H), 4.73 (s, 1H), 4.31 (s, 1H), 4.24 (t, J = 8.4 Hz, 2H), 3.95 (d, J = 8.8 Hz, 1H), 3.82 (br dd, J = 8.8, 5.4 Hz, 2H), 3.01-3.06 (m, 1H), 2.86-2.94 (m, 1H), 2.67-2.76 (m, 3H), 2.56-2.63 (m, 4H), 2.43 (s, 6H), 2.27-2.33 (m, 1H), 1.96-2.09 (m, 3H), 1.62-1.73 (m, 2H), 1.20 (s, 6H), 1.12 (s, 6H). |
| 118 | 788.36 | 789.68 | A | $^1$H NMR (300 MHz, DMSO-d$_6$) δ11.12 (s, 1H), 8.59 (s, 1H), 7.85 (m, 3H), 7.27-7.25 (m, 2H), 6.76 (m, 2H), 5.15-5.05 (m, 2H), 4.30-4.21 (m, 3H), 4.17 (s, 1H), 3.96-3.87 (m, 3H), 2.89 (m, 2H), 2.75-2.73 (m, 2H), 2.62 (m, 2H), 2.43 (m, 6H), 2.31 (m, 4H), 2.05-1.99 (m, 2H), 1.24-0.86 (m, 12H). |

TABLE 2C-continued

Degradation of AR proteins by exemplary heterobifunctional compounds of the present disclosure.

| Comp No. | Exact Mass | Observed Mass | DC50 Code* | NMR |
|---|---|---|---|---|
| 119 | 874.44 | 875.77 | A | $^1$H NMR (400 MHz, DMSO-d$_6$) δ 11.12 (s, 1H), 8.61 (s, 1H), 8.34 (s, 1H), 8.19 (s, 1H), 7.82 (dd, J = 12.4, 8.8 Hz, 2H), 7.28-7.23 (m, 2H), 6.76 (s, 2H), 5.12 (dd, J = 13.2, 5.2 Hz, 1H), 4.93 (br s, 1H), 4.49 (br d, J = 13.2 Hz, 2H), 4.30 (s, 1H), 3.94 (d, J = 9.2 Hz, 1H), 3.53-3.44 (m, 2H), 3.40 (br s, 1H), 3.24 (s, 3H), 3.00 (br t, J = 11.2 Hz, 2H), 2.88 (br d, J = 13.2 Hz, 1H), 2.65-2.58 (m, 3H), 2.58-2.53 (m, 2H), 2.43 (s, 6H), 2.37 (br s, 1H), 2.26 (br d, J = 7.2 Hz, 2H), 2.21 (br s, 2H), 2.09-2.00 (m, 1H), 1.84 (br d, J = 11.6 Hz, 2H), 1.79-1.72 (m, 1H), 1.19 (s, 6H), 1.12 (s, 6H), 1.10-0.98 (m, 2H). |
| 120 | 878.42 | 879.78 | A | $^1$H NMR (300 MHz, DMSO-d$_6$) δ 11.00 (s, 1H), 8.60 (s, 1H), 8.35 (s, 1H), 7.90 (d, J = 6.6 Hz, 1H), 7.83 (d, J = 6.3 Hz, 1H), 7.50 (d, J = 6.0 Hz, 1H), 7.25 (s, 1H), 7.02-7.00 (m, 1H), 6.86-6.80 (m, 1H), 5.13-5.09 (m, 1H), 4.85-4.78 (m, 1H), 4.60-4.40 (m, 4H), 4.30-4.20 (m, 1H), 4.00-3.90 (m, 1H), 3.70-3.55 (m, 1H), 3.00-2.80 (m, 4H), 2.65-2.55 (m, 3H), 2.48-2.30 (m, 3H), 2.28-2.10 (m, 4H), 2.05-1.95 (m, 1H), 1.90-1.82 (m, 2H), 1.80-1.62 (m, 1H), 1.30-1.00 (m, 17H), 0.95-0.85 (m, 6H). |
| 121 | 874.44 | 875.78 | A | $^1$H NMR (400 MHz, DMSO-d$_6$) δ 11.12 (s, 1H), 8.23 (d, J = 9.2 Hz, 1H), 8.17 (s, 1H), 7.86-7.80 (m, 2H), 7.38 (d, J = 9.6 Hz, 1H), 7.29-7.24 (m, 2H), 6.77 (s, 2H), 5.12 (dd, J = 13.2, 5.2 Hz, 1H), 4.94 (br s, 1H), 4.52 (br d, J = 12.0 Hz, 2H), 4.33 (s, 1H), 3.99 (d, J = 9.2 Hz, 1H), 3.49 (br d, J = 8.0 Hz, 1H), 3.40 (br s, 1H), 3.25 (s, 3H), 3.03 (br t, J = 11.6 Hz, 1H), 2.98-2.78 (m, 2H), 2.65-2.61 (m, 2H), 2.57 (br s, 1H), 2.55 (s, 1H), 2.44 (s, 6H), 2.40-2.35 (m, 2H), 2.27 (br d, J = 6.4 Hz, 2H), 2.22 (br d, J = 8.4 Hz, 2H), 2.09-2.01 (m, 1H), 1.85 (br d, J = 12.4 Hz, 3H), 1.23 (s, 6H), 1.14 (s, 6H), 1.08 (br s, 2H). |
| 122 | 872.42 | 873.63 | A | $^1$H NMR (400 MHz, CD3OD, ppm) δ 8.62 (d, J = 1.3 Hz, 1H), 7.86-7.78 (m, 2H), 7.54 (d, J = 8.6 Hz, 1H), 7.31-7.21 (m, 2H), 6.65 (s, 1H), 6.60-6.52 (m, 1H), 5.14-5.10 (m, 1H), 4.35-4.23 (m, 3H), 4.12-4.07 (m, 3H), 3.95 (s, 3H), 3.78-3.69 (m, 1H), 3.01-2.95 (m, 1H), 2.92-2.82 (m, 1H), 2.81-2.74 (m, 1H), 2.77-2.69 (m, 1H), 2.52-2.47 (m, 3H), 2.42-2.31 (m, 2H), 2.25-2.22 (m, 2H), 2.25-1.96 (m, 4H), 1.42-1.39 (m, 2H), 1.35-1.30 (m, 2H), 1.29 (s, 5H), 1.23 (s, 5H), 1.04 (d, J = 6.6 Hz, 6H). |
| 123 | 850.39 | 851.62 | A | $^1$H NMR (400 MHz, DMSO-t/$_6$) δ 10.96 (s, 1H), 8.60 (s, 1H), 8.33 (s, 1H), 7.90 (d, J = 8.8 Hz, 1H), 7.79 (d, J = 8.8 Hz, 1H), 7.50 (d, J = 8.0 Hz, 1H), 7.20 (s, 1H), 7.15-7.12 (m, 1H), 7.04-7.00 (m, 2H), 5.10-5.07 (m, 1H), 4.77-4.75 (m, 1H), 4.50-4.48 (m, 2H), 4.43-4.35 (m, 2H), 4.26-4.22 (m, 1H), 3.97-3.95 (m, 1H), 3.65-3.63 (m, 1H), 2.98-2.90 (m, 4H), 2.51-2.50 (m, 1H), 2.41-2.36 (m, 3H), 2.26-2.24 (m, 2H), 2.18-2.16 (m, 2H), 2.13-1.97 (m, 1H), 1.87-1.85 (m, 2H), 1.71 (s, 1H), 1.19-1.05 (m, 14H), 0.93-0.92 (m, 6H). |
| 124 | 894.38 | 895.62 | A | $^1$H NMR (300 MHz, DMSO-d$_6$) δ 11.10 (s, 1H), 8.60 (s, 1H), 8.30 (s, 1H), 7.93 (d, J = 6.3 Hz, 1H), 7.82-7.78 (m, 1H), 7.28 (s, 1H), 7.02 (d, J = 4.8 Hz, 1H), 6.86 (s, 1H), 6.80 (s, 1H), 5.06 (d, J = 3.9 Hz, 1H), 4.91 (s, 1H), 4.51 (d, J = 9.6 Hz, 1H), 4.43 (s, 1H), 3.96-3.92 (m, 4H), 3.70-3.60 (m, 1H), 300-2.80 (m, 4H), 2.57-2.50 (m, 1H), 2.49-2.40 (m, 2H), 2.30-2.25 (m, 2H), 2.23-2.15 (m, 2H), 2.05 (s, 1H), 2.00 (s, 1H), 1.90-1.80 (m, 2H), 1.70 (s, 1H), 1.20 (s, 6H), 1.10 (s, 6H), 1.08-1.00 (m, 2H), 0.93 (s, 6H); |
| 125 | 806.32 | 807.54 | A | $^1$H NMR (300 MHz, DMSO-de) δ 11.10 (s, 1H), 8.25 (s, 1H), 7.93-7.68 (m, 4H), 7.50 (d, J = 9.1 Hz, 1H), 7.40-7.25 (m, 2H), 7.19 (d, J = 2.4 Hz, 1H), 7.03-6.90 (m, 2H), 5.10 (dd, J = 12.6, 5.5 Hz, 2H), 4.30 (s, 1H), 4.03 (d, J = 9.2 Hz, 1H), 3.45 (d, J = 15.8 Hz, 2H), 3.21 (d, J = 15.8 Hz, 4H), 2.85 (d, J = 15.8 Hz, 2H), 2.55 (d, J = 5.5 Hz, 3H), 2.33 (d, J = 10.7 Hz, 2H), 2.05-1.46 (m, 6H), 1.39-1.01 (s, 12H). |
| 126 | 844.46 | 845.20 | D | $^1$H NMR (400 MHz, DMSO-d$_6$) d ppm 0.92 (d, J = 6.46 Hz, 6 H) 1.11 (s, 6 H) 1.19 (s, 6 H) 1.23 (s, 3 H) 1.85 (d, J = 13.30 Hz, 2 H) 1.91 (s, 2 H) 1.94-2.01 (m, 1 H) 2.10-2.28 (m, 4 H) 2.31-2.41 (m, 2 H) 2.43 (s, 6 H) 2.58 (d, J = 18.19 Hz, 1 H) 2.64-2.71 (m, 1 H) 2.82-3.04 (m, 4 H) 3.50 (s, 1 H) 3.64 (br. s 1 H) 3.94 (d, J = 8.80 Hz, 1 H) 4.20-4.33 (m, 5 H) 4.38 (d, J = 17.22 Hz, 1 H) 4.51 (d, J = 13.50 Hz, 2 H) 4.76 (br. s 1 H) 5.07 (dd, J = 13.11, 4.89 Hz, 1 H) 6.76 (s, 2 H) 6.95 (dd, J = 8.22, 1.96 Hz, 1 H) 7.00 (s, 1 H) 7.62 (d, J = 8.41 Hz, 1 H) 7.80 (d, J = 9.00 Hz, 1 H) 8.33 (s, 1 H) 8.60 (d, J = 1.17 Hz, 1 H) 10.97 (s, 1 H). |
| 127 | 880.37 | 881.70 | A | $^1$H NMR (400 MHz, DMSO-d$_6$) δ 11.11 (br s, 1H), 8.32 (s, 1H), 8.24 (d, J = 9.2 Hz, 1H), 7.91 (d, J = 8.4 Hz, 1H), 7.86-7.79 (m, 2H), 7.37 (d, J = 9.6 Hz, 1H), 7.30-7.22 (m, 3H), 7.04 (dd, J = 8.8, 2.4 Hz, 1H), 5.12 (dd, J = 13.2, 5.2 Hz, 1H), 4.94 (br s, 1H), 4.58-4.42 (m, 3H), 4.01 (d, J = 9.6 Hz, 1H), 3.49 (br d, J = 6.8 Hz, 1H), 3.25 (s, 3H), 3.10-2.96 (m, 4H), 2.87 (br d, J = 11.2 Hz, 2H), 2.63 (br s, 2H), 2.57 (br s, 1H), 2.41-2.35 (m, 2H), 2.31-2.15 (m, 4H), 2.04 (br s, 1H), 1.85 (br d, J = 12.4 Hz, 2H), 1.80-1.74 (m, 1H), 1.23 (s, 6H), 1.09 (br d, J = 13.6 Hz, 2H). |
| 128 | 857.45 | 858.78 | B | $^1$H NMR (300 MHz, Methanol-d$_4$) δ 8.31 (s, 1H), 7.90 (d, J = 8.8 Hz, 1H), 7.80 (d, J = 8.3 Hz, 1H), 7.38 (d, J = 6.9 Hz, 1H), 7.30-7.19 (m, 1H), 6.72 (s, 2H), 4.25 (s, 1H), 4.04 (s, 1H), 3.97 (s, 1H), 2.89 (d, J = 11.9 Hz, 2H), 2.77 (s, 1H), 2.48 (s, 6H), 2.39 (d, J = 6.7 Hz, 2H), 2.31 (s, 2H), 1.98 (d, J = 12.6 Hz, 2H), 1.28 (d, J = 3.2 Hz, 9H), 1.20 (s, 6H), 1.03 (d, J = 6.6 Hz, 6H), 0.10 (s, 0H). |
| 129 | 837.34 | 838.68 | B | $^1$H NMR (400 Hz, DMSO-d$_6$) δ ppm 11.39 (s, 1H), 7.87 (d, J = 8 Hz, 1H), 7.71-7.64 (m, 3H), 7.46 (d, J = 8 Hz, 1H), 7.29 (m, 2H), 7.18 (s, 1H), 6.98-6.91 (m, 3H), 4.29 (s, 1H), 4.02 (d, J = 8 Hz, 1H), 3.83 (d, J = 12 Hz, 2H), 3.41 (s, 3H), 3.25 (m, 4H), 2.73 (m, 3H), 2.68-2.63 (m, 2H), 2.38 (m, 1H), 2.18-2.12 (m, 5H), 1.90-1.76 (m, 7H), 1.18 (s, 7H), 1.09 (s, 5H). |
| 130 | 832.39 | 833.72 | B | $^1$H NMR (400 MHz, Methanol-d$_4$) δ 8.63 (d, J = 1.3 Hz, 1H), 7.86-7.79 (m, 2H), 7.54 (d, J = 8.6 Hz, 1H), 7.32-7.21 (m, 2H), 6.65 (s, 1H), 6.63 (d, J = 2.2 Hz, 1H), 6.58 (dd, J = 8.6, 2.3 Hz, 1H), 5.11 (dd, J = 12.6, 5.5 Hz, 1H), 4.34-4.25 (m, 3H), 4.07 (d, J = 0.9 Hz, 1H), 3.95 (s, 3H), 3.90 (dd, J = 9.1, 5.4 Hz, 2H), 3.81 (q, J = 8.1 Hz, 1H), 3.04 (s, 2H), 2.92-2.76 (m, 3H), 2.75 (s, 1H), 2.50 (d, J = 11.2 Hz, 2H), 2.38 (d, J = 10.4 Hz, 3H), 2.14 (s, 1H), 1.41 (d, J = 12.2 Hz, 1H), 1.30 (d, J = 5.4 Hz, 9H), 1.24 (s, 6H), 1.07 (d, J = 6.6 Hz, 6H), 0.91 (dd, J = 9.3, 6.5 Hz, 1H), 0.88 (s, 1H), 0.15-0.05 (m, 5H). |

TABLE 2C-continued

Degradation of AR proteins by exemplary heterobifunctional compounds of the present disclosure.

| Comp No. | Exact Mass | Observed Mass | DC50 Code* | NMR |
|---|---|---|---|---|
| 131 | 830.41 | 831.74 | B | $^1$H NMR (400 MHz, Methanol-d$_4$) δ 8.63 (d, J = 1.4 Hz, 1H), 7.86-7.79 (m, 2H), 7.31-7.21 (m, 2H), 6.73 (s, 2H), 5.11 (dd, J = 12.6, 5.5 Hz, 1H), 4.90 (s, 1H), 4.34-4.24 (m, 3H), 4.05 (d, J = 0.9 Hz, 1H), 3.89 (dd, J = 9.1, 5.3 Hz, 2H), 3.83-3.75 (m, 1H), 3.03 (s, 2H), 2.95-2.67 (m, 5H), 2.49 (s, 6H), 2.36 (t, J = 10.1 Hz, 2H), 2.18-2.10 (m, 1H), 1.35 (s, 1H), 1.28 (s, 7H), 1.21 (s, 6H), 1.07 (d, J = 6.6 Hz, 6H), 0.11 (s, 1H). |
| 132 | 858.44 | 859.77 | B | $^1$H NMR (400 MHz, DMSO-d$_6$) δ 11.10 (br s, 1H), 8.56 (s, 2H), 8.34 (s, 1H), 8.09 (d, J = 8.8 Hz, 1H), 7.83 (d, J = 8.2 Hz, 1H), 7.29-7.20 (m, 2H), 6.75 (s, 2H), 5.10 (dd, J = 5.6, 13.2 Hz, 1H), 4.93-4.85 (m, 1H), 4.28 (s, 1H), 4.03 (br d, J = 12.0 Hz, 2H), 3.93 (d, J = 8.8 Hz, 1H), 3.71-3.69 (m, 1H), 2.98-2.81 (m, 5H), 2.60 (br s, 1H), 2.56 (s, 1H), 2.42 (s, 6H), 2.39-2.36 (m, 1H), 2.25 (br d, J = 7.2 Hz, 2H), 2.18 (br s, 2H), 2.06-2.00 (m, 1H), 1.84 (br d, J = 10.8 Hz, 2H), 1.62 (br s, 1H), 1.22-1.17 (m, 1H), 1.19 (s, 5H), 1.17-1.13 (m, 2H), 1.11 (s, 6H), 0.92 (d, J = 6.6 Hz, 6H). |
| 133 | 816.40 | 817.71 | B | $^1$H NMR (400 MHz, DMSO-d$_6$) δ 11.14 (s, 1H), 8.41 (s, 1H), 8.06 (s, 1H), 7.90 (d, J = 8.0 Hz, 1H), 7.78 (s, 1H), 7.60 (s, 1H), 7.46 (d, J = 8.0 Hz, 1H), 6.74 (s, 2H), 5.14 (dd, J = 12.4, 5.2 Hz, 1H), 4.99 (s, 1H), 4.21 (br s, 1H), 3.69-4.11 (m, 8H), 2.80-2.98 (m, 4H), 2.65-2.68 (m, 2H), 2.44 (s, 6H), 2.16-2.32 (m, 5H), 1.90-2.12 (m, 3H), 1.22 (s, 6H), 1.11 (s, 6H). |
| 134 | 846.41 | 847.74 | B | $^1$H NMR (400 MHz, Methanol-d$_4$) δ 8.64 (d, J = 1.4 Hz, 1H), 7.87-7.79 (m, 2H), 7.54 (d, J = 8.6 Hz, 1H), 7.32-7.22 (m, 2H), 6.63 (d, J = 2.2 Hz, 1H), 6.57 (dd, J = 8.6, 2.2 Hz, 1H), 5.12 (dd, J = 12.6, 5.5 Hz, 1H), 4.35-4.26 (m, 4H), 4.19 (q, J = 6.9 Hz, 2H), 4.07 (d, J = 0.9 Hz, 1H), 3.90 (dd, J = 9.2, 5.3 Hz, 2H), 3.80 (q, J = 8.1 Hz, 1H), 3.05 (p, J = 6.8 Hz, 2H), 2.96-2.69 (m, 5H), 2.51 (s, 2H), 2.37 (t, J = 10.2 Hz, 2H), 2.19-2.10 (m, 1H), 1.80-1.69 (m, 1H), 1.48 (t, J = 7.0 Hz, 4H), 1.26 (d, J = 21.5 Hz, 14H), 1.07 (d, J = 6.6 Hz, 6H), 1.00 (t, J = 7.4 Hz, 1H), 0.12 (s, 1H). |
| 135 | 912.40 | 913.75 | B | $^1$H NMR (400 MHz, DMSO-d$_6$) δ 11.08 (s, 1H), 8.61 (m, 1H), 8.33 (s, 1H), 7.83-7.80 (d, 1H), 7.65-7.63 (s, 1H), 6.84-6.82 (m, 2H), 6.68-6.66 (s, 1H), 6.57-6.55 (m, 1H), 5.07-5.02 (m, 1H), 4.96 (m, 1H), 4.51-4.48 (m, 2H), 4.37 (s, 1H), 3.96-3.91 (m, 7H), 3.61-3.58 (m, 1H), 3.10-2.99 (d, 2H), 3.03-2.97 (m, 2H), 2.91-2.83 (m, 3 H), 2.60-2.55 (m, 1H), 2.50-2.37 (m, 4H), 2.26-2.17 (m, 2H), 2.02-1.93 (m, 1H), 1.87-1.74 (m, 3H), 1.24-1.00 (m, 14H). |
| 136 | 914.36 | 915.71 | B | $^1$H NMR (300 MHz, DMSO-d$_6$) δ 11.10 (s, 1H), 7.93-7.90 (d, 1H), 7.75-7.72 (m, 2H), 7.52-7.50 (m, 1H), 7.21 (s, 1H), 7.03-6.94 (m, 3H), 6.85-6.83 (m, 2H), 5.08-5.00 (m, 2H), 4.32 (s, 1H), 4.07 (d, 1H), 3.93-3.85 (m, 5H), 3.66-3.52 (m, 2H), 3.23 (m, 1H), 2.87-2.78 (m, 5H), 2.61 (m, 1H), 2.51-2.34 (m, 4H), 2.28-2.02 (m, 2H), 2.00-.193 (s, 1H), 1.82-1.59 (m, 3H), 1.27-1.21 (m, 7H), 1.17-1.03 (m, 7H). |
| 137 | 916.35 | 917.70 | C | $^1$H NMR (300 MHz, DMSO-<7>) δ 11.10 (s, 1H), 8.62 (s, 1H), 8.35 (s, 1H), 7.93-7.90 (d, 1H), 7.84-7.81 (d, 1H), 7.26 (s, 1H), 7.06-7.03 (d, 1H), 6.85-6.84 (m, 2H), 5.09-4.97 (m, 2H), 4.53-4.49 (m, 2H), 4.44 (s, 1H), 3.98-3.94(m, 4H), 3.61 (m, 2H), 3.29 (m, 1H), 3.06-2.83 (m, 5H), 2.62 (m, 1H), 2.43-2.25 (m, 5H), 2.03-2.00 (m, 1H), 1.87-1.83 (m, 3H), 1.25-1.05 (m, 15H). |
| 138 | 876.41 | 877.63 | D | $^1$H NMR (400 MHz, DMSO-d$_6$) δ 10.91 (s, 1H), 8.60 (s, 1H), 8.35-8.29 (m, 2H), 7.90 (d, J = 8.8 Hz, 1H), 7.81 (d, J = 8.8 Hz, 1H), 7.57 (d, J = 8.8 Hz, 1H), 7.25 (d, J = 2.4 Hz, 1H), 7.03 (dd, J = 2.4, 8.8 Hz, 1H), 6.88 (dd, J = 2.4, 8.8 Hz, 1H), 6.70 (d, J = 2.4 Hz, 1H), 4.76 (br s, 1H), 4.51 (br d, J = 12.4 Hz, 2H), 4.43 (s, 1H), 3.95 (br d, J = 9.2 Hz, 2H), 3.69-3.60 (m, 1H), 3.25-3.14 (m, 4H), 3.02-2.83 (m, 4H), 2.73-2.62 (m, 3H), 2.54 (s, 2H), 2.40-2.30 (m, 4H), 2.24 (br d, J = 6.8 Hz, 2H), 2.14 (br s, 2H), 1.85 (br d, J = 8.4 Hz, 3H), 1.69 (br s, 1H), 1.55 (s, 2H), 1.47-1.32 (m, 2H), 1.19 (s, 6H), 1.12 (s, 6H), 0.92 (d, J = 6.4 Hz, 6H). |
| 139 | 831.39 | 832.61 | D | $^1$H NMR (400 MHz, DMSO-d$_6$) δ 10.88 (s, 1H), 8.22 (s, 1H), 7.91 (d, J = 8.8 Hz, 1H), 7.74 (d, J = 8.8 Hz, 2H), 7.53-7.45 (m, 2H), 7.21 (d, J = 2.4 Hz, 1H), 6.99 (dd, J = 9.2, 17.6 Hz, 4H), 6.73 (s, 1H), 4.33 (s, 1H), 4.06 (d, J = 9.2 Hz, 1H), 3.86 (d, J = 12.4 Hz, 3H), 3.32-3.29 (m, 9H), 2.80 (t, J = 12.0 Hz, 3H), 2.59-2.54 (m, 4H), 2.22 (d, J = 6.8 Hz, 2H), 1.81 (d, J = 10.3 Hz, 4H), 1.55-1.47 (m, 2H), 1.45-1.31 (m, 2H), 1.25-1.17 (s, 8H), 1.13 (s, 6H). |
| 140 | 768.30 | 769.52 | D | $^1$H NMR (300 MHz, DMSO-de) δ 1.05-1.08 (m, 7H), 1.13 (s, 6H), 1.26-2.88 (m, 10H), 1.92-2.12 (m, 3H), 2.45-2.65 (m, 2H), 2.74-2.95 (m, 3H), 3.85-3.89 (m, 1H), 4.10-4.34 (m, 4H), 4.95-5.13 (m, 1H), 6.58-6.60 (m, 1H), 6.94-6.97 (m, 1H), 7.16-7.22 (m, 2H), 7.27-7.30 (m, 1H), 7.31-7.37 (m, 1H), 7.75-7.87 (m, 3H), 11.03 (s, 1H). |
| 141 | 876.41 | 877.64 | D | $^1$H NMR (400 MHz, DMSO-d$_6$) δ 10.91 (s, 1H), 8.60 (d, J = 1.2 Hz, 1H), 8.33 (s, 1H), 8.13 (s, 1H), 7.90 (d, J = 8.8 Hz, 1H), 7.80 (d, J = 9.2 Hz, 1H), 7.59 (d, J = 2.0, 7.6 Hz, 1H), 7.34-7.27 (m, 2H), 7.26-7.20 (m, 2H), 7.13 (dd, J = 2.4, 8.4 Hz, 1H), 7.03 (dd, J = 2.4, 8.8 Hz, 1H), 6.97 (s, 1H), 4.79 (s, 1H), 4.51 (d, J = 12.8 Hz, 2H), 4.43 (s, 1H), 3.95 (d, J = 8.8 Hz, 2H), 3.82-3.58 (m, 1H), 2.98 (t, J = 12.4 Hz, 3H), 2.74-2.68 (m, 1H), 2.57-2.52 (m, 4H), 2.30-2.10 (m, 4H), 1.91-1.81 (m, 3H), 1.75 (s, 1H), 1.60-1.48 (m, 2H), 1.42-1.30 (m, 2H), 1.19 (s, 6H), 1.13 (s, 6H), 1.10-1.04 (m, 2H), 1.00-0.91 (m, 6H). |
| 142 | 835.35 | 836.56 | D | $^1$H NMR (300 MHz, DMSO-76) δ 10.36-10.30 (d, J = 18 Hz, 1H), 7.93-7.90 (d, J = 9 Hz, 1H), 7.76-7.69 (m, 3H), 7.54-7.51 (d, J = 9 Hz, 1H), 7.47 (s, 1H), 7.36-7.30 (d, J = 18 Hz, 1H), 7.27 (s, 1H), 7.22-6.96 (m, 3H), 5.30-5.24 (m, 1H), 4.36 (s, 1H), 4.08-4.05 (d, J = 9 Hz, 1H), 3.89-3.85 (d, J = 18 Hz, 2H), 3.54 (s, 5H), 3.47 (s, 3H), 3.21-2.80 (m, 1H), 2.76-2.55 (m, 3H), 2.27-2.02 (m, 4H), 1.89-1.81 (m, 3H), 0.93 (m, 14H). |
| 143 | 816.40 | 817.72 | D | $^1$H NMR (400 MHz, DMSO-d$_6$) δ 11.14 (s, 1H), 8.55 (s, 1H), 8.47 (s, 1H), 8.38 (s, 1H), 8.02 (s, 1H), 7.89 (d, J = 8.0 Hz, 1H), 7.80 (d, J = 8.8 Hz, 1H), 7.60 (s, 1H), 7.46 (br d, J = 8.0 Hz, 1H), 6.76 (s, 2H), 5.13 (dd, J = 12.8, 5.2 Hz, 1H), 4.95-5.05 (m, 1H), 4.30 (s, 1H), 3.95 (br d, J = 9.2 Hz, 2H), 3.55-3.77 (m, 6H), 2.78-3.04 (m, 3H), 2.54-2.70 (m, 3H), 2.43 (s, 6H), 2.17-2.40 (m, 4H), 1.99-2.10 (m, 3H), 1.88-1.99 (m, 1H), 1.20 (s, 6H), 1.12 (s, 6H). |
| 144 | 962.49 | 963.85 | A | $^1$H NMR (400 MHz, DMSO-d$_6$) δ 11.12 (s, 1H), 8.76 (s, 2H), 8.14 (s, 1H), 7.84 (d, J = 8.0 Hz, 1H), 7.70 (d, J = 9.2 Hz, 1H), 7.22-7.30 (m, 2H), 6.74 (s, 2H), 5.12 (dd, J = 13.2, 5.6 Hz, 1H), 4.94 (s, 1H), 4.75 (d, J = 11.6 Hz, 2H), 4.19 (s, 1H), 4.02 (d, J = 9.6 Hz, 1H), 3.46-3.51 (m, 8H), 3.40-3.42 (m, 3H), 3.22 (s, 3H), 2.81-3.04 (m, 4H), 2.60-2.67 (m, 2H), 2.52-2.59 (m, 2H), 2.43 (s, 6H), 2.38-2.40 (m, 1H), 2.18-2.29 (m, 4H), 2.00-2.07 (m, 1H), 1.76-1.88 (m, 3H), 1.22 (s, 6H), 1.11 (s, 6H), 0.99-1.06 (m, 2H). |

TABLE 2C-continued

Degradation of AR proteins by exemplary heterobifunctional compounds of the present disclosure.

| Comp No. | Exact Mass | Observed Mass | DC50 Code* | NMR |
|---|---|---|---|---|
| 145 | 1006.52 | 1007.88 | A | $^1$H NMR (400 MHz, DMSO-d$_6$) δ 11.10 (s, 1H), 8.75 (s, 2H), 8.16 (s, 1H), 7.82 (d, J = 8.4 Hz, 1H), 7.68 (d, J = 9.2 Hz, 1H), 7.21-7.29 (m, 2H), 6.72 (s, 2H), 5.11 (dd, J = 13.2, 5.2 Hz, 1H), 4.92 (s, 1H), 4.74 (d, J = 12.4 Hz, 2H), 4.18 (s, 1H), 4.02 (d, J = 8.8 Hz, 1H), 3.47-3.51 (m, 10H), 3.43-3.47 (m, 3H), 3.38-3.42 (m, 3H), 3.22 (s, 3H), 2.83-3.05 (m, 3H), 2.52-2.67 (m, 4H), 2.42 (s, 6H), 2.35-2.39 (m, 1H), 2.15-2.30 (m, 4H), 1.98-2.08 (m, 1H), 1.71-1.88 (m, 3H), 1.21 (s, 6H), 1.10 (s, 6H), 0.96-1.07 (m, 2H). |
| 146 | 872.46 | 873.59 | A | $^1$H NMR (400 MHz, DMSO-d$_6$) δ 11.19-11.04 (m, 1H), 9.24-8.81 (m, 1H), 8.43-8.28 (m, 1H), 7.99-7.71 (m, 2H), 7.47-7.09 (m, 2H), 6.78-6.59 (m, 2H), 5.15-5.06 (m, 1H), 4.84-4.64 (m, 2H), 4.31-4.04 (m, 2H), 4.01-4.90 (m, 1H), 2.84 (d, J = 16.8 Hz, 8H), 2.44-2.38 (m, 9H), 2.21-1.57 (m, 6H), 1.38-1.33 (m, 3H), 1.31-1.26 (m, 2H), 1.26-0.99 (m, 18H). |
| 147 | 844.42 | 845.74 | A | $^1$H NMR (400 MHz, DMSO-d$_6$) δ 11.10 (s, 1H), 8.15 (s, 1H), 7.83 (d, J = 8.4 Hz, 1H), 7.73 (d, J = 8.8 Hz, 2H), 7.64 (d, J = 8.8 Hz, 1H), 7.47 (d, J = 9.2 Hz, 1H), 7.29-7.23 (m, 2H), 6.95 (d, J = 9.2 Hz, 2H), 6.64 (d, J = 2.0 Hz, 1H), 6.54 (dd, J = 8.8, 2.0 Hz, 1H), 5.11 (dd, J = 12.8, 5.4 Hz, 1H), 4.94 (br s, 1H), 4.27 (s, 1H), 4.05 (d, J = 9.2 Hz, 1H), 3.91 (s, 3H), 3.86 (br d, J = 12.8 Hz, 2H), 3.42 (br s, 2H), 2.91-2.85 (m, 1H), 2.78 (br t, J = 11.6 Hz, 2H), 2.61 (br s, 1H), 2.57 (br s, 1H), 2.55 (br d, J = 7.2 Hz, 2H), 2.41-2.33 (m, 2H), 2.24-2.17 (m, 4H), 2.09-2.00 (m, 1H), 1.81 (br d, J = 11.6 Hz, 2H), 1.64 (br s, 1H), 1.22 (s, 6H), 1.16 (br s, 1H), 1.14 (s, 6H), 0.92 (t, J = 7.2 Hz, 3H). |
| 148 | 844.42 | 845.55 | A | $^1$H NMR (400 MHz, Methanol-d$_4$) δ 7.81 (dd, J = 8.3, 1.6 Hz, 3H), 7.53 (d, J = 8.1 Hz, 2H), 7.27 (d, J = 2.2 Hz, 1H), 7.20 (dd, J = 8.3, 2.3 Hz, 1H), 6.73 (s, 2H), 5.12 (dd, J = 12.6, 5.5 Hz, 1H), 4.30 (d, J = 14.0 Hz, 1H), 4.25 (s, 1H), 4.15 (d, J = 0.9 Hz, 1H), 3.90 (dd, J = 11.4, 3.1 Hz, 1H), 3.77-3.69 (m, 1H), 3.68-3.60 (m, 1H), 3.60-3.46 (m, 2H), 3.37 (s, 0H), 3.13 (d, J = 7.0 Hz, 1H), 2.95-2.82 (m, 1H), 2.81-2.63 (m, 3H), 2.55 (dd, J = 12.9, 3.8 Hz, 1H), 2.49 (s, 6H), 2.49-2.40 (m, 3H), 2.33 (s, 3H), 2.18 (s, 3H), 1.35 (s, 1H), 1.29 (d, J = 1.5 Hz, 7H), 1.24 (s, 6H), 0.12 (s, 0H). |
| 149 | 894.48 | 895.82 | A | $^1$H NMR (400 MHz, DMSO-d$_6$) δ 11.08 (s, 1H), 7.75-7.72 (m, 2H), 7.66-7.64 (m, 1H), 7.50-7.48 (m, 1H), 6.97-6.94 (m, 2H), 6.86-6.81 (m, 2H), 6.63 (m, 1H), 6.55-6.52 (m, 1H), 5.07-5.04 (m, 1H), 5.02-4.92 (m, 1H), 4.27 (s, 1H), 4.06-4.04 (m, 1H), 3.90-3.87 (m, 2H), 3.67-3.65 (m, 1H), 2.93-2.50 (m, 4H), 2.49-2.08 (m, 5H), 2.02-1.98 (m, 2H), 1.84-1.81 (m, 2H), 1.57 (m, 1H), 1.22 (m, 8H), 1.15 (m, 8H), 0.94-0.92 (m, 6H). |
| 150 | 858.43 | 859.76 | A | $^1$H NMR (400 MHz, DMSO-d$_6$) δ 11.13 (s, 1H), 8.15 (s, 1H), 7.85-7.48 (m, 4H), 7.28 (m, 2H), 6.98 (m, 2H), 6.74 (m, 2H), 5.12-5.00 (m, 2H), 4.23 (m, 2H), 4.04 (m, 2H), 3.83-3.77 (m, 2H), 3.07-2.75 (m, 10H), 2.44 (m, 10H), 2.05-1.94 (m, 4H), 1.53 (m, 3H), 1.22-1.13 (m, 11H). |
| 151 | 844.42 | 845.54 | A | $^1$H NMR (400 MHz, Methanol-d$_4$) δ 7.81 (dd, J = 8.3, 1.4 Hz, 3H), 7.53 (d, J = 8.1 Hz, 2H), 7.27 (d, J = 2.2 Hz, 1H), 7.20 (dd, J = 8.3, 2.3 Hz, 1H), 6.73 (s, 2H), 5.12 (dd, J = 12.6, 5.4 Hz, 1H), 4.30 (d, J = 13.9 Hz, 1H), 4.25 (s, 1H), 4.15 (s, 1H), 3.90 (d, J = 8.7 Hz, 1H), 3.71 (s, 1H), 3.65 (d, J = 8.9 Hz, 1H), 3.61-3.46 (m, 2H), 3.37 (s, 1H), 3.13 (d, J = 6.9 Hz, 1H), 2.81-2.67 (m, 3H), 2.65 (s, 1H), 2.55 (d, J = 12.5 Hz, 1H), 2.49 (s, 6H), 2.49-2.40 (m, 3H), 2.33 (s, 4H), 2.18 (s, 3H), 2.14 (s, 1H), 1.33-1.27 (m, 7H), 1.24 (s, 6H), 0.12 (s, 1H). |
| 152 | 842.44 | 843.77 | A | $^1$H NMR (400 MHz, Methanol-d$_4$) δ 7.81-7.70 (m, 3H), 7.37 (d, J = 2.2 Hz, 1H), 7.28 (dt, J = 8.3, 2.0 Hz, 1H), 6.98 (d, J = 8.7 Hz, 2H), 6.73 (s, 2H), 5.12 (ddd, J = 12.4, 5.4, 1.4 Hz, 1H), 4.25 (s, 1H), 4.13 (d, J = 0.8 Hz, 1H), 3.86 (d, J = 12.4 Hz, 2H), 3.02 (s, 3H), 2.95-2.86 (m, 1H), 2.86-2.73 (m, 3H), 2.77-2.69 (m, 1H), 2.49 (s, 6H), 2.32 (d, J = 8.9 Hz, 5H), 2.18-2.08 (m, 1H), 2.08-1.92 (m, 1H), 1.92-1.77 (m, 2H), 1.74 (d, J = 10.0 Hz, 2H), 1.30 (d, J = 2.6 Hz, 6H), 1.25 (s, 1H), 1.23 (s, 6H). |
| 153 | 889.48 | 890.82 | A | $^1$H NMR (400 MHz, DMSO-d$_6$) δ 11.08 (s, 1H), 7.74-7.72 (m, 2H), 7.48-7.46 (m, 1H), 6.97-6.94 (m, 2H), 6.86-6.81 (m, 2H), 6.73 (s, 2H), 5.07-5.02 (m, 1H), 4.92 (m, 1H), 4.22 (m, 1H), 4.05-4.02 (m, 1H), 3.90-3.87 (m, 2H), 3.69-3.65 (m, 1H), 2.95-2.81 (m, 2H), 2.79-2.68 (m, 2H), 2.58-2.54 (m, 2H), 2.33 (m, 7H), 2.26-2.21 (m, 2H), 2.18-2.12 (m, 2H), 2.00-1.98 (m, 1H), 1.84-1.81 (m, 2H), 1.57 (m, 1H), 1.28 (m, 7H), 1.15 (m, 8H), 0.96 (m, 6H). |
| 154 | 842.44 | 843.76 | A | $^1$H NMR (400 MHz, Methanol-d$_4$) δ 7.81 (d, J = 8.3 Hz, 1H), 7.74 (d, J = 8.9 Hz, 2H), 7.37 (d, J = 2.3 Hz, 1H), 7.29 (dd, J = 8.3, 2.2 Hz, 1H), 7.00 (d, J = 8.9 Hz, 2H), 6.73 (s, 2H), 5.12 (dd, J = 12.6, 5.4 Hz, 1H), 5.06 (s, 1H), 4.25 (s, 1H), 4.12 (s, 1H), 3.92 (d, J = 12.7 Hz, 2H), 3.12 (s, 1H), 2.88 (s, 1H), 2.87-2.76 (m, 2H), 2.73 (d, J = 9.7 Hz, 1H), 2.49 (s, 6H), 2.33 (d, J = 11.6 Hz, 6H), 2.13 (s, 3H), 1.91 (d, J = 13.5 Hz, 4H), 1.78 (s, 1H), 1.63 (t, J = 10.7 Hz, 1H), 1.32 (d, J = 10.0 Hz, 3H), 1.29 (s, 6H), 1.22 (s, 6H), 0.11 (s, 1H). |
| 155 | 1050.54 | 1051.92 | A | $^1$H NMR (400 MHz, DMSO-d$_6$) δ 11.11 (s, 1H), 8.74 (s, 2H), 8.18 (s, 1H), 7.83 (d, J = 8.0 Hz, 1H), 7.69 (d, J = 9.2 Hz, 1H), 7.18-7.33 (m, 2H), 6.73 (s, 2H), 5.11 (dd, J = 12.8, 5.6 Hz, 1H), 4.92 (s, 1H), 4.74 (br d, J = 12.0 Hz, 2H), 4.18 (s, 1H), 4.01 (d, J = 9.2 Hz, 1H), 3.47-3.51 (m, 15H), 3.43-3.46 (m, 5H), 3.22 (s, 3H), 2.82-3.02 (m, 3H), 2.59-2.65 (m, 2H), 2.51-2.57 (m, 2H), 2.42 (s, 6H), 2.35-2.38 (m, 1H), 2.15-2.28 (m, 4H), 1.98-2.08 (m, 1H), 1.72-1.88 (m, 3H), 1.21 (s, 6H), 1.10 (s, 6H), 0.96-1.05 (m, 2H). |
| 156 | 830.37 | 831.70 | D | $^1$H NMR (400 MHz, DMSO-d$_6$) δ 7.91 (d, J = 8.8 Hz, 1H), 7.73 (d, J = 8.8 Hz, 2H), 7.49 (d, J = 8.4 Hz, 2H), 7.30 (d, J = 8.4 Hz, 1H), 7.21 (s, 1H), 7.13 (s, 1H), 6.97-6.95 (m, 3H), 4.67-4.56 (m, 2H), 4.32 (s, 1H), 4.05 (d, J = 8.8 Hz, 2H), 3.88-3.85 (m, 2H), 3.40-3.36 (m, 4H), 3.20-3.16 (m, 4H), 3.00-2.95 (m, 1H), 2.79-2.73 (m, 5H), 2.23-2.21 (m, 2H), 1.82-1.79 (m, 3H), 1.22-1.13 (m, 14H). |
| 157 | 814.41 | 815.73 | A | $^1$H NMR (300 MHz, DMSO-d$_6$) δ11.12 (s, 1H), 7.86-7.83 (m, 1H), 7.74-7.71 (m, 2H), 7.51-7.48 (m, 1H), 7.29-7.26 (m, 2H), 6.97-6.94 (m, 2H), 6.73 (s, 2H), 5.15-5.11 (m, 1H), 4.95 (m, 1H), 4.22 (s, 1H), 4.05-4.01 (m, 1H), 3.94-3.90 (m, 2H), 3.46 (m, 2H), 2.89-2.71 (m, 4H), 2.43 (m, 5H), 2.18-2.12 (m, 3H), 2.08-2.01 (m, 4H), 1.66-1.53 (m, 4H), 1.22 (m, 8H), 1.12 (m, 7H). |
| 158 | 900.45 | 901.78 | A | $^1$H NMR (400 MHz, DMSO-d$_6$) δ 11.07 (s, 1H), 8.58 (d, J = 1.2 Hz, 1H), 7.77-7.84 (m, 2H), 6.85 (d, J = 12.4 Hz, 2H), 6.75 (s, 2H), 5.05 (dd, J = 12.4, 5.2 Hz, 1H), 4.95 (s, 1H), 4.29 (s, 1H), 4.18 (s, 2H), 4.06 (s, 2H), 3.87-3.97 (m, 4H), 3.59-3.81 (m, 2H), 2.77-3.06 (m, 4H), 2.53-2.65 (m, 3H), 2.42 (s, 6H), 2.21-2.35 (m, 4H), 1.86-2.10 (m, 4H), 1.18 (s, 6H), 1.11 (s, 6H), 0.97 (d, J = 6.0 Hz, 6H). |

TABLE 2C-continued

Degradation of AR proteins by exemplary heterobifunctional compounds of the present disclosure.

| Comp No. | Exact Mass | Observed Mass | DC50 Code* | NMR |
|---|---|---|---|---|
| 159 | 891.46 | 892.80 | A | ¹H NMR (400 MHz, DMSO-d₆) δ 11.08 (s, 1H), 7.75-7.73 (m, 2H), 7.66-7.64 (m, 1H), 7.51-7.49 (m, 1H), 6.97-6.95 (m, 2H), 6.86-6.82 (m, 2H), 6.64 (m, 1H), 6.55-6.53 (m, 1H), 5.05-5.04 (m, 1H), 4.92 (m, 1H), 4.27 (m, 1H), 4.06-4.04 (m, 1H), 3.91 (m, 6H), 3.67-3.65 (m, 1H), 2.92 (m, 2H), 2.76 (m, 3H), 2.51 (m, 2H), 2.34-2.25 (m, 4H), 2.08-2.00 (m, 1H), 1.84-1.82 (m, 2H), 1.60-1.58 (m, 1H), 1.28 (m, 7H), 1.15 (m, 7H), 0.94 (m, 6H). |
| 160 | 856.45 | 857.59 | A | ¹H NMR (400 MHz, DMSO-d₆) δ 10.07-9.35 (m, 1 H), 7.85-7.81 (m, 1 H), 7.75-7.70 (m, 2 H), 7.47 (d, J = 9.2 Hz, 1H), 7.28-7.23 (m, 2 H), 6.95 (d, J = 9.2 Hz, 2 H), 6.73 (s, 2 H), 5.10 (dd, J = 12.8, 5.2 Hz, 1 H), 4.90 (t, J = 6.4 Hz, 1 H), 4.22 (s, 1 H), 4.03 (d, J = 9.2 Hz, 1 H), 3.88 (d, J = 12.8 Hz, 2 H), 3.69-3.63 (m, 1 H), 3.49 (s, 1 H), 2.94-2.83 (m, 2 H), 2.80-2.58 (m, 4 H), 2.43 (s, 6 H), 2.25 (d, J = 7.2 Hz, 2 H), 2.22-2.15 (m, 2 H), 2.05 (s, 2 H), 1.82 (d, J = 12.4 Hz, 2 H), 1.56 (s, 1 H), 1.23-1.21 (m, 6 H), 1.19-1.13 (m, 2 H), 1.11 (s, 6 H) 0.92 (d, J = 6.4 Hz, 6 H). |
| 161 | 842.44 | 843.77 | A | ¹H NMR (400 MHz, Methanol-d₄) δ 7.81 (d, J = 8.3 Hz, 1H), 7.37 (d, J = 2.2 Hz, 1H), 7.29 (dd, J = 8.3, 2.3 Hz, 1H), 7.04-6.97 (m, 2H), 6.73 (s, 2H), 5.12 (dd, J = 12.6, 5.5 Hz, 1H), 5.06 (s, 1H), 4.25 (d, J = 0.9 Hz, 1H), 4.13 (d, J = 0.9 Hz, 1H), 3.92 (d, J = 12.6 Hz, 2H), 3.13 (s, 1H), 2.96-2.81 (m, 2H), 2.81-2.66 (m, 2H), 2.49 (s, 6H), 2.33 (d, J = 10.8 Hz, 6H), 2.18-2.09 (m, 1H), 2.05 (s, 0H), 1.93 (dd, J = 17.2, 13.1 Hz, 3H), 1.91 (s, 2H), 1.79 (s, 2H), 1.70-1.58 (m, 1H), 1.38-1.29 (m, 3H), 1.29 (s, 6H), 1.23 (s, 6H). |
| 162 | 842.44 | 843.64 | A | ¹H NMR (300 MHz, DMSO-de) δ 11.10 (s, 1H), 7.83-7.82 (m, 1H), 7.73-7.71 (m, 2H), 7.47-7.43 (m, 2H), 7.37-7.35 (m, 1H), 6.93-6.91 (m, 2H), 6.72 (s, 2H), 5.13-5.10 (m, 1H), 4.30 (m, 1H), 4.22-4.17 (m, 2H), 4.04-4.02 (m, 1H), 3.81 (m, 2H), 2.93-2.86 (m, 2H), 2.77-2.71 (m, 3H), 2.61-2.56 (m, 2H), 2.43 (m, 6H), 2.22 (m, 2H), 2.08 (m, 2H), 1.83-1.66 (m, 5H), 1.52 (m, 3H), 1.36-1.27 (m, 1H), 1.22 (m, 6H), 1.12 (m, 8H). |
| 163 | 870.44 | 871.77 | A | ¹H NMR (400 MHz, DMSO-d₆) δ 11.12 (s, 1H), 8.29 (s, 1H), 8.21 (d, J = 9.2 Hz, 1H), 7.81-7.88 (m, 2H), 7.24-7.33 (m, 2H), 6.85 (d, J = 9.2 Hz, 1H), 6.77 (s, 2H), 5.13 (dd, J = 12.8, 5.2 Hz, 1H), 4.92 (t, J = 6.0 Hz, 1H), 4.32 (s, 1H), 4.13-4.22 (m, 2H), 4.03-4.10 (m, 2H), 3.98 (d, J = 9.2 Hz, 1H), 3.52-3.85 (m, 1H), 2.79-3.05 (m, 3H), 2.53-2.65 (m, 2H), 2.43 (s, 6H), 2.33-2.42 (m, 4H), 2.26-2.31 (m, 2H), 2.16-2.24 (m, 2H), 2.01-2.11 (m, 1H), 1.86-1.95 (m, 2H), 1.22 (s, 6H), 1.13 (s, 6H), 0.93 (d, J = 6.8 Hz, 6H). |
| 164 | 888.44 | 889.72 | A | ¹H NMR (400 MHz, DMSO-d₆) δ 11.06 (s, 1H), 7.73 (m, 2H), 7.46 (m, 1H), 6.96-6.72 (m, 7H), 5.03-4.96 (m, 2H), 4.22 (m, 1H), 4.02-3.92 (m, 5H), 3.59-3.52 (m, 6H), 3.04-2.87 (m, 6H), 2.42 (m, 6H), 2.14 (m, 5H), 1.99-1.91 (m, 3H), 1.69-1.50 (m, 3H), 1.21 (m, 6H), 1.11 (m, 6H). |
| 165 | 858.43 | 859.70 | A | ¹H NMR (400 MHz, DMSO-d₆) δ 11.08 (s, 1H), 7.73 (m, 2H), 7.47 (m, 1H), 6.95 (m, 2H), 6.83 (m, 2H), 6.73 (m, 2H), 5.04 (m, 1H), 4.95 (m, 1H), 4.21 (m, 1H), 4.03 (m, 1H), 3.93 (m, 5H), 3.75-3.64 (m, 2H), 2.93-2.81 (m, 1H), 2.80-2.69 (m, 3H), 2.60-2.54 (m, 2H), 2.43 (m, 8H), 2.25-2.18 (m, 2H), 2.04-1.93 (m, 1H), 1.68 (m, 2H), 1.54-1.44 (m, 2H), 1.21 (m, 7H), 1.12 (m, 6H), 0.98 (m, 3H). |
| 166 | 842.44 | 843.77 | A | ¹H NMR (400 MHz, DMSO-d₆) δ 11.12 (s, 1H), 7.83 (d, J = 8.3 Hz, 1H), 7.73 (d, J = 8.8 Hz, 2H), 7.47 (d, J = 9.3 Hz, 1H), 7.37 (d, J = 2.2 Hz, 1H), 7.31 (d, J = 8.3, 2.3 Hz, 1H), 6.94 (d, J = 8.7 Hz, 2H), 6.74 (s, 2H), 5.12 (dd, J = 12.8, 5.4 Hz, 1H), 5.02 (s, 1H), 4.23 (s, 1H), 4.04 (d, J = 9.1 Hz, 1H), 3.83 (d, J = 12.4 Hz, 2H), 2.89 (s, 1H), 2.85 (t, J = 7.4 Hz, 1H), 2.76 (t, J = 12.0 Hz, 2H), 2.64-2.51 (m, 2H), 2.44 (s, 6H), 2.42-2.33 (m, 1H), 2.17 (d, J = 9.2 Hz, 5H), 2.08-2.00 (m, 1H), 1.91 (dt, J = 13.6, 6.5 Hz, 0H), 1.85-1.74 (m, 2H), 1.68-1.58 (m, 1H), 1.22 (s, 7H), 1.14 (s, 2H), 1.12 (s, 6H). |
| 167 | 815.40 | 816.62 | A | ¹H NMR (400 MHz, DMSO-d₆) δ 11.08 (s, 1H), 7.79-7.77 (m, 2H), 7.68 (m, 1H), 7.54 (m, 1H), 7.35 (m, 1H), 7.23 (m, 1H), 7.01-6.98 (m, 2H), 6.73 (s, 2H), 5.05 (m, 1H), 4.22 (m, 1H), 4.05-4.03 (m, 1H), 3.95 (m, 1H), 3.77 (m, 2H), 3.65 (m, 2H), 3.46 (m, 4H), 3.32 (m, 2H), 2.94-2.72 (m, 2H), 2.67-2.60 (m, 6H), 2.43 (m, 7H), 2.04 (m, 1H), 1.22 (m, 6H), 1.12 (m, 6H). |
| 168 | 842.44 | 843.77 | A | ¹H NMR (400 MHz, DMSO-d₆) δ 11.10 (s, 1H), 7.83 (d, J = 8.4 Hz, 1H), 7.73 (d, J = 8.8 Hz, 2H), 7.45 (d, J = 9.2 Hz, 1H), 7.29-7.23 (m, 2H), 6.95 (d, J = 8.8 Hz, 2H), 6.73 (s, 2H), 5.11 (dd, J = 12.8, 5.4 Hz, 1H), 4.94 (br s, 1H), 4.22 (s, 1H), 4.03 (d, J = 9.2 Hz, 1H), 3.86 (br d, J = 12.4 Hz, 2H), 3.43 (br s, 2H), 2.89 (br dd, J = 5.2, 3.0 Hz, 1H), 2.78 (br t, J = 11.2 Hz, 2H), 2.61 (br d, J = 2.4 Hz, 1H), 2.57 (br s, 1H), 2.54 (br d, J = 6.4 Hz, 2H), 2.43 (s, 6H), 2.40-2.33 (m, 2H), 2.24-2.17 (m, 4H), 2.09-2.00 (m, 1H), 1.81 (br d, J = 11.2 Hz, 2H), 1.64 (br s, 1H), 1.21 (s, 6H), 1.16 (br s, 1H), 1.12 (s, 6H), 0.92 (t, J = 7.2 Hz, 3H). |
| 169 | 872.45 | 873.78 | A | ¹H NMR (400 MHz, DMSO-d₆) δ 11.09 (s, 1H), 9.96 (s, 1H), 7.76 (d, J = 8.8 Hz, 2H), 7.50 (d, J = 9.2 Hz, 1H), 7.00 (d, J = 9.2 Hz, 2H), 6.87 (s, 2H), 6.73 (s, 2H), 4.93-5.26 (m, 2H), 4.23 (s, 1H), 4.08-4.17 (m, 1H), 4.03 (d, J = 9.2 Hz, 1H), 3.86-3.98 (m, 6H), 3.77 (d, J = 17.2 Hz, 1H), 3.16 (s, 2H), 2.78-3.04 (m, 7H), 2.55-2.72 (m, 2H), 2.43 (s, 6H), 2.00 (d, J = 11.2 Hz, 3H), 1.84 (d, J = 11.2 Hz, 1H), 1.26-1.36 (m, 2H), 1.18-1.23 (m, 9H), 1.12 (s, 6H). |
| 170 | 902.46 | 903.73 | A | ¹H NMR (400 MHz, DMSO-d₆) δ 9.17-9.31 (m, 1H), 7.76 (d, J = 8.8 Hz, 2H), 7.52 (s, 1H), 7.48 (d, J = 9.2 Hz, 1H), 7.24 (s, 1H), 6.99 (d, J = 8.8 Hz, 2H), 6.74 (s, 2H), 4.97-5.18 (m, 2H), 4.17-4.30 (m, 2H), 4.04 (d, J = 8.8 Hz, 1H), 3.98 (s, 3H), 3.88-3.94 (m, 2H), 3.65 (d, J = 4.8 Hz, 2H), 3.35 (s, 4H), 3.24-3.29 (m, 1H), 3.05-3.11 (m, 1H), 2.81-3.00 (m, 6H), 2.63 (d, J = 2.8 Hz, 1H), 2.58 (s, 1H), 2.44 (s, 6H), 2.00-2.08 (m, 1H), 1.86-1.95 (m, 1H), 1.76-1.85 (m, 1H), 1.55-1.59 (m, 1H), 1.36-1.40 (m, 2H), 1.26-1.34 (m, 2H), 1.22 (s, 6H), 11.10 (s, 1H), 1.09-1.17 (m, 6H). |
| 171 | 815.40 | 816.62 | A | ¹H NMR (300 MHz, DMSO-d₆) δ 11.09 (s, 1H), 7.79-7.67 (m, 2H), 7.56-7.53 (m, 1H), 7.35 (m, 1H), 7.28-7.25 (m, 1H), 7.00-6.98 (m, 2H), 6.73 (s, 2H), 5.096-5.06 (m, 1H), 4.25-4.22 (m, 1H), 4.06-3.84 (m, 3H), 3.77-3.57 (m, 5H), 3.07-2.73 (m, 3H), 2.60 (m, 5H), 2.43 (m, 7H), 2.07-1.89 (m, 2H), 1.22 (m, 9H), 1.12 (m, 7H). |

TABLE 2C-continued

Degradation of AR proteins by exemplary heterobifunctional compounds of the present disclosure.

| Comp No. | Exact Mass | Observed Mass | DC50 Code* | NMR |
|---|---|---|---|---|
| 172 | 828.42 | 829.54 | A | $^1$H NMR (400 MHz, Methanol-$d_4$) δ 7.79 (dd, J = 8.3, 3.3 Hz, 1H), 7.76-7.69 (m, 2H), 7.43 (d, J = 2.3 Hz, 1H), 7.36-7.29 (m, 1H), 7.01-6.93 (m, 2H), 6.73 (s, 2H), 5.13 (dd, J = 12.7, 5.4 Hz, 1H), 4.25 (s, 1H), 4.19-4.11 (m, 2H), 4.08 (dd, J = 9.6, 5.4 Hz, 1H), 3.87 (t, J = 12.4 Hz, 2H), 3.24 (dd, J = 9.2, 4.8 Hz, 1H), 2.96 (s, 1H), 2.91-2.66 (m, 5H), 2.49 (s, 6H), 2.41 (dd, J = 12.1, 4.5 Hz, 1H), 2.34 (t, J = 8.3 Hz, 1H), 2.18-2.05 (m, 1H), 2.02 (d, J = 26.7 Hz, 1H), 1.91-1.83 (m, 1H), 1.83-1.72 (m, 1H), 1.36 (t, J = 5.8 Hz, 1H), 1.31 (s, 2H), 1.29 (s, 5H), 1.23 (s, 6H). |
| 173 | 828.42 | 829.75 | A | $^1$H NMR (300 MHz, DMSO-$d_6$) δ 11.11 (s, 1H), 7.83-7.69 (m, 3H), 7.49-7.46 (m, 1H), 7.23 (m, 2H), 6.94-6.91 (m, 2H), 6.71 (s, 2H), 5.11-5.08 (m, 1H), 4.91 (m, 1H), 4.20 (m, 1H), 4.02-3.87 (m, 3H), 3.68 (m, 2H), 2.86-2.49 (m, 5H), 2.20 (m, 8H), 2.04-1.81 (m, 4H), 1.68-1.44 (m, 4H), 1.19-1.09 (m, 13H), 0.96 (m, 4H). |
| 174 | 858.43 | 859.57 | A | $^1$H NMR (400 MHz, DMSO-$d_6$) δ 11.12 (s, 1H), 7.84 (m, 1H), 7.74-7.72 (m, 2H), 7.44 (m, 2H), 7.34 (m, 1H), 6.94-6.92 (m, 2H), 6.74 (m, 2H), 5.12 (m, 1H), 4.23 (m, 3H), 4.04 (m, 1H), 3.83 (m, 2H), 3.74-3.41 (m, 4H), 2.96-2.65 (m, 6H), 2.43 (m, 5H), 2.25-1.96 (m, 5H), 1.88 (m, 2H), 1.72 (m, 2H), 1.24-1.12 (m, 16H) |
| 175 | 870.44 | 871.77 | A | $^1$H NMR (400 MHz, DMSO-$d_6$) δ 11.12 (s, 1H), 8.58 (d, J = 1.2 Hz, 1H), 8.27 (s, 1H), 7.79-7.90 (m, 3H), 7.24-7.33 (m, 2H), 6.76 (s, 2H), 5.13 (dd, J = 12.8, 5.2 Hz, 1H), 4.87-4.98 (m, 1H), 4.30 (s, 1H), 4.15-4.21 (m, 2H), 4.03-4.10 (m, 2H), 3.94 (d, J = 9.2 Hz, 1H), 3.49-3.79 (m, 1H), 2.84-2.96 (m, 3H), 2.54-2.64 (m, 2H), 2.43 (s, 6H), 2.34-2.42 (m, 4H), 2.26-2.31 (m, 2H), 2.16-2.24 (m, 2H), 2.01-2.10 (m, 1H), 1.84-1.92 (m, 2H), 1.19 (s, 6H), 1.12 (s, 6H), 0.90-0.96 (m, 6H). |
| 176 | 830.40 | 831.63 | A | $^1$H NMR (400 MHz, Methanol-$d_4$) δ 7.83 (d, J = 8.3 Hz, 1H), 7.74 (d, J = 8.6 Hz, 2H), 7.54 (d, J = 8.6 Hz, 1H), 7.30 (d, J = 2.2 Hz, 1H), 7.26 (dd, J = 8.3, 2.3 Hz, 1H), 6.65 (d, J = 2.2 Hz, 1H), 6.58 (dd, J = 8.7, 2.2 Hz, 1H), 6.50 (d, J = 8.7 Hz, 2H), 5.12 (dd, J = 12.6, 5.4 Hz, 1H), 4.28 (s, 1H), 4.18-4.11 (m, 1H), 4.05 (t, J = 7.6 Hz, 2H), 3.95 (s, 3H), 3.82 (s, 1H), 3.63 (dd, J = 7.5, 5.2 Hz, 2H), 3.37 (s, 1H), 3.08 (s, 1H), 2.96-2.82 (m, 1H), 2.81-2.71 (m, 1H), 2.53 (s, 2H), 2.38 (s, 2H), 2.14 (s, 1H), 1.30 (s, 7H), 1.25 (s, 6H), 1.08 (d, J = 6.7 Hz, 6H). |
| 177 | 846.44 | 847.77 | A | $^1$H NMR (300 MHz, DMSO-$d_6$) δ 11.08 (s, 1H), 8.63 (s, 1H), 8.36 (s, 1H), 7.88-7.85 (m, 1H), 7.66-7.63 (m, 1H), 7.52-7.50 (m, 1H), 7.40-7.38 (m, 1H), 7.08-7.05 (m, 1H), 6.67-6.60 (m, 1H), 6.57 (m, 1H), 5.13-5.10 (m, 1H), 4.99 (m, 1H), 4.55-4.51 (m, 2H), 4.47-4.41 (m, 3H), 4.27-4.24 (m, 2H), 3.98-3.91 (m, 3H), 3.18-3.00 (m, 4H), 2.88-2.72 (m, 4H), 2.67 (m, 1H), 2.42-2.31 (m, 1H), 2.06-1.87 (m, 6H), 1.47-1.42 (m, 1H), 1.24-1.01 (m, 18H), 0.86 (m, 1H). |
| 178 | 801.37 | 802.51 | A | $^1$H NMR (300 MHz, DMSO-$d_6$) δ 11.12 (s, 1H), 7.85-7.83 (m, 1H), 7.75-7.73 (m, 2H), 7.51-7.49 (m, 1H), 7.28-7.21 (m, 2H), 6.98-6.96 (m, 2H), 6.55 (s, 2H), 5.14-5.05 (m, 1H), 4.42-4.39 (m, 1H), 4.22 (s, 1H), 4.04-4.02 (m, 1H), 3.69-3.66 (m, 2H), 3.07-2.94 (m, 2H), 2.93-2.81 (m, 1H), 2.64-2.53 (m, 1H), 2.46-2.37 (m, 9H), 2.07-1.83 (m, 4H), 1.45 (m, 2H), 1.21 (m, 7H), 1.13 (m, 7H). |
| 179 | 928.41 | 929.76 | A | $^1$H NMR (300 MHz, DMSO-$d_6$ + $D_2O$) δ 8.75 (s, 2H), 7.73 (m, 1H), 6.84 (m, 2H), 6.73 (s, 2H), 5.36-5.18 (m, 1H), 5.07 (m, 1H), 4.74 (m, 1H), 4.54-4.41 (m, 2H), 4.17 (s, 1H), 4.02-3.93 (m, 5H), 3.12-2.85 (m, 4H), 2.43 (m, 7H), 2.35-2.18 (m, 2H), 2.11-1.96 (m, 3H), 1.87-1.65 (m, 2H), 1.45-1.11 (m, 16H). |
| 180 | 957.50 | 958.84 | A | $^1$H NMR (400 MHz, DMSO-$d_6$) δ 11.06 (s, 1 H), 7.73 (d, J = 8.80 Hz, 2 H), 7.45 (d, J = 9.2 Hz, 1 H), 6.95 (d, J = 9.2 Hz, 2 H), 6.83 (dd, J = 10.8, 1.65 Hz, 2 H), 6.73 (s, 2 H), 5.04 (dd, J = 12.8, 5.6 Hz, 1 H), 4.95 (s, 1 H), 4.22 (s, 1 H), 4.03 (d, J = 9.2 Hz, 1 H), 3.93 (s, 3 H), 3.86 (d, J = 12.4 Hz, 2 H), 3.43-3.63 (m, 4 H), 2.73-2.99 (m, 4 H), 2.54-2.62 (m, 4 H), 2.43 (s, 6 H), 2.32-2.41 (m, 8 H), 2.16-2.27 (m, 4 H), 1.95-2.04 (m, 1 H), 1.75-1.87 (m, 2 H), 1.65 (s, 1 H), 1.21 (s, 6 H), 1.12 (s, 8H). |
| 181 | 908.50 | 909.84 | A | $^1$H NMR (300 MHz, DMSO-$d_6$) δ 11.09 (s, 1H), 7.74 (m, 2H), 7.47 (m, 1H), 6.96-6.73 (m, 6H), 5.06-4.96 (m, 2H), 4.23-3.86 (m, 5H), 3.00-2.62 (m, 8H), 2.43-2.12 (m, 11H), 2.02-1.63 (m, 5H), 1.21-1.12 (m, 15H). |
| 182 | 830.40 | 831.72 | A | $^1$H NMR (400 MHz, Methanol-$d_4$) δ 7.81 (d, J = 8.3 Hz, 1H), 7.73 (d, J = 8.8 Hz, 2H), 7.47 (d, J = 2.3 Hz, 1H), 7.34 (dd, J = 8.3, 2.2 Hz, 1H), 6.99 (d, J = 9.0 Hz, 2H), 6.73 (s, 2H), 5.12 (dd, J = 12.6, 5.5 Hz, 1H), 4.33 (t, J = 5.3 Hz, 2H), 4.24 (s, 1H), 4.12 (s, 1H), 3.78 (t, J = 4.9 Hz, 2H), 3.53 (s, 1H), 3.21 (t, J = 11.3 Hz, 2H), 2.92-2.73 (m, 3H), 2.58 (s, 2H), 2.47 (d, J = 8.8 Hz, 7H), 2.14 (s, 1H), 2.04 (d, J = 13.0 Hz, 2H), 1.75-1.64 (m, 2H), 1.29 (d, J = 6.9 Hz, 8H), 1.22 (s, 6H), 0.11 (s, 1H). |
| 183 | 829.42 | 830.64 | A | $^1$H NMR (400 MHz, DMSO-$d_6$) δ 11.08 (s, 1H), 7.81-7.79 (m, 3H), 7.69 (m, 1H), 7.46-7.43 (m, 2H), 7.34 (m, 1H), 7.26 (m, 1H), 6.74 (m, 2H), 5.08 (m, 1H), 4.23 (m, 2H), 4.06 (m, 1H), 3.77 (m, 1H), 3.60 (m, 1H), 3.43 (m, 7H), 2.87 (m, 1H), 2.67 (m, 2H), 2.43 (m, 9H), 2.17 (m, 2H), 1.99 (m, 2H), 1.23 (m, 8H), 1.13 (m, 7H). |
| 184 | 878.38 | 879.71 | A | $^1$H NMR (400 MHz, DMSO-$d_6$) δ 11.10 (s, 1H), 8.32 (s, 1H), 7.90 (d, J = 8.8 Hz, 1H), 7.83 (d, J = 8.8 Hz, 1H), 7.73 (d, J = 8.8 Hz, 2H), 7.47 (d, J = 9.2 Hz, 1H), 7.23-7.31 (m, 2H), 7.20 (d, J = 2.4 Hz, 1H), 7.00 (dd, J = 8.8, 2.4 Hz, 1H), 6.95 (d, J = 8.8 Hz, 2H), 5.11 (dd, J = 12.8, 5.2 Hz, 1H), 4.93 (s, 1H), 4.32 (s, 1H), 4.05 (d, J = 9.2 Hz, 1H), 3.86 (d, J = 12.0 Hz, 2H), 3.44-3.54 (m, 4H), 3.24 (s, 3H), 2.56-2.94 (m, 8H), 2.36 (dd, J = 14.0, 7.2 Hz, 2H), 2.17-2.29 (m, 4H), 1.99-2.08 (m, 1H), 1.81 (d, J = 11.2 Hz, 2H), 1.64 (s, 1H), 1.21 (s, 6H), 1.12 (s, 6H). |
| 185 | 844.46 | 845.80 | A | $^1$H NMR (300 MHz, DMSO-$d_6$) δ 8.67 (s, 1H), 8.25 (s, 1H), 7.53-7.43 (m, 2H), 7.04-7.02 (m, 1H), 6.72 (s, 2H), 5.18-5.15 (m, 1H), 5.07-5.02 (m, 2H), 4.65-4.62 (m, 2H), 4.49-4.42 (m, 2H), 4.35 (m, 1H), 4.24 (m, 1H), 4.04 (m, 1H), 3.77-3.73 (m, 1H), 3.17-3.06 (m, 3H), 2.96-2.83 (m, 4H), 2.78-2.52 (m, 3H), 2.47 (m, 8H), 2.21-1.96 (m, 4H), 1.41-1.32 (m, 9H), 1.26 (m, 7H), 1.19 (m, 7H). |
| 186 | 828.42 | 829.74 | A | $^1$H NMR (400 MHz, DMSO-$d_6$) δ 11.13 (br s, 1H), 9.64-9.20 (m, 1H), 7.96-7.85 (m, 1H), 7.82-7.71 (m, 2H), 7.56-7.47 (m, 1H), 7.39-7.27 (m, 2H), 7.06-6.93 (m, 2H), 6.73 (br s, 2H), 5.20-5.03 (m, 2H), 4.27-4.19 (m, 1H), 4.14-3.96 (m, 3H), 3.96-3.82 (m, 3H), 3.00-2.73 (m, 11H), 2.42-2.20 (m, 6H), 2.14-1.98 (m, 3H), 1.94-1.85 (m, 1H), 1.77-1.68 (m, 1H), 1.39-1.20 (m, 8H), 1.13-1.00 (m, 6H). |

TABLE 2C-continued

Degradation of AR proteins by exemplary heterobifunctional compounds of the present disclosure.

| Comp No. | Exact Mass | Observed Mass | DC50 Code* | NMR |
|---|---|---|---|---|
| 187 | 828.42 | 829.65 | A | ¹H NMR (400 MHz, Methanol-d₄) δ 7.83 (d, J = 8.2 Hz, 1H), 7.73 (d, J = 8.6 Hz, 2H), 7.30 (d, J = 2.2 Hz, 1H), 7.26 (dd, J = 8.3, 2.3 Hz, 1H), 6.73 (s, 2H), 6.53-6.47 (m, 2H), 5.12 (dd, J = 12.6, 5.4 Hz, 1H), 4.25 (s, 1H), 4.16-4.09 (m, 1H), 4.05 (t, J = 7.5 Hz, 2H), 3.85-3.77 (m, 1H), 3.63 (dd, J = 7.6, 5.2 Hz, 2H), 3.08 (s, 1H), 2.96-2.69 (m, 4H), 2.53 (s, 2H), 2.49 (s, 6H), 2.36 (d, J = 11.4 Hz, 2H), 1.31 (s, 0H), 1.29 (s, 6H), 1.22 (s, 6H), 1.08 (d, J = 6.6 Hz, 6H), 0.92 (s, 1H). |
| 188 | 927.49 | 928.83 | A | ¹H NMR (400 MHz, DMSO-d₆) δ 11.12 (s, 1H), 8.26 (s, 1H), 7.83 (d, J = 8.0 Hz, 1H), 7.73 (d, J = 8.8 Hz, 2H), 7.48 (d, J = 9.2 Hz, 1H), 7.22-7.32 (m, 2H), 6.95 (d, J = 8.8 Hz, 2H), 6.73 (s, 2H), 5.11 (dd, J = 12.8, 5.6 Hz, 1H), 4.93 (br s, 1H), 4.22 (s, 1H), 4.03 (d, J = 9.2 Hz, 1H), 3.86 (d, J = 12.0 Hz, 2H), 3.58-3.68 (m, 5H), 2.66-2.97 (m, 4H), 2.52-2.64 (m, 4H), 2.42 (s, 6H), 2.32-2.39 (m, 7H), 2.16-2.28 (m, 4H), 1.98-2.09 (m, 1H), 1.81 (d, J = 11.6 Hz, 2H), 1.65 (s, 1H), 1.21 (s, 6H), 1.13-1.19 (m, 2H), 1.11 (s, 6H). |
| 189 | 844.42 | 845.75 | A | ¹H NMR (300 MHz, DMSO) δ 1.08 (s, 1H), 7.73-7.71 (m, 2H), 7.50-7.48 (m, 1H), 7.00-6.94 (m, 2H), 6.85-6.82 (m, 2H), 6.73 (s, 2H), 5.07-4.96 (m, 2H), 4.22 (s, 1H), 4.04 (d, 1H), 3.93 (m, 4H), 2.93-2.72 (m, 6H), 2.42 (m, 6H), 2.21 (m, 2H), 2.06 (m, 5H), 1.62 (m, 2H), 1.52-1.50 (m, 2H), 1.34-1.21 (m, 9H), 1.11 (m, 6H). |
| 190 | 886.43 | 887.77 | A | ¹H NMR (400 MHz, DMSO-d₆) δ 11.11 (s, 1H), 7.85 (d, J = 8.2 Hz, 1H), 7.72 (d, J = 8.5 Hz, 2H), 7.65 (d, J = 8.6 Hz, 1H), 7.44 (d, J = 9.2 Hz, 1H), 7.27 (d, J = 7.8 Hz, 2H), 6.64 (d, J = 2.2 Hz, 1H), 6.58-6.50 (m, 1H), 6.41 (d, J = 8.6 Hz, 2H), 5.12 (dd, J = 12.9, 5.4 Hz, 1H), 4.95 (s, 1H), 4.27 (s, 1H), 4.04 (d, J = 9.2 Hz, 1H), 3.91 (s, 5H), 3.79 (s, 2H), 3.46 (s, 1H), 2.88 (d, J = 12.2 Hz, 1H), 2.62 (s, 1H), 2.58 (s, 3H), 2.37 (s, 3H), 2.32-2.24 (m, 2H), 2.22 (s, 2H), 2.09-2.01 (m, 1H), 1.87 (s, 2H), 1.22 (s, 7H), 1.14 (s, 6H). |
| 191 | 858.43 | 859.76 | A | ¹H NMR (400 MHz, DMSO-d₆) δ 11.10 (s, 1H), 9.33 (s, 1H), 7.75 (d, J = 8.8 Hz, 2H), 7.50 (d, J = 9.2 Hz, 1H), 6.98 (d, J = 9.2 Hz, 2H), 6.88 (d, J = 6.0 Hz, 2H), 6.73 (s, 2H), 5.05 (dd, J = 12.8, 5.6 Hz, 1H), 4.23 (s, 1H), 4.07-3.99 (m, 3H), 3.97-3.85 (m, 7H), 3.60 (m, 1H), 3.22 (d, J = 12.4 Hz, 1H), 3.12-2.75 (m, 9H), 2.43 (s, 6H), 2.01 (d, J = 5.2 Hz, 2H), 1.88 (d, J = 12.4 Hz, 1H), 1.71 (d, J = 10.4 Hz, 1H), 1.30 (s, 2H), 1.21 (s, 6H), 1.11 (s, 6H). |
| 192 | 842.44 | 843.56 | A | ¹H NMR (300 MHz, DMSO-d₆) δ 11.15 (s, 1H), 7.93-7.91 (m, 1H), 7.75-7.72 (m, 2H), 7.58-7.57 (m, 1H), 7.49-7.41 (m, 2H), 6.97-6.94 (m, 2H), 6.73 (s, 2H), 5.17-5.11 (m, 1H), 4.51-4.47 (m, 2H), 4.22 (s, 1H), 4.04-4.01 (m, 1H), 3.92-3.69 (m, 3H), 3.48-3.32 (m, 1H), 3.29-2.70 (m, 5H), 2.63 (m, 1H), 2.43 (m, 6H), 2.08 (m, 3H), 1.95-1.83 (m, 6H), 1.55 (m, 1H), 1.32-1.23 (m, 9H), 1.14-1.13 (m, 7H). |
| 193 | 828.42 | 829.74 | A | ¹H NMR (400 MHz, Methanol-d₄) δ 7.83-7.69 (m, 1H), 6.98 (d, J = 9.0 Hz, 1H), 6.73 (s, 1H), 4.19-4.04 (m, 1H), 3.87 (t, J = 12.4 Hz, 1H), 2.99-2.83 (m, 1H), 2.86-2.66 (m, 2H), 2.49 (s, 2H), 2.45-2.30 (m, 1H), 2.18-1.96 (m, 1H), 1.86 (dd, J = 11.1, 5.7 Hz, 1H), 1.83-1.71 (m, 1H), 1.26 (d, J = 26.8 Hz, 6H), 0.12 (s, 0H). |
| 194 | 846.41 | 847.73 | A | ¹H NMR (400 MHz, DMSO-d₆) δ 11.10 (s, 1H), 8.61 (d, J = 1.2 Hz, 1H), 8.33 (s, 1H), 7.83 (t, J = 8.8 Hz, 2H), 7.64 (d, J = 8.8 Hz, 1H), 7.30-7.22 (m, 2H), 6.67 (d, J = 2.0 Hz, 1H), 6.57 (dd, J = 8.8, 2.0 Hz, 1H), 5.12 (dd, J = 12.8, 5.2 Hz, 1H), 4.94 (br s, 1H), 4.49 (br d, J = 12.8 Hz, 2H), 4.38 (s, 1H), 3.96 (d, J = 9.2 Hz, 1H), 3.92 (s, 3H), 3.49-3.40 (m, 2H), 3.01 (br t, J = 11.6 Hz, 2H), 2.95-2.84 (m, 1H), 2.62 (br s, 1H), 2.58 (br s, 1H), 2.57-2.53 (m, 2H), 2.42-2.33 (m, 2H), 2.25-2.16 (m, 4H), 2.09-2.01 (m, 1H), 1.89-1.74 (m, 3H), 1.21 (s, 6H), 1.15 (s, 6H), 1.09 (br d, J = 11.6 Hz, 1H), 0.93 (t, J = 7.2 Hz, 3H). |
| 195 | 891.47 | 892.81 | A | ¹H NMR (300 MHz, DMSO-d₆) δ 11.09 (s, 1H), 8.61 (s, 1H), 8.34 (s, 1H), 7.82-7.79 (m, 1H), 6.86-6.76 (m, 4H), 5.08-5.02 (m, 1H), 4.91 (m, 1H), 4.54-4.49 (m, 2H), 4.30 (s, 1H), 3.96-3.93 (m, 1H), 3.67 (m, 1H), 3.02-2.84 (m, 4H), 2.55 (m, 1H), 2.43 (m, 6H), 2.26-2.16 (m, 4H), 2.02-1.70 (m, 4H), 1.23 (s, 8H), 1.12 (s, 9H), 0.94-0.83 (m, 6H). |
| 196 | 829.42 | 830.64 | A | ¹H NMR (400 MHz, DMSO-d₆) δ 10.89 (s, 1H), 7.62-7.58 (m, 3H), 7.49-7.47 (m, 1H), 7.26-7.24 (m, 2H), 7.14 (m, 1H), 7.05 (m, 1H), 6.54 (s, 2H), 4.90-4.85 (m, 1H), 4.03-3.96 (m, 2H), 3.87-3.84 (m, 1H), 3.58-3.56 (m, 1H), 3.39 (m, 1H), 3.23-3.22 (m, 8H), 2.69-2.64 (m, 1H), 2.44-2.37 (m, 4H), 2.23 (m, 8H), 2.03 (m, 1H), 1.87 (m, 1H), 1.07 (m, 8H), 0.93 (m, 7H). |
| 197 | 831.38 | 832.58 | A | ¹H NMR (300 MHz, DMSO-d₆) δ 11.08 (s, 1H), 7.75-7.72 (m, 2H), 7.51-7.48 (m, 1H), 6.98-6.96 (m, 2H), 6.84-6.83 (m, 2H), 6.73 (m, 3H), 5.33 (m, 1H), 5.12-4.98 (m, 2H), 4.39 (m, 1H), 4.18 (s, 1H), 4.04 (m, 1H), 3.93 (s, 3H), 3.72-3.62 (m, 2H), 3.08-2.95 (m, 3H), 2.87 (m, 1H), 2.08-1.83 (m, 5H), 1.52-1.40 (m, 3H), 1.23 (s, 12H), 1.11 (s, 7H). |
| 198 | 834.35 | 835.58 | A | ¹H NMR (400 MHz, Methanol-d₄) δ 7.82 (d, J = 8.3 Hz, 1H), 7.77-7.68 (m, 3H), 7.32-7.22 (m, 2H), 7.15 (d, J = 2.4 Hz, 1H), 7.00 (dd, J = 8.8, 2.5 Hz, 1H), 6.54-6.46 (m, 2H), 5.12 (dd, J = 12.6, 5.4 Hz, 1H), 4.30 (d, J = 0.9 Hz, 1H), 4.15 (d, J = 0.9 Hz, 1H), 4.04 (t, J = 7.6 Hz, 2H), 3.84-3.76 (m, 1H), 3.63 (d, J = 7.6, 5.2 Hz, 2H), 3.11-3.03 (m, 1H), 2.92 (s, 2H), 2.88-2.74 (m, 3H), 2.77-2.67 (m, 1H), 2.56-2.48 (m, 2H), 2.37 (t, J = 10.1 Hz, 2H), 2.19-2.10 (m, 1H), 1.30 (s, 6H), 1.24 (s, 6H), 1.07 (d, J = 6.7 Hz, 6H). |
| 199 | 888.45 | 889.79 | A | ¹H NMR (400 MHz, DMSO-d₆) δ 11.09 (s, 1H), 8.61 (d, J = 1.3 Hz, 1H), 8.34 (d, J = 1.4 Hz, 1H), 7.80 (d, J = 9.0 Hz, 1H), 7.46 (s, 1H), 7.11 (s, 1H), 6.77 (m, 2H), 5.09 (dd, J = 13.0, 5.4 Hz, 1H), 4.88 (s, 1H), 4.51 (d, J = 12.8 Hz, 2H), 4.30 (s, 1H), 3.99-3.91 (m, 4H), 3.66 (q, J = 8.2 Hz, 1H), 3.04-2.82 (m, 4H), 2.64-2.52 (m, 1H), 2.43 (s, 6H), 2.27 (s, 1H), 2.22 (dd, J = 19.4, 10.0 Hz, 3H), 2.03 (d, J = 13.1 Hz, 1H), 1.86 (d, J = 12.8 Hz, 2H), 1.70 (s, 1H), 1.20 (s, 6H), 1.12 (s, 8H), 0.93 (d, J = 6.6 Hz, 3H). |
| 200 | 886.47 | 887.82 | A | ¹H NMR (400 MHz, DMSO-d₆) δ 11.20-11.07 (m, 1H), 8.92-8.68 (m, 1H), 8.31-8.17 (m, 1H), 7.95 (s, 1H), 7.46-7.24 (m, 2H), 6.83 (s, 2H), 5.25-5.06 (m, 2H), 4.83 (d, J = 4.0, 1.6 Hz, 2H), 4.34-4.20 (m, 2H), 4.16 (s, 1H), 4.06 (d, J = 9.6 Hz, 2H), 3.63-3.53 (m, 4H), 3.12-3.02 (m, 1H), 2.95-2.86 (m, 4H), 2.68 (dt, J = 3.6, 1.6 Hz, 2H), 2.43 (s, 6H), 2.24 (s, 6H), 2.13-1.90 (m, 4H), 1.87-1.79 (m, 1H), 1.31-1.25 (m, 3H), 1.23-1.16 (m, 9H), 1.10 (s, 6H). |
| 201 | 858.43 | 859.56 | A | ¹H NMR (400 MHz, DMSO-d₆) δ 11.12 (s, 1H), 7.81 (m, 1H), 7.72-7.70 (m, 2H), 7.42-7.41 (m, 3H), 6.93-6.90 (m, 2H), 6.72 (s, 2H), 5.08 (m, 1H), 4.22 (m, 3H), 4.03-3.93 (m, 2H), 3.83-3.71 (m, 6H), 2.96-2.90 (m, 1H), 2.89-2.71 (m, 3H), 2.64 (m, 2H), 2.42 (m, 6H), 2.22 (m, 1H), 2.06-1.95 (m, 3H), 1.86 (m, 2H), 1.68 (m, 2H), 1.20 (m, 8H), 1.11 (m, 7H). |

TABLE 2C-continued

Degradation of AR proteins by exemplary heterobifunctional compounds of the present disclosure.

| Comp No. | Exact Mass | Observed Mass | DC50 Code* | NMR |
|---|---|---|---|---|
| 202 | 896.47 | 897.81 | A | $^1$H NMR (300 MHz, DMSO-d$_6$) δ 11.05 (s, 1H), 8.59 (s, 1H), 8.31 (s, 1H), 7.82-7.80 (m, 1H), 7.64-7.61 (m, 1H), 6.83-6.80 (m, 1H), 6.65-6.54 (m, 2H), 5.01 (m, 1H), 4.89 (m, 1H), 4.51-4.47 (m, 2H), 4.35 (m, 1H), 4.27-4.01 (m, 2H), 3.96-3.84 (m, 1H), 3.80-3.76 (m, 1H), 3.65-3.61(m, 3H), 3.16-3.14 (m, 1H), 3.07-2.80 (m, 5H), 2.41 (m, 2H), 2.23-2.17 (m, 3H), 2.08-1.95 (m, 2H), 1.93-1.79 (m, 2H), 1.74-1.65 (m, 1H), 1.32-0.98 (m, 11H), 0.96-0.83(m, 4H). |
| 203 | 893.45 | 894.80 | A | $^1$H NMR (400 MHz, DMSO-d$_6$) δ 11.09 (s, 1H), 8.61 (s, 1H), 8.32 (s, 1H), 7.82-7.64 (m, 2H), 6.81 (m, 2H), 6.66 (m, 2H), 5.04-4.85 (m, 2H), 4.53-4.48 (m, 2H), 4.37 (m, 1H), 3.95 (m, 4H), 3.67 (m, 1H), 2.97-2.89 (m, 4H), 2.41 (m, 4H), 2.24 (m, 4H), 2.18-1.69 (m, 4H), 1.20-0.93 (m, 20H). |
| 204 | 929.47 | 930.81 | A | $^1$H NMR (400 MHz, DMSO-d$_6$) δ 11.11 (s, 1H), 7.88 (d, J = 8.8 Hz, 1H), 7.76 (d, J = 8.8 Hz, 2H), 7.65 (d, J = 8.8 Hz, 1H), 7.50 (d, J = 9.2 Hz, 1H), 7.21-7.35 (m, 2H), 6.98 (d, J = 8.8 Hz, 2H), 6.64 (d, J = 2.0 Hz, 1H), 6.54 (dd, J = 8.8, 2.4 Hz, 1H), 5.13 (dd, J = 12.8, 5.2 Hz, 1H), 5.00-5.07 (m, 1H), 4.28 (s, 1H), 4.06 (d, J = 8.8 Hz, 1H), 3.91 (s, 8H), 3.78 (s, 3H), 3.11-3.23 (m, 6H), 2.76-2.99 (m, 4H), 2.61-2.73 (m, 4H), 2.52-2.61 (m, 2H), 2.36-2.47 (m, 2H), 2.02-2.11 (m, 1H), 1.83 (d, J = 12.0 Hz, 3H), 1.24-1.33 (m, 2H), 1.23 (s, 6H), 1.15 (s, 6H). |
| 205 | 856.45 | 857.58 | A | $^1$H NMR (400 MHz, DMSO-d$_6$) δ 9.16-8.90 (m, 1H), 7.83 (d, J = 8.0 Hz, 1 H), 7.73 (d, J = 8.4 Hz, 2 H), 7.47 (d, J = 9.2 Hz, 1 H), 7.28-7.22 (m, 2 H), 6.94 (d, J = 8.4 Hz, 2 H), 6.72 (s, 2 H), 5.10 (dd, J = 12.4, 4.8 Hz, 1 H), 4.89 (s, 1 H), 4.22 (s, 1 H), 4.03 (d, J = 9.2 Hz, 1 H), 3.87 (d, J = 12.4 Hz, 2 H), 3.68-3.63 (m, 1 H), 3.11-3.01 (m, 1 H), 2.88 (s, 3 H), 2.81-2.71 (m, 4 H), 2.42 (s, 6 H), 2.24 (d, J = 6.0 Hz, 3 H), 2.19 (d, J = 8.8 Hz, 1 H), 1.82 (d, J = 12.8 Hz, 2 H), 1.78-1.73 (m, 1 H), 1.59-1.52 (m, 1 H), 1.21 (s, 8 H), 1.11 (s, 6 H), 0.92 (d, J = 6.4 Hz, 6 H). |
| 206 | 844.43 | 845.75 | A | $^1$H NMR (400 MHz, DMSO-d$_6$) δ 11.10 (s, 1H), 8.60 (s, 1H), 8.33 (s, 1H), 7.81 (dd, J = 14.0, 8.8 Hz, 2H), 7.29-7.22 (m, 2H), 6.76 (s, 2H), 5.11 (dd, J = 12.4, 5.2 Hz, 1H), 4.94 (br s, 1H), 4.49 (br d, J = 13.2 Hz, 2H), 4.29 (s, 1H), 3.94 (d, J = 8.8 Hz, 1H), 3.47-3.38 (m, 2H), 3.00 (br t, J = 12.0 Hz, 2H), 2.94-2.83 (m, 1H), 2.61 (br s, 1H), 2.57 (br s, 1H), 2.55-2.53 (m, 2H), 2.43 (s, 6H), 2.40-2.33 (m, 2H), 2.25-2.16 (m, 4H), 2.09-1.99 (m, 1H), 1.88-1.73 (m, 3H), 1.19 (s, 6H), 1.12 (s, 6H), 1.07 (br s, 1H), 0.92 (br t, J = 7.2 Hz, 3H). |
| 207 | 874.44 | 875.77 | A | $^1$H NMR (400 MHz, DMSO-d$_6$) δ 11.09 (s, 1H), 9.24-9.42 (m, 1 H), 8.62 (s, 1 H), 8.38 (s, 1 H), 7.81 (d, J = 8.8 Hz, 1 H), 6.83-6.94 (m, 2 H), 6.76 (s, 2 H), 4.99-5.12 (m, 2 H), 4.52 (d, J = 11.2 Hz, 2 H), 4.30 (s, 1 H), 4.15 (d, J = 7.2 Hz, 1 H), 3.88-3.99 (m, 5 H), 3.46-3.57 (m, 4 H), 2.74-3.31 (m, 6 H), 2.53-2.71 (m, 3 H), 2.43 (s, 6 H), 1.76-2.23 (m, 4 H), 1.19 (s, 10 H), 1.12 (s, 6 H). |
| 208 | 850.39 | 851.71 | A | $^1$H NMR (300 MHz, DMSO-d$_6$) δ 10.98 (s, 1H), 8.58 (s, 1H), 8.31 (s, 1H), 7.90-7.86 (m, 1H), 7.81-7.78 (m, 1H), 7.46-7.41 (m, 1H), 7.30-7.22 (m, 2H), 7.03-6.94 (m, 2H), 5.12-5.06 (m, 1H), 4.80 (m, 1H), 4.51-4.36 (m, 4H), 4.25-4.20 (m, 1H), 3.95-3.92 (m, 1H), 3.68-3.55 (m, 2H), 2.95-2.91 (m, 5H), 2.28-2.15 (m, 4H), 1.99-1.98 (m, 1H), 1.85-1.73 (m, 2H), 1.70-1.55 (m, 1H), 1.28-1.06 (m, 14H), 1.03-0.98 (m, 2H), 0.87 (m, 6H). |
| 209 | 931.46 | 932.80 | A | $^1$H NMR (400 MHz, DMSO-d$_6$) δ 11.12 (s, 1H), 8.63 (s, 1H), 8.37 (s, 1H), 7.91-7.79 (m, 2H), 7.65 (d, J = 8.6 Hz, 1H), 7.32-7.26 (m, 2H), 6.67 (d, J = 1.6 Hz, 1H), 6.57 (dd, J = 8.8, 2.0 Hz, 1H), 5.13 (dd, J = 12.8, 5.6 Hz, 1H), 5.01 (br s, 1H), 4.53 (br d, J = 12.4 Hz, 2H), 4.38 (s, 1H), 3.96 (br d, J = 9.2 Hz, 1H), 3.91 (s, 3H), 3.86-3.82 (m, 1H), 3.77 (br s, 4H), 3.09 (br s, 4H), 3.01 (br d, J = 11.2 Hz, 4H), 2.88 (br d, J = 13.2 Hz, 2H), 2.62-2.54 (m, 6H), 2.35 (br d, J = 12.4 Hz, 3H), 2.06 (br dd, J = 11.2, 5.6 Hz, 1H), 2.03-1.79 (m, 4H), 1.20 (s, 7H), 1.15 (s, 6H). |
| 210 | 959.49 | 960.84 | A | $^1$H NMR (400 MHz, DMSO-d$_6$) δ 11.07 (s, 1H), 8.60 (s, 1H), 8.32 (s, 2H), 7.80 (d, J = 9.2 Hz, 1H), 6.82 (d, J = 9.2 Hz, 2H), 6.76 (s, 2H), 4.90-5.11 (m, 2H), 4.48 (d, J = 13.2 Hz, 2H), 4.29 (s, 1H), 3.90-3.97 (m, 4H), 3.46-3.61 (m, 4H), 2.82-3.05 (m, 4H), 2.52-2.64 (m, 4H), 2.43 (s, 6H), 2.36 (s, 7H), 2.18-2.28 (m, 4H), 2.00 (d, J = 5.6 Hz, 1 H), 1.84 (d, J = 11.6 Hz, 4H), 1.19 (s, 6H), 1.11 (s, 6H), 1.07 (s, 2H). |
| 211 | 888.45 | 889.80 | A | $^1$H NMR (400 MHz, DMSO-d$_6$) δ 11.23-11.03 (m, 1H), 8.27-8.19 (m, 1H), 8.16-8.12 (m, 1H), 7.92-7.79 (m, 1H), 7.71-7.58 (m, 1H), 7.38-7.23 (m, 2H), 6.75-6.60 (m, 1H), 6.58-6.49 (m, 1H), 5.18-5.08 (m, 1H), 5.00-4.90 (m, 1H), 4.83-4.69 (m, 2H), 4.26-4.18 (m, 1H), 4.11-4.04 (m, 1H), 3.93-3.89 (m, 3H), 2.94-2.77 (m, 3H), 2.64-2.53 (m, 9H), 2.25-2.22 (m, 6H), 2.12-1.99 (m, 2H), 1.88-1.79 (m, 2H), 1.37-1.24 (m, 1H), 1.24-1.18 (m, 6H), 1.13 (s, 6H), 1.08-0.88 (m, 8H). |
| 212 | 844.46 | 845.20 | A | $^1$H NMR (400 MHz, DMSO-d$_6$) d ppm 1.12 (s, 6 H) 1.19 (s, 9 H) 1.24-1.34 (m, 3 H) 1.85 (d, J = 11.93 Hz, 1 H) 1.97 (d, J = 14.87 Hz, 3 H) 2.25-2.40 (m, 2 H) 2.43 (s, 6 H) 2.54-2.71 (m, 4 H) 2.76-2.98 (m, 4 H) 2.98-3.17 (m, 3 H) 3.60 (d, J = 7.43 Hz, 1 H) 3.94 (d, J = 9.00 Hz, 1 H) 4.11-4.33 (m, 6 H) 4.39 (d, J = 16.82 Hz, 2 H) 4.53 (t, J = 6.16 Hz, 1 H) 4.97 (t, J = 6.16 Hz, 1 H) 5.05-5.20 (m, 1 H) 6.76 (s, 2 H) 7.11 (d, J = 2.35 Hz, 1 H) 7.19 (dd, J = 8.22, 2.15 Hz, 1 H) 7.55 (d, J = 8.22 Hz, 1 H) 7.81 (d, J = 9.19 Hz, 1 H) 8.37 (s, 1 H) 8.62 (s, 1 H) 8.70 (br. s 1 H) 10.99 (s, 1 H). |
| 213 | 844.42 | 845.74 | A | $^1$H NMR (400 MHz, DMSO-d$_6$) δ 11.10 (s, 1H), 7.84 (d, J = 8.3 Hz, 1H), 7.72 (d, J = 8.6 Hz, 2H), 7.50 (d, J = 2.2 Hz, 1H), 7.45 (d, J = 9.2 Hz, 1H), 7.38 (d, J = 8.3, 2.3 Hz, 1H), 6.93 (d, J = 8.7 Hz, 2H), 6.73 (s, 2H), 5.12 (dd, J = 12.9, 5.4 Hz, 1H), 4.39-4.32 (m, 1H), 4.22 (s, 2H), 4.03 (d, J = 9.2 Hz, 1H), 3.86-3.75 (m, 3H), 3.64 (s, 1H), 3.62-3.53 (m, 1H), 2.87 (dd, J = 13.9, 5.7 Hz, 1H), 2.79 (s, 1H), 2.75 (d, J = 12.1 Hz, 2H), 2.59 (d, J = 15.4 Hz, 3H), 2.43 (s, 6H), 2.32-2.24 (m, 2H), 2.10-2.00 (m, 1H), 1.84 (d, J = 12.6 Hz, 1H), 1.74 (s, 2H), 1.21 (s, 7H), 1.16 (s, 2H), 1.12 (s, 6H). |
| 214 | 924.45 | 925.79 | A | $^1$H NMR (400 MHz, DMSO-d$_6$) δ 11.11 (s, 1H), 8.06 (d, J = 8.8 Hz, 1H), 7.87 (d, J = 8.8 Hz, 1H), 7.75 (d, J = 8.8 Hz, 2H), 7.63 (d, J = 2.4 Hz, 1H), 7.47 (d, J = 9.2 Hz, 1H), 7.34 (dd, J = 8.8, 2.4 Hz, 1H), 7.27-7.31 (m, 2H), 6.98 (d, J = 8.8 Hz, 2H), 5.12 (dd, J = 12.8, 5.2 Hz, 1H), 5.03 (s, 1H), 4.37 (s, 1H), 4.07 (d, J = 9.2 Hz, 1H), 3.90 (d, J = 12.0 Hz, 2H), 3.77 (s, 6H), 3.07-3.18 (m, 6H), 2.74-2.96 (m, 4H), 2.61-2.73 (m, 4H), 2.52-2.60 (m, 2H), 2.36-2.46 (m, 2H), 2.00-2.10 (m, 1H), 1.82 (d, J = 11.6 Hz, 3H), 1.24-1.32 (m, 2H), 1.23 (s, 6H), 1.12 (s, 6H). |

TABLE 2C-continued

Degradation of AR proteins by exemplary heterobifunctional compounds of the present disclosure.

| Comp No. | Exact Mass | Observed Mass | DC50 Code* | NMR |
|---|---|---|---|---|
| 215 | 860.41 | 861.68 | A | $^1$H NMR (400 MHz, Methanol-d$_4$) δ 7.73 (d, J = 8.9 Hz, 2H), 7.09 (d, J = 1.9 Hz, 1H), 6.99 (d, J = 8.9 Hz, 2H), 6.89 (d, J = 1.9 Hz, 1H), 6.73 (s, 2H), 5.09 (dd, J = 12.4, 5.5 Hz, 1H), 4.34 (t, J = 5.3 Hz, 2H), 4.25 (s, 1H), 4.13 (d, J = 0.9 Hz, 1H), 3.95 (s, 3H), 3.86-3.76 (m, 2H), 3.49 (s, 2H), 3.23 (t, J = 11.6 Hz, 3H), 2.92-2.66 (m, 4H), 2.58 (d, J = 5.3 Hz, 2H), 2.49 (s, 8H), 2.01 (s, 1H), 1.75-1.61 (m, 2H), 1.30 (d, J = 4.8 Hz, 9H), 1.23 (s, 6H), 0.90 (s, 3H), 0.12 (s, 1H). |
| 216 | 870.43 | 871.77 | A | $^1$H NMR (400 MHz, DMSO-d$_6$) δ 11.12 (s, 1H), 7.84 (d, J = 8.1 Hz, 1H), 7.71 (d, J = 8.6 Hz, 2H), 7.65 (d, J = 8.6 Hz, 1H), 7.45 (d, J = 9.2 Hz, 1H), 7.27 (d, J = 9.5 Hz, 2H), 6.63 (d, J = 2.2 Hz, 1H), 6.57-6.49 (m, 1H), 6.40 (d, J = 8.5 Hz, 2H), 5.12 (dd, J = 12.8, 5.3 Hz, 1H), 4.92 (s, 1H), 4.26 (s, 1H), 4.04 (d, J = 9.1 Hz, 1H), 3.90 (d, J = 2.5 Hz, 4H), 3.79 (s, 2H), 3.60 (s, 1H), 2.87 (d, J = 11.8 Hz, 2H), 2.62 (s, 1H), 2.38 (s, 2H), 2.25 (s, 2H), 2.04 (d, J = 6.7 Hz, 1H), 1.85 (s, 1H), 1.21 (s, 5H), 1.14 (s, 4H), 0.95-0.89 (m, 4H). |
| 217 | 844.42 | 845.75 | A | $^1$H NMR (400 MHz, Methanol-d$_4$) δ 7.82 (d, J = 8.3 Hz, 1H), 7.77-7.69 (m, 2H), 7.54 (d, J = 8.6 Hz, 1H), 7.32-7.22 (m, 2H), 6.61 (d, J = 2.2 Hz, 1H), 6.57 (dd, J = 8.7, 2.2 Hz, 1H), 6.53-6.47 (m, 2H), 5.12 (dd, J = 12.6, 5.4 Hz, 1H), 4.26 (d, J = 1.0 Hz, 1H), 4.19 (q, J = 7.0 Hz, 2H), 4.14 (d, J = 0.9 Hz, 1H), 4.04 (t, J = 7.6 Hz, 2H), 3.79 (p, J = 8.1 Hz, 1H), 3.62 (dd, J = 7.6, 5.2 Hz, 2H), 3.05 (p, J = 6.7 Hz, 1H), 2.89 (ddd, J = 17.6, 14.1, 5.1 Hz, 1H), 2.82-2.66 (m, 4H), 2.52 (q, J = 10.5, 7.7 Hz, 2H), 2.36 (t, J = 10.4 Hz, 2H), 2.25-2.10 (m, 1H), 1.63 (s, 1H), 1.48 (t, J = 7.0 Hz, 3H), 1.33 (d, J = 18.0 Hz, 6H), 1.30 (s, 5H), 1.25 (s, 6H), 1.06 (d, J = 6.7 Hz, 6H), 0.96-0.88 (m, 1H). |
| 218 | 860.42 | 861.75 | A | $^1$H NMR (400 MHz, DMSO-d$_6$) δ 11.06 (s, 1H), 8.60 (s, 1H), 8.33 (s, 1H), 8.13 (s, 1H), 7.80 (d, J = 9.2 Hz, 1H), 6.82 (d, J = 6.4 Hz, 2H), 6.76 (s, 2H), 5.04 (dd, J = 12.8, 12.4 Hz, 1H), 4.98 (s, 1H), 4.48 (d, J = 12.8 Hz, 2H), 4.29 (s, 1H), 3.95 (s, 1H), 3.93 (s, 3H), 3.10 (s, 1H), 3.02 (t, J = 11.6 Hz, 2H), 2.94-2.81 (m, 2H), 2.60 (s, 2H), 2.54 (s, 2H), 2.43 (s, 6H), 2.38 (s, 1H), 2.25-2.17 (m, 2H), 2.14 (s, 3H), 2.12-2.07 (m, 2H), 2.03-1.96 (m, 1H), 1.83 (d, J = 11.2 Hz, 3H), 1.19 (s, 6H), 1.12 (s, 6H). |
| 219 | 933.42 | 934.76 | A | $^1$H NMR (400 MHz, DMSO-d$_6$) δ 11.12 (s, 1H), 7.85-7.93 (m, 2H), 7.75 (d, J = 8.8 Hz, 2H), 7.50 (d, J = 9.2 Hz, 1H), 7.27-7.34 (m, 2H), 7.20 (d, J = 2.0 Hz, 1H), 6.95-7.03 (m, 3H), 5.12 (dd, J = 12.8, 5.6 Hz, 1H), 5.04 (s, 1H), 4.32 (s, 1H), 4.05 (d, J = 8.8 Hz, 1H), 3.82-4.01 (m, 7H), 3.78 (s, 2H), 3.09-3.29 (m, 6H), 2.76-2.95 (m, 4H), 2.65-2.75 (m, 3H), 2.53-2.64 (m, 2H), 2.39-2.43 (m, 2H), 2.00-2.09 (m, 1H), 1.75-1.94 (m, 3H), 1.23-1.33 (m, 2H), 1.21 (s, 6H), 1.12 (s, 6H). |
| 220 | 886.43 | 887.77 | A | $^1$H NMR (400 MHz, DMSO-d$_6$) δ 11.08 (s, 1H), 7.75 (d, J = 8.7 Hz, 2H), 7.48 (d, J = 9.2 Hz, 1H), 6.98 (d, J = 8.8 Hz, 2H), 6.87-6.80 (m, 2H), 6.74 (s, 2H), 5.05 (dd, J = 12.7, 5.4 Hz, 1H), 4.23 (s, 1H), 4.04 (d, J = 9.1 Hz, 1H), 3.94 (s, 3H), 3.69 (s, 2H), 3.51 (d, J = 11.9 Hz, 2H), 3.15 (t, J = 10.9 Hz, 2H), 2.95-2.82 (m, 2H), 2.60 (d, J = 3.6 Hz, 1H), 2.55 (s, 1H), 2.46 (d, J = 7.3 Hz, 1H), 2.44 (s, 6H), 2.31 (s, 2H), 2.19 (s, 4H), 1.92 (d, J = 13.0 Hz, 2H), 1.64 (t, J = 10.6 Hz, 2H), 1.22 (s, 6H), 1.13 (s, 6H). |
| 221 | 844.42 | 845.74 | A | $^1$H NMR (400 MHz, DMSO-d$_6$) δ 11.09 (s, 1H), 7.84 (d, J = 8.3 Hz, 1H), 7.72 (d, J = 8.4 Hz, 2H), 7.51 (d, J = 2.2 Hz, 1H), 7.47 (d, J = 9.2 Hz, 1H), 7.39 (dd, J = 8.4, 2.2 Hz, 1H), 6.94 (d, J = 8.5 Hz, 2H), 6.74 (s, 2H), 5.12 (dd, J = 13.0, 5.4 Hz, 1H), 4.37 (dd, J = 10.3, 4.2 Hz, 1H), 4.22 (s, 2H), 4.03 (d, J = 9.1 Hz, 1H), 3.83 (s, 3H), 3.82-3.75 (m, 1H), 3.57 (d, J = 11.3, 7.0 Hz, 1H), 2.75 (d, J = 12.4 Hz, 2H), 2.64-2.55 (m, 1H), 2.43 (s, 6H), 2.28 (d, J = 12.8 Hz, 2H), 2.05 (d, J = 12.8 Hz, 1H), 1.84 (d, J = 12.7 Hz, 1H), 1.76 (d, J = 13.2 Hz, 2H), 1.23 (d, J = 10.7 Hz, 7H), 1.17 (s, 1H), 1.12 (s, 6H). |
| 222 | 904.45 | 905.72 | A | $^1$H NMR (400 MHz, DMSO-d$_6$) δ 11.16 (s, 1H), 9.24-9.37 (m, 1H), 8.69 (s, 1H), 8.44 (s, 1H), 7.87 (d, J = 8.8 Hz, 1H), 7.58 (s, 1H), 7.25-7.37 (m, 1H), 6.82 (s, 2H), 5.05-5.23 (m, 2H), 4.58 (d, J = 12.8 Hz, 2H), 4.36 (s, 1H), 4.20-4.34 (m, 1H), 3.96-4.09 (m, 4H), 3.72 (s, 2H), 3.40 (s, 5H), 2.91-3.15 (m, 7H), 2.60-2.71 (m, 2H), 2.49 (s, 6H), 2.07-2.21 (m, 2H), 1.85-2.02 (m, 2H), 1.38-1.53 (m, 2H), 1.28-1.38 (m, 2H), 1.26 (s, 6H), 1.18 (s, 6H). |
| 223 | 860.46 | 861.20 | A | $^1$H NMR (400 MHz, DMSO-d$_6$) d ppm 1.01-1.11 (m, 3 H) 1.11 (s, 6 H) 1.19 (s, 6 H) 1.84 (d, J = 11.93 Hz, 2 H) 2.18 (d, J = 7.83 Hz, 2 H) 2.25 (d, J = 6.46 Hz, 2 H) 2.28-2.41 (m, 4 H) 2.43 (s, 6 H) 2.54-2.70 (m, 3 H) 3.00 (t, J = 11.93 Hz, 3 H) 3.24 (s, 3 H) 3.35-3.42 (m, 3 H) 3.43-3.52 (m, 2 H) 3.94 (d, J = 9.00 Hz, 1 H) 4.19-4.41 (m, 4 H) 4.49 (d, J = 13.30 Hz, 2 H) 4.80 (br. s 1 H) 5.09 (dd, J = 13.21, 5.18 Hz, 1 H) 6.76 (s, 2 H) 7.01 (d, J = 2.35 Hz, 1 H) 7.12 (dd, J = 8.22, 2.35 Hz, 1 H) 7.50 (d, J = 8.41 Hz, 1 H) 7.80 (d, J = 9.19 Hz, 1 H) 8.33 (s, 1 H) 8.60 (d, J = 0.98 Hz, 1 H) 10.98 (br. s, 1 H). |
| 224 | 830.41 | 831.73 | A | $^1$H NMR (400 MHz, DMSO-d$_6$) δ 11.12 (s, 1H), 9.39-9.18 (m, 1H), 8.63 (s, 1H), 8.38 (s, 1H), 7.89 (d, J = 8.0 Hz, 1H), 7.82 (d, J = 8.8 Hz, 1H), 7.34-7.28 (m, 2H), 6.76 (s, 2H), 5.17-5.03 (m, 2H), 4.53 (br s, 2H), 4.30 (s, 1H), 4.15-3.89 (m, 2H), 3.18 (br d, J = 4.4 Hz, 2H), 3.07 (br d, J = 11.6 Hz, 3H), 2.88 (br d, J = 12.8 Hz, 7H), 2.78 (br s, 2H), 2.61-2.55 (m, 6H), 2.21-2.03 (m, 2H), 1.97-1.73 (m, 2H), 1.20 (s, 8H), 1.12 (s, 6H). |
| 225 | 858.43 | 859.74 | A | $^1$H NMR (400 MHz, Methanol-d$_4$) δ 7.82 (d, J = 8.2 Hz, 1H), 7.75 (d, J = 8.8 Hz, 2H), 7.31-7.21 (m, 2H), 7.01 (d, J = 9.0 Hz, 2H), 6.73 (s, 2H), 5.12 (dd, J = 12.6, 5.4 Hz, 1H), 4.25 (s, 1H), 4.13 (s, 1H), 3.93 (d, J = 12.9 Hz, 2H), 3.68-3.55 (m, 2H), 2.85 (t, J = 12.1 Hz, 2H), 2.80-2.71 (m, 1H), 2.67 (t, J = 6.4 Hz, 2H), 2.49 (s, 6H), 2.37 (d, J = 6.7 Hz, 3H), 2.15 (s, 1H), 1.96 (d, J = 12.6 Hz, 1H), 1.74 (s, 1H), 1.30 (d, J = 6.1 Hz, 9H), 1.23 (s, 6H), 0.12 (s, 2H). |
| 226 | 880.40 | 881.74 | A | $^1$H NMR (300 MHz, DMSO-d$_6$) δ 10.97 (s, 1H), 8.60 (s, 1H), 8.33 (s, 1H), 7.91 (d, 1H), 7.83 (m, 1H), 7.25 (s, 1H), 7.05-7.02 (m, 1H), 6.76-6.75 (m, 1H), 6.59 (m, 1H), 5.07-5.05 (m, 1H), 4.76 (m, 1H), 4.52-4.49 (m, 2H), 4.43 (s, 1H), 4.31 (m, 1H), 4.15 (m, 1H), 3.97 (m, 1H), 3.95-3.86 (s, 3H), 3.67-3.63 (m, 1H), 2.98-2.90 (m, 5H), 2.51(m, 1H), 2.40-2.37 (m, 4H), 2.26-2.24 (m, 2H), 2.18-2.16 (m, 2H), 2.07-1.96 (m, 1H), 1.88-1.85 (m, 2H), 1.70 (m, 1H), 1.23-1.13 (m, 12H), 0.93-0.92(m, 6H). |

TABLE 2C-continued

Degradation of AR proteins by exemplary heterobifunctional compounds of the present disclosure.

| Comp No. | Exact Mass | Observed Mass | DC50 Code* | NMR |
|---|---|---|---|---|
| 227 | 880.40 | 881.75 | A | $^1$H NMR (400 MHz, Chloroform-d) δ 8.84 (d, J = 1.3 Hz, 1H), 8.02 (d, J = 1.5 Hz, 1H), 7.98 (s, 1H), 7.78 (d, J = 8.9 Hz, 1H), 7.58 (dd, J = 8.8, 4.2 Hz, 2H), 6.99 (d, J = 2.4 Hz, 1H), 6.87-6.78 (m, 2H), 5.36 (s, 1H), 5.32 (s, 3H), 5.21 (dd, J = 13.3, 5.2 Hz, 1H), 4.78 (s, 1H), 4.57-4.44 (m, 3H), 4.35 (d, J = 16.1 Hz, 1H), 4.15 (d, J = 8.8 Hz, 1H), 4.09 (s, 1H), 3.98 (s, 3H), 3.77 (s, 2H), 2.98 (s, 3H), 2.95-2.78 (m, 1H), 2.42-2.31 (m, 1H), 2.31-2.19 (m, 1H), 2.02 (d, J = 7.0 Hz, 2H), 1.33 (s, 5H), 1.26 (d, J = 22.0 Hz, 16H), 1.00 (s, 3H), 0.90 (t, J = 6.4 Hz, 1H). |
| 228 | 856.42 | 857.75 | A | $^1$H NMR (400 MHz, Methanol-d$_4$) δ 11.93 (s, 1H), 8.65 (d, J = 8.4 Hz, 1H), 8.57 (d, J = 8.7 Hz, 2H), 8.30 (d, J = 9.2 Hz, 1H), 8.08 (d, J = 7.7 Hz, 2H), 7.79 (d, J = 8.8 Hz, 2H), 7.55 (s, 2H), 5.93 (dd, J = 12.8, 5.5 Hz, 1H), 5.79 (s, 1H), 4.86 (d, J = 9.2 Hz, 1H), 4.51 (s, 2H), 4.31 (s, 2H), 4.14 (s, 32H), 3.97 (t, J = 11.3 Hz, 2H), 3.71 (s, 2H), 3.41 (d, J = 17.6 Hz, 2H), 3.25 (s, 6H), 3.01 (s, 3H), 2.87-2.79 (m, 1H), 2.72 (s, 1H), 2.45 (s, 0H), 2.28 (d, J = 8.5 Hz, 1H), 2.05 (d, J = 7.9 Hz, 14H), 1.94 (s, 6H), 1.66 (d, J = 7.0 Hz, 1H), 0.82 (s, 12H), 0.82 (d, J = 6.7 Hz, 0H). |
| 229 | 860.42 | 861.70 | A | $^1$H NMR (400 MHz, Methanol-d$_4$) δ 8.67 (d, J = 1.3 Hz, 1H), 8.24 (s, 1H), 7.82 (d, J = 8.3 Hz, 1H), 7.31-7.20 (m, 2H), 6.74 (s, 2H), 5.12 (dd, J = 12.7, 5.5 Hz, 1H), 4.59 (d, J = 14.1 Hz, 3H), 4.27 (s, 1H), 4.06 (s, 1H), 3.68-3.58 (m, 2H), 3.06 (t, J = 12.9 Hz, 2H), 2.91-2.82 (m, 1H), 2.77 (d, J = 12.2 Hz, 1H), 2.67 (t, J = 6.4 Hz, 2H), 2.49 (s, 7H), 2.37 (d, J = 6.9 Hz, 4H), 2.00 (d, J = 13.5 Hz, 2H), 1.30 (d, J = 8.9 Hz, 9H), 1.21 (s, 6H), 0.12 (s, 2H). |
| 230 | 929.48 | 930.82 | A | $^1$H NMR (400 MHz, DMSO-d$_6$) δ 11.11 (s, 1H), 8.62 (s, 1H), 8.37 (s, 1H), 7.87 (d, J = 8.8 Hz, 1H), 7.80 (d, J = 8.8 Hz, 1H), 7.32-7.25 (m, 2H), 6.76 (s, 2H), 5.12 (dd, J = 12.8, 5.6 Hz, 1H), 5.01 (br s, 1H), 4.52 (br d, J = 12.8 Hz, 2H), 4.30 (s, 1H), 3.94 (br d, J = 8.8 Hz, 2H), 3.76 (br s, 4H), 3.08 (br s, 4H), 3.03 (br s, 4H), 2.88 (br d, J = 10.8 Hz, 2H), 2.58 (br s, 6H), 2.43 (s, 6H), 2.35 (br d, J = 13.2 Hz, 3H), 2.15-1.80 (m, 5H), 1.20 (s, 7H), 1.12 (s, 6H). |
| 231 | 906.44 | 907.79 | A | $^1$H NMR (400 MHz, DMSO) δ 11.12 (s, 1H), 8.79 (s, 2H), 7.74-7.72 (m, 1H), 6.86 (s, 1H), 6.79 (s, 1H), 6.74 (s, 2H), 5.07-5.02 (m, 1H), 4.87 (m, 1H), 4.67-4.64 (m, 2H), 4.20 (m, 1H), 4.04-4.02 (m, 1H), 3.93 (s, 3H), 3.80-3.77 (m, 1H), 3.25-3.19 (m, 1H), 3.02-2.99 (m, 1H), 2.92-2.83 (m, 1H), 2.71-2.55 (m, 4H), 2.43 (m, 9H), 2.18-2.13 (m, 2H), 2.08-1.91 (m, 3H), 1.68-1.53 (m, 2H), 1.22 (s, 6H), 1.11 (s, 6H), 0.95-0.94 (m, 6H). |
| 232 | 934.46 | 935.81 | A | $^1$H NMR (400 MHz, DMSO-d$_6$) δ 11.34-10.87 (m, 1 H), 9.70-9.23 (m, 1 H), 8.41-8.11 (m, 1 H), 7.76-7.48 (m, 1 H), 7.01-6.78 (m, 2 H), 6.69-6.41 (m, 2 H), 5.18-4.96 (m, 2 H), 4.81-4.64 (m, 2 H), 4.41-4.00 (m, 6 H), 3.95-3.86 (m, 6 H), 3.37-3.29 (m, 6 H), 3.15-2.99 (m, 2 H), 2.97-2.82 (m, 6 H), 2.70-2.65 (m, 1 H), 2.29-2.16 (m, 6 H), 2.09-1.95 (m, 2 H), 1.91-1.72 (m, 2 H), 1.26-1.04 (m, 14 H). |
| 233 | 926.44 | 927.78 | A | $^1$H NMR (400 MHz, DMSO-d$_6$) δ 11.12 (s, 1H), 8.63 (s, 1H), 8.37 (s, 1H), 8.07 (d, J = 8.8 Hz, 1H), 7.91-7.76 (m, 2H), 7.67 (d, J = 2.4 Hz, 1H), 7.38 (dd, J = 8.8, 2.4 Hz, 1H), 7.31-7.26 (m, 2H), 5.13 (dd, J = 12.8, 5.6 Hz, 1H), 5.01 (br s, 1H), 4.58-4.45 (m, 3H), 3.97 (br d, J = 8.8 Hz, 2H), 3.76 (br s, 4H), 3.08 (br s, 4H), 3.01 (br d, J = 11.6 Hz, 4H), 2.90 (br s, 2H), 2.70-2.57 (m, 6H), 2.35 (br d, J = 13.2 Hz, 3H), 2.08 (s, 2H), 2.00-1.80 (m, 3H), 1.20 (s, 7H), 1.13 (s, 6H). |
| 234 | 830.37 | 831.70 | A | $^1$H NMR (400 MHz, DMSO-d$_6$) δ 7.91 (d, J = 8.8 Hz, 1H), 7.74 (d, J = 8.8 Hz, 2H), 7.49 (d, J = 8.4 Hz, 2H), 7.30 (d, J = 8.4 Hz, 1H), 7.21 (s, 1H), 7.13 (s, 1H), 6.97-6.95 (m, 3H), 4.67-4.56 (m, 2H), 4.33 (s, 1H), 4.06 (d, J = 8.8 Hz, 1H), 3.88-3.85 (m, 2H), 3.40-3.36 (m, 4H), 3.20-3.16 (m, 4H), 3.00-2.95 (m, 1H), 2.79-2.73 (m, 5H), 2.23-2.21 (m, 2H), 1.82-1.79 (m, 3H), 1.22-1.13 (m, 14H). |
| 235 | 910.41 | 911.75 | A | $^1$H NMR (300 MHz, DMSO-d$_6$) δ 11.11 (s, 1H), 7.82-7.72 (m, 2H), 7.65 (m, 1H), 7.51 (m, 1H), 7.02-6.92 (m, 2H), 6.86-6.80 (m, 2H), 6.65 (m, 1H), 6.52 (m, 1H), 5.05-4.85 (m, 2H), 4.26 (s, 1H), 4.10-4.01 (m, 2H), 3.98-3.80 (m, 8H), 3.72-3.47 (m, 4H), 2.96-2.60 (m, 6H), 2.42-2.14 (m, 6H), 2.11-1.94 (m, 2H), 1.87-1.57 (m, 6H), 1.30-1.06 (m, 12H). |
| 236 | 858.41 | 859.74 | A | $^1$H NMR (400 MHz, Methanol-d$_4$) δ 8.68 (d, J = 1.3 Hz, 1H), 8.26 (d, J = 1.4 Hz, 1H), 7.82 (d, J = 8.3 Hz, 1H), 7.30-7.20 (m, 2H), 6.74 (s, 2H), 5.12 (dd, J = 12.6, 5.5 Hz, 1H), 4.29-4.19 (m, 3H), 4.06 (d, J = 0.9 Hz, 1H), 3.84 (t, J = 4.8 Hz, 2H), 3.46 (t, J = 11.5 Hz, 2H), 2.99 (p, J = 6.7 Hz, 1H), 2.89 (ddd, J = 17.7, 14.3, 5.1 Hz, 1H), 2.81-2.74 (m, 1H), 2.77-2.67 (m, 1H), 2.57-2.50 (m, 1H), 2.49 (s, 6H), 2.42 (s, 2H), 2.32 (td, J = 7.2, 3.9 Hz, 2H), 2.28 (s, 2H), 2.13 (d, J = 13.6 Hz, 3H), 1.72-1.60 (m, 2H), 1.29 (s, 6H), 1.22 (s, 6H). |
| 237 | 935.41 | 936.75 | B | $^1$H NMR (400 MHz, DMSO-d$_6$) δ 11.11 (s, 1H), 8.62 (d, J = 1.2 Hz, 1H), 8.37 (s, 1H), 7.93-7.85 (m, 2H), 7.81 (d, J = 8.8 Hz, 1H), 7.34-7.27 (m, 2H), 7.25 (d, J = 2.4 Hz, 1H), 7.04 (dd, J = 8.8, 2.4 Hz, 1H), 5.13 (dd, J = 12.8, 5.6 Hz, 1H), 5.02 (br s, 1H), 4.52 (br d, J = 12.8 Hz, 2H), 4.44 (s, 1H), 3.96 (br d, J = 8.8 Hz, 2H), 3.78 (br s, 4H), 3.12 (br s, 4H), 3.09-2.99 (m, 4H), 2.97-2.80 (m, 2H), 2.69-2.54 (m, 6H), 2.50-2.31 (m, 3H), 2.22-1.69 (m, 5H), 1.20 (s, 7H), 1.14 (s, 6H). |
| 238 | 902.47 | 903.81 | B | $^1$H NMR (300 MHz, DMSO-d$_6$) δ 11.06 (s, 1H), 8.62 (s, 1H), 8.31 (s, 1H), 7.78 (s, 1H), 6.82 (m, 2H), 6.75 (m, 2H), 5.07-5.00 (m, 1H), 4.92-4.87 (m, 1H), 4.53-4.48 (m, 2H), 4.29 (m, 1H), 4.27-4.17 (m, 2H), 3.93 (m, 1H), 3.64 (m, 1H), 3.05-2.77 (m, 5H), 2.62-2.53 (m, 7H), 2.28-2.11 (m, 4H), 2.08-1.93 (m, 2H), 1.91-1.80 (m, 2H), 1.78-1.63 (m, 1H), 1.36 (m, 3H), 1.19 (m, 7H), 1.11 (m, 8H), 0.93-0.91 (m, 6H). |
| 239 | 880.37 | 881.71 | B | $^1$H NMR (400 MHz, DMSO-d$_6$) δ 11.10 (s, 1H), 8.60 (s, 1H), 8.32 (s, 1H), 8.21 (s, 1H), 7.89 (d, J = 8.8 Hz, 1H), 7.73-7.86 (m, 2H), 7.19-7.30 (m, 3H), 7.03 (d, J = 8.8 Hz, 1H), 5.09-5.13 (m, 1H), 4.93 (s, 1H), 4.41-4.52 (m, 3H), 3.95 (d, J = 9.2 Hz, 1H), 3.26-3.28 (m, 3H), 3.11-3.14 (m, 1H), 2.81-3.17 (m, 3H), 2.55-2.70 (m, 6H), 2.32-2.41 (m, 3H), 2.10-2.30 (m, 5H), 2.04 (s, 1H), 1.83 (d, J = 10.4 Hz, 3H), 1.19 (s, 6H), 1.12 (s, 6H). |
| 240 | 904.45 | 905.78 | B | $^1$H NMR (400 MHz, DMSO-d$_6$) δ 11.12 (s, 1H), 9.34 (ddd, J = 5.6, 4.0, 2.0 Hz, 1H), 8.23 (br d, J = 9.6 Hz, 1H), 7.88 (br d, J = 8.8 Hz, 1H), 7.63 (d, J = 8.8 Hz, 1H), 7.40-7.25 (m, 2H), 6.64 (s, 1H), 6.54 (br d, J = 8.8 Hz, 1H), 5.16-5.01 (m, 2H), 4.73 (br d, J = 12.0 Hz, 2H), 4.20 (s, 2H), 4.07 (br d, J = 9.6 Hz, 1H), 3.90 (s, 3H), 3.65 (br s, 5H), 3.33 (s, 4H), 2.91-2.84 (m, 4H), 2.72-2.53 (m, 4H), 2.23 (s, 6H), 2.07 (s, 3H), 1.93-1.71 (m, 2H), 1.18 (s, 6H), 1.12 (s, 8H). |

TABLE 2C-continued

Degradation of AR proteins by exemplary heterobifunctional compounds of the present disclosure.

| Comp No. | Exact Mass | Observed Mass | DC50 Code* | NMR |
|---|---|---|---|---|
| 241 | 830.37 | 831.70 | B | $^1$H NMR (400 MHz, DMSO-d$_6$) δ 11.73 (br, 1H), 7.90 (d, J = 8.8 Hz, 1H), 7.73 (d, J = 8.8 Hz, 2H), 7.49 (d, J = 8.4 Hz, 2H), 7.30 (d, J = 8.4 Hz, 1H), 7.21 (s, 1H), 7.13 (s, 1H), 6.97-6.95 (m, 3H), 4.63-4.55 (m, 2H), 4.32 (s, 1H), 4.05 (d, J = 8.8 Hz, 1H), 3.88-3.85 (m, 2H), 3.40-3.36 (m, 4H), 3.20-3.16 (m, 4H), 3.00-2.95 (m, 1H), 2.79-2.73 (m, 5H), 2.23-2.21 (m, 2H), 1.82-1.79 (m, 3H), 1.22-1.13 (m, 14H). |
| 242 | 908.43 | 909.77 | B | $^1$H NMR (300 MHz, DMSO-d$_6$) δ 11.20 (s, 1H), 7.86-7.67 (m, 2H), 7.48 (m, 1H), 7.02-6.65 (m, 6H), 5.22-4.80 (m, 2H), 4.37-3.72 (m, 8H), 3.02-2.61 (m, 6H), 2.45-2.13 (m, 14H), 2.11-1.52 (m, 6H), 1.27-0.92 (m, 12H). |
| 243 | 978.43 | 979.80 | B | $^1$H NMR (400 MHz, DMSO-d$_6$) δ 1.06 (t, J = 7.2 Hz, 3H), 1.11 (s, 1H), 1.15 (s, 6H), 1.20 (s, 6H), 1.23 (s, 2H), 1.88 (s, 2H), 2.00-2.13 (m, 3H), 2.56-2.74 (m, 4H), 2.83-3.08 (m, 8H), 3.14 (d, J = 13.2 Hz, 2H), 3.70 (d, J = 10.4 Hz, 2H), 3.80 (d, J = 11.2 Hz, 1H), 3.91 (s, 3H), 3.95 (d, J = 9.2 Hz, 1H), 4.14 (s, 2H), 4.37 (s, 1H), 4.51 (d, J = 11.2 Hz, 2H), 5.04 (s, 1H), 5.09-5.23 (m, 2H), 6.57 (d, J = 8.8 Hz, 1H), 6.66 (s, 1H), 7.31 (s, 2H), 7.64 (d, J = 8.8 Hz, 1H), 7.85 (dd, J = 18.8, 8.8 Hz, 2H), 8.36 (s, 1H), 8.62 (s, 1H), 11.12 (s, 1H). |
| 244 | 932.44 | 933.58 | B | $^1$H NMR (400 MHz, DMSO-d$_6$) δ 11.16-11.03 (m, 1H), 8.27-8.18 (m, 1H), 7.87-7.79 (m, 1H), 7.91-7.75 (m, 1H), 7.69-7.61 (m, 1H), 7.43-7.32 (m, 1H), 6.92-6.82 (m, 1H), 6.79-6.72 (m, 1H), 6.70-6.64 (m, 1H), 6.61-6.53 (m, 1H), 5.13-4.98 (m, 2H), 4.57-4.47 (m, 2H), 4.46-4.36 (m, 3H), 4.03-3.98 (m, 1H), 3.91 (s, 3H), 3.50 (br d, J = 4.8 Hz, 7H), 3.11-2.98 (m, 4H), 2.70-2.58 (m, 7H), 2.36-2.25 (m, 3H), 2.10-1.88 (m, 8H), 1.74-1.64 (m, 3H), 1.25-1.14 (m, 14H). |
| 245 | 821.32 | 822.64 | B | |
| 246 | 910.42 | 911.76 | C | $^1$H NMR (400 MHz, DMSO-d$_6$) δ 11.10 (s, 1H), 8.62 (s, 1H), 8.35 (s, 1H), 7.83-7.80 (m, 1H), 6.86-6.84 (m, 2H), 6.77 (s, 2H), 5.08-5.04 (m, 1H), 4.97 (m, 1H), 4.52-4.49 (m, 2H), 4.31 (s, 1H), 3.96-3.94 (m, 4H), 3.63-3.63-3.59 (m, 1H), 3.32(m, 1H), 3.04-2.98 (m, 2H), 2.92-2.84 (m, 3H), 2.68-2.60 (m, 2H), 2.41-2.39 (m, 6H), 2.37-2.35 (m, 4H), 2.27-2.22 (m, 2H), 2.07-1.96 (m, 1H), 1.89-1.75(m, 3H), 1.23 (m, 6H), 1.18 (m, 8H). |
| 247 | 1084.47 | 1085.75 | D | $^1$H NMR (400 MHz, DMSO-d$_6$) δ 10.46-9.94 (m, 1H), 8.61 (br s, 1H), 8.35 (br s, 1H), 7.81 (br d, J = 8.8 Hz, 1H), 7.68-7.40 (m, 1H), 7.38-7.23 (m, 1H), 7.22-7.10 (m, 2H), 6.76 (s, 2H), 5.43 (br d, J = 12.0 Hz, 4H), 5.26 (br s, 1H), 4.94 (br s, 1H), 4.78 (br s, 1H), 4.51 (br d, J = 10.0 Hz, 2H), 4.30 (s, 1H), 4.14 (br s, 1H), 3.94 (br d, J = 8.8 Hz, 1H), 3.03 (br s, 5H), 2.81 (br d, J = 16.0 Hz, 3H), 2.43 (br s, 6H), 2.08 (br s, 4H), 1.92 (br s, 1H), 1.28 (br s, 4H), 1.25-1.15 (m, 18H), 1.12 (br s, 7H). |

A novel bifunctional molecule, which contains a recruiting moiety that selectively or preferentially binds to a AR protein and an E3 ubiquitin ligase recruiting moiety is described. The bifunctional molecules of the present disclosure actively ubiquitinate the mutated AR, resulting in proteasomal degradation, leading to suppression of cellular proliferation and induction of apoptosis.

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the disclosure described herein. Such equivalents are intended to be encompassed by the following claims. It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

What is claimed is:

1. A compound having the chemical structure:

PTM-L-CLM, or a pharmaceutically acceptable salt thereof, wherein:

(a) the CLM is:

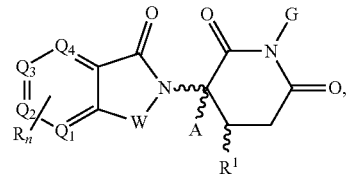

wherein:
W is selected from the group consisting of CH$_2$, C=O, NH, and N-alkyl;
G is H;
each of Q$_1$, Q$_2$, Q$_3$, and Q$_4$ represent a N or a C substituted with a group selected from H and R;
A is H;
n is an integer from 1 to 4;
each R is selected from the group consisting of H, OH, NH$_2$, unsubstituted or substituted C$_{1-4}$ alkyl, —OR$_2$, —Cl, —F, —Br, —CF$_3$, and —CN;
R$^1$ is H;
R$^2$ is C$_{1-3}$ alkyl; and
∼∼∼ represents a bond that may be stereospecific ((R) or (S)) or non-stereospecific,
wherein one R group is the point of attachment to the linker (L) or is modified to be covalently joined to the linker (L);

(b) the PTM is:

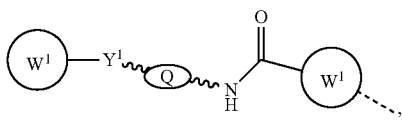

wherein:
W¹ is

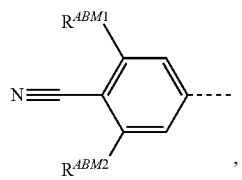

wherein $R^{ABM1}$ and $R^{ABM2}$ are each independently unsubstituted or substituted $C_1$-$C_3$ alkyl, or unsubstituted or substituted $C_1$-$C_4$ alkoxyl;
Y¹ is O or $CH_2$;
Q is a 8-10 membered fused bicyclic cycloalkyl, a 8-10 membered fused bicyclic heterocycloalkyl with 1 or 2 heteroatoms, a 7-9 membered spirocycloalkyl, or a 7-9 membered spiroheterocycloalkyl with 1 or 2 heteroatoms;
W² is a 5- or 6-membered aromatic group with 0 to 2 heteroatoms, that is optionally substituted by 1 or 2 $R^{W2}$;
each $R^{W2}$ is independently H, OH, halo, or $C_{1-3}$ alkyl;
⌇⌇⌇ represents a bond that may be stereospecific ((R) or (S)) or non-stereospecific; and
⌇ is the linker (L) attachment point; and
  (c) the L is:

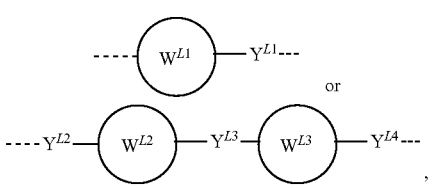

wherein:
$W^{L1}$ is a 5- or 6-membered ring with 0-3 heteroatoms or a $C_{8-11}$ spiroheterocycloalkyl with 0-3 heteroatoms, each optionally substituted with halo or methyl;
$Y^{L1}$ is a bond or $C_{1-5}$ alkyl wherein one or more C atoms are optionally replaced with O and each carbon is optionally substituted with halo, methyl, or ethyl;
$Y^{L2}$ is a bond, O, or $C_{1-3}$ alkyl, wherein each carbon is optionally substituted with halo, methyl, or ethyl;
$W^{L2}$ is a 3-7 membered ring with 0-3 heteroatoms, a $C_{5-11}$ spiroheterocycloalkyl, 6-10 membered fused bicyclic cycloalkyl, or 6-10 membered fused bicyclic heterocycloalkyl, each optionally substituted with halo or methyl;
$Y^{L3}$ is a bond or a $C_1$-$C_4$ alkyl wherein one or more C atoms are optionally replaced with O and wherein each carbon is optionally substituted with halo or $C_1$-$C_4$ alkyl;
$W^{L3}$ is a 3-7 membered ring having 0-3 heteroatoms and optionally substituted with halo or methyl; and
$Y^{L4}$ is bond or O.

2. The compound according to claim 1, or a pharmaceutically acceptable salt thereof, wherein:
(i) W is:

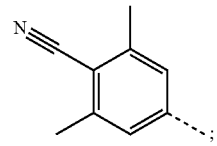

(ii) Q is selected from:

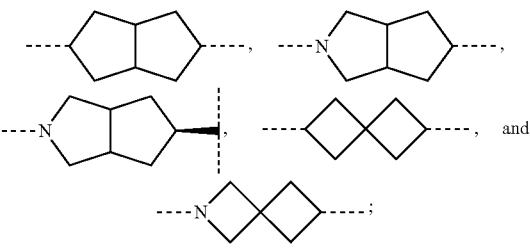

or
(iii) W² is selected from:

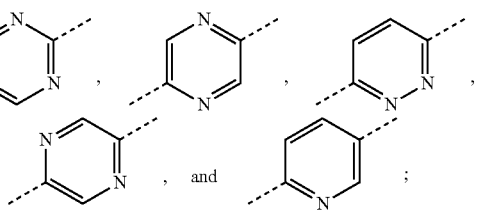

wherein the dashed lines indicate points of attachment.

3. The compound of claim 1, or a pharmaceutically acceptable salt thereof, wherein the CLM is:

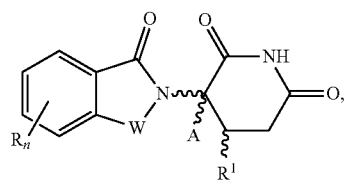

wherein:
W is $CH_2$ or C=O;
A is H;
R¹ is H;
n is 1 or 2;
each R is independently selected from a H, —Cl, —F, methyl, ethyl, methoxy, or ethoxy
wherein one R groups is modified to be covalently joined to the chemical linking group (L); and
⌇⌇⌇ represents a bond that may be stereospecific ((R) or (S)) or non-stereospecific.

4. A compound having the chemical structure:

PTM-L-CLM, or a pharmaceutically acceptable salt thereof, wherein:

(a) the CLM is:

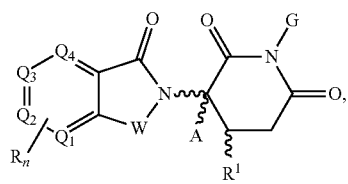

wherein:
W is selected from the group consisting of CH$_2$, C=O, NH, and N-alkyl;
G is H;
each of Q$_1$, Q$_2$, Q$_3$, and Q$_4$ represent a N or a C substituted with a group selected from H and R;
A is H;
n is an integer from 1 to 4;
each R is selected from the group consisting of H, OH, NH$_2$, unsubstituted or substituted C$_{1-4}$ alkyl, —OR$_2$, —Cl, —F, —Br, —CF$_3$, and —CN;
R$^1$ is H;
R$^2$ is C$_{1-3}$ alkyl; and
∿∿∿ represents a bond that may be stereospecific ((R) or (S)) or non-stereospecific,
wherein one R group is the point of attachment to the linker (L) or is modified to be covalently joined to the linker (L);

(b) the PTM is:

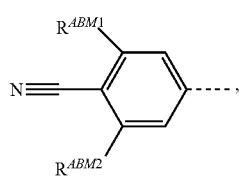

wherein:
W$^1$ is

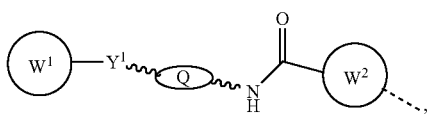

wherein R$^{ABM1}$ and R$^{ABM2}$ are each independently unsubstituted or substituted C$_1$-C$_3$ alkyl, or unsubstituted or substituted C$_1$-C$_4$ alkoxyl;
Y$^1$ is O or CH$_2$;
Q is a 8-10 membered fused bicyclic cycloalkyl, a 8-10 membered fused bicyclic heterocycloalkyl with 1 or 2 heteroatoms, a 7-9 membered spirocycloalkyl, or a 7-9 membered spiroheterocycloalkyl with 1 or 2 heteroatoms;
W$^2$ is a 5- or 6-membered aromatic group with 0 to 2 heteroatoms that is optionally substituted by 1 or 2 R$^{W2}$;
each R$^{W2}$ is independently H, OH, halo, or C$_{1-3}$ alkyl;

∿∿∿ represents a bond that may be stereospecific ((R) or (S)) or non-stereospecific; and
⌇ is the linker (L) attachment point; and
wherein the chemical linking group (L) is selected from the group consisting of:

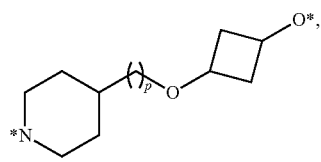

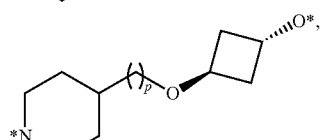

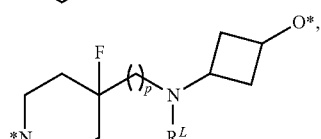

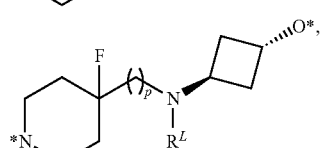

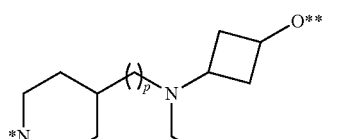

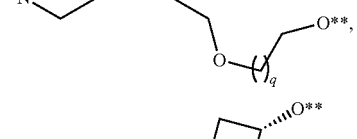

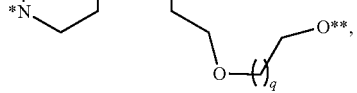

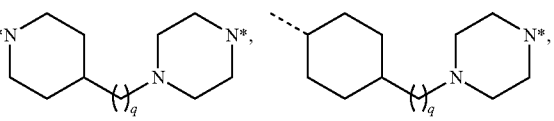

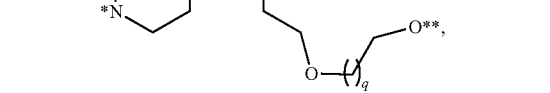

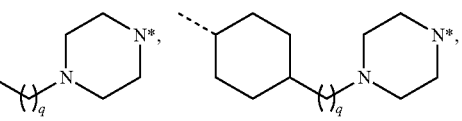

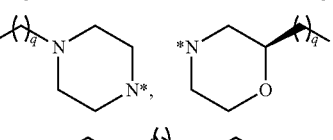

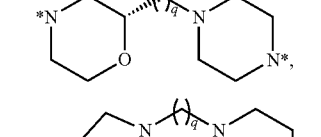

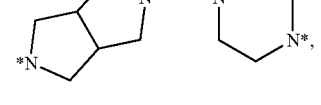

505
-continued
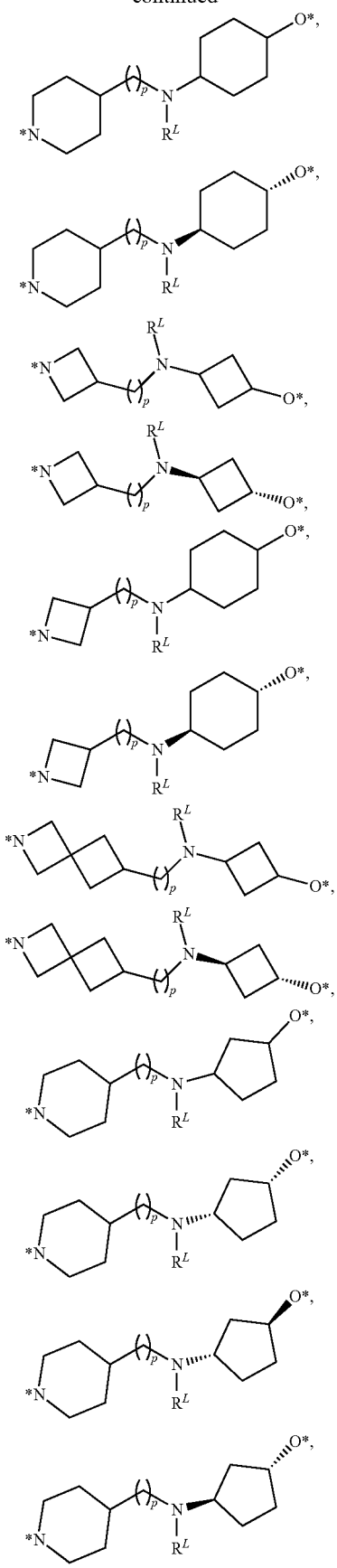
506
-continued
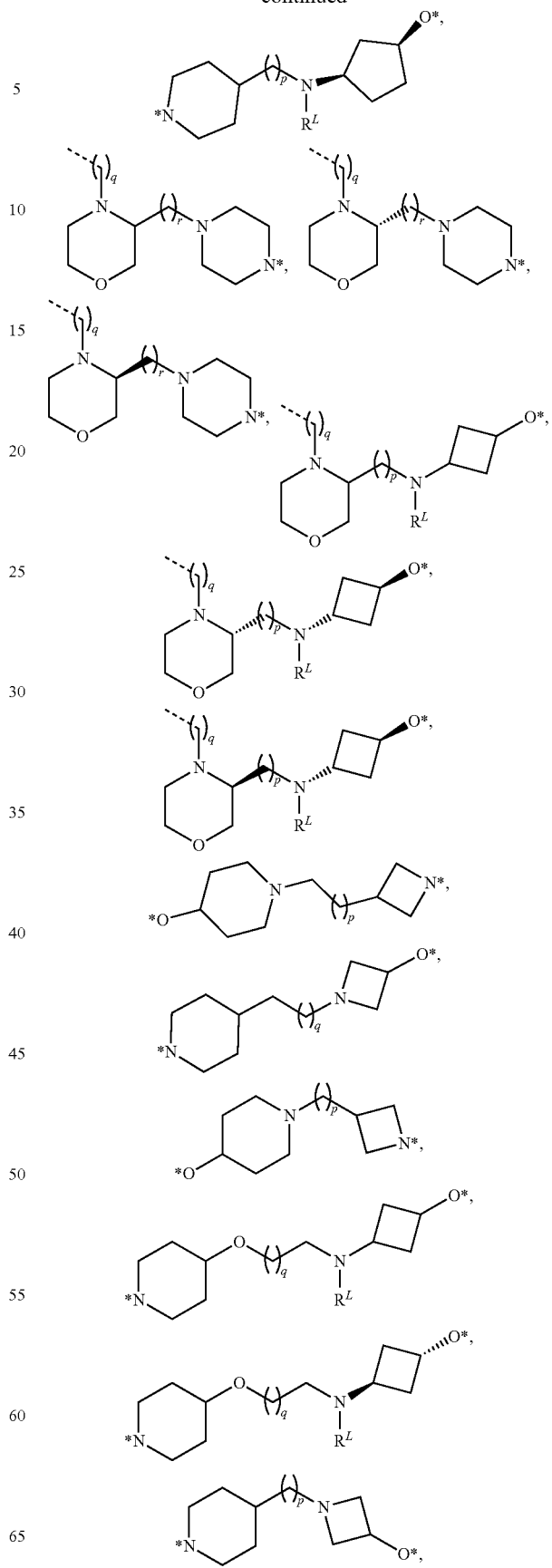

507
-continued

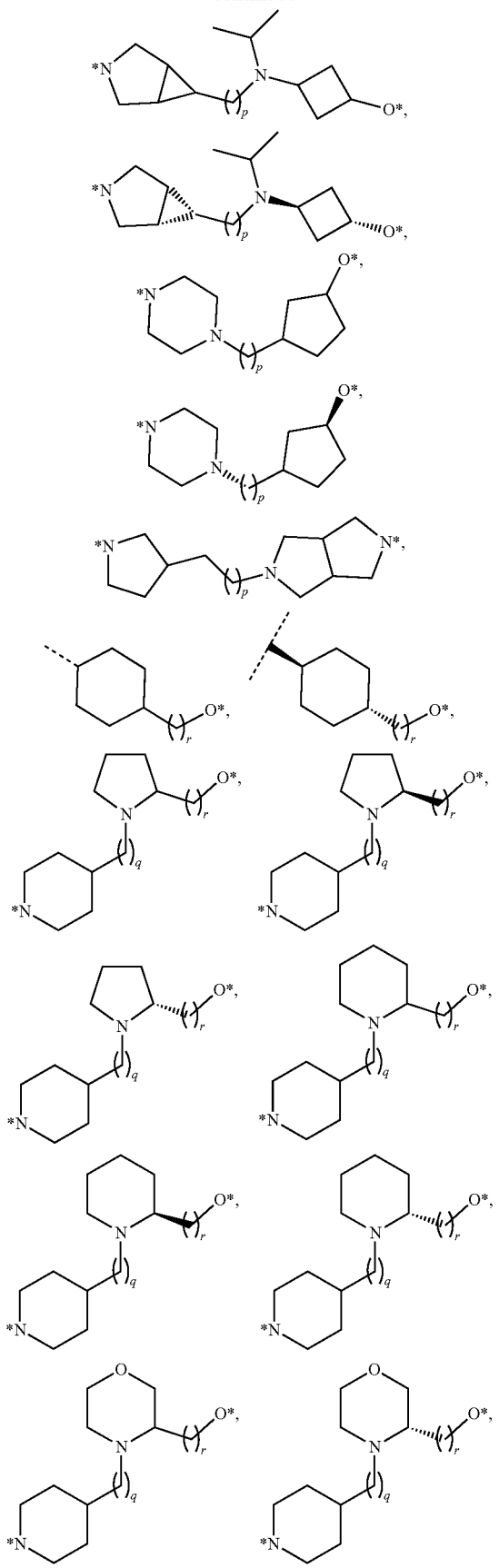

508
-continued

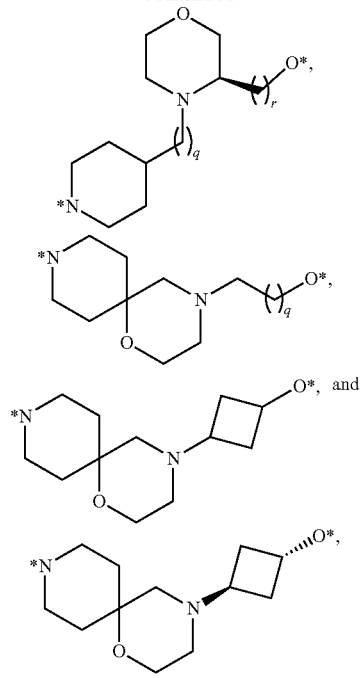

wherein:
R$^L$ is H; C$_1$-C$_4$ alkyl optionally substituted with one or more halo or C=O; or C$_1$-C$_3$ hydroxyalkyl;
p is an integer from 0 to 3;
q is an integer from 1 to 3;
r is an integer from 1 to 3;
⋯ indicates the site that is covalently linked to the CLM or PTM;
* indicates the site that is covalently linked to the CLM or PTM, or is an atom that is shared with the CLM or PTM; and
** indicates the site that is covalently linked to the CLM or is an atom that is shared with the CLM.

5. The compound according to claim 1, or a pharmaceutically acceptable salt thereof, wherein:
(a) the CLM is:

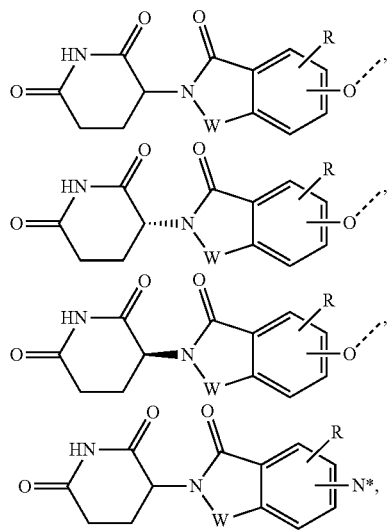

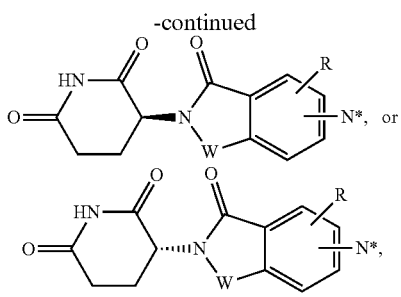

wherein:
- ⟋ of the CLM indicates the point of attachment with the chemical linking group; and
- N* is a nitrogen atom that is shared with the chemical linking group; or (b) the PTM is:

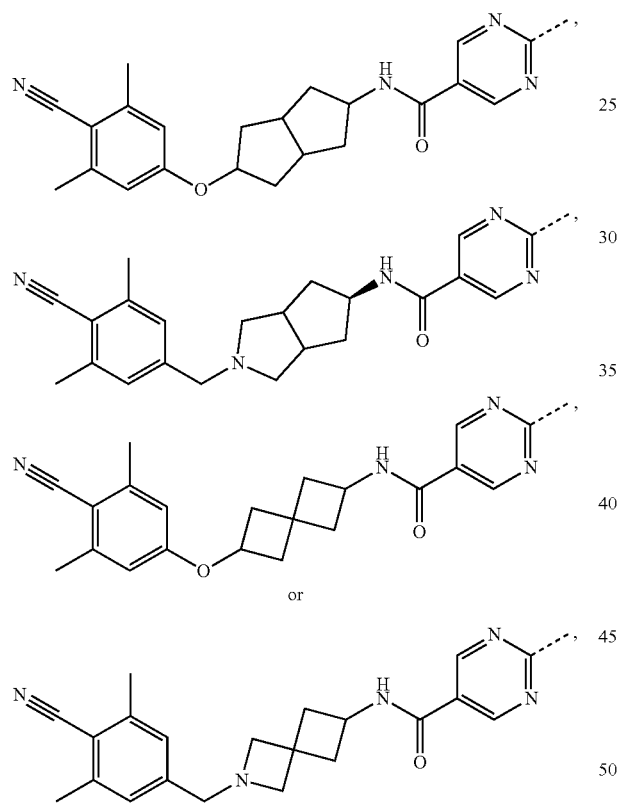

wherein ⟋ of the PTM indicates the point of attachment with the linker (L).

6. A pharmaceutical composition comprising the compound of claim 1 and a pharmaceutically acceptable carrier.

7. The pharmaceutical composition of claim 6, wherein the composition further comprises an additional bioactive agent.

8. The pharmaceutical composition of claim 7, wherein the additional bioactive agent is an anti-cancer agent.

9. A method of treating a disease, a disorder, symptom associated with the androgen receptor (AR) in a subject in need thereof, comprising administering an effective amount of the compound of claim 1, or a pharmaceutically acceptable salt thereof, to the subject, wherein the compound is effective in treating or ameliorating the disease, disorder, or at least one symptom of the disease or disorder.

10. The method of claim 9, wherein the disease or disorder is prostate cancer.

11. The method of claim 9, wherein the method further comprises administering at least one additional anti-cancer agent to the subject.

12. A pharmaceutical composition comprising the compound of claim 4 and a pharmaceutically acceptable carrier.

13. The pharmaceutical composition of claim 12, wherein the composition further comprises an additional bioactive agent.

14. The pharmaceutical composition of claim 13, wherein the additional bioactive agent is an anti-cancer agent.

15. A method of treating a disease, a disorder, or symptom associated with the androgen receptor (AR) in a subject in need thereof, comprising administering an effective amount of the compound of claim 4, or a pharmaceutically acceptable salt thereof, to the subject, wherein the compound is effective in treating or ameliorating the disease, disorder, or at least one symptom of the disease or disorder.

16. The method of claim 15, wherein the disease or disorder is prostate cancer.

17. The method of claim 15, wherein the method further comprises administering at least one additional anti-cancer agent to the subject.

18. The compound according to claim 4, or a pharmaceutically acceptable salt thereof, wherein:

(i) $W^1$ is:

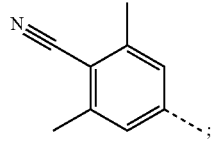

(ii) Q is selected from:

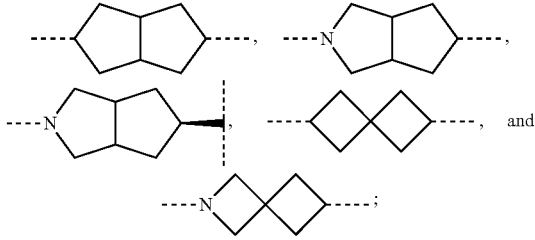

or (iii) $W^2$ is selected from:

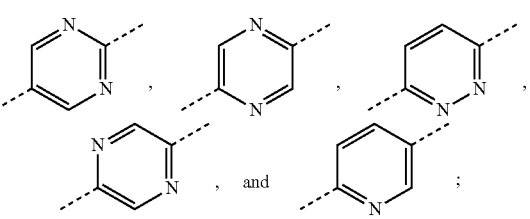

wherein the dashed lines indicate points of attachment.

19. The compound of claim 4, or a pharmaceutically acceptable salt thereof, wherein the CLM is:

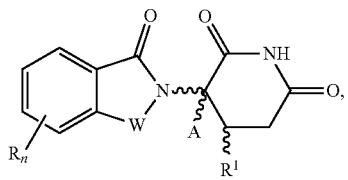

wherein:

W is $CH_2$ or C=O;

A is H;

$R^1$ is H;

n is 1 or 2;

each R is independently selected from a H, —Cl, —F, methyl, ethyl, methoxy, or ethoxy wherein one R groups is modified to be covalently joined to the chemical linking group (L); and ∿∿∿ represents a bond that may be stereospecific ((R) or (S)) or non-stereospecific.

20. The compound according to claim 4, or a pharmaceutically acceptable salt thereof, wherein:

(a) the CLM is:

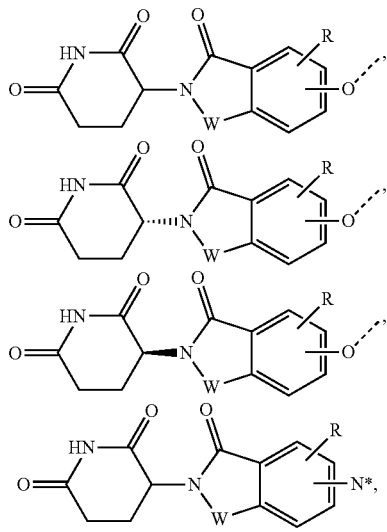

wherein:

⌇ of the CLM indicates the point of attachment with the chemical linking group; and N* is a nitrogen atom that is shared with the chemical linking group; or (b) the PTM is:

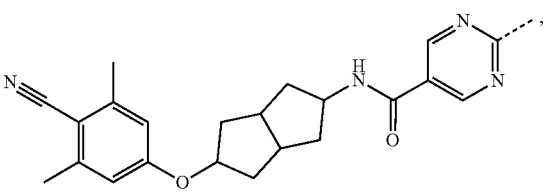

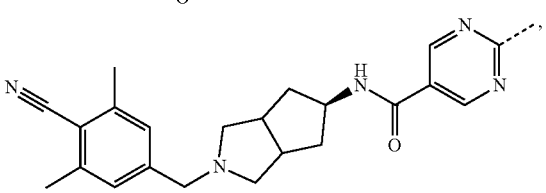

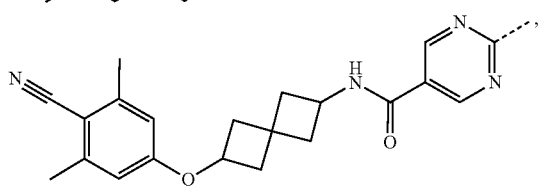

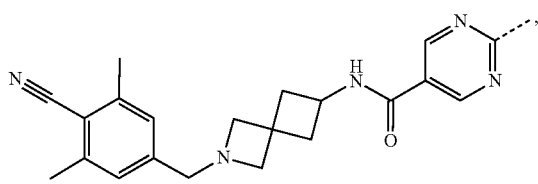

wherein ⌇ of the PTM indicates the point of attachment with the linker (L).

* * * * *